US012807571B2

(12) United States Patent
Tamiya et al.

(10) Patent No.: US 12,807,571 B2
(45) Date of Patent: Nov. 24, 2026

(54) COMPOUNDS AND METHODS FOR MODULATING RAS-PI3K

(71) Applicant: Vividion Therapeutics, Inc., San Diego, CA (US)

(72) Inventors: Junko Tamiya, Carlsbad, CA (US); Benjamin Horning, San Diego, CA (US); Karl Bedke, Oceanside, CA (US); Cynthia Berry, San Diego, CA (US); Chung-Mao Pan, San Diego, CA (US); Hideki Miyatake Ondozabal, La Jolla, CA (US); Brian Cook, San Diego, CA (US)

(73) Assignee: Vividion Therapeutics, Inc., San Diego, CA (US)

( * ) Notice: Subject to any disclaimer, the term of this patent is extended or adjusted under 35 U.S.C. 154(b) by 308 days.

(21) Appl. No.: 18/589,169

(22) Filed: Feb. 27, 2024

(65) Prior Publication Data

US 2025/0026721 A1 Jan. 23, 2025

Related U.S. Application Data

(60) Provisional application No. 63/487,431, filed on Feb. 28, 2023.

(51) Int. Cl.

| | |
|---|---|
| ***C07D 211/96*** | (2006.01) |
| ***A61K 31/4025*** | (2006.01) |
| ***A61K 31/445*** | (2006.01) |
| ***A61K 31/4523*** | (2006.01) |
| ***A61K 31/453*** | (2006.01) |
| ***A61K 31/4535*** | (2006.01) |
| ***A61K 31/454*** | (2006.01) |
| ***A61K 31/4545*** | (2006.01) |
| ***A61K 31/496*** | (2006.01) |
| ***A61K 31/5377*** | (2006.01) |
| ***A61K 31/55*** | (2006.01) |
| ***C07D 211/62*** | (2006.01) |
| ***C07D 211/78*** | (2006.01) |
| ***C07D 223/06*** | (2006.01) |
| ***C07D 401/06*** | (2006.01) |
| ***C07D 401/12*** | (2006.01) |
| ***C07D 401/14*** | (2006.01) |
| ***C07D 403/06*** | (2006.01) |
| ***C07D 405/06*** | (2006.01) |
| ***C07D 405/12*** | (2006.01) |
| ***C07D 405/14*** | (2006.01) |
| ***C07D 409/12*** | (2006.01) |
| ***C07D 409/14*** | (2006.01) |

(52) U.S. Cl.

CPC ........ *C07D 211/96* (2013.01); *A61K 31/4025* (2013.01); *A61K 31/445* (2013.01); *A61K 31/4523* (2013.01); *A61K 31/453* (2013.01); *A61K 31/4535* (2013.01); *A61K 31/454* (2013.01); *A61K 31/4545* (2013.01); *A61K 31/496* (2013.01); *A61K 31/5377* (2013.01); *A61K 31/55* (2013.01); *C07D 211/62* (2013.01); *C07D 211/78* (2013.01); *C07D 223/06* (2013.01); *C07D 401/06* (2013.01); *C07D 401/12* (2013.01); *C07D 401/14* (2013.01); *C07D 403/06* (2013.01); *C07D 405/06* (2013.01); *C07D 405/12* (2013.01); *C07D 405/14* (2013.01); *C07D 409/12* (2013.01); *C07D 409/14* (2013.01)

(58) Field of Classification Search

CPC .................................................... C07D 211/96

See application file for complete search history.

(56) References Cited

FOREIGN PATENT DOCUMENTS

WO 2009098282 A1 8/2009

OTHER PUBLICATIONS

International Search Report and Written Opinion for PCT/US2024/017497, dated Jul. 10, 2024, 14 pages.

Caulfield Thomas J. et al., "Parallel Solid-Phase Synthesis of Peptidyl Michael Acceptors", Journal of Combinatorial Chemistry, vol. 2, No. 6, Oct. 21, 2000, pp. 600-603.

Caulfield Thomas J. et al., "Parallel Solid-Phase Synthesis of Peptidyl Michael Acceptors: Supplementary Information (1)", Journal of Combinatorial Chemistry, vol. 6, No. S1, Oct. 21, 2000, pp. 1-40.

Caulfield Thomas J. et al., "Parallel Solid-Phase Synthesis of Peptidyl Michael Acceptors: Supplementary Information (2)", Journal of Combinatorial Chemistry, vol. 6, No. S2, Oct. 21, 2000, pp. 41-56.

Kumar Sandeep et al., "Piperlongumine, a piper alkaloid targets Ras/RI3K/Akt/mTOR signaling axis to inhibit tumor cell growth and proliferation in DMH/DSS induced experimental colon cancer", Biomedicine & Pharmacotherapy, vol. 109, pp. 1462-1477, Jan. 2019.

*Primary Examiner* — Yong S. Chong

(74) *Attorney, Agent, or Firm* — Quarles & Brady LLP

(57) ABSTRACT

Compounds and methods for modulating RAS-PI3K.

17 Claims, No Drawings

COMPOUNDS AND METHODS FOR MODULATING RAS-PI3K

CROSS-REFERENCE TO RELATED APPLICATIONS

The present application claims the benefit under 35 U.S.C. § 119(e) of the earlier filing date of U.S. Provisional Patent Application No. 63/487,431, filed Feb. 28, 2023, the entire content of which is incorporated herein by reference in its entirety.

FIELD OF THE DISCLOSURE

The disclosure relates to compounds and methods for modulating RAS-PI3K.

BACKGROUND OF THE DISCLOSURE

There is a need for improved cancer therapeutics and methods of treatment.

SUMMARY

Disclosed herein in some aspects are modulators of RAS-PI3K. Some such aspects relate to a RAS-PI3K agonist. Some aspects relate to a RAS-PI3K inhibitor. The RAS-PI3K modulators may include a compound described herein. The RAS-PI3K modulators may be useful in a method described herein.

In one aspect, described herein is a compound having the structure of Formula (I), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof:

Formula (I)

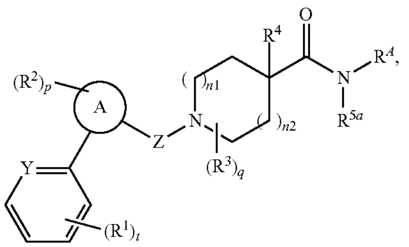

wherein,

Z is C(═O) or S(═O)$_2$;

Ring A is phenyl, 5 to 10-membered heteroaryl, $C_3$-$C_8$ cycloalkyl, $C_8$-$C_9$ spirocyclyl, or 5 to 8-membered heterocycloalkyl;

Y is N, CH, or CR$^1$;

each R$^1$ is independently halogen, —CN, —OH, —OR$^a$, —SH, —SR$^a$, —NO$_2$, —N(R$^b$)$_2$, —C(═O)R$^a$, —C(═O)OR$^a$, —C(═O)NR$^a$R$^b$, optionally substituted $C_1$-$C_6$ alkyl, optionally substituted $C_1$-$C_6$ deuteroalkyl, optionally substituted $C_2$-$C_6$ alkenyl, optionally substituted $C_2$-$C_6$ alkynyl, optionally substituted $C_1$-$C_6$ haloalkyl, optionally substituted $C_1$-$C_6$ hydroxyalkyl, or optionally substituted $C_3$-$C_6$ cycloalkyl;

each R$^2$ is independently halogen, —CN, —OH, —OR$^a$, —SH, —SR$^a$, —NO$_2$, —N(R$^b$)$_2$, —S(═O)$_2$R$^a$, —C(═O)R$^a$, —C(═O)OR$^a$, —C(═O)NR$^a$R$^b$, oxo (═O), optionally substituted $C_1$-$C_6$ alkyl, optionally substituted $C_1$-$C_6$ deuteroalkyl, optionally substituted $C_2$-$C_6$ alkenyl, optionally substituted $C_2$-$C_6$ alkynyl, optionally substituted $C_1$-$C_6$ alkylamino, optionally substituted $C_1$-$C_6$ haloalkyl, optionally substituted $C_1$-$C_6$ hydroxyalkyl, optionally substituted $C_3$-$C_6$ cycloalkyl, optionally substituted arylalkyl, or optionally substituted 4 to 6-membered heterocycloalkyl;

or two R$^2$ together with the atom(s) to which they are attached combine to form a $C_3$-$C_5$ cycloalkyl, 4 to 5-membered heterocycloalkyl, or a 5-membered heteroaryl ring;

each R$^3$ is independently halogen, —CN, —OH, —OR$^a$, $C_1$-$C_6$ alkyl, $C_1$-$C_6$ deuteroalkyl, or $C_1$-$C_6$ haloalkyl;

R$^4$ is H, halogen, —OH, —OR$^a$, or $C_1$-$C_6$ alkyl;

R$^A$ is

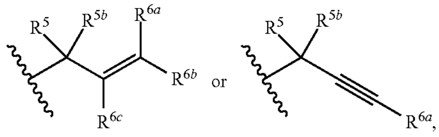

wherein

R$^5$ is H, optionally substituted $C_1$-$C_3$ alkyl, optionally substituted $C_1$-$C_3$ haloalkyl, or optionally substituted $C_1$-$C_3$ hydroxyalkyl;

R$^{6a}$ and R$^{6b}$ are each independently H, —CN, —C(═O)OR$^7$, —C(═O)N(R$^7$)$_2$, —S(═O)R$_7$, —S(═O)$_2$R$^7$, or —S(═O)(═NH)R$^7$; wherein each R$^7$ is independently optionally substituted $C_1$-$C_6$ alkyl, optionally substituted $C_3$-$C_6$ cycloalkyl, or optionally substituted 4 to 6-membered heterocycloalkyl ring;

or two R$^7$ together with the nitrogen atom to which they are attached combine to form an optionally substituted 4 to 5-membered heterocycloalkyl ring;

or R$^5$ and R$^7$ together with the atoms to which they are attached combine to form a 5-membered heterocycloalkyl ring;

R$^{6c}$ is H or —CN;

or R$^{6c}$ and R$^7$ together with the atoms to which they are attached combine to form a 4-membered heterocycloalkyl ring;

R$^{5a}$ is H; or R$^{5a}$ and R$^{6c}$ together with the nitrogen atom to which they are attached combine to form a 4-membered heterocycloalkyl ring; or R$^{5a}$ is absent and R$^{6c}$ is bound directly to the nitrogen to which R$^A$ is attached to form a 4-membered heterocyclic ring;

or R$^{5a}$ and R$^5$ together with the nitrogen and carbon atoms to which they are attached form a 4-membered heterocyclic ring;

R$^{5b}$ is H or $C_1$-$C_3$ alkyl;

each R$^a$ is independently H, $C_1$-$C_6$ alkyl, $C_1$-$C_6$ deuteroalkyl, $C_1$-$C_6$ haloalkyl, $C_1$-$C_6$ heteroalkyl, $C_2$-$C_6$ alkenyl, $C_2$-$C_6$ alkynyl, $C_3$-$C_6$ cycloalkyl, a three- to six-membered heterocycloalkyl, $C_5$-$C_8$ aryl, $C_5$-$C_8$ heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl(heterocycloalkyl); wherein each alkyl, deuteroalkyl, haloalkyl, heteroalkyl, cycloalkyl, heterocycloalkyl, aryl, heteroaryl, alkyl(aryl), alkyl(heteroaryl), alkyl(cycloalkyl) and alkyl(heterocycloalkyl) is independently optionally substituted with one, two, or three halogen, —OH, $C_1$-$C_6$ alkyl, $C_1$-$C_6$ haloalkyl, or $C_1$-$C_6$ alkoxy;

each $R^b$ is independently H, $C_1$-$C_6$ alkyl, $C_1$-$C_6$ haloalkyl, $C_1$-$C_6$ heteroalkyl, cycloalkyl, heterocycloalkyl, aryl, or heteroaryl; wherein the alkyl, heteroalkyl, cycloalkyl, heterocycloalkyl, aryl, and heteroaryl is independently optionally substituted with one, two, or three halogen, —OH, $C_1$-$C_6$ alkyl, or $C_1$-$C_6$ haloalkyl;

or two $R^b$ groups on a nitrogen atom are taken together with the nitrogen atom to which they are attached to form a heterocycloalkyl which is optionally substituted with one, two, or three $C_1$-$C_6$ alkyl, or $C_1$-$C_6$ haloalkyl;

n1 and n2 are each independently 0, 1, 2, or 3;

p is 0, 1, 2, or 3;

q is 0, 1, or 2; and t is 0, 1, 2, or 3.

In some embodiments of Formula (I), $R^4$ is halogen. In some embodiments of Formula (I), $R^{5a}$ and $R^{5b}$ are each H. In some embodiments of Formula (I), $R^5$ is $C_1$-$C_3$ alkyl. In some embodiments of Formula (I), $R^5$ is —$CH_3$ or —$CH_2CH_3$. In some embodiments of Formula (I), $R^{5a}$ and $R^{6c}$ together with the nitrogen atom to which they are attached combine together to form a 4-membered heterocycloalkyl ring.

In some embodiments, the compound of Formula (I) has the structure of Formula (Ia), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof:

Formula (Ia)

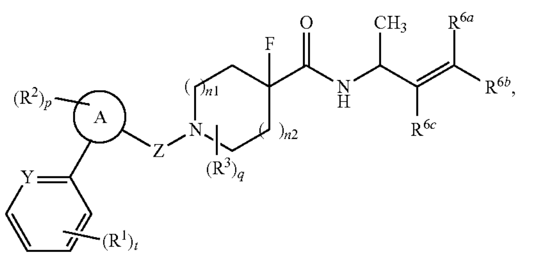

wherein,

Z is C(=O) or S(=O)$_2$;

Ring A is phenyl, 5 to 10-membered heteroaryl, $C_3$-$C_8$ cycloalkyl, $C_8$-$C_9$ spirocyclyl, or 5 to 8-membered heterocycloalkyl;

Y is CH or $CR^1$;

each $R^1$ is independently halogen, —CN, —OH, —$OR^a$, —SH, —$SR^a$, —$NO_2$, —$N(R^b)_2$, —C(=O)$R^a$, —C(=O)$OR^a$, —C(=O)$NR^aR^b$, optionally substituted $C_1$-$C_6$ alkyl, optionally substituted $C_1$-$C_6$ deuteroalkyl, optionally substituted $C_2$-$C_6$ alkenyl, optionally substituted $C_2$-$C_6$ alkynyl, optionally substituted $C_1$-$C_6$ haloalkyl, optionally substituted $C_1$-$C_6$ hydroxyalkyl, or optionally substituted $C_3$-$C_6$ cycloalkyl;

each $R^2$ is independently halogen, —CN, —OH, —$OR^a$, —SH, —$SR^a$, —$NO_2$, —$N(R^b)_2$, —S(=O)$_2R^a$, —C(=O)$R^a$, —C(=O)$OR^a$, —C(=O)$NR^aR^b$, oxo (=O), optionally substituted $C_1$-$C_6$ alkyl, optionally substituted $C_1$-$C_6$ deuteroalkyl, optionally substituted $C_2$-$C_6$ alkenyl, optionally substituted $C_2$-$C_6$ alkynyl, optionally substituted $C_1$-$C_6$ alkylamino, optionally substituted $C_1$-$C_6$ haloalkyl, optionally substituted $C_1$-$C_6$ hydroxyalkyl, optionally substituted $C_3$-$C_6$ cycloalkyl, optionally substituted arylalkyl, or optionally substituted 4 to 6-membered heterocycloalkyl;

or two $R^2$ together with the atom(s) to which they are attached combine to form a $C_3$-$C_5$ cycloalkyl, 4 to 5-membered heterocycloalkyl, or a 5-membered heteroaryl ring;

each $R^3$ is independently halogen, —CN, —OH, —$OR^a$, $C_1$-$C_6$ alkyl, $C_1$-$C_6$ deuteroalkyl, or $C_1$-$C_6$ haloalkyl;

$R^{6a}$ and $R^{6b}$ are each independently H, —CN, —C(=O)$OR^7$, —C(=O)$N(R^7)_2$, —S(=O)$R_7$, —S(=O)$_2R^7$, or —S(=O)(=NH)$R^7$; wherein each $R^7$ is independently optionally substituted $C_1$-$C_6$ alkyl, optionally substituted $C_3$-$C_6$ cycloalkyl, or optionally substituted 4 to 6-membered heterocycloalkyl ring;

or two $R^7$ together with the nitrogen atom to which they are attached combine to form an optionally substituted 4 to 5-membered heterocycloalkyl ring;

or $R^5$ and $R^7$ together with the atoms to which they are attached combine to form a 5-membered heterocycloalkyl ring;

$R^{6c}$ is H or —CN;

or $R^{6c}$ and $R^7$ together with the atoms to which they are attached combine to form a 4-membered heterocycloalkyl ring;

each $R^a$ is H, $C_1$-$C_6$ alkyl, $C_1$-$C_6$ deuteroalkyl, $C_1$-$C_6$ haloalkyl, $C_1$-$C_6$ heteroalkyl, $C_2C_6$ alkenyl, $C_2C_6$ alkynyl, $C_3$-$C_6$ cycloalkyl, a 3- to 6-membered heterocycloalkyl, $C_5$-$C_8$ aryl, $C_5$-$C_8$ heteroaryl, —$C_1$-$C_6$ alkyl (aryl), —$C_1$-$C_6$ alkyl(heteroaryl), —$C_1$-$C_6$ alkyl (cycloalkyl), or —$C_1$-$C_6$ alkyl(heterocycloalkyl); wherein each alkyl, deuteroalkyl, haloalkyl, heteroalkyl, cycloalkyl, heterocycloalkyl, aryl, heteroaryl, alkyl (aryl), alkyl(heteroaryl), alkyl(cycloalkyl) and alkyl (heterocycloalkyl) is independently optionally substituted with one, two, or three halogen, —OH, $C_1$-$C_6$ alkyl, $C_1$-$C_6$ haloalkyl, or $C_1$-$C_6$ alkoxy;

each $R^b$ is independently H, $C_1$-$C_6$ alkyl, $C_1$-$C_6$ haloalkyl, $C_1$-$C_6$ heteroalkyl, cycloalkyl, heterocycloalkyl, aryl, or heteroaryl; wherein the alkyl, heteroalkyl, cycloalkyl, heterocycloalkyl, aryl, and heteroaryl is independently optionally substituted with one, two, or three halogen, —OH, $C_1$-$C_6$ alkyl, or $C_1$-$C_6$ haloalkyl;

or two $R^b$ groups on a nitrogen atom are taken together with the nitrogen atom to which they are attached to form a heterocycloalkyl which is optionally substituted with one, two, or three $C_1$-$C_6$ alkyl, or $C_1$-$C_6$ haloalkyl;

n1 and n2 are each independently 0, 1, 2, or 3;

p is 0, 1, 2, or 3;

q is 0, 1, or 2; and t is 0, 1, 2, or 3.

In some embodiments of Formula (I) or (Ia), ring A is a $C_5$-$C_7$ cycloalkyl or 5 to 7-membered heterocycloalkyl.

In some embodiments, the compound of Formula (I) has the structure of Formula (II), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof:

Formula (II)

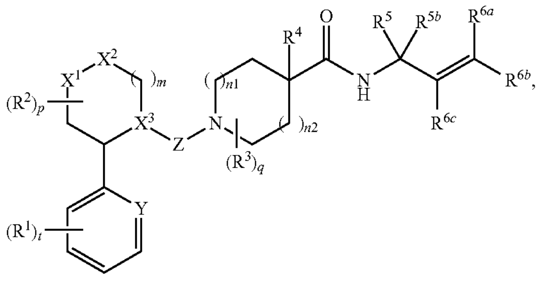

wherein, $X^1$ are $X^2$ are each independently $CH_2$, $CHR^2$, $CR^2R^2$, O, or $NR^{2a}$; wherein at least one of $X^1$ or $X^2$ is $CH_2$, $CHR^2$, or $CR^2R^2$;

$X^3$ is $CR^8$ or N, provided that when $X^3$ is N, $R^8$ is absent;

Y is N, CH, or $CR^1$;

Z is C(═O) or $S(═O)_2$;

each $R^1$ is independently halogen, —CN, —OH, —$OR^a$, optionally substituted $C_1$-$C_6$ alkyl, optionally substituted $C_1$-$C_6$ deuteroalkyl, optionally substituted $C_2$-$C_6$ alkynyl, optionally substituted $C_1$-$C_6$ haloalkyl, optionally substituted $C_1$-$C_6$ hydroxyalkyl, or optionally substituted $C_3$-$C_6$ cycloalkyl;

each $R^2$ is independently halogen, —CN, —OH, —$OR^a$, —$N(R^b)_2$, optionally substituted $C_1$-$C_6$ alkyl, optionally substituted $C_1$-$C_6$ deuteroalkyl, optionally substituted $C_2$-$C_6$ alkenyl, optionally substituted $C_2$-$C_6$ alkynyl, optionally substituted $C_1$-$C_6$ haloalkyl, optionally substituted $C_1$-$C_6$ hydroxyalkyl, optionally substituted $C_3$-$C_6$ cycloalkyl, optionally substituted arylalkyl, or optionally substituted 4 to 6-membered heterocycloalkyl;

or two $R^2$ together with the atom(s) to which they are attached combine to form a $C_3$-$C_5$ cycloalkyl;

$R^{2a}$ is H, —$S(═O)_2R^a$, —C(═O)$R^a$, —C(═O)$OR^a$, —C(═O)$NR^aR^b$, optionally substituted $C_1$-$C_6$ alkyl, optionally substituted $C_1$-$C_6$ haloalkyl, $C_3$-$C_6$ cycloalkyl, or phenyl;

each $R^3$ is independently halogen, —CN, —OH, —$OR^a$, $C_1$-$C_6$ alkyl, $C_1$-$C_6$ deuteroalkyl, or $C_1$-$C_6$ haloalkyl;

$R^4$ is H, halogen, —OH, —$OR^a$, or $C_1$-$C_6$ alkyl;

$R^5$ is H, $C_1$-$C_3$ alkyl, $C_1$-$C_3$ haloalkyl, or $C_1$-$C_3$ hydroxyalkyl;

$R^{5b}$ is H or $C_1$-$C_3$ alkyl;

$R^{6a}$ and $R^{6b}$ are each independently H, —CN, —C(═O)$OR^7$, —C(═O)$N(R^7)_2$, —S(═O)$R_7$, —$S(═O)_2R^7$, or —S(═O)(═NH)$R^7$; wherein each $R^7$ is independently optionally substituted $C_1$-$C_6$ alkyl, optionally substituted $C_3$-$C_6$ cycloalkyl, or optionally substituted 4 to 6-membered heterocycloalkyl ring;

or two $R^7$ together with the nitrogen atom to which they are attached combine to form an optionally substituted 4 to 5-membered heterocycloalkyl ring;

or $R^5$ and $R^7$ together with the atoms to which they are attached combine to form a 5-membered heterocycloalkyl ring;

$R^{6c}$ is H or —CN;

or $R^{6c}$ and $R^7$ together with the atoms to which they are attached combine to form a 4-membered heterocycloalkyl ring;

$R^8$ is absent, H, halogen, —$OCH_3$, or —$CH_3$;

each $R^a$ is independently H, $C_1$-$C_6$ alkyl, $C_1$-$C_6$ deuteroalkyl, $C_1$-$C_6$ haloalkyl, $C_1$-$C_6$ heteroalkyl, $C_2$-$C_6$alkenyl, $C_2$-$C_6$ alkynyl, $C_3$-$C_6$ cycloalkyl, 3- to 6-membered heterocycloalkyl, $C_5C_8$ aryl, $C_5C_8$ heteroaryl, —$C_1$-$C_6$ alkyl(aryl), —$C_1$-$C_6$ alkyl(heteroaryl), —$C_1$-$C_6$ alkyl (cycloalkyl), or —$C_1$-$C_6$ alkyl(heterocycloalkyl); wherein each alkyl, deuteroalkyl, haloalkyl, heteroalkyl, cycloalkyl, heterocycloalkyl, aryl, heteroaryl, alkyl (aryl), alkyl(heteroaryl), alkyl(cycloalkyl) and alkyl (heterocycloalkyl) is independently optionally substituted with one, two, or three halogen, —OH, $C_1$-$C_6$ alkyl, $C_1$-$C_6$ haloalkyl, or $C_1$-$C_6$ alkoxy;

each $R^b$ is independently H, $C_1$-$C_6$ alkyl, $C_1$-$C_6$ haloalkyl, $C_1$-$C_6$ heteroalkyl, cycloalkyl, heterocycloalkyl, aryl, or heteroaryl; wherein the alkyl, heteroalkyl, cycloalkyl, heterocycloalkyl, aryl, and heteroaryl is independently optionally substituted with one, two, or three halogen, —OH, $C_1$-$C_6$ alkyl, or $C_1$-$C_6$ haloalkyl;

or two $R^b$ groups on a nitrogen atom are taken together with the nitrogen atom to which they are attached to form a heterocycloalkyl which is optionally substituted with one, two, or three $C_1$-$C_6$ alkyl, or $C_1$-$C_6$ haloalkyl;

m is 0 or 1;

n1 and n2 are each independently 0, 1, 2, or 3;

p is 0, 1, 2, or 3;

q is 0, 1, or 2; and t is 1, 2, or 3.

In some embodiments of Formula (II), Z is —C(═O)—. In some embodiments of Formula (II), $X^3$ is $CR^8$; and $R^8$ is H. In some embodiments of Formula (II), m is 0. In some embodiments of Formula (II), $X^1$ is $NR^{2a}$; and $X^2$ is $CH_2$.

In some embodiments, the compound of Formula (II) has the structure of Formula (IIb), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof:

Formula (IIb)

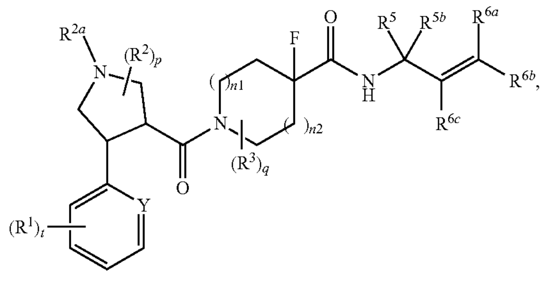

wherein,

Y is CH or $CR^1$;

each $R^1$ is independently halogen, —CN, —OH, —$OR^a$, optionally substituted $C_1$-$C_6$ alkyl, optionally substituted $C_1$-$C_6$ deuteroalkyl, optionally substituted $C_2$-$C_6$ alkynyl, optionally substituted $C_1$-$C_6$ haloalkyl, or $C_1$-$C_6$ hydroxyalkyl;

each $R^2$ is independently optionally substituted $C_1$-$C_6$ alkyl, optionally substituted $C_1$-$C_6$ deuteroalkyl, optionally substituted $C_1$-$C_6$ haloalkyl, or optionally substituted $C_3$-$C_6$ cycloalkyl;

$R^{2a}$ is H, —C(═O)$OR^a$, —C(═O)$NR^aR^b$, optionally substituted $C_1$-$C_6$ alkyl, optionally substituted $C_1$-$C_6$ haloalkyl, optionally substituted arylalkyl, or optionally substituted $C_3$-$C_6$ cycloalkyl;

each $R^3$ is independently $C_1$-$C_3$ alkyl or $C_1$-$C_3$ deuteroalkyl;

$R^5$ is H, $C_1$-$C_3$ alkyl, $C_1$-$C_3$ haloalkyl, or $C_1$-$C_3$ hydroxyalkyl;

$R^{5b}$ is H or $C_1$-$C_3$ alkyl;

$R^{6a}$ and $R^{6b}$ are each independently H, —CN, —C(═O)OR$^7$, —C(═O)N($R^7$)$_2$, —S(═O)$R_7$, —S(═O)$_2R^7$, or —S(═O)(═NH)$R^7$; wherein each $R^7$ is independently optionally substituted $C_1$-$C_6$ alkyl, optionally substituted $C_3$-$C_6$ cycloalkyl, or optionally substituted 4 to 6-membered heterocycloalkyl ring;

or two $R^7$ together with the nitrogen atom to which they are attached combine to form an optionally substituted 4 to 5-membered heterocycloalkyl ring;

or $R^5$ and $R^7$ together with the atoms to which they are attached combine to form a 5-membered heterocycloalkyl ring;

$R^{6c}$ is H or —CN;

or $R^{6c}$ and $R^7$ together with the atoms to which they are attached combine to form a 4-membered heterocycloalkyl ring;

each $R^a$ is independently H, $C_1$-$C_6$ alkyl, $C_1$-$C_6$ deuteroalkyl, $C_1$-$C_6$ haloalkyl, $C_1$-$C_6$ heteroalkyl, $C_2$-$C_6$ alkenyl, $C_2$-$C_6$ alkynyl, $C_3$-$C_6$ cycloalkyl, 3- to 6-membered heterocycloalkyl, $C_5$-$C_8$ aryl, $C_5$-$C_8$ heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl(heterocycloalkyl); wherein each alkyl, deuteroalkyl, haloalkyl, heteroalkyl, cycloalkyl, heterocycloalkyl, aryl, heteroaryl, alkyl (aryl), alkyl(heteroaryl), alkyl(cycloalkyl) and alkyl (heterocycloalkyl) is independently optionally substituted with one, two, or three halogen, —OH, $C_1$-$C_6$ alkyl, $C_1$-$C_6$ haloalkyl, or $C_1$-$C_6$ alkoxy;

each $R^b$ is independently H, $C_1$-$C_6$ alkyl, $C_1$-$C_6$ haloalkyl, $C_1$-$C_6$ heteroalkyl, cycloalkyl, heterocycloalkyl, aryl, or heteroaryl; wherein the alkyl, heteroalkyl, cycloalkyl, heterocycloalkyl, aryl, and heteroaryl is independently optionally substituted with one, two, or three halogen, —OH, $C_1$-$C_6$ alkyl, or $C_1$-$C_6$ haloalkyl;

or two $R^b$ groups on a nitrogen atom are taken together with the nitrogen atom to which they are attached to form a heterocycloalkyl which is optionally substituted with one, two, or three $C_1$-$C_6$ alkyl, or $C_1$-$C_6$ haloalkyl;

n1 and n2 are each independently 0, 1, 2, or 3;

p is 0, 1, 2, or 3;

q is 0, 1, or 2; and t is 1, 2, or 3.

In some embodiments of Formula (IIb), $R^{2a}$ is —C(═O)$R^a$, —C(═O)OR$^a$, optionally substituted $C_1$-$C_6$ alkyl, optionally substituted $C_1$-$C_6$ haloalkyl, or optionally substituted $C_3$-$C_6$ cycloalkyl; wherein each $R^a$ is independently $C_1$-$C_6$ alkyl. In some embodiments of Formula (IIb), p is 0. In some embodiments of Formula (IIb), Y is CH or CR$^1$, each $R^1$ is halogen, $R^{2a}$ is $C_1$-$C_6$ haloalkyl, $R^5$ is $C_1$-$C_3$ alkyl, $R^{5b}$ is H, $R^{6a}$ and $R^{6b}$ are each independently H or —S(═O)(═NH)$R^7$ wherein each $R^7$ is independently $C_1$-$C_6$ alkyl, or $R^5$ and $R^7$ together with the atoms to which they are attached combine to form a 5-membered heterocycloalkyl ring, $R^{6c}$ is H, n1 and n2 are each independently 1 or 2, p is 0 or 1, q is 0 or 1, and t is 1 or 2.

In some embodiments of Formula (I) or (Ia), ring A is phenyl or a 5 to 10-membered heteroaryl. In some embodiments of Formula (I) or (Ia), ring A is phenyl or pyridinyl.

In some embodiments, the compound of Formula (I) has the structure of Formula (III), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof:

Formula (III)

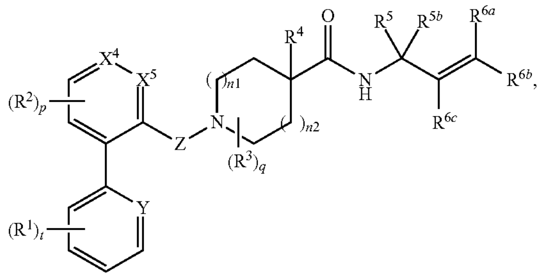

wherein,

Y is N, CH, or CR$^1$;

Z is C(═O) or S(═O)$_2$;

$X^4$ is CH, CR$^2$, or N;

$X^5$ is CH, CR$^2$, or N;

each $R^1$ is independently halogen, —CN, —OH, —OR$^a$, optionally substituted $C_1$-$C_6$ alkyl, optionally substituted $C_1$-$C_6$ deuteroalkyl, optionally substituted $C_2$-$C_6$ alkynyl, optionally substituted $C_1$-$C_6$ haloalkyl, optionally substituted $C_1$-$C_6$ hydroxyalkyl, or optionally substituted $C_3$-$C_6$ cycloalkyl;

each $R^2$ is independently halogen, —CN, —OH, —OR$^a$, —N($R^b$)$_2$, optionally substituted $C_1$-$C_6$ alkyl, optionally substituted $C_1$-$C_6$ deuteroalkyl, optionally substituted $C_2$-$C_6$ alkenyl, optionally substituted $C_2$-$C_6$ alkynyl, optionally substituted $C_1$-$C_6$ haloalkyl, optionally substituted $C_1$-$C_6$ hydroxyalkyl, optionally substituted $C_3$-$C_6$ cycloalkyl, optionally substituted arylalkyl, or optionally substituted 4 to 6-membered heterocycloalkyl;

or two $R^2$ together with the atom(s) to which they are attached combine to form a $C_3$-$C_5$ cycloalkyl, 4 to 5-membered heterocycloalkyl, or a 5-membered heteroaryl ring;

each $R^3$ is independently halogen, —CN, —OH, —OR$^a$, $C_1$-$C_6$ alkyl, $C_1$-$C_6$ deuteroalkyl, or $C_1$-$C_6$ haloalkyl;

$R^4$ is H, halogen, —OH, —OR$^a$, or $C_1$-$C_6$ alkyl;

$R^5$ is H, $C_1$-$C_3$ alkyl, $C_1$-$C_3$ haloalkyl, or $C_1$-$C_3$ hydroxyalkyl;

$R^{5b}$ is H or $C_1$-$C_3$ alkyl;

$R^{6a}$ and $R^{6b}$ are each independently H, —CN, —C(═O)OR$^7$, —C(═O)N($R^7$)$_2$, —S(═O)$R_7$, —S(═O)$_2R^7$, or —S(═O)(═NH)$R^7$; wherein each $R^7$ is independently optionally substituted $C_1$-$C_6$ alkyl, optionally substituted $C_3$-$C_6$ cycloalkyl, or optionally substituted 4 to 6-membered heterocycloalkyl ring;

or two $R^7$ together with the nitrogen atom to which they are attached combine to form an optionally substituted 4 to 5-membered heterocycloalkyl ring;

or R and $R^7$ together with the atoms to which they are attached combine to form a 5-membered heterocycloalkyl ring;

$R^{6c}$ is H or —CN;

or $R^{6c}$ and $R^7$ together with the atoms to which they are attached combine to form a 4-membered heterocycloalkyl ring;

each $R^a$ is independently H, $C_1$-$C_6$ alkyl, $C_1$-$C_6$ deuteroalkyl, $C_1$-$C_6$ haloalkyl, $C_1$-$C_6$ heteroalkyl, $C_2$-$C_6$ alkenyl, $C_2$-$C_6$ alkynyl, $C_3$-$C_6$ cycloalkyl, 3- to 6-membered heterocycloalkyl, $C_5$-$C_8$ aryl, $C_5$-$C_8$ heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl(heterocycloalkyl); wherein each alkyl, deuteroalkyl, haloalkyl, heteroalkyl, cycloalkyl, heterocycloalkyl, aryl, heteroaryl, alkyl (aryl), alkyl(heteroaryl), alkyl(cycloalkyl) and alkyl (heterocycloalkyl) is independently optionally substituted with one, two, or three halogen, —OH, $C_1$-$C_6$ alkyl, $C_1$-$C_6$ haloalkyl, or $C_1$-$C_6$ alkoxy;

each $R^b$ is independently H, $C_1$-$C_6$ alkyl, $C_1$-$C_6$ haloalkyl, $C_1$-$C_6$ heteroalkyl, cycloalkyl, heterocycloalkyl, aryl, or heteroaryl; wherein the alkyl, heteroalkyl, cycloalkyl, heterocycloalkyl, aryl, and heteroaryl is independently optionally substituted with one, two, or three halogen, —OH, $C_1$-$C_6$ alkyl, or $C_1$-$C_6$ haloalkyl;

or two $R^b$ groups on a nitrogen atom are taken together with the nitrogen atom to which they are attached to form a heterocycloalkyl which is optionally substituted with one, two, or three $C_1$-$C_6$ alkyl, or $C_1$-$C_6$ haloalkyl;

n1 and n2 are each independently 0, 1 or 2;

p is 0, 1, 2, or 3;

q is 0, 1, or 2; and t is 0, 1, 2, or 3.

In some embodiments of Formula (III), Z is —S(═O)$_2$—. In some embodiments of Formula (III), $R^4$ is halogen.

In some embodiments, the compound of Formula (III) has the structure of Formula (IIIa), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof:

Formula (IIIa)

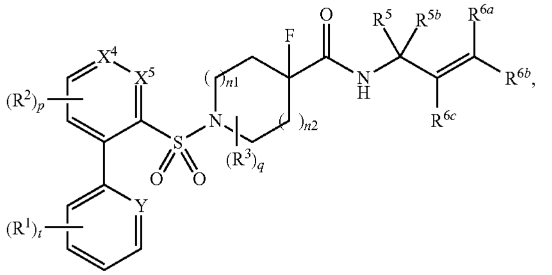

wherein,

Y is CH or $CR^1$;

$X^4$ is CH, $CR^2$, or N;

$X^5$ is CH, $CR^2$, or N;

each $R^1$ is independently halogen, —CN, —OH, —$OR^a$, optionally substituted $C_1$-$C_6$ alkyl, optionally substituted $C_1$-$C_6$ deuteroalkyl, optionally substituted $C_2$-$C_6$ alkynyl, optionally substituted $C_1$-$C_6$ haloalkyl, $C_1$-$C_6$ hydroxyalkyl, or optionally substituted $C_3$-$C_6$ cycloalkyl;

each $R^2$ is independently halogen, —CN, —OH, —$OR^a$, —$N(R^b)_2$, optionally substituted $C_1$-$C_6$ alkyl, optionally substituted $C_1$-$C_6$ deuteroalkyl, optionally substituted $C_2$-$C_6$ alkenyl, optionally substituted $C_2$-$C_6$ alkynyl, optionally substituted $C_1$-$C_6$ haloalkyl, optionally substituted $C_1$-$C_6$ hydroxyalkyl, optionally substituted $C_3$-$C_6$ cycloalkyl, optionally substituted 4 to 6-membered heterocycloalkyl, or optionally substituted arylalkyl;

each $R^3$ is independently $C_1$-$C_3$ alkyl or $C_1$-$C_3$ deuteroalkyl;

$R^5$ is H, $C_1$-$C_3$ alkyl, $C_1$-$C_3$ haloalkyl, or $C_1$-$C_3$ hydroxyalkyl;

$R^{5b}$ is H or $C_1$-$C_3$ alkyl;

$R^{6a}$ and $R^{6b}$ are each independently H, —CN, —C(═O)N$(R^7)_2$, —S(═O)$_2R^7$, or —S(═O)(═NH)$R^7$; wherein each $R^7$ is independently $C_1$-$C_3$ alkyl, or a 4-membered heterocycloalkyl ring optionally substituted with up to two fluorine atoms;

or two $R^7$ together with the nitrogen atom to which they are attached combine to form a 4-membered heterocycloalkyl ring optionally substituted with up to two fluorine atoms;

or $R^5$ and $R^7$ together with the atoms to which they are attached combine to form a 5-membered heterocycloalkyl ring;

$R^{6c}$ is H or —CN;

or $R^{6c}$ and $R^7$ together with the atoms to which they are attached combine to form a 4-membered heterocycloalkyl ring;

each $R^a$ is independently H, $C_1$-$C_6$ alkyl, $C_1$-$C_6$ deuteroalkyl, $C_1$-$C_6$ haloalkyl, $C_1$-$C_6$ heteroalkyl, $C_2$-$C_6$ alkenyl, $C_2$-$C_6$ alkynyl, $C_3$-$C_6$ cycloalkyl, 3- to 6-membered heterocycloalkyl, $C_5$-$C_8$ aryl, $C_5$-$C_8$ heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl(heterocycloalkyl); wherein each alkyl, deuteroalkyl, haloalkyl, heteroalkyl, cycloalkyl, heterocycloalkyl, aryl, heteroaryl, alkyl (aryl), alkyl(heteroaryl), alkyl(cycloalkyl) and alkyl (heterocycloalkyl) is independently optionally substituted with one, two, or three halogen, —OH, $C_1$-$C_6$ alkyl, $C_1$-$C_6$ haloalkyl, or $C_1$-$C_6$ alkoxy;

each $R^b$ is independently H, $C_1$-$C_6$ alkyl, $C_1$-$C_6$ haloalkyl, $C_1$-$C_6$ heteroalkyl, cycloalkyl, heterocycloalkyl, aryl, or heteroaryl; wherein the alkyl, heteroalkyl, cycloalkyl, heterocycloalkyl, aryl, and heteroaryl is independently optionally substituted with one, two, or three halogen, —OH, $C_1$-$C_6$ alkyl, or $C_1$-$C_6$ haloalkyl;

or two $R^b$ groups on a nitrogen atom are taken together with the nitrogen atom to which they are attached to form a heterocycloalkyl which is optionally substituted with one, two, or three $C_1$-$C_6$ alkyl, or $C_1$-$C_6$ haloalkyl;

n1 and n2 are each independently 0, 1 or 2;

p is 0, 1, 2, or 3;

q is 0, 1, or 2; and t is 0, 1, 2, or 3.

In some embodiments of Formula (III) or (IIIa), $X^4$ is CH or $CR^2$; and $X^5$ is CH or $CR^2$. In some embodiments of Formula (III) or (IIIa), $X^4$ is N; and $X^5$ is CH or $CR^2$. In some embodiments of Formula (III) or (IIIa), $X^4$ is CH or $CR^2$; and $X^5$ is N. In some embodiments of Formula (III) or (IIIa), p is 1.

In some embodiments, the compound of Formula (III) has the structure of Formula (IIIb), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof:

Formula (IIIb)

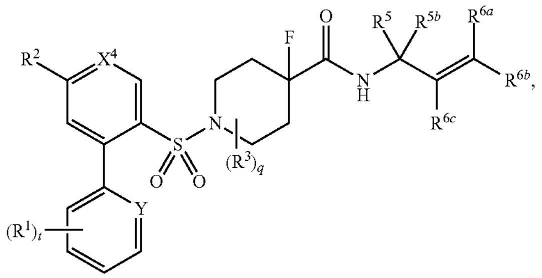

wherein, $X^4$ is CH or N;

Y is $CR^1$ or CH;

each $R^1$ is independently halogen, —CN, —$OR^a$, optionally substituted $C_1$-$C_4$ alkyl, optionally substituted $C_1$-$C_4$ deuteroalkyl, $C_2$-$C_4$ alkynyl, or $C_1$-$C_3$ fluoroalkyl;

$R^2$ is halogen, —CN, —OH, —$OR^a$, —$N(R^b)_2$, —C(=O)$R^a$, optionally substituted $C_1$-$C_4$ alkyl, optionally substituted $C_1$-$C_4$ deuteroalkyl, $C_2$-$C_4$ alkenyl, $C_2$-$C_4$ alkynyl, $C_1$-$C_3$ fluoroalkyl, optionally substituted $C_1$-$C_3$ hydroxyalkyl, optionally substituted $C_3$-$C_6$ cycloalkyl, or optionally substituted 4 to 6-membered heterocycloalkyl;

Each $R^3$ is independently —$CH_3$ or -$CD_3$;

$R^5$ is H, —$CH_3$, or —$CH_2CH_3$;

$R^{5b}$ is H or $C_1$-$C_3$ alkyl;

$R^{6a}$ and $R^{6b}$ are each independently H, —CN, —C(=O)$N(R^7)_2$, —S(=O)$_2R^7$, or —S(=O)(=NH)$R^7$; wherein each $R^7$ is independently $C_1$-$C_3$ alkyl, or a 4-membered heterocycloalkyl ring optionally substituted with up to two fluorine atoms;

or two $R^7$ together with the nitrogen atom to which they are attached combine to form a 4-membered heterocycloalkyl ring optionally substituted with up to two fluorine atoms;

or $R^5$ and $R^7$ together with the atoms to which they are attached combine to form a 5-membered heterocycloalkyl ring;

$R^{6c}$ is H or —CN;

each $R^a$ is independently $C_1$-$C_6$ alkyl, $C_3$-$C_6$ cycloalkyl, or $C_1$-$C_3$ fluoroalkyl;

each $R^b$ is independently H or $C_1$-$C_3$ alkyl;

q is 0, 1, or 2; and t is 0, 1, or 2.

In some embodiments of Formula (III), (IIIa), or (IIIb), each $R^2$ is independently halogen, —CN, —OH, —$OR^a$, —$N(R^b)_2$, —C(=O)$R^a$, optionally substituted $C_1$-$C_4$ alkyl, $C_2$-$C_4$ alkenyl, $C_2$-$C_4$ alkynyl, $C_1$-$C_3$ fluoroalkyl, optionally substituted $C_1$-$C_3$ hydroxyalkyl, optionally substituted $C_3$-$C_6$ cycloalkyl, or optionally substituted 4 to 6-membered heterocycloalkyl. In some embodiments of Formula (III), (IIIa), or (IIIb), each $R^2$ is independently Cl, Br, F, —CN, —$CH_3$, —$CH_2CH_3$, —$CH(CH_3)_2$, —$CF_3$, —$CH_2CF_3$, —$OCH_3$, —$OCH_2CH_3$, —$OCH(CH_3)_2$, —$OCF_3$, —$N(CH_3)_2$, azetidine, oxetane, pyrrolidine, piperazine, or morpholine. In some embodiments of Formula (I), (Ia), (II), (IIa), (IIb), (III), (IIIa), or (IIIb), $R^1$ is independently halogen, —CN, —OH, —$OR^a$, —C(=O)$OR^a$, —C(=O)$NR^aR^b$, optionally substituted $C_1$-$C_6$ alkyl, optionally substituted $C_2$-$C_6$ alkenyl, optionally substituted $C_2$-$C_6$ alkynyl, or optionally substituted $C_1$-$C_6$ haloalkyl. In some embodiments of Formula (I), (Ia), (II), (IIa), (IIb), (III), (IIIa), or (IIIb), each $R^1$ is independently halogen, —$OR^a$, or optionally substituted $C_1$-$C_6$ alkyl.

In some embodiments of Formula (I), (Ia), (II), (IIa), (IIb), (III), (IIIa), or (IIIb), each $R^1$ is independently Cl, Br, F, —$OCH_3$, or —$CH_3$. In some embodiments of Formula (I), (Ia), (II), (IIa), (IIb), (III), (IIIa), or (IIIb), t is 1. In some embodiments of Formula (I), (Ia), (II), (IIa), (IIb), (III), (IIIa), or (IIIb), t is 2. In some embodiments of Formula (I), (Ia), (II), (IIa), (IIb), (III), (IIIa), or (IIIb), each $R^3$ is $CH_3$. In some embodiments of Formula (I), (Ia), (II), (IIa), (IIb), (III), (IIIa) or (IIIb), q is 1. In some embodiments of Formula (I), (Ia), (II), (IIa), (IIb), (III), (IIIa) or (IIIb), q is 0. In some embodiments of Formula (I), (Ia), (II), (IIa), (IIb), (III), (IIIa), or (IIIb), n1 is 1; and n2 is 1. In some embodiments of Formula (I), (Ia), (II), (IIa), (IIb), (III), (IIIa), or (IIIb), $R^{6a}$ is S(=$O_2$)$R^7$; and $R^{6b}$ and $R^{6c}$ are each H. In some embodiments of Formula (I), (Ia), (II), (IIa), (IIb), (III), (IIIa), or (IIIb), $R^{6b}$ is S(=$O_2$)$R^7$; and $R^{6a}$ and $R^{6c}$ are each H. In some embodiments of Formula (I), (Ia), (II), (IIa), (IIb), (III), (IIIa), or (IIIb), each $R^7$ is independently optionally substituted $C_1$-$C_6$ alkyl. In some embodiments of Formula (I), (Ia), (II), (IIa), (IIb), (III), (IIIa), or (IIIb), $R^5$ and $R^7$ together with the atoms to which they are attached combine to form a 5-membered heterocycloalkyl ring. In some embodiments of Formula (I), (Ia), (II), (IIa), (IIb), (III), (IIIa), or (IIIb), $R^{6c}$ and $R^7$ together with the atoms to which they are attached combine to form a 4-membered heterocycloalkyl ring. In some embodiments of Formula (I), (Ia), (II), (IIa), (IIb), (III), (IIIa), or (IIIb), $R^{6a}$ is —C(=O)$N(R^7)_2$ and $R^{6b}$ and $R^{6c}$ are each H; or $R^{6b}$ is —C(=O)$N(R^7)_2$, and $R^{6a}$ and $R^{6c}$ are each H, wherein two $R^7$ together with the nitrogen atom to which they are attached combine to form an optionally substituted 4 to 5-membered ring.

In another aspect, provided herein is a pharmaceutical composition comprising a compound of Formula (I), (Ia), (II), (IIa), (IIb), (III), (IIIa), or (IIIb), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof; and at least one pharmaceutically acceptable excipient.

In another aspect, provided herein is a method of modulating RAS-PI3K, the method comprising administering to a subject in need thereof a therapeutically effective amount of a compound of Formula (I), (Ia), (II), (IIa), (IIb), (III), (IIIa), or (IIIb), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof. In some embodiments, the method comprises inhibition of RAS-PI3K. In some embodiments, the method comprises activation of RAS-PI3K.

In another aspect, provided herein is a method of treating a disease or condition comprising administering to a subject in need thereof a therapeutically effective amount of a compound of Formula (I), (Ia), (II), (IIa), (IIb), (III), (IIIa), or (IIIb), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof. In some embodiments, the disease or condition is mediated by the modulation of RAS-PI3K. In some embodiments, the disease is cancer. In some embodiments, the cancer is selected from the group consisting of bladder cancer, uterine cancer, head and neck cancer, esophageal cancer, ovarian cancer, liver cancer, cervical cancer, lung cancer, colorectal cancer, cholangiocarcinoma, gastric cancer, kidney cancer, and pancreatic cancer. In some embodiments, the disease or condition an immunological disease or condition. In some embodiments, the immunological condition is wound healing.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

DETAILED DESCRIPTION

RAS proteins are small GTPases known for their involvement in oncogenesis. RAS operates in a complex signaling network with multiple activators and effectors, which allows them to regulate cellular functions such as cell proliferation, differentiation, apoptosis, and senescence. Phosphatidylinositol 3-kinase (PI3K) is one of the main effector pathways of RAS, regulating cell growth, cell cycle entry, cell survival, cytoskeleton reorganization, and metabolism. It is the involvement of this pathway in human tumors that has attracted most attention. PI3K has proven to be necessary for RAS-induced transformation in vitro. Mice with mutations in the PI3K catalytic subunit p110α that block its ability to interact with RAS are highly resistant to endogenous oncogenic KRAS-induced lung tumorigenesis and HRAS-induced skin carcinogenesis. These animals also have a delayed development of the lymphatic vasculature.

Disclose herein are compounds and methods for modulating RAS-PI3K activity. Some embodiments relate to a compound or method of inhibiting RAS-PI3K activity. Some embodiments, relate to a compound or method of activating RAS-PI3K activity. The modulating of RAS-PI3K activity may be in vitro or in vivo. The compound for modulating RAS-PI3K may be formulated for administration to a subject. The RAS-PI3K modulation may be performed in a subject.

The compounds disclosed herein may be useful for treatment of diseases where RAS-PI3K activity may be a concern. In some embodiments, the compound is used for wound healing. In some embodiments, the compound is used for treatment of cancer.

Compounds of the Disclosure

Disclosed herein, in some embodiments are modulators of RAS-PI3K.

In an aspect, provided herein is a compound having the structure of Formula (I), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof:

Formula (I)

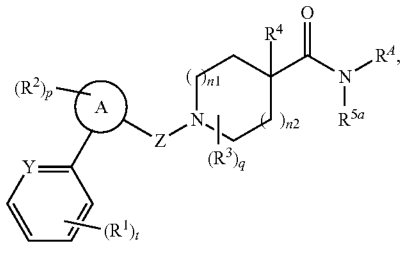

wherein,

Z is C(═O) or $S(═O)_2$;

Ring A is phenyl, 5 to 10-membered heteroaryl, $C_3$-$C_8$ cycloalkyl, $C_8$-$C_9$ spirocyclyl, or 5 to 8-membered heterocycloalkyl;

Y is N, CH, or $CR^1$;

each $R^1$ is independently halogen, —CN, —OH, —$OR^a$, —SH, —$SR^a$, —$NO_2$, —$N(R^b)_2$, —C(═O)$R^a$, —C(═O)$OR^a$, —C(═O)$NR^aR^b$, optionally substituted $C_1$-$C_6$ alkyl, optionally substituted $C_1$-$C_6$ deuteroalkyl, optionally substituted $C_2$-$C_6$ alkenyl, optionally substituted $C_2$-$C_6$ alkynyl, optionally substituted $C_1$-$C_6$ haloalkyl, optionally substituted $C_1$-$C_6$ hydroxyalkyl, or optionally substituted $C_3$-$C_6$ cycloalkyl;

each $R^2$ is independently halogen, —CN, —OH, —$OR^a$, —SH, —$SR^a$, —$NO_2$, —$N(R^b)_2$, —$S(═O)_2R^a$, —C(═O)$R^a$, —C(═O)$OR^a$, —C(═O)$NR^aR^b$, oxo (═O), optionally substituted $C_1$-$C_6$ alkyl, optionally substituted $C_1$-$C_6$ deuteroalkyl, optionally substituted $C_2$-$C_6$ alkenyl, optionally substituted $C_2$-$C_6$ alkynyl, optionally substituted $C_1$-$C_6$ alkylamino, optionally substituted $C_1$-$C_6$ haloalkyl, optionally substituted $C_1$-$C_6$ hydroxyalkyl, optionally substituted $C_3$-$C_6$ cycloalkyl, optionally substituted arylalkyl, or optionally substituted 4 to 6-membered heterocycloalkyl;

or two $R^2$ together with the atom(s) to which they are attached combine to form a $C_3$-$C_5$ cycloalkyl, 4 to 5-membered heterocycloalkyl, or a 5-membered heteroaryl ring;

each $R^3$ is independently halogen, —CN, —OH, —$OR^a$, $C_1$-$C_6$ alkyl, $C_1$-$C_6$ deuteroalkyl, or $C_1$-$C_6$ haloalkyl;

$R^4$ is H, halogen, —OH, —$OR^a$, or $C_1$-$C_6$ alkyl;

$R^A$ is

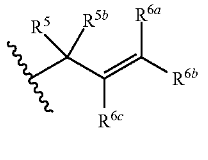

or

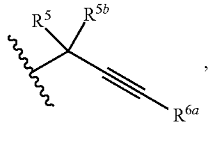

, wherein $R^5$ is H, optionally substituted $C_1$-$C_3$ alkyl, optionally substituted $C_1$-$C_3$ haloalkyl, or optionally substituted $C_1$-$C_3$ hydroxyalkyl;

$R^{6a}$ and $R^{6b}$ are each independently H, —CN, —C(═O)OR$^7$, —C(═O)N($R^7$)$_2$, —S(═O)$R_7$, —S(═O)$_2$R$^7$, or —S(═O)(═NH)R$^7$; wherein each $R^7$ is independently optionally substituted $C_1$-$C_6$ alkyl, optionally substituted $C_3$-$C_6$ cycloalkyl, or optionally substituted 4 to 6-membered heterocycloalkyl ring;

or two $R^7$ together with the nitrogen atom to which they are attached combine to form an optionally substituted 4 to 5-membered heterocycloalkyl ring;

or $R^5$ and $R^7$ together with the atoms to which they are attached combine to form a 5-membered heterocycloalkyl ring;

$R^{6c}$ is H or —CN;

or $R^{6c}$ and $R^7$ together with the atoms to which they are attached combine to form a 4-membered heterocycloalkyl ring;

$R^{5a}$ is H; or $R^{5a}$ and $R^{6c}$ together with the nitrogen atom to which they are attached combine to form a 4-membered heterocycloalkyl ring; or $R^{5a}$ is absent and $R^{6c}$ is bound directly to the nitrogen to which $R^A$ is attached to form a 4-membered heterocyclic ring;

or $R^{5a}$ and $R^5$ together with the nitrogen and carbon atoms to which they are attached form a 4-membered heterocyclic ring;

$R^{5b}$ is H or $C_1$-$C_3$ alkyl;

each $R^a$ is independently H, $C_1$-$C_6$ alkyl, $C_1$-$C_6$ deuteroalkyl, $C_1$-$C_6$ haloalkyl, $C_1$-$C_6$ heteroalkyl, $C_2$-$C_6$ alkenyl, $C_2$-$C_6$ alkynyl, $C_3$-$C_6$ cycloalkyl, 3- to 6-membered heterocycloalkyl, $C_5$-$C_8$ aryl, $C_5$-$C_8$ heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl(heterocycloalkyl); wherein each alkyl, deuteroalkyl, haloalkyl, heteroalkyl, cycloalkyl, heterocycloalkyl, aryl, heteroaryl, alkyl (aryl), alkyl(heteroaryl), alkyl(cycloalkyl), and alkyl (heterocycloalkyl) is independently optionally substituted with one, two, or three halogen, —OH, $C_1$-$C_6$ alkyl, or $C_1$-$C_6$ haloalkyl, or $C_1$-$C_6$ alkoxy;

each $R^b$ is independently H, $C_1$-$C_6$ alkyl, $C_1$-$C_6$ haloalkyl, $C_1$-$C_6$ heteroalkyl, cycloalkyl, heterocycloalkyl, aryl, or heteroaryl; wherein the alkyl, heteroalkyl, cycloalkyl, heterocycloalkyl, aryl, and heteroaryl is independently optionally substituted with one, two, or three halogen, —OH, $C_1$-$C_6$ alkyl, or $C_1$-$C_6$ haloalkyl;

or two $R^b$ groups on a nitrogen atom are taken together with the nitrogen atom to which they are attached to form a heterocycloalkyl which is optionally substituted with one, two, or three $C_1$-$C_6$ alkyl, or $C_1$-$C_6$ haloalkyl;

n1 and n2 are each independently 0, 1, 2, or 3;

p is 0, 1, 2, or 3;

q is 0, 1, or 2; and t is 0, 1, 2, or 3.

In some embodiments, provided herein is a compound having the structure of Formula (I), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof:

Formula (I)

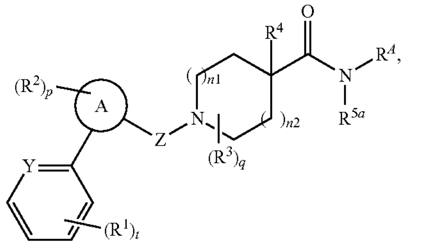

wherein,

Z is C(═O) or S(═O)$_2$;

Ring A is phenyl, pyridinyl, or 5 to 6-membered heterocycloalkyl;

Y is CH or CR$^1$;

each $R^1$ is independently halogen, —CN, —OH, —OR$^a$, $C_1$-$C_6$ alkyl, $C_1$-$C_6$ deuteroalkyl, $C_2$-$C_6$ alkynyl, $C_1$-$C_6$ haloalkyl, or $C_1$-$C_6$ hydroxyalkyl;

each $R^2$ is independently halogen, —CN, —OH, —OR$^a$, —N($R^b$)$_2$, $C_1$-$C_6$ alkyl, $C_1$-$C_6$ deuteroalkyl, $C_2$-$C_6$ alkenyl, $C_2$-$C_6$ alkynyl, $C_1$-$C_6$ haloalkyl, $C_1$-$C_6$ hydroxyalkyl, $C_3$-$C_6$ cycloalkyl, or optionally substituted 4 to 6-membered heterocycloalkyl;

each $R^3$ is independently $C_1$-$C_3$ alkyl or $C_1$-$C_3$ deuteroalkyl;

$R^4$ is F;

$R^A$ is

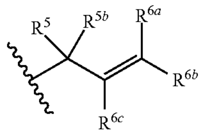

or

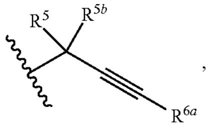

, wherein $R^5$ is H, $C_1$-$C_3$ alkyl, $C_1$-$C_3$ haloalkyl, or $C_1$-$C_3$ hydroxyalkyl;

$R^{6a}$ and $R^{6b}$ are each independently H, —CN, —C(═O)OR$^7$, —C(═O)N($R^7$)$_2$, or —S(═O)$_2$R$^7$; wherein each $R^7$ is independently optionally substituted $C_1$-$C_3$ alkyl or optionally substituted 4 to 6-membered heterocycloalkyl ring;

or two $R^7$ together with the nitrogen atom to which they are attached combine to form an optionally substituted 4 to 5-membered heterocycloalkyl ring;

or $R^5$ and $R^7$ together with the atoms to which they are attached combine to form a 5-membered heterocycloalkyl ring;

$R^{6c}$ is H;

or $R^{6c}$ and $R^7$ together with the atoms to which they are attached combine to form a 4-membered heterocycloalkyl ring;

$R^{5a}$ is H; or $R^{5a}$ and $R^{6c}$ together with the nitrogen atom to which they are attached combine to form a 4-membered heterocycloalkyl ring;

$R^{5b}$ is H or $C_1$-$C_3$ alkyl;

n1 and n2 are each independently 0, 1 or 2;

each $R^a$ is independently H, $C_1$-$C_6$ alkyl, $C_1$-$C_6$ haloalkyl, cycloalkyl, heterocycloalkyl, or aryl; wherein each alkyl, cycloalkyl, heterocycloalkyl, or aryl, is independently optionally substituted with one, two, or three halogen, —OH, $C_1$-$C_6$ alkyl, or $C_1$-$C_6$ haloalkyl;

each $R^b$ is independently H or $C_1$-$C_6$ alkyl;

or two $R^b$ groups on a nitrogen atom are taken together with the nitrogen atom to which they are attached to form a heterocycloalkyl which is optionally substituted with one, two, or three $C_1$-$C_6$ alkyl, or $C_1$-$C_6$ haloalkyl;

p is 0, 1, 2, or 3;

q is 0, 1, or 2; and t is 1, 2, or 3.

In some embodiments, provided herein is a compound having the structure of Formula (I), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof:

Formula (I)

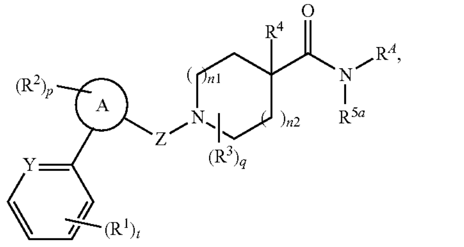

wherein,

Z is C(=O) or S(=O)$_2$;

Ring A is phenyl, pyridinyl, or 5-membered heterocycloalkyl;

Y is CH or $CR^1$;

each $R^1$ is independently Cl, Br, F, —$OCH_3$, $CH_3$, or —$CD_3$;

each $R^2$ is independently halogen, —CN, —OH, —$OR^a$, —$N(R^b)_2$, $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_3$-$C_6$ cycloalkyl, or 4 to 6-membered heterocycloalkyl;

each $R^3$ is independently —$CH_3$ or —$CD_3$;

$R^4$ is F;

$R^A$ is

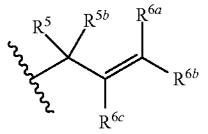

or

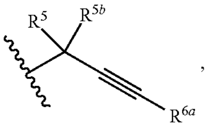

, wherein $R^5$ is H, —$CH_3$, or —$CH_2CH_3$;

$R^{6a}$ and $R^{6b}$ are each independently H, —CN, —C(=O)$OR^7$, —C(=O)$N(R^7)_2$, or —S(=O)$_2R^7$; wherein each $R^7$ is independently optionally substituted $C_1$-$C_3$ alkyl or optionally substituted 4 to 6-membered heterocycloalkyl ring;

or two $R^7$ together with the nitrogen atom to which they are attached combine to form an optionally substituted 4 to 5-membered heterocycloalkyl ring;

or $R^5$ and $R^7$ together with the atoms to which they are attached combine to form a 5-membered heterocycloalkyl ring;

$R^{6c}$ is H;

or $R^{6c}$ and $R^7$ together with the atoms to which they are attached combine to form a 4-membered heterocycloalkyl ring;

$R^{5a}$ is H; or $R^{5a}$ and $R^{6c}$ together with the nitrogen atom to which they are attached combine to form a 4-membered heterocycloalkyl ring;

$R^{5b}$ is H or $C_1$-$C_3$ alkyl;

n1 and n2 are each independently 0, 1, or 2;

each $R^a$ is independently H, $C_1$-$C_6$ alkyl, or $C_1$-$C_6$ haloalkyl;

each $R^b$ is independently H or $C_1$-$C_6$ alkyl;

p is 0, 1, 2, or 3;

q is 0, 1, or 2; and t is 1, 2, or 3.

In some embodiments, the compound of Formula (I) has the structure of Formula (Ia), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof:

Formula (Ia)

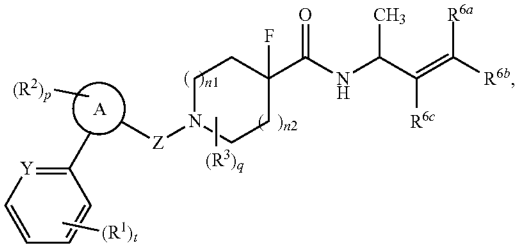

wherein,

Z is C(=O) or S(=O)$_2$;

Ring A is phenyl, 5 to 10-membered heteroaryl, $C_3$-$C_8$ cycloalkyl, $C_8$-$C_9$ spirocyclyl, or 5 to 8-membered heterocycloalkyl;

Y is CH or $CR^1$;

each $R^1$ is independently halogen, —CN, —OH, —$OR^a$, —SH, —$SR^a$, —$NO_2$, —$N(R^b)_2$, —C(=O)$R^a$, —C(=O)$OR^a$, —C(=O)$NR^aR^b$, optionally substituted $C_1$-$C_6$ alkyl, optionally substituted $C_1$-$C_6$ deuteroalkyl, optionally substituted $C_2$-$C_6$ alkenyl, optionally substituted $C_2$-$C_6$ alkynyl, optionally substituted $C_1$-$C_6$ haloalkyl, optionally substituted $C_1$-$C_6$ hydroxyalkyl, or optionally substituted $C_3$-$C_6$ cycloalkyl;

each $R^2$ is independently halogen, —CN, —OH, —$OR^a$, —SH, —$SR^a$, —$NO_2$, —$N(R^b)_2$, —S(=O)$_2R^a$, —C(=O)$R^a$, —C(=O)$OR^a$, —C(=O)$NR^aR^b$, oxo (=O), optionally substituted $C_1$-$C_6$ alkyl, optionally substituted $C_1$-$C_6$ deuteroalkyl, optionally substituted $C_2$-$C_6$ alkenyl, optionally substituted $C_2$-$C_6$ alkynyl, optionally substituted $C_1$-$C_6$ alkylamino, optionally substituted $C_1$-$C_6$ haloalkyl, optionally substituted $C_1$-$C_6$ hydroxyalkyl, optionally substituted $C_3$-$C_6$ cycloalkyl, optionally substituted arylalkyl, or optionally substituted 4 to 6-membered heterocycloalkyl;

or two $R^2$ together with the atom(s) to which they are attached combine to form a $C_3$-$C_5$ cycloalkyl, 4 to 5-membered heterocycloalkyl, or a 5-membered heteroaryl ring;

each $R^3$ is independently halogen, —CN, —OH, —$OR^a$, $C_1$-$C_6$ alkyl, $C_1$-$C_6$ deuteroalkyl, or $C_1$-$C_6$ haloalkyl;

$R^{6a}$ and $R^{6b}$ are each independently H, —CN, —C(═O)$OR^7$, —C(═O)$N(R^7)_2$, —S(═O)$R_7$, —S(═O)$_2R^7$, or —S(═O)(═NH)$R^7$; wherein each $R^7$ is independently optionally substituted $C_1$-$C_6$ alkyl, optionally substituted $C_3$-$C_6$ cycloalkyl, or optionally substituted 4 to 6-membered heterocycloalkyl ring;

or two $R^7$ together with the nitrogen atom to which they are attached combine to form an optionally substituted 4 to 5-membered heterocycloalkyl ring;

or $R^5$ and $R^7$ together with the atoms to which they are attached combine to form a 5-membered heterocycloalkyl ring;

$R^{6c}$ is H or —CN;

or $R^{6c}$ and $R^7$ together with the atoms to which they are attached combine to form a 4-membered heterocycloalkyl ring;

each $R^a$ is independently H, $C_1$-$C_6$ alkyl, $C_1$-$C_6$ deuteroalkyl, $C_1$-$C_6$ haloalkyl, $C_1$-$C_6$ heteroalkyl, $C_2$-$C_6$ alkenyl, $C_2$-$C_6$ alkynyl, $C_1$-$C_6$ cycloalkyl, 3- to 6-membered heterocycloalkyl, $C_5$-$C_8$ aryl, $C_5$-$C_8$ heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl(heterocycloalkyl); wherein each alkyl, deuteroalkyl, haloalkyl, heteroalkyl, cycloalkyl, heterocycloalkyl, aryl, heteroaryl, alkyl (aryl), alkyl(heteroaryl), alkyl(cycloalkyl) and alkyl (heterocycloalkyl) is independently optionally substituted with one, two, or three halogen, —OH, $C_1$-$C_6$ alkyl, $C_1$-$C_6$ haloalkyl, or $C_1$-$C_6$ alkoxy;

each $R^b$ is independently H, $C_1$-$C_6$ alkyl, $C_1$-$C_6$ haloalkyl, $C_1$-$C_6$ heteroalkyl, cycloalkyl, heterocycloalkyl, aryl, or heteroaryl; wherein the alkyl, heteroalkyl, cycloalkyl, heterocycloalkyl, aryl, and heteroaryl is independently optionally substituted with one, two, or three halogen, —OH, $C_1$-$C_6$ alkyl, or $C_1$-$C_6$ haloalkyl;

or two $R^b$ groups on a nitrogen atom are taken together with the nitrogen atom to which they are attached to form a heterocycloalkyl which is optionally substituted with one, two, or three $C_1$-$C_6$ alkyl, or $C_1$-$C_6$ haloalkyl;

n1 and n2 are each independently 0, 1, 2, or 3;

p is 0, 1, 2, or 3;

q is 0, 1, or 2; and t is 0, 1, 2, or 3.

In some embodiments of Formula (I) or (Ia), Y is N. In some embodiments of Formula (I) or (Ia), Y is CH or $CR^1$. In some embodiments of Formula (I) or (Ia), Y is CH. In some embodiments of Formula (I) or (Ia), Y is $CR^1$.

In some embodiments of Formula (I) or (Ia), ring A is a $C_5$-$C_7$ cycloalkyl or 5 to 7-membered heterocycloalkyl. In some embodiments of Formula (I) or (Ia), ring A is $C_3$-$C_8$ cycloalkyl. In some embodiments of Formula (I) or (Ia), ring A is a $C_5$-$C_7$ cycloalkyl. In some embodiments of Formula (I) or (Ia), ring a is a cyclopentyl. In some embodiments of Formula (I) or (Ia), ring A is a cyclohexyl. In some embodiments, ring A is a cyclohexene.

In some embodiments of Formula (I) or (Ia), ring A is a 5 to 8-membered heterocycloalkyl. In some embodiments of Formula (I) or (Ia), ring A is a heterocycloalkyl. In some embodiments of Formula (I) or (Ia), the heterocycloalkyl is monocyclic, bicyclic, or polycyclic. In some embodiments of Formula (I) or (Ia), ring A is a 5 to 7-membered heterocycloalkyl. In some embodiments of Formula (I) or (Ia), ring A is a 5 to 6-membered heterocycloalkyl. In some embodiments of Formula (I) or (Ia), ring A is a 5 membered heterocycloalkyl comprising 1 or 2 heteroatoms selected from 0 or N. In some embodiments of Formula (I) or (Ia), ring A is a 5 membered heterocycloalkyl comprising 1 heteroatom selected from 0 or N. In some embodiments, ring A is a 6-membered heterocycloalkyl. In some embodiments of Formula (I) or (Ia), ring A is a 6 membered heterocycloalkyl comprising 1 or 2 heteroatoms selected from 0 or N. In some embodiments of Formula (I) or (Ia), ring A is a 6 membered heterocycloalkyl comprising 1 heteroatom selected from 0 or N. In some embodiments of Formula (I) or (Ia), the heterocycloalkyl is piperazine, piperidine, morpholine, tetrahydropyran, pyrrolidine, or tetrahydrofuran. In some embodiments of Formula (I) or (Ia), the heterocycloalkyl is piperazine. In some embodiments of Formula (I) or (Ia), the heterocycloalkyl is piperidine, morpholine. In some embodiments of Formula (I) or (Ia), the heterocycloalkyl is tetrahydropyran. In some embodiments of Formula (I) or (Ia), the heterocycloalkyl is pyrrolidine. In some embodiments of Formula (I) or (Ia), the heterocycloalkyl is tetrahydrofuran.

In another aspect, provided herein is a compound having the structure of Formula (II), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof:

Formula (II)

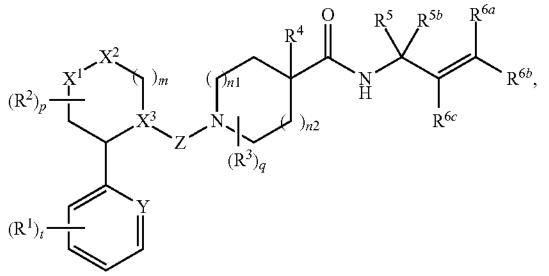

wherein, $X^1$ are $X^2$ are each independently $CH_2$, $CHR^2$, $CR^2R^2$, O, or $NR^{2a}$; wherein at least one of $X^1$ or $X^2$ is $CH_2$, $CHR^2$, or $CR^2R^2$;

$X^3$ is $CR^8$ or N, provided that when $X^3$ is N, $R^1$ is absent;

Y is N, CH, or $CR^1$;

Z is C(═O) or S(═O)$_2$;

each $R^1$ is independently halogen, —CN, —OH, —$OR^a$, optionally substituted $C_1$-$C_6$ alkyl, optionally substituted $C_1$-$C_6$ deuteroalkyl, optionally substituted $C_2$-$C_6$ alkynyl, optionally substituted $C_1$-$C_6$ haloalkyl, optionally substituted $C_1$-$C_6$ hydroxyalkyl, or optionally substituted $C_3$-$C_6$ cycloalkyl;

each $R^2$ is independently halogen, —CN, —OH, —$OR^a$, —$N(R^b)_2$, optionally substituted $C_1$-$C_6$ alkyl, optionally substituted $C_1$-$C_6$ deuteroalkyl, optionally substituted $C_2$-$C_6$ alkenyl, optionally substituted $C_2$-$C_6$ alkynyl, optionally substituted $C_1$-$C_6$ haloalkyl, optionally substituted $C_1$-$C_6$ hydroxyalkyl, optionally substituted $C_3$-$C_6$ cycloalkyl, optionally substituted arylalkyl, or optionally substituted 4 to 6-membered heterocycloalkyl;

or two $R^2$ together with the atom(s) to which they are attached combine to form a $C_3$-$C_5$ cycloalkyl;

$R^{2a}$ is H, —S(═O)$_2R^a$, —C(═O)$R^a$, —C(═O)$OR^a$, —C(═O)$NR^aR^b$, optionally substituted $C_1$-$C_6$ alkyl, optionally substituted $C_1$-$C_6$ haloalkyl, $C_3$-$C_6$ cycloalkyl, or phenyl;

each $R^3$ is independently halogen, —CN, —OH, —$OR^a$, $C_1$-$C_6$ alkyl, $C_1$-$C_6$ deuteroalkyl, or $C_1$-$C_6$ haloalkyl;

$R^4$ is H, halogen, —OH, —$OR^a$, or $C_1$-$C_6$ alkyl;

$R^5$ is H, $C_1$-$C_3$ alkyl, $C_1$-$C_3$ haloalkyl, or $C_1$-$C_3$ hydroxyalkyl;

$R^{5b}$ is H or $C_1$-$C_3$ alkyl;

$R^{6a}$ and $R^{6b}$ are each independently H, —CN, —C(=O)$OR^7$, —C(=O)$N(R^7)_2$, —S(=O)$R_7$, —S(=O)$_2R^7$, or —S(=O)(=NH)$R^7$; wherein each $R^7$ is independently optionally substituted $C_1$-$C_6$ alkyl, optionally substituted $C_3$-$C_6$ cycloalkyl, or optionally substituted 4 to 6-membered heterocycloalkyl ring;

or two $R^7$ together with the nitrogen atom to which they are attached combine to form an optionally substituted 4 to 5-membered heterocycloalkyl ring;

or $R^5$ and $R^7$ together with the atoms to which they are attached combine to form a 5-membered heterocycloalkyl ring;

$R^{6c}$ is H or —CN;

or $R^{6c}$ and $R^7$ together with the atoms to which they are attached combine to form a 4-membered heterocycloalkyl ring;

$R^8$ is absent, H, halogen, —$OCH_3$, or —$CH_3$;

each $R^a$ is independently H, $C_1$-$C_6$ alkyl, $C_1$-$C_6$ deuteroalkyl, $C_1$-$C_6$ haloalkyl, $C_1$-$C_6$ heteroalkyl, $C_2$-$C_6$ alkenyl, $C_2$-$C_6$ alkynyl, $C_3$-$C_6$ cycloalkyl, 3- to 6-membered heterocycloalkyl, $C_5$-$C_8$ aryl, $C_5$-$C_8$ heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl(heterocycloalkyl); wherein each alkyl, deuteroalkyl, haloalkyl, heteroalkyl, cycloalkyl, heterocycloalkyl, aryl, heteroaryl, alkyl (aryl), alkyl(heteroaryl), alkyl(cycloalkyl) and alkyl (heterocycloalkyl) is independently optionally substituted with one, two, or three halogen, —OH, $C_1$-$C_6$ alkyl, $C_1$-$C_6$ haloalkyl, or $C_1$-$C_6$ alkoxy;

each $R^b$ is independently H, $C_1$-$C_6$ alkyl, $C_1$-$C_6$ haloalkyl, $C_1$-$C_6$ heteroalkyl, cycloalkyl, heterocycloalkyl, aryl, or heteroaryl; wherein the alkyl, heteroalkyl, cycloalkyl, heterocycloalkyl, aryl, and heteroaryl is independently optionally substituted with one, two, or three halogen, —OH, $C_1$-$C_6$ alkyl, or $C_1$-$C_6$ haloalkyl;

or two $R^b$ groups on a nitrogen atom are taken together with the nitrogen atom to which they are attached to form a heterocycloalkyl which is optionally substituted with one, two, or three $C_1$-$C_6$ alkyl, or $C_1$-$C_6$ haloalkyl;

m is 0 or 1;

n1 and n2 are each independently 0, 1, 2, or 3;

p is 0, 1, 2, or 3;

q is 0, 1, or 2; and t is 1, 2, or 3.

In another aspect, provided herein is a compound having the structure of Formula (II), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof:

Formula (II)

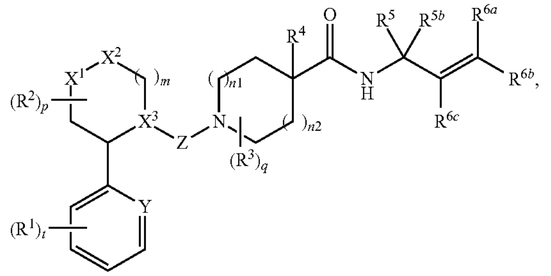

wherein, $X^1$ are $X^2$ are each independently $CH_2$, $CHR^2$, $CR^2R^2$, O, or $NR^{2a}$; wherein at least one of $X^1$ or $X^2$ is $CH_2$, $CHR^2$, or $CR^2R^2$;

$X^3$ is $CR^8$ or N, provided that when $X^3$ is N, $R^8$ is absent;

Y is CH or $CR^1$;

Z is C(=O) or S(=O)$_2$;

each $R^1$ is independently halogen, —CN, —OH, —$OR^a$, optionally substituted $C_1$-$C_6$ alkyl, optionally substituted $C_1$-$C_6$ deuteroalkyl, optionally substituted $C_2$-$C_6$ alkynyl, optionally substituted $C_1$-$C_6$ haloalkyl, or $C_1$-$C_6$ hydroxyalkyl;

each $R^2$ is independently halogen, —CN, —OH, —$OR^a$, —$N(R^b)_2$, optionally substituted $C_1$-$C_6$ alkyl, optionally substituted $C_1$-$C_6$ deuteroalkyl, optionally substituted $C_2$-$C_6$ alkenyl, optionally substituted $C_2$-$C_6$ alkynyl, optionally substituted $C_1$-$C_6$ haloalkyl, optionally substituted $C_1$-$C_6$ hydroxyalkyl, optionally substituted $C_3$-$C_6$ cycloalkyl, or optionally substituted 4 to 6-membered heterocycloalkyl;

or two $R^2$ together with the atom(s) to which they are attached combine to form a $C_3$-$C_5$ cycloalkyl;

$R^{2a}$ is H, —C(=O)$OR^a$, —C(=O)$NR^aR^b$, optionally substituted $C_1$-$C_6$ alkyl, optionally substituted $C_1$-$C_6$ haloalkyl, or optionally substituted $C_3$-$C_6$ cycloalkyl;

each $R^3$ is independently $C_1$-$C_3$ alkyl or $C_1$-$C_3$ deuteroalkyl;

$R^4$ is H or halogen;

$R^5$ is H, $C_1$-$C_3$ alkyl, $C_1$-$C_3$ haloalkyl, or $C_1$-$C_3$ hydroxyalkyl;

$R^{6a}$ and $R^{6b}$ are each independently H, —CN, —C(=O)$OR^7$, —C(=O)$N(R^7)_2$, —S(=O)$R_7$, —S(=O)$_2R^7$, or —S(=O)(=NH)$R^7$; wherein each $R^7$ is independently optionally substituted $C_1$-$C_6$ alkyl, optionally substituted $C_3$-$C_6$ cycloalkyl, or optionally substituted 4 to 6-membered heterocycloalkyl ring;

or two $R^7$ together with the nitrogen atom to which they are attached combine to form an optionally substituted 4 to 5-membered heterocycloalkyl ring;

or $R^5$ and $R^7$ together with the atoms to which they are attached combine to form a 5-membered heterocycloalkyl ring;

$R^{6c}$ is H or —CN;

or $R^{6c}$ and $R^7$ together with the atoms to which they are attached combine to form a 4-membered heterocycloalkyl ring;

$R^8$ is absent, H, halogen, —$OCH_3$, or —$CH_3$;

each $R^a$ is independently H, $C_1$-$C_6$ alkyl, $C_1$-$C_6$ haloalkyl, $C_1$-$C_6$ heteroalkyl, cycloalkyl, heterocycloalkyl, aryl, heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl (heterocycloalkyl); wherein each alkyl, heteroalkyl, cycloalkyl, heterocycloalkyl, aryl, and heteroaryl is independently optionally substituted with one, two, or three halogen, —OH, $C_1$-$C_6$ alkyl, or $C_1$-$C_6$ haloalkyl;

each $R^b$ is independently H, $C_1$-$C_6$ alkyl, $C_1$-$C_6$ haloalkyl, $C_1$-$C_6$ heteroalkyl, cycloalkyl, heterocycloalkyl, aryl, or heteroaryl; wherein the alkyl, heteroalkyl, cycloalkyl, heterocycloalkyl, aryl, and heteroaryl is independently optionally substituted with one, two, or three halogen, —OH, $C_1$-$C_6$ alkyl, or $C_1$-$C_6$ haloalkyl;

or two $R^b$ groups on a nitrogen atom are taken together with the nitrogen atom to which they are attached to form a heterocycloalkyl which is optionally substituted with one, two, or three $C_1$-$C_6$ alkyl, or $C_1$-$C_6$ haloalkyl;

m is 0 or 1;

n1 and n2 are each independently 0, 1, or 2;

p is 0, 1, 2, or 3;

q is 0, 1, or 2; and t is 1, 2, or 3.

In some embodiments, provided herein is a compound having the structure of Formula (II), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof:

Formula (II)

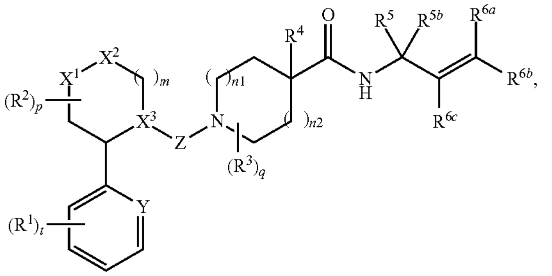

wherein, $X^1$ are $X^2$ are each independently $CH_2$, $CHR^2$, $CR^2R^2$, O, or $NR^{2a}$; wherein at least one of $X^1$ or $X^2$ is $CH_2$, $CHR^2$, or $CR^2R^2$;

$X^3$ is $CR^1$;

Y is CH or $CR^1$;

Z is C(═O);

each $R^1$ is independently Cl, Br, F, —$OCH_3$, $CH_3$ or -$CD_3$;

each $R^2$ is independently halogen, —CN, —OH, —$OR^a$, —$N(R^b)_2$, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl, or 4 to 6-membered heterocycloalkyl;

$R^{2a}$ is —C(═O)$R^a$, —C(═O)$OR^a$, $C_1$-$C_6$ haloalkyl, or $C_3$-$C_6$ cycloalkyl.

each $R^3$ is independently —$CH_3$ or -$CD_3$;

$R^4$ is F;

$R^5$ is H, —$CH_3$, or —$CH_2CH_3$;

$R^{6a}$ and $R^{6b}$ are each independently H, —CN, —C(═O)$OR^7$, —C(═O)$N(R^7)_2$, or —S(═O)$_2R^7$; wherein each $R^7$ is independently optionally substituted $C_1$-$C_3$ alkyl or optionally substituted 4 to 6-membered heterocycloalkyl ring;

or two $R^7$ together with the nitrogen atom to which they are attached combine to form an optionally substituted 4 to 5-membered heterocycloalkyl ring;

or $R^5$ and $R^7$ together with the atoms to which they are attached combine to form a 5-membered heterocycloalkyl ring;

$R^{6c}$ is H;

or $R^{6c}$ and $R^7$ together with the atoms to which they are attached combine to form a 4-membered heterocycloalkyl ring;

$R^{5a}$ is H; or $R^{5a}$ and $R^{6c}$ together with the nitrogen atom to which they are attached combine to form a 4-membered heterocycloalkyl ring;

$R^8$ is H;

each $R^a$ is independently H, $C_1$-$C_6$ alkyl, $C_1$-$C_6$ haloalkyl, cycloalkyl, heterocycloalkyl, or aryl; wherein each alkyl, cycloalkyl, heterocycloalkyl, or aryl, is independently optionally substituted with one, two, or three halogen, —OH, $C_1$-$C_6$ alkyl, or $C_1$-$C_6$ haloalkyl;

each $R^b$ is independently H or $C_1$-$C_6$ alkyl;

or two $R^b$ groups on a nitrogen atom are taken together with the nitrogen atom to which they are attached to form a heterocycloalkyl which is optionally substituted with one, two, or three $C_1$-$C_6$ alkyl, or $C_1$-$C_6$ haloalkyl;

n1 and n2 are each independently 0, 1, or 2;

m is 0 or 1;

p is 0, 1, 2, or 3;

q is 0, 1, or 2; and t is 1, 2, or 3.

In some embodiments of Formula (II), $X^3$ is $CR^8$. In some embodiments of Formula (II), $X^3$ is N.

In some embodiments of Formula (II), $R^8$ is H, halogen, $OCH_3$, or $CH_3$. In some embodiments of Formula (II), $R^8$ is halogen. In some embodiments of Formula (II), $R^8$ is F, Cl, or Br. In some embodiments of Formula (II), $R^8$ is $OCH_3$, or $CH_3$. In some embodiments of Formula (II), $R^8$ is H.

In some embodiments, the compound of Formula (II) has the structure of Formula (IIa), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof:

Formula (IIa)

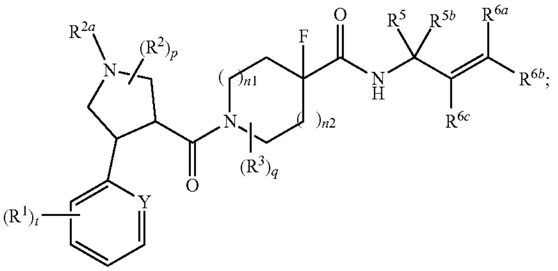

wherein, $X^1$ are $X^2$ are each independently $CH_2$, $CHR^2$, $CR^2R^2$, O, or $NR^{2a}$; wherein at least one of $X^1$ or $X^2$ is $CH_2$, $CHR^2$, or $CR^2R^2$;

$X^3$ is $CR^8$;

Y is CH or $CR^1$;

each $R^1$ is independently halogen, —CN, —OH, —$OR^a$, optionally substituted $C_1$-$C_6$ alkyl, optionally substituted $C_1$-$C_6$ deuteroalkyl, optionally substituted $C_2$-$C_6$ alkynyl, optionally substituted $C_1$-$C_6$ haloalkyl, or $C_1$-$C_6$ hydroxyalkyl;

each $R^2$ is independently optionally substituted $C_1$-$C_6$ alkyl, optionally substituted $C_1$-$C_6$ deuteroalkyl, optionally substituted $C_1$-$C_6$ haloalkyl, or optionally substituted $C_3$-$C_6$ cycloalkyl;

$R^{2a}$ is H, —C(=O)OR$^a$, —C(=O)NR$^a$R$^b$, optionally substituted $C_1$-$C_6$ alkyl, optionally substituted $C_1$-$C_6$ haloalkyl, optionally substituted arylalkyl, or optionally substituted $C_3$-$C_6$ cycloalkyl;

each $R^3$ is independently $C_1$-$C_3$ alkyl or $C_1$-$C_3$ deuteroalkyl;

$R^5$ is H, $C_1$-$C_3$ alkyl, $C_1$-$C_3$ haloalkyl, or $C_1$-$C_3$ hydroxyalkyl;

$R^{5b}$ is H or $C_1$-$C_3$ alkyl;

$R^{6a}$ and $R^{6b}$ are each independently H, —CN, —C(=O)OR$^7$, —C(=O)N(R$^7$)$_2$, —S(=O)R$_7$, —S(=O)$_2$R$^7$, or —S(=O)(=NH)R$^7$; wherein each $R^7$ is independently optionally substituted $C_1$-$C_6$ alkyl, optionally substituted $C_3$-$C_6$ cycloalkyl, or optionally substituted 4 to 6-membered heterocycloalkyl ring;

or two $R^7$ together with the nitrogen atom to which they are attached combine to form an optionally substituted 4 to 5-membered heterocycloalkyl ring;

or $R^5$ and $R^7$ together with the atoms to which they are attached combine to form a 5-membered heterocycloalkyl ring;

$R^{6c}$ is H or —CN;

or $R^{6c}$ and $R^7$ together with the atoms to which they are attached combine to form a 4-membered heterocycloalkyl ring;

$R^8$ is H, halogen, —OCH$_3$, or —CH$_3$;

each $R^a$ is independently H, $C_1$-$C_6$ alkyl, $C_1$-$C_6$ deuteroalkyl, $C_1$-$C_6$ haloalkyl, $C_1$-$C_6$ heteroalkyl, $C_2$-$C_6$ alkenyl, $C_2$-$C_6$ alkynyl, $C_3$-$C_6$ cycloalkyl, 3- to 6-membered heterocycloalkyl, $C_5$-$C_8$ aryl, $C_5$-$C_8$ heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl(heterocycloalkyl); wherein each alkyl, deuteroalkyl, haloalkyl, heteroalkyl, cycloalkyl, heterocycloalkyl, aryl, heteroaryl, alkyl (aryl), alkyl(heteroaryl), alkyl(cycloalkyl) and alkyl (heterocycloalkyl) is independently optionally substituted with one, two, or three halogen, —OH, $C_1$-$C_6$ alkyl, $C_1$-$C_6$ haloalkyl, or $C_1$-$C_6$ alkoxy;

each $R^b$ is independently H, $C_1$-$C_6$ alkyl, $C_1$-$C_6$ haloalkyl, $C_1$-$C_6$ heteroalkyl, cycloalkyl, heterocycloalkyl, aryl, or heteroaryl; wherein the alkyl, heteroalkyl, cycloalkyl, heterocycloalkyl, aryl, and heteroaryl is independently optionally substituted with one, two, or three halogen, —OH, $C_1$-$C_6$ alkyl, or $C_1$-$C_6$ haloalkyl;

or two $R^b$ groups on a nitrogen atom are taken together with the nitrogen atom to which they are attached to form a heterocycloalkyl which is optionally substituted with one, two, or three $C_1$-$C_6$ alkyl, or $C_1$-$C_6$ haloalkyl;

n1 and n2 are each independently 0, 1, 2, or 3;

p is 0, 1, 2, or 3;

q is 0, 1, or 2; and t is 1, 2, or 3.

In some embodiments of Formula (II) or (IIa), $X^1$ is CH$_2$, CHR$^2$ or CR$^2$R$^2$; and $X^2$ is CH$_2$, CHR$^2$, or CR$^2$R$^2$. In some embodiments of Formula (II) or (IIa), $X^1$ is CH$_2$, CHR$^2$, or CR$^2$R$^2$; and $X^2$ is 0 or NR$^{2a}$. In some embodiments of Formula (II) or (IIa), $X^1$ is CH$_2$, CHR$^2$, or CR$^2$R$^2$; and $X^2$ is 0. In some embodiments of Formula (II) or (IIa), $X^1$ is CH$_2$, CHR$^2$, or CR$^2$R$^2$; and $X^2$ is NR$^{2a}$. In some embodiments of Formula (II) or (IIa), $X^2$ is CH$_2$, CHR$^2$, or CR$^2$R$^2$; and $X^1$ is O or NR$^{2a}$. In some embodiments of Formula (II) or (IIa), $X^2$ is CH$_2$, CHR$^2$, or CR$^2$R$^2$; and $X^1$ is 0. In some embodiments of Formula (II) or (IIa), $X^2$ is CH$_2$, CHR$^2$, or CR$^2$R$^2$; and $X^1$ is NR$^2$a.

In some embodiments, the compound of Formula (II) has the structure of Formula (IIb), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof:

Formula (IIb)

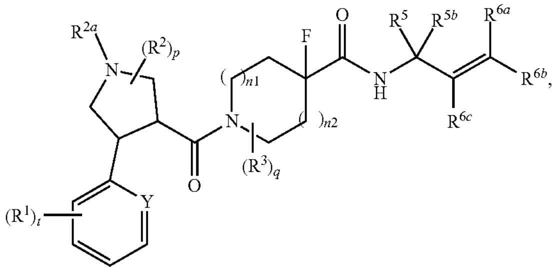

wherein,

Y is CH or CR$^1$;

each $R^1$ is independently halogen, —CN, —OH, —OR$^a$, optionally substituted $C_1$-$C_6$ alkyl, optionally substituted $C_1$-$C_6$ deuteroalkyl, optionally substituted $C_2$-$C_6$ alkynyl, optionally substituted $C_1$-$C_6$ haloalkyl, or $C_1$-$C_6$ hydroxyalkyl;

each $R^2$ is independently optionally substituted $C_1$-$C_6$ haloalkyl, or optionally substituted $C_3$-$C_6$ cycloalkyl;

$R^{2a}$ is H, —C(=O)OR$^a$, —C(=O)NR$^a$R$^b$, optionally substituted $C_1$-$C_6$ alkyl, optionally substituted $C_1$-$C_6$ haloalkyl, optionally substituted arylalkyl, or optionally substituted $C_3$-$C_6$ cycloalkyl;

each $R^3$ is independently $C_1$-$C_3$ alkyl or $C_1$-$C_3$ deuteroalkyl;

$R^5$ is H, $C_1$-$C_3$ alkyl, $C_1$-$C_3$ haloalkyl, or $C_1$-$C_3$ hydroxyalkyl;

$R^{5b}$ is H or $C_1$-$C_3$ alkyl;

$R^{6a}$ and $R^{6b}$ are each independently H, —CN, —C(=O)OR$^7$, —C(=O)N(R$^7$)$_2$, —S(=O)R$^7$, —S(=O)$_2$R$^7$, or —S(=O)(=NH)R$^7$; wherein each $R^7$ is independently optionally substituted $C_1$-$C_6$ alkyl, optionally substituted $C_3$-$C_6$ cycloalkyl, or optionally substituted 4 to 6-membered heterocycloalkyl ring;

or two $R^7$ together with the nitrogen atom to which they are attached combine to form an optionally substituted 4 to 5-membered heterocycloalkyl ring;

or $R^5$ and $R^7$ together with the atoms to which they are attached combine to form a 5-membered heterocycloalkyl ring;

$R^{6c}$ is H or —CN;

or $R^{6c}$ and $R^7$ together with the atoms to which they are attached combine to form a 4-membered heterocycloalkyl ring;

each $R^a$ is independently H, $C_1$-$C_6$ alkyl, $C_1$-$C_6$ deuteroalkyl, $C_1$-$C_6$ haloalkyl, $C_1$-$C_6$ heteroalkyl, $C_2C_6$ alkenyl, $C_2C_6$ alkynyl, $C_3C_6$ cycloalkyl, $C_3C_6$ heterocycloalkyl, $C_5C_8$ aryl, $C_5C_8$ heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl(heterocycloalkyl); wherein each alkyl, deuteroalkyl, haloalkyl, heteroalkyl, cycloalkyl, heterocycloalkyl, aryl, heteroaryl, alkyl(aryl), alkyl(heteroaryl), alkyl(cycloalkyl) and alkyl(heterocycloalkyl) is independently optionally substituted with one, two, or three halogen, —OH, $C_1$-$C_6$ alkyl, $C_1$-$C_6$ haloalkyl, or $C_1$-$C_6$ alkoxy;

each $R^b$ is independently H, $C_1$-$C_6$ alkyl, $C_1$-$C_6$ haloalkyl, $C_1$-$C_6$ heteroalkyl, cycloalkyl, heterocycloalkyl, aryl, or heteroaryl; wherein the alkyl, heteroalkyl, cycloalkyl, heterocycloalkyl, aryl, and heteroaryl is independently optionally substituted with one, two, or three halogen, —OH, $C_1$-$C_6$ alkyl, or $C_1$-$C_6$ haloalkyl;

or two $R^b$ groups on a nitrogen atom are taken together with the nitrogen atom to which they are attached to form a heterocycloalkyl which is optionally substituted with one, two, or three $C_1$-$C_6$ alkyl, or $C_1$-$C_6$ haloalkyl;

n1 and n2 are each independently 0, 1, 2, or 3;

p is 0, 1, 2, or 3;

q is 0, 1, or 2; and t is 1, 2, or 3.

In some embodiments, provided herein is a compound of Formula (IIb), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof:

Formula (IIb)

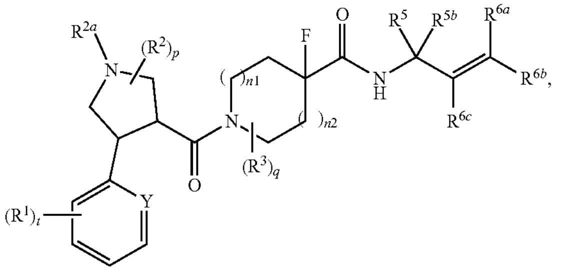

wherein,

Y is CH or $CR^1$;

each $R^1$ is independently Cl, Br, F, —$OCH_3$, $CH_3$ or $CD_3$;

each $R^2$ is independently halogen, —CN, —OH, —$OR^a$, —$N(R^b)_2$, $C_1$-$C_6$ alkyl, $C_1$-$C_6$ deuteroalkyl, $C_2$-$C_6$ alkenyl, $C_2$-$C_6$ alkynyl, $C_1$-$C_6$ haloalkyl, $C_3$-$C_6$ cycloalkyl, or 4 to 6-membered heterocycloalkyl;

$R^{2a}$ is H, $C_1$-$C_6$ alkyl, $C_1$-$C_6$ haloalkyl, or $C_3$-$C_6$ cycloalkyl;

each $R^3$ is independently —$CH_3$ or -$CD_3$;

$R^5$ is H, —$CH_3$, or —$CH_2CH_3$;

$R^{6a}$ and $R^{6b}$ are each independently H, —CN, —C(═O)$OR^7$, —C(═O)$N(R^7)_2$, or —S(═O)$_2R^7$; wherein each $R^7$ is independently optionally substituted $C_1$-$C_3$ alkyl or optionally substituted 4 to 6-membered heterocycloalkyl ring;

or two $R^7$ together with the nitrogen atom to which they are attached combine to form an optionally substituted 4 to 5-membered heterocycloalkyl ring;

or $R^5$ and $R^7$ together with the atoms to which they are attached combine to form a 5-membered heterocycloalkyl ring;

$R^{6c}$ is H;

or $R^{6c}$ and $R^7$ together with the atoms to which they are attached combine to form a 4-membered heterocycloalkyl ring;

$R^{5b}$ is H or $C_1$-$C_3$ alkyl;

each $R^a$ is independently H, $C_1$-$C_6$ alkyl, $C_1$-$C_6$ haloalkyl, cycloalkyl, heterocycloalkyl, or aryl; wherein each alkyl, cycloalkyl, heterocycloalkyl, or aryl, is independently optionally substituted with one, two, or three halogen, —OH, $C_1$-$C_6$ alkyl, or $C_1$-$C_6$ haloalkyl;

each $R^b$ is independently H or $C_1$-$C_6$ alkyl;

n1 and n2 are each independently 0, 1, or 2;

p is 0, 1, 2, or 3;

q is 0, 1, or 2; and t is 1, 2, or 3.

In some embodiments of Formula (II), (IIa), or (IIb), $R^{2a}$ is H, —S(═O)$_2R^a$, —C(═O)$R^a$, —C(═O)$OR^a$, —C(═O)$NR^aR^b$, optionally substituted $C_1$-$C_6$ alkyl, optionally substituted $C_1$-$C_6$ haloalkyl, optionally substituted $C_3$-$C_6$ cycloalkyl, or phenyl. In some embodiments of Formula (II) (IIa) or (IIb), $R^{2a}$ is —C(═O)$R^a$, —C(═O)$OR^a$, optionally substituted $C_1$-$C_6$ alkyl, optionally substituted $C_1$-$C_6$ haloalkyl, or optionally substituted $C_3$-$C_6$ cycloalkyl. In some embodiments of Formula (II), (IIa) or (IIb), $R^{2a}$ is —C(═O)$R^a$ or —C(═O)$OR^a$. In some embodiments of Formula (II), (IIa), or (IIb), $R^{2a}$ is optionally substituted $C_1$-$C_6$ alkyl or optionally substituted $C_1$-$C_6$ haloalkyl. In some embodiments of Formula (II), (IIa), or (IIb), $R^{2a}$ is —$CF_3$, —$CHF_2$, —$CH_2CF_3$, —$CH_2CHF_2$, —$CH_2CClCF_2$, —$CH_3$, or —$CH_2CH_3$. In some embodiments of Formula (II), (IIa), or (IIb), $R^{2a}$ is —$CH_2CF_3$, —$CH_2CHF_2$, or —$CH_2CClCF_2$. In some embodiments of Formula (II), (IIa), or (IIb), $R^{2a}$ is optionally substituted $C_3$-$C_6$ cycloalkyl. In some embodiments of Formula (II), (IIa), or (IIb), $R^{2a}$ is cyclopropyl, cyclobutyl, or cyclopropyl.

In some embodiments of Formula (II), (IIa), or (IIb), $R^{2a}$ is —$CF_3$, —$CHF_2$, —$CH_2CF_3$, —$CH_2CHF_2$, —$CH_2CClCF_2$, —$CH_2CF$(cyclopropyl), —$CH_2$phenyl, —$CH_2CH_2CF_3$, —$CH_2CF_2CH_3$, —$CH_2CF_2CHF_2$, —$CH_2CF_2$-(phenyl), —$CH_2CF_2CH_2CH_3$, —C(═O)$OCH_3$, —C(═O)$OC(CH_3)_3$, —C(═O)$C(CH_3)_3$, —C(═O)$CH_3$, —C(═O)phenyl, or cyclopropyl.

In some embodiments of Formula (II), (IIa), or (IIb), $R^{2a}$ is

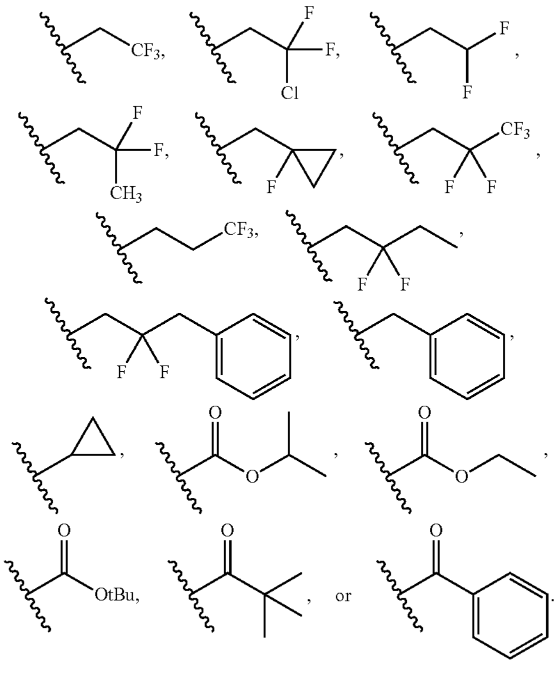

In some embodiments of Formula (II), (IIa), or (IIb), $R^{2a}$ is

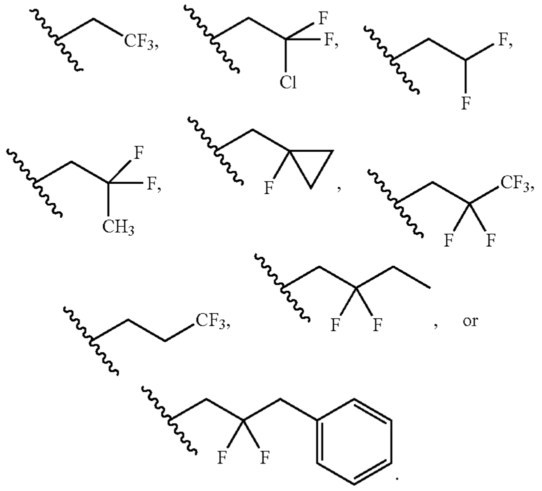

In some embodiments of Formula (II), (IIa), or (IIb), $R^{2a}$ is

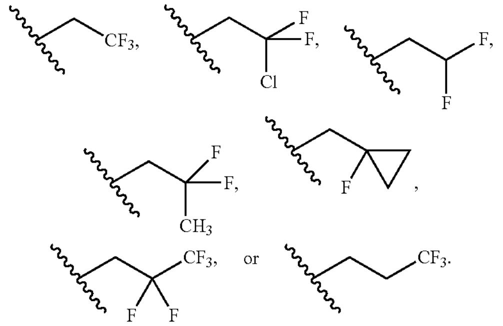

In some embodiments of Formula (II), (IIa), or (IIb), $R^{2a}$ is

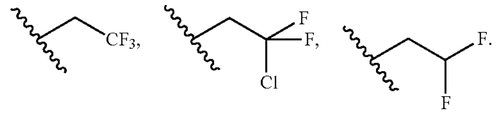 [SMILES: *CC(F)(F)F ; *CC(F)(F)Cl ; *CC(F)F]

In some embodiments of Formula (II), (IIa), or (IIb), $R^{2a}$ is

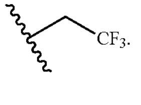 [SMILES: *CC(F)(F)F]

In some embodiments of Formula (II), (IIa), or (IIb), $R^{2a}$ is

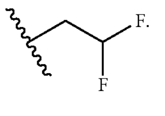 [SMILES: *CC(F)F]

In some embodiments of Formula (I) or (Ia), ring A is phenyl or a 5 to 10-membered heteroaryl. In some embodiments of Formula (I) or (Ia), ring A is a 5 to 8-membered heteroaryl comprising 1, 2, 3, or 4 heteroatoms selected from N, O, and S. In some embodiments of Formula (I) or (Ia), ring A is a 5-membered heteroaryl comprising 1, 2, or 3 heteroatoms selected from N or O. In some embodiments of Formula (I) or (Ia), ring A is a 6-membered heteroaryl comprising 1, 2, or 3 heteroatoms selected from N or O. In some embodiments of Formula (I) or (Ia), ring A is phenyl, pyridinyl, pyrimidinyl, pyridin-2-one, furanyl, isoxazolyl, or pyrrolyl. In some embodiments of Formula (I) or (Ia), ring A is phenyl or pyridinyl. In some embodiments of Formula (I) or (Ia), ring A is phenyl. In some embodiments of Formula (I) or (Ia), ring A is pyridinyl.

In another aspect, provided herein is a compound having the structure of Formula (III), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof:

Formula (III)

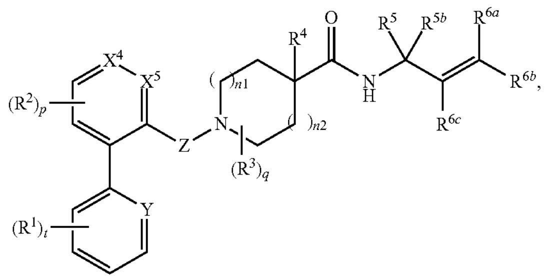

wherein,

Y is N, CH, or $CR^1$;

Z is C(=O) or $S(=O)_2$;

$X^4$ is CH, $CR^2$, or N;

$X^5$ is CH, $CR^2$, or N;

each $R^1$ is independently halogen, —CN, —OH, —$OR^a$, optionally substituted $C_1$-$C_6$ alkyl, optionally substituted $C_1$-$C_6$ deuteroalkyl, optionally substituted $C_2$-$C_6$ alkynyl, optionally substituted $C_1$-$C_6$ haloalkyl, or optionally substituted $C_1$-$C_6$ hydroxyalkyl, or optionally substituted $C_3$-$C_6$ cycloalkyl;

each $R^2$ is independently halogen, —CN, —OH, —$OR^a$, —$N(R^b)_2$, optionally substituted $C_1$-$C_6$ alkyl, optionally substituted $C_1$-$C_6$ deuteroalkyl, optionally substituted $C_2$-$C_6$ alkenyl, optionally substituted $C_2$-$C_6$ alkynyl, optionally substituted $C_1$-$C_6$ haloalkyl, optionally substituted $C_1$-$C_6$ hydroxyalkyl, optionally substituted $C_3$-$C_6$ cycloalkyl, optionally substituted arylalkyl, or optionally substituted 4 to 6-membered heterocycloalkyl;

or two $R^2$ together with the atom(s) to which they are attached combine to form a $C_3$-$C_5$ cycloalkyl, 4 to 5-membered heterocycloalkyl, or a 5-membered heteroaryl ring;

each $R^3$ is independently halogen, —CN, —OH, —$OR^a$, $C_1$-$C_6$ alkyl, $C_1$-$C_6$ deuteroalkyl, or $C_1$-$C_6$ haloalkyl;

$R^4$ is H, halogen, —OH, —$OR^a$, or $C_1$-$C_6$ alkyl;

$R^5$ is H, $C_1$-$C_3$ alkyl, $C_1$-$C_3$ haloalkyl, or $C_1$-$C_3$ hydroxyalkyl;

$R^{5b}$ is H or $C_1$-$C_3$ alkyl;

$R^{6a}$ and $R^{6b}$ are each independently H, —CN, —C(=O)$OR^7$, —C(=O)$N(R^7)_2$, —S(=O)$R_7$, —$S(=O)_2R^7$, or —S(=O)(=NH)$R^7$; wherein each $R^7$ is independently optionally substituted $C_1$-$C_6$ alkyl, optionally substituted $C_3$-$C_6$ cycloalkyl, or optionally substituted 4 to 6-membered heterocycloalkyl ring;

or two $R^7$ together with the nitrogen atom to which they are attached combine to form an optionally substituted 4 to 5-membered heterocycloalkyl ring;

or $R^1$ and $R^7$ together with the atoms to which they are attached combine to form a 5-membered heterocycloalkyl ring;

$R^{6c}$ is H or —CN;

or $R^{6c}$ and $R^7$ together with the atoms to which they are attached combine to form a 4-membered heterocycloalkyl ring;

each $R^a$ is independently H, $C_1$-$C_6$ alkyl, $C_1$-$C_6$ deuteroalkyl, $C_1$-$C_6$ haloalkyl, $C_1$-$C_6$ heteroalkyl, $C_2$-$C_6$ alkenyl, $C_2$-$C_6$ alkynyl, $C_3$-$C_6$ cycloalkyl, 3- to 6-membered heterocycloalkyl, $C_5$-$C_8$ aryl, $C_5$-$C_8$ heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl(heterocycloalkyl); wherein each alkyl, deuteroalkyl, haloalkyl, heteroalkyl, cycloalkyl, heterocycloalkyl, aryl, heteroaryl, alkyl (aryl), alkyl(heteroaryl), alkyl(cycloalkyl) and alkyl (heterocycloalkyl) is independently optionally substituted with one, two, or three halogen, —OH, $C_1$-$C_6$ alkyl, $C_1$-$C_6$ haloalkyl, or $C_1$-$C_6$ alkoxy;

each $R^b$ is independently H, $C_1$-$C_6$ alkyl, $C_1$-$C_6$ haloalkyl, $C_1$-$C_6$ heteroalkyl, cycloalkyl, heterocycloalkyl, aryl, or heteroaryl; wherein the alkyl, heteroalkyl, cycloalkyl, heterocycloalkyl, aryl, and heteroaryl is independently optionally substituted with one, two, or three halogen, —OH, $C_1$-$C_6$ alkyl, or $C_1$-$C_6$ haloalkyl;

or two $R^b$ groups on a nitrogen atom are taken together with the nitrogen atom to which they are attached to form a heterocycloalkyl which is optionally substituted with one, two, or three $C_1$-$C_6$ alkyl, or $C_1$-$C_6$ haloalkyl;

n1 and n2 are each independently 0, 1, or 2;

p is 0, 1, 2, or 3;

q is 0, 1, or 2; and t is 0, 1, 2, or 3.

In another aspect, provided herein is a compound having the structure of Formula (III), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof:

Formula (III)

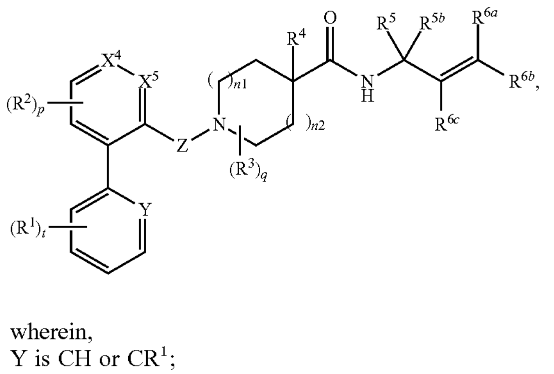

wherein,

Y is CH or $CR^1$;

Z is C(═O) or $S(═O)_2$;

$X^4$ is CH, $CR^2$, or N;

$X^5$ is CH, $CR^2$, or N;

each $R^1$ is independently halogen, —CN, —OH, —$OR^a$, optionally substituted $C_1$-$C_6$ alkyl, optionally substituted $C_1$-$C_6$ deuteroalkyl, optionally substituted $C_2$-$C_6$ alkynyl, optionally substituted $C_1$-$C_6$ haloalkyl, or $C_1$-$C_6$ hydroxyalkyl;

each $R^2$ is independently halogen, —CN, —OH, —$OR^a$, —$N(R^b)_2$, optionally substituted $C_1$-$C_6$ alkyl, optionally substituted $C_1$-$C_6$ deuteroalkyl, optionally substituted $C_2$-$C_6$ alkenyl, optionally substituted $C_2$-$C_6$ alkynyl, optionally substituted $C_1$-$C_6$ haloalkyl, optionally substituted $C_1$-$C_6$ hydroxyalkyl, optionally substituted $C_3$-$C_6$ cycloalkyl, or optionally substituted 4 to 6-membered heterocycloalkyl;

or two $R^2$ together with the atom(s) to which they are attached combine to form a $C_3$-$C_5$ cycloalkyl, 4 to 5-membered heterocycloalkyl, or a 5-membered heteroaryl ring;

each $R^3$ is independently $C_1$-$C_3$ alkyl or $C_1$-$C_3$ deuteroalkyl;

$R^4$ is halogen;

$R^5$ is H, $C_1$-$C_3$ alkyl, $C_1$-$C_3$ haloalkyl, or $C_1$-$C_3$ hydroxyalkyl;

$R^{5b}$ is H or $C_1$-$C_3$ alkyl;

$R^{6a}$ and $R^{6b}$ are each independently H, —CN, —C(═O)$OR^7$, —C(═O)$N(R^7)_2$, or —$S(═O)_2R^7$; wherein each $R^7$ is independently optionally substituted $C_1$-$C_3$ alkyl or optionally substituted 4 to 6-membered heterocycloalkyl ring;

or two $R^7$ together with the nitrogen atom to which they are attached combine to form an optionally substituted 4 to 5-membered heterocycloalkyl ring;

or $R^5$ and $R^7$ together with the atoms to which they are attached combine to form a 5-membered heterocycloalkyl ring;

$R^{6c}$ is H or —CN;

or $R^{6c}$ and $R^7$ together with the atoms to which they are attached combine to form a 4-membered heterocycloalkyl ring;

each $R^a$ is independently H, $C_1$-$C_6$ alkyl, $C_1$-$C_6$ haloalkyl, $C_1$-$C_6$ heteroalkyl, cycloalkyl, heterocycloalkyl, aryl, heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl (heterocycloalkyl); wherein each alkyl, heteroalkyl, cycloalkyl, heterocycloalkyl, aryl, and heteroaryl is independently optionally substituted with one, two, or three halogen, —OH, $C_1$-$C_6$ alkyl, or $C_1$-$C_6$ haloalkyl;

each $R^b$ is independently H, $C_1$-$C_6$ alkyl, $C_1$-$C_6$ haloalkyl, $C_1$-$C_6$ heteroalkyl, cycloalkyl, heterocycloalkyl, aryl, or heteroaryl; wherein the alkyl, heteroalkyl, cycloalkyl, heterocycloalkyl, aryl, and heteroaryl is independently optionally substituted with one, two, or three halogen, —OH, $C_1$-$C_6$ alkyl, or $C_1$-$C_6$ haloalkyl;

or two $R^b$ groups on a nitrogen atom are taken together with the nitrogen atom to which they are attached to form a heterocycloalkyl which is optionally substituted with one, two, or three $C_1$-$C_6$ alkyl, or $C_1$-$C_6$ haloalkyl;

n1 and n2 are each independently 0, 1, or 2;

p is 0, 1, 2, or 3;

q is 0, 1, or 2; and t is 0, 1, 2, or 3.

In some embodiments of Formula (III), Z is —$S(═O)_2$—.

In another aspect, provided herein is a compound having the structure of Formula (III), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof:

Formula (III)

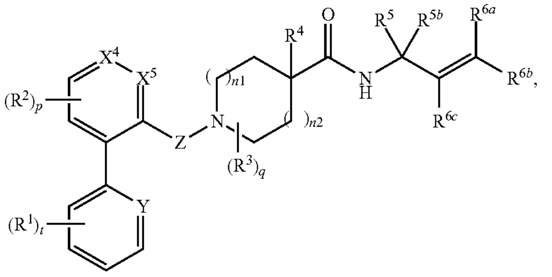

wherein,

Z is $S(=O)_2$;

$X^4$ is CH, $CR^2$, or N;

$X^5$ is CH or $CR^2$;

Y is CH or $CR^1$;

each $R^1$ is independently halogen, $-OR_a$, $C_1$-$C_6$ alkyl, $C_1$-$C_6$ deuteroalkyl, $C_2$-$C_6$ alkynyl, $C_1$-$C_6$ haloalkyl, or $C_1$-$C_6$ hydroxyalkyl;

each $R^2$ is independently halogen, —OH, $-OR_a$, $-N(R_b)_2$, $C_1$-$C_6$ alkyl, $C_1$-$C_6$ deuteroalkyl, $C_2$-$C_6$ alkenyl, $C_2$-$C_6$ alkynyl, $C_1$-$C_6$ haloalkyl, $C_3$-$C_6$ cycloalkyl, or 4 to 6-membered heterocycloalkyl;

or two $R^2$ together with the atom(s) to which they are attached combine to form a 5-membered heteroaryl ring;

each $R^3$ is independently $-CH_3$ or $-CD_3$;

$R^4$ is F;

$R^5$ is H, $-CH_3$, or $-CH_2CH_3$;

$R^{6a}$ and $R^{6b}$ are each independently H, —CN, $-C(=O)OR^7$, $-C(=O)N(R^7)_2$, or $-S(=O)_2R^7$; wherein each $R^7$ is independently optionally substituted $C_1$-$C_3$ alkyl or optionally substituted 4 to 6-membered heterocycloalkyl ring;

or two $R^7$ together with the nitrogen atom to which they are attached combine to form an optionally substituted 4 to 5-membered heterocycloalkyl ring;

or $R^5$ and $R^7$ together with the atoms to which they are attached combine to form a 5-membered heterocycloalkyl ring;

$R^{6c}$ is H;

or $R^{6c}$ and $R^7$ together with the atoms to which they are attached combine to form a 4-membered heterocycloalkyl ring; R5a is H; or R5a and R6c together with the nitrogen atom to which they are attached combine to form a 4-membered heterocycloalkyl ring;

each $R_a$ is independently H, $C_1$-$C_6$ alkyl, $C_1$-$C_6$ haloalkyl, cycloalkyl, heterocycloalkyl, or aryl; wherein each alkyl, cycloalkyl, heterocycloalkyl, or aryl, is independently optionally substituted with one, two, or three halogen, —OH, $C_1$-$C_6$ alkyl, or $C_1$-$C_6$ haloalkyl;

each $R_b$ is independently H or $C_1$-$C_6$ alkyl;

$n_1$ and $n_2$ are each independently 1 or 2;

p is 1;

q is 0, 1, or 2; and t is 1, 2, or 3.

In some embodiments, the compound of Formula (III) has the structure of Formula (IIIa), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof:

Formula (IIIa)

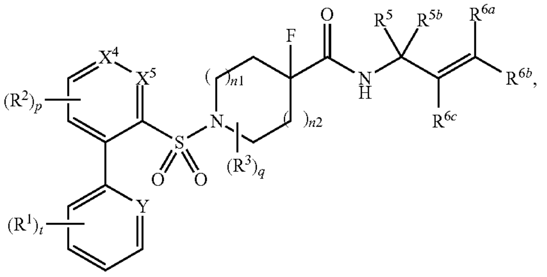

wherein,

Y is CH or $CR^1$;

$X^4$ is CH, $CR^2$, or N;

$X^5$ is CH, $CR^2$, or N;

each $R^1$ is independently halogen, —CN, —OH, $-OR^a$, optionally substituted $C_1$-$C_6$ alkyl, optionally substituted $C_1$-$C_6$ deuteroalkyl, optionally substituted $C_2$-$C_6$ alkynyl, optionally substituted $C_1$-$C_6$ haloalkyl, $C_1$-$C_6$ hydroxyalkyl, or optionally substituted $C_3$-$C_6$ cycloalkyl;

each $R^2$ is independently halogen, —CN, —OH, $-OR^a$, $-N(R^b)_2$, optionally substituted $C_1$-$C_6$ alkyl, optionally substituted $C_1$-$C_6$ deuteroalkyl, optionally substituted $C_2$-$C_6$ alkenyl, optionally substituted $C_2$-$C_6$ alkynyl, optionally substituted $C_1$-$C_6$ haloalkyl, optionally substituted $C_1$-$C_6$ hydroxyalkyl, optionally substituted $C_3$-$C_6$ cycloalkyl, optionally substituted arylalkyl, or optionally substituted 4 to 6-membered heterocycloalkyl;

each $R^3$ is independently $C_1$-$C_3$ alkyl or $C_1$-$C_3$ deuteroalkyl;

$R^5$ is H, $C_1$-$C_3$ alkyl, $C_1$-$C_3$ haloalkyl, or $C_1$-$C_3$ hydroxyalkyl;

$R^{5b}$ is H or $C_1$-$C_3$ alkyl;

$R^{6a}$ and $R^{6b}$ are each independently H, —CN, $-C(=O)N(R^7)_2$, $-S(=O)_2R^7$, or $-S(=O)(=NH)R^7$; wherein each $R^7$ is independently $C_1$-$C_3$ alkyl, or a 4-membered heterocycloalkyl ring optionally substituted with up to two fluorine atoms;

or two $R^7$ together with the nitrogen atom to which they are attached combine to form a 4-membered heterocycloalkyl ring optionally substituted with up to two fluorine atoms;

or $R^5$ and $R^7$ together with the atoms to which they are attached combine to form a 5-membered heterocycloalkyl ring;

$R^{6c}$ is H or —CN;

or $R^{6c}$ and $R^7$ together with the atoms to which they are attached combine to form a 4-membered heterocycloalkyl ring;

each $R^a$ is independently H, $C_1$-$C_6$ alkyl, $C_1$-$C_6$ deuteroalkyl, $C_1$-$C_6$ haloalkyl, $C_1$-$C_6$ heteroalkyl, $C_2$-$C_6$ alkenyl, $C_2$-$C_6$ alkynyl, $C_3$-$C_6$ cycloalkyl, 3- to 6-membered heterocycloalkyl, $C_5$-$C_8$ aryl, $C_5$-$C_8$ heteroaryl, $-C_1$-$C_6$ alkyl(aryl), $-C_1$-$C_6$ alkyl(heteroaryl), $-C_1$-$C_6$ alkyl(cycloalkyl), or $-C_1$-$C_6$ alkyl(heterocycloalkyl); wherein each alkyl, deuteroalkyl, haloalkyl, heteroalkyl, cycloalkyl, heterocycloalkyl, aryl, heteroaryl, alkyl (aryl), alkyl(heteroaryl), alkyl(cycloalkyl) and alkyl (heterocycloalkyl) is independently optionally substituted with one, two, or three halogen, —OH, $C_1$-$C_6$ alkyl, $C_1$-$C_6$ haloalkyl, or $C_1$-$C_6$ alkoxy;

each $R^b$ is independently H, $C_1$-$C_6$ alkyl, $C_1$-$C_6$ haloalkyl, $C_1$-$C_6$ heteroalkyl, cycloalkyl, heterocycloalkyl, aryl, or heteroaryl; wherein the alkyl, heteroalkyl, cycloalkyl, heterocycloalkyl, aryl, and heteroaryl is independently optionally substituted with one, two, or three halogen, —OH, $C_1$-$C_6$ alkyl, or $C_1$-$C_6$ haloalkyl;

or two $R^b$ groups on a nitrogen atom are taken together with the nitrogen atom to which they are attached to form a heterocycloalkyl which is optionally substituted with one, two, or three $C_1$-$C_6$ alkyl, or $C_1$-$C_6$ haloalkyl;

n1 and n2 are each independently 0, 1, or 2;

p is 0, 1, 2, or 3;

q is 0, 1, or 2; and t is 0, 1, 2, or 3.

In some embodiments, the compound of Formula (III) has the structure of Formula (IIIb), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof:

Formula (IIIb)

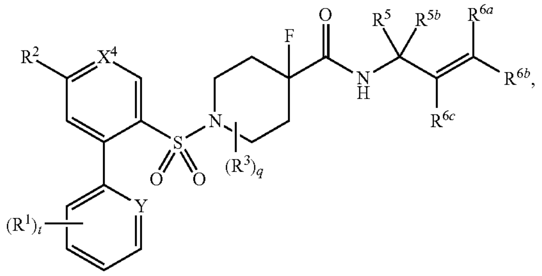

wherein, $X^4$ is CH or N;

Y is $CR^1$ or CH;

each $R^1$ is independently halogen, —CN, —$OR^a$, optionally substituted $C_1$-$C_4$ alkyl, optionally substituted $C_1$-$C_4$ deuteroalkyl, $C_2$-$C_4$ alkynyl, or $C_1$-$C_3$ fluoroalkyl;

$R^2$ is halogen, —CN, —OH, —$OR^a$, —$N(R^b)_2$, —C(=O)$R^a$, optionally substituted $C_1$-$C_4$ alkyl, optionally substituted $C_1$-$C_4$ deuteroalkyl, $C_2$-$C_4$ alkenyl, $C_2$-$C_4$ alkynyl, $C_1$-$C_3$ fluoroalkyl, optionally substituted $C_1$-$C_3$ hydroxyalkyl, optionally substituted $C_3$-$C_6$ cycloalkyl, or optionally substituted 4 to 6-membered heterocycloalkyl;

Each $R^3$ is independently —$CH_3$ or -$CD_3$;

$R^5$ is H, —$CH_3$, or —$CH_2CH_3$;

$R^{5b}$ is H or $C_1$-$C_3$ alkyl;

$R^{6a}$ and $R^{6b}$ are each independently H, —CN, —C(=O)$N(R^7)_2$, —S(=O)$_2R^7$, or —S(=O)(=NH)$R^7$; wherein each $R^7$ is independently $C_1$-$C_3$ alkyl, or a 4-membered heterocycloalkyl ring optionally substituted with up to two fluorine atoms;

or two $R^7$ together with the nitrogen atom to which they are attached combine to form a 4-membered heterocycloalkyl ring optionally substituted with up to two fluorine atoms;

or $R^5$ and $R^7$ together with the atoms to which they are attached combine to form a 5-membered heterocycloalkyl ring;

$R^{6c}$ is H or —CN;

each $R^a$ is independently $C_1$-$C_6$ alkyl, $C_3$-$C_6$ cycloalkyl, or $C_1$-$C_3$_fluoroalkyl;

each $R^b$ is independently H or $C_1$-$C_3$ alkyl;

q is 0, 1, or 2; and t is 0, 1, or 2.

In some embodiments of Formula (III) or (IIIa), $X^4$ is CH or $CR^2$ and $X^5$ is CH or $CR^2$. In some embodiments of Formula (III) or (IIIa), $X^4$ is N and $X^5$ is N.

In some embodiments of Formula (III) or (IIIa), $X^4$ is CH or $CR^2$. In some embodiments of Formula (III), (IIIa), or (IIIb), $X^4$ is CH. In some embodiments of Formula (III), (IIIa), or (IIIb), $X^4$ is N.

In some embodiments of Formula (III) or (IIIa), $X^5$ is CH or $CR^2$. In some embodiments of Formula (III) or (IIIa), $X^5$ is CH. In some embodiments of Formula (III) or (IIIa), $X^5$ is N.

In some embodiments of Formula (I), $R^A$ is

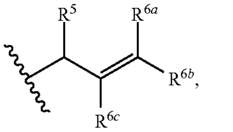

wherein $R^5$ is H, $C_1$-$C_3$ alkyl, $C_1$-$C_3$ haloalkyl, or $C_1$-$C_3$ hydroxyalkyl;

$R^{6a}$ and $R^{6b}$ are each independently H, —CN, —C(=O)$OR^7$, —C(=O)$N(R^7)_2$, —S(=O)$R_7$, —S(=O)$_2R^7$ or —S(=O)(=NH)$R^7$; wherein each $R^7$ is independently optionally substituted $C_1$-$C_6$ alkyl, optionally substituted $C_3$-$C_6$ cycloalkyl, or optionally substituted 4 to 6-membered heterocycloalkyl ring;

or two $R^7$ together with the nitrogen atom to which they are attached combine to form an optionally substituted 4 to 5-membered heterocycloalkyl ring;

or $R^5$ and $R^7$ together with the atoms to which they are attached combine to form a 5-membered heterocycloalkyl ring;

$R^{6c}$ is H or —CN;

or $R^{6c}$ and $R^7$ together with the atoms to which they are attached combine to form a 4-membered heterocycloalkyl ring.

In some embodiments of Formula (I), $R^A$ is

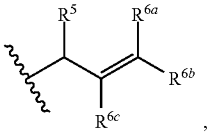

wherein $R^5$ is H, $C_1$-$C_3$ alkyl, $C_1$-$C_3$ haloalkyl, or $C_1$-$C_3$ hydroxyalkyl;

$R^{6a}$ and $R^{6b}$ are each independently H, —CN, —C(=O)$OR^7$, —C(=O)$N(R^7)_2$ or —S(=O)$_2R^7$; wherein each $R^7$ is independently optionally substituted $C_1$-$C_3$ alkyl, or optionally substituted 4 to 6-membered heterocycloalkyl ring;

or two $R^7$ together with the nitrogen atom to which they are attached combine to form an optionally substituted 4 to 5-membered heterocycloalkyl ring;

or $R^5$ and $R^7$ together with the atoms to which they are attached combine to form a 5-membered heterocycloalkyl ring;

$R^{6c}$ is H;

or $R^{6c}$ and $R^7$ together with the atoms to which they are attached combine to form a 4-membered heterocycloalkyl ring.

In some embodiments of Formula (I), $R^A$ is

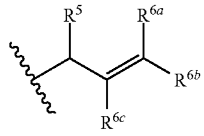
, wherein $R^5$ is $C_1$-$C_3$ alkyl;

$R^{6a}$ and $R^{6b}$ are each independently H, $—C(═O)N(R^7)_2$ or $—S(═O)_2R^7$; wherein each $R^7$ is independently optionally substituted $C_1$-$C_3$ alkyl, or optionally substituted 4 to 6-membered heterocycloalkyl ring;

or two $R^7$ together with the nitrogen atom to which they are attached combine to form an optionally substituted 4 to 5-membered heterocycloalkyl ring;

or $R^5$ and $R^7$ together with the atoms to which they are attached combine to form a 5-membered heterocycloalkyl ring;

$R^{6c}$ is H;

or $R^{6c}$ and $R^7$ together with the atoms to which they are attached combine to form a 4-membered heterocycloalkyl ring.

In some embodiments of Formula (I), (II), (IIa), (IIb), (III), (IIIa), or (IIIb), $R^5$ is $C_1$-$C_3$ alkyl, $C_1$-$C_3$ haloalkyl, or $C_1$-$C_3$ hydroxyalkyl. In some embodiments of Formula (I), (II), (IIa), (IIb), (III), (IIIa), or (IIIb), $R^5$ is $C_1$-$C_3$ haloalkyl. In some embodiments of Formula (I), (II), (IIa), (IIb), (III), (IIIa), or (IIIb), $R^5$ is $—CF^3$ or $—CH_2CF_3$. In some embodiments of Formula (I), (II), (IIa), (IIb), (III), (IIIa), or (IIIb), $R^5$ is $C_1$-$C_3$ alkyl. In some embodiments of Formula (I), (II), (IIa), (IIb), (III), (IIIa), or (IIIb), $R^5$ is $—CH_3$ or $—CH_2CH_3$. In some embodiments of Formula (I), (II), (IIa), (IIb), (III), (IIIa), or (IIIb), $R^5$ is $—CH_2CH_3$. In some embodiments of Formula (I), (II), (IIa), (IIb), (III), (IIIa), or (IIIb), $R^5$ is $C_1$-$C_3$ hydroxyalkyl. In some embodiments of Formula (I), (II), (IIa), (IIb), (III), (IIIa), or (IIIb), $R^5$ is $—CH_2OCH_3$ or $—CH_2OCH_2CH_3$. In some embodiments of Formula (I), (II), (IIa), (IIb), (III), (IIIa), or (IIIb), $R^5$ is H, $—CH_3$, $—CH_2CH_3$, $—CH_2OCF_3$, or $—CH_2OCH_3$. In some embodiments of Formula (I), (II), (IIa), (IIb), (III), (IIIa), or (IIIb), $R^5$ is H.

In some embodiments of Formula (I) or (Ia), $R^{5a}$ is H.

In some embodiments of Formula (I) or (Ia), $R^{5a}$ and $R^{6c}$ together with the nitrogen atom to which they are attached combine to form a 4-membered heterocycloalkyl ring.

In some embodiments of Formula (I), (Ia), (II), (IIa), (IIb), (III), (IIIa), or (IIIb), $R^{6a}$ is —CN, $—C(═O)OR^7$, $—C(═O)N(R^7)_2$ or $—S(═O)_2R^7$; and $R^{6b}$ and $R^{6c}$ are each H. In some embodiments of Formula (I), (Ia), (II), (IIa), (IIb), (III), (IIIa), or (IIIb), $R^{6a}$ is $—C(═O)N(R^7)_2$ or $—S(═O)_2R^7$; and $R^{6b}$ and $R^{6c}$ are each H. In some embodiments of Formula (I), (Ia), (II), (IIa), (IIb), (III), (IIIa), or (IIIb), $R^{6a}$ is $S(═O_2)R^7$; and $R^{6b}$ and $R^{6c}$ are each H.

In some embodiments of Formula (I), (Ia), (II), (IIa), (IIb), (III), (IIIa), or (IIIb), $R^{6b}$ is —CN, $—C(═O)OR^7$, $—C(═O)N(R^7)_2$ or $—S(═O)_2R^7$; and $R^{6a}$ and $R^{6c}$ are each H. In some embodiments of Formula (I), (Ia), (II), (IIa), (IIb), (III), (IIIa), or (IIIb), $R^{6b}$ is $—C(═O)N(R^7)_2$ or $—S(═O)_2R^7$; and $R^{6a}$ and $R^{6c}$ are each H. In some embodiments of Formula (I), (Ia), (II), (IIa), (IIb), (III), (IIIa), or (IIIb), $R^{6b}$ is $S(═O_2)R^7$; and $R^{6a}$ and $R^{6c}$ are each H.

In some embodiments of Formula (I), (II), (IIa), (IIb), (III), (IIIa), or (IIIb), $R^5$ and $R^7$ together with the atoms to which they are attached combine to form a 5-membered heterocycloalkyl ring.

In some embodiments of Formula (I), (Ia), (II), (IIa), (IIb), (III), (IIIa), or (IIIb), $R^{6c}$ and $R^7$ together with the atoms to which they are attached combine to form a 4-membered heterocycloalkyl ring.

In some embodiments of Formula (I), (Ia), (II), (IIa), (IIb), (III), (IIIa), or (IIIb), each $R^7$ is independently optionally substituted $C_1$-$C_3$ alkyl or optionally substituted 4 to 6-membered heterocycloalkyl ring. In some embodiments of Formula (I), (Ia), (II), (IIa), (IIb), (III), (IIIa), or (IIIb), each $R^7$ is independently $C_1$-$C_3$ alkyl. In some embodiments of Formula (I), (Ia), (II), (IIa), (IIb), (III), (IIIa), or (IIIb), each $R^7$ is independently a 4 to 6-membered heterocycloalkyl ring.

In some embodiments of Formula (I), $R^A$ is:

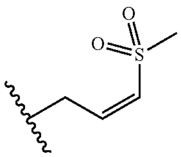
,
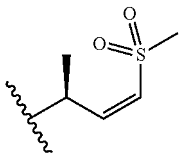
,
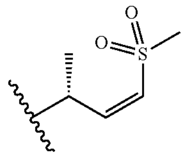
,
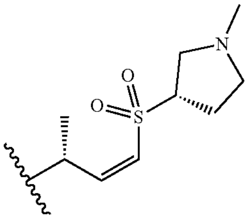
,
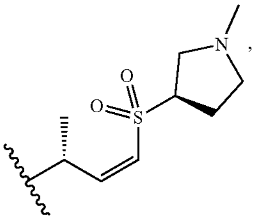
,
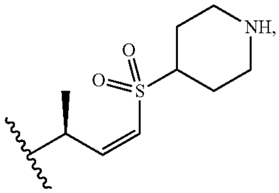
,
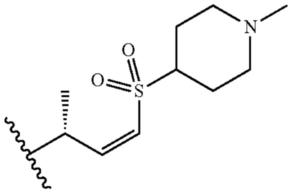
,
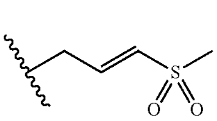
,
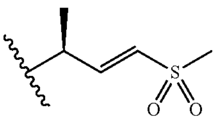
,
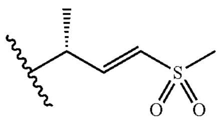
,
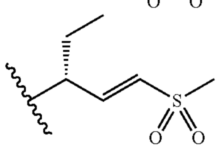
, -continued
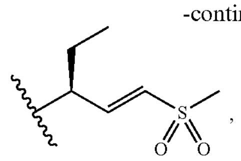
,
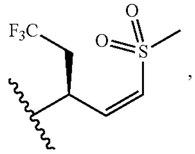
,
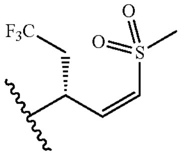
,
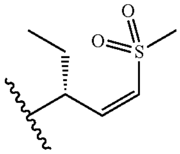
,
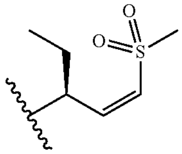
,
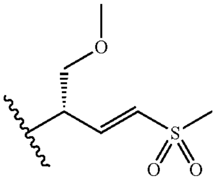
,
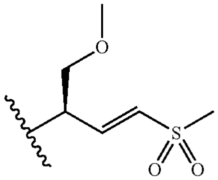
,
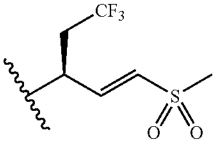
,
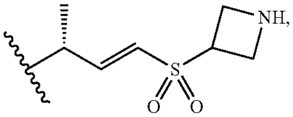
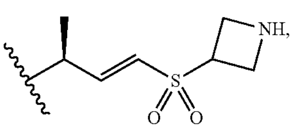
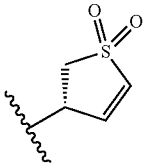
,
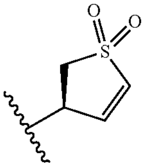
,
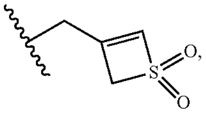
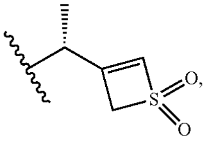
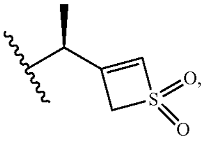
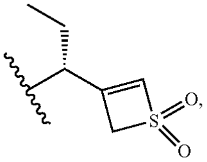
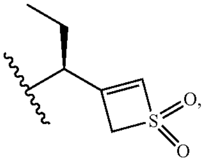
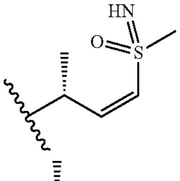
,
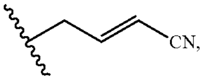
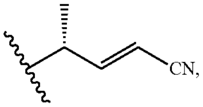
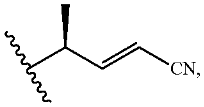
-continued
,
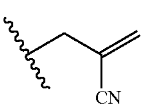
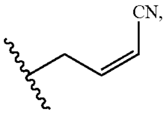
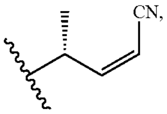
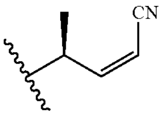
,
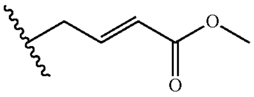
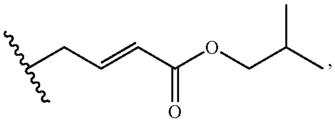
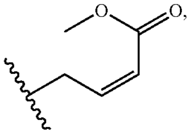
or
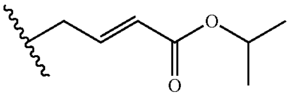
.
In some embodiments of Formula (I), $R^A$ is:
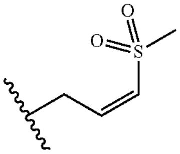
,
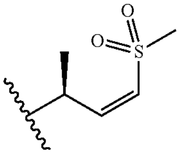
,
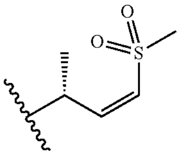
,
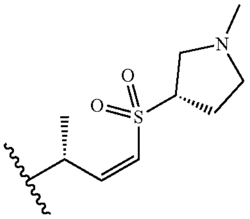
,
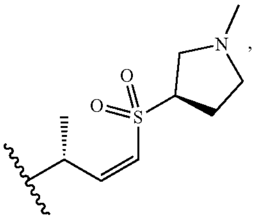
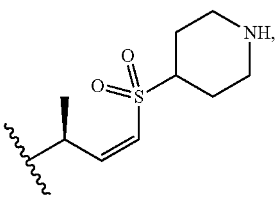
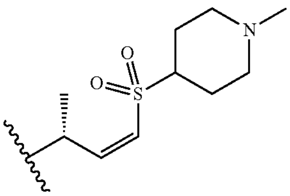
,
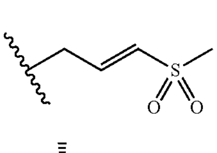
,
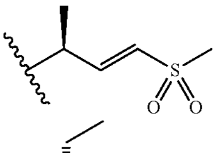
,
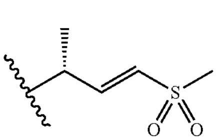
,
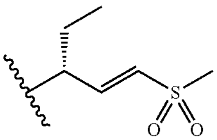
, -continued
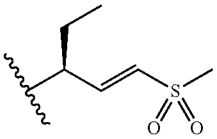
,
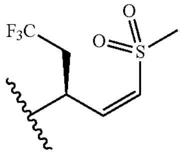
,
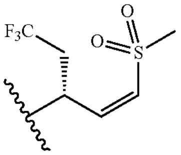
,
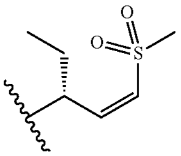
,
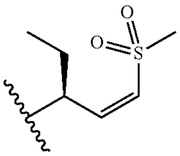
,
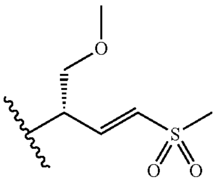
,
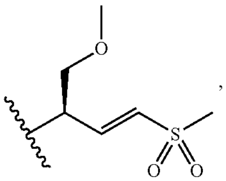
,
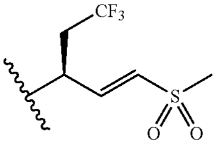
,
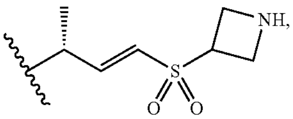
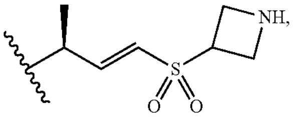
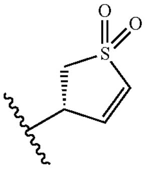
,
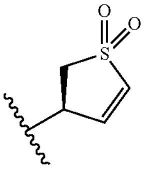
,
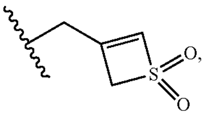
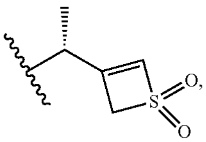
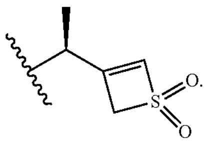
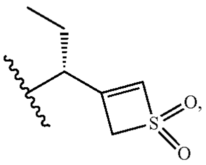
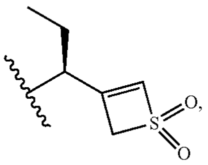
or
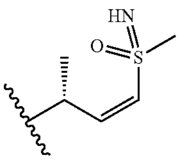
.
In some embodiments of Formula (I), $R^A$ is:
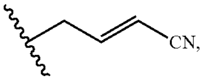
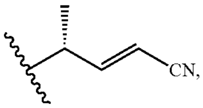
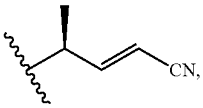
,
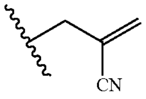
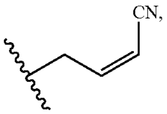
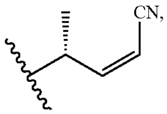
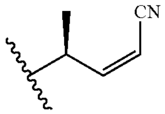
,
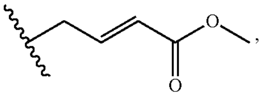
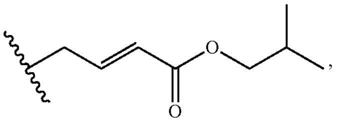
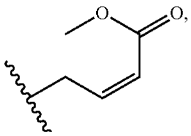
or
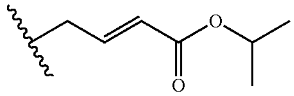
.
In some embodiments of Formula (I), $R^A$ is
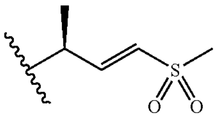
,
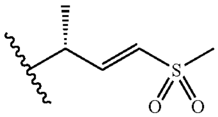
,
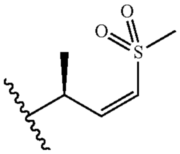
or
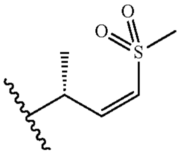
.
In some embodiments, of Formula (I), $R^A$ is
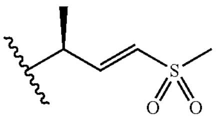
or
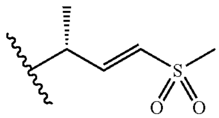
.
In some embodiments of Formula (I), $R^A$ is
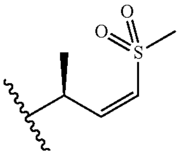
or
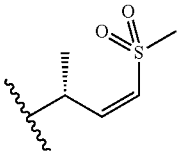
.

In some embodiments of Formula (I), $R^A$ is

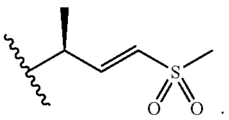 [SMILES: *[C@@H](C)/C=C/S(C)(=O)=O ; "."]

.

In some embodiments of Formula (I), $R^A$ is

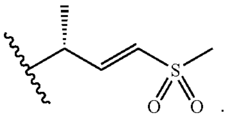 [SMILES: *[C@H](C)/C=C/S(C)(=O)=O ; "."]

.

In some embodiments of Formula (I), $R^A$ is

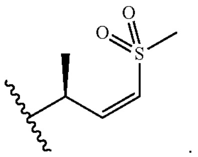 [SMILES: *[C@@H](C)/C=C\S(C)(=O)=O ; "."]

.

In some embodiments of Formula (I), $R^A$ is

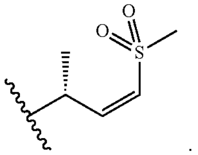 [SMILES: *[C@H](C)/C=C\S(C)(=O)=O ; "."]

.

In some embodiments of Formula (I), (Ia), (II), (IIa), (IIb), (III), (IIIa), or (IIIb), $R^{6a}$ is —C(═O)N($R^7$)$_2$, and $R^{6b}$ and $R^{6c}$ are each H; or $R^{6b}$ is —C(═O)N($R^7$)$_2$, and $R^{6a}$ and $R^{6c}$ are each H, wherein two $R^7$ together with the nitrogen atom to which they are attached combine to form an optionally substituted 4 to 5-membered ring. In some embodiments of Formula (I), (Ia), (II), (IIa), (IIb), (III), (IIIa), or (IIIb), $R^{6a}$ is —C(═O)N($R^7$)$_2$ and $R^{6b}$ and $R^{6c}$ are each H. In some embodiments, $R^{6b}$ is —C(═O)N($R^7$)$_2$ and $R^{6a}$ and $R^{6c}$ are each H.

In some embodiments of Formula (I), $R^A$ is:

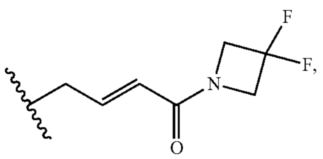

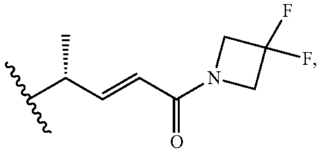

-continued

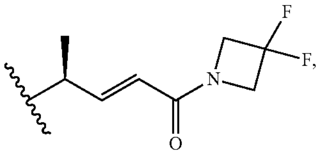

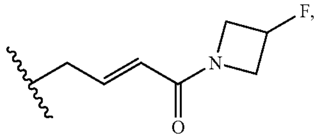

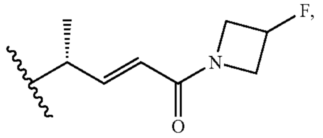

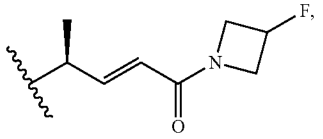

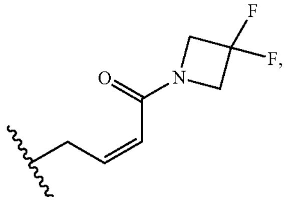

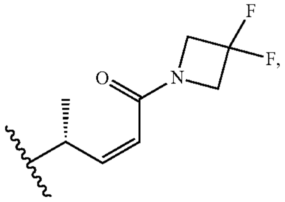

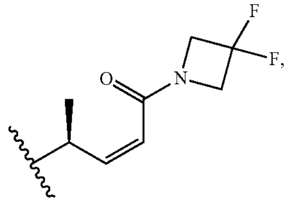

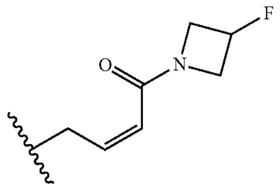

, or

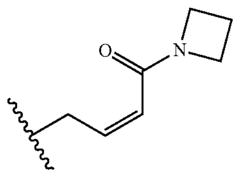

.

In some embodiments, of Formula (I), $R^A$ is

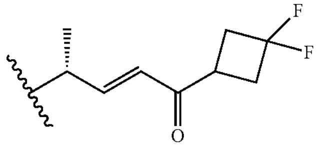

or

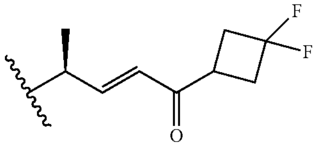

.

In some embodiments of Formula (I), $R^A$ is

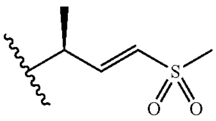,

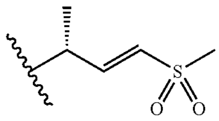,

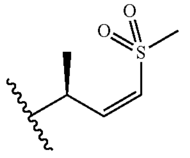,

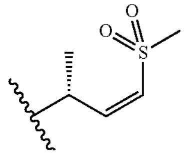.

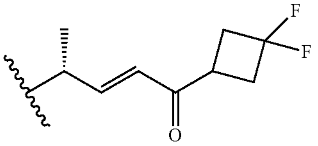, or

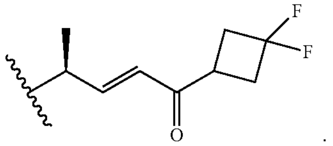.

In some embodiments of Formula (I), (Ia), (II), (IIa), (IIb), (III), (IIIa), or (IIIb), each $R^1$ is independently halogen, —CN, —OH, —$OR^a$, —SH, —$SR^a$, —$NO_2$, —$N(R^b)_2$, —C(=O)$R^a$, —C(=O)$OR^a$, —C(=O)$NR^aR^b$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ haloalkyl, or $C_1$-$C_6$ hydroxyalkyl. In some embodiments of Formula (I), (Ia), (II), (IIa), (IIb), (III), (IIIa), or (IIIb), each $R^1$ is independently halogen, —CN, —OH, —$OR^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ haloalkyl, or $C_1$-$C_6$ hydroxyalkyl. In some embodiments of Formula (I), (Ia), (II), (IIa), (IIb), (III), (IIIa), or (IIIb), each $R^1$ is independently halogen, —$OR^a$, optionally substituted $C_1$-$C_6$ alkyl, optionally substituted $C_2$-$C_6$ alkynyl, optionally substituted $C_1$-$C_6$ haloalkyl, or $C_1$-$C_6$ hydroxyalkyl. In some embodiments of Formula (I), (Ia), (II), (IIa), (IIb), (III), (IIIa), or (IIIb), each $R^1$ is independently halogen. In some embodiments of Formula (I), (Ia), (II), (IIa), (IIb), (III), (IIIa), or (IIIb), each $R^1$ is independently Br, Cl, or F. In some embodiments of Formula (I), (Ia), (II), (IIa), (IIb), (III), (IIIa), or (IIIb), each $R^1$ is independently optionally substituted $C_1$-$C_6$ alkyl. In some embodiments of Formula (I), (Ia), (II), (IIa), (IIb), (III), (IIIa), or (IIIb), each $R^1$ is independently —$CH_3$ or —$CH_2CH_3$. In some embodiments of Formula (I), (Ia), (II), (IIa), (IIb), (III), (IIIa), or (IIIb), each $R^1$ is independently —$OR^a$. In some embodiments of Formula (I), (Ia), (II), (IIa), (IIb), (III), (IIIa), or (IIIb), each $R^1$ is independently —O(alkyl), —O(haloalkyl), or —O(cycloalkyl). In some embodiments of Formula (I), (Ia), (II), (IIa), (IIb), (III), (IIIa), or (IIIb), each $R^1$ is independently —$OCH_3$, —$OCH_2CH_3$, —$OCF_3$, —O(cyclopropyl), or —O(cyclobutyl).

In some embodiments of Formula (I), (Ia), (II), (IIa), (IIb), (III), (IIIa), or (IIIb), each $R^1$ is independently Cl, F, —$CF_3$, —$CH_3$, —$CH_2CH_3$, —$OCH_3$, —O(cyclopropyl), or —O(cyclobutyl). In some embodiments of Formula (I), (Ia), (II), (IIa), (IIb), (III), (IIIa), or (IIIb), each $R^1$ is independently Cl, F, —$CH_3$, —$CH_2CH_3$, or —$OCH_3$. In some embodiments of Formula (I), (Ia), (II), (IIa), (IIb), (III), (IIIa), or (IIIb), each $R^1$ is independently Cl, F, or —$CH_3$. In some embodiments of Formula (I), (Ia), (II), (IIa), (IIb), (III), (IIIa), or (IIIb), each $R^1$ is independently $C_1$ or F. In some embodiments of Formula (I), (Ia), (II), (IIa), (IIb), (III), (IIIa), or (IIIb), each $R^1$ is independently $C_1$. In some embodiments of Formula (I), (Ia), (II), (IIa), (IIb), (III), (IIIa), or (IIIb), each $R^1$ is independently F.

In some embodiments of Formula (I), (Ia), (II), (IIa), (IIb), (III), (IIIa), or (IIIb), each $R^2$ is independently halogen, —CN, —OH, —$OR^a$, —SH, —$SR^a$, —$NO_2$, —$N(R^b)_2$, —S(=O)$_2R^a$, —C(=O)$R^a$, —C(=O)$OR^a$, —C(=O)$NR^aR^b$, oxo (=O), optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkylamino, optionally substituted $C_1$-$C_6$ haloalkyl, optionally substituted $C_1$-$C_6$ hydroxyalkyl, optionally substituted $C_3$-$C_6$ cycloalkyl, or optionally substituted 4 to 6-membered heterocycloalkyl. In some embodiments of Formula (I), (Ia), (II), (IIa), (IIb), (III), (IIIa), or (IIIb), each $R^2$ is independently halogen, —CN, —OH, —$OR^a$, —$N(R^b)_2$, optionally substituted $C_1$-$C_6$ alkyl, optionally substituted $C_2$-$C_6$ alkenyl, optionally substituted $C_1$-$C_6$ alkynyl, optionally substituted $C_1$-$C_6$ haloalkyl, optionally substituted $C_1$-$C_6$ hydroxyalkyl, optionally substituted $C_3$-$C_6$ cycloalkyl, or optionally substituted 4 to 6-membered heterocycloalkyl.

In some embodiments of Formula (I), (Ia), (II), (IIa), (IIb), (III), (IIIa), or (IIIb), each $R^2$ is independently halogen. In some embodiments of Formula (I), (Ia), (II), (IIa), (IIb), (III), (IIIa), or (IIIb), each $R^2$ is independently Cl, Br, or F. In some embodiments of Formula (I), (Ia), (II), (IIa), (IIb), (III), (IIIa), or (IIIb), each $R^2$ is independently —$OR^a$ or —$N(R^b)_2$. In some embodiments of Formula (I), (Ia), (II), (IIa), (IIb), (III), (IIIa), or (IIIb), each $R^2$ is independently —$OCH_3$, —$OCF_3$, —$OCH_2CH_3$, —$OCHF_2$, —$OCH(CH_3)_2$, —O(cyclopropyl), or —$N(CH_3)_2$. In some embodiments of Formula (I), (Ia), (II), (IIa), (IIb), (III), (IIIa), or (IIIb), each $R^2$ is independently optionally substituted $C_1$-$C_6$ alkyl. In some embodiments of Formula (I), (Ia), (II), (IIa), (IIb), (III), (IIIa), or (IIIb), each $R^2$ is independently —$CH_3$, —$CH_2CH_3$, —$CHCH_2$, or —$CH(CH_3)_2$. In some embodiments of Formula (I), (Ia), (II), (IIa), (IIb), (III), (IIIa), or (IIIb), each $R^2$ is independently optionally substituted $C_1$-$C_6$ haloalkyl or optionally substituted $C_1$-$C_6$ hydroxyalkyl. In some embodiments of Formula (I), (Ia), (II), (IIa), (IIb), (III), (IIIa), or (IIIb), each $R^2$ is independently —$CH_2OH$, —$CH_2CH_2OH$, —$CHOHCH_3$, —$CF_3$, —$CHF_2$, —$CH_2CF_3$, or —$CH_2CHF_2$. In some embodiments of Formula (I), (Ia), (II), (IIa), (IIb), (III), (IIIa), or (IIIb), each $R^2$ is independently an optionally substituted $C_3$-$C_6$ cycloalkyl or optionally substituted 4 to 6-membered heterocycloalkyl. In some embodiments of Formula (I), (Ia), (II), (IIa), (IIb), (III), (IIIa), or (IIIb), each $R^2$ is independently azetidine, oxetane, pyrrolidine, piperazine, or morpholine.

In some embodiments of Formula (I), (Ia), (II), (IIa), (IIb), (III), (IIIa), or (IIIb), each $R^2$ is independently Cl, F, Br, —CN, —OH, —$OCH_3$, —$OCF_3$, —$OCH_2CH_3$, —$OCHF_2$, —$OCH(CH_3)_2$, —O(cyclopropyl), —$N(CH_3)_2$, —$CH_3$, —$CH_2CH_3$, —$CHCH_2$, —$CH(CH_3)_2$, —$CH_2OH$, —$CH_2CH_2OH$, —$CHOHCH_3$, —$CF_3$, —$CHF_2$, —$CH_2CF_3$, —$CH_2CHF_2$, azetidine, oxetane, pyrrolidine, piperazine, or morpholine or pryrrolidin-2-one. In some embodiments of Formula (I), (Ia), (II), (IIa), (IIb), (III), (IIIa), or (IIIb), each $R^2$ is independently Cl, F, Br, —$OCH_3$, —$OCF_3$, —$OCH_2CH_3$, —$OCHF_2$, —$OCH(CH_3)_2$, —O(cyclopropyl), —$N(CH_3)_2$, —$CH_3$, —$CH_2CH_3$, —$CHCH_2$, —$CH(CH_3)_2$, —$CH_2OH$, —$CH_2CH_2OH$, —$CHOHCH_3$, —$CF_3$, —$CHF_2$, —$CH_2CF_3$, or —$CH_2CHF_2$.

In some embodiments of Formula (I), (Ia), (II), (IIa), (IIb), (III), (IIIa), or (IIIb), each $R^2$ is independently

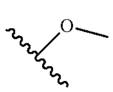 , 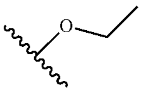 , 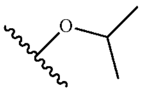 ,

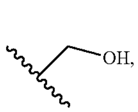 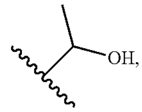 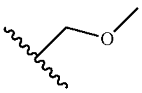 ,

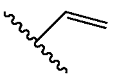 , 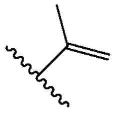 , 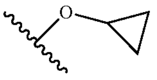 ,

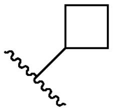 , 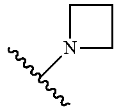 , 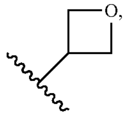

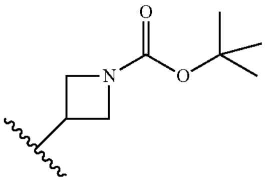 , 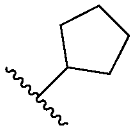 , 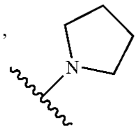 ,

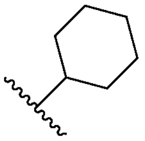 , 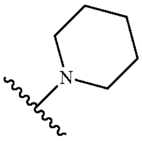 ,

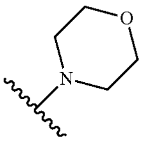 , or 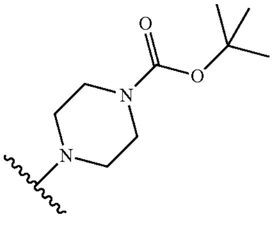 .

In some embodiments of Formula (I), (Ia), (II), (IIa), (IIb), (III), or (IIIa), two $R^2$ together with the atom(s) to which they are attached combine to form a $C_3$-$C_5$ cycloalkyl, 4 to 5-membered heterocycloalkyl, or 5-membered heteroaryl ring. In some embodiments, the two $R^2$ groups are on the same carbon atom or on adjacent atoms. In some embodiments, the two $R^2$ groups are on the same carbon atom. In some embodiments, the two $R^2$ groups are on adjacent atoms. In some embodiments of Formula (I), (Ia), (II), (IIa), (IIb), (III), or (IIIa), two $R^2$ together with the atom(s) to which they are attached combine to form a $C_3$-$C_5$ cycloalkyl ring. In some embodiments of Formula (I), (Ia), (II), (IIa), or (IIb), two $R^2$ combine with the carbon atom to which they are attached to form a cyclopropyl or cyclobutyl. In some embodiments of Formula (I), (Ia), (II), (IIa), (IIb), (III), or (IIIa), two $R^2$ together with the atom(s) to which they are attached combine to form a 4 to 5-membered heterocycloalkyl ring. In some embodiments of Formula (I), (Ia), (II), (IIa), or (IIb), two $R^2$ together with the carbon atom to which they are attached from an oxetane.

In some embodiments of Formula (I), (Ia), (II), (IIa), (IIb), (III), (IIIa), or (IIIb), each $R^3$ is independently halogen, —CN, —OH, —$OR^a$, $C_1$-$C_6$ alkyl, or $C_1$-$C_6$ haloalkyl. In some embodiments of Formula (I), (Ia), (II), (IIa), (IIb), (III), (IIIa), or (IIIb), each $R^3$ is independently halogen, —OH, —$OR^a$, or $C_1$-$C_6$ alkyl. In some embodiments of Formula (I), (Ia), (II), (IIa), (IIb), (III), (IIIa), or (IIIb), each $R^3$ is independently $C_1$-$C_6$ alkyl. In some embodiments, each $R^3$ is independently $C_1$-$C_3$ alkyl. In some embodiments of Formula (I), (Ia), (II), (IIa), (IIb), (III), (IIIa), or (IIIb), each $R^3$ is independently —$CH_3$ or —$CH_2CH_3$. In some embodiments of Formula (I), (Ia), (II), (IIa), (IIb), (III), (IIIa), or (IIIb), each $R^3$ is independently —$CH_3$. In some embodiments of Formula (I), (Ia), (II), (IIa), (IIb), (III), (IIIa), or (IIIb), each $R^3$ is independently —$CH_2CH_3$. In some embodiments of Formula (I), (Ia), (II), (IIa), (IIb), (III), (IIIa), or (IIIb), each $R^3$ is independently halogen. In some embodiments of Formula (I), (Ia), (II), (IIa), (IIb), (III), (IIIa), or (IIIb), each $R^3$ is independently F, Cl, or Br. In some embodiments of Formula (I), (Ia), (II), (IIa), (IIb), (III), (IIIa), or (IIIb), each $R^3$ is independently F. In some embodiments of Formula (I), (Ia), (II), (IIa), (IIb), (III), (IIIa), or (IIIb), each $R^3$ is independently Cl. In some embodiments of Formula (I), (Ia), (II), (IIa), (IIb), (III), (IIIa), or (IIIb), each $R^3$ is independently Br.

In some embodiments of Formula (I), (Ia), (II), or (III), two $R^3$ together with the atom(s) to which they are attached combine to form a $C_3$-$C_8$ cycloalkyl or 3 to 8-membered heterocycloalkyl ring. In some embodiments of Formula (I), (Ia), (II), or (III), two $R^3$ together with the atom(s) to which they are attached combine to form a $C_3$-$C_8$ cycloalkyl.

In some embodiments of Formula (I), (II), or (III), $R^4$ is halogen, —OH, —$OR^a$, or $C_1$-$C_6$ alkyl. In some embodiments of Formula (I), (II), or (III), $R^4$ is H or halogen. In some embodiments of Formula (I), (II), or (III), $R^4$ is halogen. In some embodiments of Formula (I), (II), or (III), $R^4$ is Cl, Br, or F. In some embodiments of Formula (I), (II), or (III), $R^4$ is F. In some embodiments of Formula (I), (II), or (III), $R^4$ is —$OR^a$ or $C_1$-$C_6$ alkyl. In some embodiments of Formula (I), (II), or (III), $R^4$ is —$OCH^3$ or —$CH^3$. In some embodiments of Formula (I), (II), or (III), $R^4$ is H.

In some embodiments of Formula (II), m is 1. In some embodiments of Formula (II), m is 0.

In some embodiments of Formula (I), (Ia), (II), (IIa), (IIb), (III), or (IIIa), n1 and n2 are each independently 0, 1, 2, or 3. In some embodiments of Formula (I), (Ia), (II), (IIa), (IIb), (III), or (IIIa), n1 and n2 are each independently 0, 1, 2. In some embodiments of Formula (I), (Ia), (II), (IIa), (IIb), (III), or (IIIa), n1 and n2 are each independently 1 or 2. In some embodiments of Formula (I), (Ia), (II), (IIa), (IIb), (III), or (IIIa), n1 and n2 are each independently 1. In some embodiments of Formula (I), (Ia), (II), (IIa), (IIb), (III), or (IIIa), n1 is 1 or 2; and n2 is 1. In some embodiments of Formula (I), (Ia), (II), (IIa), (IIb), (III), or (IIIa), n1 is 2; and n2 is 1. In some embodiments of Formula (I), (Ia), (II), (IIa), (IIb), (III), or (IIIa), n1 is 1; and n2 is 1.

In some embodiments of Formula (I), (Ia), (II), (IIa), (IIb), (III), or (IIIa), p is an integer from 0-8. In some embodiments of Formula (I), (Ia), (II), (IIa), (IIb), (III), or (IIIa), p is an integer from 0-4. In some embodiments of Formula (I), (Ia), (II), (IIa), (IIb), (III), or (IIIa), p is an integer from 0-3. In some embodiments of Formula (I), (Ia), (II), (IIa), (IIb), (III), or (IIIa), p is 0, 1, 2, 3, 4, 5, 6, 7, or 8. In some embodiments of Formula (I), (Ia), (II), (IIa), (IIb), (III), or (IIIa), p is 0, 1, 2, 3, or 4. In some embodiments of Formula (I), (Ia), (II), (IIa), (IIb), (III), or (IIIa), p is 0, 1, 2, or 3. In some embodiments of Formula (I), (Ia), (II), (IIa), (IIb), (III), or (IIIa), p is 0, 1, or 2. In some embodiments of Formula (I), (Ia), (II), (IIa), (IIb), (III), or (IIIa), p is 1 or 2. In some embodiments of Formula (I), (Ia), (II), (IIa), (IIb), (III), or (IIIa), p is 3. In some embodiments of Formula (I), (Ia), (II), (IIa), (IIb), (III), or (IIIa), p is 2. In some embodiments of Formula (I), (Ia), (II), (IIa), (IIb), (III), or (IIIa), p is 1. In some embodiments of Formula (I), (Ia), (II), (IIa), (IIb), (III), or (IIIa), p is 0.

In some embodiments of Formula (I), (Ia), (II), (IIa), (IIb), (III), (IIIa) or (IIIb), q is an integer from 0-12. In some embodiments of Formula (I), (Ia), (II), (IIa), (IIb), (III), (IIIa) or (IIIb), q is an integer from 0-8. In some embodiments of Formula (I), (Ia), (II), (IIa), (IIb), (III), (IIIa) or (IIIb), q is an integer from 0-2. In some embodiments of Formula (I), (Ia), (II), (IIa), (IIb), (III), (IIIa), or (IIIb), q is 0, 1, 2, 3, 4, 5, 6, 7, or 8. In some embodiments of Formula (I), (Ia), (II), (IIa), (IIb), (III), (IIIa), or (IIIb), q is 0, 1, 2, 3, or 4. In some embodiments of Formula (I), (Ia), (II), (IIa), (IIb), (III), (IIIa), or (IIIb), q is 0, 1, 2, or 3. In some embodiments of Formula (I), (Ia), (II), (IIa), (IIb), (III), (IIIa), or (IIIb), q is 0, 1 or 2. In some embodiments of Formula (I), (Ia), (II), (IIa), (IIb), (III), (IIIa), or (IIIb), q is 0 or 1. In some embodiments of Formula (I), (Ia), (II), (IIa), (IIb), (III), (IIIa), or (IIIb), q is 3. In some embodiments of Formula (I), (Ia), (II), (IIa), (IIb), (III), (IIIa), or (IIIb), q is 2. In some embodiments of Formula (I), (Ia), (II), (IIa), (IIb), (III), (IIIa), or (IIIb), q is 1. In some embodiments of Formula (I), (Ia), (II), (IIa), (IIb), (III), (IIIa), or (IIIb), q is 0.

In some embodiments of Formula (I), (Ia), (II), (IIa), (IIb), (III), (IIIa), or (IIIb), t is 0, 1, 2, or 3. In some embodiments of Formula (I), (Ia), (II), (IIa), (IIb), (III), IIIa), or (IIIb), t is 0, 1 or 2. In some embodiments of Formula (I), (Ia), (II), (IIa), (IIb), (III), (IIIa), or (IIIb), t is 0 or 1. In some embodiments of Formula (I), (Ia), (II), (IIa), (IIb), (III), (IIIa), or (IIIb), t is 3. In some embodiments of Formula (I), (Ia), (II), (IIa), (IIb), (III), (IIIa), or (IIIb), t is 2. In some embodiments of Formula (I), (Ia), (II), (IIa), (IIb), (III), (IIIa), or (IIIb), t is 1. In some embodiments of Formula (I), (Ia), (II), (IIa), (IIb), (III), (IIIa), or (IIIb), t is 0.

In some embodiments of Formula (I), (Ia), (II), (IIa), (IIb), (III), (IIIa), or (IIIb), each $R^a$ is independently H, $C_1$-$C_6$ alkyl, $C_1$-$C_6$ haloalkyl, $C_1$-$C_6$ heteroalkyl, cycloalkyl, heterocycloalkyl, aryl, heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl(heterocycloalkyl); wherein each alkyl, heteroalkyl, cycloalkyl, heterocycloalkyl, aryl, and heteroaryl is independently optionally substituted with one, two, or three halogen, —OH, $C_1$-$C_6$ alkyl, or $C_1$-$C_6$ haloalkyl. In some embodiments, each $R^a$ is independently $C_1$-$C_6$ alkyl, $C_1$-$C_6$ heteroalkyl, cycloalkyl, heterocycloalkyl, aryl, or heteroaryl; wherein the alkyl, heteroalkyl, cycloalkyl, heterocycloalkyl, aryl, and heteroaryl is independently optionally substituted with one, two, or three halogen, —OH, $C_1$-$C_6$ alkyl, or $C_1$-$C_6$ haloalkyl. In some embodiments each $R^a$ is independently $C_1$-$C_6$ alkyl or $C_1$-$C_6$ heteroalkyl; wherein the alkyl or heteroalkyl is independently optionally substituted with one, two, or three halogen, —OH, $C_1$-$C_6$ alkyl, or $C_1$-$C_6$ haloalkyl.

In some embodiments of Formula (I), (Ia), (II), (IIa), (IIb), (III), (IIIa), or (IIIb), each $R^b$ is independently H, $C_1$-$C_6$ alkyl, $C_1$-$C_6$ haloalkyl, $C_1$-$C_6$ heteroalkyl, cycloalkyl, heterocycloalkyl, aryl, or heteroaryl; wherein the alkyl, heteroalkyl, cycloalkyl, heterocycloalkyl, aryl, and heteroaryl is independently optionally substituted with one, two, or three halogen, —OH, $C_1$-$C_6$ alkyl, or $C_1$-$C_6$ haloalkyl. In some embodiments, each $R^b$ is independently hydrogen, $C_1$-$C_6$ alkyl, $C_1$-$C_6$ heteroalkyl, cycloalkyl, heterocycloalkyl, aryl, or heteroaryl; wherein the alkyl, heteroalkyl, cycloalkyl, heterocycloalkyl, aryl, and heteroaryl is independently optionally substituted with one, two, or three halogen, —OH, $C_1$-$C_6$ alkyl, or $C_1$-$C_6$ haloalkyl. In some embodiments, each $R^b$ is independently H, $C_1$-$C_6$ alkyl or $C_1$-$C_6$ heteroalkyl; wherein the alkyl or heteroalkyl is independently optionally substituted with one, two, or three halogen, —OH, $C_1$-$C_6$ alkyl, or $C_1$-$C_6$ haloalkyl. In some embodiments, each $R^b$ is hydrogen.

In some embodiments of Formula (I), (Ia), (II), (IIa), (IIb), (III), or (IIIa), two $R^b$ groups on a nitrogen atom are taken together with the nitrogen atom to which they are attached to form a heterocycloalkyl which is optionally substituted with one, two, or three $C_1$-$C_6$ alkyl, or $C_1$-$C_6$ haloalkyl. In some embodiments, two $R^b$ groups on a nitrogen atom are taken together with the nitrogen atom to which they are attached to form a 3- to 7-membered heterocycloalkyl which is optionally substituted with one, two, or three $C_1$-$C_6$ alkyl, or $C_1$-$C_6$ haloalkyl. In some embodiments, two $R^b$ groups on a nitrogen atom are taken together with the nitrogen atom to which they are attached to form a 5- or 6-membered heterocycloalkyl which is optionally substituted with one, two, or three $C_1$-$C_6$ alkyl, or $C_1$-$C_6$ haloalkyl. In some embodiments, two $R^b$ groups on a nitrogen atom are taken together with the nitrogen atom to which they are attached to form pyrrolidine, piperidine, or morpholine, which is optionally substituted with one, two, or three $C_1$-$C_6$ alkyl, or $C_1$-$C_6$ haloalkyl. In some embodiments, two $R^b$ groups on a nitrogen atom are taken together with the nitrogen atom to which they are attached to form pyrrolidine, piperidine, or morpholine.

The compounds of Formula (I), (Ia), (II), (IIa), (IIb), (III), (IIIa), and (IIIb) can be present in chiral or achiral form. The form may either be racemic or R or S configuration. The compounds of Formula (I), (Ia), (II), (IIa), (IIb), (III), (IIIa), and (IIIb) may be stereoisomers. The compounds may be atropisomers or pharmaceutically acceptable salts of an atropisomer.

Compounds of the disclosure include, but are not limited to the compound of Table 1, or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof.

All stereocenters labeled with (S) or (R) are known, absolute stereochemistry. In cases where the stereochemistry is pure but unknown, the stereocenter is drawn and defined as (*S) or (*R). Stereochemistry that is drawn but not labeled is in the correct cis or trans configuration but are racemic and designated as "rac" or RS.

TABLE 1

| Compounds of the Disclosure. | | |
|---|---|---|
| Structure | Cmp. No. | IUPAC |
| 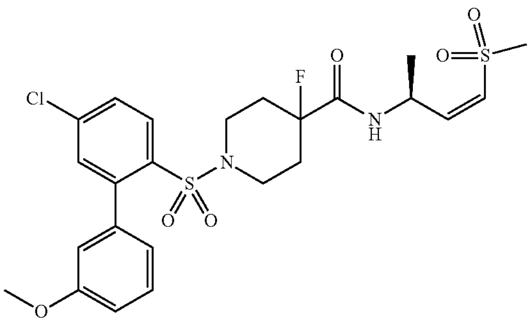 | 1 | (S,Z)-1-((5-chloro-3'-methoxy-[1,1'-biphenyl]-2-yl)sulfonyl)-4-fluoro-N-(4-(methylsulfonyl)but-3-en-2-yl)piperidine-4-carboxamide |
| 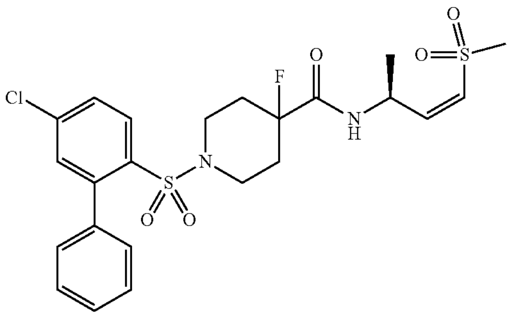 [SMILES: C[C@@H](/C=C\S(C)(=O)=O)NC(=O)C1(F)CCN(S(=O)(=O)c2ccc(Cl)cc2-c2ccccc2)CC1] | 2 | (S,Z)-1-((5-chloro-[1,1'-biphenyl]-2-yl)sulfonyl)-4-fluoro-N-(4-(methylsulfonyl)but-3-en-2-yl)piperidine-4-carboxamide |
| 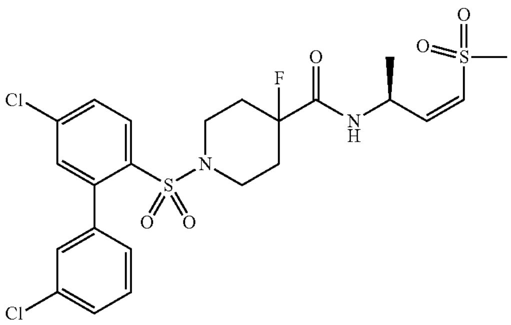 [SMILES: C[C@@H](/C=C\S(C)(=O)=O)NC(=O)C1(F)CCN(S(=O)(=O)c2ccc(Cl)cc2-c2cccc(Cl)c2)CC1] | 3 | (S,Z)-1-((3',5-dichloro-[1,1'-biphenyl]-2-yl)sulfonyl)-4-fluoro-N-(4-(methylsulfonyl)but-3-en-2-yl)piperidine-4-carboxamide |
| 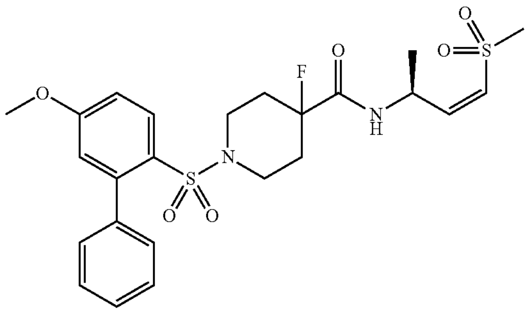 | 4 | (S,Z)-4-fluoro-1-((5-methoxy-[1,1'-biphenyl]-2-yl)sulfonyl)-N-(4-(methylsulfonyl)but-3-en-2-yl)piperidine-4-carboxamide |

TABLE 1-continued

| Compounds of the Disclosure. | | |
|---|---|---|
| Structure | Cmp. No. | IUPAC |
| 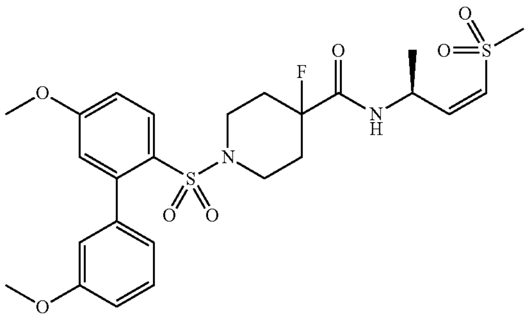 | 5 | (S,Z)-1-((3',5-dimethoxy-[1,1'-biphenyl]-2-yl)sulfonyl)-4-fluoro-N-(4-(methylsulfonyl) but-3-en-2-yl)piperidine-4-carboxamide |
| 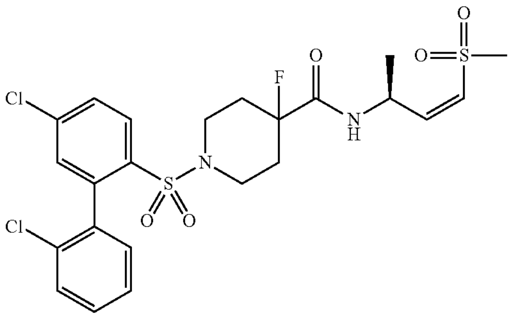 [SMILES: C[C@@H](/C=C\S(C)(=O)=O)NC(=O)C1(F)CCN(S(=O)(=O)c2ccc(Cl)cc2-c2ccccc2Cl)CC1] | 6 | (S,Z)-1-((2',5-dichloro-[1,1'-biphenyl]-2-yl)sulfonyl)-4-fluoro-N-(4-(methylsulfonyl) but-3-en-2-yl)piperidine-4-carboxamide |
| 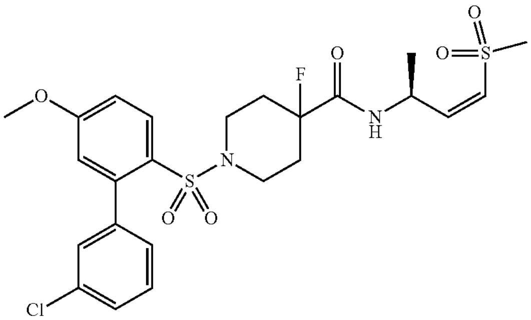 | 7 | (S,Z)-1-((3'-chloro-5-methoxy-[1,1'-biphenyl]-2-yl)sulfonyl)-4-fluoro-N-(4-(methylsulfonyl)but-3-en-2-yl)piperidine-4-carboxamide |
| 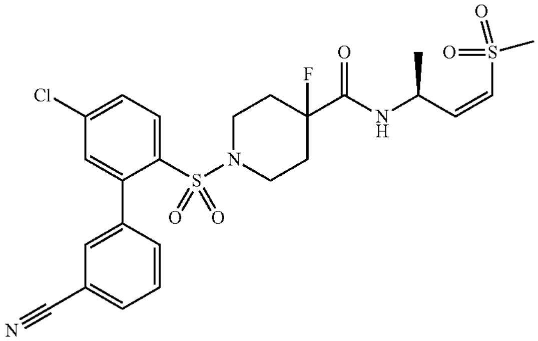 [SMILES: C[C@@H](/C=C\S(C)(=O)=O)NC(=O)C1(F)CCN(S(=O)(=O)c2ccc(Cl)cc2-c2cccc(C#N)c2)CC1] | 8 | (S,Z)-1-((5-chloro-3'-cyano-[1,1'-biphenyl]-2-yl)sulfonyl)-4-fluoro-N-(4-(methylsulfonyl)but-3-en-2-yl)piperidine-4-carboxamide |

TABLE 1-continued

| Compounds of the Disclosure. | | |
|---|---|---|
| Structure | Cmp. No. | IUPAC |
| 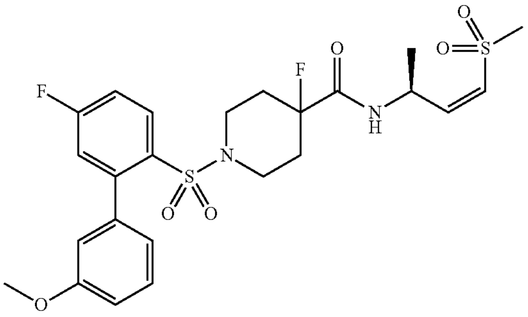 | 9 | (S,Z)-4-fluoro-1-((5-fluoro-3'-methoxy-[1,1'-biphenyl]-2-yl)sulfonyl)-N-(4-(methylsulfonyl)but-3-en-2-yl)piperidine-4-carboxamide |
| 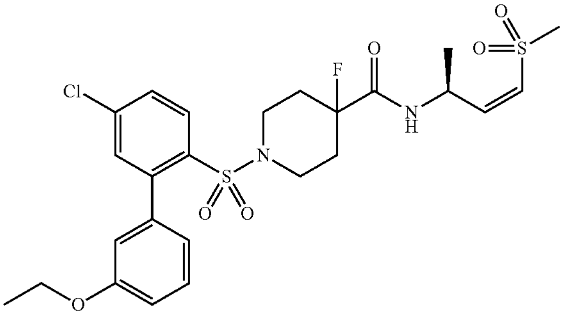 [SMILES: CCOc1cccc(-c2cc(Cl)ccc2S(=O)(=O)N2CCC(F)(C(=O)N[C@@H](C)/C=C\S(C)(=O)=O)CC2)c1] | 10 | (S,Z)-1-((5-chloro-3'-ethoxy-[1,1'-biphenyl]-2-yl)sulfonyl)-4-fluoro-N-(4-(methylsulfonyl)but-3-en-2-yl)piperidine-4-carboxamide |
| 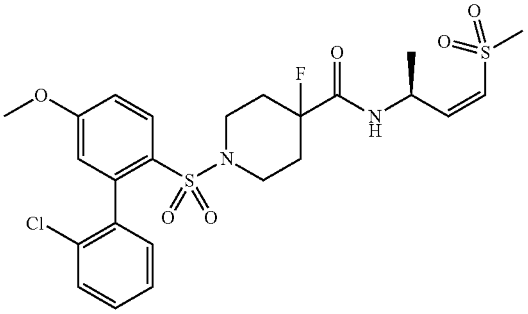 | 11 | (S,Z)-1-((2'-chloro-5-methoxy-[1,1'-biphenyl]-2-yl)sulfonyl)-4-fluoro-N-(4-(methylsulfonyl)but-3-en-2-yl)piperidine-4-carboxamide |
| 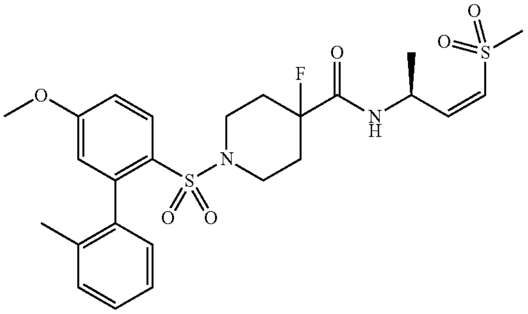 | 12 | (S,Z)-4-fluoro-1-((5-methoxy-2'-methyl-[1,1'-biphenyl]-2-yl)sulfonyl)-N-(4-(methylsulfonyl)but-3-en-2-yl)piperidine-4-carboxamide |

TABLE 1-continued

Compounds of the Disclosure.

| Structure | Cmp. No. | IUPAC |
|---|---|---|
| 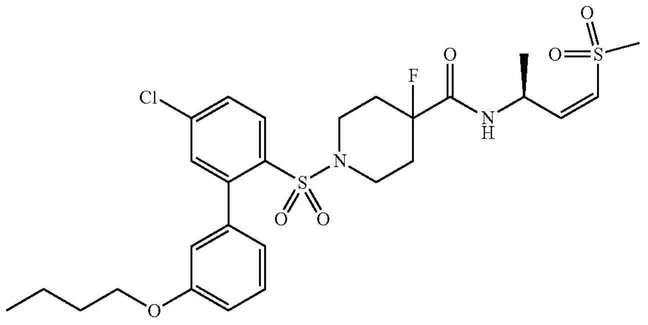 [SMILES: CCCCOc1cccc(-c2cc(Cl)ccc2S(=O)(=O)N2CCC(F)(C(=O)N[C@@H](C)/C=C\S(C)(=O)=O)CC2)c1] | 13 | (S,Z)-1-((3'-butoxy-5-chloro-[1,1'-biphenyl]-2-yl)sulfonyl)-4-fluoro-N-(4-(methylsulfonyl)but-3-en-2-yl)piperidine-4-carboxamide |
| 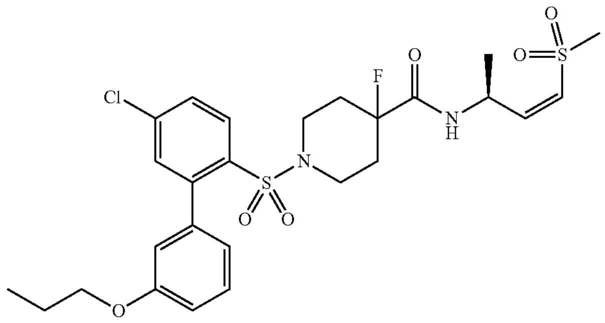 [SMILES: CCCOc1cccc(-c2cc(Cl)ccc2S(=O)(=O)N2CCC(F)(C(=O)N[C@@H](C)/C=C\S(C)(=O)=O)CC2)c1] | 14 | (S,Z)-1-((5-chloro-3'-propoxy-[1,1'-biphenyl]-2-yl)sulfonyl)-4-fluoro-N-(4-(methylsulfonyl)but-3-en-2-yl)piperidine-4-carboxamide |
| 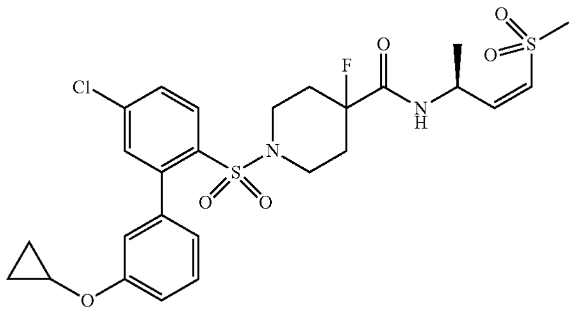 [SMILES: C[C@@H](/C=C\S(C)(=O)=O)NC(=O)C1(F)CCN(S(=O)(=O)c2ccc(Cl)cc2-c2cccc(OC3CC3)c2)CC1] | 15 | (S,Z)-1-((5-chloro-3'-cyclopropoxy-[1,1'-biphenyl]-2-yl)sulfonyl)-4-fluoro-N-(4-(methylsulfonyl)but-3-en-2-yl)piperidine-4-carboxamide |
| 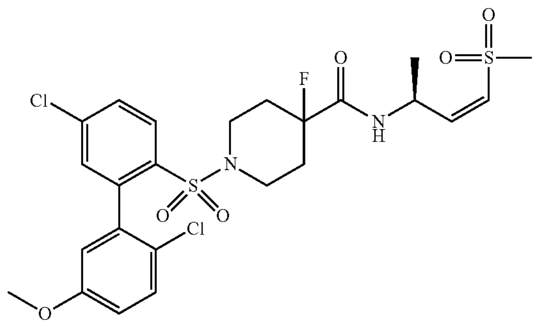 | 16 | (S,Z)-1-((2',5-dichloro-5'-methoxy-[1,1'-biphenyl]-2-yl)sulfonyl)-4-fluoro-N-(4-(methylsulfonyl)but-3-en-2-yl)piperidine-4-carboxamide |

TABLE 1-continued

Compounds of the Disclosure.

| Structure | Cmp. No. | IUPAC |
| --- | --- | --- |
| 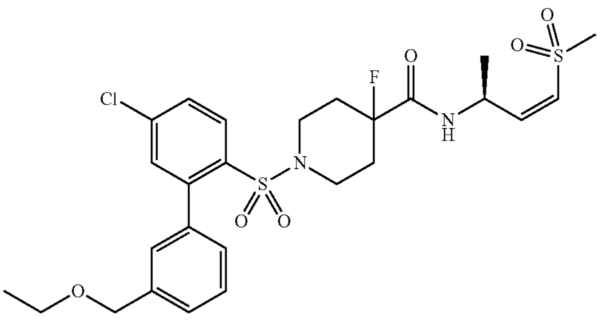 [SMILES: CCOCc1cccc(-c2cc(Cl)ccc2S(=O)(=O)N2CCC(F)(C(=O)N[C@@H](C)/C=C\S(C)(=O)=O)CC2)c1] | 17 | (S,Z)-1-((5-chloro-3'-(ethoxymethyl)-[1,1'-biphenyl]-2-yl)sulfonyl)-4-fluoro-N-(4-(methylsulfonyl)but-3-en-2-yl)piperidine-4-carboxamide |
| 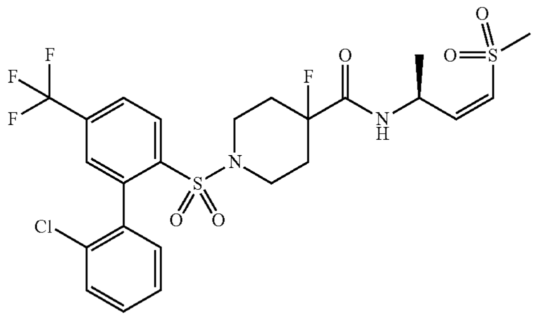 [SMILES: C[C@@H](/C=C\S(C)(=O)=O)NC(=O)C1(F)CCN(S(=O)(=O)c2ccc(C(F)(F)F)cc2-c2ccccc2Cl)CC1] | 18 | (S,Z)-1-((2'-chloro-5-(trifluoromethyl)-[1,1'-biphenyl]-2-yl)sulfonyl)-4-fluoro-N-(4-(methylsulfonyl)but-3-en-2-yl)piperidine-4-carboxamide |
| 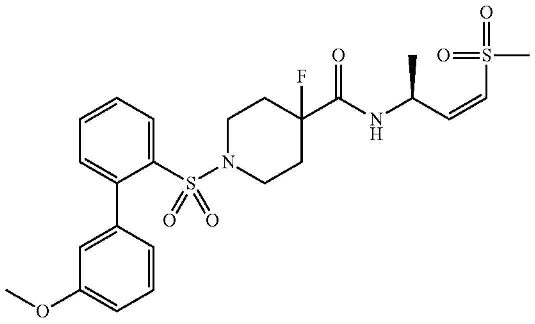 | 19 | (S,Z)-4-fluoro-1-((3'-methoxy-[1,1'-biphenyl]-2-yl)sulfonyl)-N-(4-(methylsulfonyl)but-3-en-2-yl)piperidine-4-carboxamide |
| 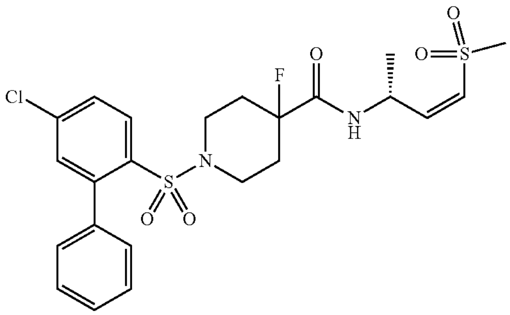 [SMILES: C[C@H](/C=C\S(C)(=O)=O)NC(=O)C1(F)CCN(S(=O)(=O)c2ccc(Cl)cc2-c2ccccc2)CC1] | 20 | (R,Z)-1-((5-chloro-[1,1'-biphenyl]-2-yl)sulfonyl)-4-fluoro-N-(4-(methylsulfonyl)but-3-en-2-yl)piperidine-4-carboxamide |

TABLE 1-continued

| Compounds of the Disclosure. | | |
|---|---|---|
| Structure | Cmp. No. | IUPAC |
| 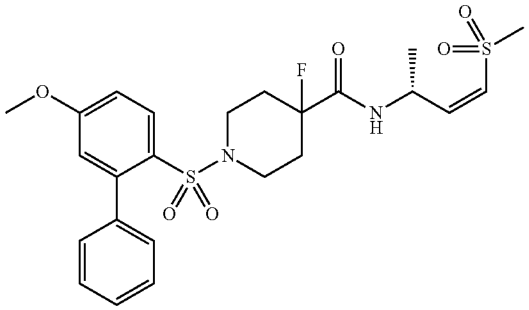 | 21 | (R,Z)-4-fluoro-1-((5-methoxy-[1,1'-biphenyl]-2-yl)sulfonyl)-N-(4-(methylsulfonyl)but-3-en-2-yl)piperidine-4-carboxamide |
| 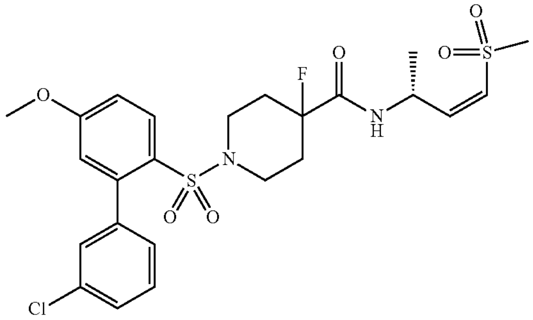 | 22 | (R,Z)-1-((3'-chloro-5-methoxy-[1,1'-biphenyl]-2-yl)sulfonyl)-4-fluoro-N-(4-(methylsulfonyl)but-3-en-2-yl)piperidine-4-carboxamide |
| 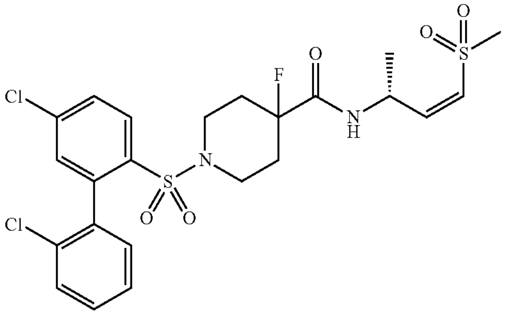 [SMILES: C[C@H](/C=C\S(C)(=O)=O)NC(=O)C1(F)CCN(S(=O)(=O)c2ccc(Cl)cc2-c2ccccc2Cl)CC1] | 23 | (R,Z)-1-((2',5-dichloro-[1,1'-biphenyl]-2-yl)sulfonyl)-4-fluoro-N-(4-(methylsulfonyl) but-3-en-2-yl)piperidine-4-carboxamide |
| 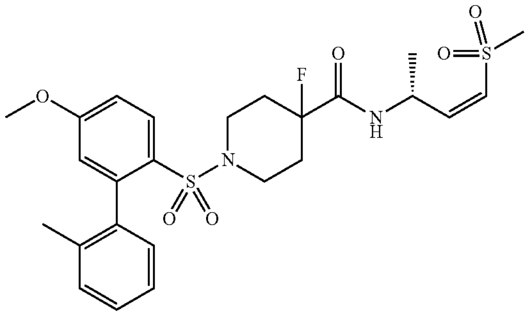 | 24 | (R,Z)-4-fluoro-1-((5-methoxy-2'-methyl-[1,1'-biphenyl]-2-yl)sulfonyl)-N-(4-(methylsulfonyl)but-3-en-2-yl)piperidine-4-carboxamide |

TABLE 1-continued

Compounds of the Disclosure.

| Structure | Cmp. No. | IUPAC |
| --- | --- | --- |
| 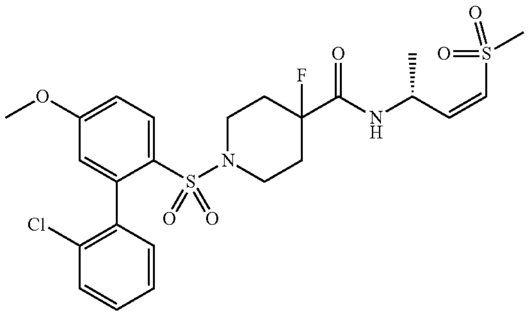 | 25 | (R,Z)-1-((2'-chloro-5-methoxy-[1,1'-biphenyl]-2-yl)sulfonyl)-4-fluoro-N-(4-(methylsulfonyl)but-3-en-2-yl)piperidine-4-carboxamide |
| 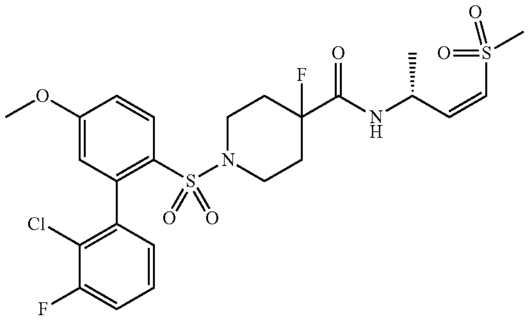 | 26 | (R,Z)-1-((2'-chloro-3'-fluoro-5-methoxy-[1,1'-biphenyl]-2-yl)sulfonyl)-4-fluoro-N-(4-(methylsulfonyl)but-3-en-2-yl)piperidine-4-carboxamide |
| 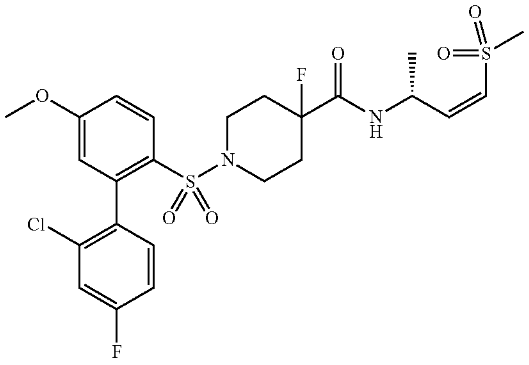 | 27 | (R,Z)-1-((2'-chloro-4'-fluoro-5-methoxy-[1,1'-biphenyl]-2-yl)sulfonyl)-4-fluoro-N-(4-(methylsulfonyl)but-3-en-2-yl)piperidine-4-carboxamide |
| 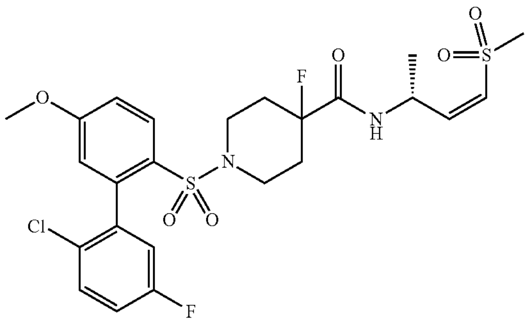 | 28 | (R,Z)-1-((2'-chloro-5'-fluoro-5-methoxy-[1,1'-biphenyl]-2-yl)sulfonyl)-4-fluoro-N-(4-(methylsulfonyl)but-3-en-2-yl)piperidine-4-carboxamide |

TABLE 1-continued

Compounds of the Disclosure.

| Structure | Cmp. No. | IUPAC |
|---|---|---|
| 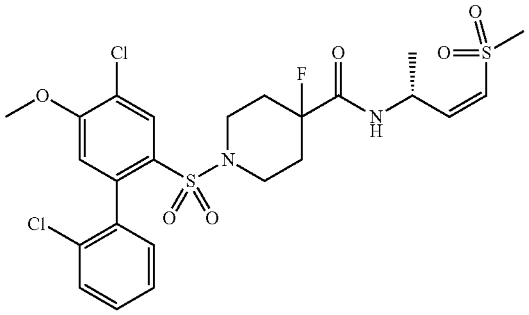 | 29 | (R,Z)-1-((2',4-dichloro-5-methoxy-[1,1'-biphenyl]-2-yl)sulfonyl)-4-fluoro-N-(4-(methylsulfonyl)but-3-en-2-yl)piperidine-4-carboxamide |
| 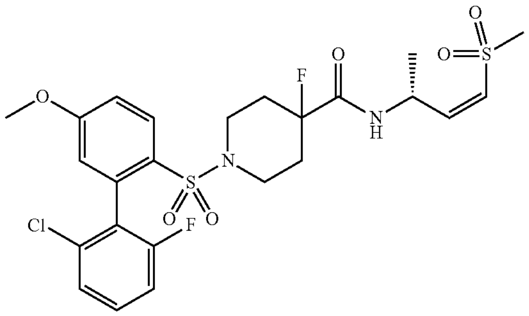 | 30 | 1-((2'-chloro-6'-fluoro-5-methoxy-[1,1'-biphenyl]-2-yl)sulfonyl)-4-fluoro-N-((R,Z)-4-(methylsulfonyl)but-3-en-2-yl)piperidine-4-carboxamide |
| 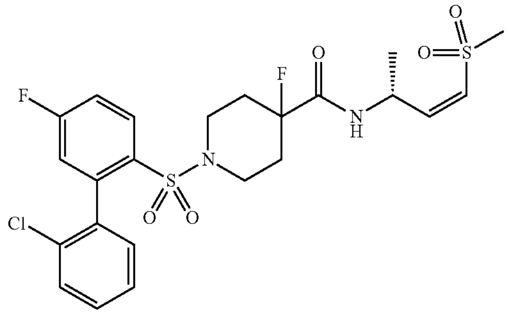 [SMILES: C[C@H](/C=C\S(C)(=O)=O)NC(=O)C1(F)CCN(S(=O)(=O)c2ccc(F)cc2-c2ccccc2Cl)CC1] | 31 | (R,Z)-1-((2'-chloro-5-fluoro-[1,1'-biphenyl]-2-yl)sulfonyl)-4-fluoro-N-(4-(methylsulfonyl)but-3-en-2-yl)piperidine-4-carboxamide |
| 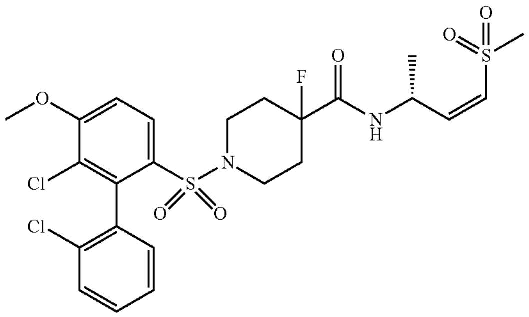 | 32 | 1-((2',6-dichloro-5-methoxy-[1,1'-biphenyl]-2-yl)sulfonyl)-4-fluoro-N-((R,Z)-4-(methylsulfonyl)but-3-en-2-yl)piperidine-4-carboxamide |

TABLE 1-continued

| Structure | Cmp. No. | IUPAC |
|---|---|---|
| Compounds of the Disclosure. | | |
| 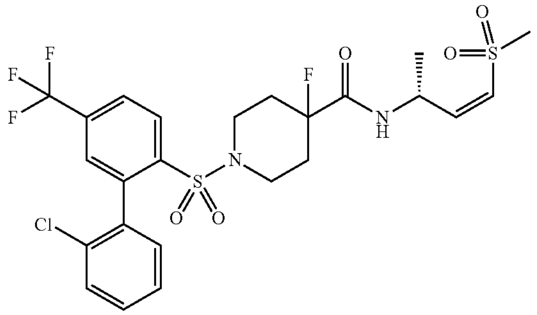 [SMILES: C[C@H](/C=C\S(C)(=O)=O)NC(=O)C1(F)CCN(S(=O)(=O)c2ccc(C(F)(F)F)cc2-c2ccccc2Cl)CC1] | 33 | (R,Z)-1-((2'-chloro-5-(trifluoromethyl)-[1,1'-biphenyl]-2-yl)sulfonyl)-4-fluoro-N-(4-(methylsulfonyl)but-3-en-2-yl)piperidine-4-carboxamide |
| 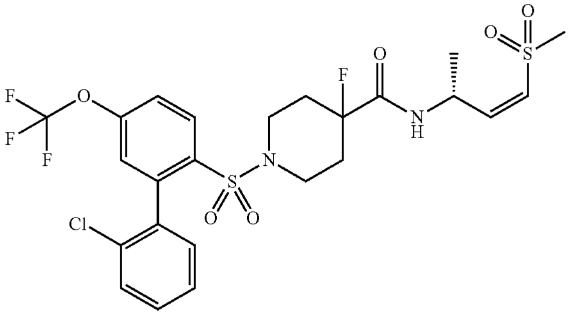 [SMILES: C[C@H](/C=C\S(C)(=O)=O)NC(=O)C1(F)CCN(S(=O)(=O)c2ccc(OC(F)(F)F)cc2-c2ccccc2Cl)CC1] | 34 | (R,Z)-1-((2'-chloro-5-(trifluoromethoxy)-[1,1'-biphenyl]-2-yl)sulfonyl)-4-fluoro-N-(4-(methylsulfonyl)but-3-en-2-yl)piperidine-4-carboxamide |
| 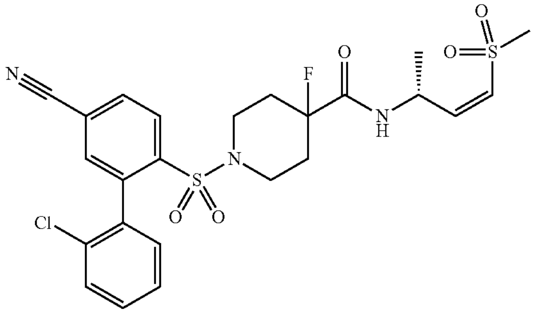 [SMILES: C[C@H](/C=C\S(C)(=O)=O)NC(=O)C1(F)CCN(S(=O)(=O)c2ccc(C#N)cc2-c2ccccc2Cl)CC1] | 35 | (R,Z)-1-((2'-chloro-5-cyano-[1,1'-biphenyl]-2-yl)sulfonyl)-4-fluoro-N-(4-(methylsulfonyl) but-3-en-2-yl)piperidine-4-carboxamide |
| 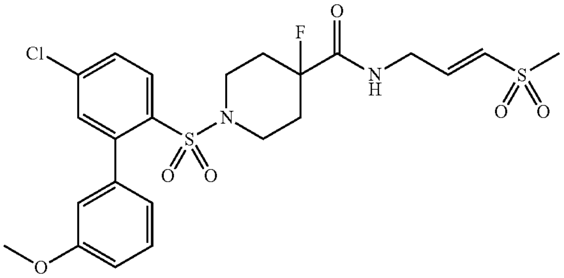 | 36 | (E)-1-((5-chloro-3'-methoxy-[1,1'-biphenyl]-2-yl)sulfonyl)-4-fluoro-N-(3-(methylsulfonyl)allyl)piperidine-4-carboxamide |
| 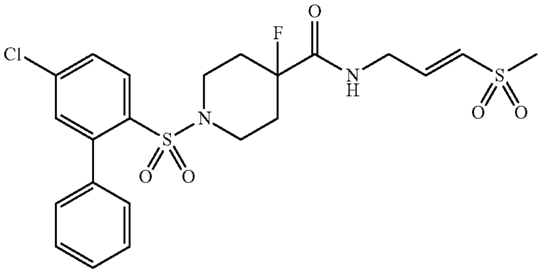 [SMILES: CS(=O)(=O)/C=C/CNC(=O)C1(F)CCN(S(=O)(=O)c2ccc(Cl)cc2-c2ccccc2)CC1] | 37 | (E)-1-((5-chloro-[1,1'-biphenyl]-2-yl)sulfonyl)-4-fluoro-N-(3-(methylsulfonyl)allyl)piperidine-4-carboxamide |

TABLE 1-continued

Compounds of the Disclosure.

| Structure | Cmp. No. | IUPAC |
|---|---|---|
| 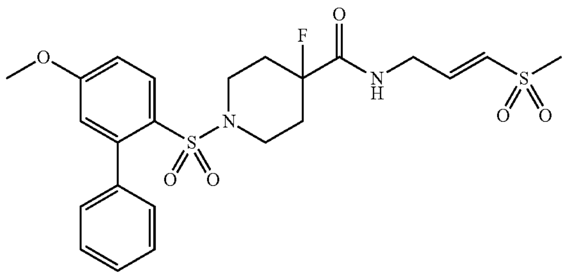 | 38 | (E)-4-fluoro-1-((5-methoxy-[1,1'-biphenyl]-2-yl)sulfonyl)-N-(3-(methylsulfonyl)allyl)piperidine-4-carboxamide |
| 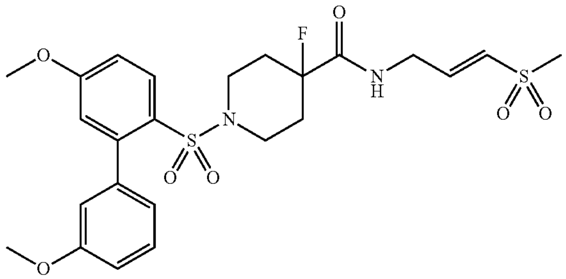 | 39 | (E)-1-((3',5-dimethoxy-[1,1'-biphenyl]-2-yl)sulfonyl)-4-fluoro-N-(3-(methylsulfonyl)allyl)piperidine-4-carboxamide |
| 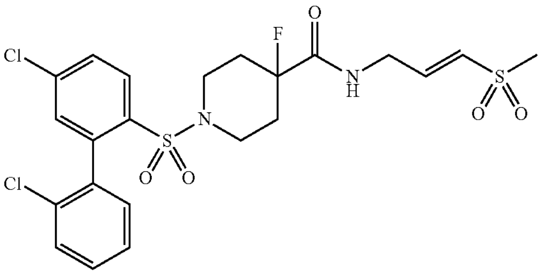 [SMILES: CS(=O)(=O)/C=C/CNC(=O)C1(F)CCN(S(=O)(=O)c2ccc(Cl)cc2-c2ccccc2Cl)CC1] | 40 | (E)-1-((2',5-dichloro-[1,1'-biphenyl]-2-yl)sulfonyl)-4-fluoro-N-(3-(methylsulfonyl)allyl)piperidine-4-carboxamide |
| 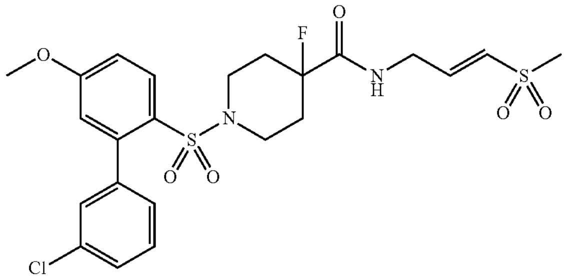 | 41 | (E)-1-((3'-chloro-5-methoxy-[1,1'-biphenyl]-2-yl)sulfonyl)-4-fluoro-N-(3-(methylsulfonyl)allyl)piperidine-4-carboxamide |
| 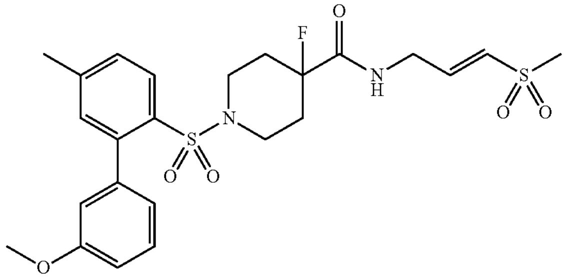 | 42 | (E)-4-fluoro-1-((3'-methoxy-5-methyl-[1,1'-biphenyl]-2-yl)sulfonyl)-N-(3-(methylsulfonyl)allyl)piperidine-4-carboxamide |

TABLE 1-continued

| Compounds of the Disclosure. | | |
|---|---|---|
| Structure | Cmp. No. | IUPAC |
| 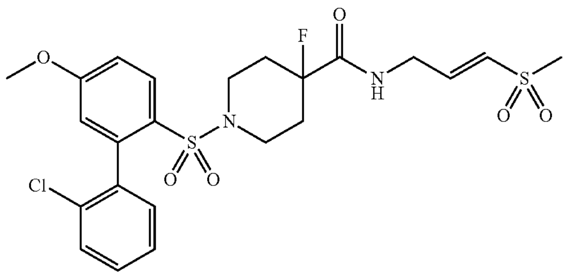 | 43 | (E)-1-((2'-chloro-5-methoxy-[1,1'-biphenyl]-2-yl)sulfonyl)-4-fluoro-N-(3-(methylsulfonyl)allyl)piperidine-4-carboxamide |
| 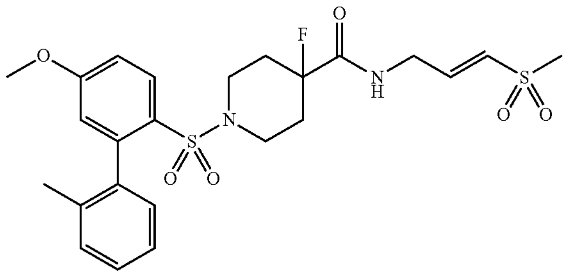 | 44 | (E)-4-fluoro-1-((5-methoxy-2'-methyl-[1,1'-biphenyl]-2-yl)sulfonyl)-N-(3-(methylsulfonyl)allyl)piperidine-4-carboxamide |
| 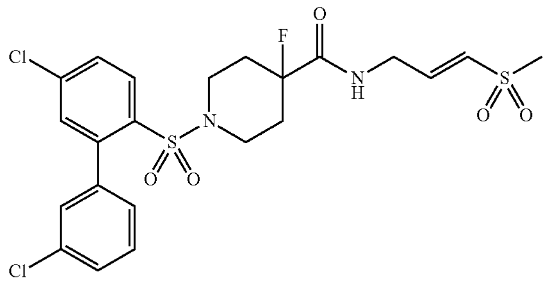 [SMILES: CS(=O)(=O)/C=C/CNC(=O)C1(F)CCN(S(=O)(=O)c2ccc(Cl)cc2-c2cccc(Cl)c2)CC1] | 45 | (E)-1-((3',5-dichloro-[1,1'-biphenyl]-2-yl)sulfonyl)-4-fluoro-N-(3-(methylsulfonyl)allyl)piperidine-4-carboxamide |
| 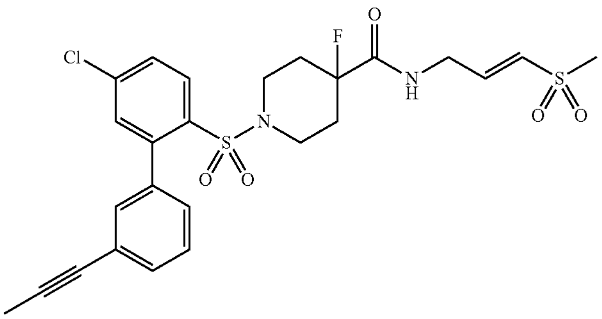 [SMILES: CC#Cc1cccc(-c2cc(Cl)ccc2S(=O)(=O)N2CCC(F)(C(=O)NC/C=C/S(C)(=O)=O)CC2)c1] | 46 | (E)-1-((5-chloro-3'-(prop-1-yn-1-yl)-[1,1'-biphenyl]-2-yl)sulfonyl)-4-fluoro-N-(3-(methylsulfonyl)allyl)piperidine-4-carboxamide |
| 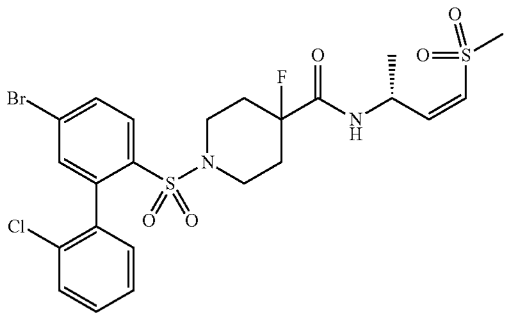 [SMILES: C[C@H](/C=C\S(C)(=O)=O)NC(=O)C1(F)CCN(S(=O)(=O)c2ccc(Br)cc2-c2ccccc2Cl)CC1] | 47 | (R,Z)-1-((5-bromo-2'-chloro-[1,1'-biphenyl]-2-yl)sulfonyl)-4-fluoro-N-(4-(methylsulfonyl)but-3-en-2-yl)piperidine-4-carboxamide |

TABLE 1-continued

| Compounds of the Disclosure. | | |
|---|---|---|
| Structure | Cmp. No. | IUPAC |
| 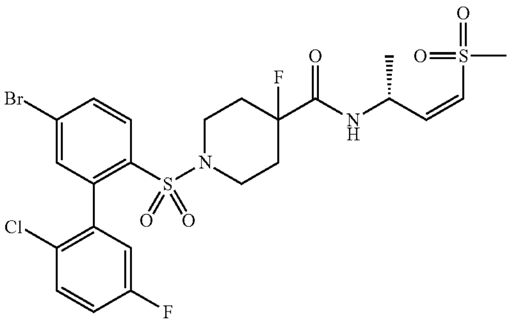 [SMILES: C[C@H](/C=C\S(C)(=O)=O)NC(=O)C1(F)CCN(S(=O)(=O)c2ccc(Br)cc2-c2cc(F)ccc2Cl)CC1] | 48 | (R,Z)-1-((5-bromo-2'-chloro-5'-fluoro-[1,1'-biphenyl]-2-yl)sulfonyl)-4-fluoro-N-(4-(methylsulfonyl)but-3-en-2-yl)piperidine-4-carboxamide |
| 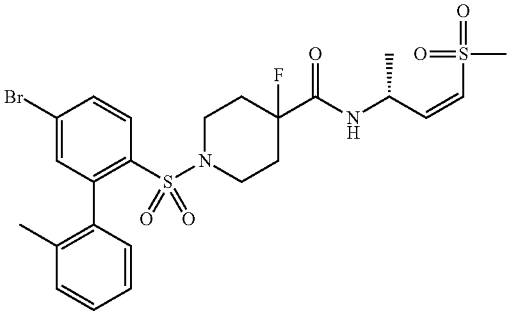 [SMILES: Cc1ccccc1-c1cc(Br)ccc1S(=O)(=O)N1CCC(F)(C(=O)N[C@H](C)/C=C\S(C)(=O)=O)CC1] | 49 | (R,Z)-1-((5-bromo-2'-methyl-[1,1'-biphenyl]-2-yl)sulfonyl)-4-fluoro-N-(4-(methylsulfonyl)but-3-en-2-yl)piperidine-4-carboxamide |
| 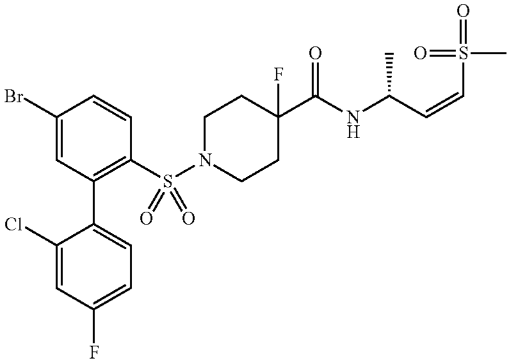 [SMILES: C[C@H](/C=C\S(C)(=O)=O)NC(=O)C1(F)CCN(S(=O)(=O)c2ccc(Br)cc2-c2ccc(F)cc2Cl)CC1] | 50 | (R,Z)-1-((5-bromo-2'-chloro-4'-fluoro-[1,1'-biphenyl]-2-yl)sulfonyl)-4-fluoro-N-(4-(methylsulfonyl)but-3-en-2-yl)piperidine-4-carboxamide |
| 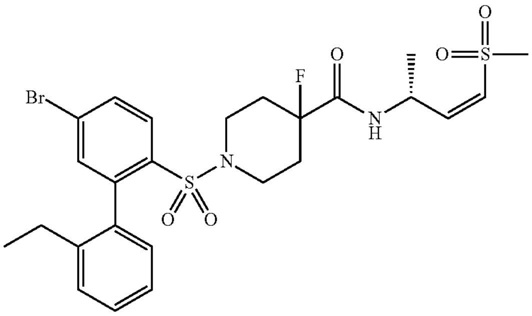 [SMILES: CCc1ccccc1-c1cc(Br)ccc1S(=O)(=O)N1CCC(F)(C(=O)N[C@H](C)/C=C\S(C)(=O)=O)CC1] | 51 | (R,Z)-1-((5-bromo-2'-ethyl-[1,1'-biphenyl]-2-yl)sulfonyl)-4-fluoro-N-(4-(methylsulfonyl)but-3-en-2-yl)piperidine-4-carboxamide |

TABLE 1-continued

| Structure | Cmp. No. | IUPAC |
|---|---|---|
| Compounds of the Disclosure. | | |
| 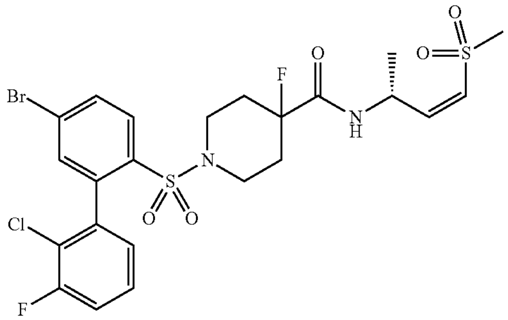 [SMILES: C[C@H](/C=C\S(C)(=O)=O)NC(=O)C1(F)CCN(S(=O)(=O)c2ccc(Br)cc2-c2cccc(F)c2Cl)CC1] | 52 | (R,Z)-1-((5-bromo-2'-chloro-3'-fluoro-[1,1'-biphenyl]-2-yl)sulfonyl)-4-fluoro-N-(4-(methylsulfonyl)but-3-en-2-yl)piperidine-4-carboxamide |
| 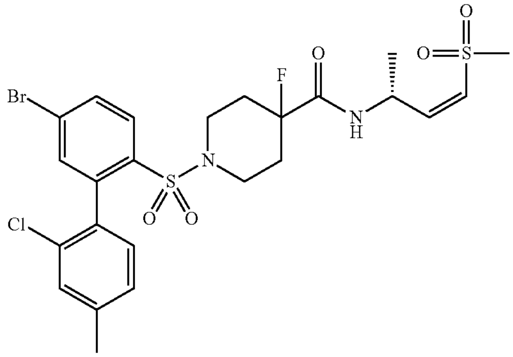 [SMILES: Cc1ccc(-c2cc(Br)ccc2S(=O)(=O)N2CCC(F)(C(=O)N[C@H](C)/C=C\S(C)(=O)=O)CC2)c(Cl)c1] | 53 | (R,Z)-1-((5-bromo-2'-chloro-4'-methyl-[1,1'-biphenyl]-2-yl)sulfonyl)-4-fluoro-N-(4-(methylsulfonyl)but-3-en-2-yl)piperidine-4-carboxamide |
| 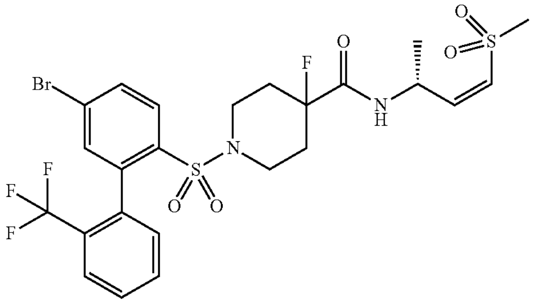 [SMILES: C[C@H](/C=C\S(C)(=O)=O)NC(=O)C1(F)CCN(S(=O)(=O)c2ccc(Br)cc2-c2ccccc2C(F)(F)F)CC1] | 54 | (R,Z)-1-((5-bromo-2'-(trifluoromethyl)-[1,1'-biphenyl]-2-yl)sulfonyl)-4-fluoro-N-(4-(methylsulfonyl)but-3-en-2-yl)piperidine-4-carboxamide |
| 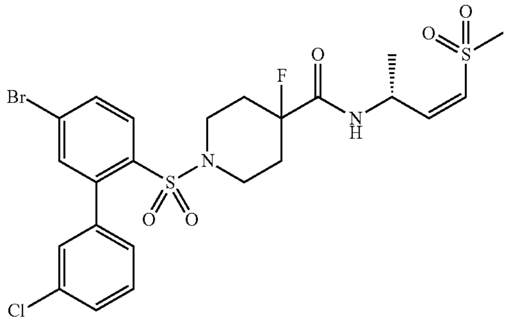 [SMILES: C[C@H](/C=C\S(C)(=O)=O)NC(=O)C1(F)CCN(S(=O)(=O)c2ccc(Br)cc2-c2cccc(Cl)c2)CC1] | 55 | (R,Z)-1-((5-bromo-3'-chloro-[1,1'-biphenyl]-2-yl)sulfonyl)-4-fluoro-N-(4-(methylsulfonyl)but-3-en-2-yl)piperidine-4-carboxamide |

TABLE 1-continued

| Compounds of the Disclosure. | | |
|---|---|---|
| Structure | Cmp. No. | IUPAC |
| 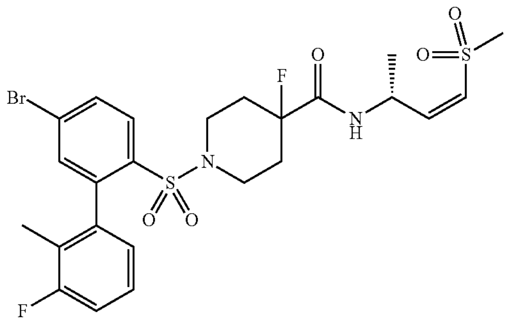 [SMILES: Cc1c(F)cccc1-c1cc(Br)ccc1S(=O)(=O)N1CCC(F)(C(=O)N[C@H](C)/C=C\S(C)(=O)=O)CC1] | 56 | (R,Z)-1-((5-bromo-3'-fluoro-2'-methyl-[1,1'-biphenyl]-2-yl)sulfonyl)-4-fluoro-N-(4-(methylsulfonyl)but-3-en-2-yl)piperidine-4-carboxamide |
| 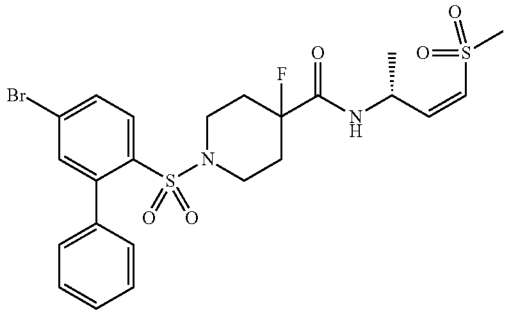 [SMILES: C[C@H](/C=C\S(C)(=O)=O)NC(=O)C1(F)CCN(S(=O)(=O)c2ccc(Br)cc2-c2ccccc2)CC1] | 57 | (R,Z)-1-((5-bromo-[1,1'-biphenyl]-2-yl)sulfonyl)-4-fluoro-N-(4-(methylsulfonyl)but-3-en-2-yl)piperidine-4-carboxamide |
| 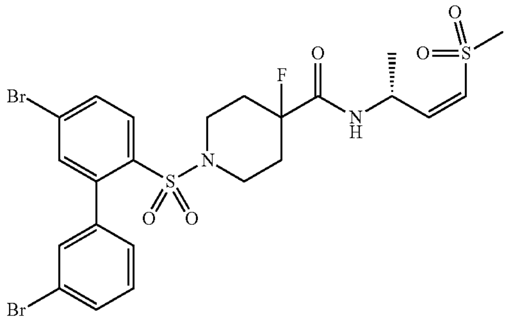 [SMILES: C[C@H](/C=C\S(C)(=O)=O)NC(=O)C1(F)CCN(S(=O)(=O)c2ccc(Br)cc2-c2cccc(Br)c2)CC1] | 58 | (R,Z)-1-((3',5-dibromo-[1,1'-biphenyl]-2-yl)sulfonyl)-4-fluoro-N-(4-(methylsulfonyl) but-3-en-2-yl)piperidine-4-carboxamide |
| 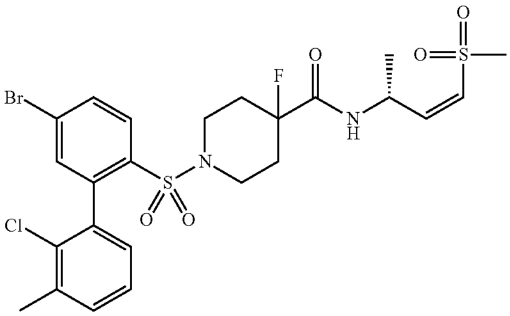 [SMILES: Cc1cccc(-c2cc(Br)ccc2S(=O)(=O)N2CCC(F)(C(=O)N[C@H](C)/C=C\S(C)(=O)=O)CC2)c1Cl] | 59 | (R,Z)-1-((5-bromo-2'-chloro-3'-methyl-[1,1'-biphenyl]-2-yl)sulfonyl)-4-fluoro-N-(4-(methylsulfonyl)but-3-en-2-yl)piperidine-4-carboxamide |

TABLE 1-continued

Compounds of the Disclosure.

| Structure | Cmp. No. | IUPAC |
|---|---|---|
| 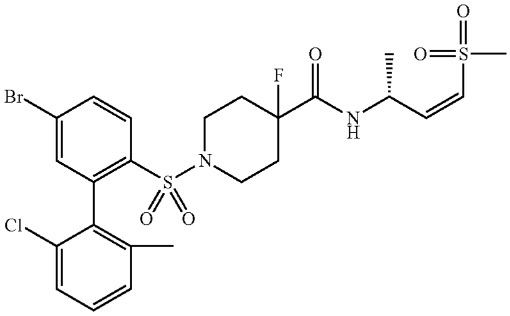 [SMILES: Cc1cccc(Cl)c1-c1cc(Br)ccc1S(=O)(=O)N1CCC(F)(C(=O)N[C@H](C)/C=C\S(C)(=O)=O)CC1] | 60 | 1-((5-bromo-2'-chloro-6'-methyl-[1,1'-biphenyl]-2-yl)sulfonyl)-4-fluoro-N-((R,Z)-4-(methylsulfonyl)but-3-en-2-yl)piperidine-4-carboxamide |
| 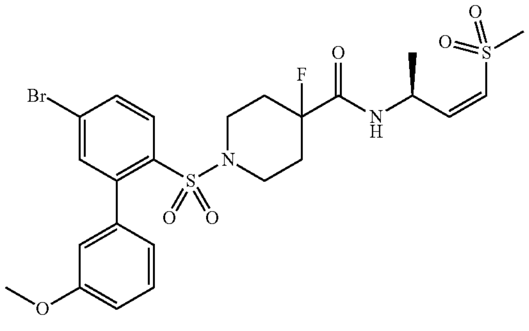 | 61 | (S,Z)-1-((5-bromo-3'-methoxy-[1,1'-biphenyl]-2-yl)sulfonyl)-4-fluoro-N-(4-(methylsulfonyl)but-3-en-2-yl)piperidine-4-carboxamide |
| 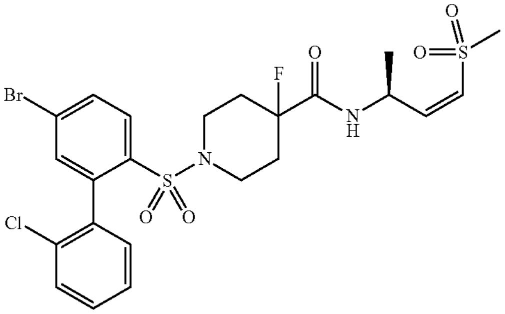 [SMILES: C[C@@H](/C=C\S(C)(=O)=O)NC(=O)C1(F)CCN(S(=O)(=O)c2ccc(Br)cc2-c2ccccc2Cl)CC1] | 62 | (S,Z)-1-((5-bromo-2'-chloro-[1,1'-biphenyl]-2-yl)sulfonyl)-4-fluoro-N-(4-(methylsulfonyl) but-3-en-2-yl)piperidine-4-carboxamide |
| 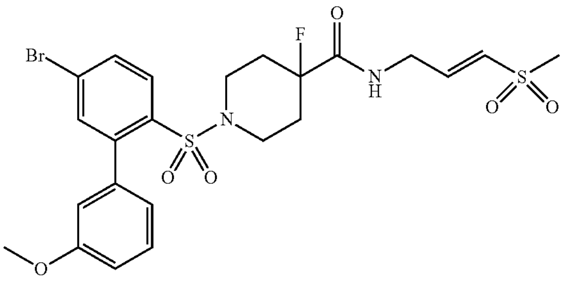 | 63 | (E)-1-((5-bromo-3'-methoxy-[1,1'-biphenyl]-2-yl)sulfonyl)-4-fluoro-N-(3-(methylsulfonyl)allyl)piperidine-4-carboxamide |
| 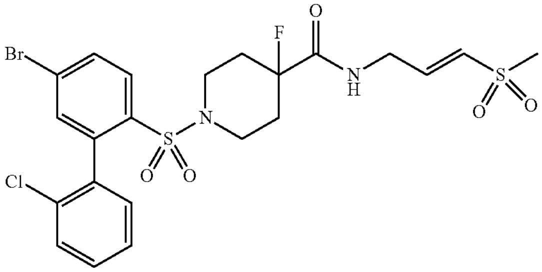 [SMILES: CS(=O)(=O)/C=C/CNC(=O)C1(F)CCN(S(=O)(=O)c2ccc(Br)cc2-c2ccccc2Cl)CC1] | 64 | (E)-1-((5-bromo-2'-chloro-[1,1'-biphenyl]-2-yl)sulfonyl)-4-fluoro-N-(3-(methylsulfonyl)allyl)piperidine-4-carboxamide |

TABLE 1-continued

| Compounds of the Disclosure. | | |
|---|---|---|
| Structure | Cmp. No. | IUPAC |
| 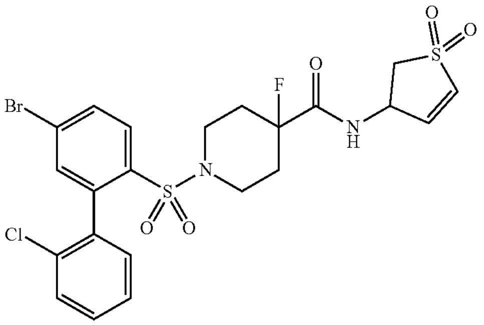 [SMILES: O=C(NC1C=CS(=O)(=O)C1)C1(F)CCN(S(=O)(=O)c2ccc(Br)cc2-c2ccccc2Cl)CC1] | 65 | rac-1-((5-bromo-2'-chloro-[1,1'-biphenyl]-2-yl)sulfonyl)-N-(1,1-dioxido-2,3-dihydrothiophen-3-yl)-4-fluoropiperidine-4-carboxamide |
| 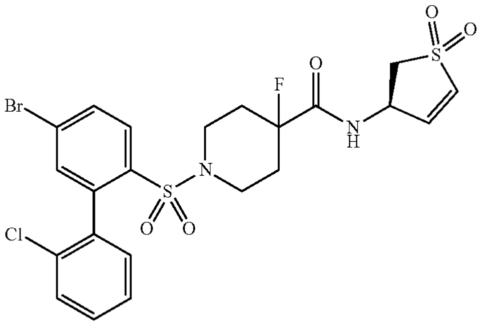 [SMILES: O=C(N[C@@H]1C=CS(=O)(=O)C1)C1(F)CCN(S(=O)(=O)c2ccc(Br)cc2-c2ccccc2Cl)CC1] | 66 | (R)-1-((5-bromo-2'-chloro-[1,1'-biphenyl]-2-yl)sulfonyl)-N-(1,1-dioxido-2,3-dihydrothiophen-3-yl)-4-fluoropiperidine-4-carboxamide |
| 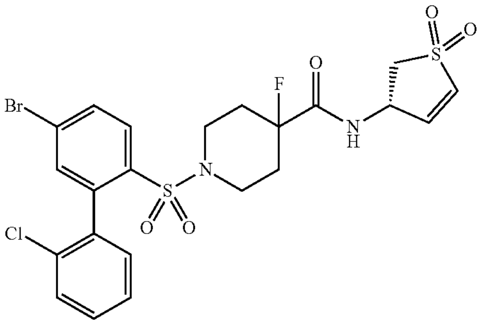 [SMILES: O=C(N[C@H]1C=CS(=O)(=O)C1)C1(F)CCN(S(=O)(=O)c2ccc(Br)cc2-c2ccccc2Cl)CC1] | 67 | (S)-1-((5-bromo-2'-chloro-[1,1'-biphenyl]-2-yl)sulfonyl)-N-(1,1-dioxido-2,3-dihydrothiophen-3-yl)-4-fluoropiperidine-4-carboxamide |
| 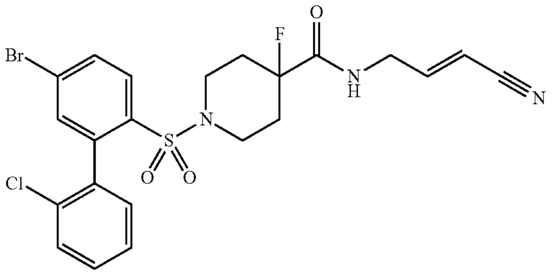 | 68 | (E)-1-((5-bromo-2'-chloro-[1,1'-biphenyl]-2-yl)sulfonyl)-N-(3-cyanoallyl)-4-fluoropiperidine-4-carboxamide |
| 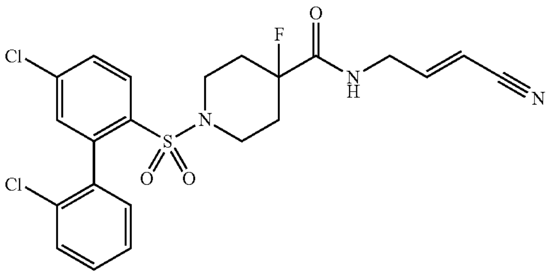 [SMILES: N#C/C=C/CNC(=O)C1(F)CCN(S(=O)(=O)c2ccc(Cl)cc2-c2ccccc2Cl)CC1] | 69 | (E)-N-(3-cyanoallyl)-1-((2',5-dichloro-[1,1'-biphenyl]-2-yl)sulfonyl)-4-fluoropiperidine-4-carboxamide |

TABLE 1-continued

| Compounds of the Disclosure. | | |
|---|---|---|
| Structure | Cmp. No. | IUPAC |
| 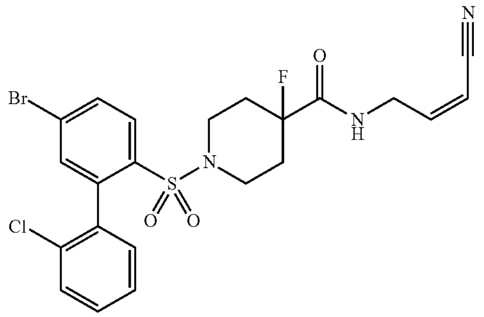 [SMILES: N#C/C=C\CNC(=O)C1(F)CCN(S(=O)(=O)c2ccc(Br)cc2-c2ccccc2Cl)CC1] | 70 | (Z)-1-((5-bromo-2'-chloro-[1,1'-biphenyl]-2-yl)sulfonyl)-N-(3-cyanoallyl)-4-fluoropiperidine-4-carboxamide |
| 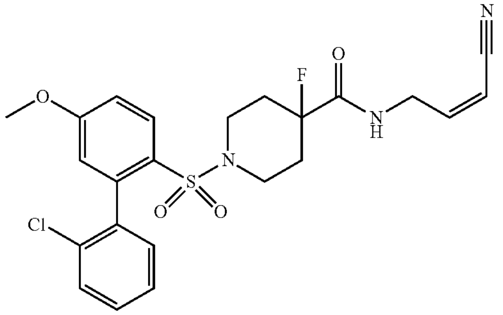 [SMILES: COc1ccc(S(=O)(=O)N2CCC(F)(C(=O)NC/C=C\C#N)CC2)c(-c2ccccc2Cl)c1] | 71 | (Z)-1-((2'-chloro-5-methoxy-[1,1'-biphenyl]-2-yl)sulfonyl)-N-(3-cyanoallyl)-4-fluoropiperidine-4-carboxamide |
| 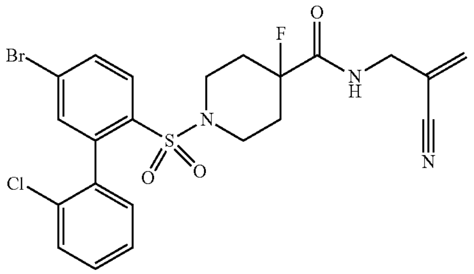 [SMILES: C=C(C#N)CNC(=O)C1(F)CCN(S(=O)(=O)c2ccc(Br)cc2-c2ccccc2Cl)CC1] | 72 | 1-((5-bromo-2'-chloro-[1,1'-biphenyl]-2-yl)sulfonyl)-N-(2-cyanoallyl)-4-fluoropiperidine-4-carboxamide |
| 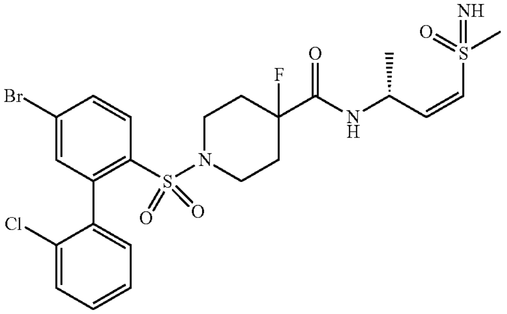 [SMILES: C[C@H](/C=C\S(C)(=N)=O)NC(=O)C1(F)CCN(S(=O)(=O)c2ccc(Br)cc2-c2ccccc2Cl)CC1] | 73 | 1-((5-bromo-2'-chloro-[1,1'-biphenyl]-2-yl)sulfonyl)-4-fluoro-N-((2R,Z)-4-((RS)-(S-methylsulfonimidoyl)but-3-en-2-yl)piperidine-4-carboxamide |

TABLE 1-continued

| Compounds of the Disclosure. | | |
|---|---|---|
| Structure | Cmp. No. | IUPAC |
| 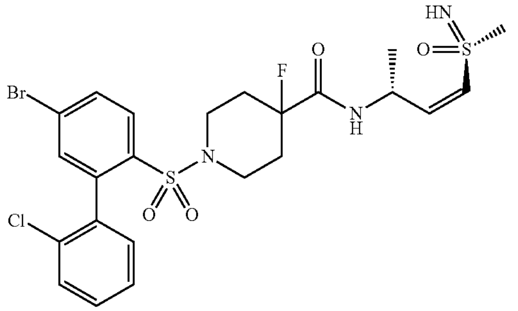 [SMILES: C[C@H](/C=C\[S@](C)(=N)=O)NC(=O)C1(F)CCN(S(=O)(=O)c2ccc(Br)cc2-c2ccccc2Cl)CC1] | 74 | 1-((5-bromo-2'-chloro-[1,1'-biphenyl]-2-yl)sulfonyl)-4-fluoro-N-((R,Z)-4-((*R)-S-methylsulfonimidoyl)but-3-en-2-yl)piperidine-4-carboxamide |
| 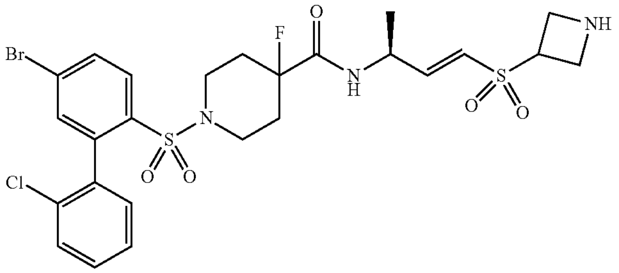 [SMILES: C[C@@H](/C=C/S(=O)(=O)C1CNC1)NC(=O)C1(F)CCN(S(=O)(=O)c2ccc(Br)cc2-c2ccccc2Cl)CC1] | 75 | (S,E)-N-(4-(azetidin-3-ylsulfonyl)but-3-en-2-yl)-1-((5-bromo-2'-chloro-[1,1'-biphenyl]-2-yl)sulfonyl)-4-fluoropiperidine-4-carboxamide |
| 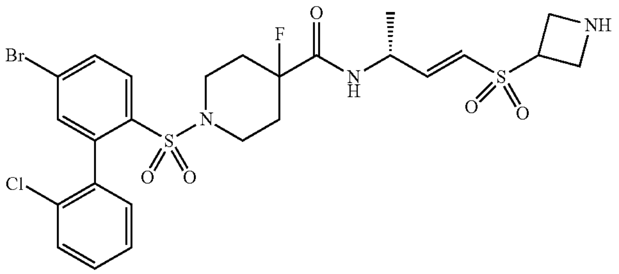 [SMILES: C[C@H](/C=C/S(=O)(=O)C1CNC1)NC(=O)C1(F)CCN(S(=O)(=O)c2ccc(Br)cc2-c2ccccc2Cl)CC1] | 76 | (R,E)-N-(4-(azetidin-3-ylsulfonyl)but-3-en-2-yl)-1-((5-bromo-2'-chloro-[1,1'-biphenyl]-2-yl)sulfonyl)-4-fluoropiperidine-4-carboxamide |
| 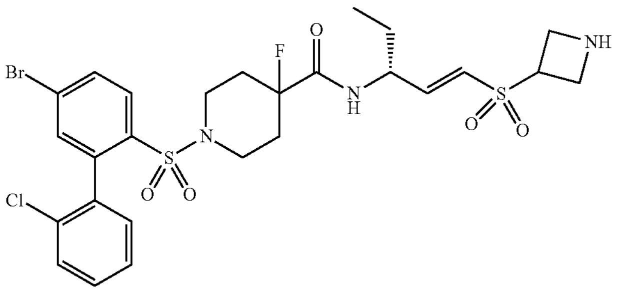 [SMILES: CC[C@H](/C=C/S(=O)(=O)C1CNC1)NC(=O)C1(F)CCN(S(=O)(=O)c2ccc(Br)cc2-c2ccccc2Cl)CC1] | 77 | (R,E)-N-(1-(azetidin-3-ylsulfonyl)pent-1-en-3-yl)-1-((5-bromo-2'-chloro-[1,1'-biphenyl]-2-yl)sulfonyl)-4-fluoropiperidine-4-carboxamide |
| 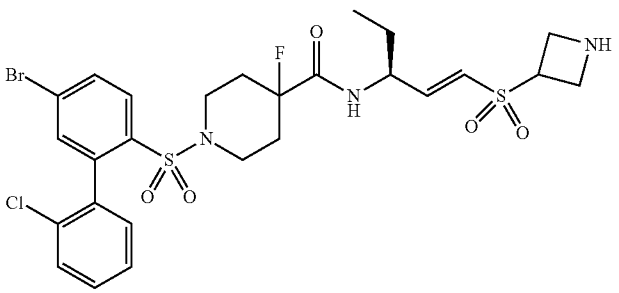 [SMILES: CC[C@@H](/C=C/S(=O)(=O)C1CNC1)NC(=O)C1(F)CCN(S(=O)(=O)c2ccc(Br)cc2-c2ccccc2Cl)CC1] | 78 | (S,E)-N-(1-(azetidin-3-ylsulfonyl)pent-1-en-3-yl)-1-((5-bromo-2'-chloro-[1,1'-biphenyl]-2-yl)sulfonyl)-4-fluoropiperidine-4-carboxamide |

TABLE 1-continued

| Compounds of the Disclosure. | | |
|---|---|---|
| Structure | Cmp. No. | IUPAC |
| 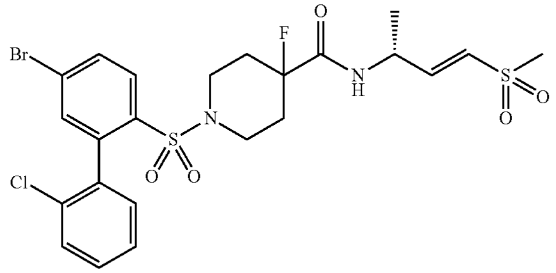 [SMILES: C[C@H](/C=C/S(C)(=O)=O)NC(=O)C1(F)CCN(S(=O)(=O)c2ccc(Br)cc2-c2ccccc2Cl)CC1] | 79 | (R,E)-1-((5-bromo-2'-chloro-[1,1'-biphenyl]-2-yl)sulfonyl)-4-fluoro-N-(4-(methylsulfonyl)but-3-en-2-yl)piperidine-4-carboxamide |
| 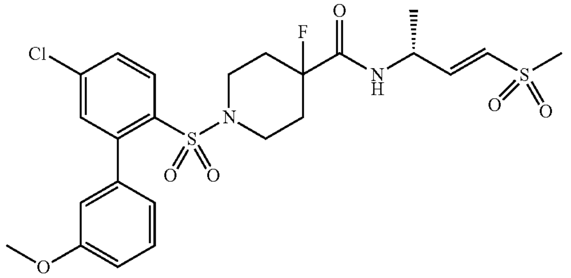 | 80 | (R,E)-1-((5-chloro-3'-methoxy-[1,1'-biphenyl]-2-yl)sulfonyl)-4-fluoro-N-(4-(methylsulfonyl)but-3-en-2-yl)piperidine-4-carboxamide |
| 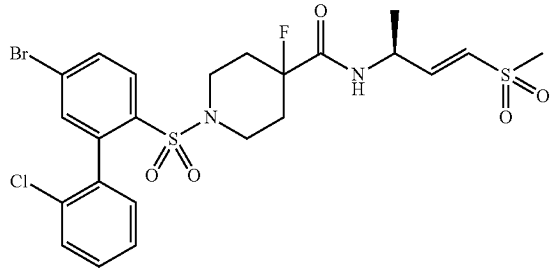 [SMILES: C[C@@H](/C=C/S(C)(=O)=O)NC(=O)C1(F)CCN(S(=O)(=O)c2ccc(Br)cc2-c2ccccc2Cl)CC1] | 81 | (S,E)-1-((5-bromo-2'-chloro-[1,1'-biphenyl]-2-yl)sulfonyl)-4-fluoro-N-(4-(methylsulfonyl)but-3-en-2-yl)piperidine-4-carboxamide |
| 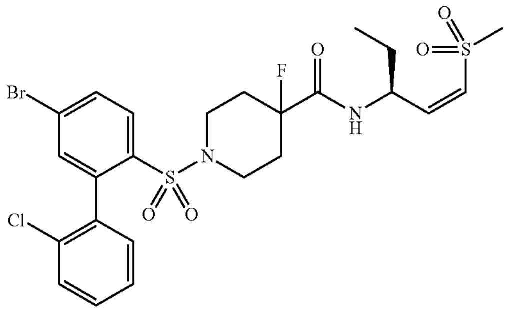 [SMILES: CC[C@@H](/C=C\S(C)(=O)=O)NC(=O)C1(F)CCN(S(=O)(=O)c2ccc(Br)cc2-c2ccccc2Cl)CC1] | 82 | (S,Z)-1-((5-bromo-2'-chloro-[1,1'-biphenyl]-2-yl)sulfonyl)-4-fluoro-N-(1-(methylsulfonyl)pent-1-en-3-yl)piperidine-4-carboxamide |
| 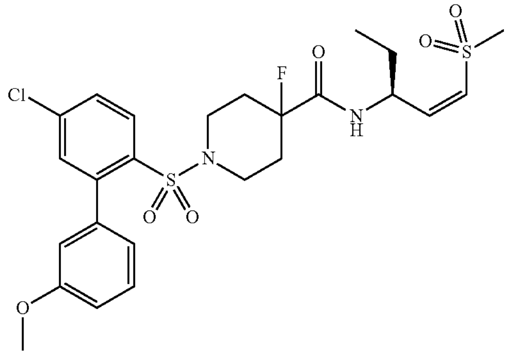 [SMILES: CC[C@@H](/C=C\S(C)(=O)=O)NC(=O)C1(F)CCN(S(=O)(=O)c2ccc(Cl)cc2-c2cccc(OC)c2)CC1] | 83 | (S,Z)-1-((5-chloro-3'-methoxy-[1,1'-biphenyl]-2-yl)sulfonyl)-4-fluoro-N-(1-(methylsulfonyl)pent-1-en-3-yl)piperidine-4-carboxamide |

TABLE 1-continued

Compounds of the Disclosure.

| Structure | Cmp. No. | IUPAC |
|---|---|---|
| 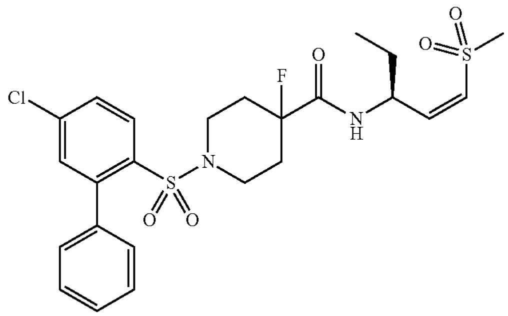 [SMILES: CC[C@@H](/C=C\S(C)(=O)=O)NC(=O)C1(F)CCN(S(=O)(=O)c2ccc(Cl)cc2-c2ccccc2)CC1] | 84 | (S,Z)-1-((5-chloro-[1,1'-biphenyl]-2-yl)sulfonyl)-4-fluoro-N-(1-(methylsulfonyl)pent-1-en-3-yl)piperidine-4-carboxamide |
| 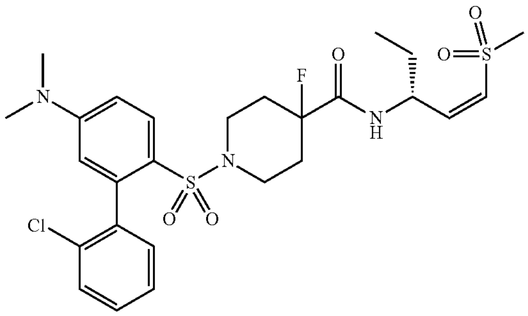 | 85 | (R,Z)-1-((2'-chloro-5-(dimethylamino)-[1,1'-biphenyl]-2-yl)sulfonyl)-4-fluoro-N-(1-(methylsulfonyl)pent-1-en-3-yl)piperidine-4-carboxamide |
| 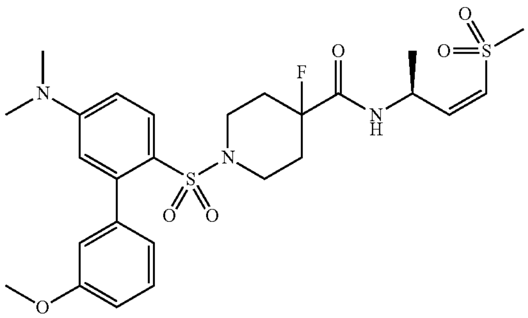 | 86 | (S,Z)-1-((5-(dimethylamino)-3'-methoxy-[1,1'-biphenyl]-2-yl)sulfonyl)-4-fluoro-N-(4-(methylsulfonyl)but-3-en-2-yl)piperidine-4-carboxamide |
| 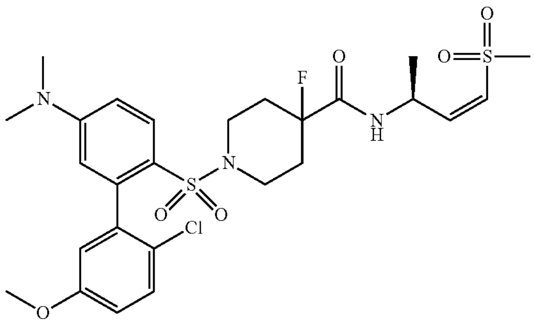 | 87 | (S,Z)-1-((2'-chloro-5-(dimethylamino)-5'-methoxy-[1,1'-biphenyl]-2-yl)sulfonyl)-4-fluoro-N-(4-(methylsulfonyl)but-3-en-2-yl)piperidine-4-carboxamide |

TABLE 1-continued

| Compounds of the Disclosure. | | |
|---|---|---|
| Structure | Cmp. No. | IUPAC |
| 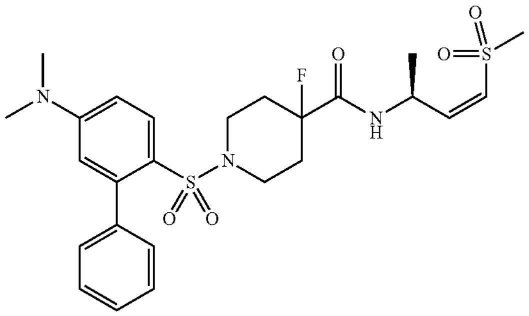 | 88 | (S,Z)-1-((5-(dimethylamino)-[1,1'-biphenyl]-2-yl)sulfonyl)-4-fluoro-N-(4-(methylsulfonyl)but-3-en-2-yl)piperidine-4-carboxamide |
| 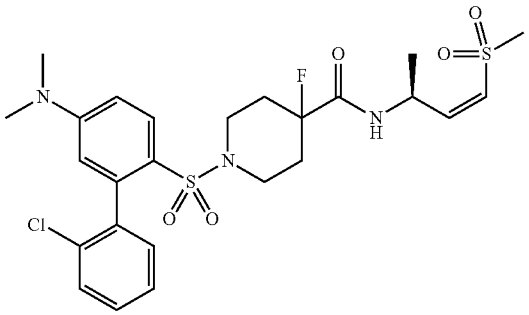 | 89 | (S,Z)-1-((2'-chloro-5-(dimethylamino)-[1,1'-biphenyl]-2-yl)sulfonyl)-4-fluoro-N-(4-(methylsulfonyl)but-3-en-2-yl)piperidine-4-carboxamide |
| 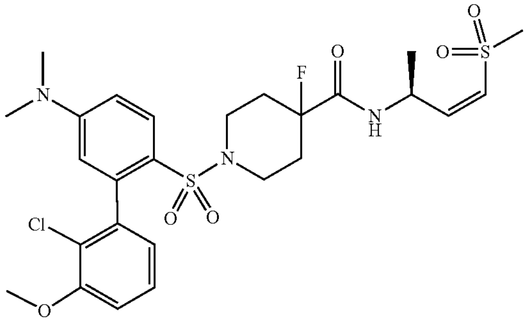 | 90 | (S,Z)-1-((2'-chloro-5-(dimethylamino)-3'-methoxy-[1,1'-biphenyl]-2-yl)sulfonyl)-4-fluoro-N-(4-(methylsulfonyl)but-3-en-2-yl)piperidine-4-carboxamide |
| 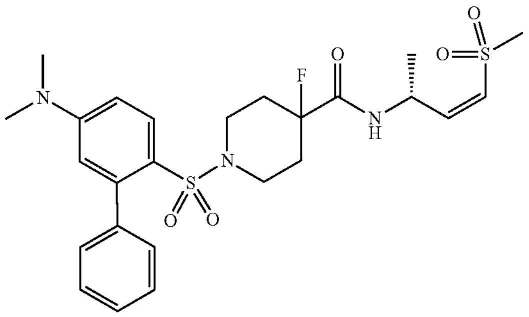 | 91 | (R,Z)-1-((5-(dimethylamino)-[1,1'-biphenyl]-2-yl)sulfonyl)-4-fluoro-N-(4-(methylsulfonyl)but-3-en-2-yl)piperidine-4-carboxamide |

TABLE 1-continued

Compounds of the Disclosure.

| Structure | Cmp. No. | IUPAC |
|---|---|---|
| 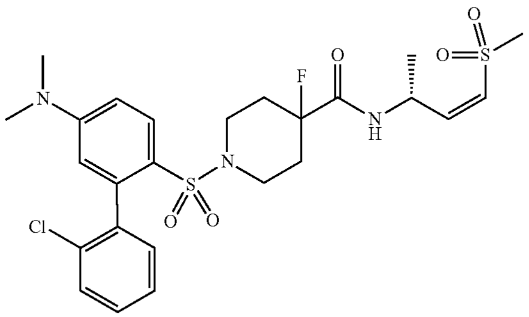 | 92 | (R,Z)-1-((2'-chloro-5-(dimethylamino)-[1,1'-biphenyl]-2-yl)sulfonyl)-4-fluoro-N-(4-(methylsulfonyl)but-3-en-2-yl)piperidine-4-carboxamide |
| 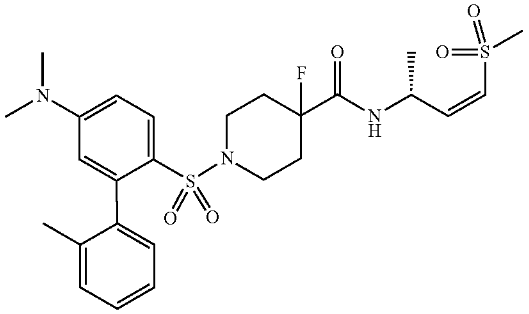 | 93 | (R,Z)-1-((5-(dimethylamino)-2'-methyl-[1,1'-biphenyl]-2-yl)sulfonyl)-4-fluoro-N-(4-(methylsulfonyl)but-3-en-2-yl)piperidine-4-carboxamide |
| 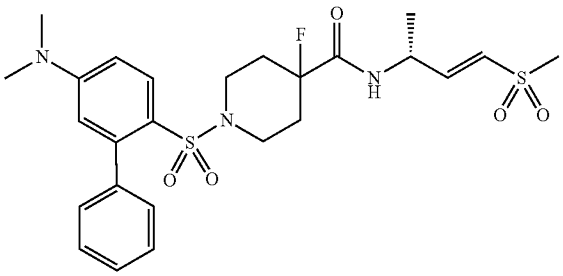 | 94 | (E)-1-((5-(dimethylamino)-[1,1'-biphenyl]-2-yl)sulfonyl)-4-fluoro-N-(3-(methylsulfonyl)allyl)piperidine-4-carboxamide |
| 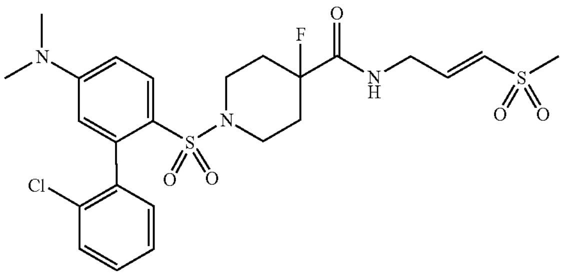 | 95 | (E)-1-((2'-chloro-5-(dimethylamino)-[1,1'-biphenyl]-2-yl)sulfonyl)-4-fluoro-N-(3-(methylsulfonyl)allyl)piperidine-4-carboxamide |
| 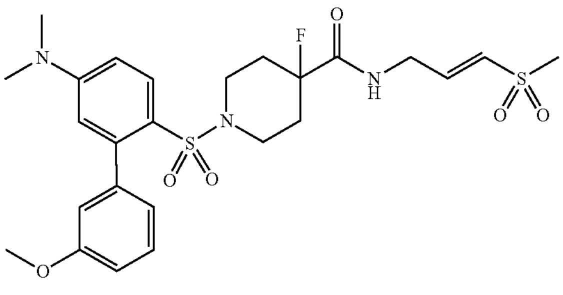 | 96 | (E)-1-((5-(dimethylamino)-3'-methoxy-[1,1'-biphenyl]-2-yl)sulfonyl)-4-fluoro-N-(3-(methylsulfonyl)allyl)piperidine-4-carboxamide |

TABLE 1-continued

| Compounds of the Disclosure. | | |
|---|---|---|
| Structure | Cmp. No. | IUPAC |
| 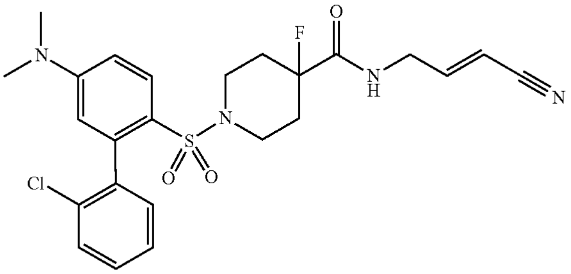 [SMILES: CN(C)c1ccc(S(=O)(=O)N2CCC(F)(C(=O)NC/C=C/C#N)CC2)c(-c2ccccc2Cl)c1] | 97 | (E)-1-((2'-chloro-5-(dimethylamino)-[1,1'-biphenyl]-2-yl)sulfonyl)-N-(3-cyanoallyl)-4-fluoropiperidine-4-carboxamide |
| 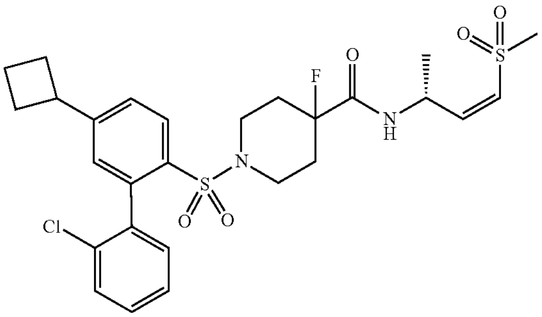 [SMILES: C[C@H](/C=C\S(C)(=O)=O)NC(=O)C1(F)CCN(S(=O)(=O)c2ccc(C3CCC3)cc2-c2ccccc2Cl)CC1] | 98 | (R,Z)-1-((2'-chloro-5-cyclobutyl-[1,1'-biphenyl]-2-yl)sulfonyl)-4-fluoro-N-(4-(methylsulfonyl)but-3-en-2-yl)piperidine-4-carboxamide |
| 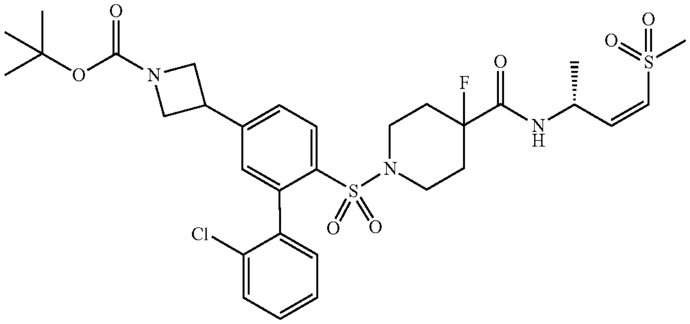 [SMILES: C[C@H](/C=C\S(C)(=O)=O)NC(=O)C1(F)CCN(S(=O)(=O)c2ccc(C3CN(C(=O)OC(C)(C)C)C3)cc2-c2ccccc2Cl)CC1] | 99 | tert-butyl (R,Z)-3-(2'-chloro-6-((4-fluoro-4-((4-(methylsulfonyl)but-3-en-2-yl)carbamoyl)piperidin-1-yl)sulfonyl)-[1,1'-biphenyl]-3-yl)azetidine-1-carboxylate |
| 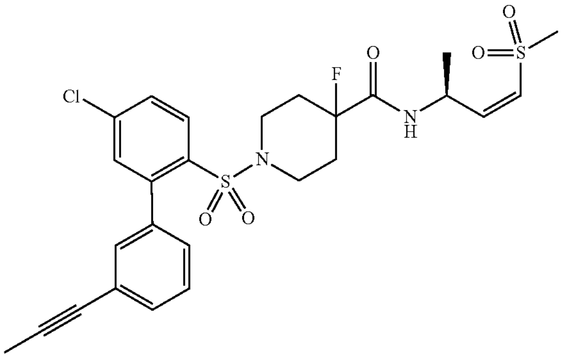 [SMILES: CC#Cc1cccc(-c2cc(Cl)ccc2S(=O)(=O)N2CCC(F)(C(=O)N[C@@H](C)/C=C\S(C)(=O)=O)CC2)c1] | 100 | (S,Z)-1-((5-chloro-3'-(prop-1-yn-1-yl)-[1,1'-biphenyl]-2-yl)sulfonyl)-4-fluoro-N-(4-(methylsulfonyl)but-3-en-2-yl)piperidine-4-carboxamide |

TABLE 1-continued

| Compounds of the Disclosure. | | |
|---|---|---|
| Structure | Cmp. No. | IUPAC |
| 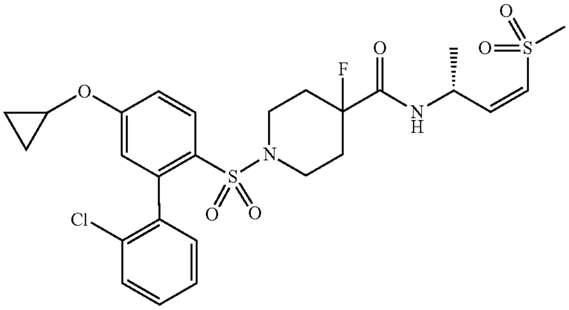 [SMILES: C[C@H](/C=C\S(C)(=O)=O)NC(=O)C1(F)CCN(S(=O)(=O)c2ccc(OC3CC3)cc2-c2ccccc2Cl)CC1] | 101 | (R,Z)-1-((2'-chloro-5-cyclopropoxy-[1,1'-biphenyl]-2-yl)sulfonyl)-4-fluoro-N-(4-(methylsulfonyl)but-3-en-2-yl)piperidine-4-carboxamide |
| 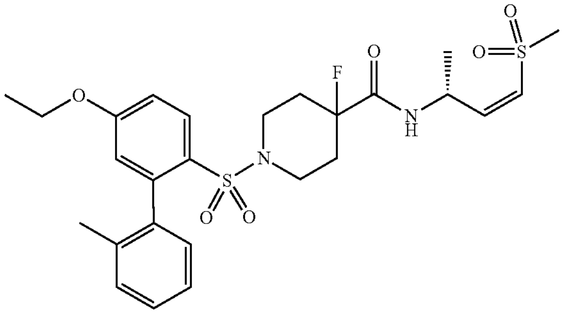 [SMILES: CCOc1ccc(S(=O)(=O)N2CCC(F)(C(=O)N[C@H](C)/C=C\S(C)(=O)=O)CC2)c(-c2ccccc2C)c1] | 102 | (R,Z)-1-((5-ethoxy-2'-methyl-[1,1'-biphenyl]-2-yl)sulfonyl)-4-fluoro-N-(4-(methylsulfonyl)but-3-en-2-yl)piperidine-4-carboxamide |
| 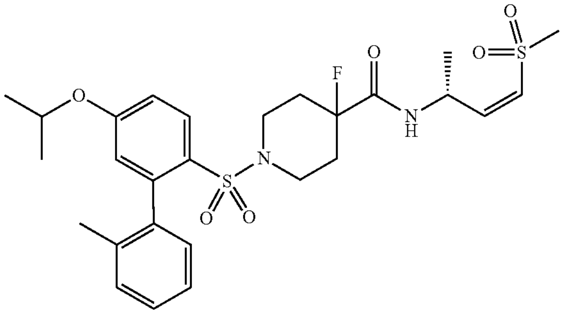 [SMILES: Cc1ccccc1-c1cc(OC(C)C)ccc1S(=O)(=O)N1CCC(F)(C(=O)N[C@H](C)/C=C\S(C)(=O)=O)CC1] | 103 | (R,Z)-4-fluoro-1-((5-isopropoxy-2'-methyl-[1,1'-biphenyl]-2-yl)sulfonyl)-N-(4-(methylsulfonyl)but-3-en-2-yl)piperidine-4-carboxamide |
| 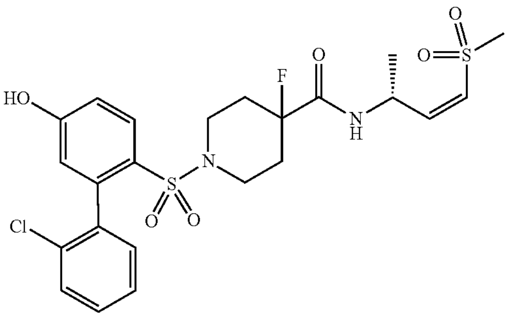 [SMILES: C[C@H](/C=C\S(C)(=O)=O)NC(=O)C1(F)CCN(S(=O)(=O)c2ccc(O)cc2-c2ccccc2Cl)CC1] | 104 | (R,Z)-1-((2'-chloro-5-hydroxy-[1,1'-biphenyl]-2-yl)sulfonyl)-4-fluoro-N-(4-(methylsulfonyl)but-3-en-2-yl)piperidine-4-carboxamide |

TABLE 1-continued

Compounds of the Disclosure.

| Structure | Cmp. No. | IUPAC |
|---|---|---|
| 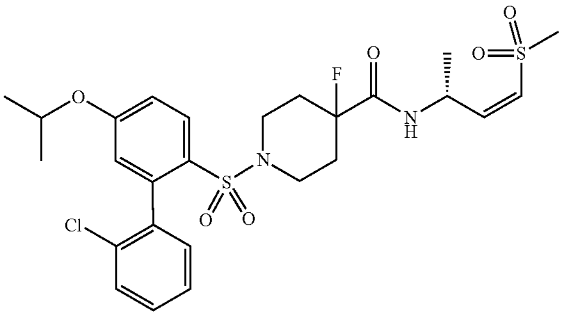 [SMILES: CC(C)Oc1ccc(S(=O)(=O)N2CCC(F)(C(=O)N[C@H](C)/C=C\S(C)(=O)=O)CC2)c(-c2ccccc2Cl)c1] | 105 | (R,Z)-1-((2'-chloro-5-isopropoxy-[1,1'-biphenyl]-2-yl)sulfonyl)-4-fluoro-N-(4-(methylsulfonyl)but-3-en-2-yl)piperidine-4-carboxamide |
| 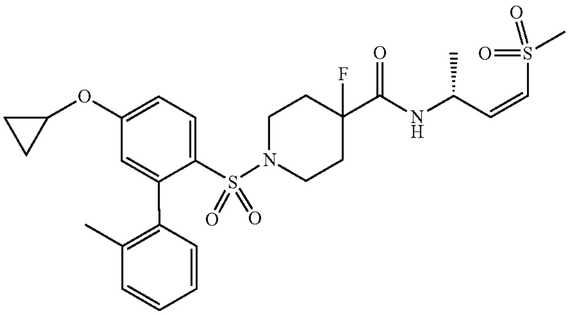 [SMILES: Cc1ccccc1-c1cc(OC2CC2)ccc1S(=O)(=O)N1CCC(F)(C(=O)N[C@H](C)/C=C\S(C)(=O)=O)CC1] | 106 | (R,Z)-1-((5-cyclopropoxy-2'-methyl-[1,1'-biphenyl]-2-yl)sulfonyl)-4-fluoro-N-(4-(methylsulfonyl)but-3-en-2-yl)piperidine-4-carboxamide |
| 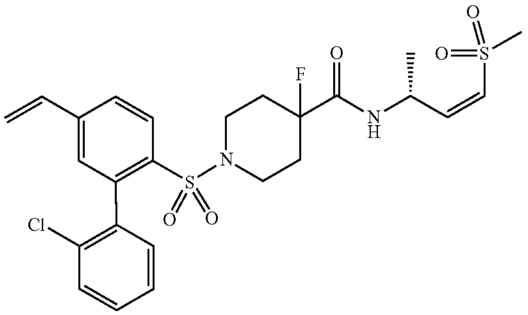 [SMILES: C=Cc1ccc(S(=O)(=O)N2CCC(F)(C(=O)N[C@H](C)/C=C\S(C)(=O)=O)CC2)c(-c2ccccc2Cl)c1] | 107 | (R,Z)-1-((2'-chloro-5-vinyl-[1,1'-biphenyl]-2-yl)sulfonyl)-4-fluoro-N-(4-(methylsulfonyl) but-3-en-2-yl)piperidine-4-carboxamide |
| 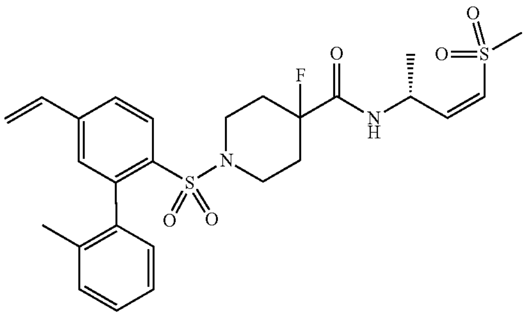 [SMILES: C=Cc1ccc(S(=O)(=O)N2CCC(F)(C(=O)N[C@H](C)/C=C\S(C)(=O)=O)CC2)c(-c2ccccc2C)c1] | 108 | (R,Z)-4-fluoro-1-((2'-methyl-5-vinyl-[1,1'-biphenyl]-2-yl)sulfonyl)-N-(4-(methylsulfonyl)but-3-en-2-yl)piperidine-4-carboxamide |

TABLE 1-continued

| Compounds of the Disclosure. | | |
|---|---|---|
| Structure | Cmp. No. | IUPAC |
| 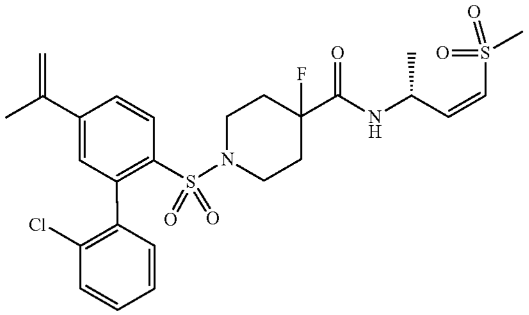 [SMILES: C=C(C)c1ccc(S(=O)(=O)N2CCC(F)(C(=O)N[C@H](C)/C=C\S(C)(=O)=O)CC2)c(-c2ccccc2Cl)c1] | 109 | (R,Z)-1-((2'-chloro-5-(prop-1-en-2-yl)-[1,1'-biphenyl]-2-yl)sulfonyl)-4-fluoro-N-(4-(methylsulfonyl)but-3-en-2-yl)piperidine-4-carboxamide |
| 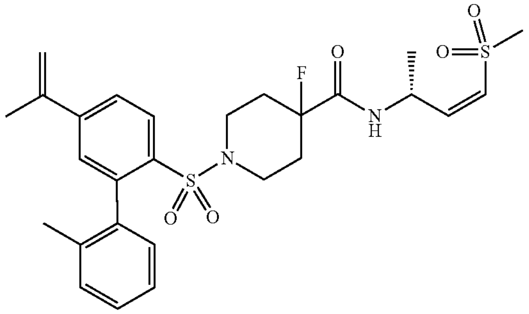 [SMILES: C=C(C)c1ccc(S(=O)(=O)N2CCC(F)(C(=O)N[C@H](C)/C=C\S(C)(=O)=O)CC2)c(-c2ccccc2C)c1] | 110 | (R,Z)-4-fluoro-1-((2'-methyl-5-(prop-1-en-2-yl)-[1,1'-biphenyl]-2-yl)sulfonyl)-N-(4-(methylsulfonyl)but-3-en-2-yl)piperidine-4-carboxamide |
| 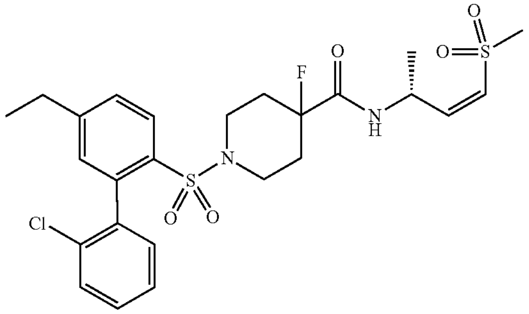 [SMILES: CCc1ccc(S(=O)(=O)N2CCC(F)(C(=O)N[C@H](C)/C=C\S(C)(=O)=O)CC2)c(-c2ccccc2Cl)c1] | 111 | (R,Z)-1-((2'-chloro-5-ethyl-[1,1'-biphenyl]-2-yl)sulfonyl)-4-fluoro-N-(4-(methylsulfonyl) but-3-en-2-yl)piperidine-4-carboxamide |
| 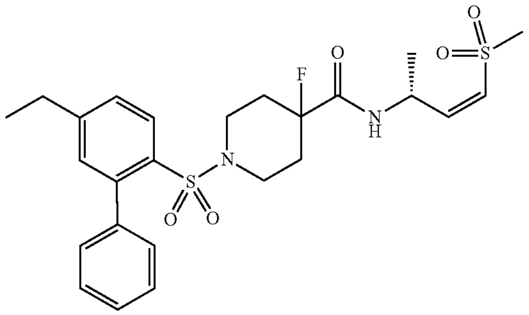 [SMILES: CCc1ccc(S(=O)(=O)N2CCC(F)(C(=O)N[C@H](C)/C=C\S(C)(=O)=O)CC2)c(-c2ccccc2)c1] | 112 | (R,Z)-1-((5-ethyl-[1,1'-biphenyl]-2-yl) sulfonyl)-4-fluoro-N-(4-(methylsulfonyl)but-3-en-2-yl)piperidine-4-carboxamide |

TABLE 1-continued

| Compounds of the Disclosure. | | |
|---|---|---|
| Structure | Cmp. No. | IUPAC |
| 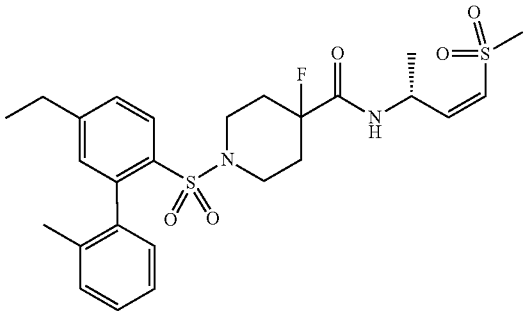 [SMILES: CCc1ccc(S(=O)(=O)N2CCC(F)(C(=O)N[C@H](C)/C=C\S(C)(=O)=O)CC2)c(-c2ccccc2C)c1] | 113 | (R,Z)-1-((5-ethyl-2'-methyl-[1,1'-biphenyl]-2-yl)sulfonyl)-4-fluoro-N-(4-(methylsulfonyl) but-3-en-2-yl)piperidine-4-carboxamide |
| 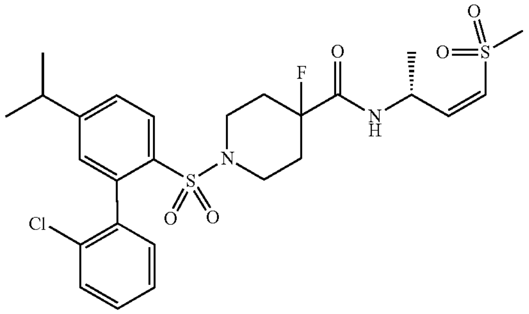 [SMILES: CC(C)c1ccc(S(=O)(=O)N2CCC(F)(C(=O)N[C@H](C)/C=C\S(C)(=O)=O)CC2)c(-c2ccccc2Cl)c1] | 114 | (R,Z)-1-((2'-chloro-5-isopropyl-[1,1'-biphenyl]-2-yl)sulfonyl)-4-fluoro-N-(4-(methylsulfonyl)but-3-en-2-yl)piperidine-4-carboxamide |
| 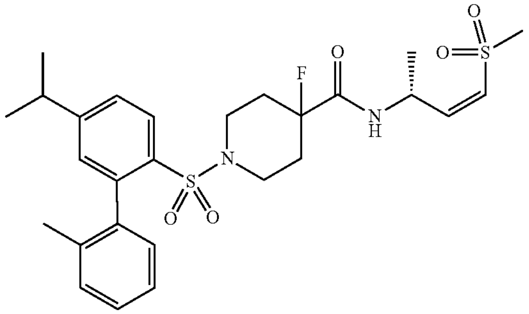 [SMILES: Cc1ccccc1-c1cc(C(C)C)ccc1S(=O)(=O)N1CCC(F)(C(=O)N[C@H](C)/C=C\S(C)(=O)=O)CC1] | 115 | (R,Z)-4-fluoro-1-((5-isopropyl-2'-methyl-[1,1'-biphenyl]-2-yl)sulfonyl)-N-(4-(methylsulfonyl)but-3-en-2-yl)piperidine-4-carboxamide |
| 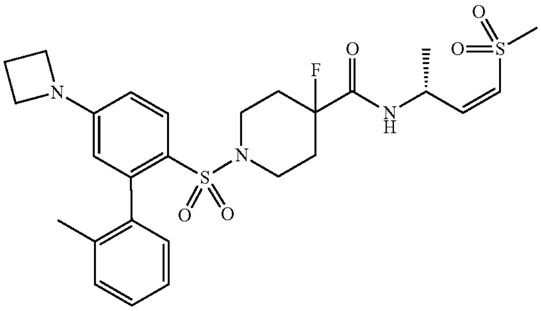 [SMILES: Cc1ccccc1-c1cc(N2CCC2)ccc1S(=O)(=O)N1CCC(F)(C(=O)N[C@H](C)/C=C\S(C)(=O)=O)CC1] | 116 | (R,Z)-1-((5-(azetidin-1-yl)-2'-methyl-[1,1'-biphenyl]-2-yl)sulfonyl)-4-fluoro-N-(4-(methylsulfonyl)but-3-en-2-yl)piperidine-4-carboxamide |

TABLE 1-continued

| Compounds of the Disclosure. | | |
|---|---|---|
| Structure | Cmp. No. | IUPAC |
| 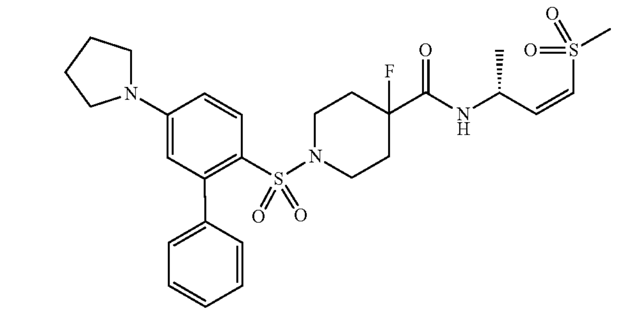 [SMILES: C[C@H](/C=C\S(C)(=O)=O)NC(=O)C1(F)CCN(S(=O)(=O)c2ccc(N3CCCC3)cc2-c2ccccc2)CC1] | 117 | (R,Z)-4-fluoro-N-(4-(methylsulfonyl)but-3-en-2-yl)-1-((5-(pyrrolidin-1-yl)-[1,1'-biphenyl]-2-yl)sulfonyl)piperidine-4-carboxamide |
| 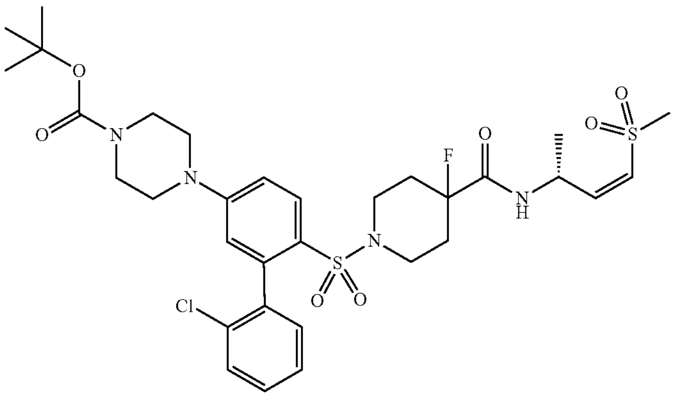 [SMILES: C[C@H](/C=C\S(C)(=O)=O)NC(=O)C1(F)CCN(S(=O)(=O)c2ccc(N3CCN(C(=O)OC(C)(C)C)CC3)cc2-c2ccccc2Cl)CC1] | 118 | tert-butyl (R,Z)-4-(2'-chloro-6-((4-fluoro-4-((4-(methylsulfonyl)but-3-en-2-yl)carbamoyl)piperidin-1-yl)sulfonyl)-[1,1'-biphenyl]-3-yl)piperazine-1-carboxylate |
| 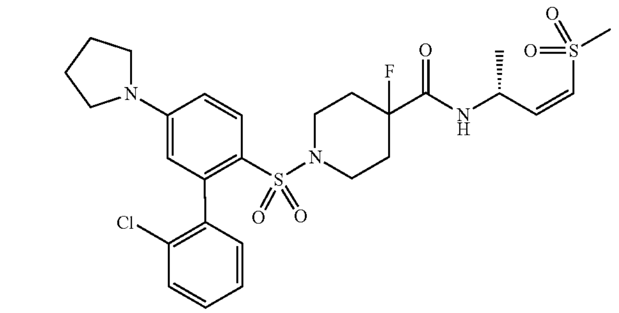 [SMILES: C[C@H](/C=C\S(C)(=O)=O)NC(=O)C1(F)CCN(S(=O)(=O)c2ccc(N3CCCC3)cc2-c2ccccc2Cl)CC1] | 119 | (R,Z)-1-((2'-chloro-5-(pyrrolidin-1-yl)-[1,1'-biphenyl]-2-yl)sulfonyl)-4-fluoro-N-(4-(methylsulfonyl)but-3-en-2-yl)piperidine-4-carboxamide |
| 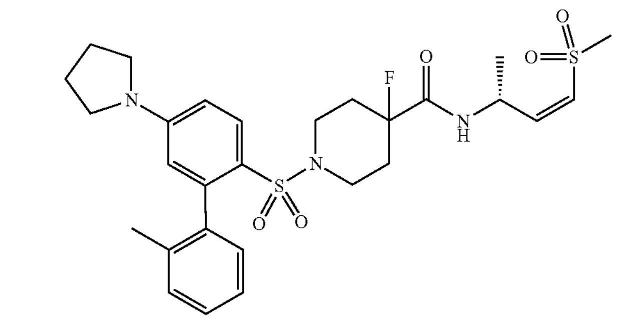 [SMILES: Cc1ccccc1-c1cc(N2CCCC2)ccc1S(=O)(=O)N1CCC(F)(C(=O)N[C@H](C)/C=C\S(C)(=O)=O)CC1] | 120 | (R,Z)-4-fluoro-1-((2'-methyl-5-(pyrrolidin-1-yl)-[1,1'-biphenyl]-2-yl)sulfonyl)-N-(4-(methylsulfonyl)but-3-en-2-yl)piperidine-4-carboxamide |

TABLE 1-continued

| Compounds of the Disclosure. | | |
|---|---|---|
| Structure | Cmp. No. | IUPAC |
| 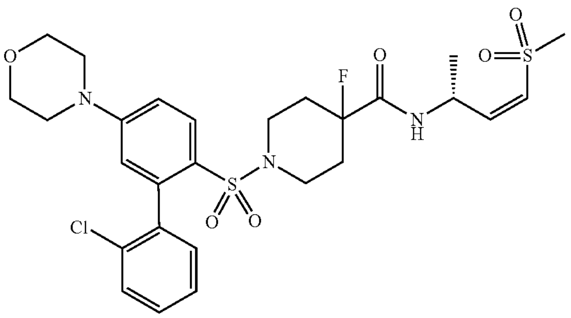 [SMILES: C[C@H](/C=C\S(C)(=O)=O)NC(=O)C1(F)CCN(S(=O)(=O)c2ccc(N3CCOCC3)cc2-c2ccccc2Cl)CC1] | 121 | (R,Z)-1-((2'-chloro-5-morpholino-[1,1'-biphenyl]-2-yl)sulfonyl)-4-fluoro-N-(4-(methylsulfonyl)but-3-en-2-yl)piperidine-4-carboxamide |
| 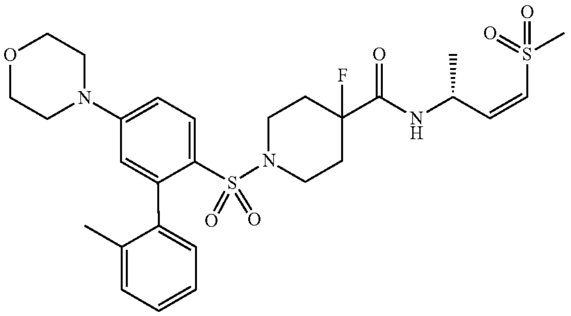 [SMILES: Cc1ccccc1-c1cc(N2CCOCC2)ccc1S(=O)(=O)N1CCC(F)(C(=O)N[C@H](C)/C=C\S(C)(=O)=O)CC1] | 122 | (R,Z)-4-fluoro-1-((2'-methyl-5-morpholino-[1,1'-biphenyl]-2-yl)sulfonyl)-N-(4-(methylsulfonyl)but-3-en-2-yl)piperidine-4-carboxamide |
| 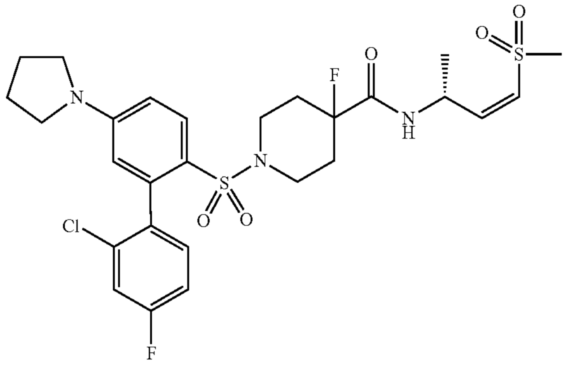 [SMILES: C[C@H](/C=C\S(C)(=O)=O)NC(=O)C1(F)CCN(S(=O)(=O)c2ccc(N3CCCC3)cc2-c2ccc(F)cc2Cl)CC1] | 123 | (R,Z)-1-((2'-chloro-4'-fluoro-5-(pyrrolidin-1-yl)-[1,1'-biphenyl]-2-yl)sulfonyl)-4-fluoro-N-(4-(methylsulfonyl)but-3-en-2-yl)piperidine-4-carboxamide |
| 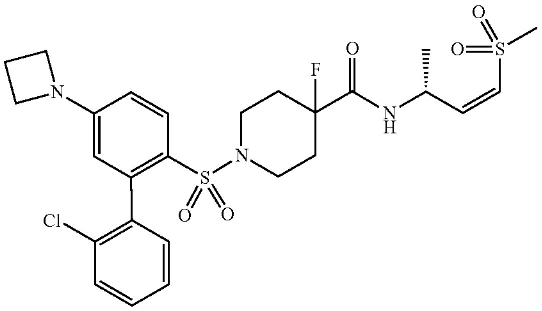 [SMILES: C[C@H](/C=C\S(C)(=O)=O)NC(=O)C1(F)CCN(S(=O)(=O)c2ccc(N3CCC3)cc2-c2ccccc2Cl)CC1] | 124 | (R,Z)-1-((5-(azetidin-1-yl)-2'-chloro-[1,1'-biphenyl]-2-yl)sulfonyl)-4-fluoro-N-(4-(methylsulfonyl)but-3-en-2-yl)piperidine-4-carboxamide |

TABLE 1-continued

| Compounds of the Disclosure. | | |
|---|---|---|
| Structure | Cmp. No. | IUPAC |
| 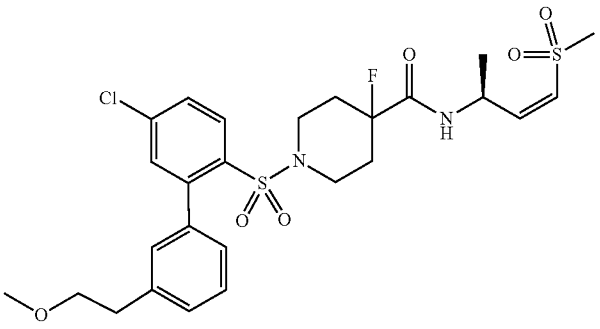 | 125 | (S,Z)-1-((5-chloro-3'-(2-methoxyethyl)-[1,1'-biphenyl]-2-yl)sulfonyl)-4-fluoro-N-(4-(methylsulfonyl)but-3-en-2-yl)piperidine-4-carboxamide |
| 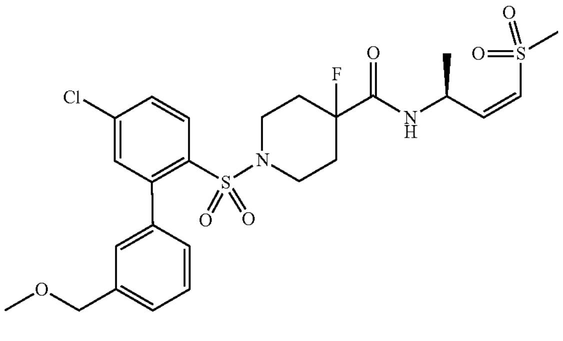 | 126 | (S,Z)-1-((5-chloro-3'-(methoxymethyl)-[1,1'-biphenyl]-2-yl)sulfonyl)-4-fluoro-N-(4-(methylsulfonyl)but-3-en-2-yl)piperidine-4-carboxamide |
| 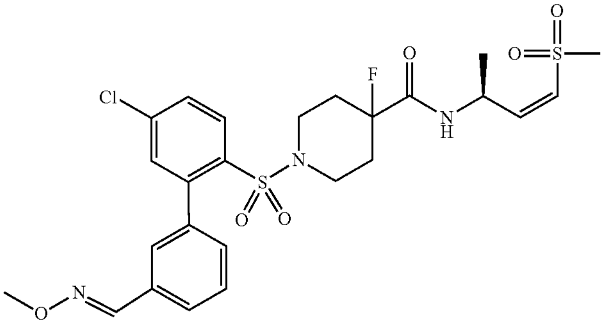 | 127 | 1-((5-chloro-3'-((E)-(methoxyimino)methyl)-[1,1'-biphenyl]-2-yl)sulfonyl)-4-fluoro-N-((S,Z)-4-(methylsulfonyl)but-3-en-2-yl) piperidine-4-carboxamide |
| 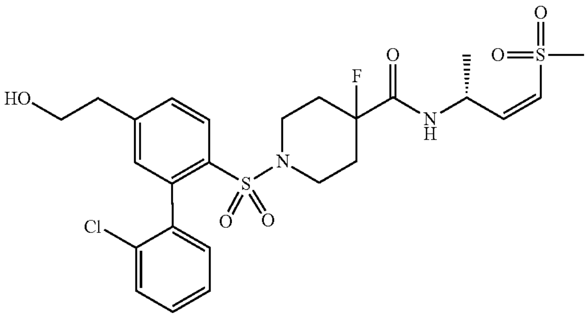 [SMILES: C[C@H](/C=C\S(C)(=O)=O)NC(=O)C1(F)CCN(S(=O)(=O)c2ccc(CCO)cc2-c2ccccc2Cl)CC1] | 128 | (R,Z)-1-((2'-chloro-5-(2-hydroxyethyl)-[1,1'-biphenyl]-2-yl)sulfonyl)-4-fluoro-N-(4-(methylsulfonyl)but-3-en-2-yl)piperidine-4-carboxamide |

TABLE 1-continued

| Structure | Cmp. No. | IUPAC |
|---|---|---|
| Compounds of the Disclosure. | | |
| 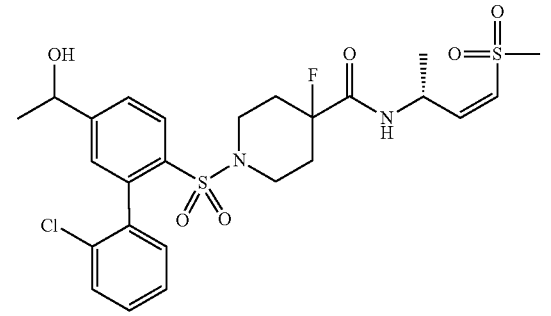 [SMILES: CC(O)c1ccc(S(=O)(=O)N2CCC(F)(C(=O)N[C@H](C)/C=C\S(C)(=O)=O)CC2)c(-c2ccccc2Cl)c1] | 129 | 1-((2'-chloro-5-(1-hydroxyethyl)-[1,1'-biphenyl]-2-yl)sulfonyl)-4-fluoro-N-((R,Z)-4-(methylsulfonyl)but-3-en-2-yl)piperidine-4-carboxamide |
| 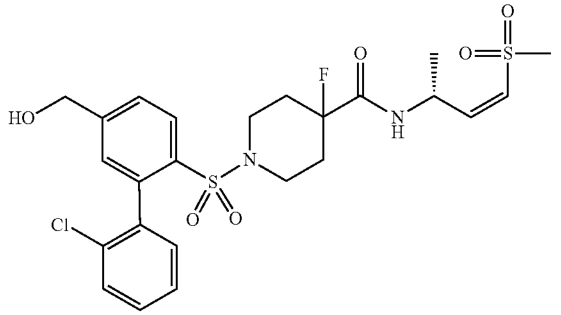 [SMILES: C[C@H](/C=C\S(C)(=O)=O)NC(=O)C1(F)CCN(S(=O)(=O)c2ccc(CO)cc2-c2ccccc2Cl)CC1] | 130 | (R,Z)-1-((2'-chloro-5-(hydroxymethyl)-[1,1'-biphenyl]-2-yl)sulfonyl)-4-fluoro-N-(4-(methylsulfonyl)but-3-en-2-yl)piperidine-4-carboxamide |
| 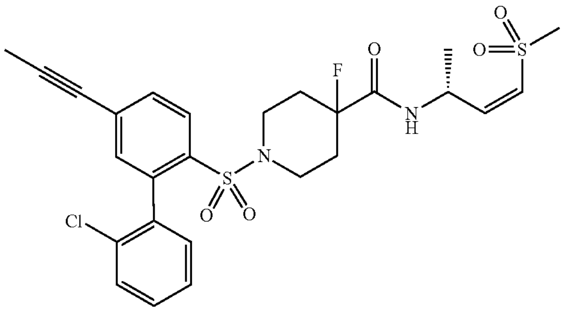 [SMILES: CC#Cc1ccc(S(=O)(=O)N2CCC(F)(C(=O)N[C@H](C)/C=C\S(C)(=O)=O)CC2)c(-c2ccccc2Cl)c1] | 131 | (R,Z)-1-((2'-chloro-5-(prop-1-yn-1-yl)-[1,1'-biphenyl]-2-yl)sulfonyl)-4-fluoro-N-(4-(methylsulfonyl)but-3-en-2-yl)piperidine-4-carboxamide |
| 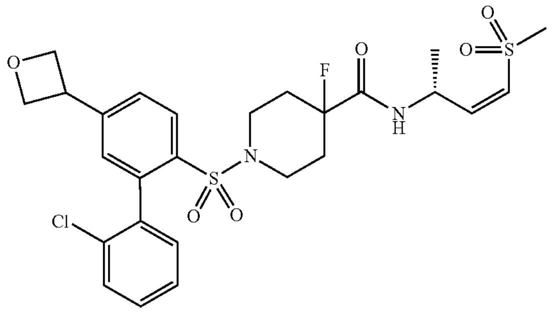 [SMILES: C[C@H](/C=C\S(C)(=O)=O)NC(=O)C1(F)CCN(S(=O)(=O)c2ccc(C3COC3)cc2-c2ccccc2Cl)CC1] | 132 | (R,Z)-1-((2'-chloro-5-(oxetan-3-yl)-[1,1'-biphenyl]-2-yl)sulfonyl)-4-fluoro-N-(4-(methylsulfonyl)but-3-en-2-yl)piperidine-4-carboxamide |

TABLE 1-continued

Compounds of the Disclosure.

| Structure | Cmp. No. | IUPAC |
| --- | --- | --- |
| 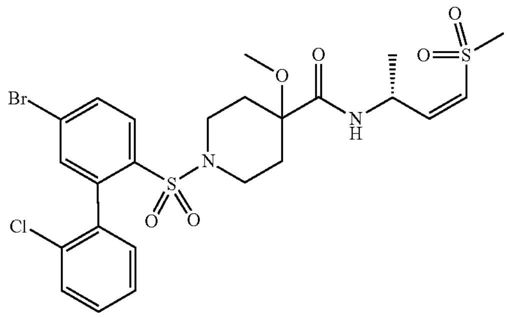 [SMILES: COC1(C(=O)N[C@H](C)/C=C\S(C)(=O)=O)CCN(S(=O)(=O)c2ccc(Br)cc2-c2ccccc2Cl)CC1] | 133 | (R,Z)-1-((5-bromo-2'-chloro-[1,1'-biphenyl]-2-yl)sulfonyl)-4-methoxy-N-(4-(methylsulfonyl)but-3-en-2-yl)piperidine-4-carboxamide |
| 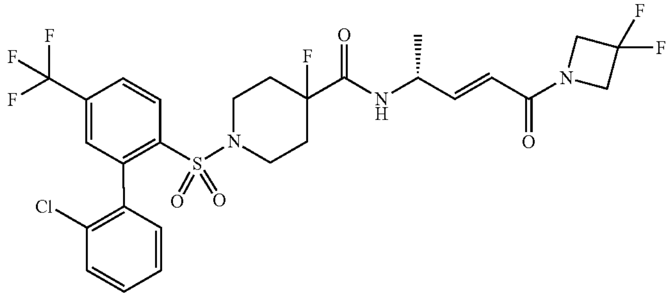 [SMILES: C[C@H](/C=C/C(=O)N1CC(F)(F)C1)NC(=O)C1(F)CCN(S(=O)(=O)c2ccc(C(F)(F)F)cc2-c2ccccc2Cl)CC1] | 134 | (R,E)-1-((2'-chloro-5-(trifluoromethyl)-[1,1'-biphenyl]-2-yl)sulfonyl)-N-(5-(3,3-difluoroazetidin-1-yl)-5-oxopent-3-en-2-yl)-4-fluoropiperidine-4-carboxamide |
| 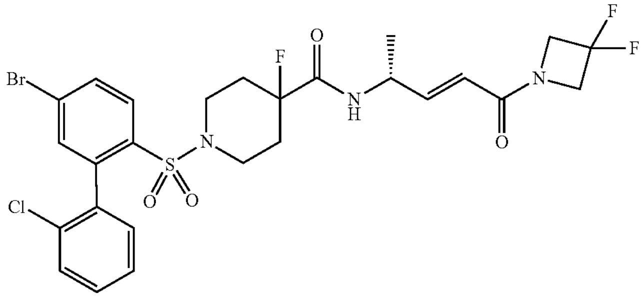 [SMILES: C[C@H](/C=C/C(=O)N1CC(F)(F)C1)NC(=O)C1(F)CCN(S(=O)(=O)c2ccc(Br)cc2-c2ccccc2Cl)CC1] | 135 | (R,E)-1-((5-bromo-2'-chloro-[1,1'-biphenyl]-2-yl)sulfonyl)-N-(5-(3,3-difluoroazetidin-1-yl)-5-oxopent-3-en-2-yl)-4-fluoropiperidine-4-carboxamide |
| 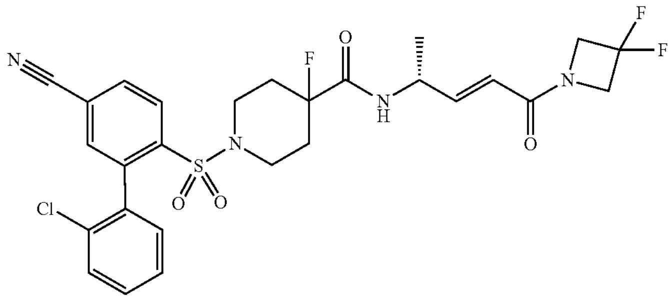 [SMILES: C[C@H](/C=C/C(=O)N1CC(F)(F)C1)NC(=O)C1(F)CCN(S(=O)(=O)c2ccc(C#N)cc2-c2ccccc2Cl)CC1] | 136 | (R,E)-1-((2'-chloro-5-cyano-[1,1'-biphenyl]-2-yl)sulfonyl)-N-(5-(3,3-difluoroazetidin-1-yl)-5-oxopent-3-en-2-yl)-4-fluoropiperidine-4-carboxamide |
| 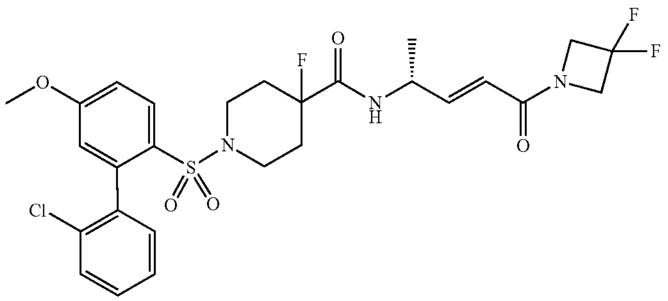 [SMILES: COc1ccc(S(=O)(=O)N2CCC(F)(C(=O)N[C@H](C)/C=C/C(=O)N3CC(F)(F)C3)CC2)c(-c2ccccc2Cl)c1] | 137 | (R,E)-1-((2'-chloro-5-methoxy-[1,1'-biphenyl]-2-yl)sulfonyl)-N-(5-(3,3-difluoroazetidin-1-yl)-5-oxopent-3-en-2-yl)-4-fluoropiperidine-4-carboxamide |

TABLE 1-continued

| Compounds of the Disclosure. | | |
|---|---|---|
| Structure | Cmp. No. | IUPAC |
| 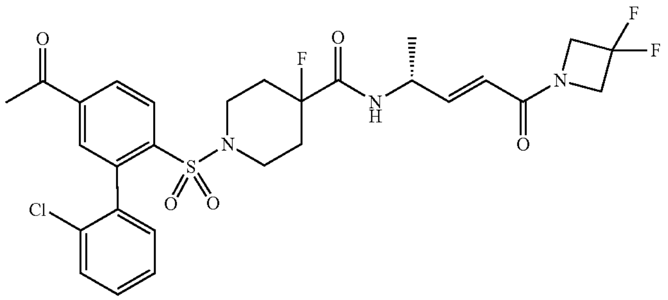 [SMILES: CC(=O)c1ccc(S(=O)(=O)N2CCC(F)(C(=O)N[C@H](C)/C=C/C(=O)N3CC(F)(F)C3)CC2)c(-c2ccccc2Cl)c1] | 138 | (R,E)-1-((5-acetyl-2'-chloro-[1,1'-biphenyl]-2-yl)sulfonyl)-N-(5-(3,3-difluoroazetidin-1-yl)-5-oxopent-3-en-2-yl)-4-fluoropiperidine-4-carboxamide |
| 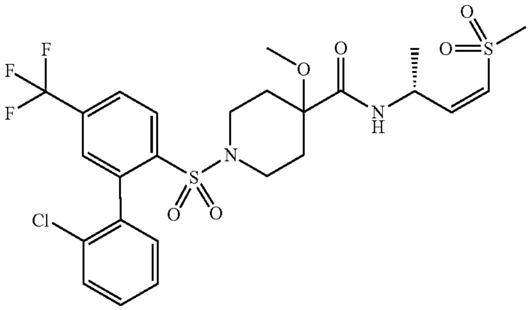 [SMILES: COC1(C(=O)N[C@H](C)/C=C\S(C)(=O)=O)CCN(S(=O)(=O)c2ccc(C(F)(F)F)cc2-c2ccccc2Cl)CC1] | 139 | (R,Z)-1-((2'-chloro-5-(trifluoromethyl)-[1,1'-biphenyl]-2-yl)sulfonyl)-4-methoxy-N-(4-(methylsulfonyl)but-3-en-2-yl)piperidine-4-carboxamide |
| 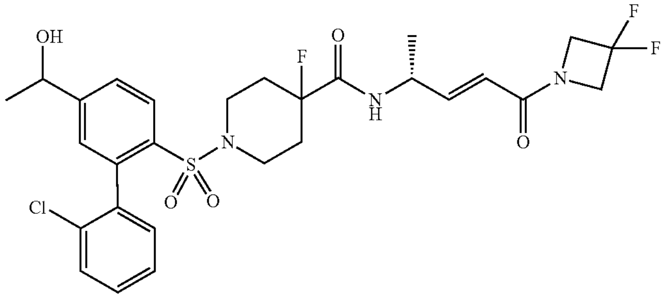 [SMILES: CC(O)c1ccc(S(=O)(=O)N2CCC(F)(C(=O)N[C@H](C)/C=C/C(=O)N3CC(F)(F)C3)CC2)c(-c2ccccc2Cl)c1] | 140 | 1-((2'-chloro-5-(1-hydroxyethyl)-[1,1'-biphenyl]-2-yl)sulfonyl)-N-((R,E)-5-(3,3-difluoroazetidin-1-yl)-5-oxopent-3-en-2-yl)-4-fluoropiperidine-4-carboxamide |
| 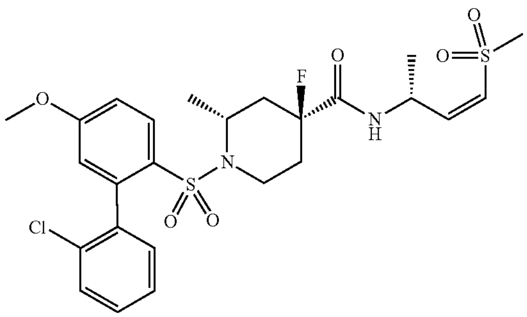 | 141 | (2R,4S)-1-((2'-chloro-5-methoxy-[1,1'-biphenyl]-2-yl)sulfonyl)-4-fluoro-2-methyl-N-((R,Z)-4-(methylsulfonyl)but-3-en-2-yl)piperidine-4-carboxamide |

TABLE 1-continued

| Compounds of the Disclosure. | | |
|---|---|---|
| Structure | Cmp. No. | IUPAC |
| 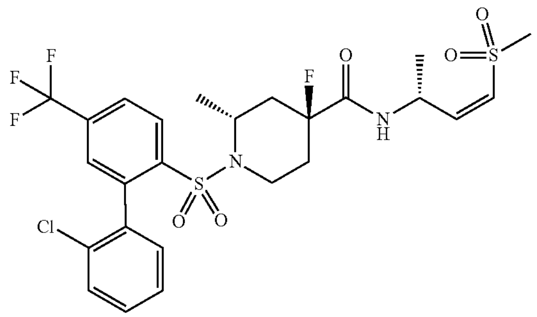 [SMILES: C[C@H](/C=C\S(C)(=O)=O)NC(=O)[C@]1(F)CCN(S(=O)(=O)c2ccc(C(F)(F)F)cc2-c2ccccc2Cl)[C@H](C)C1] | 142 | (2R,4S)-1-((2'-chloro-5-(trifluoromethyl)-[1,1'-biphenyl]-2-yl)sulfonyl)-4-fluoro-2-methyl-N-((R,Z)-4-(methylsulfonyl)but-3-en-2-yl)piperidine-4-carboxamide |
| 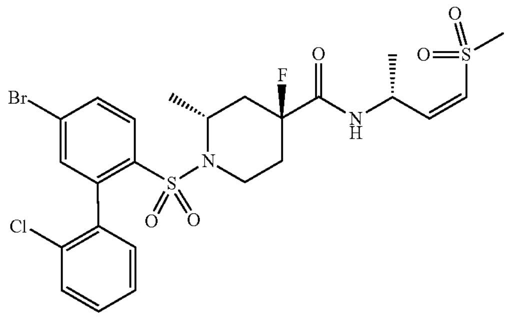 [SMILES: C[C@H](/C=C\S(C)(=O)=O)NC(=O)[C@]1(F)CCN(S(=O)(=O)c2ccc(Br)cc2-c2ccccc2Cl)[C@H](C)C1] | 143 | (2R,4S)-1-((5-bromo-2'-chloro-[1,1'-biphenyl]-2-yl)sulfonyl)-4-fluoro-2-methyl-N-((R,Z)-4-(methylsulfonyl)but-3-en-2-yl)piperidine-4-carboxamide |
| 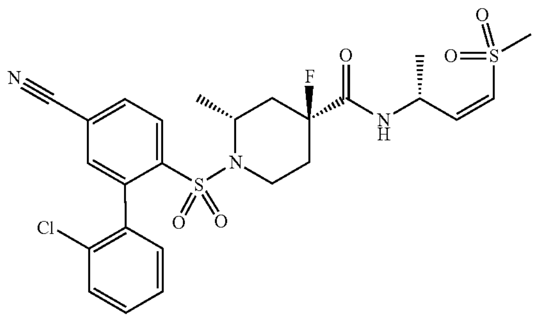 [SMILES: C[C@H](/C=C\S(C)(=O)=O)NC(=O)[C@]1(F)CCN(S(=O)(=O)c2ccc(C#N)cc2-c2ccccc2Cl)[C@H](C)C1] | 144 | (2R,4S)-1-((2'-chloro-5-cyano-[1,1'-biphenyl]-2-yl)sulfonyl)-4-fluoro-2-methyl-N-((R,Z)-4-(methylsulfonyl)but-3-en-2-yl)piperidine-4-carboxamide |
| 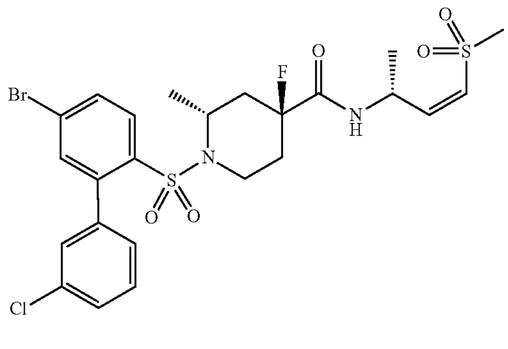 [SMILES: C[C@H](/C=C\S(C)(=O)=O)NC(=O)[C@]1(F)CCN(S(=O)(=O)c2ccc(Br)cc2-c2cccc(Cl)c2)[C@H](C)C1] | 145 | (2R,4S)-1-((5-bromo-3'-chloro-[1,1'-biphenyl]-2-yl)sulfonyl)-4-fluoro-2-methyl-N-((R,Z)-4-(methylsulfonyl)but-3-en-2-yl)piperidine-4-carboxamide |

TABLE 1-continued

| Structure | Cmp. No. | IUPAC |
|---|---|---|
| 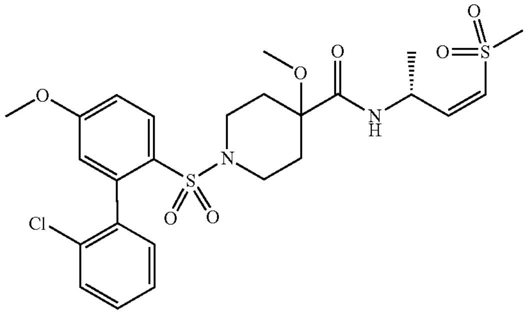 | 146 | (R,Z)-1-((2'-chloro-5-methoxy-[1,1'-biphenyl]-2-yl)sulfonyl)-4-methoxy-N-(4-(methylsulfonyl)but-3-en-2-yl)piperidine-4-carboxamide |
| 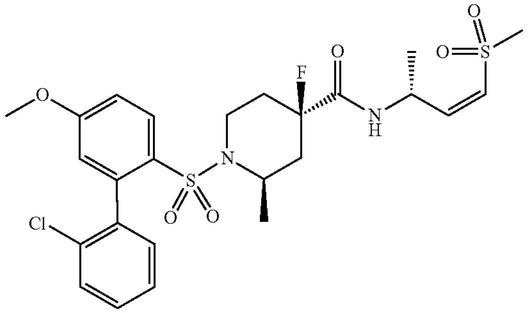 | 147 | (2*R,4*R)-1-((2'-chloro-5-methoxy-[1,1'-biphenyl]-2-yl)sulfonyl)-4-fluoro-2-methyl-N-((R,Z)-4-(methylsulfonyl)but-3-en-2-yl)piperidine-4-carboxamide |
| 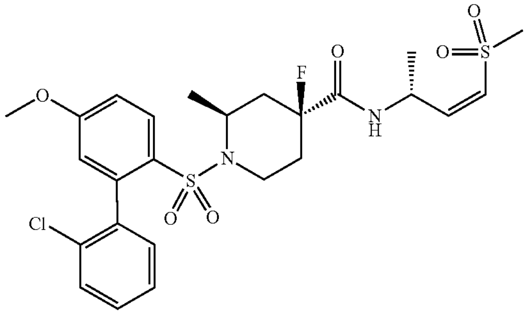 | 148 | (2*S,4*S)-1-((2'-chloro-5-methoxy-[1,1'-biphenyl]-2-yl)sulfonyl)-4-fluoro-2-methyl-N-((R,Z)-4-(methylsulfonyl)but-3-en-2-yl)piperidine-4-carboxamide |
| 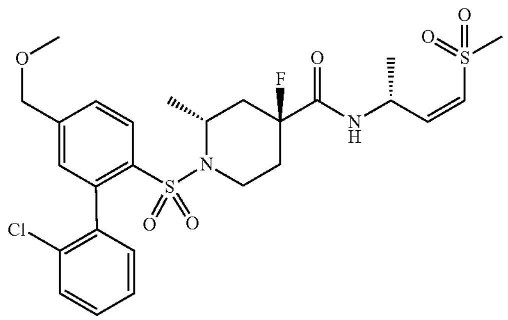 [SMILES: COCc1ccc(S(=O)(=O)N2CC[C@@](F)(C(=O)N[C@H](C)/C=C\S(C)(=O)=O)C[C@H]2C)c(-c2ccccc2Cl)c1] | 149 | (2R,4S)-1-((2'-chloro-5-(methoxymethyl)-[1,1'-biphenyl]-2-yl)sulfonyl)-4-fluoro-2-methyl-N-((R,Z)-4-(methylsulfonyl)but-3-en-2-yl)piperidine-4-carboxamide |

Compounds of the Disclosure.

TABLE 1-continued

Compounds of the Disclosure.

| Structure | Cmp. No. | IUPAC |
|---|---|---|
| 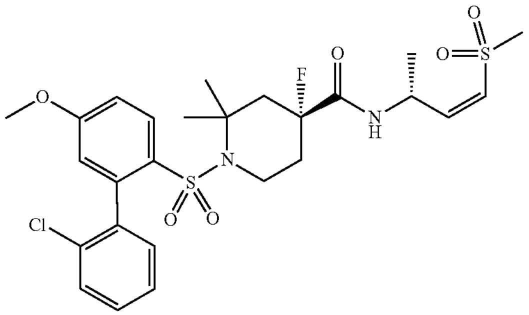 | 150 | (*R)-1-((2'-chloro-5-methoxy-[1,1'-biphenyl]-2-yl)sulfonyl)-4-fluoro-2,2-dimethyl-N-((R,Z)-4-(methylsulfonyl)but-3-en-2-yl)piperidine-4-carboxamide |
| 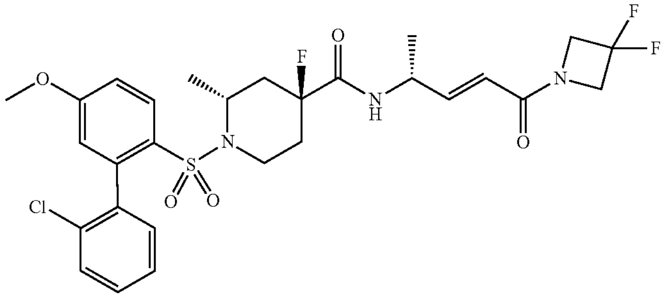 [SMILES: COc1ccc(S(=O)(=O)N2CC[C@@](F)(C(=O)N[C@H](C)/C=C/C(=O)N3CC(F)(F)C3)C[C@H]2C)c(-c2ccccc2Cl)c1] | 151 | (2R,4S)-1-((2'-chloro-5-methoxy-[1,1'-biphenyl]-2-yl)sulfonyl)-N-((R,E)-5-(3,3-difluoroazetidin-1-yl)-5-oxopent-3-en-2-yl)-4-fluoro-2-methylpiperidine-4-carboxamide |
| 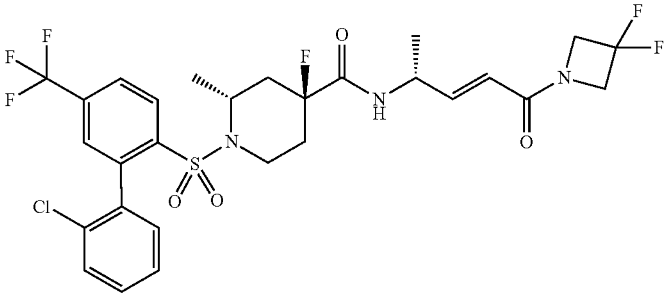 [SMILES: C[C@H](/C=C/C(=O)N1CC(F)(F)C1)NC(=O)[C@]1(F)CCN(S(=O)(=O)c2ccc(C(F)(F)F)cc2-c2ccccc2Cl)[C@H](C)C1] | 152 | (2R,4S)-1-((2'-chloro-5-(trifluoromethyl)-[1,1'-biphenyl]-2-yl)sulfonyl)-N-((R,E)-5-(3,3-difluoroazetidin-1-yl)-5-oxopent-3-en-2-yl)-4-fluoro-2-methylpiperidine-4-carboxamide |
| 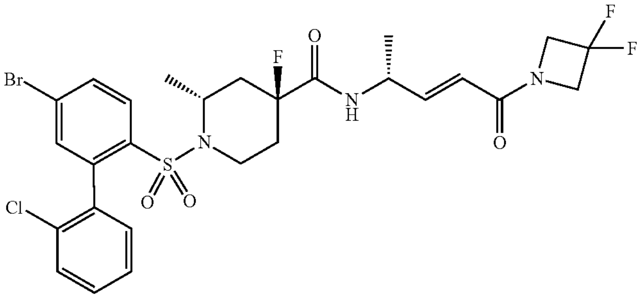 [SMILES: C[C@H](/C=C/C(=O)N1CC(F)(F)C1)NC(=O)[C@]1(F)CCN(S(=O)(=O)c2ccc(Br)cc2-c2ccccc2Cl)[C@H](C)C1] | 153 | (2R,4S)-1-((5-bromo-2'-chloro-[1,1'-biphenyl]-2-yl)sulfonyl)-N-((R,E)-5-(3,3-difluoroazetidin-1-yl)-5-oxopent-3-en-2-yl)-4-fluoro-2-methylpiperidine-4-carboxamide |
| 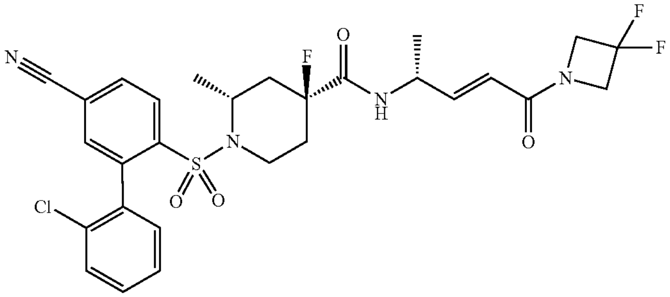 [SMILES: C[C@H](/C=C/C(=O)N1CC(F)(F)C1)NC(=O)[C@]1(F)CCN(S(=O)(=O)c2ccc(C#N)cc2-c2ccccc2Cl)[C@H](C)C1] | 154 | (2R,4S)-1-((2'-chloro-5-cyano-[1,1'-biphenyl]-2-yl)sulfonyl)-N-((R,E)-5-(3,3-difluoroazetidin-1-yl)-5-oxopent-3-en-2-yl)-4-fluoro-2-methylpiperidine-4-carboxamide |

TABLE 1-continued

| Compounds of the Disclosure. | | |
|---|---|---|
| Structure | Cmp. No. | IUPAC |
| 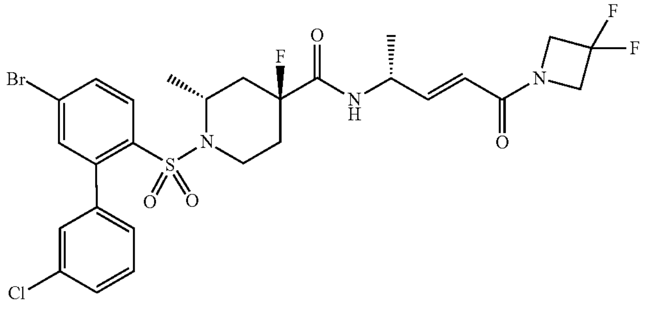 [SMILES: C[C@H](/C=C/C(=O)N1CC(F)(F)C1)NC(=O)[C@]1(F)CCN(S(=O)(=O)c2ccc(Br)cc2-c2cccc(Cl)c2)[C@H](C)C1] | 155 | (2R,4S)-1-((5-bromo-3'-chloro-[1,1'-biphenyl]-2-yl)sulfonyl)-N-((R,E)-5-(3,3-difluoroazetidin-1-yl)-5-oxopent-3-en-2-yl)-4-fluoro-2-methylpiperidine-4-carboxamide |
| 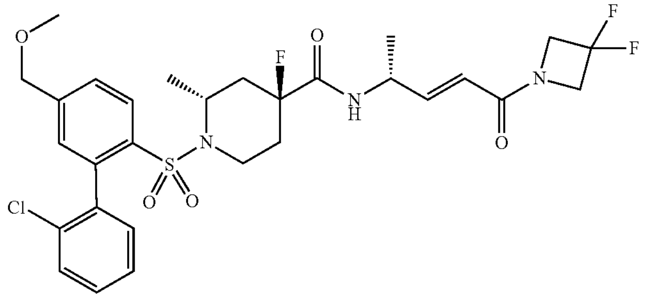 [SMILES: COCc1ccc(S(=O)(=O)N2CC[C@@](F)(C(=O)N[C@H](C)/C=C/C(=O)N3CC(F)(F)C3)C[C@H]2C)c(-c2ccccc2Cl)c1] | 156 | (2R,4S)-1-((2'-chloro-5-(methoxymethyl)-[1,1'-biphenyl]-2-yl)sulfonyl)-N-((R,E)-5-(3,3-difluoroazetidin-1-yl)-5-oxopent-3-en-2-yl)-4-fluoro-2-methylpiperidine-4-carboxamide |
| 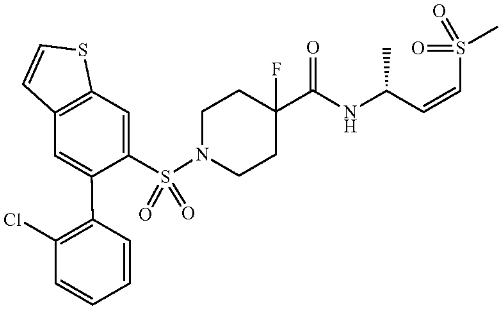 [SMILES: C[C@H](/C=C\S(C)(=O)=O)NC(=O)C1(F)CCN(S(=O)(=O)c2cc3sccc3cc2-c2ccccc2Cl)CC1] | 157 | (R,Z)-1-((5-(2-chlorophenyl)benzo[b]thiophen-6-yl)sulfonyl)-4-fluoro-N-(4-(methylsulfonyl)but-3-en-2-yl)piperidine-4-carboxamide |
| 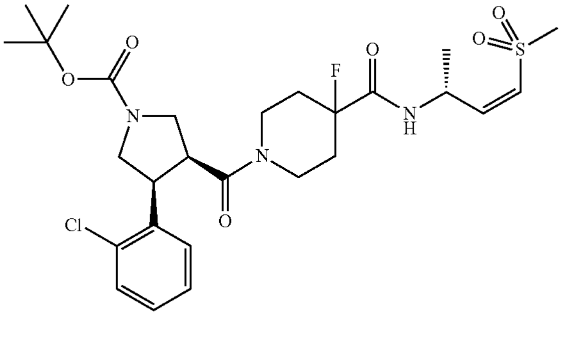 [SMILES: C[C@H](/C=C\S(C)(=O)=O)NC(=O)C1(F)CCN(C(=O)[C@@H]2CN(C(=O)OC(C)(C)C)C[C@@H]2c2ccccc2Cl)CC1] | 158 | tert-butyl cis-(3RS,4RS)-3-(2-chlorophenyl)-4-(4-fluoro-4-(((R,Z)-4-(methylsulfonyl)but-3-en-2-yl)carbamoyl)piperidine-1-carbonyl)pyrrolidine-1-carboxylate |

TABLE 1-continued

Compounds of the Disclosure.

| Structure | Cmp. No. | IUPAC |
|---|---|---|
| 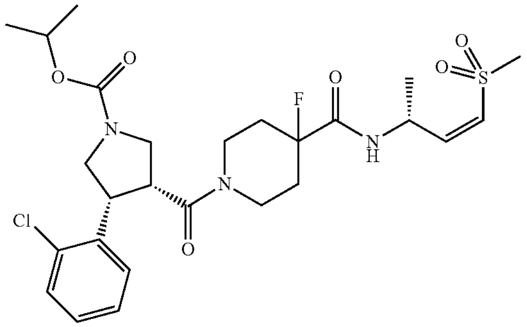 [SMILES: CC(C)OC(=O)N1C[C@H](C(=O)N2CCC(F)(C(=O)N[C@H](C)/C=C\S(C)(=O)=O)CC2)[C@H](c2ccccc2Cl)C1] | 159 | isopropyl (3R,4R)-3-(2-chlorophenyl)-4-(4-fluoro-4-(((R,Z)-4-(methylsulfonyl) but-3-en-2-yl)carbamoyl)piperidine-1-carbonyl)pyrrolidine-1-carboxylate |
| 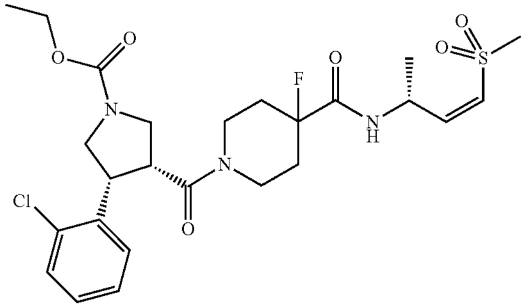 [SMILES: CCOC(=O)N1C[C@H](C(=O)N2CCC(F)(C(=O)N[C@H](C)/C=C\S(C)(=O)=O)CC2)[C@H](c2ccccc2Cl)C1] | 160 | ethyl (3R,4R)-3-(2-chlorophenyl)-4-(4-fluoro-4-(((R,Z)-4-(methylsulfonyl)but-3-en-2-yl)carbamoyl) piperidine-1-carbonyl)pyrrolidine-1-carboxylate |
| 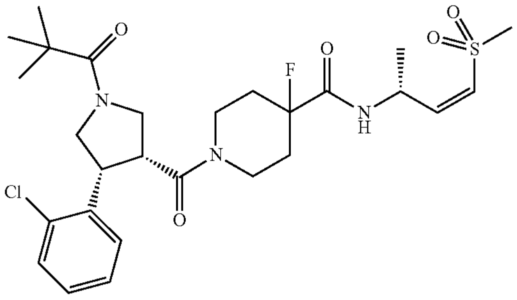 [SMILES: C[C@H](/C=C\S(C)(=O)=O)NC(=O)C1(F)CCN(C(=O)[C@H]2CN(C(=O)C(C)(C)C)C[C@H]2c2ccccc2Cl)CC1] | 161 | 1-((3R,4R)-4-(2-chlorophenyl)-1-pivaloylpyrrolidine-3-carbonyl)-4-fluoro-N-((R,Z)-4-(methylsulfonyl)but-3-en-2-yl)piperidine-4-carboxamide |
| 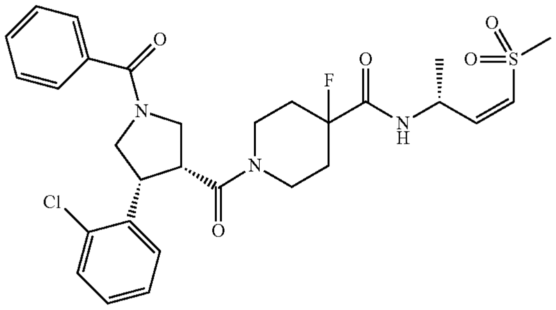 [SMILES: C[C@H](/C=C\S(C)(=O)=O)NC(=O)C1(F)CCN(C(=O)[C@H]2CN(C(=O)c3ccccc3)C[C@H]2c2ccccc2Cl)CC1] | 162 | 1-((3R,4R)-1-benzoyl-4-(2-chlorophenyl) pyrrolidine-3-carbonyl)-4-fluoro-N-((R,Z)-4-(methylsulfonyl)but-3-en-2-yl)piperidine-4-carboxamide |

TABLE 1-continued

| Compounds of the Disclosure. | | |
|---|---|---|
| Structure | Cmp. No. | IUPAC |
| 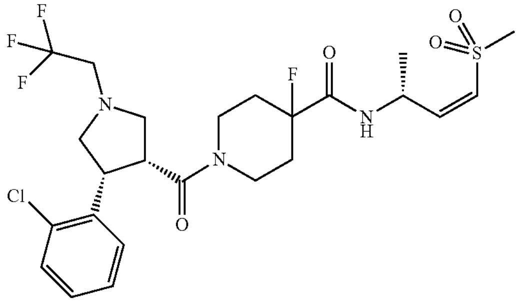 [SMILES: C[C@H](/C=C\S(C)(=O)=O)NC(=O)C1(F)CCN(C(=O)[C@H]2CN(CC(F)(F)F)C[C@H]2c2ccccc2Cl)CC1] | 163 | 1-((3R,4R)-4-(2-chlorophenyl)-1-(2,2,2-trifluoroethyl)pyrrolidine-3-carbonyl)-4-fluoro-N-((R,Z)-4-(methylsulfonyl)but-3-en-2-yl)piperidine-4-carboxamide |
| 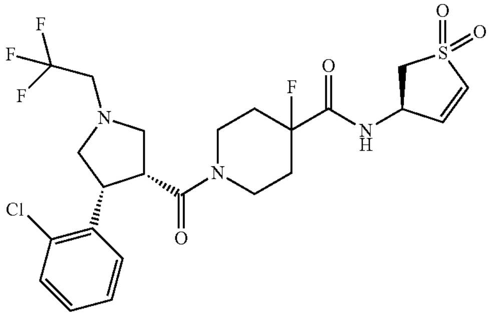 [SMILES: O=C([C@H]1CN(CC(F)(F)F)C[C@H]1c1ccccc1Cl)N1CCC(F)(C(=O)N[C@@H]2C=CS(=O)(=O)C2)CC1] | 164 | 1-((3R,4R)-4-(2-chlorophenyl)-1-(2,2,2-trifluoroethyl)pyrrolidine-3-carbonyl)-N-((R)-1,1-dioxido-2,3-dihydrothiophen-3-yl)-4-fluoropiperidine-4-carboxamide |
| 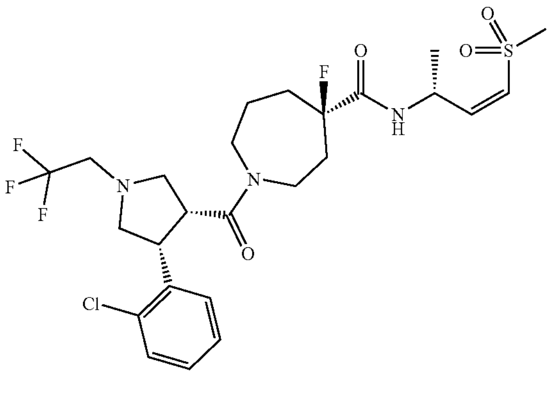 [SMILES: C[C@H](/C=C\S(C)(=O)=O)NC(=O)[C@@]1(F)CCCN(C(=O)[C@H]2CN(CC(F)(F)F)C[C@H]2c2ccccc2Cl)CC1] | 165 | (R)-1-((3R,4R)-4-(2-chlorophenyl)-1-(2,2,2-trifluoroethyl)pyrrolidine-3-carbonyl)-4-fluoro-N-((R,Z)-4-(methylsulfonyl)but-3-en-2-yl)azepane-4-carboxamide |
| 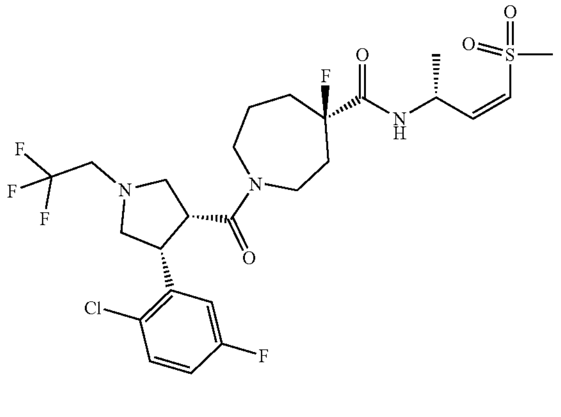 [SMILES: C[C@H](/C=C\S(C)(=O)=O)NC(=O)[C@@]1(F)CCCN(C(=O)[C@H]2CN(CC(F)(F)F)C[C@H]2c2cc(F)ccc2Cl)CC1] | 166 | (R)-1-((3*R,4*R)-4-(2-chloro-5-fluorophenyl)-1-(2,2,2-trifluoroethyl) pyrrolidine-3-carbonyl)-4-fluoro-N-((R,Z)-4-(methylsulfonyl)but-3-en-2-yl)azepane-4-carboxamide |

TABLE 1-continued

| Compounds of the Disclosure. | | |
|---|---|---|
| Structure | Cmp. No. | IUPAC |
| 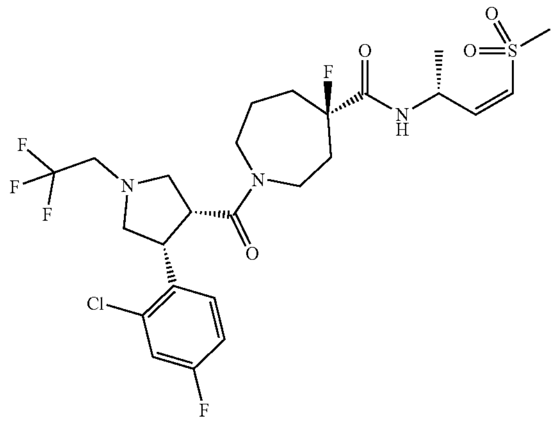 [SMILES: C[C@H](/C=C\S(C)(=O)=O)NC(=O)[C@@]1(F)CCCN(C(=O)[C@H]2CN(CC(F)(F)F)C[C@H]2c2ccc(F)cc2Cl)CC1] | 167 | (R)-1-((3*R,4*R)-4-(2-chloro-4-fluorophenyl)-1-(2,2,2-trifluoroethyl) pyrrolidine-3-carbonyl)-4-fluoro-N-((R,Z)-4-(methylsulfonyl)but-3-en-2-yl)azepane-4-carboxamide |
| 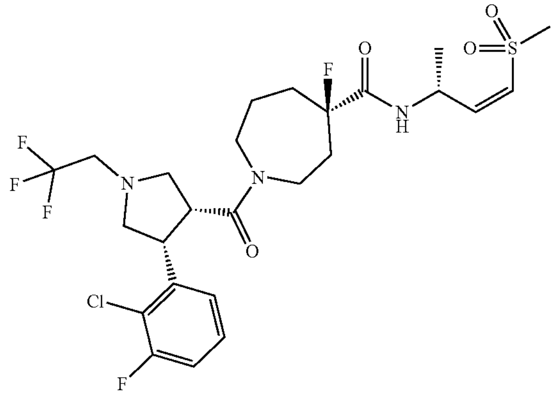 [SMILES: C[C@H](/C=C\S(C)(=O)=O)NC(=O)[C@@]1(F)CCCN(C(=O)[C@H]2CN(CC(F)(F)F)C[C@H]2c2cccc(F)c2Cl)CC1] | 168 | (R)-1-((3*R,4*R)-4-(2-chloro-3-fluorophenyl)-1-(2,2,2-trifluoroethyl) pyrrolidine-3-carbonyl)-4-fluoro-N-((R,Z)-4-(methylsulfonyl)but-3-en-2-yl)azepane-4-carboxamide |
| 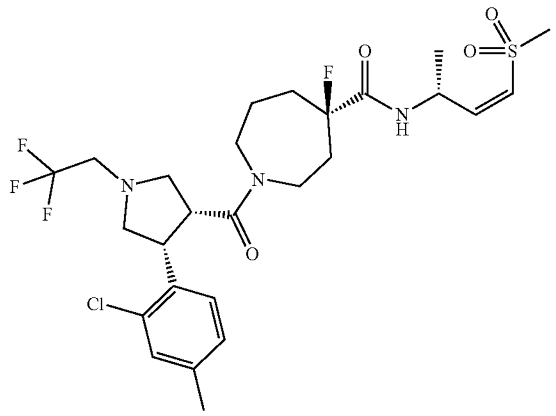 [SMILES: Cc1ccc([C@@H]2CN(CC(F)(F)F)C[C@@H]2C(=O)N2CCC[C@](F)(C(=O)N[C@H](C)/C=C\S(C)(=O)=O)CC2)c(Cl)c1] | 169 | (R)-1-((3*R,4*R)-4-(2-chloro-4-methylphenyl)-1-(2,2,2-trifluoroethyl) pyrrolidine-3-carbonyl)-4-fluoro-N-((R,Z)-4-(methylsulfonyl)but-3-en-2-yl)azepane-4-carboxamide |

TABLE 1-continued

| Compounds of the Disclosure. | | |
|---|---|---|
| Structure | Cmp. No. | IUPAC |
| 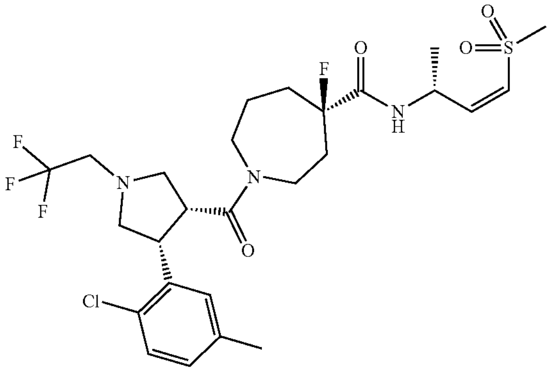 [SMILES: Cc1ccc(Cl)c([C@@H]2CN(CC(F)(F)F)C[C@@H]2C(=O)N2CCC[C@](F)(C(=O)N[C@H](C)/C=C\S(C)(=O)=O)CC2)c1] | 170 | (R)-1-((3*R,4*R)-4-(2-chloro-5-methylphenyl)-1-(2,2,2-trifluoroethyl) pyrrolidine-3-carbonyl)-4-fluoro-N-((R,Z)-4-(methylsulfonyl)but-3-en-2-yl)azepane-4-carboxamide |
| 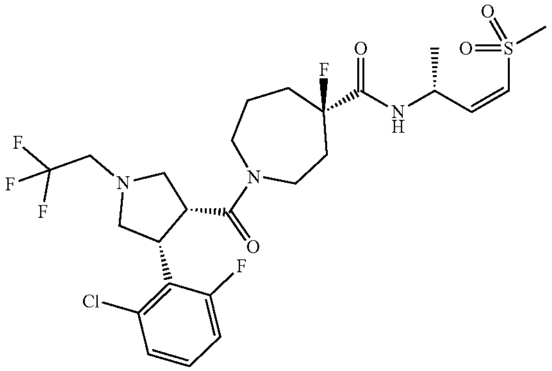 [SMILES: C[C@H](/C=C\S(C)(=O)=O)NC(=O)[C@@]1(F)CCCN(C(=O)[C@H]2CN(CC(F)(F)F)C[C@H]2c2c(F)cccc2Cl)CC1] | 171 | (R)-1-((3R,4R)-4-(2-chloro-6-fluorophenyl)-1-(2,2,2-trifluoroethyl)pyrrolidine-3-carbonyl)-4-fluoro-N-((R,Z)-4-(methylsulfonyl)but-3-en-2-yl)azepane-4-carboxamide |
| 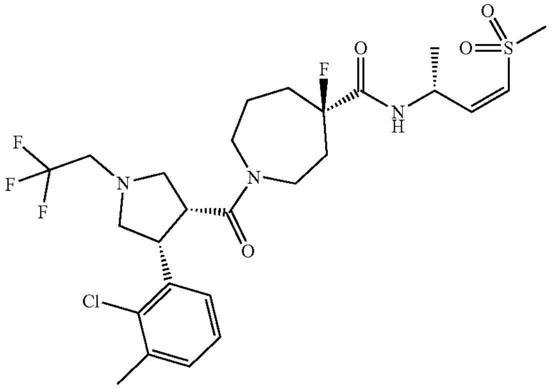 [SMILES: Cc1cccc([C@@H]2CN(CC(F)(F)F)C[C@@H]2C(=O)N2CCC[C@](F)(C(=O)N[C@H](C)/C=C\S(C)(=O)=O)CC2)c1Cl] | 172 | (R)-1-((3*R,4*R)-4-(2-chloro-3-methylphenyl)-1-(2,2,2-trifluoroethyl) pyrrolidine-3-carbonyl)-4-fluoro-N-((R,Z)-4-(methylsulfonyl)but-3-en-2-yl)azepane-4-carboxamide |
| 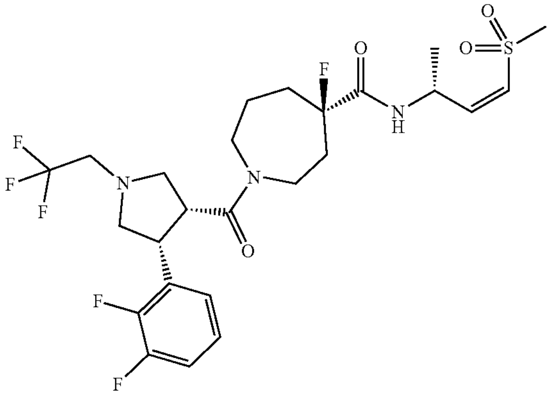 [SMILES: C[C@H](/C=C\S(C)(=O)=O)NC(=O)[C@@]1(F)CCCN(C(=O)[C@H]2CN(CC(F)(F)F)C[C@H]2c2cccc(F)c2F)CC1] | 173 | (R)-1-((3*R,4*R)-4-(2,3-difluorophenyl)-1-(2,2,2-trifluoroethyl)pyrrolidine-3-carbonyl)-4-fluoro-N-((R,Z)-4-(methylsulfonyl)but-3-en-2-yl)azepane-4-carboxamide |

TABLE 1-continued

Compounds of the Disclosure.

| Structure | Cmp. No. | IUPAC |
|---|---|---|
| 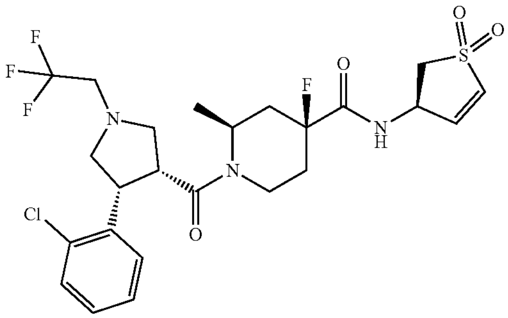 | 174 | (2*S,4*S)-1-((3R,4R)-4-(2-chlorophenyl)-1-(2,2,2-trifluoroethyl)pyrrolidine-3-carbonyl)-N-((R)-1,1-dioxido-2,3-dihydrothiophen-3-yl)-4-fluoro-2-methylpiperidine-4-carboxamide |
| 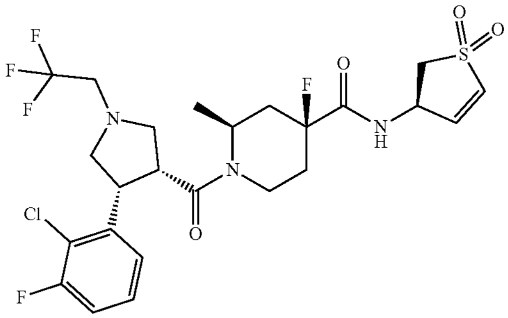 | 175 | (2*S,4*S)-1-((3*R,4*R)-4-(2-chloro-3-fluorophenyl)-1-(2,2,2-trifluoroethyl)pyrrolidine-3-carbonyl)-N-((R)-1,1-dioxido-2,3-dihydrothiophen-3-yl)-4-fluoro-2-methylpiperidine-4-carboxamide |
| 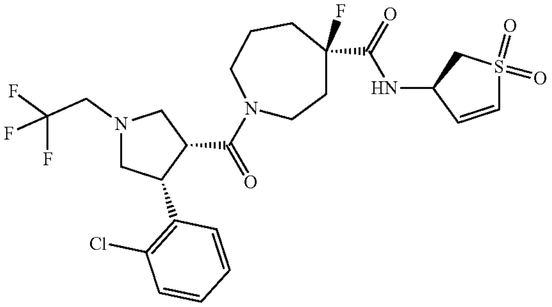 [SMILES: O=C([C@H]1CN(CC(F)(F)F)C[C@H]1c1ccccc1Cl)N1CCC[C@](F)(C(=O)N[C@@H]2C=CS(=O)(=O)C2)CC1] | 176 | (R)-1-((3R,4R)-4-(2-chlorophenyl)-1-(2,2,2-trifluoroethyl)pyrrolidine-3-carbonyl)-N-((R)-1,1-dioxido-2,3-dihydrothiophen-3-yl)-4-fluoroazepane-4-carboxamide |
| 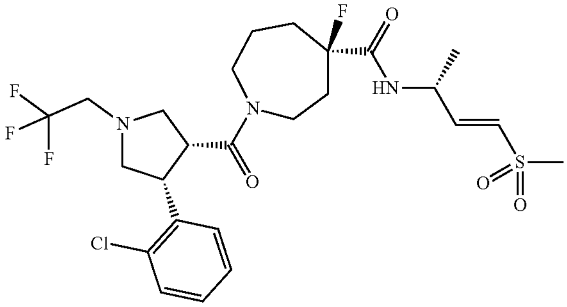 [SMILES: C[C@H](/C=C/S(C)(=O)=O)NC(=O)[C@@]1(F)CCCN(C(=O)[C@H]2CN(CC(F)(F)F)C[C@H]2c2ccccc2Cl)CC1] | 177 | (R)-1-((3R,4R)-4-(2-chlorophenyl)-1-(2,2,2-trifluoroethyl)pyrrolidine-3-carbonyl)-4-fluoro-N-((R,E)-4-(methylsulfonyl)but-3-en-2-yl)azepane-4-carboxamide |

TABLE 1-continued

| Compounds of the Disclosure. | | |
|---|---|---|
| Structure | Cmp. No. | IUPAC |
| 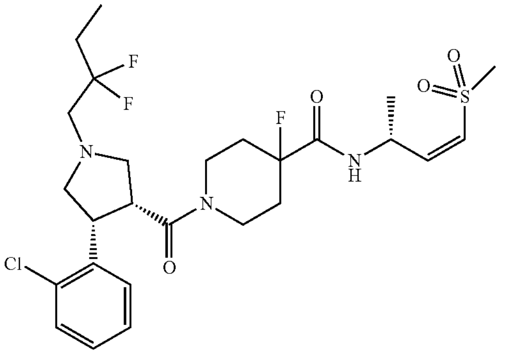 [SMILES: CCC(F)(F)CN1C[C@H](C(=O)N2CCC(F)(C(=O)N[C@H](C)/C=C\S(C)(=O)=O)CC2)[C@H](c2ccccc2Cl)C1] | 178 | 1-((3R,4R)-4-(2-chlorophenyl)-1-(2,2-difluorobutyl)pyrrolidine-3-carbonyl)-4-fluoro-N-((R,Z)-4-(methylsulfonyl)but-3-en-2-yl)piperidine-4-carboxamide |
| 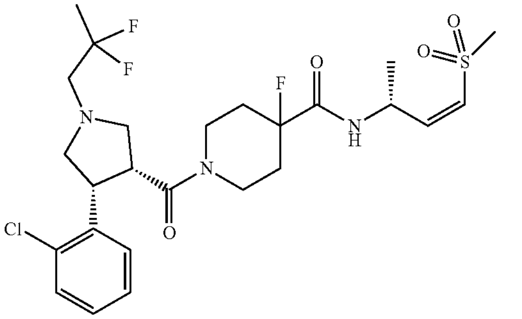 [SMILES: C[C@H](/C=C\S(C)(=O)=O)NC(=O)C1(F)CCN(C(=O)[C@H]2CN(CC(C)(F)F)C[C@H]2c2ccccc2Cl)CC1] | 179 | 1-((3R,4R)-4-(2-chlorophenyl)-1-(2,2-difluoropropyl)pyrrolidine-3-carbonyl)-4-fluoro-N-((R,Z)-4-(methylsulfonyl)but-3-en-2-yl)piperidine-4-carboxamide |
| 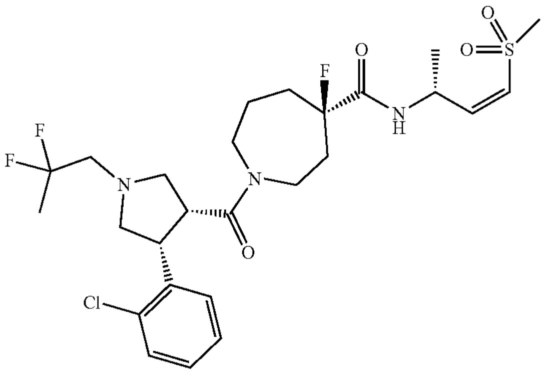 [SMILES: C[C@H](/C=C\S(C)(=O)=O)NC(=O)[C@@]1(F)CCCN(C(=O)[C@H]2CN(CC(C)(F)F)C[C@H]2c2ccccc2Cl)CC1] | 180 | (R)-1-((3R,4R)-4-(2-chlorophenyl)-1-(2,2-difluoropropyl)pyrrolidine-3-carbonyl)-4-fluoro-N-((R,Z)-4-(methylsulfonyl)but-3-en-2-yl)azepane-4-carboxamide |
| 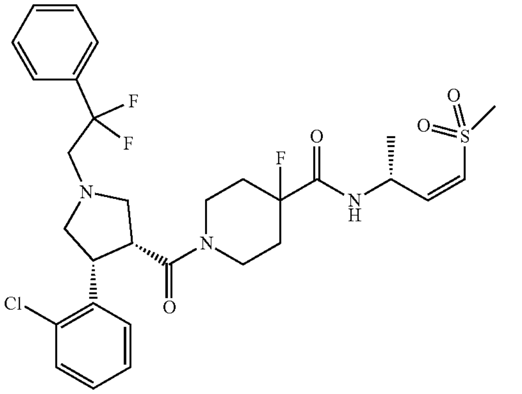 [SMILES: C[C@H](/C=C\S(C)(=O)=O)NC(=O)C1(F)CCN(C(=O)[C@H]2CN(CC(F)(F)c3ccccc3)C[C@H]2c2ccccc2Cl)CC1] | 181 | 1-((3R,4R)-4-(2-chlorophenyl)-1-(2,2-difluoro-2-phenylethyl)pyrrolidine-3-carbonyl)-4-fluoro-N-((R,Z)-4-(methylsulfonyl)but-3-en-2-yl)piperidine-4-carboxamide |

TABLE 1-continued

| Compounds of the Disclosure. | | |
|---|---|---|
| Structure | Cmp. No. | IUPAC |
| 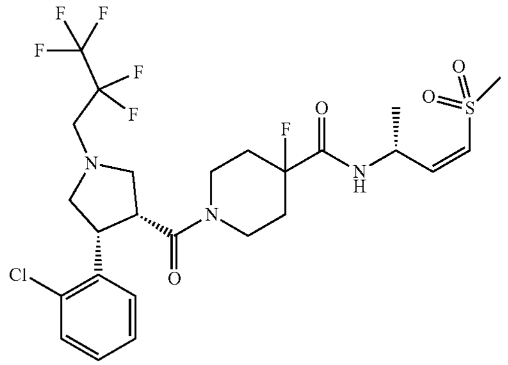 [SMILES: C[C@H](/C=C\S(C)(=O)=O)NC(=O)C1(F)CCN(C(=O)[C@H]2CN(CC(F)(F)C(F)(F)F)C[C@H]2c2ccccc2Cl)CC1] | 182 | 1-((3R,4R)-4-(2-chlorophenyl)-1-(2,2,3,3,3-pentafluoropropyl)pyrrolidine-3-carbonyl)-4-fluoro-N-((R,Z)-4-(methylsulfonyl)but-3-en-2-yl)piperidine-4-carboxamide |
| 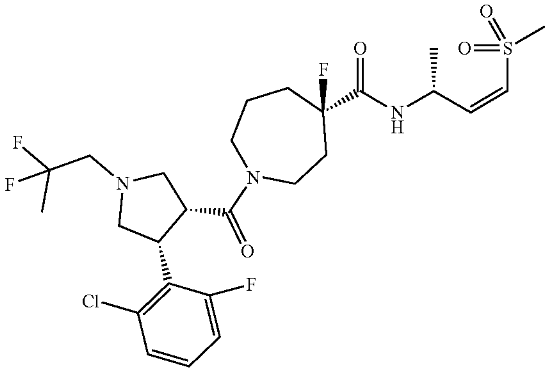 [SMILES: C[C@H](/C=C\S(C)(=O)=O)NC(=O)[C@@]1(F)CCCN(C(=O)[C@H]2CN(CC(C)(F)F)C[C@H]2c2c(F)cccc2Cl)CC1] | 183 | (R)-1-((3R,4R)-4-(2-chloro-6-fluorophenyl)-1-(2,2-difluoropropyl)pyrrolidine-3-carbonyl)-4-fluoro-N-((R,Z)-4-(methylsulfonyl)but-3-en-2-yl)azepane-4-carboxamide |
| 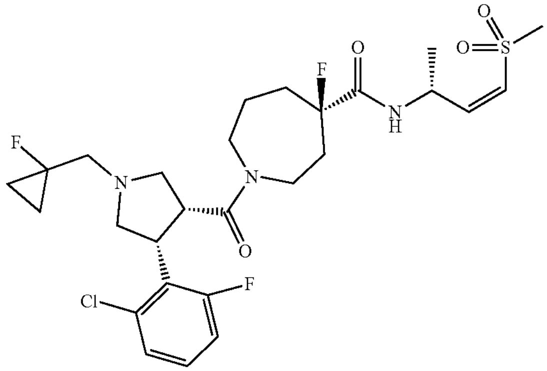 [SMILES: C[C@H](/C=C\S(C)(=O)=O)NC(=O)[C@@]1(F)CCCN(C(=O)[C@H]2CN(CC3(F)CC3)C[C@H]2c2c(F)cccc2Cl)CC1] | 184 | (R)-1-((3*R,4*R)-4-(2-chloro-6-fluorophenyl)-1-((1-fluorocyclopropyl)methyl)pyrrolidine-3-carbonyl)-4-fluoro-N-((R,Z)-4-(methylsulfonyl)but-3-en-2-yl)azepane-4-carboxamide |
| 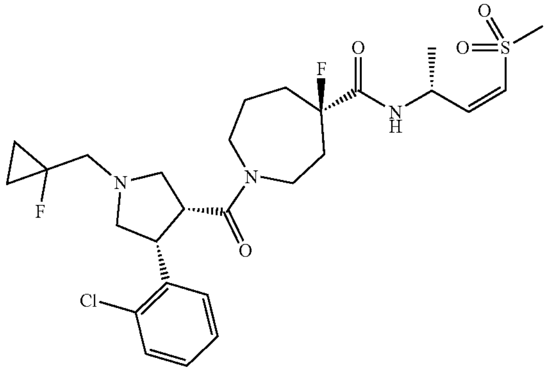 [SMILES: C[C@H](/C=C\S(C)(=O)=O)NC(=O)[C@@]1(F)CCCN(C(=O)[C@H]2CN(CC3(F)CC3)C[C@H]2c2ccccc2Cl)CC1] | 185 | (R)-1-((3R,4R)-4-(2-chlorophenyl)-1-((1-fluorocyclopropyl)methyl)pyrrolidine-3-carbonyl)-4-fluoro-N-((R,Z)-4-(methylsulfonyl)but-3-en-2-yl)azepane-4-carboxamide |

TABLE 1-continued

Compounds of the Disclosure.

| Structure | Cmp. No. | IUPAC |
|---|---|---|
| 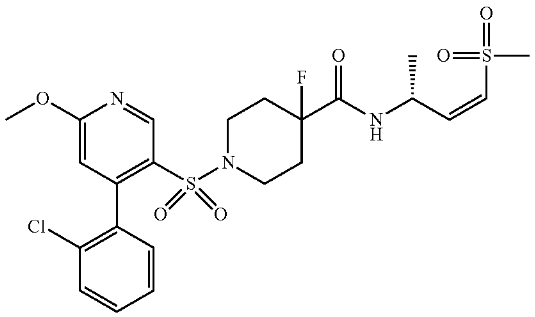 | 186 | (R,Z)-1-((4-(2-chlorophenyl)-6-methoxypyridin-3-yl)sulfonyl)-4-fluoro-N-(4-(methylsulfonyl)but-3-en-2-yl)piperidine-4-carboxamide |
| 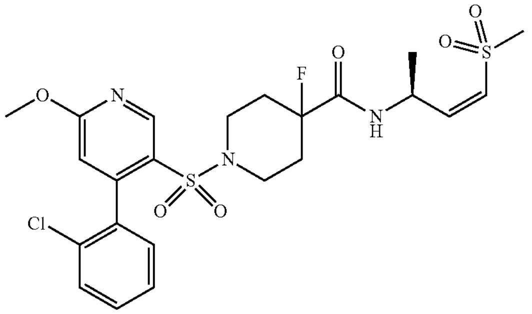 | 187 | (S,Z)-1-((4-(2-chlorophenyl)-6-methoxypyridin-3-yl)sulfonyl)-4-fluoro-N-(4-(methylsulfonyl)but-3-en-2-yl)piperidine-4-carboxamide |
| 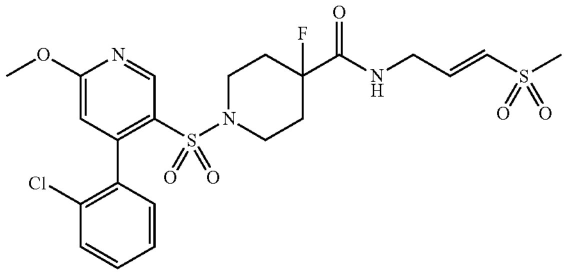 | 188 | (E)-1-((4-(2-chlorophenyl)-6-methoxypyridin-3-yl)sulfonyl)-4-fluoro-N-(3-(methylsulfonyl)allyl)piperidine-4-carboxamide |
| 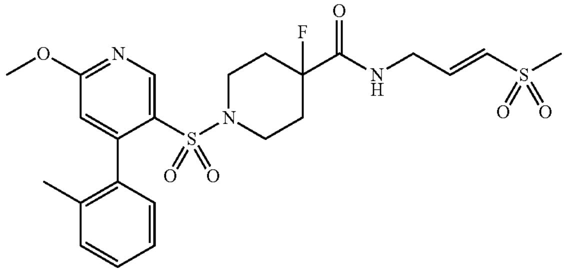 | 189 | (E)-4-fluoro-1-((6-methoxy-4-(o-tolyl)pyridin-3-yl)sulfonyl)-N-(3-(methylsulfonyl)allyl)piperidine-4-carboxamide |
| 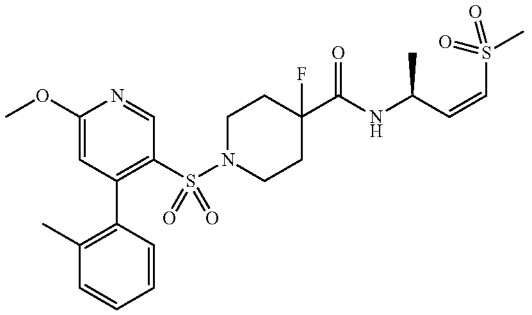 | 190 | (S,Z)-4-fluoro-1-((6-methoxy-4-(o-tolyl)pyridin-3-yl)sulfonyl)-N-(4-(methylsulfonyl)but-3-en-2-yl)piperidine-4-carboxamide |

TABLE 1-continued

| Compounds of the Disclosure. | | |
|---|---|---|
| Structure | Cmp. No. | IUPAC |
| 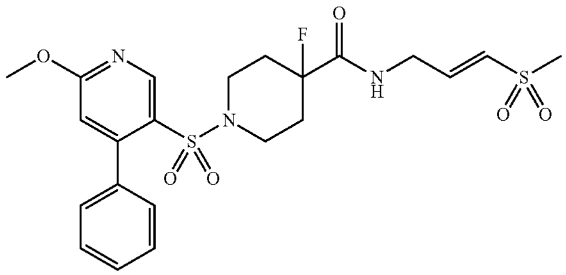 | 191 | (E)-4-fluoro-1-((6-methoxy-4-phenylpyridin-3-yl)sulfonyl)-N-(3-(methylsulfonyl)allyl)piperidine-4-carboxamide |
| 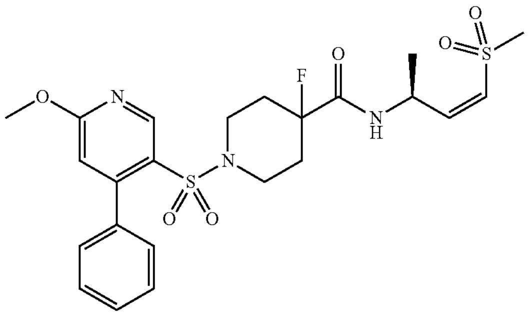 | 192 | (S,Z)-4-fluoro-1-((6-methoxy-4-phenylpyridin-3-yl)sulfonyl)-N-(4-(methylsulfonyl)but-3-en-2-yl)piperidine-4-carboxamide |
| 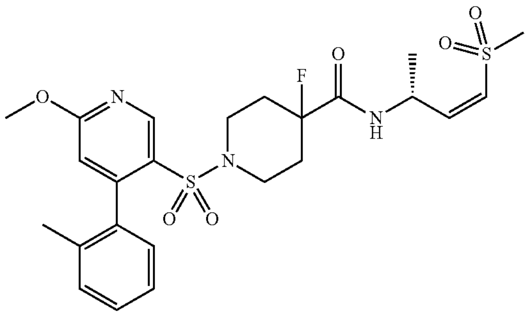 | 193 | (R,Z)-4-fluoro-1-((6-methoxy-4-(o-tolyl)pyridin-3-yl)sulfonyl)-N-(4-(methylsulfonyl)but-3-en-2-yl)piperidine-4-carboxamide |
| 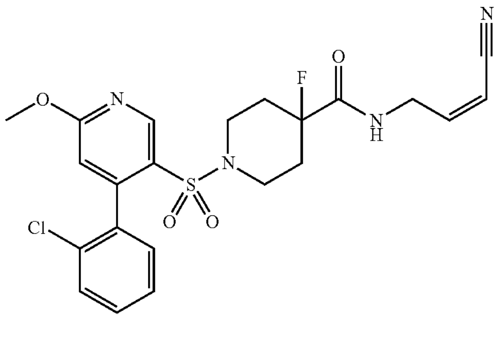 [SMILES: COc1cc(-c2ccccc2Cl)c(S(=O)(=O)N2CCC(F)(C(=O)NC/C=C\C#N)CC2)cn1] | 194 | (Z)-1-((4-(2-chlorophenyl)-6-methoxypyridin-3-yl)sulfonyl)-N-(3-cyanoallyl)-4-fluoropiperidine-4-carboxamide |

TABLE 1-continued

| Compounds of the Disclosure. | | |
|---|---|---|
| Structure | Cmp. No. | IUPAC |
| 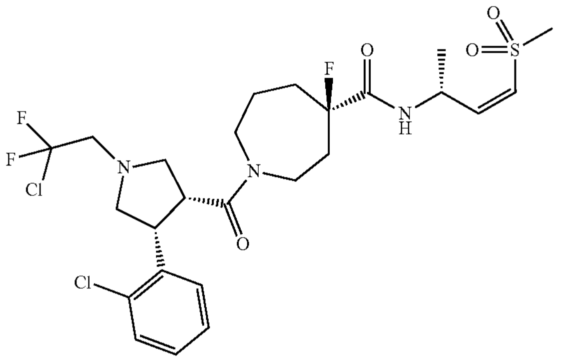 [SMILES: C[C@H](/C=C\S(C)(=O)=O)NC(=O)[C@@]1(F)CCCN(C(=O)[C@H]2CN(CC(F)(F)Cl)C[C@H]2c2ccccc2Cl)CC1] | 195 | (R)-1-((3R,4R)-1-(2-chloro-2,2-difluoroethyl)-4-(2-chlorophenyl)pyrrolidine-3-carbonyl)-4-fluoro-N-((R,Z)-4-(methylsulfonyl)but-3-en-2-yl)azepane-4-carboxamide |
| 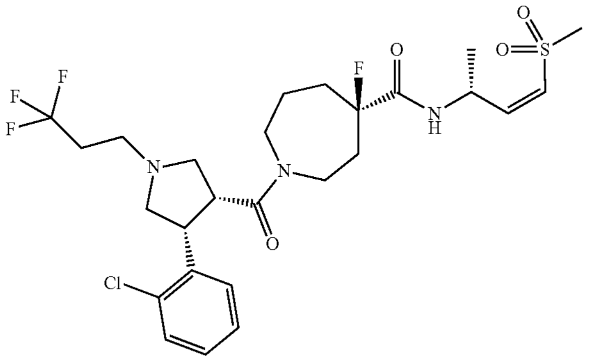 [SMILES: C[C@H](/C=C\S(C)(=O)=O)NC(=O)[C@@]1(F)CCCN(C(=O)[C@H]2CN(CCC(F)(F)F)C[C@H]2c2ccccc2Cl)CC1] | 196 | (R)-1-((3R,4R)-4-(2-chlorophenyl)-1-(3,3,3-trifluoropropyl)pyrrolidine-3-carbonyl)-4-fluoro-N-((R,Z)-4-(methylsulfonyl)but-3-en-2-yl)azepane-4-carboxamide |
| 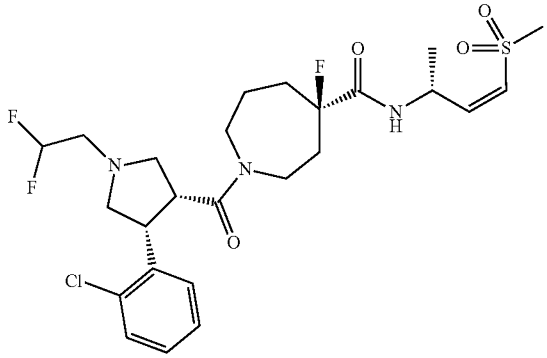 [SMILES: C[C@H](/C=C\S(C)(=O)=O)NC(=O)[C@@]1(F)CCCN(C(=O)[C@H]2CN(CC(F)F)C[C@H]2c2ccccc2Cl)CC1] | 197 | (R)-1-((3R,4R)-4-(2-chlorophenyl)-1-(2,2-difluoroethyl)pyrrolidine-3-carbonyl)-4-fluoro-N-((R,Z)-4-(methylsulfonyl)but-3-en-2-yl) azepane-4-carboxamide |
| 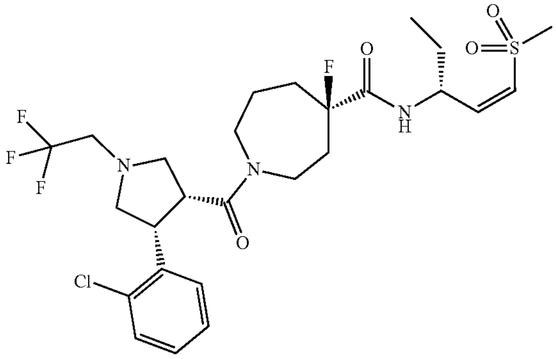 [SMILES: CC[C@H](/C=C\S(C)(=O)=O)NC(=O)[C@@]1(F)CCCN(C(=O)[C@H]2CN(CC(F)(F)F)C[C@H]2c2ccccc2Cl)CC1] | 198 | (R)-1-((3R,4R)-4-(2-chlorophenyl)-1-(2,2,2-trifluoroethyl)pyrrolidine-3-carbonyl)-4-fluoro-N-((R,Z)-1-(methylsulfonyl)pent-1-en-3-yl)azepane-4-carboxamide |

TABLE 1-continued

Compounds of the Disclosure.

| Structure | Cmp. No. | IUPAC |
|---|---|---|
| 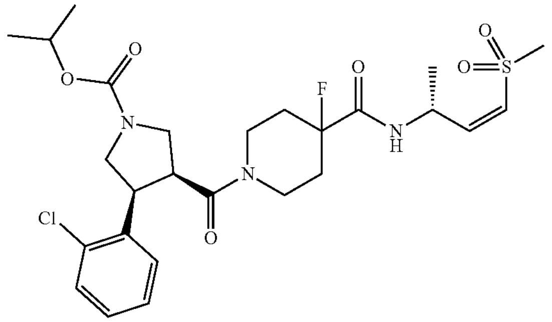 [SMILES: CC(C)OC(=O)N1C[C@H](c2ccccc2Cl)[C@H](C(=O)N2CCC(F)(C(=O)N[C@H](C)/C=C\S(C)(=O)=O)CC2)C1] | 199 | isopropyl (3S,4S)-3-(2-chlorophenyl)-4-(4-fluoro-4-(((R,Z)-4-(methylsulfonyl)but-3-en-2-yl)carbamoyl)piperidine-1-carbonyl) pyrrolidine-1-carboxylate |
| 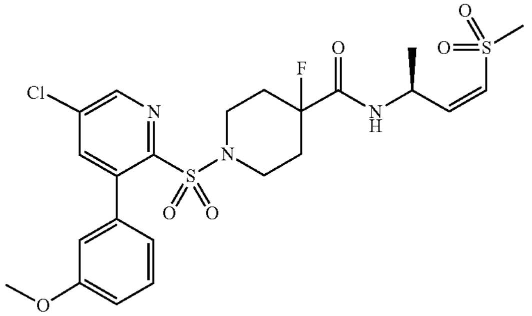 | 200 | (S,Z)-1-((5-chloro-3-(3-methoxyphenyl) pyridin-2-yl)sulfonyl)-4-fluoro-N-(4-(methylsulfonyl) but-3-en-2-yl)piperidine-4-carboxamide |
| 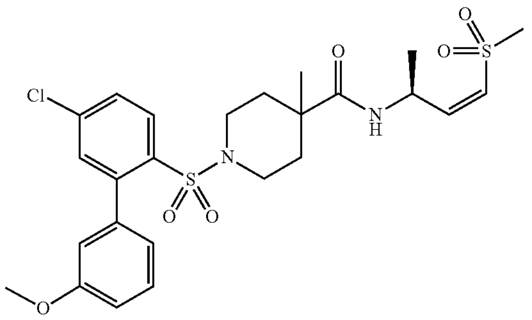 | 201 | (S,Z)-1-((5-chloro-3'-methoxy-[1,1'-biphenyl]-2-yl)sulfonyl)-4-methyl-N-(4-(methylsulfonyl)but-3-en-2-yl)piperidine-4-carboxamide |
| 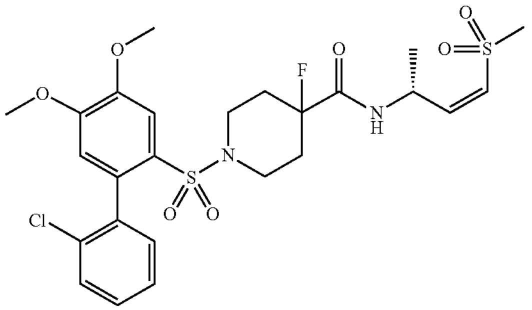 | 202 | (R,Z)-1-((2'-chloro-4,5-dimethoxy-[1,1'-biphenyl]-2-yl)sulfonyl)-4-fluoro-N-(4-(methylsulfonyl)but-3-en-2-yl)piperidine-4-carboxamide |

TABLE 1-continued

| Compounds of the Disclosure. | | |
|---|---|---|
| Structure | Cmp. No. | IUPAC |
| 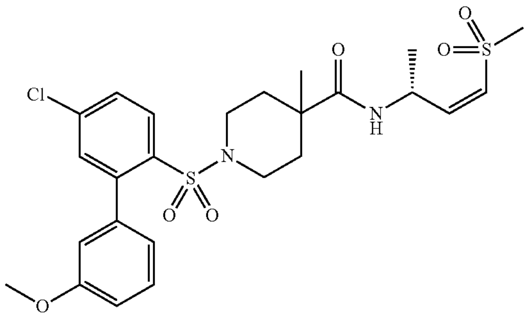 | 203 | (R,Z)-1-((5-chloro-3'-methoxy-[1,1'-biphenyl]-2-yl)sulfonyl)-4-methyl-N-(4-(methylsulfonyl)but-3-en-2-yl)piperidine-4-carboxamide |
| 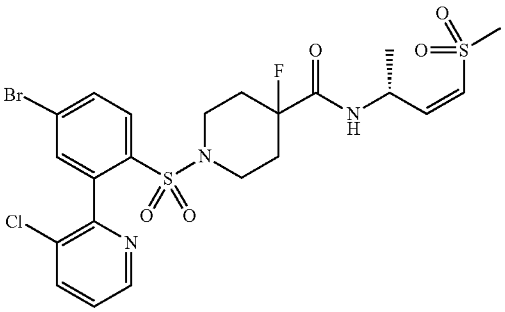 [SMILES: C[C@H](/C=C\S(C)(=O)=O)NC(=O)C1(F)CCN(S(=O)(=O)c2ccc(Br)cc2-c2ncccc2Cl)CC1] | 204 | (R,Z)-1-((4-bromo-2-(3-chloropyridin-2-yl)phenyl)sulfonyl)-4-fluoro-N-(4-(methylsulfonyl)but-3-en-2-yl)piperidine-4-carboxamide |
| 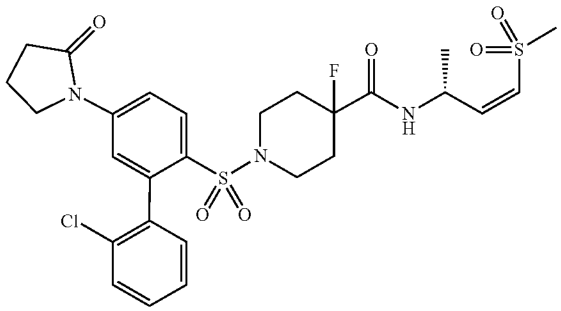 [SMILES: C[C@H](/C=C\S(C)(=O)=O)NC(=O)C1(F)CCN(S(=O)(=O)c2ccc(N3CCCC3=O)cc2-c2ccccc2Cl)CC1] | 205 | (R,Z)-1-((2'-chloro-5-(2-oxopyrrolidin-1-yl)-[1,1'-biphenyl]-2-yl)sulfonyl)-4-fluoro-N-(4-(methylsulfonyl)but-3-en-2-yl)piperidine-4-carboxamide |
| 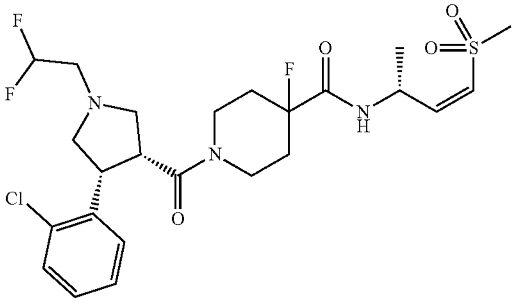 [SMILES: C[C@H](/C=C\S(C)(=O)=O)NC(=O)C1(F)CCN(C(=O)[C@H]2CN(CC(F)F)C[C@H]2c2ccccc2Cl)CC1] | 206 | 1-((3R,4R)-4-(2-chlorophenyl)-1-(2,2-difluoroethyl)pyrrolidine-3-carbonyl)-4-fluoro-N-((R,Z)-4-(methylsulfonyl)but-3-en-2-yl)piperidine-4-carboxamide |

TABLE 1-continued

| Compounds of the Disclosure. | | |
|---|---|---|
| Structure | Cmp. No. | IUPAC |
| 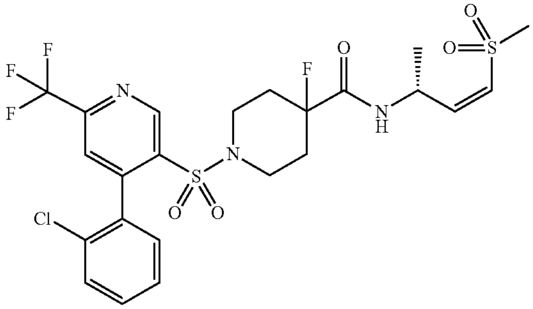 [SMILES: C[C@H](/C=C\S(C)(=O)=O)NC(=O)C1(F)CCN(S(=O)(=O)c2cnc(C(F)(F)F)cc2-c2ccccc2Cl)CC1] | 207 | (R,Z)-1-((4-(2-chlorophenyl)-6-(trifluoromethyl)pyridin-3-yl)sulfonyl)-4-fluoro-N-(4-(methylsulfonyl)but-3-en-2-yl)piperidine-4-carboxamide |
| 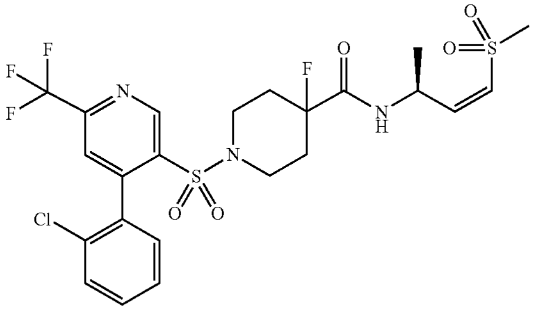 [SMILES: C[C@@H](/C=C\S(C)(=O)=O)NC(=O)C1(F)CCN(S(=O)(=O)c2cnc(C(F)(F)F)cc2-c2ccccc2Cl)CC1] | 208 | (S,Z)-1-((4-(2-chlorophenyl)-6-(trifluoromethyl)pyridin-3-yl)sulfonyl)-4-fluoro-N-(4-(methylsulfonyl)but-3-en-2-yl)piperidine-4-carboxamide |
| 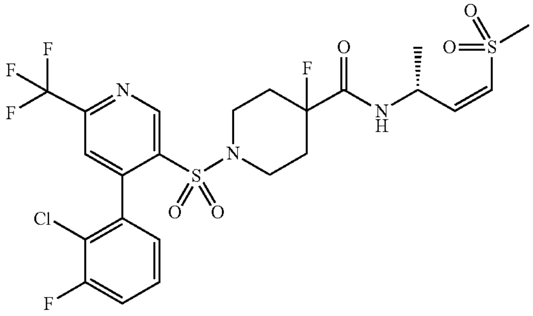 [SMILES: C[C@H](/C=C\S(C)(=O)=O)NC(=O)C1(F)CCN(S(=O)(=O)c2cnc(C(F)(F)F)cc2-c2cccc(F)c2Cl)CC1] | 209 | (R,Z)-1-((4-(2-chloro-3-fluorophenyl)-6-(trifluoromethyl)pyridin-3-yl)sulfonyl)-4-fluoro-N-(4-(methylsulfonyl)but-3-en-2-yl)piperidine-4-carboxamide |
| 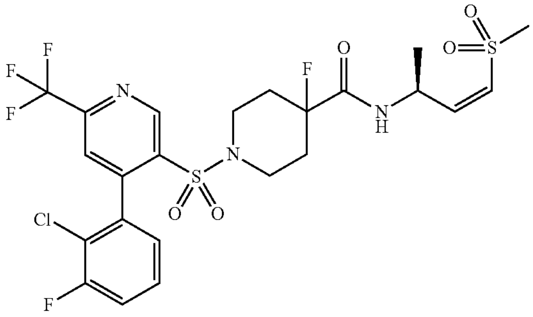 [SMILES: C[C@@H](/C=C\S(C)(=O)=O)NC(=O)C1(F)CCN(S(=O)(=O)c2cnc(C(F)(F)F)cc2-c2cccc(F)c2Cl)CC1] | 210 | (S,Z)-1-((4-(2-chloro-3-fluorophenyl)-6-(trifluoromethyl)pyridin-3-yl)sulfonyl)-4-fluoro-N-(4-(methylsulfonyl)but-3-en-2-yl)piperidine-4-carboxamide |

TABLE 1-continued

Compounds of the Disclosure.

| Structure | Cmp. No. | IUPAC |
|---|---|---|
| 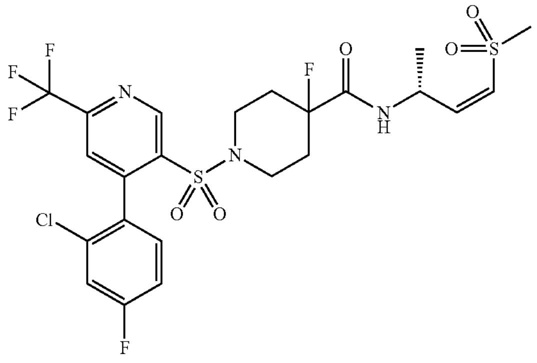 [SMILES: C[C@H](/C=C\S(C)(=O)=O)NC(=O)C1(F)CCN(S(=O)(=O)c2cnc(C(F)(F)F)cc2-c2ccc(F)cc2Cl)CC1] | 211 | (R,Z)-1-((4-(2-chloro-4-fluorophenyl)-6-(trifluoromethyl)pyridin-3-yl)sulfonyl)-4-fluoro-N-(4-(methylsulfonyl)but-3-en-2-yl)piperidine-4-carboxamide |
| 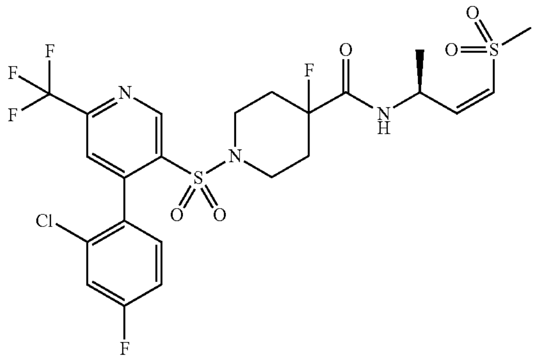 [SMILES: C[C@@H](/C=C\S(C)(=O)=O)NC(=O)C1(F)CCN(S(=O)(=O)c2cnc(C(F)(F)F)cc2-c2ccc(F)cc2Cl)CC1] | 212 | (S,Z)-1-((4-(2-chloro-4-fluorophenyl)-6-(trifluoromethyl)pyridin-3-yl)sulfonyl)-4-fluoro-N-(4-(methylsulfonyl)but-3-en-2-yl)piperidine-4-carboxamide |
| 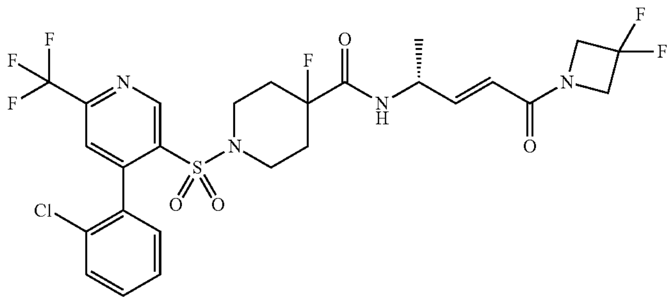 [SMILES: C[C@H](/C=C/C(=O)N1CC(F)(F)C1)NC(=O)C1(F)CCN(S(=O)(=O)c2cnc(C(F)(F)F)cc2-c2ccccc2Cl)CC1] | 213 | (R,E)-1-((4-(2-chlorophenyl)-6-(trifluoromethyl)pyridin-3-yl)sulfonyl)-N-(5-(3,3-difluoroazetidin-1-yl)-5-oxopent-3-en-2-yl)-4-fluoropiperidine-4-carboxamide |
| 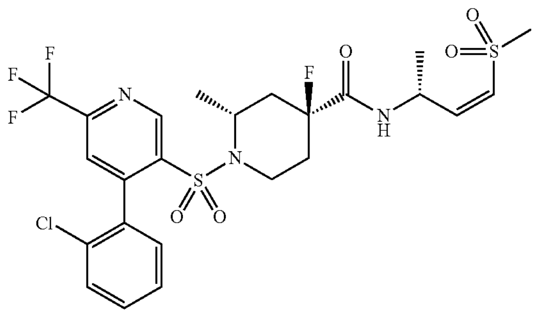 [SMILES: C[C@H](/C=C\S(C)(=O)=O)NC(=O)[C@]1(F)CCN(S(=O)(=O)c2cnc(C(F)(F)F)cc2-c2ccccc2Cl)[C@H](C)C1] | 214 | (2R,4S)-1-((4-(2-chlorophenyl)-6-(trifluoromethyl)pyridin-3-yl)sulfonyl)-4-fluoro-2-methyl-N-((R,Z)-4-(methylsulfonyl)but-3-en-2-yl)piperidine-4-carboxamide |

TABLE 1-continued

Compounds of the Disclosure.

| Structure | Cmp. No. | IUPAC |
|---|---|---|
| 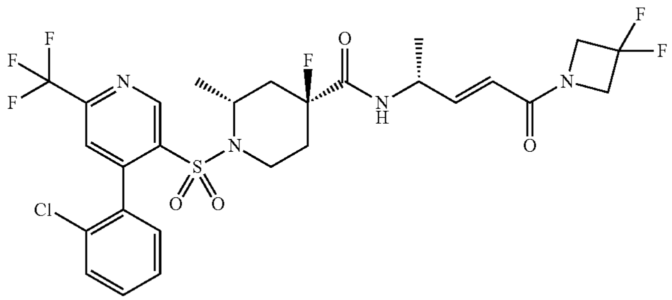 [SMILES: C[C@H](/C=C/C(=O)N1CC(F)(F)C1)NC(=O)[C@]1(F)CCN(S(=O)(=O)c2cnc(C(F)(F)F)cc2-c2ccccc2Cl)[C@H](C)C1] | 215 | (2R,4S)-1-((4-(2-chlorophenyl)-6-(trifluoromethyl)pyridin-3-yl)sulfonyl)-N-((R,E)-5-(3,3-difluoroazetidin-1-yl)-5-oxopent-3-en-2-yl)-4-fluoro-2-methylpiperidine-4-carboxamide |
| 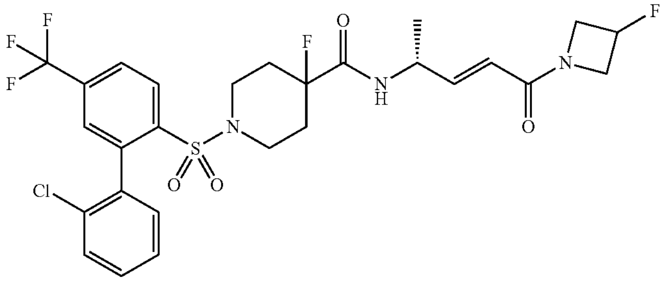 [SMILES: C[C@H](/C=C/C(=O)N1CC(F)C1)NC(=O)C1(F)CCN(S(=O)(=O)c2ccc(C(F)(F)F)cc2-c2ccccc2Cl)CC1] | 216 | (R,E)-1-((2'-chloro-5-(trifluoromethyl)-[1,1'-biphenyl]-2-yl)sulfonyl)-4-fluoro-N-(5-(3-fluoroazetidin-1-yl)-5-oxopent-3-en-2-yl)piperidine-4-carboxamide |
| 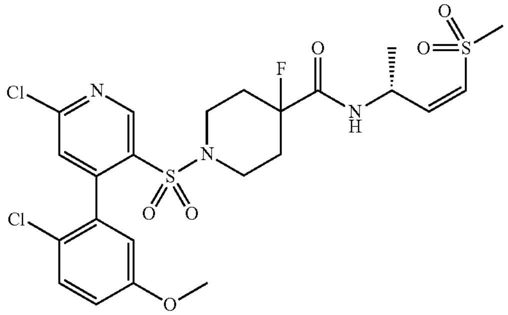 [SMILES: COc1ccc(Cl)c(-c2cc(Cl)ncc2S(=O)(=O)N2CCC(F)(C(=O)N[C@H](C)/C=C\S(C)(=O)=O)CC2)c1] | 217 | (R,Z)-1-((6-chloro-4-(2-chloro-5-methoxyphenyl)pyridin-3-yl)sulfonyl)-4-fluoro-N-(4-(methylsulfonyl)but-3-en-2-yl)piperidine-4-carboxamide |
| 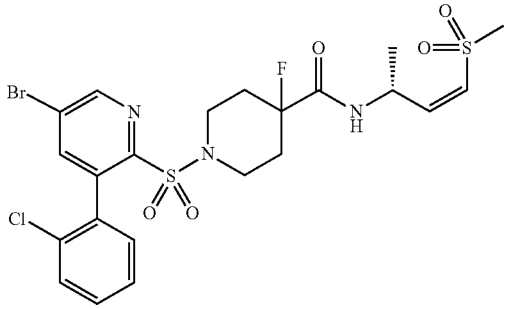 [SMILES: C[C@H](/C=C\S(C)(=O)=O)NC(=O)C1(F)CCN(S(=O)(=O)c2ncc(Br)cc2-c2ccccc2Cl)CC1] | 218 | (R,Z)-1-((5-bromo-3-(2-chlorophenyl)pyridin-2-yl)sulfonyl)-4-fluoro-N-(4-(methylsulfonyl)but-3-en-2-yl)piperidine-4-carboxamide |
| 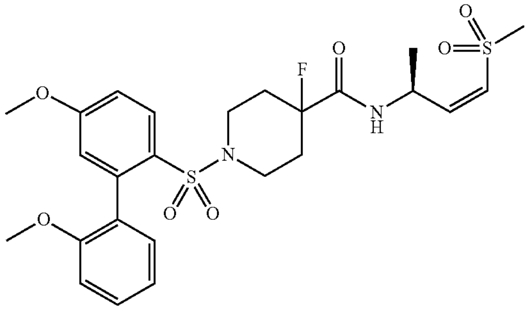 | 219 | (S,Z)-1-((2',5-dimethoxy-[1,1'-biphenyl]-2-yl)sulfonyl)-4-fluoro-N-(4-(methylsulfonyl)but-3-en-2-yl)piperidine-4-carboxamide |

TABLE 1-continued

| Structure | Cmp. No. | IUPAC |
|---|---|---|
| Compounds of the Disclosure. | | |
| 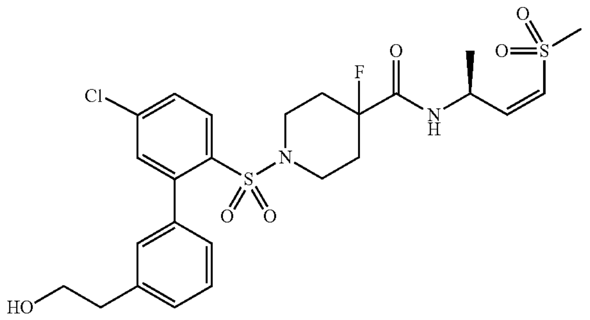 [SMILES: C[C@@H](/C=C\S(C)(=O)=O)NC(=O)C1(F)CCN(S(=O)(=O)c2ccc(Cl)cc2-c2cccc(CCO)c2)CC1] | 220 | (S,Z)-1-((5-chloro-3'-(2-hydroxyethyl)-[1,1'-biphenyl]-2-yl)sulfonyl)-4-fluoro-N-(4-(methylsulfonyl)but-3-en-2-yl)piperidine-4-carboxamide |
| 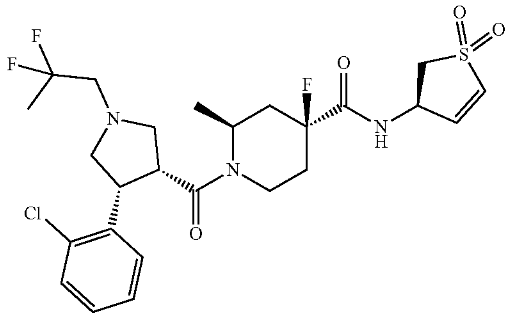 [SMILES: C[C@H]1C[C@](F)(C(=O)N[C@@H]2C=CS(=O)(=O)C2)CCN1C(=O)[C@H]1CN(CC(C)(F)F)C[C@H]1c1ccccc1Cl] | 221 | (2*S,4*S)-1-((3R,4R)-4-(2-chlorophenyl)-1-(2,2-difluoropropyl)pyrrolidine-3-carbonyl)-N-((R)-1,1-dioxido-2,3-dihydrothiophen-3-yl)-4-fluoro-2-methylpiperidine-4-carboxamide |
| 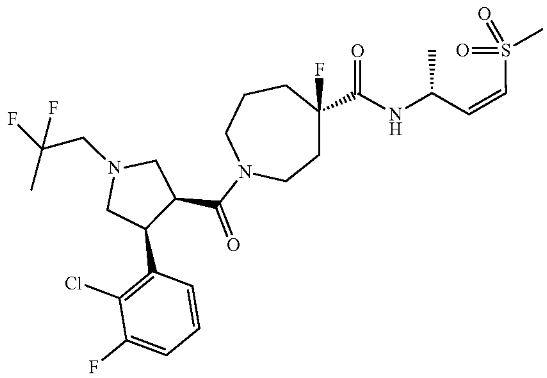 [SMILES: C[C@H](/C=C\S(C)(=O)=O)NC(=O)[C@@]1(F)CCCN(C(=O)[C@@H]2CN(CC(C)(F)F)C[C@@H]2c2cccc(F)c2Cl)CC1] | 222 | (R)-1-((3*S,4*S)-4-(2-chloro-3-fluorophenyl)-1-(2,2-difluoropropyl)pyrrolidine-3-carbonyl)-4-fluoro-N-((R,Z)-4-(methylsulfonyl)but-3-en-2-yl)azepane-4-carboxamide |
| 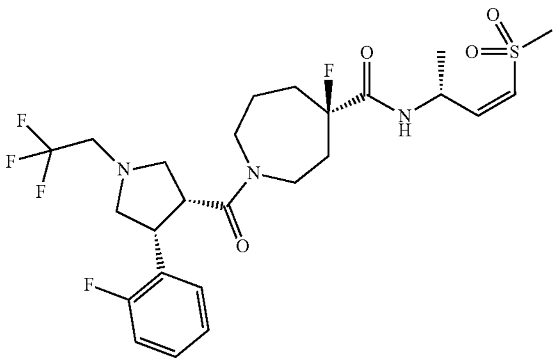 [SMILES: C[C@H](/C=C\S(C)(=O)=O)NC(=O)[C@@]1(F)CCCN(C(=O)[C@H]2CN(CC(F)(F)F)C[C@H]2c2ccccc2F)CC1] | 223 | (R)-4-fluoro-1-((3*R,4*R)-4-(2-fluorophenyl)-1-(2,2,2-trifluoroethyl)pyrrolidine-3-carbonyl)-N-((R,Z)-4-(methylsulfonyl)but-3-en-2-yl) azepane-4-carboxamide |

TABLE 1-continued

Compounds of the Disclosure.

| Structure | Cmp. No. | IUPAC |
|---|---|---|
| 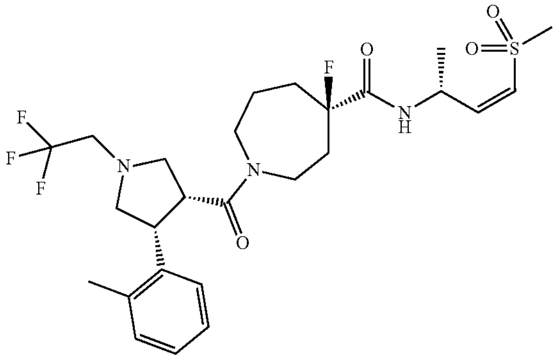 | 224 | (R)-4-fluoro-N-((R,Z)-4-(methylsulfonyl)but-3-en-2-yl)-1-((3*R,4*R)-4-(o-tolyl)-1-(2,2,2-trifluoroethyl)pyrrolidine-3-carbonyl) azepane-4-carboxamide |
| 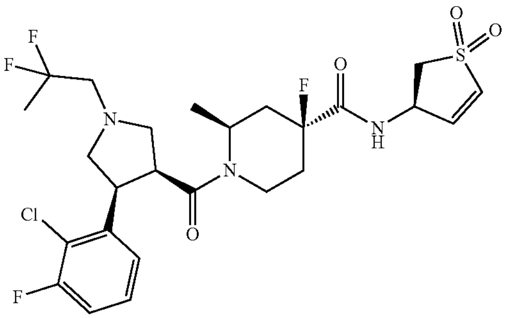 [SMILES: C[C@H]1C[C@](F)(C(=O)N[C@@H]2C=CS(=O)(=O)C2)CCN1C(=O)[C@@H]1CN(CC(C)(F)F)C[C@@H]1c1cccc(F)c1Cl] | 225 | (2*S,4*S)-1-((3*S,4*S)-4-(2-chloro-3-fluorophenyl)-1-(2,2-difluoropropyl) pyrrolidine-3-carbonyl)-N-((R)-1,1-dioxido-2,3-dihydrothiophen-3-yl)-4-fluoro-2-methylpiperidine-4-carboxamide |
| 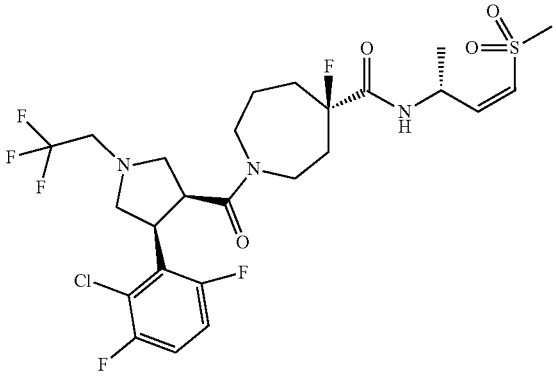 [SMILES: C[C@H](/C=C\S(C)(=O)=O)NC(=O)[C@@]1(F)CCCN(C(=O)[C@@H]2CN(CC(F)(F)F)C[C@@H]2c2c(F)ccc(F)c2Cl)CC1] | 226 | (R)-1-((3*S,4*S)-4-(2-chloro-3,6-difluorophenyl)-1-(2,2,2-trifluoroethyl)pyrrolidine-3-carbonyl)-4-fluoro-N-((R,Z)-4-(methylsulfonyl)but-3-en-2-yl)azepane-4-carboxamide |
| 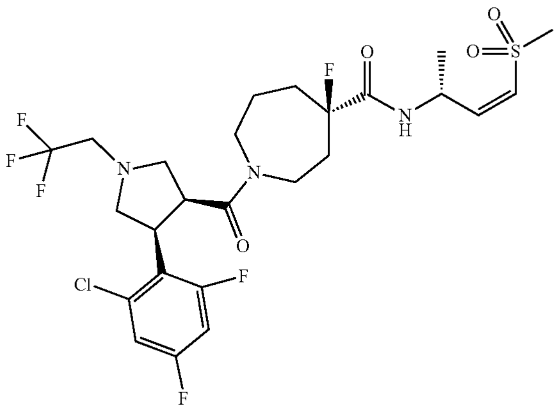 [SMILES: C[C@H](/C=C\S(C)(=O)=O)NC(=O)[C@@]1(F)CCCN(C(=O)[C@@H]2CN(CC(F)(F)F)C[C@@H]2c2c(F)cc(F)cc2Cl)CC1] | 227 | (R)-1-((3*S,4*S)-4-(2-chloro-4,6-difluorophenyl)-1-(2,2,2-trifluoroethyl)pyrrolidine-3-carbonyl)-4-fluoro-N-((R,Z)-4-(methylsulfonyl)but-3-en-2-yl)azepane-4-carboxamide |

TABLE 1-continued

Compounds of the Disclosure.

| Structure | Cmp. No. | IUPAC |
|---|---|---|
| 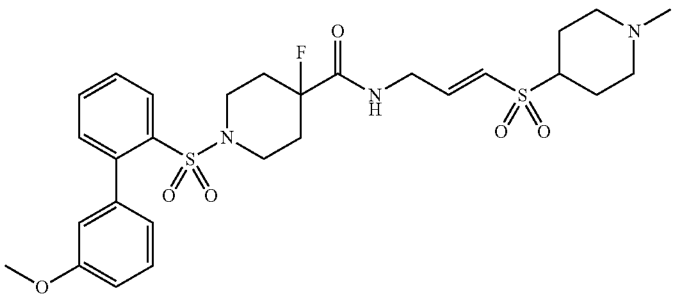 | 228 | (E)-4-fluoro-1-((3'-methoxy-[1,1'-biphenyl]-2-yl)sulfonyl)-N-(3-((1-methylpiperidin-4-yl)sulfonyl)allyl)piperidine-4-carboxamide |
| 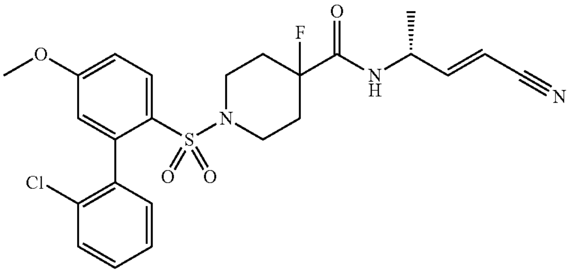 [SMILES: COc1ccc(S(=O)(=O)N2CCC(F)(C(=O)N[C@H](C)/C=C/C#N)CC2)c(-c2ccccc2Cl)c1] | 229 | (R,E)-1-((2'-chloro-5-methoxy-[1,1'-biphenyl]-2-yl)sulfonyl)-N-(4-cyanobut-3-en-2-yl)-4-fluoropiperidine-4-carboxamide |
| 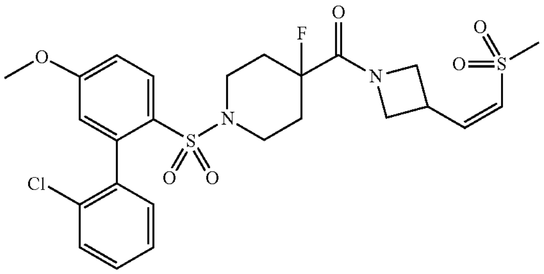 | 230 | (Z)-(1-((2'-chloro-5-methoxy-[1,1'-biphenyl]-2-yl)sulfonyl)-4-fluoropiperidin-4-yl)(3-(2-(methylsulfonyl)vinyl)azetidin-1-yl)methanone |
| 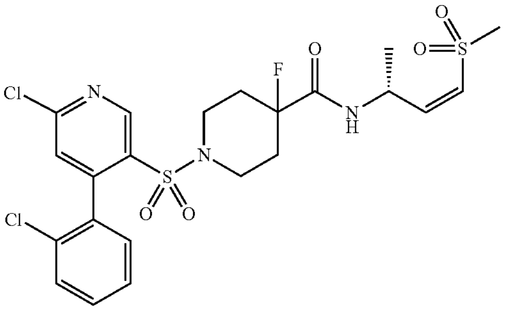 [SMILES: C[C@H](/C=C\S(C)(=O)=O)NC(=O)C1(F)CCN(S(=O)(=O)c2cnc(Cl)cc2-c2ccccc2Cl)CC1] | 231 | (R,Z)-1-((6-chloro-4-(2-chlorophenyl) pyridin-3-yl)sulfonyl)-4-fluoro-N-(4-(methylsulfonyl)but-3-en-2-yl)piperidine-4-carboxamide |
| 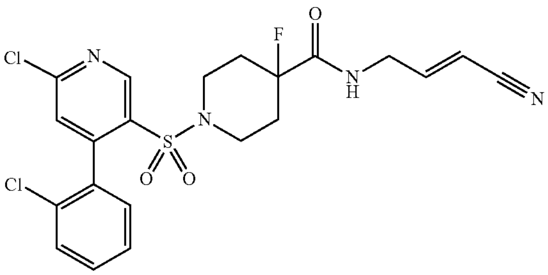 [SMILES: N#C/C=C/CNC(=O)C1(F)CCN(S(=O)(=O)c2cnc(Cl)cc2-c2ccccc2Cl)CC1] | 232 | (E)-1-((6-chloro-4-(2-chlorophenyl)pyridin-3-yl)sulfonyl)-N-(3-cyanoallyl)-4-fluoropiperidine-4-carboxamide |

TABLE 1-continued

| Compounds of the Disclosure. | | |
|---|---|---|
| Structure | Cmp. No. | IUPAC |
| 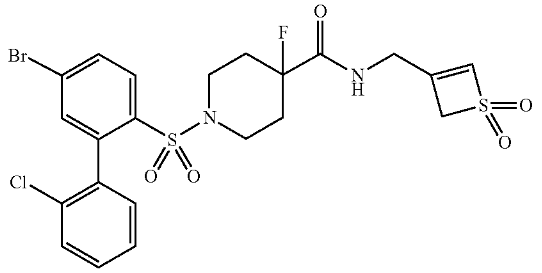 [SMILES: O=C(NCC1=CS(=O)(=O)C1)C1(F)CCN(S(=O)(=O)c2ccc(Br)cc2-c2ccccc2Cl)CC1] | 233 | 1-((5-bromo-2'-chloro-[1,1'-biphenyl]-2-yl)sulfonyl)-N-((1,1-dioxido-2H-thiet-3-yl)methyl)-4-fluoropiperidine-4-carboxamide |
| 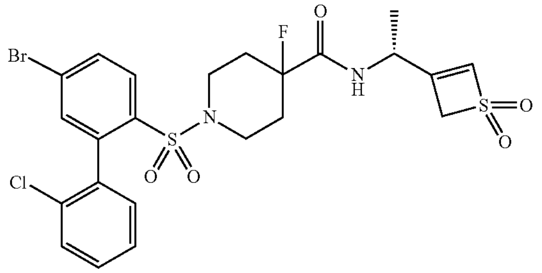 [SMILES: C[C@@H](NC(=O)C1(F)CCN(S(=O)(=O)c2ccc(Br)cc2-c2ccccc2Cl)CC1)C1=CS(=O)(=O)C1] | 234 | (*R)-1-((5-bromo-2'-chloro-[1,1'-biphenyl]-2-yl)sulfonyl)-N-(1-(1,1-dioxido-2H-thiet-3-yl)ethyl)-4-fluoropiperidine-4-carboxamide |
| 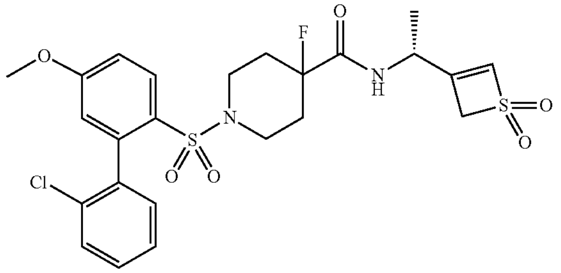 [SMILES: COc1ccc(S(=O)(=O)N2CCC(F)(C(=O)N[C@H](C)C3=CS(=O)(=O)C3)CC2)c(-c2ccccc2Cl)c1] | 235 | (R)-1-((2'-chloro-5-methoxy-[1,1'-biphenyl]-2-yl)sulfonyl)-N-(1-(1,1-dioxido-2H-thiet-3-yl)ethyl)-4-fluoropiperidine-4-carboxamide |
| 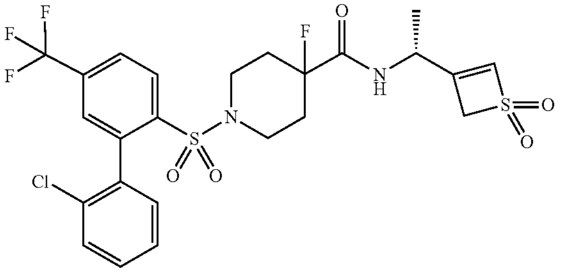 [SMILES: C[C@@H](NC(=O)C1(F)CCN(S(=O)(=O)c2ccc(C(F)(F)F)cc2-c2ccccc2Cl)CC1)C1=CS(=O)(=O)C1] | 236 | (R)-1-((2'-chloro-5-(trifluoromethyl)-[1,1'-biphenyl]-2-yl)sulfonyl)-N-(1-(1,1-dioxido-2H-thiet-3-yl)ethyl)-4-fluoropiperidine-4-carboxamide |
| 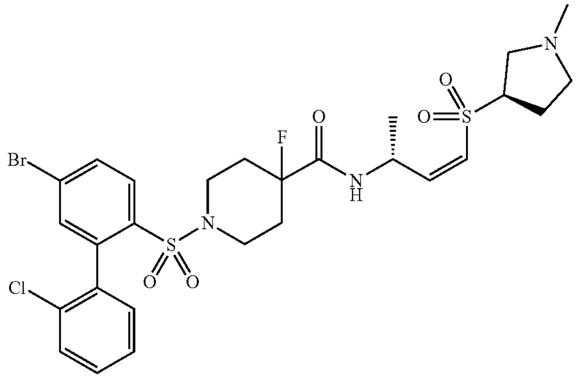 [SMILES: C[C@H](/C=C\S(=O)(=O)[C@@H]1CCN(C)C1)NC(=O)C1(F)CCN(S(=O)(=O)c2ccc(Br)cc2-c2ccccc2Cl)CC1] | 237 | 1-((5-bromo-2'-chloro-[1,1'-biphenyl]-2-yl)sulfonyl)-4-fluoro-N-((R,Z)-4-(((*R)-1-methylpyrrolidin-3-yl)sulfonyl)but-3-en-2-yl)piperidine-4-carboxamide |

TABLE 1-continued

Compounds of the Disclosure.

| Structure | Cmp. No. | IUPAC |
|---|---|---|
| 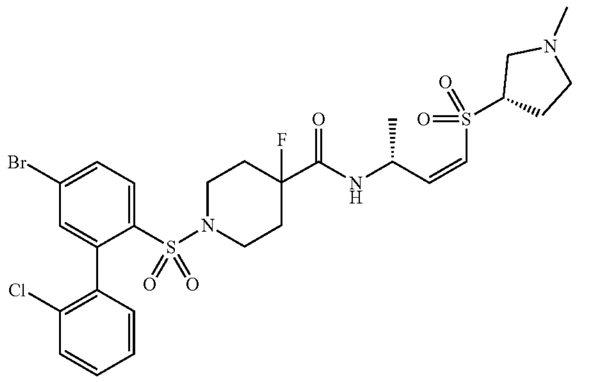 [SMILES: C[C@H](/C=C\S(=O)(=O)[C@H]1CCN(C)C1)NC(=O)C1(F)CCN(S(=O)(=O)c2ccc(Br)cc2-c2ccccc2Cl)CC1] | 238 | 1-((5-bromo-2'-chloro-[1,1'-biphenyl]-2-yl)sulfonyl)-4-fluoro-N-((R,Z)-4-(((*S)-1-methylpyrrolidin-3-yl)sulfonyl)but-3-en-2-yl)piperidine-4-carboxamide |
| 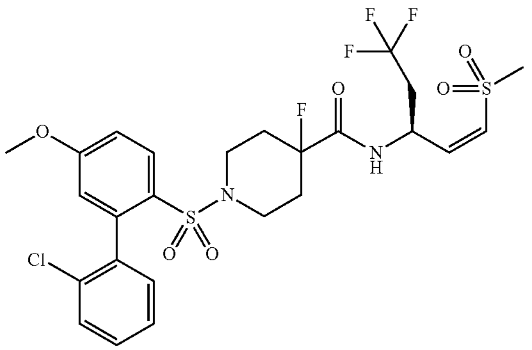 | 239 | (*S,Z)-1-((2'-chloro-5-methoxy-[1,1'-biphenyl]-2-yl)sulfonyl)-4-fluoro-N-(5,5,5-trifluoro-1-(methylsulfonyl)pent-1-en-3-yl)piperidine-4-carboxamide |
| 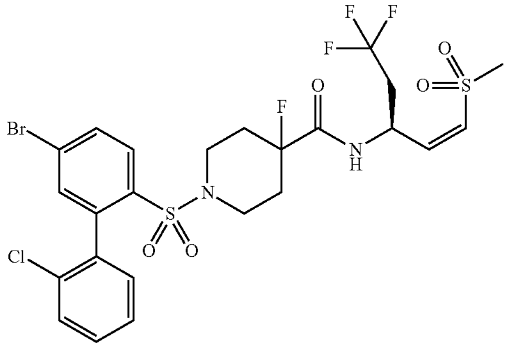 [SMILES: CS(=O)(=O)/C=C\[C@H](CC(F)(F)F)NC(=O)C1(F)CCN(S(=O)(=O)c2ccc(Br)cc2-c2ccccc2Cl)CC1] | 240 | (*S,Z)-1-((5-bromo-2'-chloro-[1,1'-biphenyl]-2-yl)sulfonyl)-4-fluoro-N-(5,5,5-trifluoro-1-(methylsulfonyl)pent-1-en-3-yl)piperidine-4-carboxamide |
| 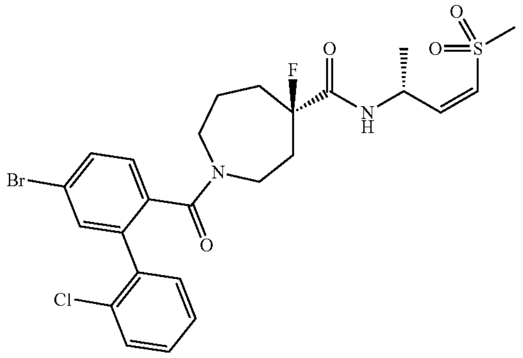 [SMILES: C[C@H](/C=C\S(C)(=O)=O)NC(=O)[C@@]1(F)CCCN(C(=O)c2ccc(Br)cc2-c2ccccc2Cl)CC1] | 241 | (R)-1-(5-bromo-2'-chloro-[1,1'-biphenyl]-2-carbonyl)-4-fluoro-N-((R,Z)-4-(methylsulfonyl)but-3-en-2-yl)azepane-4-carboxamide |

TABLE 1-continued

Compounds of the Disclosure.

| Structure | Cmp. No. | IUPAC |
|---|---|---|
| 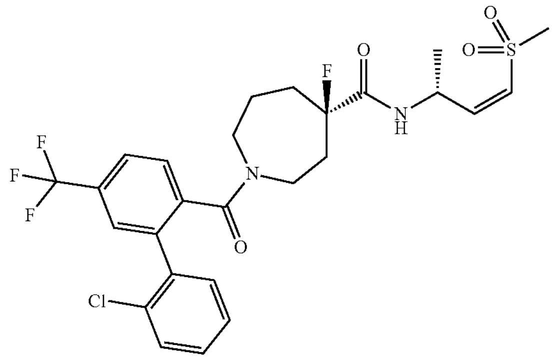 [SMILES: C[C@H](/C=C\S(C)(=O)=O)NC(=O)[C@@]1(F)CCCN(C(=O)c2ccc(C(F)(F)F)cc2-c2ccccc2Cl)CC1] | 242 | (R)-1-(2'-chloro-5-(trifluoromethyl)-[1,1'-biphenyl]-2-carbonyl)-4-fluoro-N-((R,Z)-4-(methylsulfonyl)but-3-en-2-yl)azepane-4-carboxamide |
| 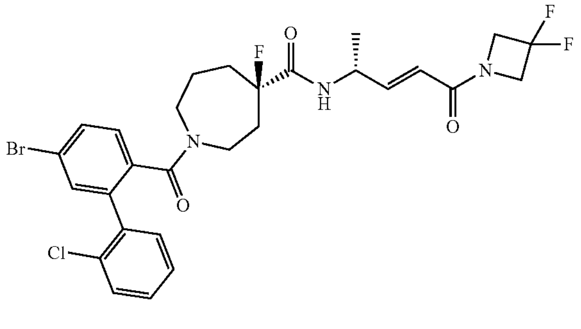 [SMILES: C[C@H](/C=C/C(=O)N1CC(F)(F)C1)NC(=O)[C@@]1(F)CCCN(C(=O)c2ccc(Br)cc2-c2ccccc2Cl)CC1] | 243 | (R)-1-(5-bromo-2'-chloro-[1,1'-biphenyl]-2-carbonyl)-N-((R,E)-5-(3,3-difluoroazetidin-1-yl)-5-oxopent-3-en-2-yl)-4-fluoroazepane-4-carboxamide |
| 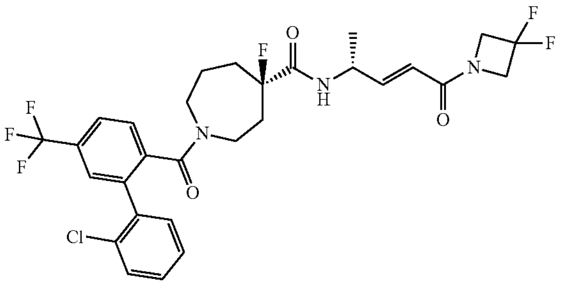 [SMILES: C[C@H](/C=C/C(=O)N1CC(F)(F)C1)NC(=O)[C@@]1(F)CCCN(C(=O)c2ccc(C(F)(F)F)cc2-c2ccccc2Cl)CC1] | 244 | (R)-1-(2'-chloro-5-(trifluoromethyl)-[1,1'-biphenyl]-2-carbonyl)-N-((R,E)-5-(3,3-difluoroazetidin-1-yl)-5-oxopent-3-en-2-yl)-4-fluoroazepane-4-carboxamide |
| 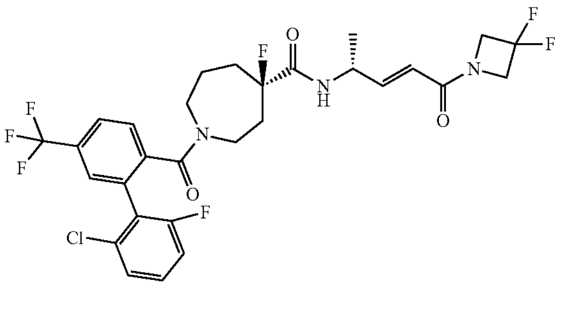 [SMILES: C[C@H](/C=C/C(=O)N1CC(F)(F)C1)NC(=O)[C@@]1(F)CCCN(C(=O)c2ccc(C(F)(F)F)cc2-c2c(F)cccc2Cl)CC1] | 245 | (4R)-1-(2'-chloro-6'-fluoro-5-(trifluoromethyl)-[1,1'-biphenyl]-2-carbonyl)-N-((R,E)-5-(3,3-difluoroazetidin-1-yl)-5-oxopent-3-en-2-yl)-4-fluoroazepane-4-carboxamide |

TABLE 1-continued

| Compounds of the Disclosure. | | |
|---|---|---|
| Structure | Cmp. No. | IUPAC |
| 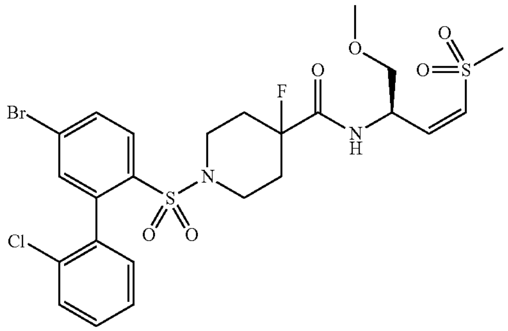 [SMILES: COC[C@@H](/C=C\S(C)(=O)=O)NC(=O)C1(F)CCN(S(=O)(=O)c2ccc(Br)cc2-c2ccccc2Cl)CC1] | 246 | (R,Z)-1-((5-bromo-2'-chloro-[1,1'-biphenyl]-2-yl)sulfonyl)-4-fluoro-N-(1-methoxy-4-(methylsulfonyl)but-3-en-2-yl)piperidine-4-carboxamide |
| 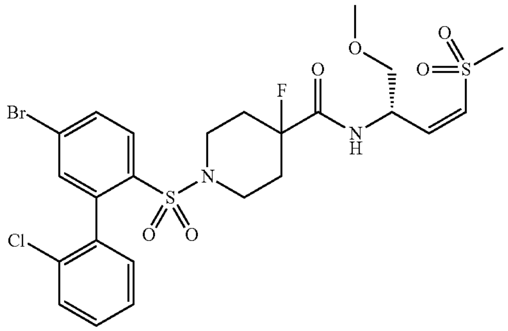 [SMILES: COC[C@H](/C=C\S(C)(=O)=O)NC(=O)C1(F)CCN(S(=O)(=O)c2ccc(Br)cc2-c2ccccc2Cl)CC1] | 247 | (S,Z)-1-((5-bromo-2'-chloro-[1,1'-biphenyl]-2-yl)sulfonyl)-4-fluoro-N-(1-methoxy-4-(methylsulfonyl)but-3-en-2-yl)piperidine-4-carboxamide |
| 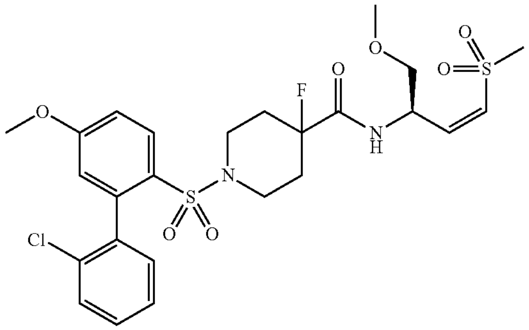 | 248 | (R,Z)-1-((2'-chloro-5-methoxy-[1,1'-biphenyl]-2-yl)sulfonyl)-4-fluoro-N-(1-methoxy-4-(methylsulfonyl)but-3-en-2-yl)piperidine-4-carboxamide |
| 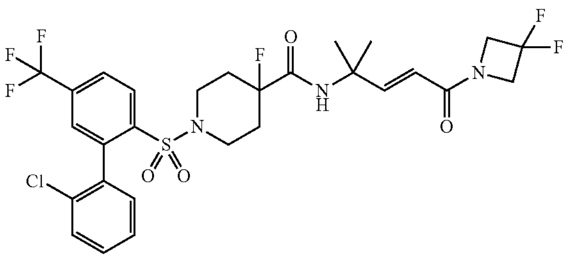 [SMILES: CC(C)(/C=C/C(=O)N1CC(F)(F)C1)NC(=O)C1(F)CCN(S(=O)(=O)c2ccc(C(F)(F)F)cc2-c2ccccc2Cl)CC1] | 249 | (E)-1-((2'-chloro-5-(trifluoromethyl)-[1,1'-biphenyl]-2-yl)sulfonyl)-N-(5-(3,3-difluoroazetidin-1-yl)-2-methyl-5-oxopent-3-en-2-yl)-4-fluoropiperidine-4-carboxamide |

TABLE 1-continued

Compounds of the Disclosure.

| Structure | Cmp. No. | IUPAC |
|---|---|---|
| 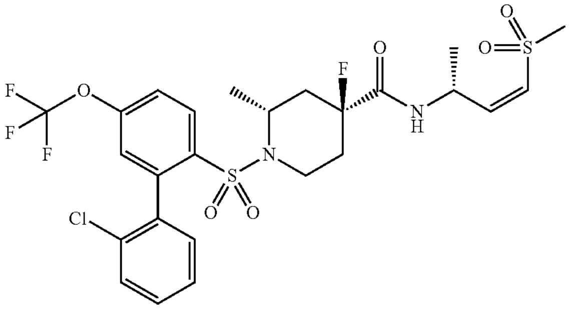 [SMILES: C[C@H](/C=C\S(C)(=O)=O)NC(=O)[C@]1(F)CCN(S(=O)(=O)c2ccc(OC(F)(F)F)cc2-c2ccccc2Cl)[C@H](C)C1] | 250 | (2R,4S)-1-((2'-chloro-5-(trifluoromethoxy)-[1,1'-biphenyl]-2-yl)sulfonyl)-4-fluoro-2-methyl-N-((R,Z)-4-(methylsulfonyl)but-3-en-2-yl)piperidine-4-carboxamide |
| 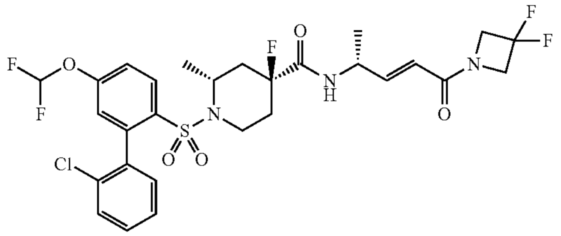 [SMILES: C[C@H](/C=C/C(=O)N1CC(F)(F)C1)NC(=O)[C@]1(F)CCN(S(=O)(=O)c2ccc(OC(F)F)cc2-c2ccccc2Cl)[C@H](C)C1] | 251 | (2R,4S)-1-((2'-chloro-5-(difluoromethoxy)-[1,1'-biphenyl]-2-yl)sulfonyl)-N-((R,E)-5-(3,3-difluoroazetidin-1-yl)-5-oxopent-3-en-2-yl)-4-fluoro-2-methylpiperidine-4-carboxamide |
| 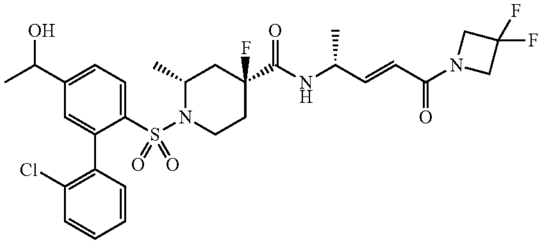 [SMILES: CC(O)c1ccc(S(=O)(=O)N2CC[C@@](F)(C(=O)N[C@H](C)/C=C/C(=O)N3CC(F)(F)C3)C[C@H]2C)c(-c2ccccc2Cl)c1] | 252 | (2R,4S)-1-((2'-chloro-5-((RS)-1-hydroxyethyl)-[1,1'-biphenyl]-2-yl)sulfonyl)-N-((R,E)-5-(3,3-difluoroazetidin-1-yl)-5-oxopent-3-en-2-yl)-4-fluoro-2-methylpiperidine-4-carboxamide |
| 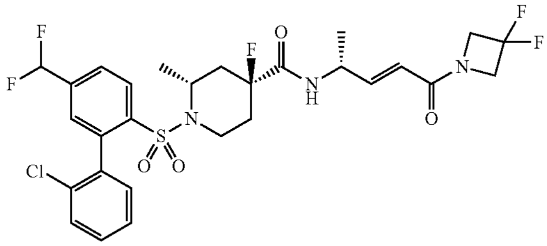 [SMILES: C[C@H](/C=C/C(=O)N1CC(F)(F)C1)NC(=O)[C@]1(F)CCN(S(=O)(=O)c2ccc(C(F)F)cc2-c2ccccc2Cl)[C@H](C)C1] | 253 | (2R,4S)-1-((2'-chloro-5-(difluoromethyl)-[1,1'-biphenyl]-2-yl)sulfonyl)-N-((R,E)-5-(3,3-difluoroazetidin-1-yl)-5-oxopent-3-en-2-yl)-4-fluoro-2-methylpiperidine-4-carboxamide |
| 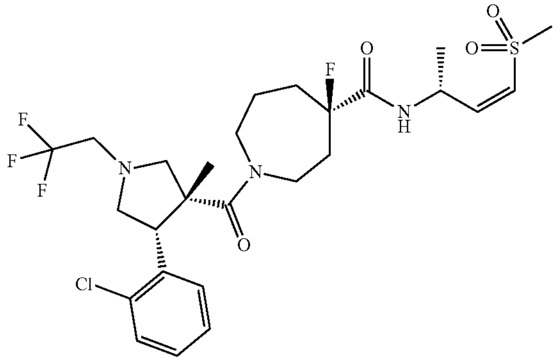 [SMILES: C[C@H](/C=C\S(C)(=O)=O)NC(=O)[C@@]1(F)CCCN(C(=O)[C@@]2(C)CN(CC(F)(F)F)C[C@H]2c2ccccc2Cl)CC1] | 254 | (R)-1-((3R,4R)-4-(2-chlorophenyl)-3-methyl-1-(2,2,2-trifluoroethyl)pyrrolidine-3-carbonyl)-4-fluoro-N-((R,Z)-4-(methylsulfonyl)but-3-en-2-yl)azepane-4-carboxamide |

TABLE 1-continued

Compounds of the Disclosure.

| Structure | Cmp. No. | IUPAC |
|---|---|---|
| 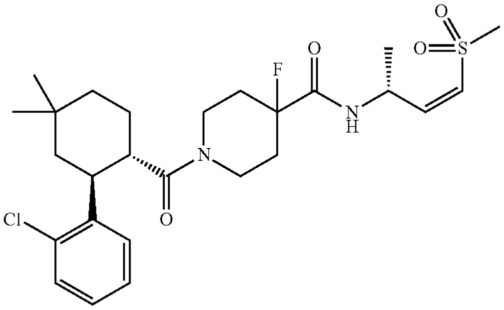 | 255 | 1-((1*S,2*S)-2-(2-chlorophenyl)-4,4-dimethylcyclohexane-1-carbonyl)-4-fluoro-N-((R,Z)-4-(methylsulfonyl)but-3-en-2-yl)piperidine-4-carboxamide |
| 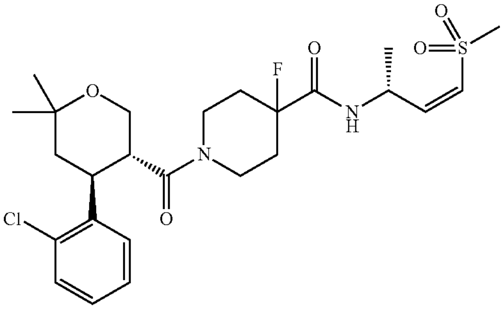 | 256 | 1-((3*R,4*S)-4-(2-chlorophenyl)-6,6-dimethyltetrahydro-2H-pyran-3-carbonyl)-4-fluoro-N-((R,Z)-4-(methylsulfonyl)but-3-en-2-yl)piperidine-4-carboxamide |
| 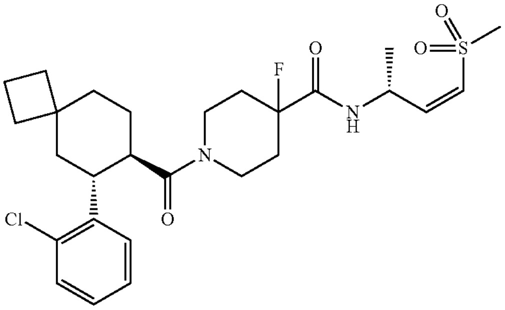 [SMILES: C[C@H](/C=C\S(C)(=O)=O)NC(=O)C1(F)CCN(C(=O)[C@@H]2CCC3(CCC3)C[C@H]2c2ccccc2Cl)CC1] | 257 | 1-((6*R,7*R)-6-(2-chlorophenyl)spiro[3.5]nonane-7-carbonyl)-4-fluoro-N-((R,Z)-4-(methylsulfonyl)but-3-en-2-yl)piperidine-4-carboxamide |
| 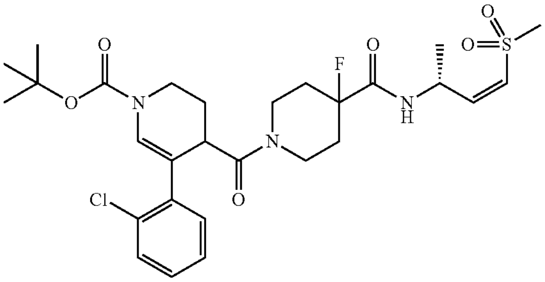 [SMILES: C[C@H](/C=C\S(C)(=O)=O)NC(=O)C1(F)CCN(C(=O)C2CCN(C(=O)OC(C)(C)C)C=C2c2ccccc2Cl)CC1] | 258 | tert-butyl 5-(2-chlorophenyl)-4-(4-fluoro-4-(((R,Z)-4-(methylsulfonyl)but-3-en-2-yl)carbamoyl)piperidine-1-carbonyl)-3,4-dihydropyridine-1(2H)-carboxylate |
| 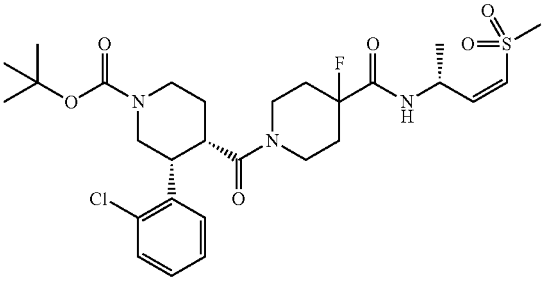 [SMILES: C[C@H](/C=C\S(C)(=O)=O)NC(=O)C1(F)CCN(C(=O)[C@H]2CCN(C(=O)OC(C)(C)C)C[C@H]2c2ccccc2Cl)CC1] | 259 | tert-butyl (3*R,4*S)-3-(2-chlorophenyl)-4-(4-fluoro-4-(((R,Z)-4-(methylsulfonyl)but-3-en-2-yl)carbamoyl)piperidine-1-carbonyl)piperidine-1-carboxylate |

TABLE 1-continued

| Structure | Cmp. No. | IUPAC |
|---|---|---|
| Compounds of the Disclosure. | | |
| 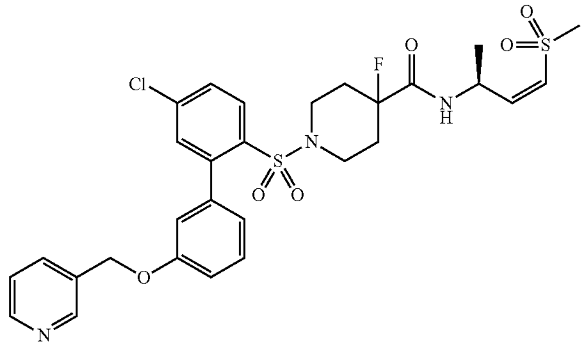 [SMILES: C[C@@H](/C=C\S(C)(=O)=O)NC(=O)C1(F)CCN(S(=O)(=O)c2ccc(Cl)cc2-c2cccc(OCc3cccnc3)c2)CC1] | 260 | (S,Z)-1-((5-chloro-3'-(pyridin-3-ylmethoxy)-[1,1'-biphenyl]-2-yl)sulfonyl)-4-fluoro-N-(4-(methylsulfonyl)but-3-en-2-yl)piperidine-4-carboxamide |
| 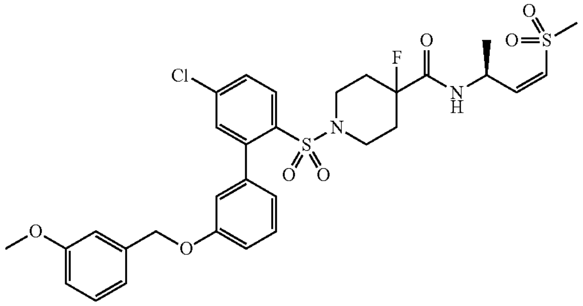 | 261 | (S,Z)-1-((5-chloro-3'-((3-methoxybenzyl)oxy)-[1,1'-biphenyl]-2-yl)sulfonyl)-4-fluoro-N-(4-(methylsulfonyl)but-3-en-2-yl)piperidine-4-carboxamide |
| 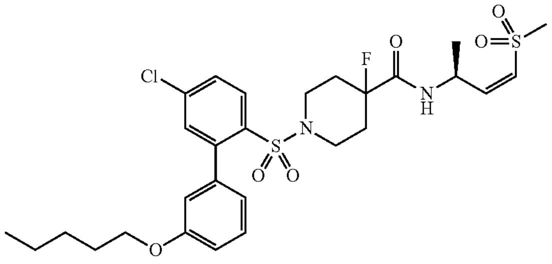 [SMILES: CCCCCOc1cccc(-c2cc(Cl)ccc2S(=O)(=O)N2CCC(F)(C(=O)N[C@@H](C)/C=C\S(C)(=O)=O)CC2)c1] | 262 | (S,Z)-1-((5-chloro-3'-(pentyloxy)-[1,1'-biphenyl]-2-yl)sulfonyl)-4-fluoro-N-(4-(methylsulfonyl)but-3-en-2-yl)piperidine-4-carboxamide |
| 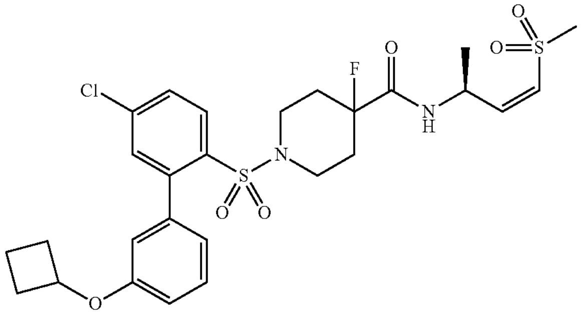 [SMILES: C[C@@H](/C=C\S(C)(=O)=O)NC(=O)C1(F)CCN(S(=O)(=O)c2ccc(Cl)cc2-c2cccc(OC3CCC3)c2)CC1] | 263 | (S,Z)-1-((5-chloro-3'-cyclobutoxy-[1,1'-biphenyl]-2-yl)sulfonyl)-4-fluoro-N-(4-(methylsulfonyl)but-3-en-2-yl)piperidine-4-carboxamide |
| 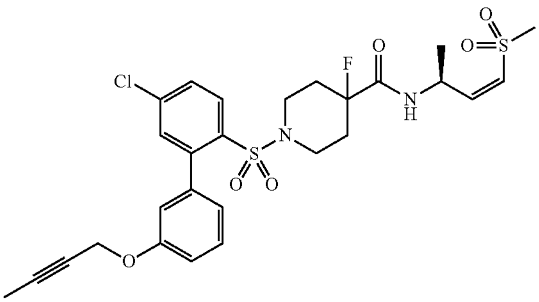 [SMILES: CC#CCOc1cccc(-c2cc(Cl)ccc2S(=O)(=O)N2CCC(F)(C(=O)N[C@@H](C)/C=C\S(C)(=O)=O)CC2)c1] | 264 | (S,Z)-1-((3'-(but-2-yn-1-yloxy)-5-chloro-[1,1'-biphenyl]-2-yl)sulfonyl)-4-fluoro-N-(4-(methylsulfonyl)but-3-en-2-yl)piperidine-4-carboxamide |

TABLE 1-continued

| Compounds of the Disclosure. | | |
|---|---|---|
| Structure | Cmp. No. | IUPAC |
| 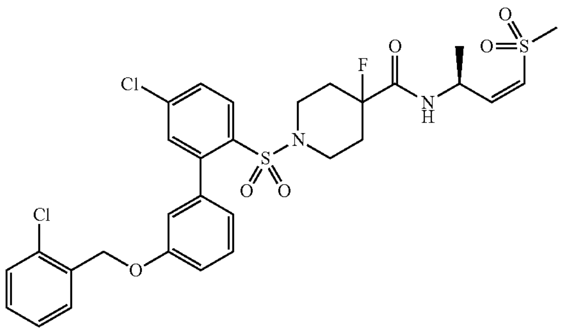 [SMILES: C[C@@H](/C=C\S(C)(=O)=O)NC(=O)C1(F)CCN(S(=O)(=O)c2ccc(Cl)cc2-c2cccc(OCc3ccccc3Cl)c2)CC1] | 265 | (S,Z)-1-((5-chloro-3'-((2-chlorobenzyl)oxy)-[1,1'-biphenyl]-2-yl)sulfonyl)-4-fluoro-N-(4-(methylsulfonyl)but-3-en-2-yl)piperidine-4-carboxamide |
| 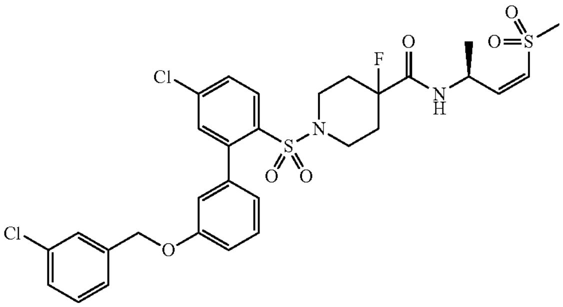 [SMILES: C[C@@H](/C=C\S(C)(=O)=O)NC(=O)C1(F)CCN(S(=O)(=O)c2ccc(Cl)cc2-c2cccc(OCc3cccc(Cl)c3)c2)CC1] | 266 | (S,Z)-1-((5-chloro-3'-((3-chlorobenzyl)oxy)-[1,1'-biphenyl]-2-yl)sulfonyl)-4-fluoro-N-(4-(methylsulfonyl)but-3-en-2-yl)piperidine-4-carboxamide |
| 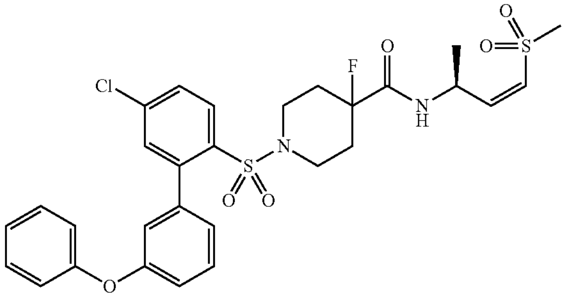 [SMILES: C[C@@H](/C=C\S(C)(=O)=O)NC(=O)C1(F)CCN(S(=O)(=O)c2ccc(Cl)cc2-c2cccc(Oc3ccccc3)c2)CC1] | 267 | (S,Z)-1-((5-chloro-3'-phenoxy-[1,1'-biphenyl]-2-yl)sulfonyl)-4-fluoro-N-(4-(methylsulfonyl)but-3-en-2-yl)piperidine-4-carboxamide |
| 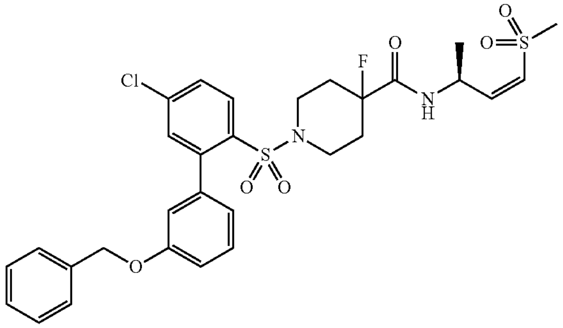 [SMILES: C[C@@H](/C=C\S(C)(=O)=O)NC(=O)C1(F)CCN(S(=O)(=O)c2ccc(Cl)cc2-c2cccc(OCc3ccccc3)c2)CC1] | 268 | (S,Z)-1-((3'-(benzyloxy)-5-chloro-[1,1'-biphenyl]-2-yl)sulfonyl)-4-fluoro-N-(4-(methylsulfonyl)but-3-en-2-yl)piperidine-4-carboxamide |

TABLE 1-continued

| Structure | Cmp. No. | IUPAC |
|---|---|---|
| Compounds of the Disclosure. | | |
| 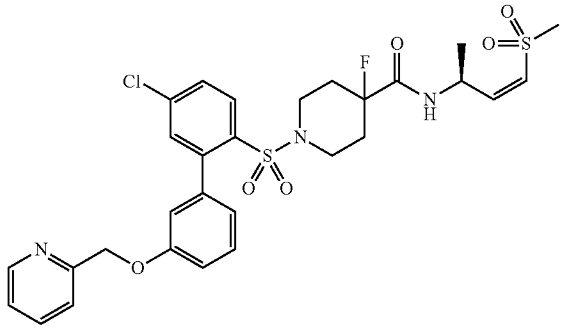 [SMILES: C[C@@H](/C=C\S(C)(=O)=O)NC(=O)C1(F)CCN(S(=O)(=O)c2ccc(Cl)cc2-c2cccc(OCc3ccccn3)c2)CC1] | 269 | (S,Z)-1-((5-chloro-3'-(pyridin-2-ylmethoxy)-[1,1'-biphenyl]-2-yl)sulfonyl)-4-fluoro-N-(4-(methylsulfonyl)but-3-en-2-yl)piperidine-4-carboxamide |
| 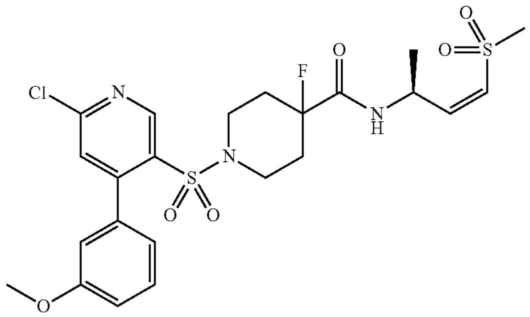 | 270 | (S,Z)-1-((6-chloro-4-(3-methoxyphenyl) pyridin-3-yl)sulfonyl)-4-fluoro-N-(4-(methylsulfonyl) but-3-en-2-yl)piperidine-4-carboxamide |
| 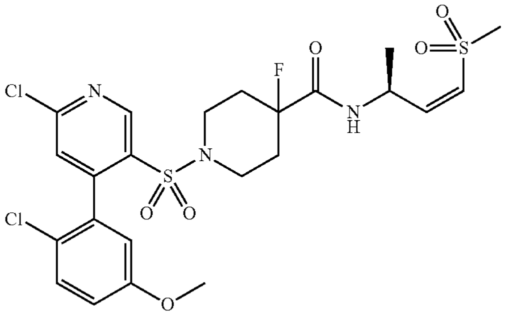 [SMILES: COc1ccc(Cl)c(-c2cc(Cl)ncc2S(=O)(=O)N2CCC(F)(C(=O)N[C@@H](C)/C=C\S(C)(=O)=O)CC2)c1] | 271 | (S,Z)-1-((6-chloro-4-(2-chloro-5-methoxyphenyl)pyridin-3-yl)sulfonyl)-4-fluoro-N-(4-(methylsulfonyl) but-3-en-2-yl)piperidine-4-carboxamide |
| 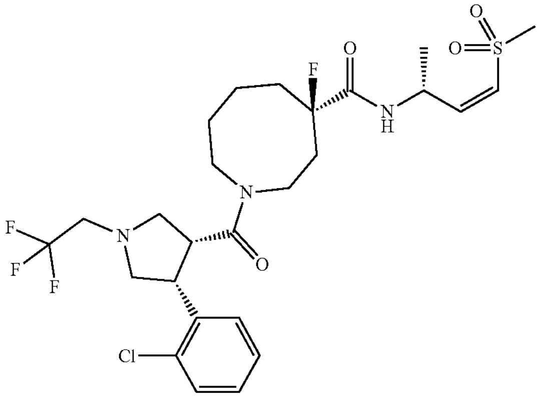 [SMILES: C[C@H](/C=C\S(C)(=O)=O)NC(=O)[C@@]1(F)CCCCN(C(=O)[C@H]2CN(CC(F)(F)F)C[C@H]2c2ccccc2Cl)CC1] | 272 | (*R)-1-((3R,4R)-4-(2-chlorophenyl)-1-(2,2,2-trifluoroethyl)pyrrolidine-3-carbonyl)-4-fluoro-N-((R,Z)-4-(methylsulfonyl)but-3-en-2-yl)azocane-4-carboxamide |

TABLE 1-continued

| Compounds of the Disclosure. | | |
|---|---|---|
| Structure | Cmp. No. | IUPAC |
| 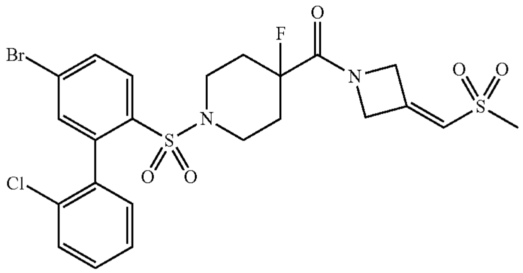 [SMILES: CS(=O)(=O)C=C1CN(C(=O)C2(F)CCN(S(=O)(=O)c3ccc(Br)cc3-c3ccccc3Cl)CC2)C1] | 273 | (1-((5-bromo-2'-chloro-[1,1'-biphenyl]-2-yl)sulfonyl)-4-fluoropiperidin-4-yl)(3-((methylsulfonyl)methylene)azetidin-1-yl)methanone |
| 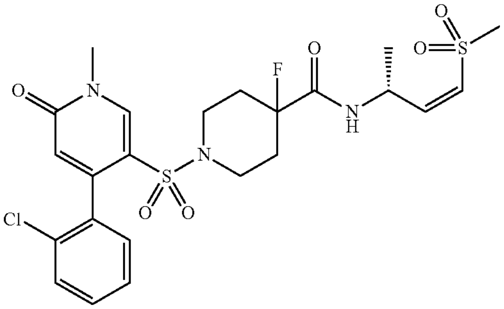 [SMILES: C[C@H](/C=C\S(C)(=O)=O)NC(=O)C1(F)CCN(S(=O)(=O)c2cn(C)c(=O)cc2-c2ccccc2Cl)CC1] | 274 | (R,Z)-1-((4-(2-chlorophenyl)-1-methyl-6-oxo-1,6-dihydropyridin-3-yl)sulfonyl)-4-fluoro-N-(4-(methylsulfonyl)but-3-en-2-yl)piperidine-4-carboxamide |
| 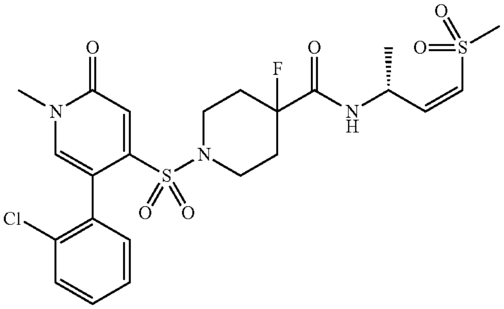 | 275 | (R,Z)-1-((5-(2-chlorophenyl)-1-methyl-2-oxo-1,2-dihydropyridin-4-yl)sulfonyl)-4-fluoro-N-(4-(methylsulfonyl)but-3-en-2-yl)piperidine-4-carboxamide |
| 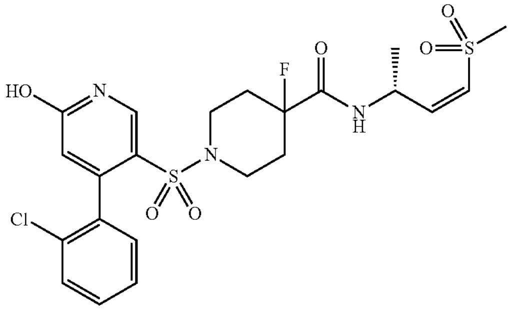 [SMILES: C[C@H](/C=C\S(C)(=O)=O)NC(=O)C1(F)CCN(S(=O)(=O)c2cnc(O)cc2-c2ccccc2Cl)CC1] | 276 | (R,Z)-1-((4-(2-chlorophenyl)-6-hydroxypyridin-3-yl)sulfonyl)-4-fluoro-N-(4-(methylsulfonyl) but-3-en-2-yl)piperidine-4-carboxamide |
| 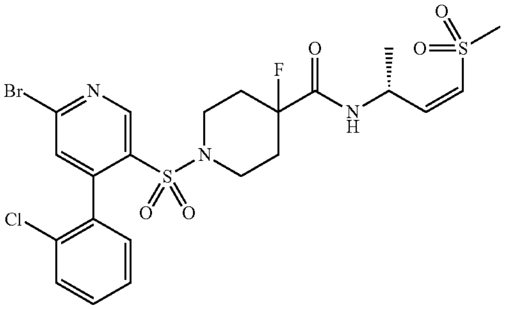 [SMILES: C[C@H](/C=C\S(C)(=O)=O)NC(=O)C1(F)CCN(S(=O)(=O)c2cnc(Br)cc2-c2ccccc2Cl)CC1] | 277 | (R,Z)-1-((6-bromo-4-(2-chlorophenyl) pyridin-3-yl)sulfonyl)-4-fluoro-N-(4-(methylsulfonyl)but-3-en-2-yl)piperidine-4-carboxamide |

TABLE 1-continued

Compounds of the Disclosure.

| Structure | Cmp. No. | IUPAC |
|---|---|---|
| 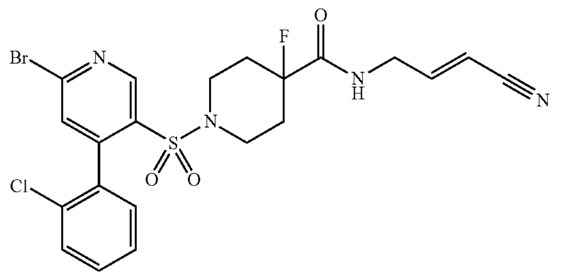 [SMILES: N#C/C=C/CNC(=O)C1(F)CCN(S(=O)(=O)c2cnc(Br)cc2-c2ccccc2Cl)CC1] | 278 | (E)-1-((6-bromo-4-(2-chlorophenyl)pyridin-3-yl)sulfonyl)-N-(3-cyanoallyl)-4-fluoropiperidine-4-carboxamide |
| 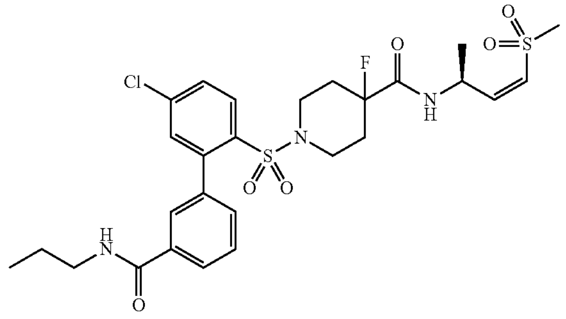 [SMILES: CCCNC(=O)c1cccc(-c2cc(Cl)ccc2S(=O)(=O)N2CCC(F)(C(=O)N[C@@H](C)/C=C\S(C)(=O)=O)CC2)c1] | 279 | (S,Z)-1-((5-chloro-3'-(propylcarbamoyl)-[1,1'-biphenyl]-2-yl)sulfonyl)-4-fluoro-N-(4-(methylsulfonyl)but-3-en-2-yl)piperidine-4-carboxamide |
| 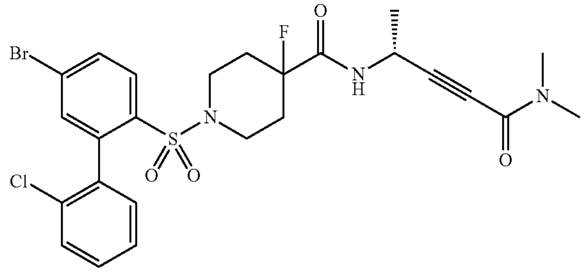 [SMILES: C[C@H](C#CC(=O)N(C)C)NC(=O)C1(F)CCN(S(=O)(=O)c2ccc(Br)cc2-c2ccccc2Cl)CC1] | 280 | (R)-1-((5-bromo-2'-chloro-[1,1'-biphenyl]-2-yl)sulfonyl)-N-(5-(dimethylamino)-5-oxopent-3-yn-2-yl)-4-fluoropiperidine-4-carboxamide |
| 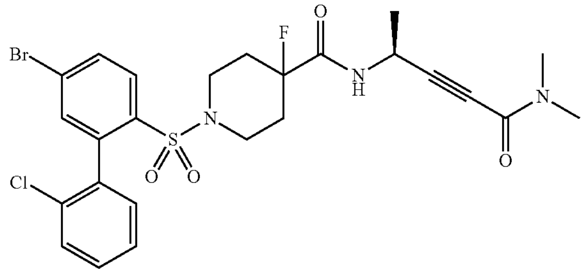 [SMILES: C[C@@H](C#CC(=O)N(C)C)NC(=O)C1(F)CCN(S(=O)(=O)c2ccc(Br)cc2-c2ccccc2Cl)CC1] | 281 | (S)-1-((5-bromo-2'-chloro-[1,1'-biphenyl]-2-yl)sulfonyl)-N-(5-(dimethylamino)-5-oxopent-3-yn-2-yl)-4-fluoropiperidine-4-carboxamide |
| 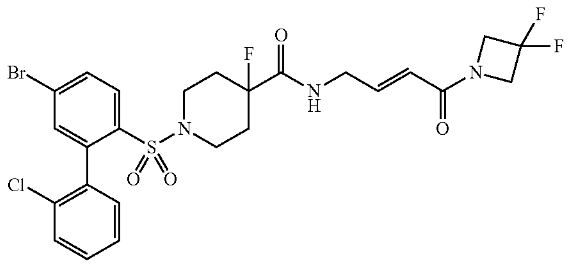 [SMILES: O=C(/C=C/CNC(=O)C1(F)CCN(S(=O)(=O)c2ccc(Br)cc2-c2ccccc2Cl)CC1)N1CC(F)(F)C1] | 282 | (E)-1-((5-bromo-2'-chloro-[1,1'-biphenyl]-2-yl)sulfonyl)-N-(4-(3,3-difluoroazetidin-1-yl)-4-oxobut-2-en-1-yl)-4-fluoropiperidine-4-carboxamide |

TABLE 1-continued

| Compounds of the Disclosure. | | |
|---|---|---|
| Structure | Cmp. No. | IUPAC |
| 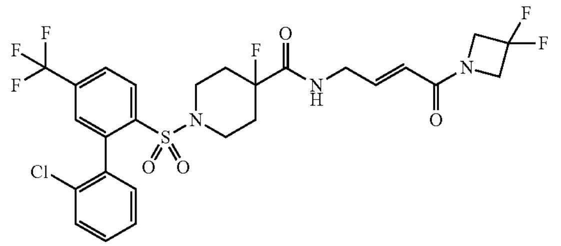 [SMILES: O=C(/C=C/CNC(=O)C1(F)CCN(S(=O)(=O)c2ccc(C(F)(F)F)cc2-c2ccccc2Cl)CC1)N1CC(F)(F)C1] | 283 | (E)-1-((2'-chloro-5-(trifluoromethyl)-[1,1'-biphenyl]-2-yl)sulfonyl)-N-(4-(3,3-difluoroazetidin-1-yl)-4-oxobut-2-en-1-yl)-4-fluoropiperidine-4-carboxamide |
| 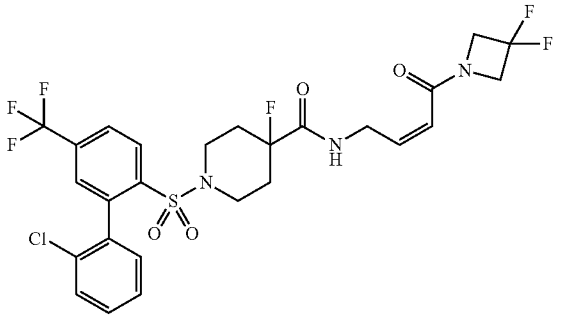 [SMILES: O=C(/C=C\CNC(=O)C1(F)CCN(S(=O)(=O)c2ccc(C(F)(F)F)cc2-c2ccccc2Cl)CC1)N1CC(F)(F)C1] | 284 | (Z)-1-((2'-chloro-5-(trifluoromethyl)-[1,1'-biphenyl]-2-yl)sulfonyl)-N-(4-(3,3-difluoroazetidin-1-yl)-4-oxobut-2-en-1-yl)-4-fluoropiperidine-4-carboxamide |
| 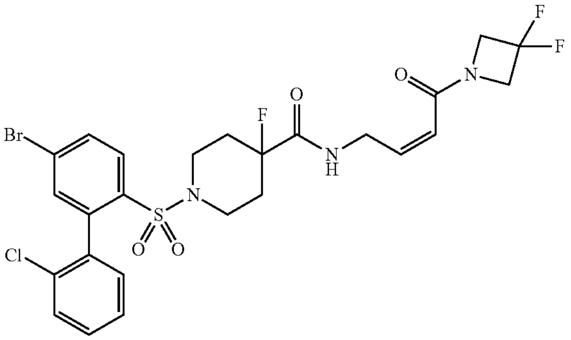 [SMILES: O=C(/C=C\CNC(=O)C1(F)CCN(S(=O)(=O)c2ccc(Br)cc2-c2ccccc2Cl)CC1)N1CC(F)(F)C1] | 285 | (Z)-1-((5-bromo-2'-chloro-[1,1'-biphenyl]-2-yl)sulfonyl)-N-(4-(3,3-difluoroazetidin-1-yl)-4-oxobut-2-en-1-yl)-4-fluoropiperidine-4-carboxamide |
| 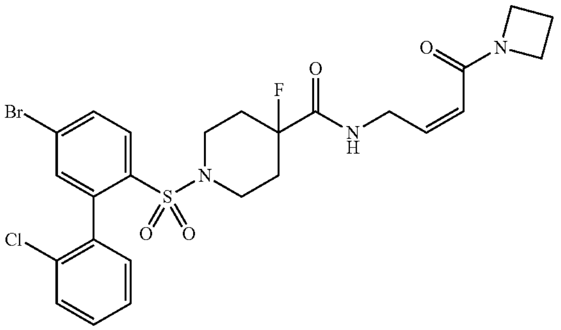 [SMILES: O=C(/C=C\CNC(=O)C1(F)CCN(S(=O)(=O)c2ccc(Br)cc2-c2ccccc2Cl)CC1)N1CCC1] | 286 | (Z)-N-(4-(azetidin-1-yl)-4-oxobut-2-en-1-yl)-1-((5-bromo-2'-chloro-[1,1'-biphenyl]-2-yl)sulfonyl)-4-fluoropiperidine-4-carboxamide |

TABLE 1-continued

Compounds of the Disclosure.

| Structure | Cmp. No. | IUPAC |
|---|---|---|
| 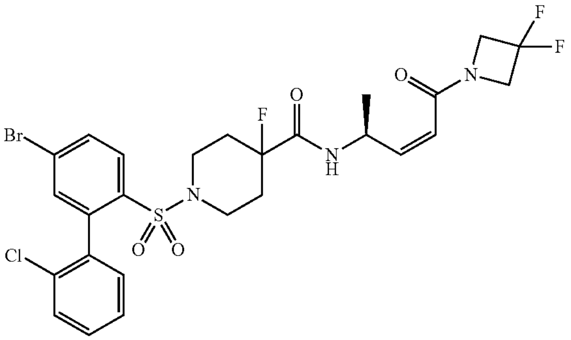 [SMILES: C[C@@H](/C=C\C(=O)N1CC(F)(F)C1)NC(=O)C1(F)CCN(S(=O)(=O)c2ccc(Br)cc2-c2ccccc2Cl)CC1] | 287 | (S,Z)-1-((5-bromo-2'-chloro-[1,1'-biphenyl]-2-yl)sulfonyl)-N-(5-(3,3-difluoroazetidin-1-yl)-5-oxopent-3-en-2-yl)-4-fluoropiperidine-4-carboxamide |
| 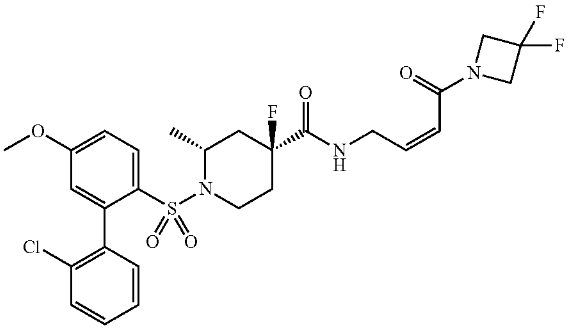 [SMILES: COc1ccc(S(=O)(=O)N2CC[C@@](F)(C(=O)NC/C=C\C(=O)N3CC(F)(F)C3)C[C@H]2C)c(-c2ccccc2Cl)c1] | 288 | (2R,4S)-1-((2'-chloro-5-methoxy-[1,1'-biphenyl]-2-yl)sulfonyl)-N-((Z)-4-(3,3-difluoroazetidin-1-yl)-4-oxobut-2-en-1-yl)-4-fluoro-2-methylpiperidine-4-carboxamide |
| 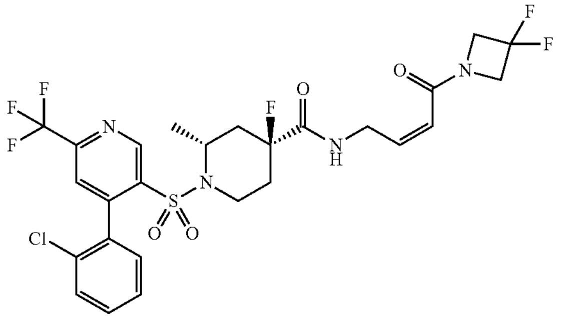 [SMILES: C[C@@H]1C[C@](F)(C(=O)NC/C=C\C(=O)N2CC(F)(F)C2)CCN1S(=O)(=O)c1cnc(C(F)(F)F)cc1-c1ccccc1Cl] | 289 | (2R,4S)-1-((4-(2-chlorophenyl)-6-(trifluoromethyl)pyridin-3-yl)sulfonyl)-N-((Z)-4-(3,3-difluoroazetidin-1-yl)-4-oxobut-2-en-1-yl)-4-fluoro-2-methylpiperidine-4-carboxamide |
| 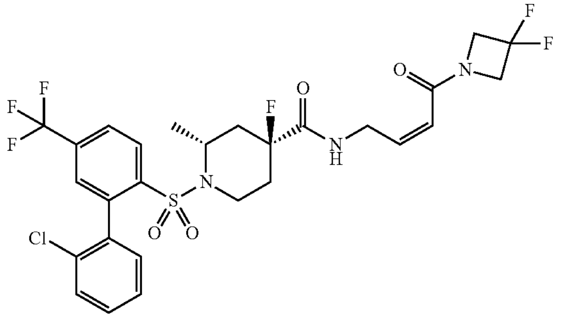 [SMILES: C[C@@H]1C[C@](F)(C(=O)NC/C=C\C(=O)N2CC(F)(F)C2)CCN1S(=O)(=O)c1ccc(C(F)(F)F)cc1-c1ccccc1Cl] | 290 | (2R,4S)-1-((2'-chloro-5-(trifluoromethyl)-[1,1'-biphenyl]-2-yl)sulfonyl)-N-((Z)-4-(3,3-difluoroazetidin-1-yl)-4-oxobut-2-en-1-yl)-4-fluoro-2-methylpiperidine-4-carboxamide |

TABLE 1-continued

| Compounds of the Disclosure. | | |
|---|---|---|
| Structure | Cmp. No. | IUPAC |
| 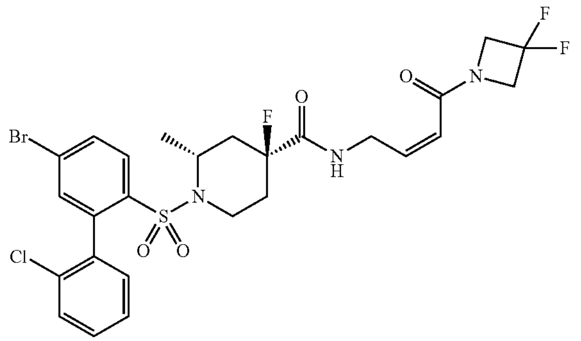 [SMILES: C[C@@H]1C[C@](F)(C(=O)NC/C=C\C(=O)N2CC(F)(F)C2)CCN1S(=O)(=O)c1ccc(Br)cc1-c1ccccc1Cl] | 291 | (2R,4S)-1-((5-bromo-2'-chloro-[1,1'-biphenyl]-2-yl)sulfonyl)-N-((Z)-4-(3,3-difluoroazetidin-1-yl)-4-oxobut-2-en-1-yl)-4-fluoro-2-methylpiperidine-4-carboxamide |
| 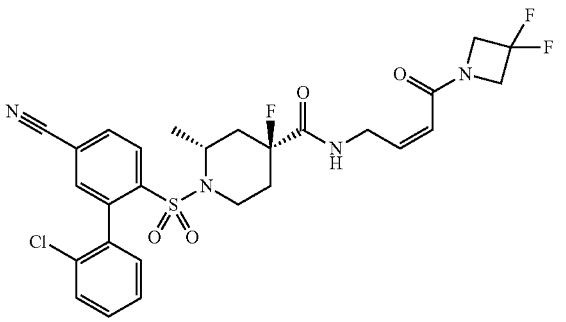 [SMILES: C[C@@H]1C[C@](F)(C(=O)NC/C=C\C(=O)N2CC(F)(F)C2)CCN1S(=O)(=O)c1ccc(C#N)cc1-c1ccccc1Cl] | 292 | (2R,4S)-1-((2'-chloro-5-cyano-[1,1'-biphenyl]-2-yl)sulfonyl)-N-((Z)-4-(3,3-difluoroazetidin-1-yl)-4-oxobut-2-en-1-yl)-4-fluoro-2-methylpiperidine-4-carboxamide |
| 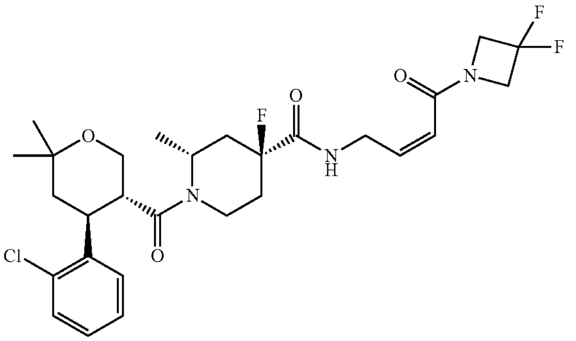 [SMILES: C[C@@H]1C[C@](F)(C(=O)NC/C=C\C(=O)N2CC(F)(F)C2)CCN1C(=O)[C@H]1COC(C)(C)C[C@@H]1c1ccccc1Cl] | 293 | (2*R,4*S)-1-((3*R,4*S)-4-(2-chlorophenyl)-6,6-dimethyltetrahydro-2H-pyran-3-carbonyl)-N-((Z)-4-(3,3-difluoroazetidin-1-yl)-4-oxobut-2-en-1-yl)-4-fluoro-2-methylpiperidine-4-carboxamide |
| 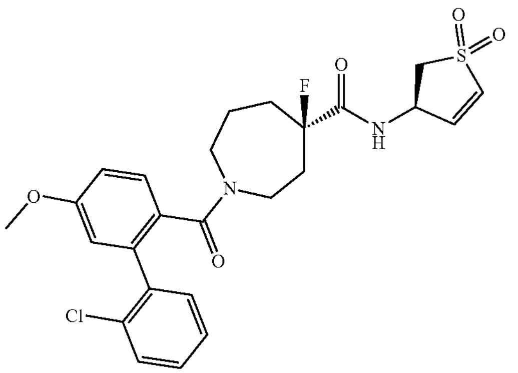 [SMILES: COc1ccc(C(=O)N2CCC[C@](F)(C(=O)N[C@@H]3C=CS(=O)(=O)C3)CC2)c(-c2ccccc2Cl)c1] | 294 | (R)-1-(2'-chloro-5-methoxy-[1,1'-biphenyl]-2-carbonyl)-N-((R)-1,1-dioxido-2,3-dihydrothiophen-3-yl)-4-fluoroazepane-4-carboxamide |

TABLE 1-continued

| Compounds of the Disclosure. | | |
|---|---|---|
| Structure | Cmp. No. | IUPAC |
| 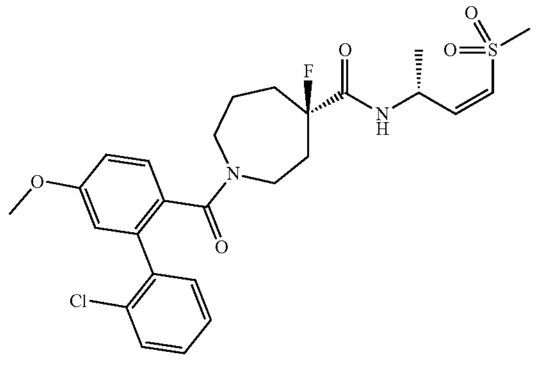 | 295 | (R)-1-(2'-chloro-5-methoxy-[1,1'-biphenyl]-2-carbonyl)-4-fluoro-N-((R,Z)-4-(methylsulfonyl)but-3-en-2-yl)azepane-4-carboxamide |
| 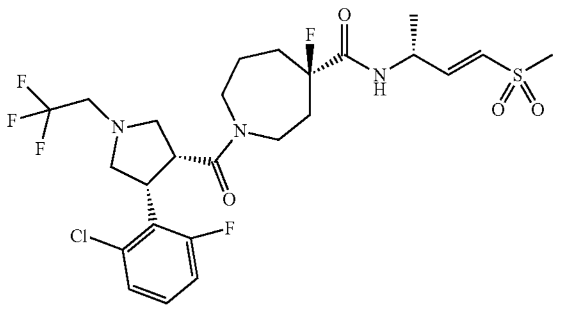 [SMILES: C[C@H](/C=C/S(C)(=O)=O)NC(=O)[C@@]1(F)CCCN(C(=O)[C@H]2CN(CC(F)(F)F)C[C@H]2c2c(F)cccc2Cl)CC1] | 296 | (R)-1-((3R,4R)-4-(2-chloro-6-fluorophenyl)-1-(2,2,2-trifluoroethyl)pyrrolidine-3-carbonyl)-4-fluoro-N-((R,E)-4-(methylsulfonyl)but-3-en-2-yl)azepane-4-carboxamide |
| 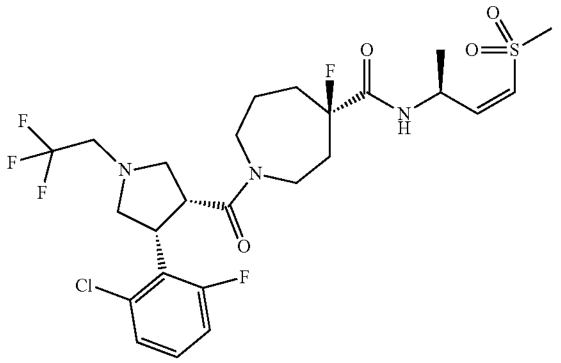 [SMILES: C[C@@H](/C=C\S(C)(=O)=O)NC(=O)[C@@]1(F)CCCN(C(=O)[C@H]2CN(CC(F)(F)F)C[C@H]2c2c(F)cccc2Cl)CC1] | 297 | (R)-1-((3R,4R)-4-(2-chloro-6-fluorophenyl)-1-(2,2,2-trifluoroethyl)pyrrolidine-3-carbonyl)-4-fluoro-N-((S,Z)-4-(methylsulfonyl)but-3-en-2-yl)azepane-4-carboxamide |
| 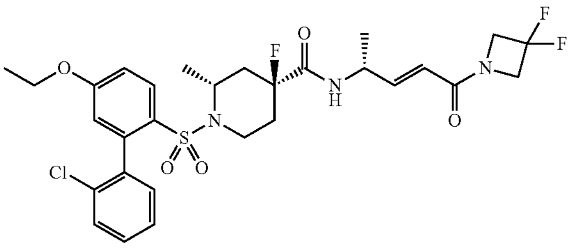 [SMILES: CCOc1ccc(S(=O)(=O)N2CC[C@@](F)(C(=O)N[C@H](C)/C=C/C(=O)N3CC(F)(F)C3)C[C@H]2C)c(-c2ccccc2Cl)c1] | 298 | (2R,4S)-1-((2'-chloro-5-ethoxy-[1,1'-biphenyl]-2-yl)sulfonyl)-N-((R,E)-5-(3,3-difluoroazetidin-1-yl)-5-oxopent-3-en-2-yl)-4-fluoro-2-methylpiperidine-4-carboxamide |

TABLE 1-continued

| Structure | Cmp. No. | IUPAC |
|---|---|---|
| Compounds of the Disclosure. | | |
| 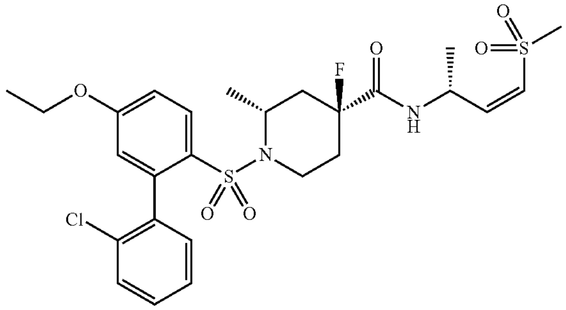 [SMILES: CCOc1ccc(S(=O)(=O)N2CC[C@@](F)(C(=O)N[C@H](C)/C=C\S(C)(=O)=O)C[C@H]2C)c(-c2ccccc2Cl)c1] | 299 | (2R,4S)-1-((2'-chloro-5-ethoxy-[1,1'-biphenyl]-2-yl)sulfonyl)-4-fluoro-2-methyl-N-((R,Z)-4-(methylsulfonyl)but-3-en-2-yl)piperidine-4-carboxamide |
| 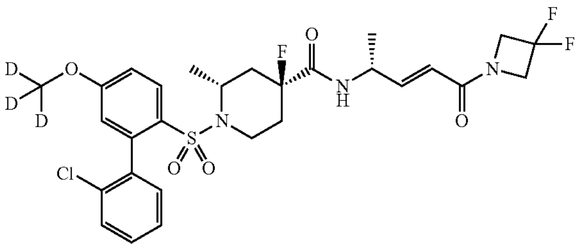 [SMILES: [2H]C([2H])([2H])Oc1ccc(S(=O)(=O)N2CC[C@@](F)(C(=O)N[C@H](C)/C=C/C(=O)N3CC(F)(F)C3)C[C@H]2C)c(-c2ccccc2Cl)c1] | 300 | (2R,4S)-1-((2'-chloro-5-(methoxy-d3)-[1,1'-biphenyl]-2-yl)sulfonyl)-N-((R,E)-5-(3,3-difluoroazetidin-1-yl)-5-oxopent-3-en-2-yl)-4-fluoro-2-methylpiperidine-4-carboxamide |
| 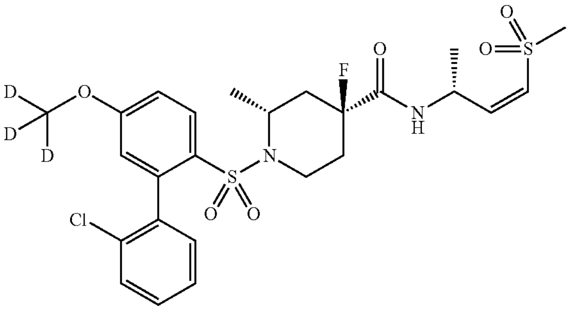 [SMILES: [2H]C([2H])([2H])Oc1ccc(S(=O)(=O)N2CC[C@@](F)(C(=O)N[C@H](C)/C=C\S(C)(=O)=O)C[C@H]2C)c(-c2ccccc2Cl)c1] | 301 | (2R,4S)-1-((2'-chloro-5-(methoxy-d3)-[1,1'-biphenyl]-2-yl)sulfonyl)-4-fluoro-2-methyl-N-((R,Z)-4-(methylsulfonyl)but-3-en-2-yl)piperidine-4-carboxamide |
| 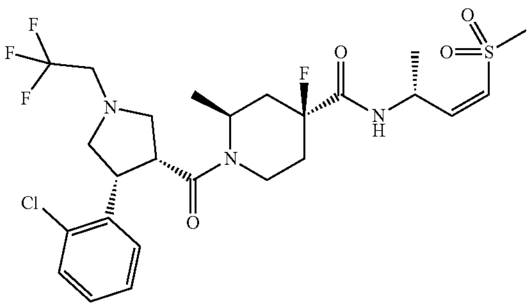 [SMILES: C[C@H](/C=C\S(C)(=O)=O)NC(=O)[C@]1(F)CCN(C(=O)[C@H]2CN(CC(F)(F)F)C[C@H]2c2ccccc2Cl)[C@@H](C)C1] | 302 | (2*S,4*S)-1-((3R,4R)-4-(2-chlorophenyl)-1-(2,2,2-trifluoroethyl)pyrrolidine-3-carbonyl)-4-fluoro-2-methyl-N-((R,Z)-4-(methylsulfonyl)but-3-en-2-yl)piperidine-4-carboxamide |

TABLE 1-continued

Compounds of the Disclosure.

| Structure | Cmp. No. | IUPAC |
|---|---|---|
| 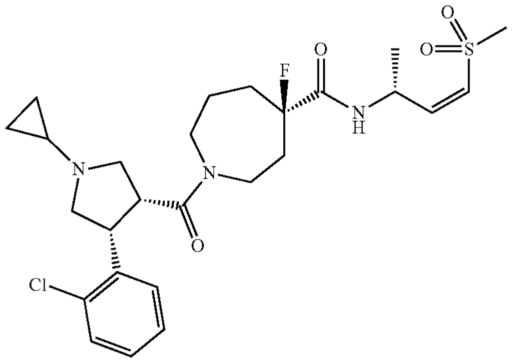 [SMILES: C[C@H](/C=C\S(C)(=O)=O)NC(=O)[C@@]1(F)CCCN(C(=O)[C@H]2CN(C3CC3)C[C@H]2c2ccccc2Cl)CC1] | 303 | (R)-1-((3R,4R)-4-(2-chlorophenyl)-1-cyclopropylpyrrolidine-3-carbonyl)-4-fluoro-N-((R,Z)-4-(methylsulfonyl)but-3-en-2-yl)azepane-4-carboxamide |
| 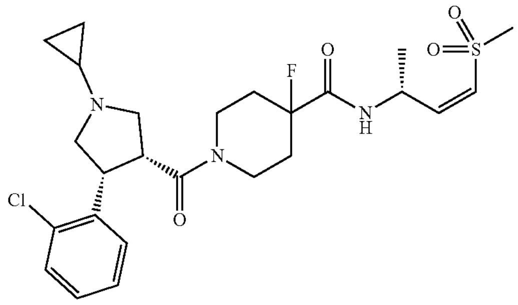 [SMILES: C[C@H](/C=C\S(C)(=O)=O)NC(=O)C1(F)CCN(C(=O)[C@H]2CN(C3CC3)C[C@H]2c2ccccc2Cl)CC1] | 304 | 1-((3R,4R)-4-(2-chlorophenyl)-1-cyclopropylpyrrolidine-3-carbonyl)-4-fluoro-N-((R,Z)-4-(methylsulfonyl)but-3-en-2-yl)piperidine-4-carboxamide |
| 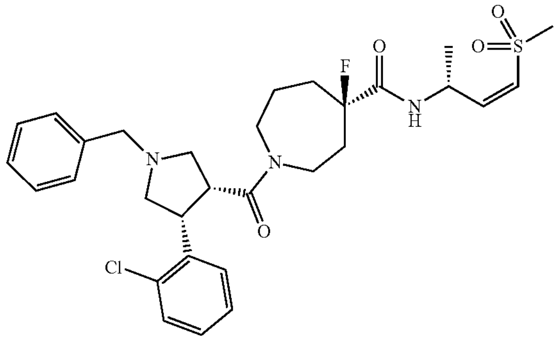 [SMILES: C[C@H](/C=C\S(C)(=O)=O)NC(=O)[C@@]1(F)CCCN(C(=O)[C@H]2CN(Cc3ccccc3)C[C@H]2c2ccccc2Cl)CC1] | 305 | (R)-1-((3*R,4*R)-1-benzyl-4-(2-chlorophenyl)pyrrolidine-3-carbonyl)-4-fluoro-N-((R,Z)-4-(methylsulfonyl)but-3-en-2-yl)azepane-4-carboxamide |
| 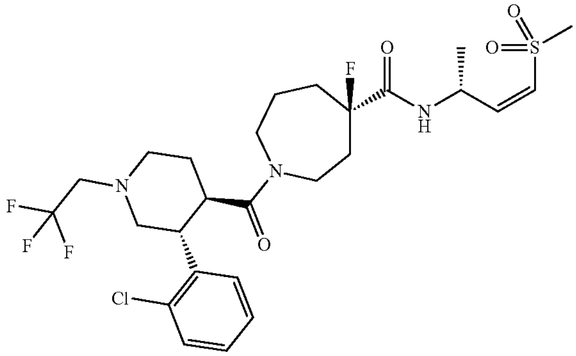 [SMILES: C[C@H](/C=C\S(C)(=O)=O)NC(=O)[C@@]1(F)CCCN(C(=O)[C@@H]2CCN(CC(F)(F)F)C[C@H]2c2ccccc2Cl)CC1] | 306 | (R)-1-((3*R,4*R)-3-(2-chlorophenyl)-1-(2,2,2-trifluoroethyl)piperidine-4-carbonyl)-4-fluoro-N-((R,Z)-4-(methylsulfonyl)but-3-en-2-yl)azepane-4-carboxamide |

TABLE 1-continued

Compounds of the Disclosure.

| Structure | Cmp. No. | IUPAC |
|---|---|---|
| 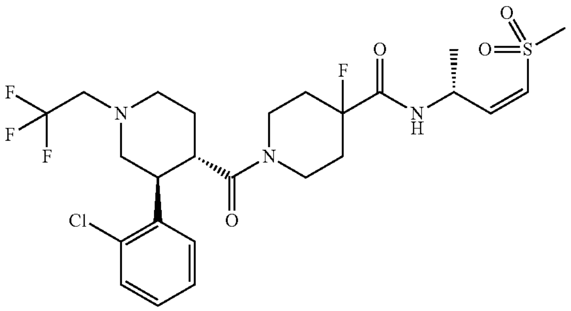 [SMILES: C[C@H](/C=C\S(C)(=O)=O)NC(=O)C1(F)CCN(C(=O)[C@H]2CCN(CC(F)(F)F)C[C@@H]2c2ccccc2Cl)CC1] | 307 | 1-((3*S,4*S)-3-(2-chlorophenyl)-1-(2,2,2-trifluoroethyl)piperidine-4-carbonyl)-4-fluoro-N-((R,Z)-4-(methylsulfonyl)but-3-en-2-yl)piperidine-4-carboxamide |
| 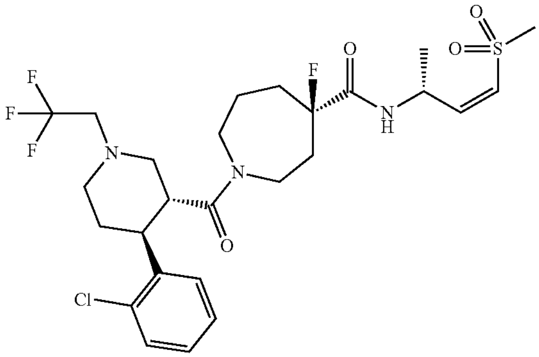 [SMILES: C[C@H](/C=C\S(C)(=O)=O)NC(=O)[C@@]1(F)CCCN(C(=O)[C@H]2CN(CC(F)(F)F)CC[C@@H]2c2ccccc2Cl)CC1] | 308 | (R)-1-((3*R,4*S)-4-(2-chlorophenyl)-1-(2,2,2-trifluoroethyl)piperidine-3-carbonyl)-4-fluoro-N-((R,Z)-4-(methylsulfonyl)but-3-en-2-yl) azepane-4-carboxamide |
| 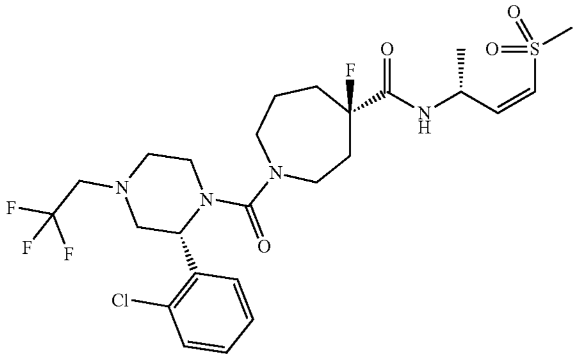 [SMILES: C[C@H](/C=C\S(C)(=O)=O)NC(=O)[C@@]1(F)CCCN(C(=O)N2CCN(CC(F)(F)F)C[C@H]2c2ccccc2Cl)CC1] | 309 | (R)-1-((*R)-2-(2-chlorophenyl)-4-(2,2,2-trifluoroethyl)piperazine-1-carbonyl)-4-fluoro-N-((R,Z)-4-(methylsulfonyl)but-3-en-2-yl)azepane-4-carboxamide |
| 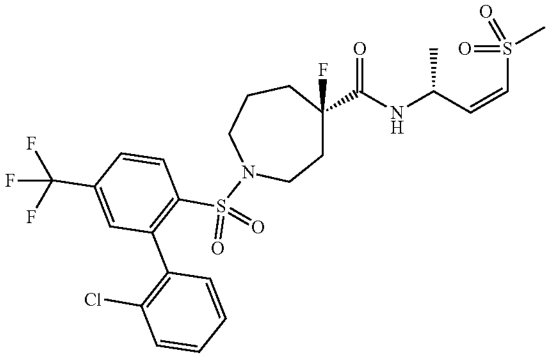 [SMILES: C[C@H](/C=C\S(C)(=O)=O)NC(=O)[C@@]1(F)CCCN(S(=O)(=O)c2ccc(C(F)(F)F)cc2-c2ccccc2Cl)CC1] | 310 | (R)-1-((2'-chloro-5-(trifluoromethyl)-[1,1'-biphenyl]-2-yl)sulfonyl)-4-fluoro-N-((R,Z)-4-(methylsulfonyl)but-3-en-2-yl)azepane-4-carboxamide |

TABLE 1-continued

Compounds of the Disclosure.

| Structure | Cmp. No. | IUPAC |
|---|---|---|
| 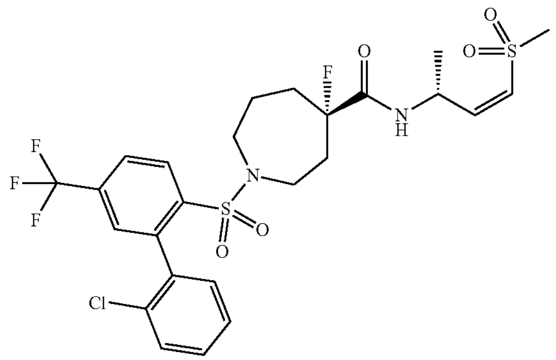 [SMILES: C[C@H](/C=C\S(C)(=O)=O)NC(=O)[C@]1(F)CCCN(S(=O)(=O)c2ccc(C(F)(F)F)cc2-c2ccccc2Cl)CC1] | 311 | (S)-1-((2'-chloro-5-(trifluoromethyl)-[1,1'-biphenyl]-2-yl)sulfonyl)-4-fluoro-N-((R,Z)-4-(methylsulfonyl)but-3-en-2-yl)azepane-4-carboxamide |
| 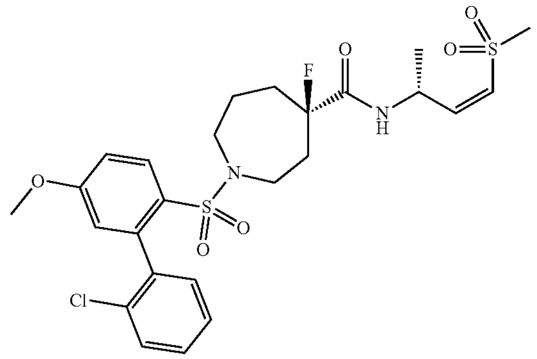 | 312 | (R)-1-((2'-chloro-5-methoxy-[1,1'-biphenyl]-2-yl)sulfonyl)-4-fluoro-N-((R,Z)-4-(methylsulfonyl)but-3-en-2-yl)azepane-4-carboxamide |
| 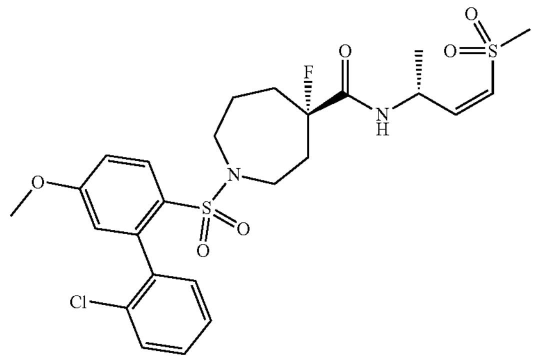 | 313 | (S)-1-((2'-chloro-5-methoxy-[1,1'-biphenyl]-2-yl)sulfonyl)-4-fluoro-N-((R,Z)-4-(methylsulfonyl)but-3-en-2-yl)azepane-4-carboxamide |
| 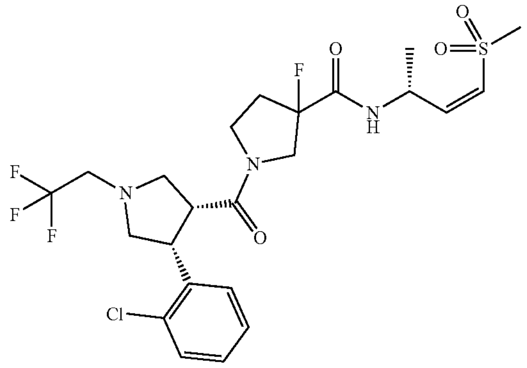 [SMILES: C[C@H](/C=C\S(C)(=O)=O)NC(=O)C1(F)CCN(C(=O)[C@H]2CN(CC(F)(F)F)C[C@H]2c2ccccc2Cl)C1] | 314 | 1-((3R,4R)-4-(2-chlorophenyl)-1-(2,2,2-trifluoroethyl)pyrrolidine-3-carbonyl)-3-fluoro-N-((R,Z)-4-(methylsulfonyl)but-3-en-2-yl)pyrrolidine-3-carboxamide |

Any combination of the groups described above for the various variables is contemplated herein. Throughout the specification, groups and substituents thereof are chosen by one skilled in the field to provide stable moieties and compounds.

Further Forms of Compounds

In some aspects, a compound disclosed herein possesses one or more stereocenters and each stereocenter exists independently in either the R or S configuration. The compounds presented herein include all diastereomeric, enantiomeric, and epimeric forms as well as the appropriate mixtures thereof. Furthermore, the compounds may exist as atropisomers. The compounds and methods provided herein include all cis, trans, syn, anti, entgegen (E), and zusammen (Z) isomers as well as the appropriate mixtures thereof. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley and Sons, Inc., 1981. In one aspect, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. In some embodiments, the design of a prodrug increases the effective water solubility. An example, without limitation, of a prodrug is a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically, or therapeutically active form of the compound. In certain embodiments, a prodrug is enzymatically metabolized by one or more steps or processes to the biologically, pharmaceutically, or therapeutically active form of the compound.

In one aspect, prodrugs are designed to alter the metabolic stability or the transport characteristics of a drug, to mask side effects or toxicity, to improve the flavor of a drug, or to alter other characteristics or properties of a drug. By virtue of knowledge of pharmacokinetic, pharmacodynamic processes, and drug metabolism in vivo, once a pharmaceutically active compound is known, the design of prodrugs of the compound is possible. (See, for example, Nogrady (1985) *Medicinal Chemistry A Biochemical Approach*, Oxford University Press, New York, pages 388-392; Silverman (1992), The Organic Chemistry of Drug Design and Drug Action, Academic Press, Inc., San Diego, pages 352-401, Rooseboom et al., *Pharmacological Reviews,* 56:53-102, 2004; Aesop Cho, "Recent Advances in Oral Prodrug Discovery", *Annual Reports in Medicinal Chemistry*, Vol. 41, 395-407, 2006; T. Higuchi and V. Stella, *Pro-drugs as Novel Delivery Systems*, Vol. 14 of the A.C.S. Symposium Series).

In some embodiments, some of the herein-described compounds may be a prodrug for another derivative or active compound.

In some embodiments, sites on the aromatic ring portion of compounds described herein are susceptible to various metabolic reactions Therefore incorporation of appropriate substituents on the aromatic ring structures will reduce, minimize or eliminate this metabolic pathway. In specific embodiments, the appropriate substituent to decrease or eliminate the susceptibility of the aromatic ring to metabolic reactions is, by way of example only, a halogen, or an alkyl group.

In another embodiment, the compounds described herein are labeled isotopically (e.g., with a radioisotope) or by another other means, including, but not limited to, the use of chromophores or fluorescent moieties, bioluminescent labels, or chemiluminescent labels.

The compounds disclosed herein, in some embodiments, are used in different enriched isotopic forms, e.g., enriched in the content of $^{2}H$, $^{3}H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, compounds described herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^{2}H$), tritium (3H), iodine-125 ($^{125}I$) or carbon-14 ($^{14}C$). Isotopic substitution with $^{2}H$, $^{11}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, and $^{125}I$ are all contemplated. All isotopic variations of the compounds of the present invention, whether radioactive or not, are encompassed within the scope of the present invention.

In some embodiments of a compound disclosed herein, one or more of $R^1$, $R^2$, $R^3$, $R^4$, $R^5$, $R^{5a}$, $R^{6a}$, $R^{6b}$, $R^{6c}$, $R^7$, and $R^8$ groups comprise deuterium at a percentage higher than the natural abundance of deuterium.

In some embodiments of a compound disclosed herein, one or more hydrogens are replaced with one or more deuteriums in one or more of the following groups $R^1$, $R^2$, $R^3$, $R^4$, $R^5$, $R^{5a}$, $R^{6a}$, $R^{6b}$, $R^{6c}$, $R^7$, and $R^8$.

In some embodiments of a compound disclosed herein, the abundance of deuterium in each of $R^1$, $R^2$, $R^3$, $R^4$, $R^5$, $R^{5a}$, $R^{6a}$, $R^{6b}$, $R^{6c}$, $R^7$, and $R^8$ is independently at least 1%, at least 10%, at least 20%, at least 30%, at least 40%, at least 50%, at least 60%, at least 70%, at least 80%, at least 90%, or 100% of a total number of hydrogen and deuterium.

In certain embodiments, the compounds disclosed herein have some or all of the $^{1}H$ atoms replaced with $^{2}H$ atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

In additional or further embodiments, the compounds described herein are metabolized upon administration to an organism in need to produce a metabolite that is then used to produce a desired effect, including a desired therapeutic effect.

"Pharmaceutically acceptable" as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a compound disclosed herein with acids. Pharmaceutically acceptable salts are also obtained by reacting a compound disclosed herein with a base to form a salt.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g., lithium, sodium, potassium), an alkaline earth ion (e.g., magnesium, or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms, particularly solvates. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Pharmaceutical Compositions

In another aspect, provided herein is a compound of Formula (I), (Ia), (II), (IIa), (IIb), (III), (IIIa), or (IIIb), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof, for use in the manufacture of a medicament.

In one aspect, the compounds described herein (e.g., compound of Formula (I), (Ia), (II), (IIa), (IIb), (III), (IIIa), or (IIIb), or pharmaceutically acceptable salts thereof, or a stereoisomer thereof, or a pharmaceutically acceptable salt of a stereoisomer thereof, or an atropisomer thereof, or a pharmaceutically acceptable salt of an atropisomer thereof) are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition, as used herein, refers to a mixture of a compound disclosed herein with other chemical components (i.e., pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism.

Pharmaceutical formulations described herein are administrable to a subject in a variety of ways by multiple administration routes, including but not limited to, oral, parenteral (e.g., intravenous, subcutaneous, intramuscular, intramedullary injections, intrathecal, direct intraventricular, intraperitoneal, intralymphatic, intranasal injections), intranasal, buccal, topical or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the compounds disclosed herein are administered orally.

In some embodiments, the compounds disclosed herein are administered topically. In such embodiments, the compound disclosed herein is formulated into a variety of topically administrable compositions, such as solutions, suspensions, lotions, gels, pastes, shampoos, scrubs, rubs, smears, medicated sticks, medicated bandages, balms, creams or ointments. In one aspect, the compounds disclosed herein are administered topically to the skin.

In another aspect, the compounds disclosed herein are administered by inhalation.

In another aspect, the compounds disclosed herein are formulated for intranasal administration. Such formulations include nasal sprays, nasal mists, and the like.

In another aspect, the compounds disclosed herein are formulated as eye drops.

In any of the aforementioned aspects are further embodiments in which the effective amount of the compound disclosed herein is: (a) systemically administered to the mammal; and/or (b) administered orally to the mammal; and/or (c) intravenously administered to the mammal; and/or (d) administered by inhalation to the mammal; and/or (e) administered by nasal administration to the mammal; or and/or (f) administered by injection to the mammal; and/or (g) administered topically to the mammal; and/or (h) administered by ophthalmic administration; and/or (i) administered rectally to the mammal; and/or (j) administered non-systemically or locally to the mammal.

In any of the aforementioned aspects are further embodiments comprising single administrations of the effective amount of the compound disclosed herein, including further embodiments in which (i) the compound is administered once; (ii) the compound is administered to the mammal multiple times over the span of one day; (iii) the compound is administered continually; or (iv) the compound is administered continuously.

In any of the aforementioned aspects are further embodiments comprising multiple administrations of the effective amount of the compound disclosed herein, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound disclosed herein is temporarily suspended or the dose of the compound being administered is temporarily reduced; at the end of the drug holiday, dosing of the compound is resumed. In one embodiment, the length of the drug holiday varies from 2 days to 1 year.

In certain embodiments, the compound disclosed herein is administered in a local rather than systemic manner.

In some embodiments, the compound disclosed herein is administered topically. In some embodiments, the compound disclosed herein is administered systemically.

In some embodiments, the pharmaceutical formulation is in the form of a tablet. In other embodiments, pharmaceutical formulations of the compounds disclosed herein are in the form of a capsule.

In one aspect, liquid formulation dosage forms for oral administration are in the form of aqueous suspensions or solutions selected from the group including, but not limited to, aqueous oral dispersions, emulsions, solutions, elixirs, gels, and syrups.

For administration by inhalation, a compound disclosed herein is formulated for use as an aerosol, a mist, or a powder.

For buccal or sublingual administration, the compositions may take the form of tablets, lozenges, or gels formulated in a conventional manner.

In some embodiments, compounds disclosed herein are prepared as transdermal dosage forms.

In one aspect, a compound disclosed herein is formulated into a pharmaceutical composition suitable for intramuscular, subcutaneous, or intravenous injection.

In some embodiments, the compound disclosed herein is be administered topically and can be formulated into a variety of topically administrable compositions, such as solutions, suspensions, lotions, gels, pastes, medicated sticks, balms, creams, or ointments.

In some embodiments, the compounds disclosed herein are formulated in rectal compositions such as enemas, rectal gels, rectal foams, rectal aerosols, suppositories, jelly suppositories, or retention enemas.

Methods of Treatment

In another aspect, provided herein is a compound of Formula (I), (Ia), (II), (IIa), (IIb), (III), (IIIa), or (IIIb), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof, for use in a method of modulating RAS-PI3K. In some embodiments, the method comprises inhibiting RAS-PI3K. In some embodiments, the method comprises activating RAS-PI3K.

In another aspect, provided herein is a compound of Formula (I), (Ia), (II), (IIa), (IIb), (III), (IIIa), or (IIIb), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof, for use in a method of treating a disease or condition. In some embodiments, provided herein is a method of treating a disease or condition, the method comprising administering to a subject in need thereof, a therapeutically effective amount of a compound of Formula (I), (Ia), (II), (IIa), (IIb), (III), (IIIa), or (IIIb), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof. In some embodiments, the disease or condition is mediated by RAS-PI3K. In some embodiments, the disease is cancer.

In another aspect, provided herein is a compound of Formula (I), (Ia), (II), (IIa), (IIb), (III), (IIIa), or (IIIb), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof, for use in the manufacture of a medicament for modulating RAS-PI3K.

In another aspect, provided herein is a compound of Formula (I), (Ia), (II), (IIa), (IIb), (III), (IIIa), or (IIIb), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof, for use in treating cancer in a subject in need thereof.

In another aspect, provided herein is a compound of Formula (I), (Ia), (II), (IIa), (IIb), (III), (IIIa), or (IIIb), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof, for use in the manufacture of a medicament for treating a cancer in a subject in need thereof.

In some embodiments, the disease mediated by RAS-PI3K is a cancer. In some embodiments, the cancer is selected from the group consisting of bladder cancer, uterine cancer, head and neck cancer, esophageal cancer, ovarian cancer, liver cancer, lung cancer, colorectal cancer, cervical cancer, cholangiocarcinoma, gastric cancer, kidney cancer, and pancreatic cancer.

In another aspect, provided herein is a compound of Formula (I), (Ia), (II), (IIa), (IIb), (III), (IIIa), or (IIIb), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof, for use in a method of treating an immunological disease or condition.

In another aspect, provided herein is a compound of Formula (I), (Ia), (II), (IIa), (IIb), (III), (IIIa), or (IIIb), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof, for use in the manufacture of a medicament for treating an immunological disease or condition in a subject in need thereof.

In some embodiments, the immunological disease or condition is selected from Psoriasis, Psoriatic Arthritis, Crohn's disease, Ulcerative colitis, Lupus (including Systemic Lupus Erythematous, Cutaneous lupus, Lupus nephritis), Rheumatoid arthritis, Juvenile Idiopathic arthritis, Still's disease, Spondyloarthritis, and Scleroderma, acute cytokine release syndrome associated with viral infections such as COVID, with cell therapies such as CAR-T and with gene therapy.

In another aspect, provided herein is a compound of Formula (I), (Ia), (II), (IIa), (IIb), (III), (IIIa), or (IIIb), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof, for use in a method of treating a disease or condition.

In some embodiments, administration of a compound of Formula (I), (Ia), (II), (IIa), (IIb), (III), (IIIa), or (IIIb), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof, promotes wound healing.

In another aspect, provided herein is a use of a compound of Formula (I), (Ia), (II), (IIa), (IIb), (III), (IIIa), or (IIIb), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof, for the treatment of an immunological disease or condition or cancer.

Dosing and Treatment Regimens

In one aspect, the compounds disclosed herein are used in the preparation of medicaments for the treatment of diseases or conditions described herein. In addition, a method for treating any of the diseases or conditions described herein in a subject in need of such treatment, involves administration of pharmaceutical compositions that include at least one compound disclosed herein or a pharmaceutically acceptable salt, active metabolite, prodrug, or solvate thereof, in therapeutically effective amounts to said subject.

In some embodiments, the compositions containing the compound disclosed herein are administered for prophylactic and/or therapeutic treatments. In certain therapeutic applications, the compositions are administered to a patient or subject already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions containing the compounds disclosed herein are administered to a patient susceptible to or otherwise at risk of a particular disease, disorder or condition.

In some embodiments, the dose of drug being administered may be temporarily reduced or temporarily suspended for a certain length of time (i.e., a "drug holiday"). Doses employed for adult human treatment are typically in the range of 0.01 mg-5000 mg per day or from about 1 mg to about 1000 mg per day. In one embodiment, the desired dose is conveniently presented in a single dose or in divided doses.

Combination Treatments

In certain instances, it is appropriate to administer at least one compound disclosed herein in combination with another therapeutic agent.

In one specific embodiment, a compound disclosed herein is co-administered with a second therapeutic agent, wherein the compound disclosed herein and the second therapeutic agent modulate different aspects of the disease, disorder or condition being treated, thereby providing a greater overall benefit than administration of either therapeutic agent alone.

For combination therapies described herein, dosages of the co-administered compounds vary depending on the type of co-drug(s) employed, on the specific drug(s) employed, on the disease or condition being treated and so forth. In additional embodiments, when co-administered with one or more other therapeutic agents, the compound provided herein is administered either simultaneously with the one or more other therapeutic agents, or sequentially.

If administration is simultaneous, the multiple therapeutic agents are, by way of example only, provided in a single, unified form, or in multiple forms.

DEFINITIONS

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. Further, headings provided herein are for convenience only and do not interpret the scope or meaning of the claimed invention.

The terms below, as used herein, have the following meanings, unless indicated otherwise:

"Oxo" refers to the =O substituent.

"Alkyl" refers to a straight or branched hydrocarbon chain radical, having from one to twenty carbon atoms, and which is attached to the rest of the molecule by a single bond. An alkyl comprising up to 10 carbon atoms is referred to as a $C_1$-$C_{10}$ alkyl, likewise, for example, an alkyl comprising up to 6 carbon atoms is a $C_1$-$C_6$ alkyl. Alkyls (and other moieties defined herein) comprising other numbers of carbon atoms are represented similarly. Alkyl groups include, but are not limited to, $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (i-propyl), n-butyl, i-butyl, s-butyl, n-pentyl, 1,1-dimethylethyl (t-butyl), 3-methylhexyl, 2-methylhexyl, 1-ethyl-propyl, and the like. In some embodiments, the alkyl is methyl or ethyl. Unless stated otherwise specifically in the specification, an alkyl group may be optionally substituted as described below.

"Alkylene" refers to a straight or branched divalent hydrocarbon chain linking the rest of the molecule to a radical group. In some embodiments, the alkylene is $-CH_2-$, $-CH_2CH_2-$, or $-CH_2CH_2CH_2-$. In some embodiments, the alkylene is $-CH_2-$. In some embodiments, the alkylene is $-CH_2CH_2-$. In some embodiments, the alkylene is $-CH_2CH_2CH_2-$.

"Alkoxy" refers to a radical of the formula —OR where R is an alkyl radical as defined. Unless stated otherwise specifically in the specification, an alkoxy group may be optionally substituted as described below. Representative alkoxy groups include, but are not limited to, methoxy, ethoxy, propoxy, butoxy, pentoxy. In some embodiments, the alkoxy is methoxy. In some embodiments, the alkoxy is ethoxy.

"Heteroalkyl" refers to an alkyl radical as described above where one or more carbon atoms of the alkyl is replaced with a O, N (i.e., NH, N-alkyl) or S atom. "Heteroalkylene" refers to a straight or branched divalent heteroalkyl chain linking the rest of the molecule to a radical group. Unless stated otherwise specifically in the specification, the heteroalkyl or heteroalkylene group may be optionally substituted as described below. Representative heteroalkyl groups include, but are not limited to $-OCH_2OMe$, $-OCH_2CH_2OMe$, or $-OCH_2CH_2OCH_2CH_2NH_2$. Representative heteroalkylene groups include, but are not limited to $-OCH_2CH_2O-$, $-OCH_2CH_2OCH_2CH_2O-$, or $-OCH_2CH_2OCH_2CH_2OCH_2CH_2O-$.

"Alkylamino" refers to a radical of the formula —NHR or —NRR where each R is, independently, an alkyl radical as defined above. Unless stated otherwise specifically in the specification, an alkylamino group may be optionally substituted as described below.

The term "aromatic" refers to a planar ring having a delocalized π-electron system containing 4n+2 π electrons, where n is an integer. Aromatics can be optionally substituted. The term "aromatic" includes both aryl groups (e.g., phenyl, naphthalenyl) and heteroaryl groups (e.g., pyridinyl, quinolinyl).

"Aryl" refers to an aromatic ring wherein each of the atoms forming the ring is a carbon atom. Aryl groups can be optionally substituted. Examples of aryl groups include, but are not limited to, phenyl and naphthyl. In some embodiments, the aryl is phenyl. Depending on the structure, an aryl group can be a monoradical or a diradical (i.e., an arylene group). Unless stated otherwise specifically in the specification, the term "aryl" or the prefix "ar-" (such as in "aralkyl") is meant to include aryl radicals that are optionally substituted.

"Carboxy" refers to $-CO_2H$. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to:

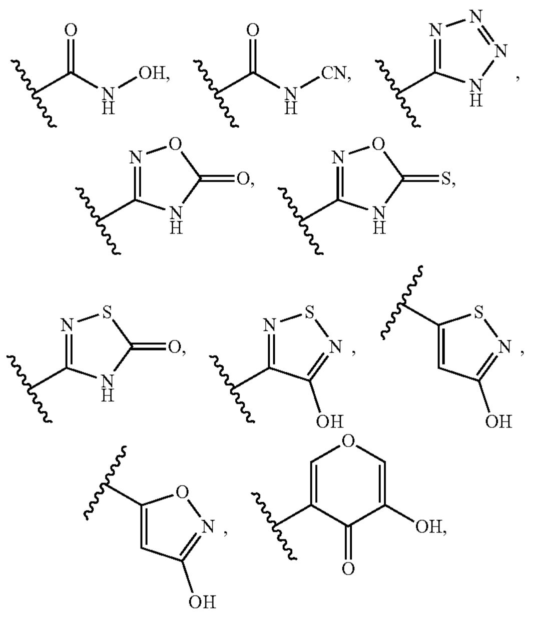

and the like.

"Cycloalkyl" refers to a monocyclic or polycyclic non-aromatic radical, wherein each of the atoms forming the ring (i.e., skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms. Representative cycloalkyls include, but are not limited to, cycloalkyls having from three to ten carbon atoms, from three to eight carbon atoms, from three to six carbon atoms, or from three to five carbon atoms. In some embodiments, a cycloalkyl is a $C_3$-$C_6$cycloalkyl. In some embodiments, the cycloalkyl is monocyclic, bicyclic or polycyclic. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, bicyclo[1.1.1]pentyl, bicyclo[3.3.0]octane, bicyclo[4.3.0]nonane, bicyclo[2.1.1]hexane, bicyclo[2.2.1]heptane, bicyclo[2.2.2]octane, bicyclo[3.2.2]nonane, bicyclo[3.3.2]decane, norbornyl, decalinyl and adamantyl. In some embodiments, the cycloalkyl is monocyclic. Monocyclic cyclcoalkyl radicals include, for example, cyclopropyl, cyclobutyl, cyclopentyl, cyclohexyl, cycloheptyl, and cyclooctyl. In some embodiments, the monocyclic cyclcoalkyl is cyclopropyl, cyclobutyl, cyclopentyl or cyclohexyl. In some embodiments, the cycloalkyl is bicyclic. Bicyclic cycloalkyl groups include fused bicyclic cycloalkyl groups, spiro bicyclic cycloalkyl groups, and bridged bicyclic cycloalkyl groups. In some embodiments, cycloalkyl groups are selected from among spiro[2.2]pentyl, bicyclo[1.1.1]pentyl, bicyclo[3.3.0]octane, bicyclo[4.3.0]nonane, bicyclo[2.1.1]hexane, bicyclo[2.2.1]heptane, bicyclo[2.2.2]octane, bicyclo[3.2.2]nonane, bicyclo[3.3.2]decane, norbornyl, 3,4-dihydronaphthalen-1(2H)-one and decalinyl. In some embodiments, the cycloalkyl is polycyclic. Polycyclic radicals include, for example, adamantyl. In some embodiments, the polycyclic cycloalkyl is adamantyl. Unless otherwise stated specifically in the specification, a cycloalkyl group may be optionally substituted.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" refers to an alkoxy radical, as defined above, that is substituted by one or more halo radicals, as defined above, e.g., trifluoromethoxy, difluoromethoxy, fluoromethoxy, trichloromethoxy, 2,2,2-trifluoroethoxy, 1,2-difluoroethoxy, 3-bromo-2-fluoropropoxy, 1,2-dibromoethoxy, and the like. Unless stated otherwise specifically in the specification, a haloalkoxy group may be optionally substituted.

"Heterocycloalkyl" or "heterocyclyl" or "heterocyclic ring" refers to a stable 3- to 14-membered non-aromatic ring radical comprising 2 to 10 carbon atoms and from one to 4 heteroatoms selected from the group consisting of nitrogen, oxygen, and sulfur. Unless stated otherwise specifically in the specification, the heterocycloalkyl radical may be a monocyclic, bicyclic ring (which may include a fused bicyclic heterocycloalkyl (when fused with an aryl or a heteroaryl ring, the heterocycloalkyl is bonded through a non-aromatic ring atom), bridged heterocycloalkyl or spiro heterocycloalkyl), or polycyclic. In some embodiments, the heterocycloalkyl is monocyclic or bicyclic. In some embodiments, the heterocycloalkyl is monocyclic. In some embodiments, the heterocycloalkyl is bicyclic. The nitrogen, carbon or sulfur atoms in the heterocyclyl radical may be optionally oxidized. The nitrogen atom may be optionally quaternized. The heterocycloalkyl radical is partially or fully saturated. Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl. The term heterocycloalkyl also includes all ring forms of carbohydrates, including but not limited to monosaccharides, disaccharides and oligosaccharides. Unless otherwise noted, heterocycloalkyls have from 2 to 10 carbons in the ring. In some embodiments, heterocycloalkyls have from 2 to 8 carbons in the ring. In some embodiments, heterocycloalkyls have from 2 to 8 carbons in the ring and 1 or 2 N atoms. In some embodiments, heterocycloalkyls have from 2 to 10 carbons, 0-2 N atoms, 0-2 O atoms, and 0-1 S atoms in the ring. In some embodiments, heterocycloalkyls have from 2 to 10 carbons, 1-2 N atoms, 0-1 O atoms, and 0-1 S atoms in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e., skeletal atoms of the heterocycloalkyl ring). Unless stated otherwise specifically in the specification, a heterocycloalkyl group may be optionally substituted.

"Heteroaryl" refers to an aryl group that includes one or more ring heteroatoms selected from nitrogen, oxygen and sulfur. The heteroaryl is monocyclic or bicyclic. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, furazanyl, indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Illustrative examples of bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, heteroaryl is pyridinyl, pyrazinyl, pyrimidinyl, thiazolyl, thienyl, thiadiazolyl or furyl. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$ heteroaryl. In some embodiments, monocyclic heteroaryl is a $C_1$-$C_5$ heteroaryl. In some embodiments, monocyclic heteroaryl is a 5-membered or 6-membered heteroaryl. In some embodiments, a bicyclic heteroaryl is a $C_6$-$C_9$ heteroaryl.

The term "optionally substituted" or "substituted" means that the referenced group may be substituted with one or more additional group(s) individually and independently selected from alkyl, haloalkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halogen, acyl, acyloxy, —$CO_2$H, —$CO_2$alkyl, nitro, and amino, including mono- and di-substituted amino groups (e.g., —$NH_2$, —NHR, —$NR_2$), and the protected derivatives thereof. In some embodiments, optional substituents are independently selected from alkyl, alkoxy, haloalkyl, cycloalkyl, halogen, —CN, —$NH_2$, —$NH(CH_3)$, —$N(CH_3)_2$, —OH, —$CO_2H$, and —$CO_2$alkyl. In some embodiments, optional substituents are independently selected from fluoro, chloro, bromo, iodo, —$CH_3$, —$CH_2CH_3$, —$CF_3$, —$OCH_3$, and —$OCF_3$. In some embodiments, substituted groups are substituted with one or two of the preceding groups. In some embodiments, an optional substituent on an aliphatic carbon atom (acyclic or cyclic) includes oxo (═O).

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

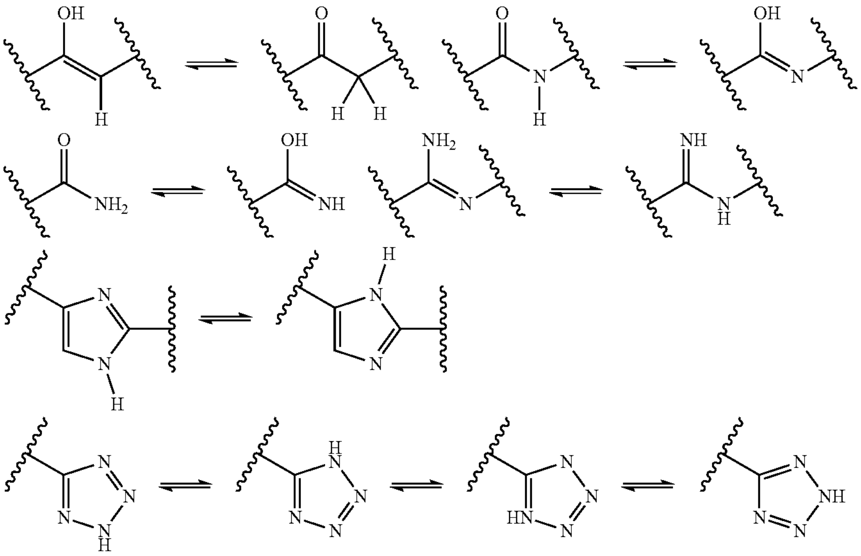

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. An "effective amount" is an amount sufficient for a compound to accomplish a stated purpose relative to the absence of the compound (e.g., achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The term "pharmaceutical combination" as used herein, means a product that results from the mixing or combining of more than one active ingredient and includes both fixed and non-fixed combinations of the active ingredients. The term "fixed combination" means that the active ingredients, e.g., a compound of Formula (I) and a co-agent, are both administered to a patient simultaneously in the form of a single entity or dosage. The term "non-fixed combination" means that the active ingredients, e.g., a compound of Formula (I) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g., the administration of three or more active ingredients.

The term "subject" or "patient" encompasses mammals. Examples of mammals include, but are not limited to, humans. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

TABLE 2

Abbreviations.

| Acronym | Term |
|---|---|
| $^1H$ NMR | Proton nuclear magnetic resonance |
| ACN, MeCN | Acetonitrile |
| aq. | Aqueous |
| BINAP | (2,2'-Bis(diphenylphosphino)-1,1'-binaphthyl) |
| Boc | tert-Butyloxycarbonyl |
| DAST | Diethylaminosulfur trifluoride |
| DCE | Dichloroethane |
| DCM | Dichloromethane |
| DEA | Diethylamine |
| Deoxo-Fluor ® | Bis(2-methoxyethyl)aminosulfur trifluoride |
| DIAD | Diisopropyl azodicarboxylate |
| DIPEA | Diisopropylethylamine |
| DMA | Dimethylacetamide |
| DMAP | 4-Dimethylaminopyridine |
| DME | 1,2-Dimethoxyethane |
| DMF | Dimethylformamide |
| DMSO | Dimethylsulfoxide |
| EA, EtOAc | Ethyl acetate |
| ESI | Electrospray ionization |
| FCC | Normal phase silica gel column chromatography |
| h, hr(s) | Hour(s) |
| HATU | 1-[Bis(dimethylamino)methylene]-1H-1,2,3-triazolo[4,5-b]pyridinium 3-oxid hexafluorophosphate |
| HPLC | High performance liquid chromatography |
| KHMDS | Potassium bis(trimethylsilyl)amide |
| KOtBu | Potassium tert-butoxide |
| LDA | Lithium diisopropylamide |
| LiHMDS | Lithium bis(trimethylsilyl)amide |
| m-CPBA | meta-Chloroperoxybenzoic acid |
| min | Minutes |
| MTBE | Methyl tert-butyl ether |
| m/z | Mass-to-charge ratio |
| NBS | N-Bromosuccinimide |
| NCS | N-Chlorosuccinimide |
| NFSI | N-Fluorobenzenesulfonimide |
| NMP | N-Methyl-2-pyrrolidone |
| $Pd_2(dba)_3$ | Tris(dibenzylideneacetone)dipalladium(0) |
| $Pd(dppf)Cl_2$ | [1,1'-Bis(diphenylphosphino)ferrocene]dichloropalladium(II) |
| PE | Petroleum ether |
| ppm | Parts per million |
| psi | Pounds per square inch |
| PTFE | Polytetrafluoroethylene |
| quant. | Quantitative |
| RP-HPLC | Reverse phase high performance liquid chromatography |
| Rt | Retention time |
| rt | Room temperature |
| RuPhos Pd G4 | [Dicyclohexyl(2',6'-diisopropoxy-2-biphenylyl)phosphine-κP](methanesulfonatato-κO)[2'-(methylamino-κN)-2-biphenylyl-κ$C^2$]palladium |
| sat. | Saturated |
| Selectfluor ® | 1-Chloromethyl-4-fluoro-1,4-diazoniabicyclo[2.2.2]octane bis(tetrafluoroborate) |
| SFC | Supercritical fluid chromatography |
| SPhos Pd G4 | (SP-4-3)-[Dicyclohexyl(2',6'-dimethoxy[1,1'-biphenyl]-2-yl)phosphine-κP](methanesulfonato-κO)[2'-(methylamino-κN)[1,1'-biphenyl]-2-yl-κC]palladium |
| $T_3P$ ® | 2,4,6-Tripropyl-1,3,5,2,4,6-trioxatriphosphorinane-2,4,6-trioxide |
| TEA | Triethylamine |
| TFA | Trifluoroacetic acid |
| THF | Tetrahydrofuran |

TABLE 2-continued

| Abbreviations. | |
|---|---|
| Acronym | Term |
| TLC | Thin layer chromatography |
| TMSCl | Trimethylsilyl chloride |
| TsOH | p-Toluenesulfonic acid |
| XantPhos | 4,5-Bis(diphenylphosphino)-9,9-dimethylxanthene |
| XPhos | Dicyclohexyl[2',4',6'-tris(propan-2-yl)[1,1'-biphenyl]-2-yl]phosphane |

Example 1. Synthesis of the Compounds of the Disclosure

Scheme 1. Synthesis of Intermediate (R,Z)-4-(methylsulfonyl)but-3-en-2-amine

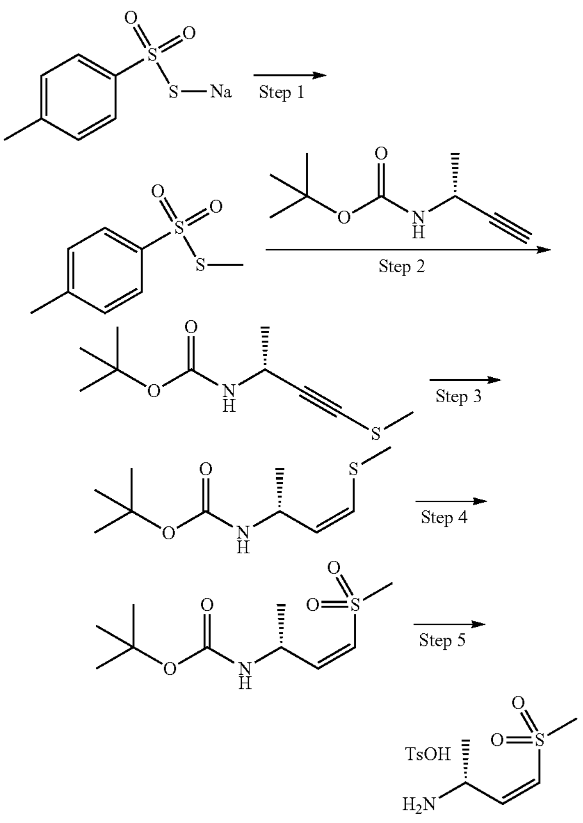

Step 1. To a solution of sodium 4-methylbenzenesulfonothioate (30 g, 143 mmol, 1.0 eq) in DMF (100 mL, 1.4 M) was added iodomethane (8.9 mL, 143 mmol, 1.0 eq). The reaction was stirred for 24 h at 25 °C under $N_2$. The reaction mixture was quenched with water (300 mL) and extracted with EtOAc (300 mL×2). The combined organic layers were washed with brine (300 mL×3), dried over $Na_2SO_4$, filtered, and concentrated under reduced pressure. The resulting residue was purified by FCC on silica (PE:EtOAc=50:1) to give S-methyl 4-methylbenzenesulfonothioate (27 g, 133 mmol, 94% yield) as a white solid. $^1H$ NMR (400 MHz, $CDCl_3$) δ ppm 7.81 (d, J=8.4 Hz, 2H), 7.35 (d, J=8.4 Hz, 2H), 2.50 (s, 3H), 2.46 (s, 3H).

Step 2. n-Butyllithium (39.7 mL, 99.3 mmol, 2.1 eq) was added dropwise to a stirred solution of tert-butyl(R)-but-3-yn-2-ylcarbamate (8.0 g, 47.3 mmol, 1.0 eq) and N,N,N,N-tetramethylethylenediamine (5.5 g, 47.3 mmol, 1.0 eq) in anhydrous THF (30 mL, 0.24 M) at 0 °C under $N_2$ atmosphere. After 30 minutes, S-methyl 4-methylbenzenesulfonothioate (10 g, 49.6 mmol, 1.1 eq) in THF (80 mL, 0.60 M) was added. The reaction was stirred at 0 °C for 2 h before being quenched by sat. aq. $NH_4Cl$ (200 mL) at 0 °C and extracted with ethyl acetate (200 mL×3). The combined organic layers were washed with brine (200 mL), dried over anhydrous $Na_2SO_4$, filtered, and concentrated under reduced pressure. The resulting residue was purified by FCC on silica (PE:EtOAc=5:1) to afford tert-butyl (R)-(4-(methylthio)but-3-yn-2-yl)carbamate (9.0 g, 41.8 mmol, 88% yield) as a white solid. $^1H$ NMR (400 MHz, $CDCl_3$) δ ppm 4.65-4.76 (m, 1H), 4.50-4.63 (m, 1H), 2.37 (s, 3H), 1.46 (s, 9H), 1.39 (d, J=6.88 Hz, 3H).

Step 3. tert-Butyl (R)-(4-(methylthio)but-3-yn-2-yl)carbamate (3.0 g, 13.9 mmol, 1.0 eq), Lindlar catalyst (900 mg), and hexene (6 mL) were taken up in methanol (30 mL, 0.46 M). The reaction was stirred under $H_2$ (30 psi) at 25 °C for 3 h. The mixture was filtered concentrated under vacuum. The resulting residue was purified by FCC (PE:EtOAc=3:1) to afford tert-butyl(R,Z)-(4-(methylthio)but-3-en-2-yl)carbamate (2.6 g, 12.0 mmol, 86% yield) as a white solid. $^1H$ NMR (400 MHz, DMSO-$d_6$) δ ppm 5.96 (d, J=9.6 Hz, 1H), 5.43 (dd, J=8.0, 9.5 Hz, 1H), 4.63-4.34 (m, 2H), 2.28 (s, 3H), 1.45 (s, 9H), 1.22 (d, J=6.4 Hz, 3H).

Step 4. To a solution of tert-butyl(R,Z)-(4-(methylthio)but-3-en-2-yl)carbamate (2.6 g, 12.0 mmol, 1.0 eq) in DCM (10 mL, 1.2 M) was added 3-chloroperbenzoic acid (6.2 g, 35.9 mmol, 3.0 eq) in portions over 5 min. The reaction was stirred at 25 °C for 2 h before being diluted with sat. aq. $Na_2SO_3$ (100 mL×2) and extracted with DCM (200 mL). The extract was washed with sat. aq. $NaHCO_3$ (100 mL×2) then washed with brine (200 mL), dried over $Na_2SO_4$, filtered, and concentrated under reduced pressure. The resulting residue was purified by FCC on silica (PE:EtOAc=1:1) to afford tert-butyl(R,Z)-(4-(methylsulfonyl)but-3-en-2-yl)carbamate (2.4 g, 9.47 mmol, 79% yield) as a white solid. $^1H$ NMR (400 MHz, $CDCl_3$) δ ppm 6.31-6.22 (m, 1H), 6.21-6.11 (m, 1H), 4.63 (s, 1H), 3.19 (s, 3H), 1.42 (s, 9H), 1.31 (d, J=6.8 Hz, 3H).

Step 5. tert-Butyl(R,Z)-(4-(methylsulfonyl)but-3-en-2-yl)carbamate (2.4 g, 9.47 mmol, 1.0 eq) and p-toluenesulfonic acid monohydrate (1.8 g, 9.47 mmol, 1.0 eq) were taken up in MeCN (30 mL, 0.32 M). The reaction was stirred at 40 °C for 16 h. The mixture was concentrated under vacuum to afford (R,Z)-4-(methylsulfonyl)but-3-en-2-amine (TsOH salt, 3.0 g, 9.33 mmol, 99% yield) as a white solid, which was used in the next step directly. $^1H$ NMR (400 MHz, $CDCl_3$) δ ppm 8.13 (br s, 1H), 7.51 (d, J=8.0 Hz, 2H), 7.14 (d, J=8.0 Hz, 2H), 6.75 (d, J=11.2 Hz, 1H), 6.37 (dd, J=9.6, 11.2 Hz, 1H), 5.09 (br s, 2H), 4.95-4.75 (m, 1H), 3.12 (s, 3H), 2.29 (s, 3H), 1.31 (d, J=6.8 Hz, 3H).

Intermediate (S,Z)-4-(methylsulfonyl)but-3-en-2-amine, 4-methylbenzenesulfonic acid salt was synthesized in an analogous manner to (R,Z)-4-(methylsulfonyl)but-3-en-2-amine starting with tert-butyl(S)-but-3-yn-2-ylcarbamate.

Scheme 2. Synthesis of Intermediate ethyl 4-fluoropiperidine-4-carboxylate

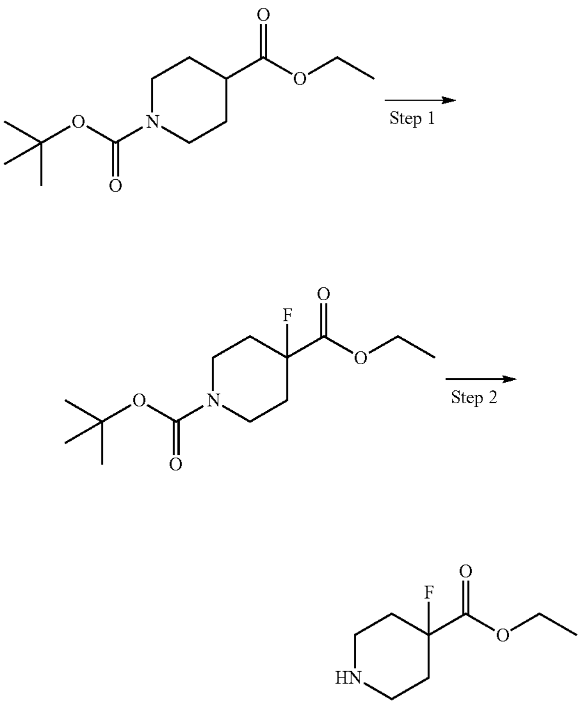

Step 1. To a solution of 1-tert-butyl 4-ethyl piperidine-1,4-dicarboxylate (54 g, 209.9 mmol, 1 eq) in THF (500 mL) was added 2 M LDA (157 mL, 315 mmol, 1.5 eq) dropwise at −45 °C and the mixture was stirred at −45 °C for 0.5 hour. Then to the mixture was added NFSI (82.7 g, 262 mmol, 1.3 eq) in THF (500 mL) dropwise and the resulting solution was stirred at −45 °C for 1 hr and at −45~15 °C for 1 hr. The reaction was quenched with sat. aq. $NH_4Cl$ (1 L) and extracted with EtOAc (1 L×2). The combined organic phases were washed with brine (1 L×2), dried over $Na_2SO_4$, filtered, concentrated and purified by FCC (PE:EtOAc=9:1) to give 1-tert-butyl 4-ethyl 4-fluoropiperidine-1,4-dicarboxylate as a light yellow oil (47.3 g, 172 mmol, 82% yield). $^1H$ NMR (400 MHz, $CDCl_3$) δ ppm 4.26 (q, J=7.2 Hz, 2H), 4.09-3.94 (m, 2H), 3.11 (br s, 2H), 2.05 (s, 1H), 1.99-1.88 (m, 3H), 1.48 (s, 9H), 1.32 (t, J=7.2 Hz, 3H).

Step 2. A mixture of 1-tert-butyl 4-ethyl 4-fluoropiperidine-1,4-dicarboxylate (30 g, 109 mmol, 1 eq) in HCl/EtOAc (4 M, 350 mL) was stirred at 25 °C for 1 hr. The reaction was concentrated to give a crude product as a pink solid. The crude product was washed with a mixture solvent MTBE/PE (1:1, 100 mL×3) to give ethyl 4-fluoropiperidine-4-carboxylate as a light pink solid (22.3 g, 106 mmol, 97%). $^1H$ NMR (400 MHz, Methanol-$d_4$) δ ppm 4.28 (q, J=7.1 Hz, 2H), 3.48-3.39 (m, 2H), 3.30-3.20 (m, 2H), 2.42-2.18 (m, 4H), 1.32 (t, J=7.2 Hz, 3H).

Intermediate methyl 4-fluoropiperidine-4-carboxylate was prepared from 1-tert-butyl 4-methyl 4-fluoropiperidine-1,4-dicarboxylate in a manner analogous to Step 2 of the synthesis of ethyl 4-fluoropiperidine-4-carboxylate.

Scheme 3. Synthesis of (S,Z)-1-((5-chloro-3′-methoxy-[1,1′-biphenyl]-2-yl)sulfonyl)-4-fluoro-N-(4-(methylsulfonyl)but-3-en-2-yl)piperidine-4-carboxamide (Compound 1)

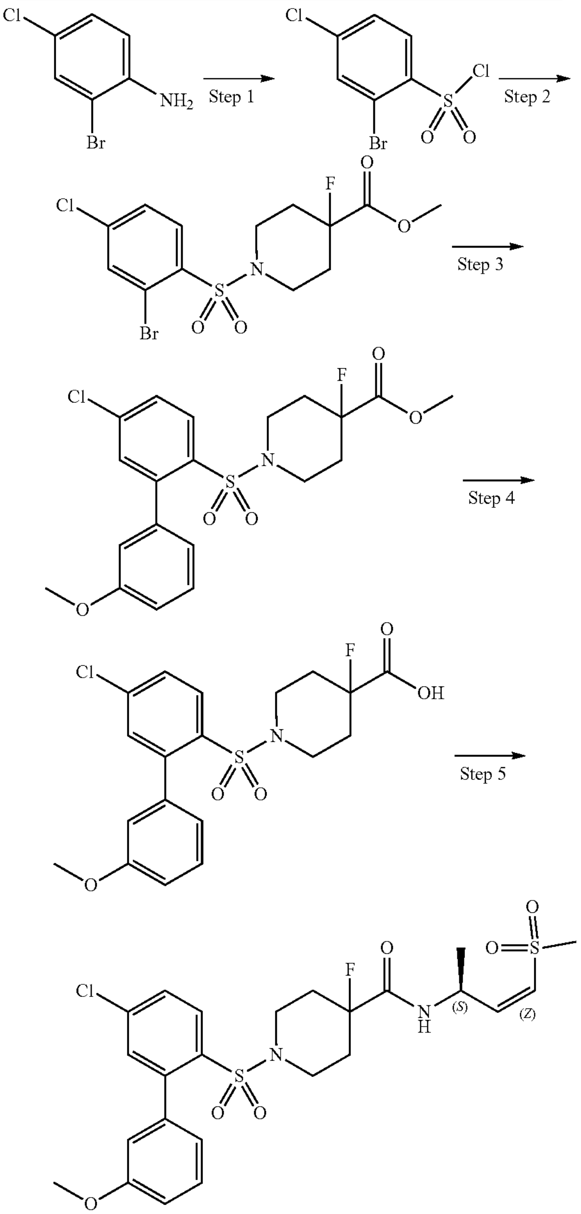

Step 1. 2-Bromo-4-chloroaniline (1.5 g, 7.26 mmol, 1.0 eq) was added in one portion to a mixture of concentrated hydrochloric acid (3 mL) and glacial acetic acid (1 mL) in a beaker equipped with a mechanical stirrer. The thick pink hydrochloride salt was cooled in an ice bath to 0 °C. A solution of sodium nitrite (553 mg, 8.0 mmol, 1.1 eq) in water (1.5 mL) was added dropwise at a rate such that the temperature did not exceed 0 °C. This mixture was stirred for 45 min at 0 °C. In a separate beaker, sulfur dioxide gas was bubbled through 5 mL of glacial acetic acid under vigorous stirring for 30 minutes. Copper(I) chloride (274 mg) was added to this solution and bubbling of sulfur dioxide gas was continued until the yellow-green suspension became blue-green and most of the solids dissolved (about 30 minutes). This mixture was cooled to 0 °C in an ice bath with stirring and to it was added the diazotization mixture in portions over 30 minutes, after which period the ice bath was removed and the mixture was allowed to warm to rt. The mixture was stirred for an additional 30 minutes. The reaction was poured into ice water (10 mL) and the precipitated gummy solid was extracted with MTBE (20 mL×3). The combined extracts were washed with sat. aq. sodium bicarbonate (30 mL) until neutral and washed with water (30 mL×2), dried over $Na_2SO_4$, filtered, and concentrated under vacuum to yield 2-bromo-4-chloro-benzenesulfonyl chloride as a dark green solid (1.4 g, 4.72 mmol, 65%). $^1$H NMR (400 MHz, $CDCl_3$) δ ppm 8.14 (d, J=8.8 Hz, 1H), 7.88 (d, J=2.2 Hz, 1H), 7.54 (dd, J=8.6, 2.0 Hz, 1H).

Step 2. To a solution of methyl 4-fluoropiperidine-4-carboxylate (300 mg, 1.52 mmol, 1 eq) in DCM (5 mL, 0.3 M) was added TEA (307 mg, 3.04 mmol, 2 eq) and 2-bromo-4-chloro-benzenesulfonyl chloride (572 mg, 1.97 mmol, 1.3 eq) at 0 °C. The reaction was stirred at 25 °C for 2 hrs. The reaction mixture was poured into water (10 mL) and extracted with DCM (10 mL×3). The combined organic layers were washed with brine (10 mL×2), dried over $Na_2SO_4$, filtered and concentrated under reduced pressure. The residue was purified by FCC on silica (PE:EtOAc=8:2) to provide methyl 1-(2-bromo-4-chloro-phenyl)sulfonyl-4-fluoro-piperidine-4-carboxylate (600 mg, 1.45 mmol, 95% yield) as a yellow oil. [M+H] calculated for $C_{13}H_{14}BrClFNO_4S$, 415; found 416.

Step 3. To a solution of methyl 1-(2-bromo-4-chloro-phenyl)sulfonyl-4-fluoro-piperidine-4-carboxylate (200 mg, 0.48 mmol, 1.0 eq) and 3-methoxyphenylboronic acid (80.6 mg, 0.53 mmol, 1.1 eq) in toluene (9 mL, 0.04 M) and water (3 mL, 0.04 M) was added $Na_2CO_3$ (153 mg, 1.45 mmol, 3.0 eq) and $Pd(PPh_3)_4$(55.7 mg, 0.05 mmol, 0.1 eq) at 25 °C under $N_2$. The mixture was stirred at 80 °C for 18 h. After cooling to rt, the reaction mixture was poured into water (15 mL) and extracted with EtOAc (15 mL×3). The combined organic layers were washed with brine (10 mL×2), dried over $Na_2SO_4$, filtered and concentrated under reduced pressure. The residue was purified by flash silica gel chromatography (PE:EtOAc=80:20) to provide methyl 1-[4-chloro-2-(3-methoxyphenyl)phenyl]sulfonyl-4-fluoro-piperidine-4-carboxylate (160 mg, 0.36 mmol, 75% yield) as a yellow oil. $^1$H NMR (400 MHz, $CDCl_3$) δ ppm 8.02 (d, J=8.7 Hz, 1H), 7.40 (dd, J=8.6, 2.2 Hz, 1H), 7.23-7.31 (m, 2H), 6.84-6.95 (m, 3H), 3.77 (s, 3H), 3.70 (s, 3H), 3.12 (br d, J=13.1 Hz, 2H), 2.50-2.60 (m, 2H), 1.65-1.81 (m, 4H). [M+H] calculated for $C_{20}H_{21}ClFNO_5S$, 441; found 442.

Step 4. To a solution of methyl 1-[4-chloro-2-(3-methoxyphenyl)phenyl]sulfonyl-4-fluoro-piperidine-4-carboxylate (160 mg, 0.36 mmol, 1.0 eq) in THF (6 mL, 0.05 M) and water (2 mL, 0.05 M) was added LiOH (43.4 mg, 1.81 mmol, 5.0 eq). The mixture was stirred at 50 °C for 3 hrs. After cooling to rt, the mixture was acidified with 1N HCl to pH=4-5, poured into water (10 mL) and extracted with EtOAc (10 mL×3). The combined organic layers were washed with brine (10 mL×2), dried over $Na_2SO_4$, filtered and concentrated under reduced pressure. Compound 1-[4-chloro-2-(3-methoxyphenyl)phenyl]sulfonyl-4-fluoro-piperidine-4-carboxylic acid was obtained as a yellow oil (140 mg, 0.33 mmol, 90%).

Step 5. To a solution of 1-[4-chloro-2-(3-methoxyphenyl)phenyl]sulfonyl-4-fluoro-piperidine-4-carboxylic acid (50 mg, 0.12 mmol, 1 eq) in DCM (3 mL, 0.04 M) was added (S,Z)-4-(methylsulfonyl)but-3-en-2-amine (TsOH salt, 41 mg, 0.13 mmol, 1.1 eq), HATU (67 mg, 0.18 mmol, 1.5 eq) and DIPEA (38 mg, 0.29 mmol, 2.5 eq) at 0 °C. The mixture was stirred at 25 °C for 2 h. The reaction mixture was poured into water (10 mL) and extracted with EtOAc (10 mL×3). The combined organic layers were washed with brine (10 mL×2), dried over $Na_2SO_4$, filtered and concentrated under reduced pressure. The residue was purified by prep-TLC (DCM:MeOH=20:1) to give (S,Z)-1-((5-chloro-3'-methoxy-[1,1'-biphenyl]-2-yl)sulfonyl)-4-fluoro-N-(4-(methylsulfonyl)but-3-en-2-yl)piperidine-4-carboxamide (Compound 1) (35 mg, 0.06 mmol, 53%). $^1$H NMR (400 MHz, DMSO-$d_6$) δ ppm 8.36 (br d, J=7.9 Hz, 1H), 8.04 (d, J=8.5 Hz, 1H), 7.70 (dd, J=8.6, 2.2 Hz, 1H), 7.47 (d, J=2.3 Hz, 1H), 7.34 (t, J=8.0 Hz, 1H), 6.93-7.03 (m, 3H), 6.45 (d, J=11.2 Hz, 1H), 6.26 (dd, J=11.1, 9.6 Hz, 1H), 5.25-5.41 (m, 1H), 3.78 (s, 3H), 3.12 (s, 5H), 2.52-2.56 (m, 2H), 1.58-1.84 (m, 4H), 1.20 (d, J=6.78 Hz, 3H). [M+H] calculated for $C_{24}H_{28}ClFN_2O_6S_2$, 558.1; found 559.1.

Compounds 2-18, Compounds 219-220, and Compounds 267-268 were synthesized in a manner analogous to Compound 1 starting with the appropriate aniline in Step 1 and the appropriate boronic acid in Step 3. Either methyl 4-fluoropiperidine-4-carboxylate or ethyl 4-fluoropiperidine-4-carboxylate was used in Step 2.

Compound 19 and Compound 200 were synthesized from the appropriate sulfonyl chloride in a manner analogous to Steps 2-5 of Compound 1.

Intermediates 4-fluoro-1-((3'-methoxy-[1,1'-biphenyl]-2-yl)sulfonyl)piperidine-4-carboxylic acid and 1-((2'-chloro-5-methoxy-[1,1'-biphenyl]-2-yl)sulfonyl)-4-fluoropiperidine-4-carboxylic acid were synthesized from the appropriate sulfonyl chloride and boronic acid in a manner analogous to Steps 2-4 of Compound 1.

Compound 201 was synthesized in a manner analogous to Compound 1 using ethyl 4-methyl-4-piperidinecarboxylate hydrochloride in Step 2.

Compound 203 was synthesized in a manner analogous to Compound 201 using (R,Z)-4-(methylsulfonyl)but-3-en-2-amine, TsOH salt in Step 5.

Intermediate ethyl 1-((5-chloro-3'-hydroxy-[1,1'-biphenyl]-2-yl)sulfonyl)-4-fluoropiperidine-4-carboxylate was prepared in a manner analogous to Compound 1, Steps 1-3, using 3-hydroxyphenylboronic acid in Step 3.

Scheme 4. Synthesis of Intermediate 1-[ethoxy(methylsulfonylmethyl)phosphoryl]oxyethane

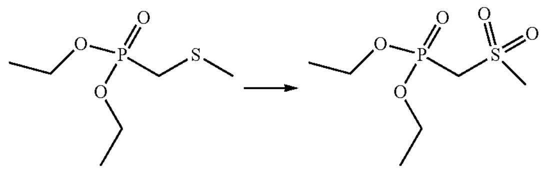

To a mixture of diethyl (methylthiomethyl)phosphonate (20 g, 101 mmol, 1 eq) in MeCN (160 mL, 0.42 M) and water (80 mL, 0.42 M) was added oxone (185 g, 303 mmol, 3 eq) in portions at 0-5 °C. The mixture was stirred at 25 °C for 2 h. The reaction mixture was filtered and the filtrate was quenched with sat. aq. $Na_2SO_3$ (200 mL) at 0-5 °C, then the mixture was concentrated under reduced pressure to remove MeCN. The residue was extracted with DCM (100 mL×2). The combined organic layers were washed with brine (100 mL×1), dried over anhydrous $Na_2SO_4$, filtered and concentrated under reduced pressure to give 1-[ethoxy(methylsulfonylmethyl)phosphoryl]oxyethane (21 g, 91.2 mmol, 90%) as a white solid. $^1$H NMR (400 MHz, $CDCl_3$) δ ppm 4.20-4.32 (m, 4H), 3.59 (d, J=16.4 Hz, 2H), 3.21 (s, 3H), 1.38 (t, J=7.1 Hz, 6H).

Scheme 5. Synthesis of Intermediate (E)-3-(methylsulfonyl)prop-2-en-1-amine

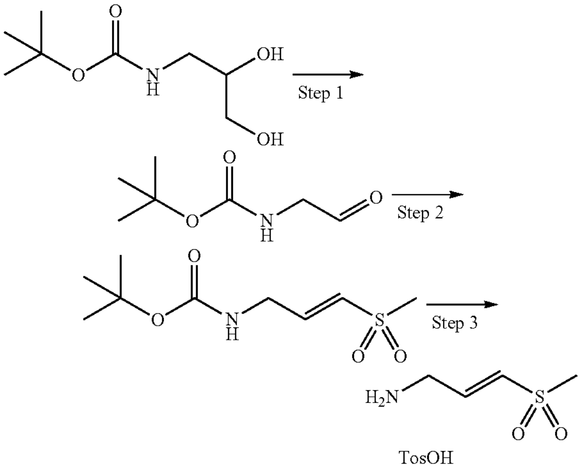

Step 1. To a suspension of tert-butyl N-(2,3-dihydroxypropyl)carbamate (2.5 g, 13.1 mmol, 1 eq) in water (20 mL, 0.65 M) was added $NaIO_4$ (3.1 g, 14.4 mmol, 1.1 eq) at 0 °C. The flask was covered in foil to protect $NaIO_4$ from light. The mixture was stirred for 4 h at 0 °C under $N_2$. The mixture was extracted with DCM (10 mL×5). The organic layer was dried over $Na_2SO_4$, filtered and concentrated under reduced pressure to give tert-butyl N-(2-oxoethyl) carbamate (1.6 g, 9.80 mmol, 75%) as a colorless oil. $^1H$ NMR (400 MHz, $CDCl_3$) δ ppm 9.65 (s, 1H), 5.21 (br s, 1H), 4.07 (br d, J=4.5 Hz, 2H), 1.45 (s, 9H).

Step 2. To a suspension of 1-[ethoxy(methylsulfonylmethyl)phosphoryl]oxyethane (13.6 g, 59.07 mmol, 1 eq) and potassium carbonate (24.5 g, 177 mmol, 3 eq) in THF (140 mL, 0.42 M) was added tert-butyl N-(2-oxoethyl)carbamate (8.5 g, 53.2 mmol, 0.9 eq) at 25 °C under $N_2$. The mixture was stirred at 50 °C for 8 h. After cooling to rt, the mixture was diluted with water (150 mL) and extracted with EtOAc (100 mL×3). The combined organic layers were dried over $Na_2SO_4$, filtered, and concentrated under reduced pressure. The residue was purified by FCC (PE:EtOAc=4:1 to 1:1) to give tert-butyl N-[(E)-3 methylsulfonylallyl]carbamate (8.5 g, 36.1 mmol, 61%) as a yellow oil. $^1H$ NMR (400 MHz, $CDCl_3$) δ ppm 6.89-6.96 (m, 1H), 6.46-6.55 (m, 1H), 4.77-4.91 (m, 1H), 3.93-4.05 (m, 2H), 1.46 (s, 9H), 2.95 (s, 3H).

Step 3. To a solution of tert-butyl N-[(E)-3-methylsulfonylallyl]carbamate (8.5 g, 36.3 mmol, 1 eq) in MeCN (85 mL, 0.43 M) was added p-toluenesulfonic acid monohydrate (8.3 g, 43.5 mmol, 1.2 eq). The mixture was stirred at 60 °C for 12 h. Then the reaction was filtered and concentrated under reduced pressure to give 4-methylbenzenesulfonate; (E)-3-methylsulfonylprop-2-en-1-amine (6.7 g, 21.9 mmol, 60%) as a white solid. $^1H$NMR (400 MHz, DMSO-$d_6$) δ ppm 8.04 (br s, 3H), 7.45-7.52 (m, 2H), 7.11 (d, J=7.8 Hz, 2H), 6.97 (dt, J=15.48, 1.6 Hz, 1H), 6.73 (dt, J=15.42, 5.6 Hz, 1H), 3.74 (dd, J=5.57, 1.6 Hz, 2H), 3.05 (s, 3H), 2.28 (s, 3H).

Compounds 36-45 were synthesized in a manner analogous to Compound 1 starting with the appropriate aniline in Step 1, the appropriate boronic acid in Step 3 and using (E)-3-methylsulfonylprop-2-en-1-amine in Step 5. Either methyl 4-fluoropiperidine-4-carboxylate or ethyl 4-fluoropiperidine-4-carboxylate was used in Step 2.

Intermediate 3-((methylsulfonyl)methylene)azetidine was synthesized in a manner analogous to (E)-3-(methylsulfonyl)prop-2-en-1-amine, Steps 2-3, starting with tert-butyl 3-oxoazetidine-1-carboxylate in Step 2.

Scheme 6. Synthesis of 1-[4-bromo-2-(2-chlorophenyl)phenyl]sulfonyl-4-fluoro-N-[(Z,1R)-1-methyl-3-methylsulfonyl-allyl]piperidine-4-carboxamide (Compound 47)

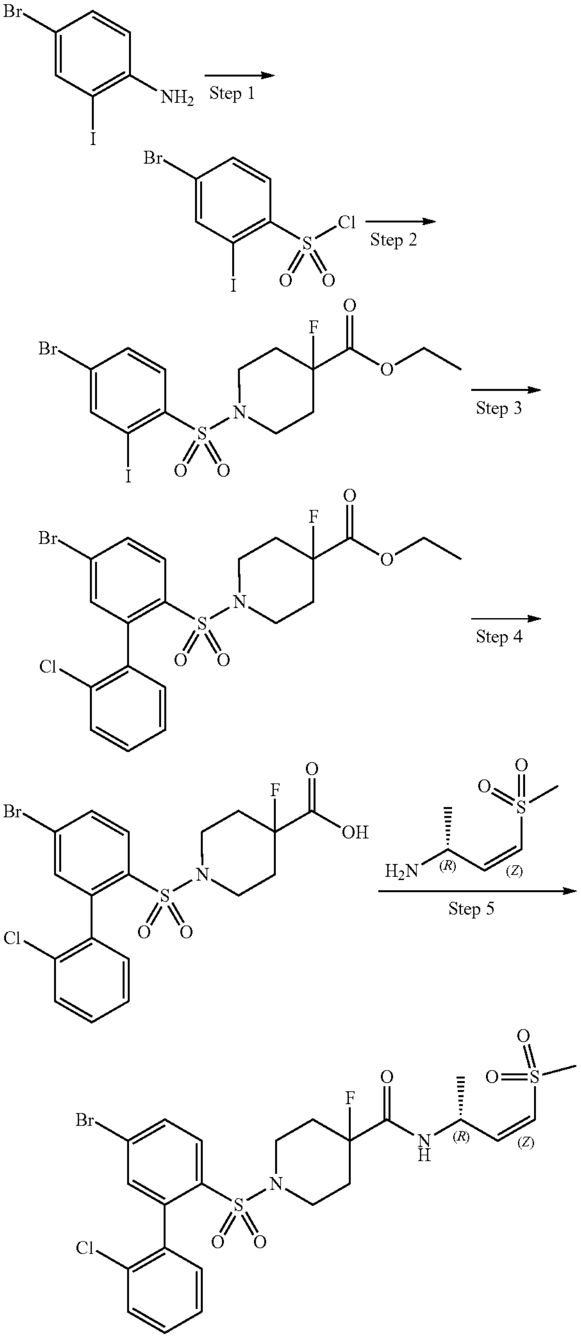

Step 1. To a solution of 4-bromo-2-iodo-aniline (1 g, 3.36 mmol, 1 eq) in concentrated HCl (15 mL)/acetic acid (5 mL, 0.09 M) was added $NaNO_2$ (254 mg, 3.70 mmol, 1.1 eq) at 0 °C. This mixture 1 was stirred at 0 °C for 1 hour. In a separate flask, $SO_2$ was bubbled through acetic acid (33 mL, 0.09 M) for about 10 min at 0 °C before CuCl (99 mg, 1.01 mmol, 0.3 eq) was added. $SO_2$ was bubbled through mixture 2 for about 10 min. Mixture 1 was added to the mixture 2 at 0 °C. The resulting mixture was stirred at 0 °C~20 °C for 1 hour. The reaction mixture was quenched with water (30 mL) and extracted with MTBE (30 mL×2). The combined organic layers were washed with sat. aq. sodium bicarbonate (30 mL×2) and 30 mL brine. The organic layer was then separated and dried ($Na_2SO_4$) before evaporation in vacuo. The crude material was purified by FCC (PE:EtOAc 50:1) to give 4-bromo-2-iodo-benzenesulfonyl chloride (4 g, 10.5 mmol, 62% yield) as a yellow oil. $^1$H NMR (400 MHz, $CDCl_3$) δ ppm 7.72 (dd, J=8.6, 1.9 Hz, 1H), 8.07 (d, J=8.6 Hz, 1H), 8.37 (d, J=1.9 Hz, 1H).

Step 2. To a solution of 4-bromo-2-iodo-benzenesulfonyl chloride (3.6 g, 9.44 mmol, 1 eq) and ethyl 4-fluoropiperidine-4-carboxylate hydrochloride (2.0 g, 9.44 mmol, 1 eq) in DCM (10 mL, 0.9 M) was added triethylamine (2.9 g, 28.3 mmol, 3 eq) dropwise at 0 °C. The resulting mixture was stirred at 20 °C for 1 hour. The reaction mixture was quenched with water (15 mL) and extracted with DCM (15 mL×2). The combined organic layers were washed with 20 mL brine. The organic layer was then separated and dried ($Na_2SO_4$) before evaporation in vacuo. The crude material was then purified by FCC to give ethyl 1-(4-bromo-2-iodo-phenyl)sulfonyl-4-fluoro-piperidine-4-carboxylate (4.3 g, 8.3 mmol, 87% yield) as a yellow solid. $^1$H NMR (400 MHz, $CDCl_3$) δ ppm 8.28 (d, J=1.88 Hz, 1H), 7.99 (d, J=8.50 Hz, 1H), 7.64 (dd, J=8.44, 1.94 Hz, 1H), 4.27 (q, J=7.13 Hz, 2H), 3.75 (dt, J=13.01, 2.56 Hz, 2H), 3.18 (td, J=12.76, 2.75 Hz, 2H), 2.12-2.31 (m, 2H), 1.99-2.08 (m, 2H), 1.32 (t, J=7.13 Hz, 3H).

Step 3. To a solution of ethyl 1-(4-bromo-2-iodo-phenyl) sulfonyl-4-fluoro-piperidine-4-carboxylate (878 mg, 1.69 mmol, 1 eq) in 1,4-dioxane (9 mL, 0.2 M) and 1 M aq. $K_3PO_4$ (2.7 mL) was added 2-chlorophenylboronic acid (290 mg, 1.86 mmol, 1.1 eq) and tetrakis(triphenylphosphine)palladium(0) (195 mg, 0.169 mmol, 0.1 eq). The mixture was stirred at 80 °C under nitrogen for 16 hrs. The mixture was diluted with water (100 mL) and extracted with EtOAc (150 mL×3). The combined organic layers were washed with brine (100 mL×2), dried over $Na_2SO_4$, filtered, and concentrated under reduced pressure. The residue was purified by prep-TLC (PE:EtOAc 3:1) to give ethyl 1-[4-bromo-2-(2-chlorophenyl)phenyl]sulfonyl-4-fluoro-piperidine-4-carboxylate (400 mg, 0.79 mmol, 47% yield) as a yellow oil. $^1$H NMR (400 MHz, $CDCl_3$) δ ppm 8.01 (d, J=8.5 Hz, 1H), 7.67 (dd, J=1.9, 8.5 Hz, 1H), 7.55-7.44 (m, 2H), 7.43-7.27 (m, 3H), 4.22 (q, J=7.0 Hz, 2H), 3.24 (br d, J=13.4 Hz, 1H), 3.07 (br d, J=13.3 Hz, 1H), 2.98-2.85 (m, 1H), 2.72-2.58 (m, 1H), 2.04-1.79 (m, 4H), 1.34-1.27 (m, 3H). [M+H] calculated for $C_{20}H_{20}BrClFNO_4S$, 505; found 506.

Step 4. Ethyl 1-[4-bromo-2-(2-chlorophenyl)phenyl] sulfonyl-4-fluoro-piperidine-4-carboxylate (460 mg, 0.911 mmol, 1 eq) and lithium hydroxide monohydrate (115 mg, 2.73 mmol, 3 eq) were taken up in THF (6 mL, 0.11 M) and water (2 mL, 0.11 M). The mixture was stirred at 25 °C for 2 h. The mixture was concentrated to remove organic solvent and acidified with 6 M HCl to adjust pH to 2~4. The precipitate was filtered to afford 1-[4-bromo-2-(2-chlorophenyl)phenyl]sulfonyl-4-fluoro-piperidine-4-carboxylic acid (400 mg, 0.84 mmol, 92% yield) as a white solid.

Step 5. 1-[4-Bromo-2-(2-chlorophenyl)phenyl]sulfonyl-4-fluoro-piperidine-4-carboxylic acid (500 mg, 1.05 mmol, 1 eq), (R,Z)-4-(methylsulfonyl)but-3-en-2-amine (TsOH salt, 438 mg, 1.36 mmol, 1.3 eq), 2,4,6-tripropyl-1,3,5,2,4,6-trioxatriphosphorinane-2,4,6-trioxide (1.7 g, 2.62 mmol, 2.5 eq) and DIPEA (407 mg, 3.15 mmol, 3 eq) were combined in DCM (5 mL, 0.21 M). The mixture was stirred at 25 °C for 2 h. The mixture was diluted with water (10 mL) and extracted with EtOAc (20 mL). The extract was washed with brine (20 mL), dried over $Na_2SO_4$, and filtered. The filtrate was concentrated in vacuo and purified by column chromatography (PE:EtOAc 10:1-1:1) to afford 1-[4-bromo-2-(2-chlorophenyl)phenyl]sulfonyl-4-fluoro-N-[(Z,1R)-1-methyl-3-methylsulfonyl-allyl]piperidine-4-carboxamide (Compound 47) as a white solid (428 mg, 0.70 mmol, 66.5% yield). $^1$H NMR (400 MHz, DMSO-$d_6$) δ ppm 8.37 (br d, J=6.0 Hz, 1H), 7.99-7.92 (m, 1H), 7.92-7.86 (m, 1H), 7.60 (d, J=2.0 Hz, 1H), 7.58-7.51 (m, 1H), 7.49-7.41 (m, 1H), 7.39 (d, J=4.1 Hz, 2H), 6.45 (d, J=11.3 Hz, 1H), 6.28 (dd, J=9.5, 11.1 Hz, 1H), 5.44-5.27 (m, 1H), 3.21-3.05 (m, 5H), 2.79-2.69 (m, 1H), 2.65-2.56 (m, 1H), 2.02-1.61 (m, 4H), 1.20 (d, J=6.9 Hz, 3H). [M+H] calculated for $C_{23}H_{25}BrClFN_2O_5S_2$, 606; found 607.

Compounds 20-35 were synthesized in a manner analogous to Compound 47 using the appropriate aniline in Step 1 and the appropriate boronic acid in Step 3. Either methyl 4-fluoropiperidine-4-carboxylate or ethyl 4-fluoropiperidine-4-carboxylate was used in Step 2.

Compounds 48-58 were synthesized in a manner analogous to Compound 47 using the appropriate boronic acid in Step 3. Either methyl 4-fluoropiperidine-4-carboxylate or ethyl 4-fluoropiperidine-4-carboxylate was used in Step 2.

Compounds 59-60 were synthesized in a manner analogous to Compound 47 using the appropriate pinacol boronate ester in Step 3 in the place of the boronic acid. Either methyl 4-fluoropiperidine-4-carboxylate or ethyl 4-fluoropiperidine-4-carboxylate was used in Step 2.

Compounds 61-62 were synthesized in a manner analogous to Compound 47 using the appropriate boronic acid in Step 3 and (S,Z)-4-(methylsulfonyl)but-3-en-2-amine, TsOH salt in Step 5. Either methyl 4-fluoropiperidine-4-carboxylate or ethyl 4-fluoropiperidine-4-carboxylate was used in Step 2.

Compounds 63-64 were synthesized in a manner analogous to Compound 47 using the appropriate boronic acid in Step 3 and (E)-3-(methylsulfonyl)prop-2-en-1-amine, TsOH salt in Step 5. Either methyl 4-fluoropiperidine-4-carboxylate or ethyl 4-fluoropiperidine-4-carboxylate was used in Step 2.

Compound 65 was synthesized in a manner analogous to Compound 47 using 3-amino-2,3-dihydrothiophene 1,1-dioxide in Step 5.

Compound 66 was synthesized in a manner analogous to Compound 47 using (R)-3-amino-2,3-dihydrothiophene 1,1-dioxide in Step 5.

Compound 67 was synthesized in a manner analogous to Compound 47 using (S)-3-amino-2,3-dihydrothiophene 1,1-dioxide in Step 5.

Compound 202 was synthesized in a manner analogous to Compound 47 starting with 2-bromo-4,5-dimethoxybenzenesulfonyl chloride in Step 2.

Compound 204 was synthesized in a manner analogous to Compound 47 using 3-chloro-2-(tributylstannyl)pyridine in Step 3 and reacting under microwave irradiation at 140 °C for 1 h.

Compound 273 was synthesized in a manner analogous to Compound 47 using 3-((methylsulfonyl)methylene)azetidine in Step 5.

Scheme 7. Synthesis of Intermediate (E)-4-aminobut-2-enenitrile

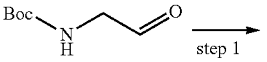

-continued

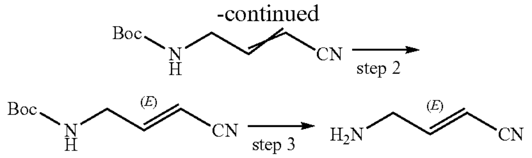

Step 1. To a solution of N-boc-2-aminoacetaldehyde (11 g, 69.1 mmol, 1.0 eq) in THF (130 mL, 0.53 M) was added diethyl cyanomethylphosphonate (12.2 g, 69.1 mmol, 1 eq) and $K_2CO_3$ (19.1 g, 138 mmol, 2 eq) at 0 °C. The mixture was stirred at 25 °C for 12 h. The reaction mixture was poured into water (100 mL) and extracted with EtOAc (100 mL×3). The combined organic phase was washed with brine (80 mL), dried over by $Na_2SO_4$, filtered, and concentrated under reduced pressure. The residue was purified by column chromatography to give tert-butyl(3-cyanoallyl)carbamate (8 g, 43.9 mmol, 63%) as a yellow oil.

Step 2. Crude tert-butyl N-(3-cyanoallyl)carbamate (4 g, 22 mmol, 1 eq) was purified by prep-HPLC to give tert-butyl N-[(E)-3-cyanoallyl]carbamate (1 g, 5.5 mmol, 25%) and tert-butyl N-[(Z)-3-cyanoallyl]carbamate (300 mg, 1.64 mmol, 7.5%).

Step 3. To a solution of tert-butyl N-[(E)-3-cyanoallyl] carbamate (100 mg, 0.55 mmol, 1 eq) in DCM (3 mL, 0.15 M) was added TFA (0.5 mL) under $N_2$. The reaction was stirred at 25 °C for 2 h. The reaction mixture was concentrated under reduced pressure to give (E)-4-aminobut-2-enenitrile; 2,2,2-trifluoroacetic acid (80 mg, 0.408 mmol, 74%) as a yellow oil. $^1H$ NMR (400 MHz, Methanol-$d_4$) δ ppm 6.77 (dt, J=16.4, 6.2 Hz, 1H), 5.92 (d, J=16.4 Hz, 1H), 3.77 (d, J=6.1 Hz, 2H).

Intermediate (Z)-4-aminobut-2-enenitrile was synthesized in an analogous manner as (E)-4-aminobut-2-enenitrile, Step 3, using tert-butyl N-[(Z)-3-cyanoallyl]carbamate.

Compound 68 was synthesized in a manner analogous to Compound 47 using (E)-4-aminobut-2-enenitrile in Step 5.

Compound 69 was synthesized in a manner analogous to Compound 68 starting with the appropriate aniline in Step 1.

Compound 70 was synthesized in a manner analogous to Compound 47 using (Z)-4-aminobut-2-enenitrile in Step 5.

Compound 71 was synthesized in a manner analogous to Compound 1 using (Z)-4-aminobut-2-enenitrile in Step 5.

Intermediate (R,E)-4-aminopent-2-enenitrile was synthesized in a manner analogous to (E)-4-aminobut-2-enenitrile starting from 1,1-dimethylethyl N-[(1R)-1-methyl-2-oxo-ethyl]carbamate in Step 1.

Compound 229 was synthesized in a manner analogous to Compound 1, Step 5, using (R,E)-4-aminopent-2-enenitrile and 1-((2'-chloro-5-methoxy-[1,1'-biphenyl]-2-yl)sulfonyl)-4-fluoropiperidine-4-carboxylic acid in Step 5.

Scheme 8. Synthesis of Intermediate 2-(aminomethyl)acrylonitrile

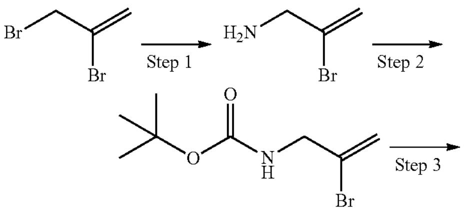

-continued

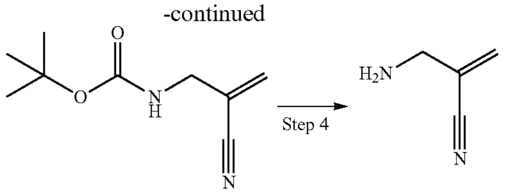

Step 1. To a solution of hexamethylenetetramine (7 g, 49.9 mmol, 1 eq) in chloroform (50 mL, 1.0 M) was added 2,3-dibromopropene (10.2 g, 50.9 mmol, 1.02 eq) at 70 °C. The mixture was stirred at 70 °C for 3 hrs. The mixture was cooled in an ice batch and the salt was collected by filtration to give the crude solid. The solid was dissolved in a warm solution of 40 mL of water, 200 mL of EtOH and 45 mL of conc. HCl. A white precipitate of $NH_4Cl$ formed and the reaction mixture was allowed to stand at 25 °C for 16 h. The white solid was removed again by filtration and the mother liquid was concentrated and dried to give 2-bromoprop-2-en-1-amine; hydrochloride (13.5 g, 78.3 mmol) as a white solid.

Step 2. 2-Bromoprop-2-en-1-amine; hydrochloride (1 g, 5.80 mmol, 1 eq) and di-tert-butyl dicarbonate (1.5 g, 6.95 mmol, 1.2 eq) were taken up in DCM (20 mL, 0.29 M). The mixture was stirred at 20 °C for 10 h. The mixture was diluted with $H_2O$ (15 mL) and extracted with DCM (80 mL). The extract was washed with brine (30 mL), dried over $Na_2SO_4$ and filtered. The filtrate was concentrated in vacuo and purified by column chromatography to afford tert-butyl N-(2-bromoallyl)carbamate (600 mg, 2.54 mmol, 44% yield) as a white solid.

Step 3. To a mixture of tert-butyl N-(2-bromoallyl)carbamate (200 mg, 0.85 mmol, 1 eq) in DMF (2 mL, 0.42 M) was added $Zn(CN)_2$ (149 mg, 1.27 mmol, 1.5 eq) and $Pd(PPh_3)_4$(98 mg, 0.085 mmol, 0.1 eq). The mixture was stirred at 110 °C for 12 hrs. After cooling to rt, the reaction mixture was poured into water (5 mL) and extracted with EtOAc (20 mL×3). The combined organic layers were washed with brine (10 mL), dried over $Na_2SO_4$, filtered, and concentrated under reduced pressure. The residue was purified by column chromatography to afford tert-butyl N-(2-cyanoallyl)carbamate (80 mg, 0.44 mmol, 52% yield) as a white solid.

Step 4. To a solution of tert-butyl N-(2-cyanoallyl)carbamate (80 mg, 0.44 mmol, 1 eq) in DCM (0.3 mL, 1.5 M) was added TFA (0.1 mL). The mixture was stirred at 20 °C for 2 hrs. Solvent was removed by vacuum to afford 2-(aminomethyl)prop-2-enenitrile (23 mg, 0.28 mmol, 64% yield) as a yellow oil, which was used in the next step directly. $^1H$ NMR (400 MHz, MeOD-$d_4$) δ ppm 6.37 (s, 1H), 6.28 (s, 1H), 3.82 (s, 2H).

Compound 72 was synthesized in a manner analogous to Compound 47 using 2-(aminomethyl)prop-2-enenitrile in Step 5.

Scheme 9. Synthesis of 1-((5-bromo-2'-chloro-[1,1'-biphenyl]-2-yl)sulfonyl)-4-fluoro-N-((2R,Z)-4-(S-methylsulfonimidoyl) but-3-en-2-yl)piperidine-4-carboxamide (Compound 73)

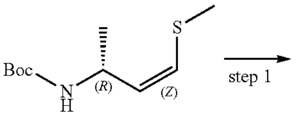

-continued

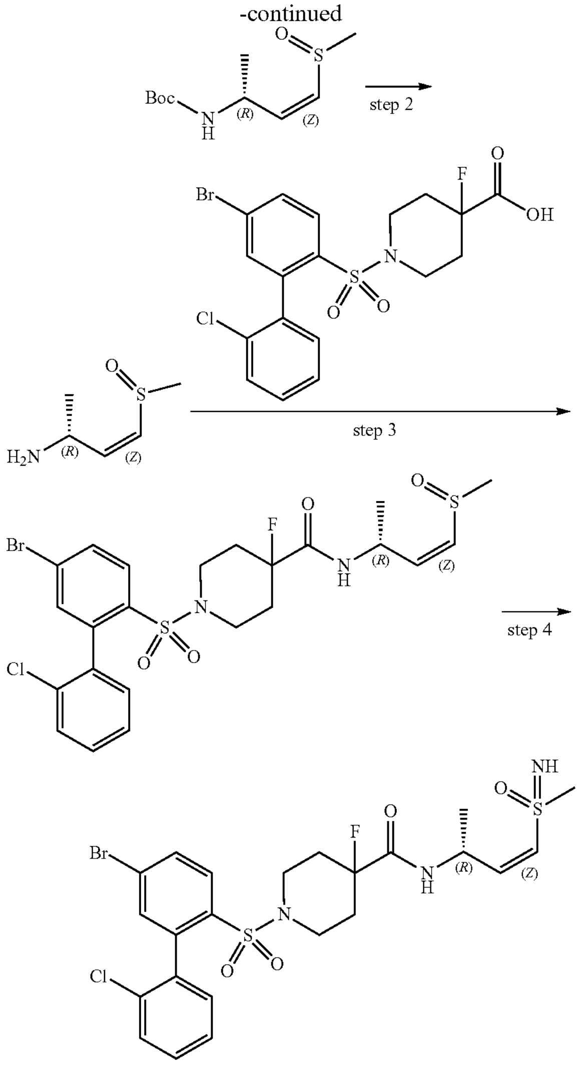

Step 1. To a solution of tert-butyl(R,Z)-(4-(methylthio)but-3-en-2-yl)carbamate (0.8 g, 3.68 mmol, 1 eq) in EtOAc (10 mL, 0.37 M) was added m-CPBA (667 mg, 3.68 mmol, 1 eq) at 0 °C and the reaction was stirred at 20 °C for 4 h. The solution was diluted with aq. $Na_2SO_3$ (20 mL) and extracted with EtOAc (20 mL×3). The combined organic layers were washed with brine (10 mL×3), dried over $Na_2SO_4$, filtered, and concentrated under reduced pressure. The residue was purified by column chromatography (PE:EtOAc=0:1) to give tert-butyl ((2R,Z)-4-(methylsulfinyl)but-3-en-2-yl)carbamate (0.65 g, 2.8 mmol, 76%).

Step 2. To a solution of tert-butyl ((2R,Z)-4-(methylsulfinyl)but-3-en-2-yl)carbamate (300 mg, 1.29 mmol, 1 eq) in MeCN (3 mL, 0.43 M) was added 4-methylbenzenesulfonic acid (332 mg, 1.93 mmol, 1.5 eq) at 15 °C and the reaction was stirred at 50 °C for 18 h. The solution was evaporated to get the crude (2R,Z)-4-(methylsulfinyl)but-3-en-2-amine (350 mg, 1.1 mmol, 89%).

Step 3. To a solution of 1-[4-bromo-2-(2-chlorophenyl)phenyl]sulfonyl-4-fluoro-piperidine-4-carboxylic acid (100 mg, 0.21 mmol, 1 eq) and (2R,Z)-4-(methylsulfinyl)but-3-en-2-amine (28 mg, 0.21 mmol, 1 eq) in DCM (3 mL, 0.07 M) was added DIPEA (81.3 mg, 0.63 mmol, 3 eq) and $T_3P$ (0.2 mL, 1.5 eq, 60%) at 15 °C. The reaction was stirred at 15 °C for 1 h. The solution was diluted with $H_2O$ (10 mL) and extracted with DCM (10 mL×3). The combined organic layers were washed with brine (20 mL), dried over $Na_2SO_4$, filtered, and concentrated under reduced pressure. The residue was purified by prep-TLC (DCM:MeOH=10:1). The product 1-((5-bromo-2'-chloro-[1,1'-biphenyl]-2-yl)sulfonyl)-4-fluoro-N-((2R,Z)-4-(methylsulfinyl)but-3-en-2-yl)piperidine-4-carboxamide (60 mg, 0.11 mmol, 48%) was obtained as a yellow oil.

Step 4. To a solution of 1-((5-bromo-2'-chloro-[1,1'-biphenyl]-2-yl)sulfonyl)-4-fluoro-N-((2R,Z)-4-(methylsulfinyl)but-3-en-2-yl)piperidine-4-carboxamide (60 mg, 0.10 mmol, 1 eq) in methanol (3 mL, 0.03 M) was added $PhI(OAc)_2$ (163 mg, 0.30 mmol, 3 eq) and $NH_4COONH_2$ (131 mg, 1.00 mmol, 10 eq). The reaction was stirred at 15 °C for 16 h. The mixture was filtrated, and the filtrate was concentrated under reduced pressure. The residue was purified by prep-HPLC to give 1-((5-bromo-2'-chloro-[1,1'-biphenyl]-2-yl)sulfonyl)-4-fluoro-N-((2R,Z)-4-(S-methylsulfonimidoyl)but-3-en-2-yl)piperidine-4-carboxamide (Compound 73) (32.6 mg, 0.05 mmol, 53%) as a yellow oil. $^1H$ NMR (400 MHz, $CDCl_3$) δ ppm 8.56 (br t, J=6.7 Hz, 1H), 8.01-7.92 (m, 1H), 7.92-7.86 (m, 1H), 7.61 (d, J=1.9 Hz, 1H), 7.55 (d, J=7.6 Hz, 1H), 7.49-7.42 (m, 1H), 7.39 (d, J=4.4 Hz, 2H), 6.85-6.62 (m, 2H), 5.39-5.20 (m, 1H), 3.79-3.61 (m, 3H), 3.15 (br s, 2H), 2.76-2.56 (m, 4H), 2.01-1.63 (m, 4H), 1.25 (d, J=6.8 Hz, 3H). [M+H] calculated for $C_{23}H_{26}BrClFN_3O_4S_2$, 605; found 606.

Compound 74 was synthesized in an analogous manner to Compound 73 starting with the chiral sulfoxide in Step 3.

Scheme 10. Synthesis of Intermediate 2-trimethylsilylethyl 3-[(E,3S)-3-aminobut-1-enyl]sulfonylazetidine-1-carboxylate

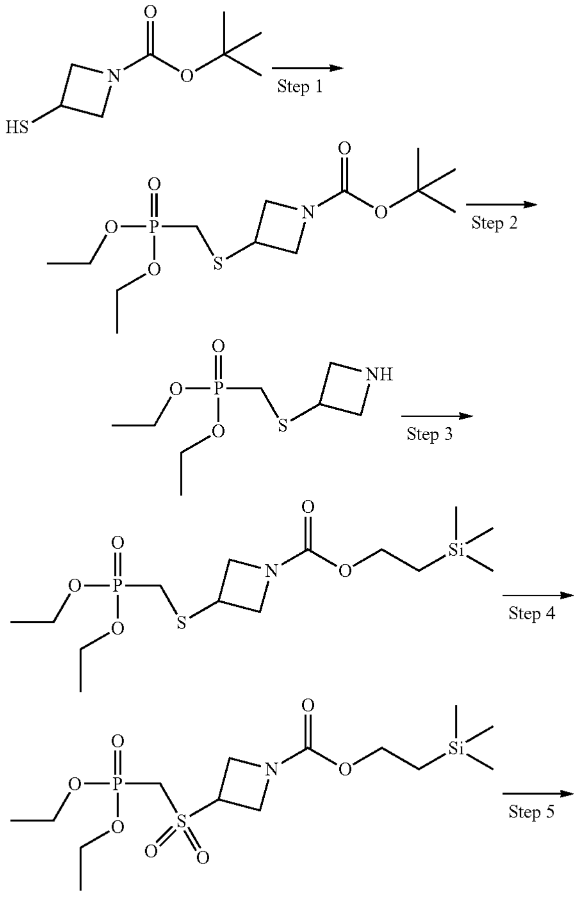

-continued

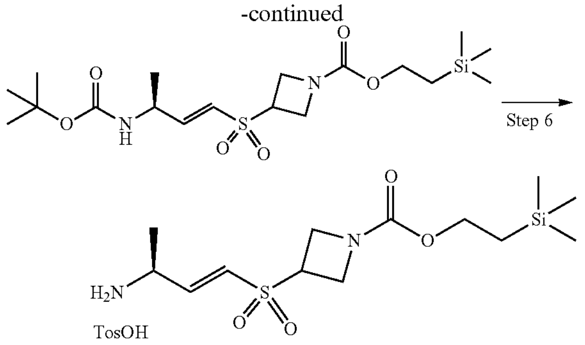

Step 1. To a solution of tert-butyl 3-sulfanylazetidine-1-carboxylate (6 g, 31.7 mmol, 1 eq) in THF (60 mL) at 0 °C was added NaH (1.4 g, 34.87 mmol, 1.1 eq). The mixture was stirred at 0 °C for 1 h. Diethyl iodomethylphosphonate (9.7 g, 34.9 mmol, 1.1 eq) was added and the reaction was stirred at 25 °C for 1 hr. The reaction mixture was poured into aq. sat. $NH_4Cl$ (50 mL) and extracted with EtOAc (30 mL×3). The combined organic layers were washed with brine (10 mL×2), dried over $Na_2SO_4$, filtered, and concentrated under reduced pressure. The crude tert-butyl 3-(diethoxyphosphorylmethylsulfanyl)azetidine-1-carboxylate (11.1 g, 32.7 mmol) was obtained as a yellow oil, which was used in the next step without further purification.

Step 2. To tert-butyl 3-(diethoxyphosphorylmethylsulfanyl) azetidine-1-carboxylate (11.1 g, 32.7 mmol, 1 eq) in DCM (30 mL, 0.55 M) was added TFA (30 mL, 0.55 M). The mixture was stirred at 20 °C for 8 hrs. The mixture was concentrated under vacuum to obtain 3-(diethoxyphosphorylmethylsulfanyl) azetidin-1-ium; 2,2,2-trifluoroacetate (11.6 g, 34.0 mmol, 100%) as a yellow oil, which was used in the next step without further purification.

Step 3. To a solution of 3-(diethoxyphosphorylmethylsulfanyl) azetidin-1-ium; 2,2,2-trifluoroacetate (11.6 g, 34.0 mmol, 1.0 eq) in methanol (50 mL) and DCM (50 mL) was added (2,5-dioxopyrrolidin-1-yl) 2-trimethylsilylethyl carbonate (9.7 g, 37.5 mmol, 1.1 eq) and triethylamine (10.3 g, 102 mmol, 3 eq). The mixture was stirred at 30 °C for 5 h. The reaction mixture was poured into water (45 mL) and extracted with EtOAc (45 mL×3). The combined organic layers were washed with brine (50 mL), dried over $Na_2SO_4$, filtered, and concentrated under reduced pressure. The crude 2-trimethylsilylethyl 3-(diethoxyphosphorylmethylsulfanyl) azetidine-1-carboxylate (12.7 g, 33.11 mmol, 97%) was obtained as a yellow oil, which was used in the next step without further purification.

Step 4. To a solution of 2-trimethylsilylethyl 3-(diethoxyphosphorylmethylsulfanyl) azetidine-1-carboxylate (16.7 g, 43.5 mmol, 1 eq) in DCM (100 mL, 0.44 M) was added 3-chloroperbenzoic acid (19.4 g, 95.8 mmol, 2.2 eq) at 0 °C. The mixture was stirred at 20 °C for 12 hrs. The reaction mixture was poured into sat. aq. $Na_2SO_3$ (100 mL) and extracted with DCM (50 mL×3). The combined organic layers were washed with brine (100 mL), dried over $Na_2SO_4$, filtered, and concentrated under reduced pressure. The crude was purified by column chromatography to give 2-trimethylsilylethyl 3-(diethoxyphosphorylmethylsulfonyl) azetidine-1-carboxylate (7.7 g, 18.5 mmol, 43%).

Step 5. A solution of 2-trimethylsilylethyl 3-(diethoxyphosphorylmethylsulfonyl) azetidine-1-carboxylate (1 g, 2.41 mmol, 1 eq) in THF (20 mL, 0.12 M) was cooled to −78 °C. Then lithium bis(trimethylsilyl)amide (2.6 mL, 2.64 mmol, 1.1 eq) was added. The mixture was stirred at −78 °C for 1 hr. tert-Butyl (S)-(1-oxopropan-2-yl)carbamate (458 mg, 2.65 mmol, 1.1 eq) was added. After 10 min, the mixture was heated to 20 °C and stirred for 1 hr. The reaction mixture was poured into sat. aq. $NH_4Cl$ (100 mL) and extracted with EtOAc (30 mL×3). The combined organic layers were washed with brine (10 mL×2), dried over $Na_2SO_4$, filtered and concentrated under reduced pressure. The crude was purified by column chromatography to give 2-trimethylsilylethyl 3-[(E,3S)-3-(tert-butoxycarbonylamino) but-1-enyl] sulfonylazetidine-1-carboxylate (0.8 g, 1.84 mmol, 76%) as a yellow oil.

Step 6. To 2-trimethylsilylethyl 3-[(E,3S)-3-(tert-butoxycarbonylamino)but-1-enyl]sulfonylazetidine-1-carboxylate (0.8 g, 1.84 mmol, 1 eq) in MeCN (5 mL, 0.37 M) was added p-toluenesulfonic acid monohydrate (350 mg, 1.84 mmol, 1 eq). The mixture was stirred at 20 °C for 2 hrs. The mixture was filtered to give 4-methylbenzenesulfonate; 2-trimethylsilylethyl 3-[(E,3S)-3-aminobut-1-enyl]sulfonylazetidine-1-carboxylate (500 mg, 0.99 mmol, 54%) as a white solid.

Intermediates 2-trimethylsilylethyl 3-[(E,3R)-3-aminobut-1-enyl]sulfonylazetidine-1-carboxylate, 2-(trimethylsilyl)ethyl(S,E)-3-((3-aminopent-1-en-1-yl)sulfonyl)azetidine-1-carboxylate, and 2-(trimethylsilyl)ethyl(R,E)-3-((3-aminopent-1-en-1-yl)sulfonyl)azetidine-1-carboxylate were synthesized in a manner analogous to 2-trimethylsilylethyl 3-[(E,3S)-3-aminobut-1-enyl]sulfonylazetidine-1-carboxylate starting with the appropriate aldehyde in Step 5.

Scheme 11. Synthesis of (S,E)-N-(4-(azetidin-3-ylsulfonyl)but-3-en-2-yl)-1-((5-bromo-2′-chloro-[1,1′-biphenyl]-2-yl)sulfonyl)-4-fluoropiperidine-4-carboxamide (Compound 75)

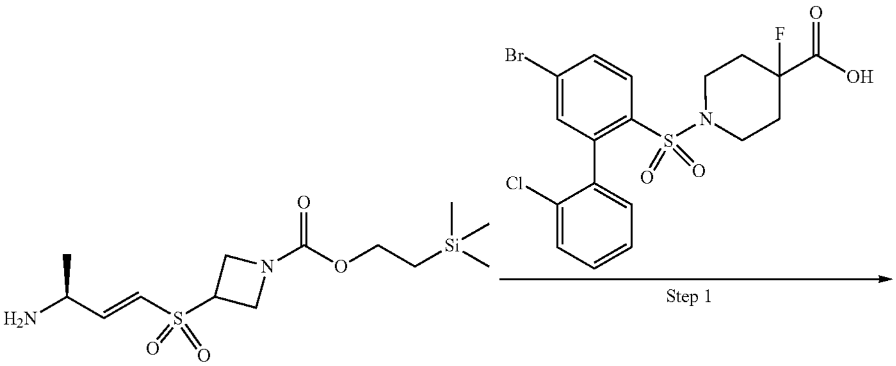

-continued

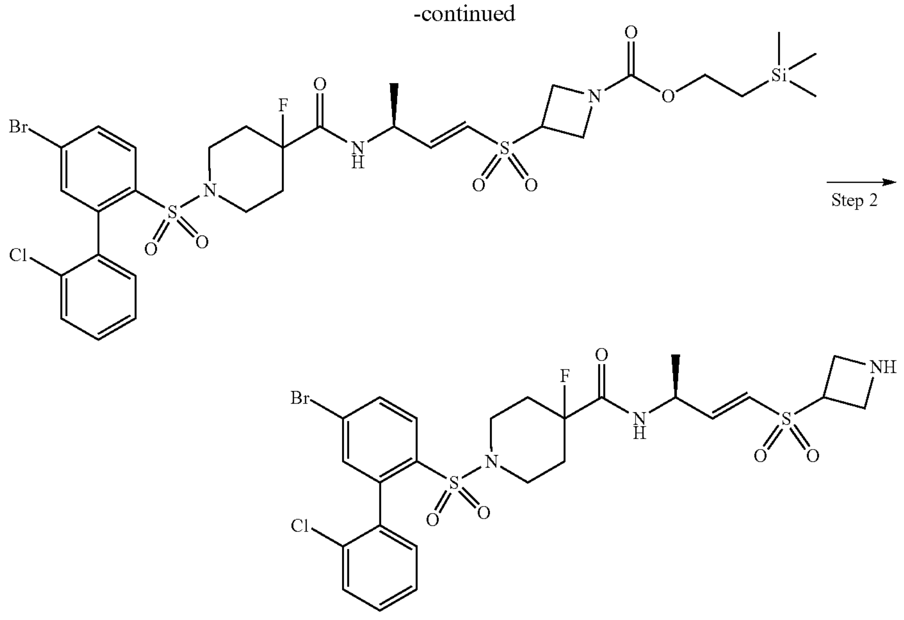

Step 1. To a solution of 1-[4-bromo-2-(2-chlorophenyl) phenyl]sulfonyl-4-fluoro-piperidine-4-carboxylic acid (150 mg, 0.315 mmol, 1 eq) and 4-methylbenzenesulfonate; 2-trimethylsilylethyl 3-[(E,3S)-3-aminobut-1-enyl]sulfonylazetidine-1-carboxylate (239 mg, 0.472 mmol, 1.5 eq) in MeCN (1 mL, 0.31 M) was added 1-methylimidazole (77.5 mg, 0.94 mmol, 3 eq) and N-[chloro(dimethylamino)methylidene]-N-methylmethanaminium hexafluorophosphate (132 mg, 0.472 mmol, 1.5 eq). The mixture was stirred at 25 °C for 1 hour. The mixture was purified by column chromatography to give 2-(trimethylsilyl)ethyl(S,E)-3-((3-(1-((5-bromo-2'-chloro-[1,1'-biphenyl]-2-yl)sulfonyl)-4-fluoropiperidine-4-carboxamido)but-1-en-1-yl)sulfonyl) azetidine-1-carboxylate (200 mg, 0.25 mmol, 80%).

Step 2. To 2-(trimethylsilyl)ethyl(S,E)-3-((3-(1-((5-bromo-2'-chloro-[1,1'-biphenyl]-2-yl)sulfonyl)-4-fluoropiperidine-4-carboxamido)but-1-en-1-yl)sulfonyl)azetidine-1-carboxylate (200 mg, 0.252 mmol, 1 eq) in DCM (1 mL) was added TFA (0.3 mL). The mixture was stirred at 20 °C for 1 hour. The mixture was concentrated under vacuum and purified by prep-HPLC to give (S,E)-N-(4-(azetidin-3-ylsulfonyl)but-3-en-2-yl)-1-((5-bromo-2'-chloro-[1,1'-biphenyl]-2-yl)sulfonyl)-4-fluoropiperidine-4-carboxamide (Compound 75) (117.9 mg, 0.18 mmol, 72%). $^1H$ NMR (400 MHz, DMSO-$d_6$) δ ppm 9.18-8.98 (m, 2H), 8.52-8.42 (m, 1H), 7.97-7.85 (m, 2H), 7.59 (d, J=2.0 Hz, 1H), 7.53 (d, J=7.9 Hz, 1H), 7.48-7.35 (m, 3H), 6.85 (dd, J=5.0, 15.2 Hz, 1H), 6.65 (dd, J=1.2, 15.3 Hz, 1H), 4.65-4.54 (m, 1H), 4.49-4.37 (m, 1H), 4.29-4.18 (m, 2H), 4.12-4.00 (m, 2H), 3.19-3.09 (m, 2H), 2.78-2.67 (m, 1H), 2.63-2.52 (m, 1H), 1.97-1.67 (m, 4H), 1.22 (d, J=7.0 Hz, 3H). [M+H] calculated for $C_{25}H_{28}BrClFN_3O_5S_2$, 647; found 648.

Compounds 76-78 were synthesized from the appropriate intermediate in a manner analogous to Compound 75.

Scheme 12. Synthesis of Intermediate (R,E)-4-methylsulfonylbut-3-en-2-amine

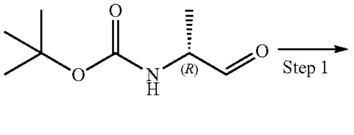

-continued

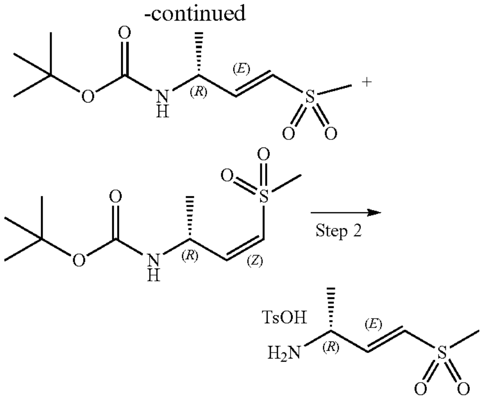

Step 1. To a solution of diethyl ((methylsulfonyl)methyl) phosphonate (2.7 g, 11.5 mmol, 1.0 eq) in THF (60 mL) was added NaH (462 mg, 1 eq, 11.5 mmol, 60%) at 0 °C. The mixture was stirred at 0 °C for 0.5 h before (R)-tert-butyl (1-oxopropan-2-yl)carbamate (2 g, 11.5 mmol, 1.0 eq) in THF (10 mL) was added to the mixture. The reaction was stirred at 0 °C for 1 h. The reaction was quenched with water (50 mL) and extracted with EtOAc (30 mL×3). The organic layers were combined and dried over $Na_2SO_4$, filtered, and concentrated to give a crude mixture. The residue was purified by prep-HPLC to give the tert-butyl(R,E)-(4-(methylsulfonyl)but-3-en-2-yl)carbamate (950 mg, 3.81 mmol, 33%) as a white solid and tert-butyl(R,Z)-(4-(methylsulfonyl)but-3-en-2-yl)carbamate (160 mg, 0.64 mmol, 5.6%) as a white solid.

Step 2. To a solution of tert-butyl(R,E)-(4-(methylsulfonyl)but-3-en-2-yl)carbamate (200 mg, 0.8 mmol, 1 eq) in MeCN (3 mL) was added 4-methylbenzenesulfonic acid (138 mg, 0.8 mmol, 1 eq). The mixture was stirred at 60 °C for 12 h. The reaction was concentrated to give 4-methylbenzenesulfonic acid; (R,E)-4-methylsulfonylbut-3-en-2-amine (200 mg, 0.62 mmol, 78%) as a white solid. $^1H$ NMR (400 MHz, Methanol-$d_4$) δ ppm 7.71 (d, J=8.1 Hz, 2H), 7.24

(d, J=8 Hz, 2H), 6.92-7.01 (m, 1H), 6.81-6.89 (m, 1H), 4.18 (q, J=6.5 Hz, 1H), 3.02 (s, 3H), 2.37 (s, 3H), 1.47 (d, J=6.8 Hz, 3H).

Intermediate (S,E)-4-methylsulfonylbut-3-en-2-amine was synthesized in a manner analogous to (R,E)-4-methylsulfonylbut-3-en-2-amine.

Compound 79 was synthesized in a manner analogous to Compound 47 using (R,E)-4-methylsulfonylbut-3-en-2-amine in Step 5.

Compound 80 was synthesized in a manner analogous to Compound 1 using (R,E)-4-methylsulfonylbut-3-en-2-amine in Step 5.

Compound 81 was synthesized in a manner analogous to Compound 47 using (S,E)-4-methylsulfonylbut-3-en-2-amine in Step 5.

Scheme 13. Synthesis of Intermediate bis(2,2,2-trifluoroethyl) ((methylsulfonyl)methyl)phosphonate

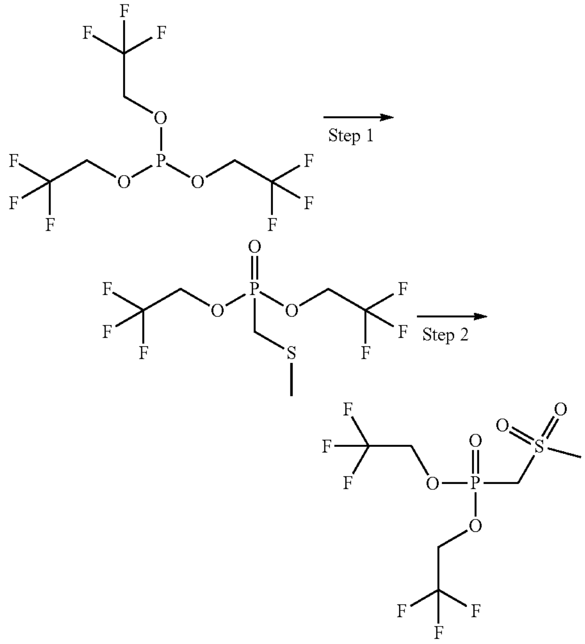

Step 1. A mixture of chloromethyl methyl sulfide (1.5 mg, 15.2 mmol, 1 eq) and tris(2,2,2-trifluoroethyl)phosphite (5 g, 15.2 mmol, 1 eq) was heated at 160 °C for 7 h and then 140 °C for 16 h. The reaction was concentrated directly to give 1,1,1-trifluoro-2-[methylsulfanylmethyl(2,2,2-trifluoroethoxy)phosphoryl]oxy-ethane (4 g, 13.1 mmol, 86%) as a colorless oil, which was used directly in the next step.

Step 2. To a solution of 1,1,1-trifluoro-2-[methylsulfanylmethyl(2,2,2-trifluoroethoxy)phosphoryl]oxy-ethane (4 g, 13.1 mmol, 1 eq) in DCM (100 mL, 0.13 M) was added m-CPBA (6.6 g, 32.7 mmol, 2.2 eq) in portions at 0 °C, then the mixture was stirred at 20 °C for 15 h. The reaction was quenched with 10% aq. $Na_2S_2O_3$ (100 mL) and sat. aq. $NaHCO_3$ (100 mL). Then the mixture was extracted with DCM (100 mL×2). The organic layers were combined, dried over $Na_2SO_4$ and concentrated to give a crude product, which was purified by column chromatography to give bis(2,2,2-trifluoroethyl) ((methylsulfonyl)methyl)phosphonate (3.5 g, 10.3 mmol, 79%) as a white solid.

Scheme 14. Synthesis of Intermediate (S,Z)-1-(methylsulfonyl)pent-1-en-3-amine

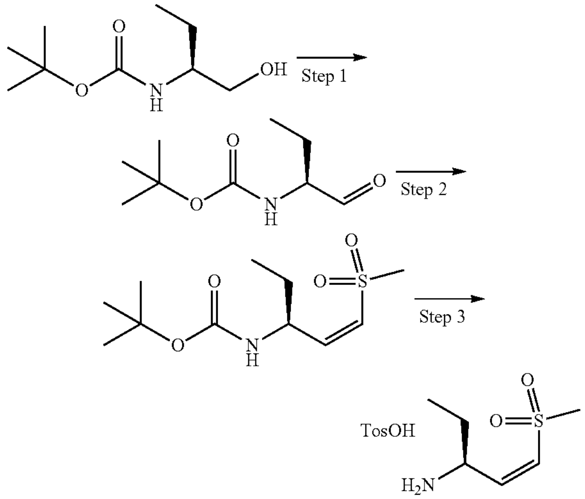

Step 1. To a solution of tert-butyl N-[(1S)-1-(hydroxymethyl)propyl]carbamate (0.5 g, 2.64 mmol, 1 eq) in DCM (10 mL, 0.26 M) was added Dess-Martin periodinane (1.2 g, 2.77 mmol, 1.1 eq) at 0 °C and the mixture was stirred for 10 mins. Then the mixture was warmed up 20 °C and stirred for 16 h. The reaction mixture was quenched by 10% aq. $Na_2S_2O_4$ (20 mL). The organic layer was washed with sat. aq. $NaHCO_3$ (20 mL), dried over $Na_2SO_4$, filtered, and concentrated to dryness. The crude was then purified by column chromatography to give the product tert-butyl N-[(1S)-1-formylpropyl]carbamate (360 mg, 1.92 mmol, 73%) as a colorless oil.

Step 2. To a solution of bis(2,2,2-trifluoroethyl) ((methylsulfonyl)methyl)phosphonate (650 mg, 1.92 mmol, 1 eq) in THF (8 mL, 0.16 M) was added NaH (76.9 mg, 1.92 mmol, 1 eq) in portions at 0 °C and this was stirred for 0.5 h. Then tert-butyl N-[(1S)-1-formylpropyl]carbamate (360 mg, 1.92 mmol, 1 eq) in THF (4 mL, 0.16 M) was added dropwise at 0 °C and stirred for 2 h. The reaction mixture was quenched by addition of aq. sat. $NH_4Cl$ (10 mL) at 0 °C, and then extracted with EtOAc (10 mL×2). The combined organic layers were washed with brine (10 mL), dried over $Na_2SO_4$, filtered, and concentrated under reduced pressure. The residue was purified by column chromatography to give tert-butyl N-[(Z,1S)-1-ethyl-3-methylsulfonyl-allyl]carbamate (210 mg, 0.80 mmol, 41%) as a yellow oil and tert-butyl N-[(E,1S)-1-ethyl-3-methylsulfonyl-allyl]carbamate (190 mg, 0.72 mmol, 37%) as a yellow oil.

Step 3. To a solution of tert-butyl N-[(Z, 1S)-1-ethyl-3-methylsulfonyl-allyl]carbamate (210 mg, 0.80 mmol, 1 eq) in MeCN (6 mL, 0.13 M) was added p-toluenesulfonic acid monohydrate (152 mg, 0.80 mmol, 1 eq). The mixture was stirred at 65 °C for 16 h. The reaction mixture was concentrated to give the product 4-methylbenzenesulfonic acid; (S,Z)-1-(methylsulfonyl)pent-1-en-3-amine (267 mg, 0.80 mmol, 100%) as a yellow solid.

Intermediate (R,Z)-1-(methylsulfonyl)pent-1-en-3-amine was synthesized in a manner analogous to (S,Z)-1-(methylsulfonyl)pent-1-en-3-amine.

Compound 82 was synthesized in a manner analogous to Compound 47 using (S,Z)-1-(methylsulfonyl)pent-1-en-3-amine in Step 5.

Compound 83 was synthesized in a manner analogous to Compound 1 using (S,Z)-1-(methylsulfonyl)pent-1-en-3-amine in Step 5.

Compound 84 was synthesized in a manner analogous to Compound 83 using the appropriate boronic acid in Step 3.

Intermediate (Z)-3-(2-(methylsulfonyl)vinyl)azetidine was synthesized in a manner analogous to (S,Z)-1-(methylsulfonyl)pent-1-en-3-amine starting with tert-butyl 3-formylazetidine-1-carboxylate in Step 2.

Compound 230 was synthesized in a manner analogous to Compound 1, Step 5, using (Z)-3-(2-(methylsulfonyl)vinyl) azetidine and 1-((2'-chloro-5-methoxy-[1,1'-biphenyl]-2-yl) sulfonyl)-4-fluoropiperidine-4-carboxylic acid in Step 5.

Scheme 15. Synthesis of 1-[4-(dimethylamino)-2-(3-methoxyphenyl) phenyl]sulfonyl-4-fluoro-N-[rac-(Z,1S)-1-methyl-3-methylsulfonyl-allyl]piperidine-4-carboxamide (Compound 86)

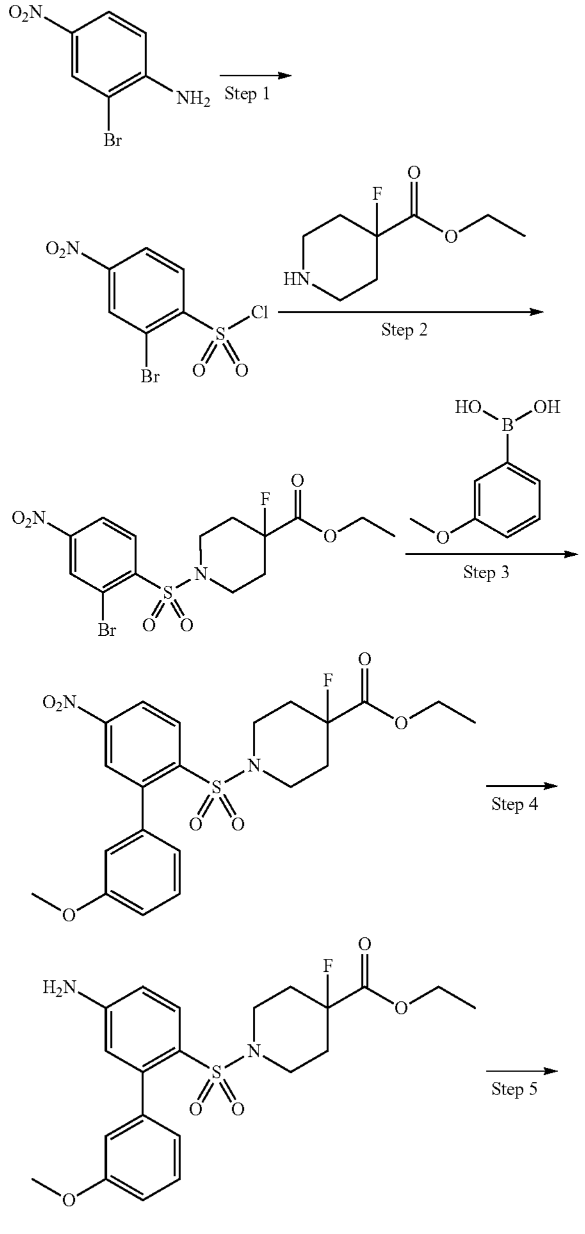

-continued

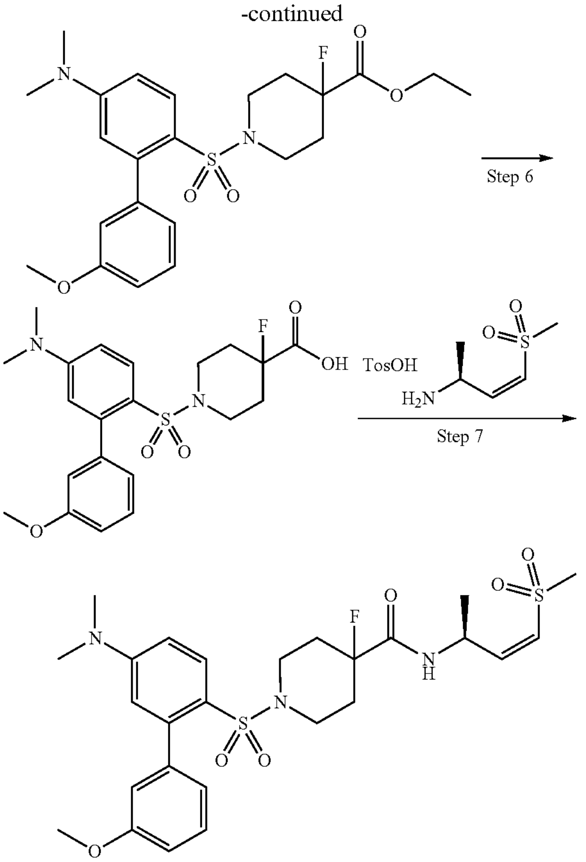

Step 1. 2-Bromo-4-nitro-aniline (1 g, 4.61 mmol, 1.0 eq) was added to the mixture of HCl (2.4 mL) and acetic acid (0.7 mL, 0.47 M). Once a white solid precipitated, the beaker was placed in ice-ethanol bath. At −10 °C, a solution of $NaNO_2$ (350 mg, 5.07 mmol, 1.1 eq) in water (1 mL, 0.47 M) was added. This mixture was stirred at −10 °C for another 1 hr. At the same time, $SO_2$ was bubbled through acetic acid (8 mL, 0.47 M) separately and CuCl (150 mg, 1.52 mmol, 0.3 eq) was added. $SO_2$ was continued to bubble until the color of the suspension changed from yellow-green to blue-green. The whole process took about 30 min for completion. When the temperature reached 10 °C, the above diazotization reaction mixture was added over 30 min carefully. The mixture was poured into ice water. EtOAc (50 mL) was used for extraction. The organic layer was washed with $NaHCO_3$ (60 mL), dried over $Na_2SO_4$, filtered and concentrated. 2-Bromo-4-nitro-benzenesulfonyl chloride was obtained as a yellow oil (1 g, 3.32 mmol, 72% yield). $^1$H NMR (400 MHz, $CDCl_3$) δ ppm 8.71 (d, J=1.5 Hz, 1H), 8.42-8.38 (m, 2H).

Step 2. At 0 °C, 2-bromo-4-nitro-benzenesulfonyl chloride (772 mg, 2.57 mmol, 1.7 eq) was added to a mixture of ethyl 4-fluoropiperidine-4-carboxylate hydrochloride (320 mg, 1.51 mmol, 1 eq) and TEA (306 mg, 3.02 mmol, 2 eq) in DCM (5 mL, 0.30 M). The resulting mixture was stirred at 25 °C for 2 hrs. The reaction mixture was poured into water (15 mL) and extracted with DCM (15 mL×3). The combined organic layers were washed with brine (10 mL×2), dried over $Na_2SO_4$, filtered and concentrated under reduced pressure. The residue was purified by column chromatography (PE:EtOAc=10:0-8:2). Ethyl 1-(2-bromo-4-nitro-phenyl)sulfonyl-4-fluoro-piperidine-4-carboxylate was obtained as a yellow oil (450 mg, 1.02 mmol, 68% yield). $^1$H NMR (400 MHz, $CDCl_3$) δ ppm 8.60 (d, J=1.6 Hz, 1H), 8.35-8.25 (m, 2H), 4.27 (q, J=7.1 Hz, 2H), 3.91-3.79 (m, 2H), 3.23 (dt, J=2.7, 12.8 Hz, 2H), 2.31-2.01 (m, 4H), 1.33 (t, J=7.1 Hz, 3H).

Step 3. A solution of ethyl 1-(2-bromo-4-nitro-phenyl) sulfonyl-4-fluoro-piperidine-4-carboxylate (400 mg, 0.91 mmol, 1.0 eq), 3-methoxyphenylboronic acid (415 mg, 2.73 mmol, 3.0 eq) and $K_2CO_3$ (483 mg, 4.55 mmol, 5 eq) in toluene (9 mL, 0.08 M) and water (3 mL, 0.08 M) was placed under $N_2$. $Pd(PPh_3)_4$ (105 mg, 0.09 mmol, 0.1 eq) was added and the mixture was stirred at 80 °C for 16 hrs. The reaction was quenched with water (30 mL) and extracted with EtOAc (30 mL×3). The organic layers were combined and washed with brine (50 mL). The organic layer was dried over $Na_2SO_4$, filtered, and the filtrate was concentrated to give the crude product. The residue was purified by column chromatography (PE:EtOAc=10:0-7:3). Ethyl 4-fluoro-1-[2-(3-methoxyphenyl)-4-nitro-phenyl]sulfonyl-piperidine-4-carboxylate was obtained as a colorless oil (320 mg, 0.69 mmol, 75%). $^1$H NMR (400 MHz, $CDCl_3$) δ ppm 8.39-8.28 (m, 2H), 8.20 (d, J=2.1 Hz, 1H), 7.39 (t, J=8.0 Hz, 1H), 7.04-6.97 (m, 3H), 4.23 (q, J=7.2 Hz, 2H), 3.86 (s, 3H), 3.22 (br d, J=13.1 Hz, 2H), 2.70-2.57 (m, 2H), 1.98-1.75 (m, 4H), 1.30 (t, J=7.1 Hz, 3H). [M+H] calculated for $C_{21}H_{23}FN_2O_7S$, 466; found 467.

Step 4. Fe (240 mg, 4.29 mmol, 5 eq) was added to a mixture of ethyl 4-fluoro-1-[2-(3-methoxyphenyl)-4-nitro-phenyl]sulfonyl-piperidine-4-carboxylate (400 mg, 0.86 mmol, 1 eq) and $NH_4Cl$ (229 mg, 4.29 mmol, 5 eq) in ethanol (10 mL, 0.07 M) and water (2 mL, 0.07 M). The resulting mixture was stirred at 80 °C for 3 hrs. After filtration, the filtrate was concentrated. The residue was purified by column chromatography (PE:EtOAc=10:0-7:3). Ethyl 1-[4-amino-2-(3-methoxyphenyl)phenyl]sulfonyl-4-fluoro-piperidine-4-carboxylate was obtained as a yellow oil (320 mg, 0.73 mmol, 85%). $^1$H NMR (400 MHz, $CDCl_3$) δ ppm 7.92 (d, J=8.7 Hz, 1H), 7.33-7.28 (m, 1H), 7.05-7.00 (m, 1H), 6.98 (d, J=7.6 Hz, 1H), 6.91 (dd, J=1.9, 8.2 Hz, 1H), 6.67 (dd, J=2.5, 8.6 Hz, 1H), 6.55 (d, J=2.4 Hz, 1H), 4.21 (q, J=7.2 Hz, 2H), 4.14 (s, 2H), 3.84 (s, 3H), 3.19 (br d, J=12.6 Hz, 2H), 2.65-2.53 (m, 2H), 1.89-1.70 (m, 4H), 1.29 (t, J=7.2 Hz, 3H). [M+H] calculated for $C_{21}H_{25}FN_2O_5S$, 436; found 437.

Step 5. $NaBH_3CN$ (63 mg, 1.01 mmol, 2.2 eq) was added to a mixture of ethyl 1-[4-amino-2-(3-methoxyphenyl)phenyl]sulfonyl-4-fluoro-piperidine-4-carboxylate (200 mg, 0.46 mmol, 1 eq) and paraformaldehyde (27.5 mg, 0.92 mmol, 2 eq) in acetic acid (1.8 mL, 0.25 M). The resulting mixture was stirred at 25 °C for 0.5 hr, then the mixture was heated to 65 °C and stirred for 2 hrs. The pH was adjusted to around 10 with NaOH aq. (5 M), and then diluted with EtOAc (80 mL). The layers were separated and the aqueous layer was extracted with EtOAc (50 mL×2). The combined organic layers were washed with brine (50 mL×2), dried over $Na_2SO_4$, filtered and concentrated under reduced pressure. The residue was purified by column chromatography (PE:EtOAc=100:0-85:15). Ethyl 1-[4-(dimethylamino)-2-(3-methoxyphenyl)phenyl]sulfonyl-4-fluoro-piperidine-4-carboxylate was obtained as a yellow solid (170 mg, 0.37 mmol, 79%). $^1$H NMR (400 MHz, $CDCl_3$) δ ppm 7.97 (d, J=9.0 Hz, 1H), 7.33-7.28 (m, 1H), 7.05 (d, J=2.2 Hz, 1H), 7.01 (d, J=7.5 Hz, 1H), 6.92 (dd, J=1.8, 8.3 Hz, 1H), 6.66 (dd, J=2.8, 9.0 Hz, 1H), 6.52 (d, J=2.8 Hz, 1H), 4.22 (q, J=7.1 Hz, 2H), 3.85 (s, 3H), 3.20 (br d, J=13.0 Hz, 2H), 3.06 (s, 6H), 2.67-2.53 (m, 2H), 1.91-1.69 (m, 4H), 1.29 (t, J=7.2 Hz, 3H).

Step 6. To a solution of ethyl 1-[4-(dimethylamino)-2-(3-methoxyphenyl)phenyl]sulfonyl-4-fluoro-piperidine-4-carboxylate (170 mg, 0.37 mmol, 1.0 eq) in THF (6 mL, 0.05 M) and water (2 mL, 0.05 M) was added $LiOH \cdot H_2O$ (123 mg, 2.93 mmol, 8 eq). The mixture was stirred at 50 °C for 3 hrs. The mixture was acidified with 1N HCl to pH=4, poured into water (10 mL) and extracted with EtOAc (10 mL×3). The combined organic layers were washed with brine (10 mL×2), dried over $Na_2SO_4$, filtered and concentrated under reduced pressure to give 1-[4-(dimethylamino)-2-(3-methoxyphenyl)phenyl]sulfonyl-4-fluoro-piperidine-4-carboxylic acid as a yellow oil (160 mg, 0.37 mmol, 100%). $^1$H NMR (400 MHz, $CDCl_3$) δ ppm 7.97 (d, J=9.0 Hz, 1H), 7.31 (t, J=7.9 Hz, 1H), 7.07-7.00 (m, 2H), 6.92 (dd, J=2.1, 8.3 Hz, 1H), 6.67 (dd, J=2.6, 9.0 Hz, 1H), 6.53 (d, J=2.6 Hz, 1H), 3.84 (s, 3H), 3.22 (br d, J=12.9 Hz, 2H), 3.06 (s, 6H), 2.69-2.58 (m, 2H), 1.90-1.72 (m, 4H).

Step 7. HATU (78 mg, 0.21 mmol, 1.5 eq) was added to a mixture of 1-[4-(dimethylamino)-2-(3-methoxyphenyl)phenyl]sulfonyl-4-fluoro-piperidine-4-carboxylic acid (60 mg, 0.14 mmol, 1 eq), (S,Z)-4-(methylsulfonyl)but-3-en-2-amine (44 mg, 0.14 mmol, 1 eq) and DIPEA (44 mg, 0.34 mmol, 2.5 eq) in DCM (3 mL, 0.05 M). The resulting mixture was stirred at 25 °C for 2 hrs. The reaction mixture was poured into $H_2O$ (10 mL) and extracted with DCM (10 mL×3). The combined organic layers were washed with brine (10 mL), dried over $Na_2SO_4$, filtered and concentrated under reduced pressure. The residue was purified by prep-HPLC. 1-[4-(Dimethylamino)-2-(3-methoxyphenyl)phenyl]sulfonyl-4-fluoro-N-[rac-(Z, 1S)-1-methyl-3-methylsulfonyl-allyl]piperidine-4-carboxamide (Compound 86) was obtained as a white solid (21.6 mg, 0.04 mmol, 27% yield). $^1$H NMR (400 MHz, DMSO-$d_6$) δ ppm 8.32 (br d, J=7.7 Hz, 1H), 7.78 (d, J=9.0 Hz, 1H), 7.31-7.24 (m, 1H), 6.96-6.89 (m, 3H), 6.78 (dd, J=2.8, 9.2 Hz, 1H), 6.50-6.41 (m, 2H), 6.26 (dd, J=9.6, 11.1 Hz, 1H), 5.40-5.26 (m, 1H), 3.77 (s, 3H), 3.12 (s, 3H), 3.06 (br d, J=12.7 Hz, 2H), 3.01 (s, 6H), 2.43 (br d, J=12.7 Hz, 2H), 1.75-1.56 (m, 4H), 1.19 (d, J=6.9 Hz, 3H). [M+H] calculated for $C_{26}H_{34}FN_3O_6S_2$, 567; found 568.

Compounds 87-90 were synthesized in a manner analogous to Compound 86 using the appropriate boronic acid in Step 3. Either methyl 4-fluoropiperidine-4-carboxylate or ethyl 4-fluoropiperidine-4-carboxylate was used in Step 2.

Compound 85 was synthesized in a manner analogous to Compound 86 using the appropriate boronic acid in Step 3 and (R,Z)-1-(methylsulfonyl)pent-1-en-3-amine in Step 7.

Compounds 91-93 were synthesized in a manner analogous to Compound 86 using the appropriate boronic acid in Step 3 and (R,Z)-4-(methylsulfonyl)but-3-en-2-amine in Step 7. Either methyl 4-fluoropiperidine-4-carboxylate or ethyl 4-fluoropiperidine-4-carboxylate was used in Step 2.

Compounds 94-96 were synthesized in a manner analogous to Compound 86 using the appropriate boronic acid in Step 3 and (E)-3-methylsulfonylprop-2-en-1-amine in Step 7. Either methyl 4-fluoropiperidine-4-carboxylate or ethyl 4-fluoropiperidine-4-carboxylate was used in Step 2.

Compound 97 was synthesized in a manner analogous to Compound 86 using the appropriate boronic acid in Step 3 and (E)-4-aminobut-2-enenitrile in Step 7.

Scheme 16. Synthesis of Intermediate ethyl 1-[2-(2-chlorophenyl)-4-cyclobutyl-phenyl]sulfonyl-4-fluoro-piperidine-4-carboxylate

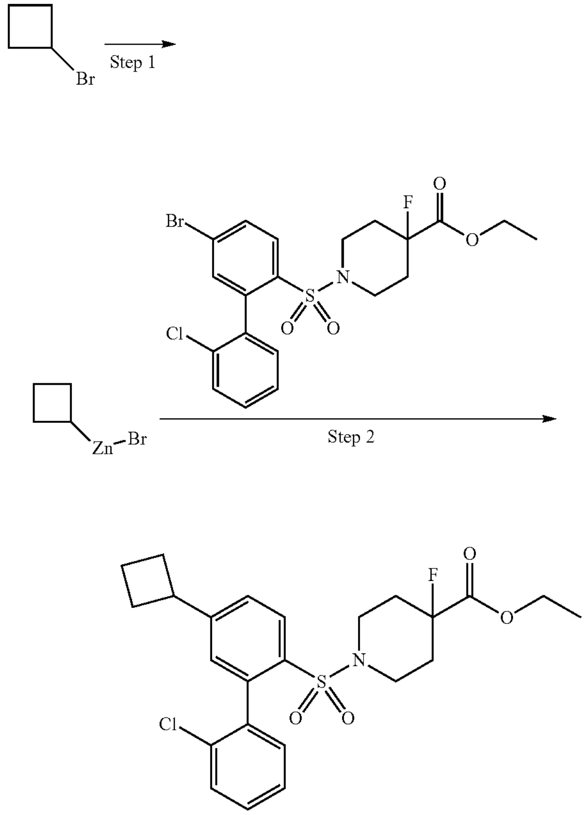

Step 1. To a solution of magnesium (88 mg, 3.33 mmol, 1.5 eq) in THF (10 mL, 0.22 M) was added bromocyclobutane (300 mg, 2.22 mmol, 1 eq). The reaction mixture was stirred for 1 h at 25 °C. To the reaction mixture was added dichlorozinc (909 mg, 6.67 mmol, 3 eq) and this was stirred for another 1 h. The zinc reagent was used for the next step directly without purification.

Step 2. To a solution of bromo(cyclobutyl)zinc (300 mg, 1.5 mmol, 1 eq) in THF (10 mL) was added ethyl 1-[4-bromo-2-(2-chlorophenyl)phenyl]sulfonyl-4-fluoro-piperidine-4-carboxylate (100 mg, 0.20 mmol, 0.13 eq), CuI (100 mg), and Pd(dppf)$Cl_2$ (100 mg) under $N_2$. The reaction mixture was stirred for 16 h at 25 °C. The reaction was quenched with 20 mL of sat. aq. $NH_4Cl$ and extracted with EtOAc (20 mL). The crude product was purified by prep-TLC (PE:EtOAc=3:1) to give ethyl 1-[2-(2-chlorophenyl)-4-cyclobutyl-phenyl]sulfonyl-4-fluoro-piperidine-4-carboxylate (40 mg, 0.08 mmol, 40% yield) as a yellow solid. $^1$H NMR (400 MHz, $CDCl_3$) δ ppm 8.05 (d, J=8.3 Hz, 1H), 7.40-7.53 (m, 2H), 7.28-7.36 (m, 3H), 7.13 (s, 1H), 4.14-4.29 (m, 2H), 3.62 (q, J=8.8 Hz, 1H), 3.26 (br d, J=13.2 Hz, 1H), 3.12 (br d, J=15.8 Hz, 1H), 2.84-2.96 (m, 1H), 2.58-2.70 (m, 1H), 2.31-2.44 (m, 3H), 1.95-2.24 (m, 7H), 1.76-1.91 (m, 4H), 1.24-1.31 (m, 4H).

Ethyl 1-[4-bromo-2-(2-chlorophenyl)phenyl]sulfonyl-4-fluoro-piperidine-4-carboxylate was converted to Compound 98 in a manner analogous to Steps 4 and 5 of Compound 47.

Scheme 17. Synthesis of Intermediate ethyl 1-[4-(1-tert-butoxycarbonylazetidin-3-yl)-2-(2-chlorophenyl)phenyl]sulfonyl-4-fluoro-piperidine-4-carboxylate

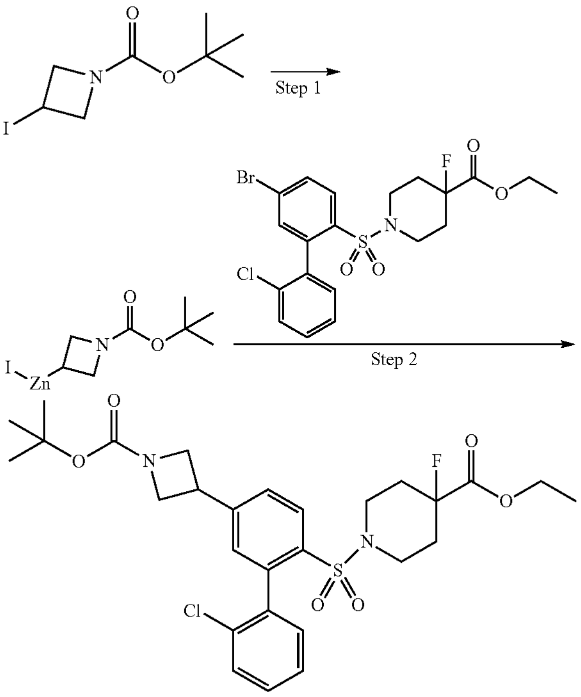

Step 1. To a solution of Zn (289 mg, 6.62 mmol, 2.5 eq) in DMA (8 mL, 0.33 M) was added 1,2-dibromoethane (299 mg, 1.59 mmol, 0.6 eq) and TMSCl (0.14 ml, 1.06 mmol, 0.4 eq) at 50 °C and the reaction was stirred at 50 °C for 30 min. Then 1-boc-3-iodoazetidine (750 mg, 2.65 mmol, 1 eq) was added at 50 °C and this was stirred at 50 °C for 30 min. The reaction mixture of (1-tert-butoxycarbonylazetidin-3-yl)-iodo-zinc (923 mg, 2.65 mmol, 100%) was used for the next step directly.

Step 2. To a solution of ethyl 1-[4-bromo-2-(2-chlorophenyl)phenyl]sulfonyl-4-fluoro-piperidine-4-carboxylate (400 mg, 0.79 mmol, 1 eq) in DMA (5 mL, 0.16 M) was added CuI (15 mg, 0.047 mmol, 0.06 eq), Pd(dppf)$Cl_2$(78 mg, 0.039 mmol, 0.05 eq) and (1-tert-butoxycarbonylazetidin-3-yl)-iodo-zinc (828 mg, 2.38 mmol, 3 eq, in DMA) at 15 °C. The mixture was stirred at 80 °C for 2 h under $N_2$. The solution was diluted with water (15 mL) and extracted with EtOAc (10 mL×3). The combined organic layers were washed with brine (30 mL×2), dried over $Na_2SO_4$, filtered and concentrated. The crude product was purified by column chromatography (PE:EtOAc=1:0 to 10:1) to give ethyl 1-[4-(1-tert-butoxycarbonylazetidin-3-yl)-2-(2-chlorophenyl)phenyl]sulfonyl-4-fluoro-piperidine-4-carboxylate (500 mg, 0.8 mmol, 100%) as a brown solid. $^1$HNMR (400 MHz, $CDCl_3$) δ ppm 8.13 (d, J=8.3 Hz, 1H), 7.52-7.42 (m, 3H), 7.39-7.32 (m, 2H), 7.26 (d, J=1.8 Hz, 1H), 4.37 (dt, J=2.4, 8.7 Hz, 2H), 4.18-4.09 (m, 1H), 4.04-3.95 (m, 2H), 3.87-3.70 (m, 1H), 3.32-3.07 (m, 2H), 2.94-2.86 (m, 1H), 2.66 (dt, J=2.7, 12.9 Hz, 1H), 2.04-1.76 (m, 4H), 1.46 (s, 9H), 1.33-1.28 (m, 3H).

Ethyl 1-[4-(1-tert-butoxycarbonylazetidin-3-yl)-2-(2-chlorophenyl)phenyl]sulfonyl-4-fluoro-piperidine-4-carboxylate was converted to Compound 99 in a manner analogous to Steps 4 and 5 of Compound 47.

Scheme 18. Synthesis of Intermediate (3-prop-1-ynylphenyl)boronic acid

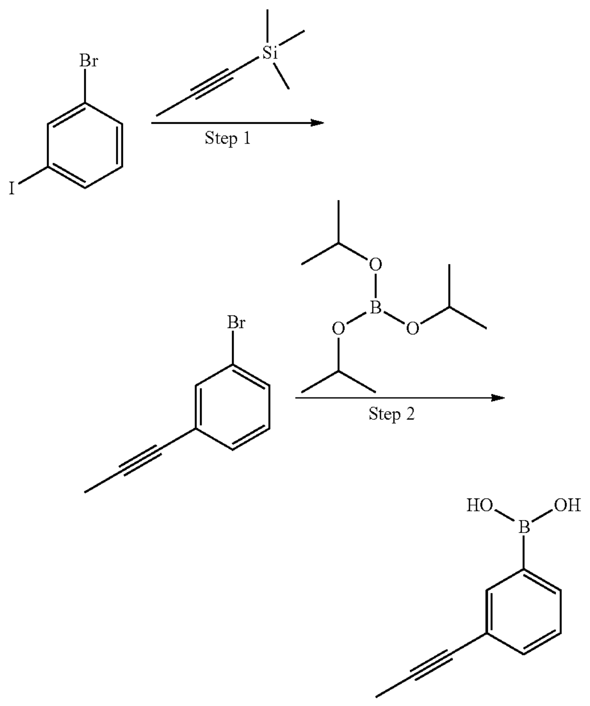

Step 1. To a solution of 1-bromo-3-iodobenzene (3 g, 10.6 mmol, 1 eq) in toluene (30 mL, 0.35 M) was added CuI (604 mg, 3.18 mmol, 0.3 eq) and $Pd(PPh_3)_4$(300 mg). This was stirred for 5 min. Then to the mixture was added 1-(trimethylsilyl)-1-propyne (1.2 g, 10.6 mmol, 1 eq), TEA (3.5 g, 35.0 mmol, 3.3 eq) and TBAF (1 M, 10.6 mL, 1.0 eq) at rt. The resulting mixture was stirred at 20 °C for 5 h. The reaction mixture was quenched with water (50 mL), extracted with MTBE (20 mL×3) and the organic layers were combined. The organic phase was washed with brine (50 mL), dried over $Na_2SO_4$, filtered, and concentrated to give the crude product. The crude product was purified by column chromatography (PE=100%) to give 1-bromo-3-prop-1-ynyl-benzene (2 g, 10.2 mmol, 96%) as a colorless oil. $^1H$ NMR (400 MHz, $CDCl_3$) δ ppm 7.54 (t, J=1.6 Hz, 1H), 7.40 (dt, J=8.0, 1.3 Hz, 1H), 7.31 (d, J=7.8 Hz, 1H), 7.08-7.19 (m, 1H), 2.05 (s, 3H).

Step 2. To a solution of 1-bromo-3-(prop-1-yn-1-yl)benzene (500 mg, 2.56 mmol, 1 eq) and triisopropyl borate (530 mg, 2.82 mmol, 1.1 eq) in THF (3 mL, 0.85 M) and toluene (9 mL) was added n-BuLi (1.1 mL, 1.1 eq, 1M) at −78 °C. The reaction was stirred at −78 °C for 30 min. The mixture was warmed to 15 °C and stirred at 15 °C for 1 h. The reaction mixture was cooled to −78 °C and 3 M HCl was added to adjust pH to 2 and this was stirred at 15 °C for 15 min. Potassium hydroxide was added to adjust the pH to 8. 2-Methyl-tetrahydrofuran was added and the solution was filtered. The product (3-prop-1-ynylphenyl)boronic acid (350 mg, 2.18 mmol, 85%) was obtained as a white solid. $^1H$ NMR (400 MHz, DMSO-$d_6$) δ ppm 7.55-7.82 (m, 2H), 6.95-7.23 (m, 2H), 2.01 (s, 3H).

Compound 100 was synthesized in a manner analogous to Compound 1 using (3-prop-1-ynylphenyl)boronic acid in Step 3.

Compound 46 was synthesized in a manner analogous to Compound 100 using (E)-3-(methylsulfonyl)prop-2-en-1-amine in Step 5.

Scheme 19. Synthesis of Intermediate 1-((2′-chloro-5-cyclopropoxy-[1,1′-biphenyl]-2-yl)sulfonyl)-4-fluoropiperidine-4-carboxylic acid

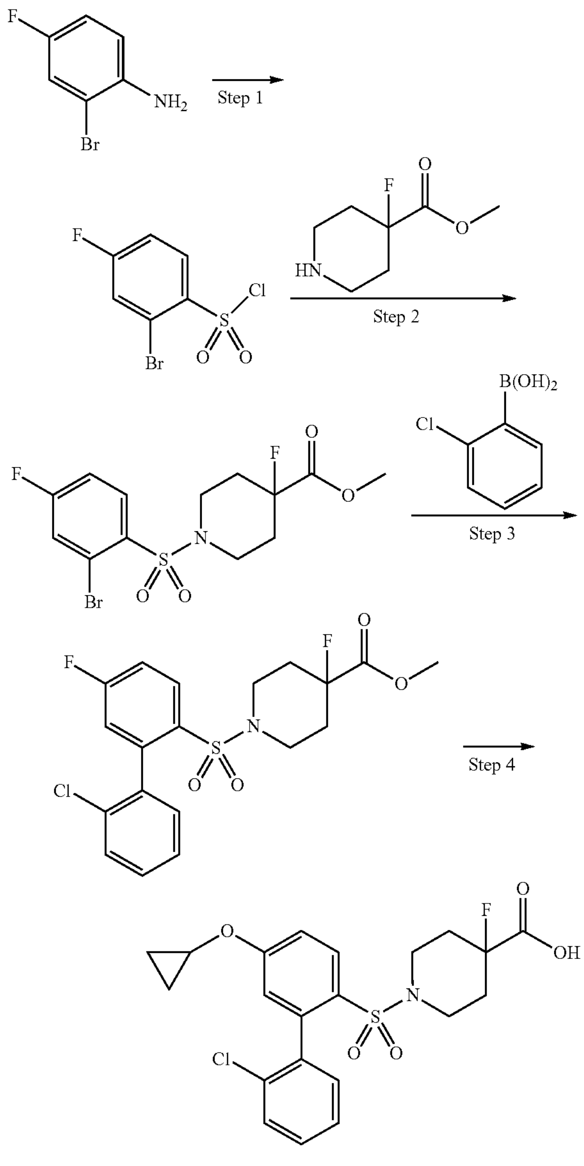

Step 1. To a solution of 2-bromo-4-fluoroaniline (15 g, 78.9 mmol, 1 eq) in HCl/acetic acid (v/v 3:1, 44 mL, 1.3 M) was added $NaNO_2$ (6 g, 86.8 mmol, 1.1 eq) at 0 °C. This mixture 1 was stirred at 0 °C for 1 h. In a separate flask, $SO_2$ was bubbled through acetic acid (50 mL, 1.3 M) for about 10 min at 0 °C before CuCl (2.3 g, 23.7 mmol, 0.3 eq) was added. $SO_2$ was bubbled through mixture 2 for about 10 min. Mixture 1 was added to mixture 2 at 0 °C. The resulting the mixture was stirred at 0-20 °C for 1 h. The reaction mixture was quenched by water (300 mL) and extracted with MTBE (300 mL×2). The organic layers were washed with sat. aq. sodium bicarbonate (300 mL×2) and 300 mL of brine. The organic layer was then separated, dried over $Na_2SO_4$, filtered, and concentrated to dryness. The crude was then purified by column chromatography (PE:EtOAc=50:1) to give 2-bromo-4-fluoro-benzenesulfonyl chloride (10 g, 36.6 mmol, 46%) as a yellow oil. $^1H$ NMR (400 MHz, $CDCl_3$) δ ppm 8.24 (dd, J=9.1, 5.4 Hz, 1H), 7.61 (dd, J=7.8, 2.6 Hz, 1H), 7.27 (s, 1H).

Step 2. To a solution of 2-bromo-4-fluoro-benzenesulfonyl chloride (5 g, 18.3 mmol, 1 eq) and ethyl 4-fluoropiperidine-4-carboxylate hydrochloride (3.9 g, 18.3 mmol, 1 eq) in DCM (100 mL, 0.18 M) was added TEA (5.5 g, 54.8 mmol, 3 eq) dropwise at 0 °C. The resulting mixture was stirred at 0 °C for 1 h. The mixture was quenched with $H_2O$ (80 mL) and extracted with DCM (100 mL×2). The organic layers were washed with 120 mL of brine. The organic layer was then separated, dried over $Na_2SO_4$, filtered, and concentrated to dryness. The crude product was then purified by column chromatography (PE:EtOAc=3:1) to give the product ethyl 1-(2-bromo-4-fluoro-phenyl)sulfonyl-4-fluoro-piperidine-4-carboxylate as a yellow solid. $^1$H NMR (400 MHz, $CDCl_3$) δ ppm 8.14 (dd, J=8.9, 5.8 Hz, 1H), 7.51 (dd, J=8.0, 2.5 Hz, 1H), 7.17 (ddd, J=8.9, 7.4, 2.6 Hz, 1H), 4.27 (q, J=7.2 Hz, 2H), 3.80 (dt, J=12.9, 2.6 Hz, 2H), 3.16 (td, J=12.7, 2.8 Hz, 2H), 2.10-2.29 (m, 2H), 2.06 (br s, 1H), 1.99-2.05 (m, 1H), 1.32 (t, J=7.1 Hz, 3H).

Step 3. To a solution of ethyl 1-(2-bromo-4-fluoro-phenyl)sulfonyl-4-fluoro-piperidine-4-carboxylate (1.5 g, 3.64 mmol, 1 eq) in 1,4-dioxane/water (v/v 10:1, 22 mL, 0.18 M) was added 2-chlorophenylboronic acid (1.1 g, 7.28 mmol, 2 eq) and $K_2CO_3$ (1 g, 7.28 mmol, 2.0 eq). The mixture was placed under $N_2$ and Pd(dppf)$Cl_2$ (500 mg) was added. The resulting mixture was stirred at 90 °C for 12 h. After cooling to rt, the reaction mixture was quenched by $H_2O$ (30 mL) and extracted with EtOAc (20 mL×2). The organic layers were washed with 30 mL of brine. The organic was then separated, dried over $Na_2SO_4$, filtered, and concentrated to dryness. The crude was then purified by column chromatography to give the product ethyl 1-[2-(2-chlorophenyl)-4-fluoro-phenyl]sulfonyl-4-fluoro-piperidine-4-carboxylate (1 g, 2.25 mmol, 62%) as a yellow oil. $^1$H NMR (400 MHz, $CDCl_3$) δ ppm 8.18 (dd, J=5.6, 8.8 Hz, 1H), 7.52-7.47 (m, 1H), 7.46-7.41 (m, 1H), 7.40-7.31 (m, 2H), 7.25-7.19 (m, 1H), 7.04 (dd, J=2.6, 8.8 Hz, 1H), 4.28-4.16 (m, 2H), 3.25 (br dd, J=2.1, 13.4 Hz, 1H), 3.08 (td, J=2.3, 13.3 Hz, 1H), 2.98-2.87 (m, 1H), 2.73-2.58 (m, 1H), 2.16-1.76 (m, 5H), 1.31-1.27 (m, 3H).

Step 4. To a solution of ethyl 1-[2-(2-chlorophenyl)-4-fluoro-phenyl]sulfonyl-4-fluoro-piperidine-4-carboxylate (150 mg, 0.34 mmol, 1 eq) in DMF (2 mL, 0.17 M) was added NaH (27 mg, 0.68 mmol, 2.0 eq, 60%) at 0 °C. The reaction mixture was stirred for 30 mins, then cyclopropanol (196 mg, 3.38 mmol, 10 eq) was added dropwise at 0 °C. The resulting mixture was stirred at 25 °C for 1 h. The reaction mixture was quenched with $H_2O$ (10 mL) and extracted with MTBE (10 mL). The aqueous phase was adjusted with aq. HCl until pH=4 and extracted with EtOAc (5 mL×2). The combined organic layers were washed with 10 mL of brine, dried over $Na_2SO_4$ and filtered. The filtrate was concentrated to give 1-((2'-chloro-5-cyclopropoxy-[1,1'-biphenyl]-2-yl)sulfonyl)-4-fluoropiperidine-4-carboxylic acid (100 mg, 0.22 mmol, 65% yield) as a yellow oil.

Compound 101 was synthesized from 1-((2'-chloro-5-cyclopropoxy-[1,1'-biphenyl]-2-yl)sulfonyl)-4-fluoropiperidine-4-carboxylic acid in a manner analogous to Step 5 of Compound 47.

Compounds 102-103 were synthesized in a manner analogous to Compound 101 using the appropriate boronic acid in Step 3 and the appropriate alcohol in Step 4.

Compounds 104-105 was synthesized in a manner analogous to Compound 101 using the appropriate alcohol in Step 4.

Compound 106 was synthesized in a manner analogous to Compound 101 using the appropriate boronic acid in Step 3.

Scheme 20. Synthesis of Intermediate methyl 1-[2-(2-chlorophenyl)-4-vinyl-phenyl]sulfonyl-4-fluoro-piperidine-4-carboxylate

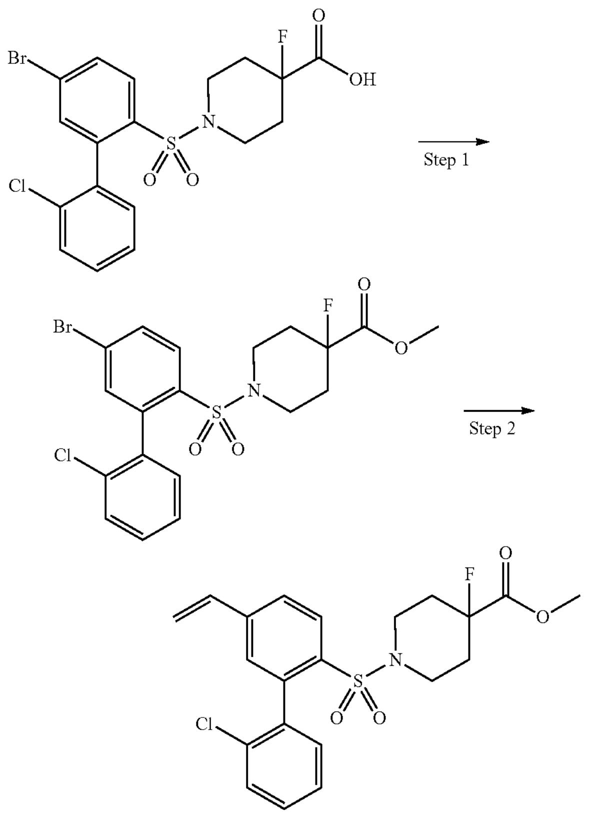

Step 1. To a solution of 1-[4-bromo-2-(2-chlorophenyl)phenyl]sulfonyl-4-fluoro-piperidine-4-carboxylic acid (200 mg, 0.42 mmol, 1 eq) in methanol (6 mL, 0.07 M) was added $SOCl_2$ (0.1 mL, 0.84 mmol, 2 eq) at 0 °C. The mixture was stirred at 60 °C for 3 h. After cooling to rt, the reaction mixture was poured into ice water (15 mL) and extracted with EtOAc (15 mL×3). The combined organic layers were washed with brine (10 mL×2), dried over $Na_2SO_4$, filtered and concentrated under reduced pressure. The crude product was purified by column chromatography (PE:EtOAc=1:0 to 10:1) and methyl 1-[4-bromo-2-(2-chlorophenyl)phenyl]sulfonyl-4-fluoro-piperidine-4-carboxylate (140 mg, 0.29 mmol, 68%) was obtained as a yellow solid. $^1$H NMR (400 MHz, $CDCl_3$) δ ppm 7.98-8.04 (m, 1H), 7.62-7.70 (m, 1H), 7.47-7.51 (m, 2H), 7.40-7.43 (m, 1H), 7.31-7.39 (m, 2H), 3.79 (s, 3H), 3.26 (dt, J=13.5, 2.4 Hz, 1H), 3.04-3.12 (m, 1H), 2.93 (td, J=12.8, 3.1 Hz, 1H), 2.59-2.69 (m, 1H), 1.75-2.10 (m, 4H).

Step 2. To a solution of methyl 1-[4-bromo-2-(2-chlorophenyl)phenyl]sulfonyl-4-fluoro-piperidine-4-carboxylate (100 mg, 0.21 mmol, 1 eq) in ethanol (5 mL, 0.04 M) was added potassium vinyltrifluoroborate (33 mg, 0.25 mmol, 1.2 eq) and TEA (41 mg, 0.41 mmol, 2 eq). The mixture was stirred at 20 °C for 10 min. Then Pd(dppf)$Cl_2$·$CH_2Cl_2$ (50 mg, 0.021 mmol, 0.1 eq) was added to the mixture. The mixture was stirred at 85 °C for 12 h. After cooling to rt, the mixture was diluted with water (5 mL) and extracted with EtOAc (5 mL×3). The combined organic layers were washed with brine (5 mL×2), dried over $Na_2SO_4$, filtered and concentrated under reduced pressure. The residue was purified by prep-TLC (PE:EtOAc=3:1, $R_f$(product)=0.6).

Methyl 1-[2-(2-chlorophenyl)-4-vinyl-phenyl]sulfonyl-4-fluoro-piperidine-4-carboxylate (75 mg, 0.17 mmol, 84%) was obtained as a colorless oil. $^1H$ NMR (400 MHz, $CDCl_3$) δ ppm 8.10 (d, J=8.3 Hz, 1H), 7.52-7.63 (m, 1H), 7.41-7.51 (m, 2H), 7.30-7.38 (m, 3H), 6.76 (dd, J=17.5, 10.9 Hz, 1H), 5.86-5.95 (m, 1H), 5.86-5.95 (m, 1H), 5.42-5.50 (m, 1H), 3.64-3.83 (m, 3H), 3.28 (br d, J=14.9 Hz, 1H), 3.12 (br d, J=10.8 Hz, 1H), 2.83-2.98 (m, 2H), 2.60-2.73 (m, 1H), 2.60-2.73 (m, 1H), 1.91-2.04 (m, 2H), 1.75-1.90 (m, 2H). [M+H] calculated for $C_{21}H_{21}ClFNO_4S$, 437, found 438.

Compound 107 was synthesized in a manner analogous to Compound 47, Steps 4-5, using methyl 1-[2-(2-chlorophenyl)-4-vinyl-phenyl]sulfonyl-4-fluoro-piperidine-4-carboxylate.

Intermediate methyl 4-fluoro-1-((2'-methyl-5-vinyl-[1,1'-biphenyl]-2-yl)sulfonyl)piperidine-4-carboxylate was prepared in a manner analogous to methyl 1-[2-(2-chlorophenyl)-4-vinyl-phenyl]sulfonyl-4-fluoro-piperidine-4-carboxylate starting from 1-((5-bromo-2'-methyl-[1,1'-biphenyl]-2-yl)sulfonyl)-4-fluoropiperidine-4-carboxylic acid.

Compound 108 was synthesized in a manner analogous to Compound 47, Steps 4-5, using methyl 4-fluoro-1-((2'-methyl-5-vinyl-[1,1'-biphenyl]-2-yl)sulfonyl)piperidine-4-carboxylate.

Compounds 109-110 were synthesized in a manner analogous to Compound 107 using the appropriate carboxylic acid in Step 1 and potassium trifluoro(isopropenyl)borate in Step 2.

Scheme 21. Synthesis of Intermediate ethyl 1-[2-(2-chlorophenyl)-4-ethyl-phenyl]sulfonyl-4-fluoro-piperidine-4-carboxylate

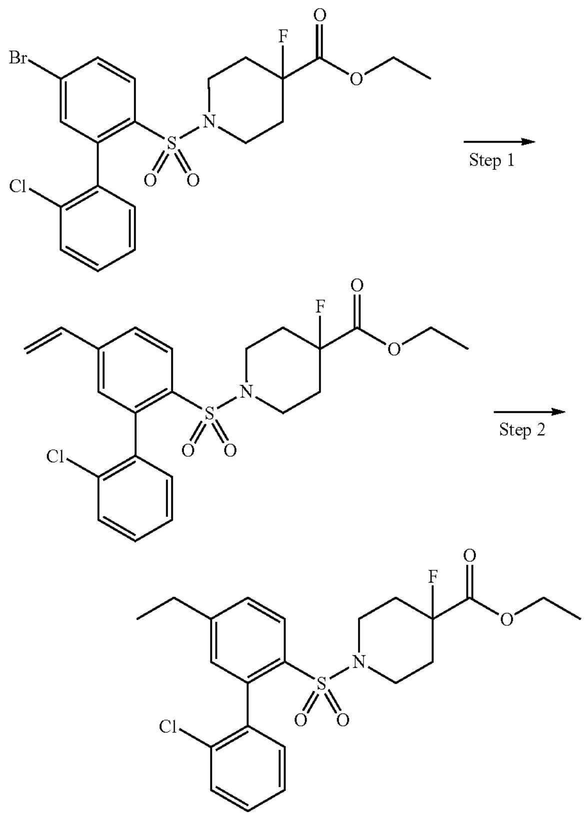

Step 1. To a solution of ethyl 1-[4-bromo-2-(2-chlorophenyl)phenyl]sulfonyl-4-fluoro-piperidine-4-carboxylate (100 mg, 0.19 mmol, 1 eq) in ethanol (5 mL, 0.04 M) was added potassium vinyltrifluoroborate (32 mg, 0.24 mmol, 1.2 eq) and TEA (40 mg, 0.40 mmol, 2 eq). The mixture was stirred at 20 °C for 10 min. Then $Pd(dppf)Cl_2{\cdot}CH_2Cl_2$(50 mg, 0.019 mol, 0.1 eq) was added to the mixture. The mixture was stirred at 85 °C for 12 h. After cooling to rt, the mixture was diluted with water (5 mL) and extracted with EtOAc (5 mL×3). The combined organic layers were washed with brine (5 mL×2), dried over $Na_2SO_4$, filtered and concentrated under reduced pressure. The residue was purified by prep-TLC (PE:EtOAc=3:1). Ethyl 1-[2-(2-chlorophenyl)-4-vinyl-phenyl]sulfonyl-4-fluoro-piperidine-4-carboxylate (70 mg, 0.15 mmol, 79%) was obtained as a colorless oil. $^1H$ NMR (400 MHz, $CDCl_3$) δ ppm 8.09 (d, J=8.3 Hz, 1H), 7.54 (dd, J=1.8, 8.3 Hz, 1H), 7.50-7.46 (m, 1H), 7.45-7.42 (m, 1H), 7.38-7.30 (m, 3H), 6.75 (dd, J=10.9, 17.6 Hz, 1H), 5.89 (d, J=17.6 Hz, 1H), 5.47-5.42 (m, 1H), 4.26-4.17 (m, 2H), 3.27 (td, J=2.2, 13.3 Hz, 1H), 3.12 (td, J=2.2, 13.3 Hz, 1H), 2.91 (dt, J=2.9, 12.7 Hz, 1H), 2.66 (dt, J=2.8, 12.8 Hz, 1H), 2.14-1.77 (m, 4H), 1.29 (t, J=7.2 Hz, 3H).

Step 2. To a solution of ethyl 1-[2-(2-chlorophenyl)-4-vinyl-phenyl]sulfonyl-4-fluoro-piperidine-4-carboxylate (60 mg, 0.13 mmol, 1 eq) in methanol (5 mL, 0.03 M) was added Pd/C (100 mg, 5%, wetted with ca. 55% water). The mixture was stirred at 20 °C under $H_2$ for 30 min. The mixture was filtered and concentrated under reduced pressure to give ethyl 1-[2-(2-chlorophenyl)-4-ethyl-phenyl]sulfonyl-4-fluoro-piperidine-4-carboxylate (50 mg, 0.11 mmol, 83%) as a colorless oil.

Compound 111 was synthesized in a manner analogous to Compound 47, Steps 4-5, using ethyl 1-[2-(2-chlorophenyl)-4-ethyl-phenyl]sulfonyl-4-fluoro-piperidine-4-carboxylate.

Intermediates ethyl 1-((5-ethyl-2'-methyl-[1,1'-biphenyl]-2-yl)sulfonyl)-4-fluoropiperidine-4-carboxylate and ethyl 1-((5-ethyl-[1,1'-biphenyl]-2-yl)sulfonyl)-4-fluoropiperidine-4-carboxylate were prepared in a manner analogous to ethyl 1-[2-(2-chlorophenyl)-4-ethyl-phenyl]sulfonyl-4-fluoro-piperidine-4-carboxylate starting from the appropriately substituted biphenyl sulfonamide.

Compounds 112-113 were synthesized in a manner analogous to Compound 111 using the appropriate intermediate in Step 1.

Intermediate ethyl 1-((2'-chloro-5-isopropyl-[1,1'-biphenyl]-2-yl)sulfonyl)-4-fluoropiperidine-4-carboxylate was prepared in a manner analogous to ethyl 1-[2-(2-chlorophenyl)-4-ethyl-phenyl]sulfonyl-4-fluoro-piperidine-4-carboxylate using potassium trifluoro(isopropenyl)borate in Step 1.

Compound 114 was synthesized in a manner analogous to Compound 47, Steps 4-5, using ethyl 1-((2'-chloro-5-isopropyl-[1,1'-biphenyl]-2-yl)sulfonyl)-4-fluoropiperidine-4-carboxylate.

Intermediate ethyl 4-fluoro-1-((5-isopropyl-2'-methyl-[1,1'-biphenyl]-2-yl)sulfonyl)piperidine-4-carboxylate was prepared in a manner analogous to ethyl 1-((2'-chloro-5-isopropyl-[1,1'-biphenyl]-2-yl)sulfonyl)-4-fluoropiperidine-4-carboxylate using the appropriately substituted biphenyl sulfonamide.

Compound 115 was synthesized in a manner analogous to Compound 47, Steps 4-5, using ethyl 4-fluoro-1-((5-isopropyl-2'-methyl-[1,1'-biphenyl]-2-yl)sulfonyl)piperidine-4-carboxylate.

Scheme 22. Synthesis of Intermediate 1-[4-(azetidin-1-yl)-2-(o-tolyl)phenyl]sulfonyl-4-fluoro-piperidine-4-carboxylic acid

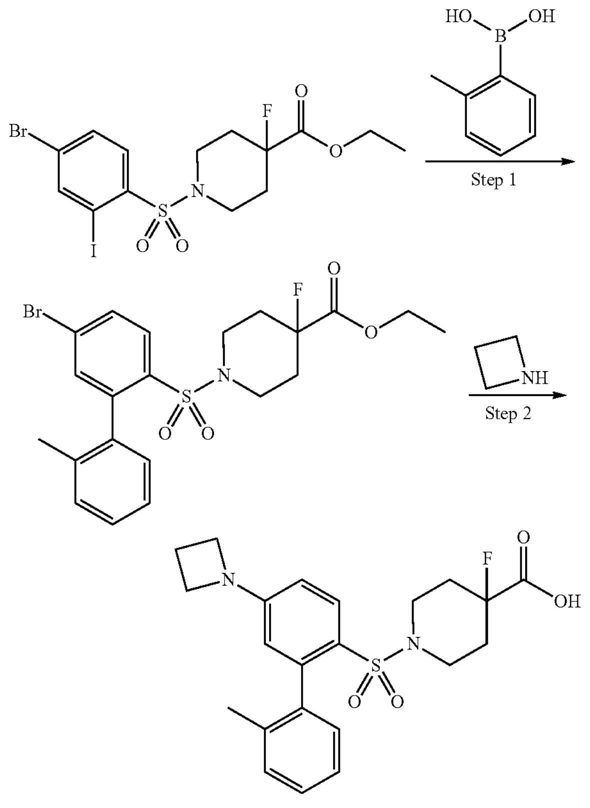

Step 1. To a solution of ethyl 1-(4-bromo-2-iodo-phenyl) sulfonyl-4-fluoro-piperidine-4-carboxylate (200 mg, 0.38 mmol, 1 eq) in 1,4-dioxane (3 mL, 0.12 M) was added o-tolylboronic acid (78 mg, 0.58 mmol, 1.5 eq), $Na_2CO_3$ (140 mg, 0.96 mmol, 2.5 eq) in water (0.38 mL, 0.17 M), and $Pd(dppf)Cl_2$ (0.15 eq, 0.058 mmol, 59 mg). The reaction was heated to 90 °C and stirred for 16 h. After cooling to rt, the reaction mixture was quenched with water (10 mL) and extracted with EtOAc (10 mL×2). The organic phase was dried over $Na_2SO_4$, filtered, and evaporated under vacuum. The crude product was purified by prep-TLC (PE:EtOAc=3:1) to give ethyl 1-[4-bromo-2-(o-tolyl)phenyl]sulfonyl-4-fluoro-piperidine-4-carboxylate (154 mg, 0.32 mmol, 83%) as a colorless oil. $^1H$ NMR (400 MHz, $CDCl_3$) δ ppm 8.00 (d, J=8.6 Hz, 1H), 7.64 (dd, J=8.6, 2.2 Hz, 1H), 7.40-7.50 (m, 1H), 7.28 (br d, J=3.1 Hz, 2H), 7.19-7.25 (m, 2H), 4.19-4.25 (m, 2H), 3.16 (br d, J=12.5 Hz, 2H), 2.61-2.75 (m, 2H), 2.07-2.12 (m, 3H), 1.82-2.05 (m, 4H), 1.25-1.30 (m, 3H).

Step 2. To a solution of ethyl 1-[4-bromo-2-(o-tolyl) phenyl]sulfonyl-4-fluoro-piperidine-4-carboxylate (154 mg, 0.32 mmol, 1 eq) in 1,4-dioxane (3 mL, 0.1 M) was added azetidine (22 mg, 0.38 mmol, 1.2 eq), t-BuONa (91 mg, 0.95 mmol, 3 eq), $Pd_2(dba)_3$ (14 mg, 0.016 mmol, 0.05 eq) and XantPhos (18 mg, 0.03 mmol, 0.1 eq). The reaction was heated to 100 °C and stirred for 16 h. After cooling to rt, the mixture was quenched with water (10 mL) and adjusted to pH 3 with 1N HCl. The aqueous phase was extracted with ethyl acetate (10 mL×3). The combined organic layers were washed with brine (20 mL), dried over $Na_2SO_4$, filtered and concentrated under reduced pressure to give 1-[4-(azetidin-1-yl)-2-(o-tolyl)phenyl]sulfonyl-4-fluoro-piperidine-4-carboxylic acid (120 mg, 0.27 mmol, 87%) as a yellow solid. $^1H$ NMR (400 MHz, $CDCl_3$) δ ppm 7.84 (d, J=8.7 Hz, 1H), 7.31-7.58 (m, 4H), 7.06-7.13 (m, 2H), 3.90 (br t, J=7.3 Hz, 4H), 3.06-3.23 (m, 4H), 2.46-2.74 (m, 4H), 2.31-2.41 (m, 2H), 2.05 (s, 3H). [M+H] calculated for $C_{22}H_{25}FN_2O_4S$ 432, found 433.

Compound 116 was synthesized in a manner analogous to Compound 47, Step 5, using 1-[4-(azetidin-1-yl)-2-(o-tolyl) phenyl]sulfonyl-4-fluoro-piperidine-4-carboxylic acid.

Compound 117 was synthesized in a manner analogous to Compound 116 starting from methyl 1-(4-bromo-2-phenyl-phenyl)sulfonyl-4-fluoro-piperidine-4-carboxylate and using pyrrolidine and BINAP instead of XantPhos as a reagent.

Intermediate ethyl 1-((2'-chloro-5-(2-oxopyrrolidin-1-yl)-[1,1'-biphenyl]-2-yl)sulfonyl)-4-fluoropiperidine-4-carboxylate was synthesized in a manner analogous to 1-[4-(azetidin-1-yl)-2-(o-tolyl)phenyl]sulfonyl-4-fluoro-piperidine-4-carboxylic acid using 2-chlorophenylboronic acid in Step 1 and 2-pyrrolidone in Step 2.

Compound 205 was synthesized in a manner analogous to Compound 47, Steps 4-5, from ethyl 1-((2'-chloro-5-(2-oxopyrrolidin-1-yl)-[1,1'-biphenyl]-2-yl)sulfonyl)-4-fluoropiperidine-4-carboxylate.

Scheme 23. Synthesis of Intermediate tert-butyl 4-[3-(2-chlorophenyl)-4-[(4-ethoxycarbonyl-4-fluoro-1-piperidyl)sulfonyl]penyl] piperazine-1-carboxylate

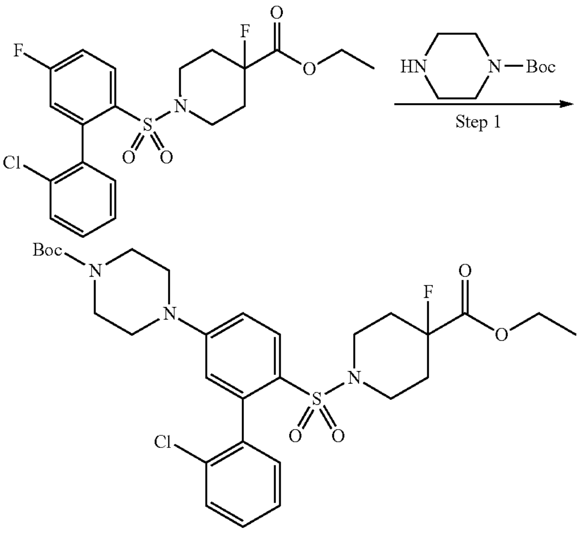

Step 1. To a solution of ethyl 1-[2-(2-chlorophenyl)-4-fluoro-phenyl]sulfonyl-4-fluoro-piperidine-4-carboxylate (100 mg, 0.23 mmol, 1 eq) in MeCN (2 mL, 0.11 M) was added tert-butyl piperazin-4-ium-1-carboxylate (50 mg, 0.27 mmol, 1.2 eq) and DIPEA (58 mg, 0.46 mmol, 2 eq) at rt. The reaction was slowly heated to 100 °C and stirred for 36 h. Then the mixture was heated at 130 °C for 16 h. When the reaction was complete and cooled to rt, the reaction was quenched with water (10 mL), and the aqueous solution was extracted with EtOAc (10 mL×3). The combined organic layers were dried over $Na_2SO_4$, filtered, and evaporated under reduced pressure. The crude product was purified by prep-TLC to give tert-butyl 4-[3-(2-chlorophenyl)-4-[(4-ethoxycarbonyl-4-fluoro-1-piperidyl)sulfonyl]phenyl]piperazine-1-carboxylate (50 mg, 0.08 mmol, 36%) as a white solid. $^1$H NMR (400 MHz, $CDCl_3$) δ ppm 7.99 (d, J=8.9 Hz, 1H), 7.40-7.51 (m, 2H), 7.30-7.35 (m, 2H), 6.90 (dd, J=9.0, 2.6 Hz, 1H), 6.70 (d, J=2.5 Hz, 1H), 4.23 (q, J=7.1 Hz, 2H), 3.58 (br d, J=5.3 Hz, 4H), 3.34 (br d, J=5.1 Hz, 4H), 3.25 (br d, J=13.0 Hz, 1H), 3.13 (br d, J=11.5 Hz, 1H), 2.82-2.94 (m, 1H), 2.62-2.71 (m, 1H), 1.76-2.03 (m, 4H), 1.56-1.58 (m, 9H), 1.29-1.32 (m, 3H).

Compound 118 was synthesized in a manner analogous to Compound 47, Steps 4-5, using tert-butyl 4-[3-(2-chlorophenyl)-4-[(4-ethoxycarbonyl-4-fluoro-1-piperidyl)sulfonyl]phenyl]piperazine-1-carboxylate.

Compounds 119 and 121 were synthesized in a manner analogous to Compound 118 using the appropriate amine in Step 4.

Compounds 120, 122, and 123 were synthesized in a manner analogous to Compound 118 using the appropriate boronic acid in Step 3 and amine in Step 4.

Compound 124 was synthesized by combining ethyl 1-(2-bromo-4-fluoro-phenyl)sulfonyl-4-fluoro-piperidine-4-carboxylate and azetidine in a manner analogous to Step 4 of tert-butyl 4-[3-(2-chlorophenyl)-4-[(4-ethoxycarbonyl-4-fluoro-1-piperidyl)sulfonyl]phenyl]piperazine-1-carboxylate followed by a coupling with 2-chlorophenylboronic acid in a manner analogous to Step 3 of tert-butyl 4-[3-(2-chlorophenyl)-4-[(4-ethoxycarbonyl-4-fluoro-1-piperidyl)sulfonyl]phenyl]piperazine-1-carboxylate followed by hydrolysis and coupling with (R,Z)-4-(methylsulfonyl)but-3-en-2-amine.

Scheme 24. Synthesis of Intermediate 1-[4-chloro-2-[3-(2-methoxyethyl)phenyl]phenyl] sulfonyl-4-fluoro-piperidine-4-carboxylic acid

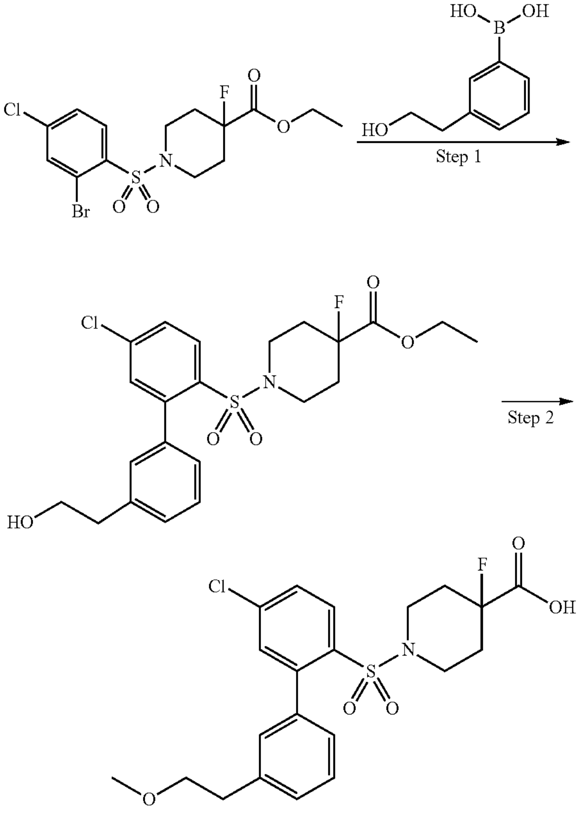

Step 1. To a solution of ethyl 1-(2-bromo-4-chloro-phenyl)sulfonyl-4-fluoro-piperidine-4-carboxylate (150 mg, 0.35 mmol, 1 eq) in 1,4-dioxane (2 mL, 0.16 M) was added [3-(2-hydroxyethyl)phenyl]boronic acid (70 mg, 0.420 mmol, 1.2 eq), $K_2CO_3$ (96 mg, 0.70 mmol, 2 eq) in water (0.2 mL, 0.16 M), and Pd(dppf)$Cl_2$ (45 mg, 0.035 mmol, 0.1 eq). The reaction mixture was heated to 90 °C and stirred for 2 h. After cooling to rt, the mixture was quenched with the water (5 mL) and extracted with EtOAc (5 mL×3). The organic phase was dried over $Na_2SO_4$, filtered and evaporated under vacuum. The crude product was purified by prep-TLC to give ethyl 1-[4-chloro-2-[3-(2-hydroxyethyl)phenyl]phenyl]sulfonyl-4-fluoro-piperidine-4-carboxylate (100 mg, 0.21 mmol, 61%) as a yellow oil. $^1$H NMR (400 MHz, $CDCl_3$) δ ppm 8.08 (d, J=8.6 Hz, 1H), 7.48 (dd, J=8.6, 2.2 Hz, 1H), 7.37-7.42 (m, 1H), 7.35-7.37 (m, 1H), 7.33 (s, 1H), 7.29 (s, 2H), 4.22 (q, J=7.1 Hz, 2H), 3.15 (br d, J=12.9 Hz, 2H), 2.93 (t, J=6.2 Hz, 2H), 2.52-2.63 (m, 2H), 1.74-1.94 (m, 4H), 1.29 (t, J=7.2 Hz, 3H).

Step 2. Ethyl 1-[4-chloro-2-[3-(2-hydroxyethyl)phenyl]phenyl]sulfonyl-4-fluoro-piperidine-4-carboxylate (100 mg, 0.21 mmol, 1 eq) was taken up in THF (2 mL, 1.2 M) and placed under $N_2$. NaH (10 mg, 0.43 mmol, 2.0 eq) was added in portions at 0 °C. After 5 min, $CH_3I$ (90 mg, 0.64 mmol, 3 eq) was added and the resulting solution was stirred for 1 h at 0 °C. The reaction mixture was warmed to rt. The reaction was then quenched by the addition of water (5 mL) and acidified with 1N HCl until pH=3. The aqueous phase was extracted with ethyl acetate (5 mL×3). The separated organic phase was dried over $Na_2SO_4$, filtered, and evaporated to dryness to give 1-[4-chloro-2-[3-(2-methoxyethyl)phenyl]phenyl]sulfonyl-4-fluoro-piperidine-4-carboxylic acid (100 mg, 0.22 mmol, 100%) as a yellow oil. $^1$H NMR (400 MHz, $CDCl_3$) δ ppm 8.11 (d, J=8.6 Hz, 1H), 7.47 (dd, J=8.6, 2.2 Hz, 1H), 7.33-7.40 (m, 2H), 7.29 (s, 3H), 3.69 (t, J=6.7 Hz, 2H), 3.38 (s, 3H), 3.10 (br d, J=12.9 Hz, 2H), 2.95 (t, J=6.7 Hz, 2H), 2.54-2.66 (m, 2H), 1.73-1.93 (m, 5H). [M+H] calculated for $C_{21}H_{23}ClFNO_5S$, 455, found 456.

Compound 125 was synthesized from 1-[4-chloro-2-[3-(2-methoxyethyl)phenyl]phenyl]sulfonyl-4-fluoro-piperidine-4-carboxylic acid in a manner analogous to Step 5 of Compound 1.

Compound 126 was synthesized in a manner analogous to Compound 125 starting with [3-(hydroxymethyl)phenyl]boronic acid.

Scheme 25. Synthesis of Intermediate ethyl 1-[4-chloro-2-[3-[(E)-methoxyiminomethyl]phenyl]phenyl]sulfonyl-4-fluoro-piperidine-4-carboxylate

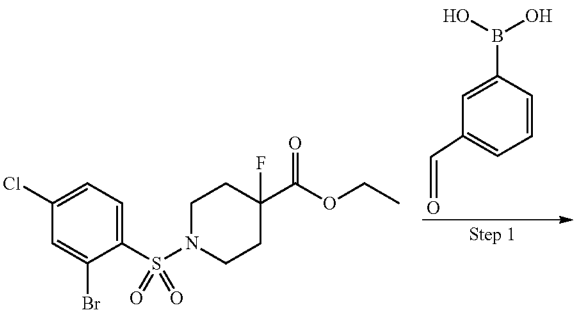

-continued

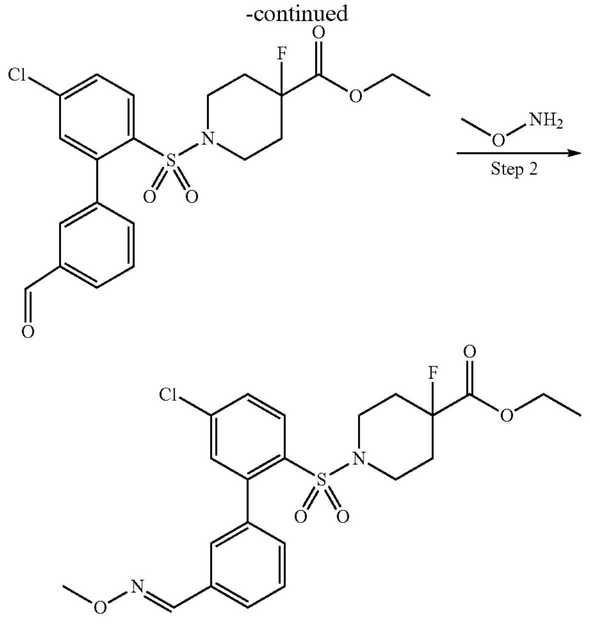

Step 1. To a solution of ethyl 1-(2-bromo-4-chloro-phenyl)sulfonyl-4-fluoro-piperidine-4-carboxylate (0.1 g, 0.23 mmol, 1 eq) in 1,4-dioxane/water (v/v 3:1. 2.0 mL, 0.15 M) was added 3-formylphenylboronic acid (0.04 g, 0.30 mmol, 1.3 eq), $K_2CO_3$ (1.9 g, 0.69 mmol, 3 eq), and Pd(dppf)$Cl_2$ (500 mg, 0.023 mmol, 0.1 eq). The reaction was stirred for 16 h at 90 °C under $N_2$. After cooling to rt, the reaction mixture was diluted with water (30 mL) and extracted with EtOAc (30 mL×3). The combined aqueous layer was acidified with 1N HCl to pH=5 then concentrated. Ethyl 1-[4-chloro-2-(3-formylphenyl)phenyl]sulfonyl-4-fluoro-piperidine-4-carboxylate (0.1 g, 0.26 mmol) was obtained as a yellow solid. $^1$H NMR (400 MHz, $CDCl_3$) δ ppm 10.08 (s, 1H), 8.09 (d, J=8.5 Hz, 1H), 7.89-7.99 (m, 2H), 7.73 (d, J=7.6 Hz, 1H), 7.59-7.65 (m, 1H), 7.54 (dd, J=8.5, 2.1 Hz, 1H), 7.37 (d, J=2.1 Hz, 1H), 4.22 (q, J=7.1 Hz, 2H), 3.18 (br d, J=13.3 Hz, 2H), 2.59-2.73 (m, 2H), 1.70-1.91 (m, 4H), 1.28-1.31 (m, 2H).

Step 2. To a solution of ethyl 1-[4-chloro-2-(3-formylphenyl)phenyl]sulfonyl-4-fluoro-piperidine-4-carboxylate (50 mg, 0.11 mmol, 1 eq) and O-methylhydroxylamine hydrochloride (11 mg, 0.13 mmol, 1.2 eq) in methanol/DCM (v/v 1:1, 2 mL, 0.05 M) was added $Na_2CO_3$ (11 mg, 0.11 mmol, 1 eq) until pH 7-8. To the solution was added AcOH (one drop) and the mixture was stirred at 20 °C for 15 min. The reaction mixture was quenched with water (5 mL) and extracted with DCM (5 mL×3). The combined organic layers were washed with brine (12 mL), dried over $Na_2SO_4$, filtered, concentrated and purified by prep-TLC (PE:EtOAc=3:1) to give ethyl 1-[4-chloro-2-[3-[(E)-methoxyiminomethyl]phenyl]phenyl]sulfonyl-4-fluoro-piperidine-4-carboxylate (36 mg, 0.07 mmol, 68%) as a colorless oil. $^1$H NMR (400 MHz, $CDCl_3$) δ ppm 8.07-8.11 (m, 2H), 7.60-7.65 (m, 2H), 7.49 (dd, J=8.5, 2.0 Hz, 1H), 7.42-7.45 (m, 2H), 7.36 (d, J=2.1 Hz, 1H), 4.22 (q, J=7.1 Hz, 2H), 3.98 (s, 3H), 3.18 (br d, J=12.9 Hz, 2H), 2.59-2.70 (m, 2H), 1.74-1.93 (m, 4H), 1.29 (t, J=7.2 Hz, 3H).

Compound 127 was synthesized from ethyl 1-[4-chloro-2-[3-[(E)-methoxyiminomethyl]phenyl]phenyl]sulfonyl-4-fluoro-piperidine-4-carboxylate in a manner analogous to Steps 4 and 5 of Compound 1.

Scheme 26. Synthesis of Intermediates 1-[2-(2-chlorophenyl)-4-(2-hydroxyethyl)phenyl]sulfonyl-4-fluro-piperidine-4-carboxylic acid and 1-[2-(2-chlorophenyl)-4-(1-hydroxyethyl)phenyl]sulfonyl-4-fluro-piperidine-4-carboxylic acid

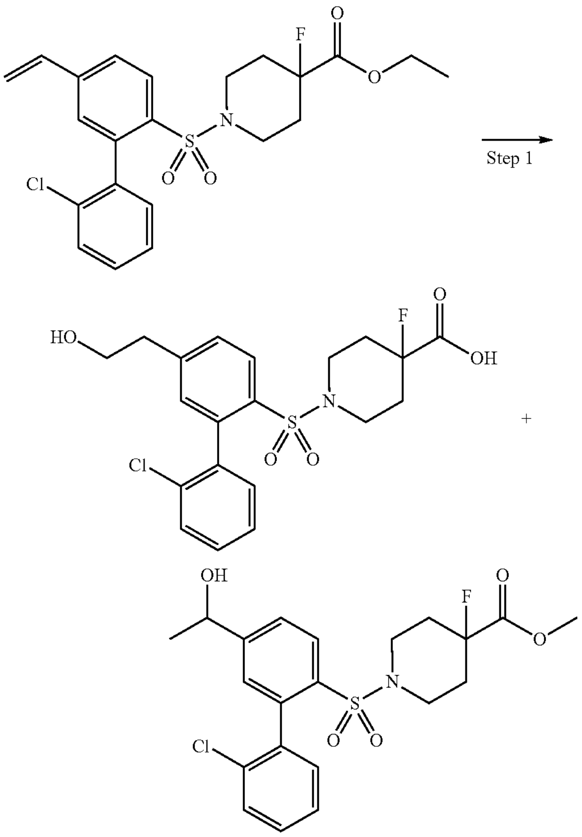

Step 1. To a solution of $BH_3$·THF (0.93 mL, 0.93 mmol, 1 M, 1.5 eq) was added a solution of ethyl 1-[2-(2-chlorophenyl)-4-vinyl-phenyl]sulfonyl-4-fluoro-piperidine-4-carboxylate (280 mg, 0.62 mmol, 1.0 eq) in THF (5 mL, 0.12 M) dropwise at 0 °C. The mixture was stirred at 25 °C for 1 h. A solution of NaOH (1 M, 4 mL) was added to the mixture at 0 °C followed by $H_2O_2$(0.53 mL, 6.2 mmol, 10 eq). The mixture was stirred at 0 °C for 30 min then 25 °C for 30 min. The mixture was diluted with aq. $Na_2SO_3$ (40 mL) and extracted with DCM (20 mL). The organic phase was washed with sat. aq. $NaHCO_3$ (20 mL×2), then washed with brine (20 mL), dried over $Na_2SO_4$, filtered and concentrated. Purification by prep-HPLC afforded 1-[2-(2-chlorophenyl)-4-(2-hydroxyethyl)phenyl]sulfonyl-4-fluoro-piperidine-4-carboxylic acid (50 mg, 0.12 mmol, 18%) as a white solid and 1-[2-(2-chlorophenyl)-4-(1-hydroxyethyl)phenyl]sulfonyl-4-fluoro-piperidine-4-carboxylic acid (25 mg, 0.06 mmol, 9%) as a white solid.

Compound 128 was synthesized from 1-[2-(2-chlorophenyl)-4-(2-hydroxyethyl)phenyl]sulfonyl-4-fluoro-piperidine-4-carboxylic acid in a manner analogous to Step 5 of Compound 47.

Compound 129 was synthesized from 1-[2-(2-chlorophenyl)-4-(1-hydroxyethyl)phenyl]sulfonyl-4-fluoro-piperidine-4-carboxylic acid in a manner analogous to Step 5 of Compound 47.

Scheme 27. Synthesis of Intermediate ethyl 1-[2-(2-chlorophenyl)-4-(hydroxymethyl)phenyl]sulfonyl-4-fluoro-piperidine-4-carboxylate

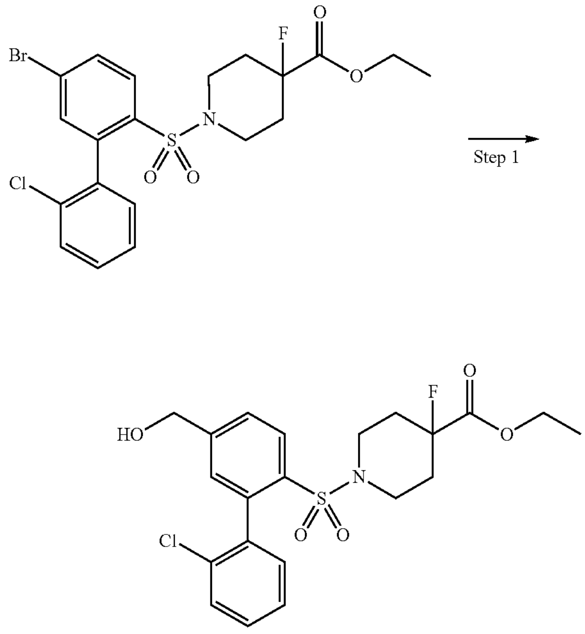

Step 1. To a solution of ethyl 1-[4-bromo-2-(2-chlorophenyl)phenyl]sulfonyl-4-fluoro-piperidine-4-carboxylate (50 mg, 0.099 mmol, 1 eq) in DMF (5 mL, 0.12 M) was added $Pd(PPh_3)_4$(69 mg, 0.059 mmol, 0.1 eq) and tributylstannylmethanol (191 mg, 0.59 mmol, 1 eq). The solution was purged with $N_2$ and stirred at 100 °C for 12 h. After cooling to rt, the reaction mixture was quenched with water (10 mL), extracted with EtOAc (20 mL×2). The combined organic layers were washed with brine (10 mL), dried over $Na_2SO_4$, filtered and concentrated under reduced pressure. The crude product was purified by prep-TLC (PE:EtOAc=3:1) to give ethyl 1-[2-(2-chlorophenyl)-4-(hydroxymethyl)phenyl]sulfonyl-4-fluoro-piperidine-4-carboxylate (70 mg, 0.15 mmol, 26%) as a colorless oil.

Compound 130 was synthesized from ethyl 1-[2-(2-chlorophenyl)-4-(hydroxymethyl)phenyl]sulfonyl-4-fluoro-piperidine-4-carboxylate in a manner analogous to Steps 4 and 5 of Compound 47.

Scheme 28. Synthesis of Intermediate ethyl 1-((2′-chloro-5-(prop-1-yn-1-yl)-[1,1′-biphenyl]-2-yl)sulfonyl)-4-fluoropiperidine-4-carboxylate

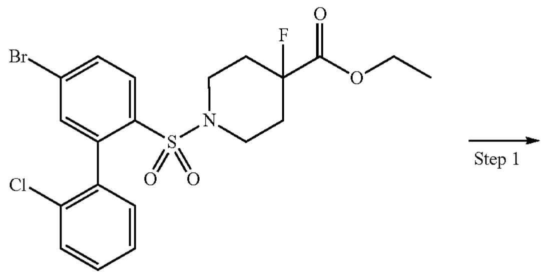

-continued

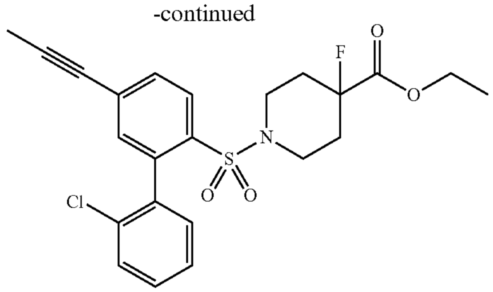

Step 1. To a solution of ethyl 1-[4-bromo-2-(2-chlorophenyl)phenyl]sulfonyl-4-fluoro-piperidine-4-carboxylate (150 mg, 0.30 mmol, 1 eq) and propargyltrimethylsilane (67 mg, 0.59 mmol, 2 eq) in TEA (1 mL) was added $Pd(PPh_3)_2Cl_2$ (21 mg, 0.03 mmol, 0.1 eq). The mixture was stirred at 70 °C for 16 h. After cooling to rt, the reaction mixture was concentrated. The residue was quenched with $NH_4Cl$ (10 mL) and extracted with EtOAc (3 mL×2). The combined organic layers were washed with 10 mL of brine, dried over $Na_2SO_4$ and filtered. The filtrate was concentrated under reduced pressure. The crude product was purified by prep-HPLC (neutral conditions) to give ethyl 1-((2'-chloro-5-(prop-1-yn-1-yl)-[1,1'-biphenyl]-2-yl)sulfonyl)-4-fluoropiperidine-4-carboxylate (60 mg, 0.11 mmol, 95% yield) as a white solid.

Compound 131 was synthesized from ethyl 1-((2'-chloro-5-(prop-1-yn-1-yl)-[1,1'-biphenyl]-2-yl)sulfonyl)-4-fluoropiperidine-4-carboxylate in a manner analogous to Steps 4 and 5 of Compound 47.

Scheme 29. Synthesis of Intermediate ethyl 1-((2′-chloro-5-(oxetan-3-yl)-[1,1′-biphenyl]-2-yl)sulfonyl)-4-fluoropiperidine-4-carboxylate

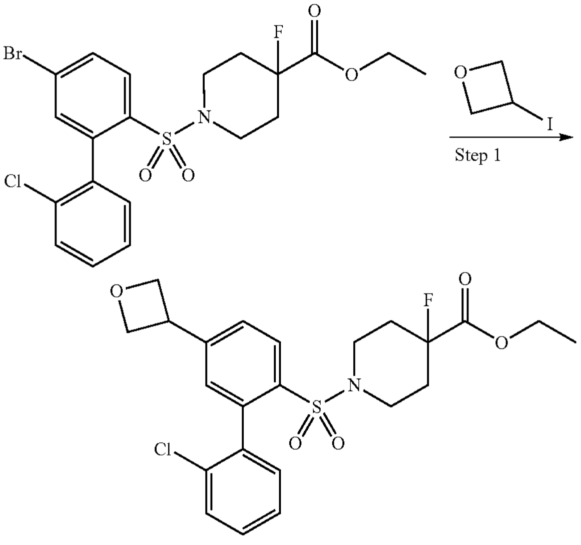

Step 1. A mixture of ethyl 1-[4-bromo-2-(2-chlorophenyl)phenyl]sulfonyl-4-fluoro-piperidine-4-carboxylate (200 mg, 0.39 mmol, 1 eq), 3-iodooxetane (146 mg, 0.79 mmol, 2 eq), (4,4'-di-tert-butyl-2,2'-bipyridine)bis[3,5-difluoro-2-[5-(trifluoromethyl)-2-pyridinyl]phenyl]iridium(III) hexafluorophosphate (4.4 mg, 0.004 mmol, 0.01 eq), dichloro(dimethoxyethane)nickel (0.4 mg, 0.002 mmol, 0.005 eq), sodium carbonate (84 mg, 0.79 mmol, 2 eq), tris(trimethylsilyl)

silane (98 mg, 0.39 mmol, 1 eq) and 4,4-di-tert-butyl-2,2-dipyridyl (0.5 mg, 0.002 mmol, 0.005 eq) in dimethoxyethane (10 mL, 0.04 M) was stirred at 25 °C under 34 watt blue LED irradiation for 16 h. The reaction was quenched with water (30 mL) and extracted with EtOAc (20 mL×2). The combined organic phases were washed with brine (40 mL), dried over $Na_2SO_4$, filtered, concentrated and purified by column chromatography (PE:EtOAc=5:1 to 3:1) to give ethyl 1-((2'-chloro-5-(oxetan-3-yl)-[1,1'-biphenyl]-2-yl)sulfonyl)-4-fluoropiperidine-4-carboxylate (125 mg, 0.42 mmol, 52% yield) as a colorless oil. $^1H$ NMR (400 MHz, $CDCl_3$) δ ppm 8.07 (d, J=8.2 Hz, 1H), 7.48 (dd, J=1.8, 8.2 Hz, 1H), 7.44-7.40 (m, 1H), 7.39-7.35 (m, 1H), 7.29-7.27 (m, 2H), 7.19 (s, 1H), 5.05 (ddd, J=2.3, 6.1, 8.3 Hz, 2H), 4.70 (dt, J=1.9, 6.3 Hz, 2H), 4.26-4.12 (m, 3H), 3.20 (td, J=2.2, 13.2 Hz, 1H), 3.04 (td, J=2.3, 13.3 Hz, 1H), 2.85 (s, 1H), 2.59 (dt, J=2.8, 12.8 Hz, 1H), 1.96-1.67 (m, 4H), 1.22 (t, J=7.1 Hz, 3H).

Compound 132 was synthesized from ethyl 1-((2'-chloro-5-(oxetan-3-yl)-[1,1'-biphenyl]-2-yl)sulfonyl)-4-fluoropiperidine-4-carboxylate in a manner analogous to Steps 4 and 5 of Compound 47.

Scheme 30. Synthesis of Intermediate methyl 4-methoxypiperidine-4-carboxylate

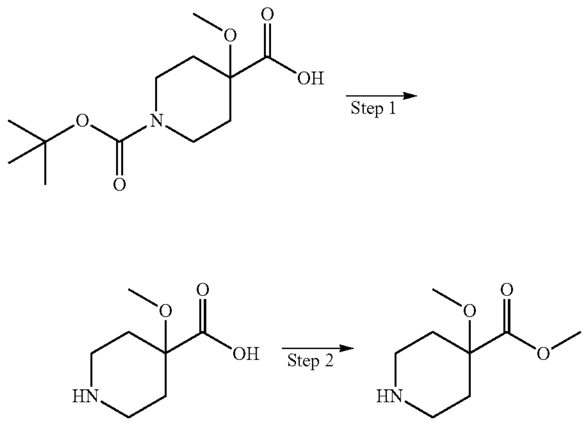

Step 1. To a solution of 1-tert-butoxycarbonyl-4-methoxy-piperidine-4-carboxylic acid (500 mg, 1.93 mmol, 1 eq) was added HCl/1,4-dioxane (4 M, 5 mL) and the reaction was stirred at 25 °C for 2 hours. The reaction solution was concentrated in vacuo to give 4-methoxypiperidine-4-carboxylic acid (300 mg, 98% yield) as a white solid. $^1H$ NMR (400 MHz, Methanol-$d_4$) δ ppm 2.96 (s, 3H), 2.95 (br s, 4H), 1.70-1.94 (m, 4H).

Step 2. To a solution of 4-methoxypiperidine-4-carboxylic acid (300 mg, 1.88 mmol, 1 eq) in methanol (3 mL, 0.6 M) was added thionyl chloride (404 mg, 3.39 mmol) and the reaction was stirred at 25 °C for 2 h. The solvent was evaporated to give methyl 4-methoxypiperidine-4-carboxylate (310 mg, 1.79 mmol, 95%) as a yellow solid. $^1H$ NMR (400 MHz, Methanol-$d_4$) δ ppm 2.05-2.25 (m, 4H), 3.09-3.28 (m, 4H), 3.28 (s, 3H), 3.79 (s, 3H).

Compound 133 was synthesized analogous to Compound 47 using methyl 4-methoxypiperidine-4-carboxylate instead of ethyl 4-fluoropiperidine-4-carboxylate in Step 2.

Scheme 31. Synthesis of Intermediate (E,4R)-4-amino-1-(3,3-difluoroazetidin-1-yl)pent-2-en-1-one

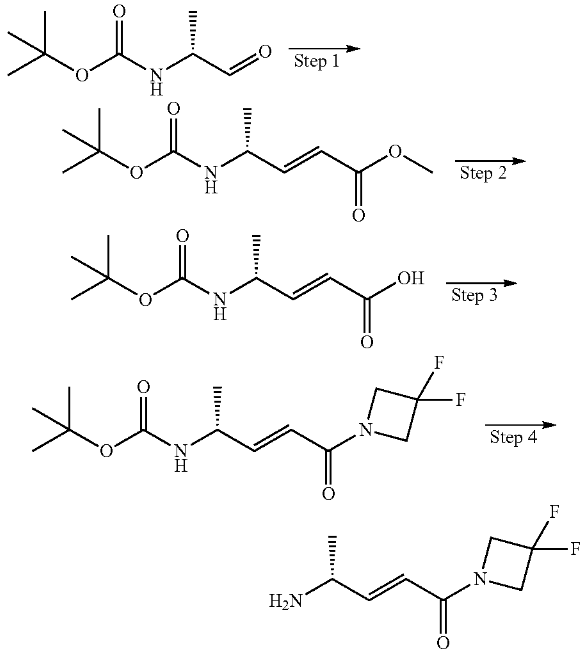

Step 1. To a solution of trimethyl phosphonoacetate (18.9 g, 104 mmol, 1.2 eq) in THF (40 mL, 2.2 M) was added LiHMDS (40 ml, 1.4 eq, 1 M) at −70 °C and this was stirred at −70 °C for 1 h. To this mixture was added tert-butyl (R)-(1-oxopropan-2-yl)carbamate (15 g, 86.6 mmol, 1.0 eq) in THF (20 mL) and the reaction was stirred at −70 °C for 1 h. The reaction mixture was quenched with sat. aq. $NH_4Cl$ (80 mL) and extracted with EtOAc (50 mL×3). Then organic layers were combined, dried over $Na_2SO_4$, filtered, and concentrated under reduced pressure. The crude product was purified by FCC on silica (PE:EtOAc=1:0-5:1) then prep-HPLC to give methyl(E,4R)-4-(tert-butoxycarbonylamino)pent-2-enoate (2.5 g, 10.9 mmol, 13%). $^1H$ NMR (400 MHz, $CDCl_3$) δ ppm 6.88 (dd, J=5.0, 15.7 Hz, 1H), 5.91 (dd, J=1.6, 15.7 Hz, 1H), 4.61-4.33 (m, 2H), 3.74 (s, 3H), 1.44 (s, 9H), 1.27 (d, J=7.0 Hz, 3H).

Step 2. To a solution of methyl(E,4R)-4-(tert-butoxycarbonylamino)pent-2-enoate (200 mg, 0.87 mmol, 1.0 eq) in THF (3 mL, 0.22 M) and water (1 mL, 0.22 M) was added lithium hydroxide hydrate (110 mg, 2.62 mmol, 3.0 eq). The reaction solution was stirred at 25 °C for 12 h. The reaction solution was adjusted to pH 4 and extracted with EtOAc (10 mL×3). The combined organic layers were washed with brine (20 mL), dried over $Na_2SO_4$, and filtered. The filtrate was concentrated to give (E,4R)-4-(tert-butoxycarbonylamino)pent-2-enoic acid (190 mg, 0.88 mmol, quant. yield) as a colorless oil, which was used in the next step directly without purification. $^1H$ NMR (400 MHz, $CDCl_3$) δ ppm 6.98 (br dd, J=4.4, 15.8 Hz, 1H), 5.92 (dd, J=1.4, 15.7 Hz, 1H), 4.64-4.37 (m, 1H), 1.46 (s, 9H), 1.29 (d, J=6.9 Hz, 3H).

Step 3. To a solution of (E,4R)-4-(tert-butoxycarbonylamino)pent-2-enoic acid (1.5 g, 6.97 mmol, 1 eq), 3,3-difluoroazetidine HCl (1.1 g, 8.36 mmol, 1.2 eq), and $T_3P$ (3.3 g, 10.4 mmol, 1.5 eq) in DCM (5 mL, 1.4 M) was added DIPEA (2.3 g, 17.4 mmol, 2.5 eq). The reaction solution was stirred at 25 °C for 2 h. The reaction mixture was purified by column chromatography (PE:EtOAc=5:1) to give tert-butyl N—[(E,1R)-4-(3,3-difluoroazetidin-1-yl)-1-methyl-4-oxo-but-2-enyl]carbamate (1.4 g, 4.82 mmol, 69%) as a white solid. $^1$H NMR (400 MHz, $CDCl_3$) δ ppm 6.82 (br dd, J=5.4, 15.1 Hz, 1H), 5.93 (dd, J=1.2, 15.3 Hz, 1H), 4.59-4.30 (m, 6H), 1.45 (s, 9H), 1.28 (d, J=6.9 Hz, 3H). [M+H] calculated for $C_{13}H_{20}F_2N_2O_3$, 290, found 291.

Step 4. To a solution of tert-butyl N-[(E,1R)-4-(3,3-difluoroazetidin-1-yl)-1-methyl-4-oxo-but-2-enyl]carbamate (300 mg, 1.03 mmol, 1 eq) in MeCN (5 mL, 0.21 M) was added 4-methylbenzenesulfonic acid (890 mg, 5.17 mmol, 5.0 eq). The reaction solution was stirred at 65 °C for 12 h. The reaction solution was concentrated to give the 4-methylbenzenesulfonic acid salt of (E,4R)-4-amino-1-(3,3-difluoroazetidin-1-yl)pent-2-en-1-one (300 mg, 0.83 mmol, 80%).

Intermediate (R,E)-4-amino-1-(3-fluoroazetidin-1-yl)pent-2-en-1-one was synthesized in a manner analogous to (E,4R)-4-amino-1-(3,3-difluoroazetidin-1-yl)pent-2-en-1-one using 3-fluoroazetidine HCl in Step 3.

Intermediate (E)-4-amino-1-(3,3-difluoroazetidin-1-yl)-4-methylpent-2-en-1-one was synthesized in a manner analogous to (E,4R)-4-amino-1-(3,3-difluoroazetidin-1-yl)pent-2-en-1-one using 1,1-dimethylethyl N-(1,1-dimethyl-2-oxoethyl)carbamate in Step 1.

Intermediate (E)-4-amino-1-(3,3-difluoroazetidin-1-yl)but-2-en-1-one was synthesized in a manner analogous to (E,4R)-4-amino-1-(3,3-difluoroazetidin-1-yl)pent-2-en-1-one using tert-butyl(2-oxoethyl)carbamate in Step 1.

Compound 282 was synthesized in a manner analogous to Compound 47 using (E)-4-amino-1-(3,3-difluoroazetidin-1-yl)but-2-en-1-one in Step 5.

Scheme 32. Synthesis of 1-[2-(2-chlorophenyl)-4-(trifluoromethyl)phenyl]sulfonyl-4-fluoro-N-[(E,1R)-4-(3,3-difluoroazetidin-1-yl)-1-methyl-4-oxo-but-2-enyl]piperidine-4-carboxamide (Compound 134)

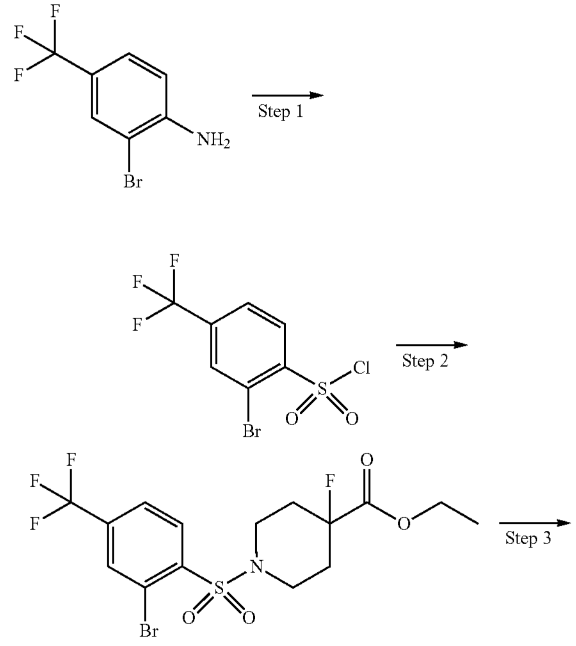

-continued

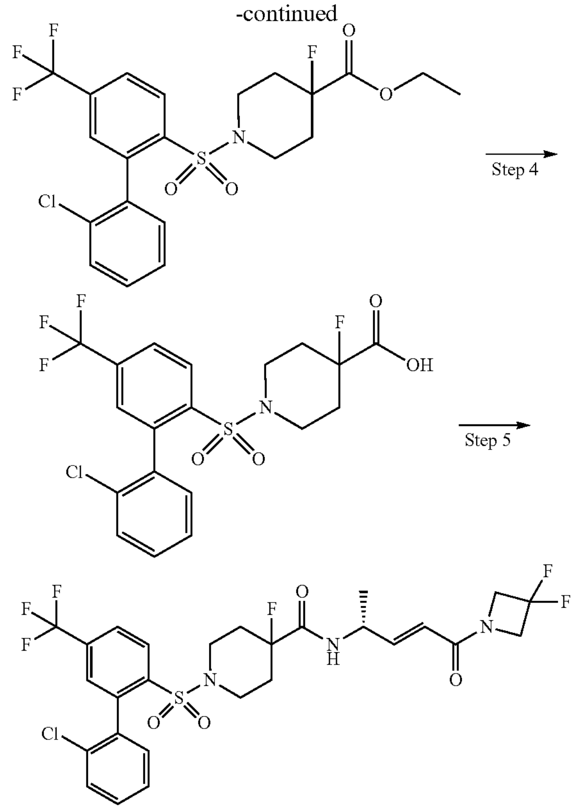

Step 1. To a solution of 2-bromo-4-(trifluoromethyl) aniline (10 g, 41.7 mmol, 1 eq) in HCl/acetic acid (v/v 3:1, 20 mL, 0.48 M) was added sodium nitrite (3.2 g, 45.8 mmol, 1.1 eq) at 0 °C. Mixture 1 was stirred at 0 °C for 1 h. $SO_2$ was bubbled through acetic acid (60 mL, 0.69 M) for 10 min at 0 °C before cuprous chloride (1.2 g, 12.5 mmol, 0.3 eq) was added. $SO_2$ was bubbled through mixture 2 for 10 min. Then, mixture 1 was added to the mixture 2 at 0 °C. The resulting mixture was stirred at 0-20 °C for 1 h. The reaction mixture was quenched with $H_2O$ (100 mL) and extracted with MTBE (60 mL×3). The organic layers were washed with $NaHCO_3$ (50 mL×2) and brine (30 mL). The combined organic layers were separated, dried over $Na_2SO_4$, filtered, and concentrated to dryness. The residue was purified by column chromatography (PE) to give 2-bromo-4-(trifluoromethyl)benzenesulfonyl chloride (3.8 g, 11.7 mmol, 28%) as a yellow solid. $^1$H NMR (400 MHz, DMSO-$d_6$) δ ppm 8.07-8.11 (m, 1H), 7.90 (s, 1H), 7.70-7.75 (m, 1H).

Step 2. To a solution of ethyl 4-fluoropiperidine-4-carboxylate hydrochloride (2.2 g, 10.5 mmol, 1 eq) in DCM (40 mL, 0.26 M) was added TEA (3.2 g, 31.5 mmol, 3 eq) and 2-bromo-4-(trifluoromethyl)benzenesulfonyl chloride (3.4 g, 10.5 mmol, 1 eq). The mixture was stirred at 20 °C for 2 h. The reaction mixture was poured into sat. aq. $NH_4Cl$ (20 mL) and extracted with DCM (20 mL×3). The combined organic layers were washed with brine (20 mL×2), dried over $Na_2SO_4$, filtered and concentrated under reduced pressure. The residue was purified by column chromatography (PE:EtOAc=1:0-3:1) to give ethyl 1-[2-bromo-4-(trifluoromethyl)phenyl]sulfonyl-4-fluoro-piperidine-4-carboxylate (4.8 g, 10.4 mmol, 99%) as a white solid. $^1$H NMR (400 MHz, $CDCl_3$) δ ppm 8.21-8.27 (m, 1H), 7.99-8.04 (m, 1H), 7.72 (dd, J=8.3, 1.0 Hz, 1H), 4.24-4.30 (m, 2H), 3.80-3.87 (m, 2H), 3.21 (td, J=12.8, 2.8 Hz, 2H), 2.12-2.30 (m, 2H), 2.07-2.10 (m, 1H), 2.02 (br s, 1H), 1.32 (t, J=7.1 Hz, 3H).

Step 3. To a solution of ethyl 1-[2-bromo-4-(trifluoromethyl)phenyl]sulfonyl-4-fluoro-piperidine-4-carboxylate (3.5 g, 7.57 mmol, 1 eq) in 1,4-dioxane/water (v/v 10:1, 44 mL, 0.17 M) was added 2-chlorophenylboronic acid (1.8 g, 11.4 mmol, 1.5 eq), sodium carbonate (2 g, 18.9 mmol, 2.5 eq) and tetrakis(triphenylphosphine)palladium(0) (0.88 g, 0.76 mmol, 0.1 eq) under $N_2$. The mixture was stirred at 90 °C for 16 h. After cooling to rt, the reaction mixture was poured into sat. aq. $NH_4Cl$ (30 mL) and extracted with EtOAc (40 mL×3). The combined organic layers were washed with brine (50 mL×2), dried over $Na_2SO_4$, filtered, and concentrated under reduced pressure. The residue was purified by column chromatography (PE:EtOAc=10:0-9:1) to give ethyl 1-[2-(2-chlorophenyl)-4-(trifluoromethyl)phenyl]sulfonyl-4-fluoro-piperidine-4-carboxylate as a white solid. $^1$H NMR (400 MHz, $CDCl_3$) δ ppm 8.30 (d, J=8.3 Hz, 1H), 7.80 (dd, J=8.3, 1.2 Hz, 1H), 7.59 (d, J=1.3 Hz, 1H), 7.50-7.54 (m, 1H), 7.43-7.47 (m, 1H), 7.34-7.42 (m, 2H), 4.24 (q, J=7.1 Hz, 2H), 3.22-3.35 (m, 1H), 3.03-3.15 (m, 1H), 2.96 (td, J=12.8, 2.9 Hz, 1H), 2.59-2.72 (m, 1H), 1.93-2.13 (m, 2H), 1.78-1.91 (m, 2H), 1.30 (t, J=7.2 Hz, 3H). [M+H] calculated for $C_{21}H_{20}ClF_4NO_4S$, 493, found 494.

Step 4. To a solution of ethyl 1-[2-(2-chlorophenyl)-4-(trifluoromethyl)phenyl]sulfonyl-4-fluoro-piperidine-4-carboxylate (3.5 g, 6.51 mmol, 1 eq) in THF/water (v/v 3:1, 40 mL, 0.16 M) was added LiOH·$H_2O$ (820 mg, 19.5 mmol, 3 eq). The mixture was stirred at 20 °C for 3 h. The pH was adjusted to around 4 with HCl. The mixture was extracted with EtOAc (20 mL×3). The combined organic layers were washed with brine (30 mL×2), dried over $Na_2SO_4$, filtered and concentrated under reduced pressure to give 1-[2-(2-chlorophenyl)-4-(trifluoromethyl)phenyl]sulfonyl-4-fluoro-piperidine-4-carboxylic acid (3 g, 6.44 mmol, 99%) as a yellow solid. $^1$H NMR (400 MHz, DMSO-$d_6$) δ ppm 8.26 (d, J=8.4 Hz, 1H), 8.06 (dd, J=8.4, 1.4 Hz, 1H), 7.74 (d, J=1.1 Hz, 1H), 7.54-7.61 (m, 1H), 7.38-7.51 (m, 3H), 3.16 (br dd, J=12.2, 1.8 Hz, 2H), 2.59-2.83 (m, 2H), 1.75-1.97 (m, 4H).

Step 5. To a solution of 1-[2-(2-chlorophenyl)-4-(trifluoromethyl)phenyl]sulfonyl-4-fluoro-piperidine-4-carboxylic acid (100 mg, 0.21 mmol, 1 eq) in DCM (2 mL, 0.11 M) was added 4-methylbenzenesulfonic acid salt of (E,4R)-4-amino-1-(3,3-difluoroazetidin-1-yl)pent-2-en-1-one (156 mg, 0.43 mmol, 2 eq), $T_3P$ (205 mg, 0.32 mmol, 1.5 eq), and DIPEA (69 mg, 0.54 mmol, 2.5 eq). The mixture was stirred at 25 °C for 1 h. The reaction was purified by prep-TLC (PE:EtOAc=1:2) to give 1-[2-(2-chlorophenyl)-4-(trifluoromethyl)phenyl]sulfonyl-4-fluoro-N-[(E,1R)-4-(3,3-difluoroazetidin-1-yl)-1-methyl-4-oxo-but-2-enyl]piperidine-4-carboxamide (Compound 134) (27 mg, 0.04 mmol, 19%) as a white solid. $^1$H NMR (400 MHz, DMSO-$d_6$) δ ppm 8.34 (dd, J=1.7, 8.2 Hz, 1H), 8.26 (d, J=8.4 Hz, 1H), 8.06 (dd, J=1.4, 8.4 Hz, 1H), 7.74 (s, 1H), 7.58 (d, J=7.9 Hz, 1H), 7.52-7.39 (m, 3H), 6.66 (dd, J=5.9, 15.5 Hz, 1H), 5.93 (dd, J=1.2, 15.4 Hz, 1H), 4.62 (br t, J=10.9 Hz, 2H), 4.56-4.48 (m, 1H), 4.31 (br t, J=11.4 Hz, 2H), 3.24-3.18 (m, 2H), 2.78 (dt, J=2.6, 12.6 Hz, 1H), 2.69-2.58 (m, 1H), 2.06-1.75 (m, 4H), 1.19 (d, J=7.0 Hz, 3H). [M+H] calculated for $C_{27}H_{26}ClF_6N_3O_4S$, 637; found 638.

Compounds 135-138 were synthesized analogous to Compound 134 using the appropriate starting aniline.

Compound 139 was synthesized analogous to Compound 134 using methyl 4-methoxypiperidine-4-carboxylate instead of ethyl 4-fluoropiperidine-4-carboxylate in Step 2 and using (R,Z)-4-(methylsulfonyl)but-3-en-2-amine in Step 5.

Compound 216 was synthesized analogous to Compound 134 using (R,E)-4-amino-1-(3-fluoroazetidin-1-yl)pent-2-en-1-one in Step 5.

Compound 249 was synthesized analogous to Compound 134 using (E)-4-amino-1-(3,3-difluoroazetidin-1-yl)-4-methylpent-2-en-1-one in Step 5.

Compound 283 was synthesized in a manner analogous to Compound 134 using (E)-4-amino-1-(3,3-difluoroazetidin-1-yl)but-2-en-1-one in Step 5.

Intermediate 1-[4-acetyl-2-(2-chlorophenyl)phenyl]sulfonyl-4-fluoro-piperidine-4-carboxylic acid was synthesized analogous to 1-[2-(2-chlorophenyl)-4-(trifluoromethyl)phenyl]sulfonyl-4-fluoro-piperidine-4-carboxylic acid.

Scheme 33. Synthesis of Intermediate 1-[2-(2-chlorophenyl)-4-(1-hydroxyethyl)phenyl]sulfonyl-4-fluoro-piperidine-4-carboxylic acid

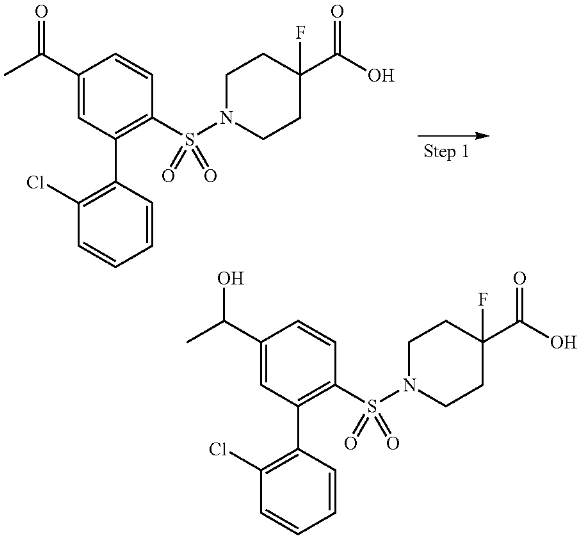

Step 1. To a solution of 1-[4-acetyl-2-(2-chlorophenyl)phenyl]sulfonyl-4-fluoro-piperidine-4-carboxylic acid (120 mg, 0.27 mmol, 1 eq) in methanol (2 mL, 0.14 M) was added sodium borohydride (50 mg, 1.32 mmol, 4.8 eq) and this was stirred at 25 °C for 16 h. The reaction mixture was filtered and the filtrate was concentrated under reduced pressure to give a residue, which was purified by prep-HPLC to give 1-[2-(2-chlorophenyl)-4-(1-hydroxyethyl)phenyl]sulfonyl-4-fluoro-piperidine-4-carboxylic acid (70 mg, 0.16 mmol, 58%) as a white solid. $^1$H NMR (400 MHz, DMSO-$d_6$) δ ppm 7.94 (d, J=8.3 Hz, 1H), 7.61 (dd, J=8.2, 1.3 Hz, 1H), 7.52 (d, J=7.8 Hz, 1H), 7.31-7.46 (m, 3H), 7.26 (d, J=1.5 Hz, 1H), 5.33-5.53 (m, 1H), 4.76-4.89 (m, 1H), 3.99-4.22 (m, 1H), 3.03-3.13 (m, 2H), 2.61-2.72 (m, 1H), 2.53-2.59 (m, 1H), 1.59-1.99 (m, 4H), 1.35 (dd, J=6.5, 2.1 Hz, 3H).

Compound 140 was synthesized analogous to Compound 134, Step 5, using 1-[2-(2-chlorophenyl)-4-(1-hydroxyethyl)phenyl]sulfonyl-4-fluoro-piperidine-4-carboxylic acid.

Intermediate (2R,4S)-1-((2'-chloro-5-(1-hydroxyethyl)-[1,1'-biphenyl]-2-yl)sulfonyl)-4-fluoro-2-methylpiperidine-4-carboxylic acid was synthesized in a manner analogous to 1-[2-(2-chlorophenyl)-4-(1-hydroxyethyl)phenyl]sulfonyl-4-fluoro-piperidine-4-carboxylic acid using (2R,4S)-1-((5-acetyl-2'-chloro-[1,1'-biphenyl]-2-yl)sulfonyl)-4-fluoro-2-methylpiperidine-4-carboxylic acid.

Compound 252 was synthesized in a manner analogous to Compound 134, Step 5, using (2R,4S)-1-((2'-chloro-5-(1-hydroxyethyl)-[1,1'-biphenyl]-2-yl)sulfonyl)-4-fluoro-2-methylpiperidine-4-carboxylic acid.

Scheme 34. Synthesis of Intermediate 2'-chloro-5-methoxy-[1,1'-biphenyl]-2-sulfonyl chloride

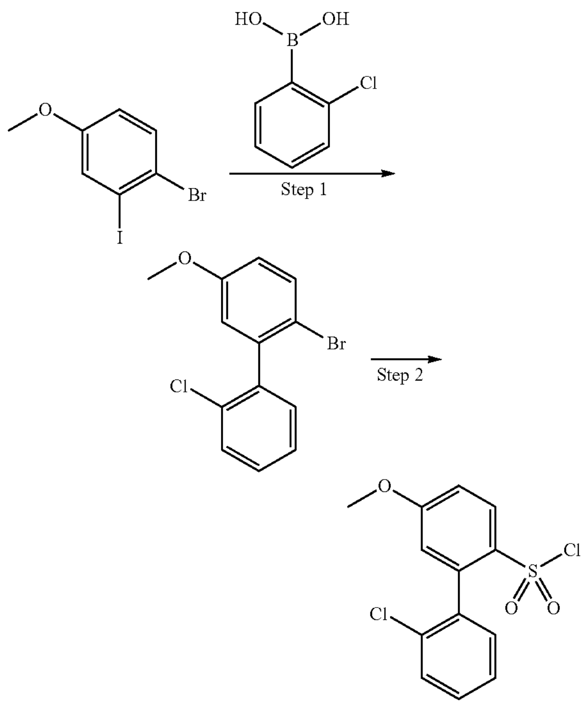

Step 1. To a mixture of 1-bromo-2-iodo-4-methoxy-benzene (45 g, 144 mmol, 1 eq) in 1,4-dioxane/water (v/v 10:1, 550 mL, 0.26 M) was added 2-chlorophenylboronic acid (2.7 g, 173 mmol, 1.2 eq), $K_2CO_3$ (50 g, 364 mmol, 2.5 eq) and Pd(dppf)$Cl_2$ (3.6 g, 12.2 mmol, 0.08 eq). The mixture was stirred at 90 °C for 12 h under $N_2$. After cooling to rt, the reaction mixture was diluted with water (300 mL) and extracted with EtOAc (300 mL×2). The combined organic layers were washed with brine (300 mL), dried over $Na_2SO_4$, filtered, and concentrated under reduced pressure. The residue was purified by column chromatography (PE:EtOAc=1:0-10:1) to give 1-bromo-2-(2-chlorophenyl)-4-methoxy-benzene (40 g, 269 mmol, 94%) as a yellow oil.

Step 2. To a solution of 1-bromo-2-(2-chlorophenyl)-4-methoxy-benzene (40 g, 134 mmol, 1.0 eq) in THF (400 mL, 0.34 M) at −78 °C was added n-BuLi (100 mL, 252 mmol, 1.9 eq) and this was stirred for 30 min. To the solution was added a solution of $SO_2$ in THF (sat. 400 mL). The reaction was stirred at 25 °C for 16 h. The reaction mixture was concentrated to remove solvent. n-Hexane was added to the residue and the mixture was stirred for 10 min. The mixture was filtered and the filter cake was dissolved in AcOH (150 mL) before NCS (20 g, 151 mmol, 1.2 eq) was added. The resulting reaction was stirred at 25 °C for 1 h. The reaction mixture was poured into water (600 mL) and extracted with EtOAc (600 mL×3). The combined organic layers were washed with brine (200 mL), dried over $Na_2SO_4$, filtered, and concentrated under reduced pressure. The residue was purified by column chromatography (PE:EtOAc=1:0-95:5). 2'-Chloro-5-methoxy-[1,1'-biphenyl]-2-sulfonyl chloride (35 g, 110.34 mmol, 41% yield) was obtained as a yellow oil.

Scheme 35. Synthesis of Intermediate 2-(2-chlorophenyl)-4-(trifluoromethyl)benzenesulfonyl chloride

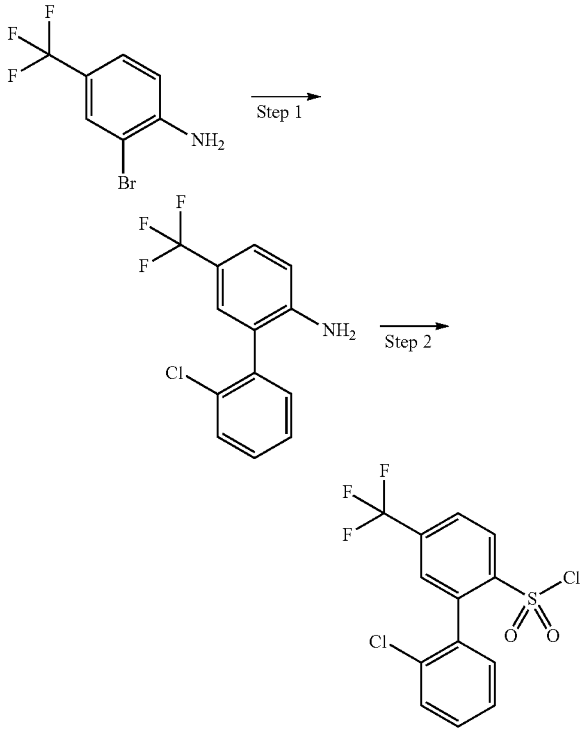

Step 1. To a solution of 2-bromo-4-(trifluoromethyl) aniline (1.0 g, 4.17 mmol, 1.0 eq) in dimethoxyethane/water (v/v 1:1, 20 mL, 0.21 M) was added 2-chlorophenylboronic acid (0.80 g, 4.99 mmol, 1.2 eq), sodium carbonate (1.3 g, 12.5 mmol, 3.0 eq), and Pd($PPh_3$)$_4$(481 mg, 0.417 mmol, 0.1 eq). The reaction was placed under $N_2$ and stirred at 80 °C for 16 h. After cooling to rt, the reaction was quenched with water (20 mL) and extracted with EtOAc (30 mL×3). The combined organic phases were washed with brine (20 mL), dried over $Na_2SO_4$, filtered, and concentrated under reduced pressure. The resulting residue was purified by FCC on silica (PE:EtOAc=1:0 to 10:1) to give 2-(2-chlorophenyl)-4-(trifluoromethyl)aniline (670 mg, 2.47 mmol, 59% yield) as a yellow oil. $^1$H NMR (400 MHz, $CDCl_3$) δ ppm 7.56-7.50 (m, 1H), 7.44 (dd, J=8.5, 1.7 Hz, 1H), 7.40-7.30 (m, 4H), 6.81 (d, J=8.4 Hz, 1H).

Step 2. To a solution of 2-(2-chlorophenyl)-4-(trifluoromethyl) aniline (300 mg, 1.10 mmol, 1.0 eq) in HCl/acetic acid (v/v 3:1, 1.3 mL, 2.8 M) was added a solution of sodium nitrite (84 mg, 1.21 mmol, 1.1 eq) in water (0.10 mL, 2.8 M) dropwise at 0 °C. This mixture 1 was stirred for 1 h at 0 °C. In a separate beaker, sulfur dioxide gas was bubbled through glacial acetic acid (3.0 mL) under vigorous stirring for 20 minutes. Cuprous chloride (32.8 mg, 0.331 mmol, 0.3 eq) was added and bubbling of sulfur dioxide gas was continued until the yellow-green suspension became close to black and most of the solids dissolved (about 30 minutes). Mixture 1 was added to this solution and the reaction was allowed to warm to 20 °C. The reaction was stirred for 2 h before being poured into water (20 mL) and extracted with MTBE (10 mL×2). The combined organic phases were washed with sat. aq. $NaHCO_3$ (50 mL), dried over $Na_2SO_4$, and filtered. The filtrate was concentrated under reduced pressure to give 2-(2-chlorophenyl)-4-(trifluoromethyl)benzenesulfonyl chloride (200 mg, 0.563 mmol, 51% yield) as a yellow oil. $^1$H NMR (400 MHz, $CDCl_3$) δ ppm 8.39 (d, J=8.4 Hz, 1H), 7.93 (dd, J=1.4, 8.5 Hz, 1H), 7.76-7.66 (m, 2H), 7.61-7.50 (m, 3H).

Intermediates 2-(2-chlorophenyl)-4-cyano-benzenesulfonyl chloride, 5-bromo-2'-chloro-[1,1'-biphenyl]-2-sulfonyl chloride, and 5-bromo-3'-chloro-[1,1'-biphenyl]-2-sulfonyl chloride were synthesized in a manner analogous to 2-(2-chlorophenyl)-4-(trifluoromethyl)benzenesulfonyl chloride using the appropriate aniline and boronic acid in Step 1.

Scheme 36. Synthesis of Intermediate rac-(2R,4S)-1-tert-butoxycarbonyl-4-fluoro-2-methyl-piperidine-4-carboxylic acid

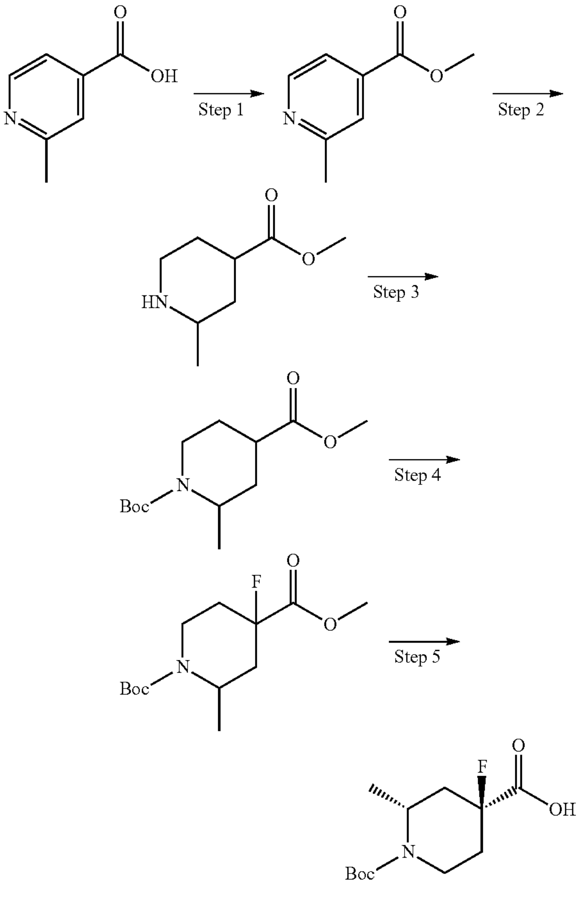

Step 1. To a solution of 2-methylpyridine-4-carboxylic acid (50 g, 365 mmol, 1.0 eq) in methanol (500 mL, 0.73 M) was added $SOCl_2$ (50 mL) at 0 °C. The reaction solution was stirred at 60 °C for 6 h. The reaction solution was concentrated to give methyl 2-methylpyridine-4-carboxylate (55 g, 364 mmol, 100%) as a white solid. The crude material was used directly in the next step.

Step 2. To a solution of methyl 2-methylpyridine-4-carboxylate (50 g, 331 mmol, 1 eq) in methanol (400 mL, 0.83 M) was added di-tert-butyl dicarbonate (145 g, 663 mmol. 2.0 eq) and $PtO_2$ (3.5 g) under Ar. The reaction solution was stirred at 25 °C for 12 h under $H_2$ (45 psi). The reaction solution was filtered and the filtrate was concentrated to give methyl 2-methylpiperidine-4-carboxylate (50 g, 318 mmol, 96%) as a white solid.

Step 3. To a solution of methyl 2-methylpiperidine-4-carboxylate (50 g, 318 mmol, 1 eq) in THF (300 mL, 1.1 M) was added di-tert-butyl dicarbonate (69 g, 318 mmol, 1.0 eq) and TEA (133 mL, 954 mmol, 3 eq) at 0 °C. The reaction solution was stirred at 0-25 °C for 12 h. The reaction solution was concentrated. The crude product was purified by column chromatography (PE:EtOAc=1:0-5:1) to give 1-(tert-butyl) 4-methyl 2-methylpiperidine-1,4-dicarboxylate (52 g, 202 mmol, 64%) as a colorless oil. $^1$H NMR (400 MHz, $CDCl_3$, 298 K) 6 ppm 4.21-4.15 (m, 1H), 3.87-3.79 (m, 1H), 3.71 (s, 3H), 3.10 (ddd, J=4.1, 12.0, 13.9 Hz, 1H), 2.59 (t, J=5.7 Hz, 1H), 2.03-1.87 (m, 3H), 1.81-1.69 (m, 1H), 1.46 (s, 9H), 1.08 (d, J=6.9 Hz, 3H).

Step 4. To a solution of 1-tert-butyl 4-methyl 2-methylpiperidine-1,4-dicarboxylate (10 g, 38.9 mmol, 1 eq) in THF (300 mL) was added LDA (39 mL, 77.7 mmol, 2 eq) dropwise at −30 °C and the mixture was stirred at −30 °C for 1.5 h. To the mixture was added N-fluorobenzenesulfonimide (18.4 g, 58.3 mmol, 1.5 eq) in THF (10 mL) dropwise at −30 °C and the resulting solution was stirred at −30-15 °C for 2 h. The reaction was quenched with aq. sat. $NH_4Cl$ (200 mL) and extracted with EtOAc (200 mL×2). The combined organic phases were washed with brine (40 mL×2), dried over $Na_2SO_4$, filtered, concentrated and purified by column chromatography (PE:EtOAc=1:0-3:1) then prep-HPLC to give 1-tert-butyl 4-methyl 4-fluoro-2-methyl-piperidine-1,4-dicarboxylate (8 g, 29.10 mmol, 75% yield) as a white solid.

Step 5. A solution of 1-tert-butyl 4-methyl 4-fluoro-2-methyl-piperidine-1,4-dicarboxylate (20 g, 72.6 mmol, 1.0 eq) and $LiOH{\cdot}H_2O$ (9.1 g, 218 mmol, 3.0 eq) in THF (200 mL, 0.27 M) and water (70 mL, 0.27 M) was stirred at 25 °C for 2 h. The mixture was extracted with EtOAc (20 mL). The aqueous phase was adjusted to pH 2 by 1M HCl, diluted with water (50 mL), and extracted with EtOAc (70 mL×4). The combined organic phases were concentrated to give rac-(2R,4S)-1-tert-butoxycarbonyl-4-fluoro-2-methyl-piperidine-4-carboxylic acid (19 g, 72.7 mmol, 100%) as a colorless oil, which was used for next step directly. $^1$H NMR (400 MHz, $CDCl_3$, 298 K) 6 ppm 4.26-4.17 (m, 1H), 4.01-3.91 (m, 1H), 3.24-3.14 (m, 1H), 2.33-2.21 (m, 1H), 2.16-2.13 (m, 1H), 2.04-1.88 (m, 2H), 1.47 (s, 9H), 1.20 (d, J=6.8 Hz, 3H).

Scheme 37. Synthesis of Intermediate (2R,4S)-4-fluoro-2-methyl-N-((R,Z)-4-(methylsulfonyl)but-3-en-2-yl)piperidine-4-carboxamide

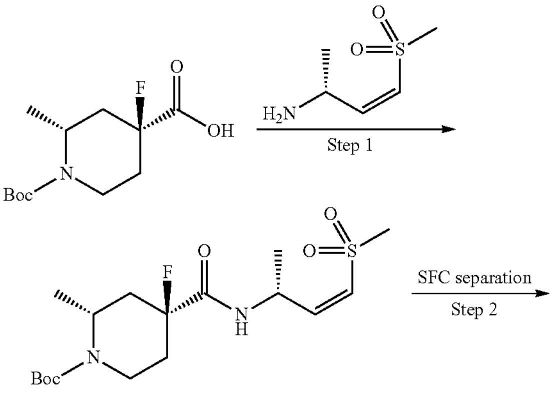

-continued

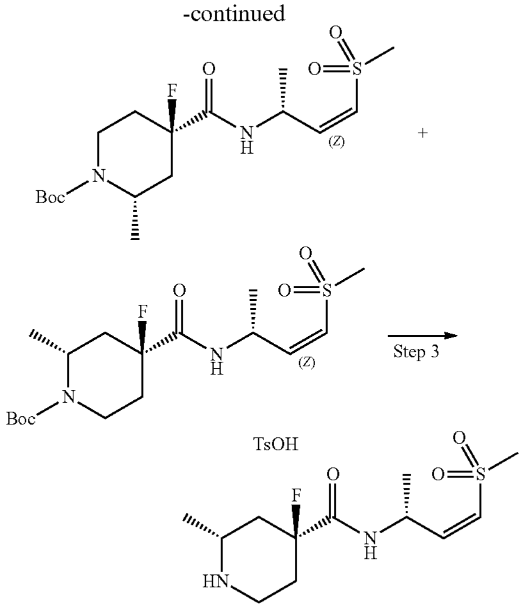

Step 1. To a solution of rac-(2R,4S)-1-tert-butoxycarbonyl-4-fluoro-2-methyl-piperidine-4-carboxylic acid (42 g, 161 mmol, 1.0 eq) and (R,Z)-4-(methylsulfonyl)but-3-en-2-amine, TsOH salt (56.8 g, 177 mmol, 1.1 eq) in DMF (420 mL, 0.38 M) was added HATU (73.3 g, 193 mmol, 1.2 eq) and DIPEA (62.3 g, 482 mmol, 3 eq) dropwise at 25 °C. The reaction solution was stirred at 25 °C for 0.5 h. The reaction solution was quenched with water (500 mL) and extracted with EtOAc (100 mL×4). The combined organic phases were washed with brine (300 mL), dried over $Na_2SO_4$, filtered, and concentrated. The crude product was purified by column chromatography to give tert-butyl(rac-2R,4S)-4-fluoro-2-methyl-4-(((R,Z)-4-(methylsulfonyl)but-3-en-2-yl)carbamoyl)piperidine-1-carboxylate (75 g).

Step 2. tert-Butyl(rac-2R,4S)-4-fluoro-2-methyl-4-(((R,Z)-4-(methylsulfonyl)but-3-en-2-yl)carbamoyl)piperidine-1-carboxylate was separated by SFC (Stationary phase: IC (25×5 cm); Mobile phase: 35% iPrOH/$CO_2$ with 0.1% $NH_4OH$) to give tert-butyl(2S,4R)-4-fluoro-2-methyl-4-[[(Z,1R)-1-methyl-3-methylsulfonyl-allyl]carbamoyl]piperidine-1-carboxylate (Rt=8.85 min, 33 g, 84.1 mmol) as a colorless oil and tert-butyl(2R,4S)-4-fluoro-2-methyl-4-[[(Z,1R)-1-methyl-3-methylsulfonyl-allyl]carbamoyl]piperidine-1-carboxylate (Rt=9.95 min, 33 g, 84.1 mmol) as a colorless oil. $^1H$ NMR (400 MHz, DMSO-$d_6$) δ ppm 8.43 (dd, J=1.9, 7.7 Hz, 1H), 6.47 (d, J=11.1 Hz, 1H), 6.30 (dd, J=9.6, 11.1 Hz, 1H), 5.45-5.30 (m, 1H), 3.97 (td, J=6.5, 9.2 Hz, 1H), 3.80-3.66 (m, 1H), 3.16-3.05 (m, 4H), 2.21-2.05 (m, 1H), 2.02-1.94 (m, 1H), 1.89-1.69 (m, 2H), 1.23 (d, J=6.9 Hz, 3H), 1.11 (d, J=6.5 Hz, 3H).

Step 3. To a solution of tert-butyl(2R,4S)-4-fluoro-2-methyl-4-[[(Z,1R)-1-methyl-3-methylsulfonyl-allyl]carbamoyl]piperidine-1-carboxylate (33 g, 84.1 mmol, 1 eq) in MeCN (330 mL, 0.25 M) was added p-toluenesulfonic acid monohydrate (17.6 g, 92.5 mmol, 1.1 eq) and this was stirred at 60 °C for 12 h. The mixture was concentrated to give crude 4-methylbenzenesulfonic acid salt of (2R,4S)-4-fluoro-2-methyl-N-((R,Z)-4-(methylsulfonyl)but-3-en-2-yl)piperidine-4-carboxamide (35.5 g, 76.4 mmol, 91% yield) as a colorless oil, which was used in the next step directly.

Intermediate (2R,4S)-N-((R,E)-5-(3,3-difluoroazetidin-1-yl)-5-oxopent-3-en-2-yl)-4-fluoro-2-methylpiperidine-4-carboxamide was synthesized in a manner analogous to (2R,4S)-4-fluoro-2-methyl-N-((R,Z)-4-(methylsulfonyl)but-3-en-2-yl)piperidine-4-carboxamide starting with the separation of rac-(2R,4S)-1-tert-butoxycarbonyl-4-fluoro-2-methyl-piperidine-4-carboxylic acid by chiral SFC to give (2R,4S)-1-tert-butoxycarbonyl-4-fluoro-2-methyl-piperidine-4-carboxylic acid and (2S,4R)-1-tert-butoxycarbonyl-4-fluoro-2-methyl-piperidine-4-carboxylic acid. Coupling with (E,4R)-4-amino-1-(3,3-difluoroazetidin-1-yl)pent-2-en-1-one and removal of the tert-butyl carbamate provided the title compound.

Scheme 38. Synthesis of (2R,4S)-1-((2′-chloro-5-methoxy-[1,1′-biphenyl]-2-yl)sulfonyl)-4-fluoro-2-methyl-N-((R,Z)-4-(methylsulfonyl)but-3-en-2-yl)piperidine-4-carboxamide (Compound 141)

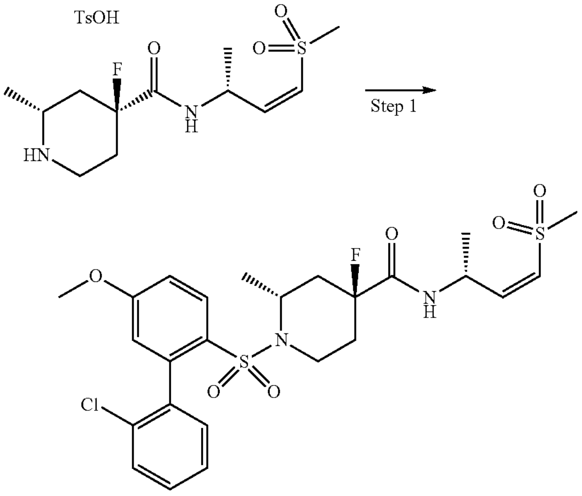

Step 1. To a solution of 4-methylbenzenesulfonic acid salt of (2R,4S)-4-fluoro-2-methyl-N-((R,Z)-4-(methylsulfonyl)but-3-en-2-yl)piperidine-4-carboxamide (35.5 g, 76.4 mmol, 1 eq) in DCM (500 mL, 0.15 M) was added DIPEA (29.6 g, 229 mmol, 3 eq). A solution of 2-(2-chlorophenyl)-4-methoxy-benzenesulfonyl chloride (29 g, 91.7 mmol, 1.2 eq) in DCM (15 mL) was added dropwise at 0 °C. The mixture was stirred at 30 °C for 12 h. The reaction mixture was poured into water (300 mL) and extracted with DCM (100 mL×3). The combined organic layers were washed with brine (100 mL×2), dried over $Na_2SO_4$, filtered and concentrated under reduced pressure. The residue was purified by column chromatography (PE:EtOAc=10:0-3:7) then slurried with MTBE (60 mL) to give (2R,4S)-1-[2-(2-chlorophenyl)-4-methoxy-phenyl]sulfonyl-4-fluoro-2-methyl-N-[(Z,1R)-1-methyl-3-methylsulfonyl-allyl]piperidine-4-carboxamide (Compound 141) (20.9 g, 36.1 mmol, 47%) as a white solid. $^1H$ NMR (400 MHz, DMSO-$d_6$, 298 K) 6 ppm 8.41-8.30 (m, 1H), 7.98 (dd, J=2.2, 8.9 Hz, 1H), 7.61-7.51 (m, 1H), 7.45-7.30 (m, 3H), 7.16 (td, J=3.2, 8.9 Hz, 1H), 6.88-6.80 (m, 1H), 6.44 (d, J=11.1 Hz, 1H), 6.26 (dd, J=9.6, 11.0 Hz, 1H), 5.34 (td, J=7.8, 15.7 Hz, 1H), 3.85 (s, 3H), 3.43-3.33 (m, 1H), 3.12 (d, J=2.5 Hz, 3H), 2.96-2.74 (m, 1H), 2.66-2.58 (m, 1H), 2.36-2.23 (m, 1H), 2.13-1.52 (m, 4H), 1.20 (d, J=6.9 Hz, 3H), 1.09-0.99 (m, 3H). [M+H] calculated for $C_{25}H_{30}ClFN_2O_6S_2$, 572; found 573.

Compounds 142-145 were synthesized in a manner analogous to Compound 141 starting with the appropriate sulfonyl chloride.

Compounds 151-155 were synthesized from (2R,4S)-N-((R,E)-5-(3,3-difluoroazetidin-1-yl)-5-oxopent-3-en-2-yl)-4-fluoro-2-methylpiperidine-4-carboxamide and the appropriate sulfonyl chloride in a manner analogous to Compound 141.

Scheme 39. Synthesis of 1-[2-(2-chlorophenyl)-4-methoxy-phenyl]sulfonyl-4-methoxy-N-[(Z,R)-1-methyl-3-methylsulfonyl-allyl]piperidine-4-carboxamide (Compound 146)

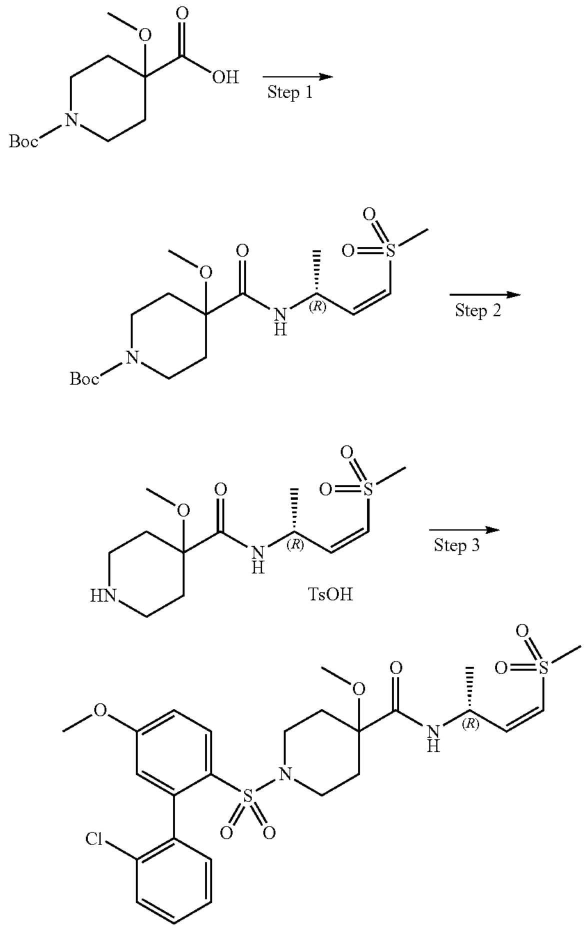

Step 1. To a solution of 1-tert-butoxycarbonyl-4-methoxy-piperidine-4-carboxylic acid (400 mg, 1.54 mmol, 1 eq) and (R,Z)-4-(methylsulfonyl)but-3-en-2-amine, TsOH salt (545 mg, 1.7 mmol, 1.1 eq) in DCM (2 mL, 0.77 M) was added DIPEA (598 mg, 4.6 mmol, 3 eq) and 2,4,6-tripropyl-1,3,5,2,4,6-trioxatriphosphorinane-2,4,6-trioxide (1.5 g, 2.3 mmol, 1.5 eq). The mixture was stirred at 25 °C for 2 h. The reaction mixture was diluted with water (5 mL) and extracted with DCM (5 mL×2), dried over $Na_2SO_4$ and filtered. The filtrate was concentrated under reduced pressure. The residue was purified by column chromatography (PE:EtOAc=1:0-1:1) to give tert-butyl 4-methoxy-4-[[(Z,1R)-1-methyl-3-methylsulfonyl-allyl]carbamoyl]piperidine-1-carboxylate (420 mg, 1.1 mmol, 70% yield) as a colorless oil. $^1$H NMR (400 MHz, DMSO-$d_6$) δ ppm 8.16 (d, J=8.0 Hz, 1H), 6.44 (d, J=11.4 Hz, 1H), 6.29 (dd, J=9.5, 11.1 Hz, 1H), 5.42-5.30 (m, 1H), 3.69 (br d, J=9.3 Hz, 2H), 3.11 (d, J=6.0 Hz, 3H), 3.04-2.90 (m, 2H), 1.99 (s, 3H), 1.75-1.62 (m, 4H), 1.39 (s, 9H), 1.22-1.19 (m, 3H).

Step 2. To a solution of tert-butyl 4-methoxy-4-[[(Z,1R)-1-methyl-3-methylsulfonyl-allyl]carbamoyl]piperidine-1-carboxylate (420 mg, 1.1 mmol, 1 eq) in MeCN (5 mL, 0.22 M) was added p-toluenesulfonic acid monohydrate (225 mg, 1.2 mmol, 1.1 eq). The mixture was stirred at 65 °C for 4 h. The reaction mixture was concentrated under reduced pressure to give 4-methoxy-N-[(Z,1R)-1-methyl-3-methylsulfonyl-allyl]piperidine-4-carboxamide 4-methylbenzenesulfonic acid salt (180 mg, 1.04 mmol, 96% yield) as a yellow solid.

Step 3. To a solution of 4-methoxy-N-[(Z,1R)-1-methyl-3-methylsulfonyl-allyl]piperidine-4-carboxamide, 4-methylbenzenesulfonic acid (200 mg, 0.43 mmol, 1 eq) in DCM (1 mL, 0.43 M) was added 2-(2-chlorophenyl)-4-methoxy-benzenesulfonyl chloride (205 mg, 0.65 mmol, 1.5 eq) and DIPEA (167 mg, 1.3 mmol, 3 eq). The mixture was stirred at 25 °C for 2 h. The reaction mixture was concentrated under reduced pressure to give a residue, which was purified by prep-HPLC to give 1-[2-(2-chlorophenyl)-4-methoxy-phenyl]sulfonyl-4-methoxy-N-[(Z,1R)-1-methyl-3-methyl-sulfonyl-allyl]piperidine-4-carboxamide (Compound 146) (47 mg, 0.08 mmol, 19% yield) as a white solid. $^1$H NMR (400 MHz, DMSO-$d_6$) δ ppm 8.11 (d, J=8.0 Hz, 1H), 7.93 (d, J=8.9 Hz, 1H), 7.50 (d, J=7.7 Hz, 1H), 7.44-7.31 (m, 3H), 7.18 (dd, J=2.7, 9.0 Hz, 1H), 6.83 (d, J=2.6 Hz, 1H), 6.43 (d, J=11.2 Hz, 1H), 6.30-6.23 (m, 1H), 5.40-5.28 (m, 1H), 3.85 (s, 3H), 3.11 (s, 3H), 3.02 (s, 3H), 3.00-2.92 (m, 2H), 2.65-2.52 (m, 2H), 1.74-1.56 (m, 4H), 1.19 (d, J=6.9 Hz, 3H). [M+H] calculated for $C_{25}H_{31}ClN_2O_7S_2$, 570; found 571.

Intermediate 4-fluoro-N-[(Z,1R)-1-methyl-3-methyl-sulfonyl-allyl]piperidine-4-carboxamide, 4-methylbenzene-sulfonic acid salt was synthesized in a manner analogous to 4-methoxy-N-[(Z,1R)-1-methyl-3-methylsulfonyl-allyl]piperidine-4-carboxamide, 4-methylbenzenesulfonic acid salt.

Scheme 40. Synthesis of Intermediates (2*R,4*R)-4-fluoro-1-[(4-methoxyphenyl)methyl]-2-methyl-N-[(Z,1R)-1-methyl-3-methylsulfonyl-allyl]piperidine-4-carboxamide and (2*S,4*S)-4-fluoro-1-[(4-methoxyphenyl)methyl]-2-methyl-N-[(Z,1R)-1-methyl-3-methylsulfonyl-allyl]piperidine-4-carboxamide

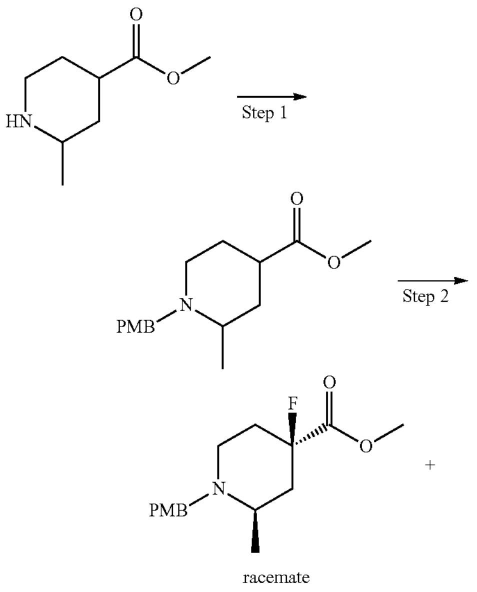

-continued

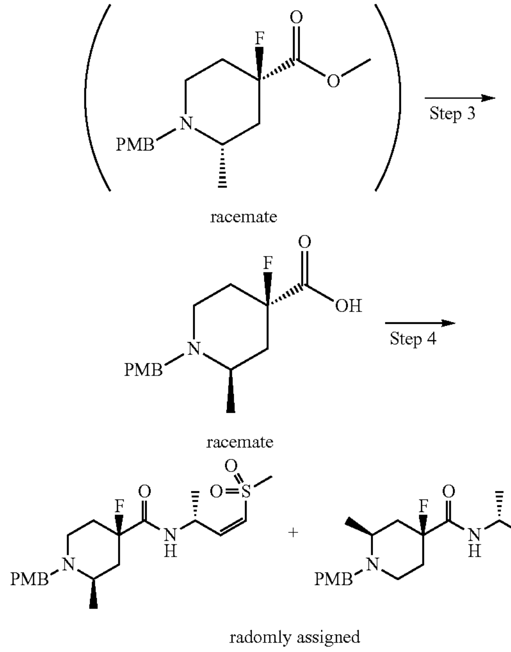

Step 1. To a solution of methyl 2-methylpiperidine-4-carboxylate (2.6 g, 13.4 mmol, 1 eq) in DMF (260 mL, 0.06 M) was added $K_2CO_3$ (5.6 g, 40.3 mmol, 3 eq) and 4-methoxybenzyl chloride (2.5 g, 16.1 mmol, 1.2 eq). The reaction mixture was stirred at 25 °C for 12 h. The mixture was poured into $H_2O$ (100 mL) and extracted with EtOAc (70 mL×3). The combined organic phases were washed with brine (100 mL), dried over $Na_2SO_4$, filtered and concentrated. The crude was purified by column chromatography to give methyl 1-[(4-methoxyphenyl)methyl]-2-methyl-piperidine-4-carboxylate (3.5 g, 12.6 mmol, 94% yield) as a colorless oil. $^1$H NMR (400 MHz, $CDCl_3$) δ ppm 7.26-7.19 (m, 2H), 6.88-6.82 (m, 2H), 4.04 (d, J=13.3 Hz, 1H), 3.82-3.79 (m, 3H), 3.71-3.64 (m, 3H), 3.08 (d, J=13.3 Hz, 1H), 2.91-2.80 (m, 1H), 2.66-2.48 (m, 1H), 2.40-2.18 (m, 2H), 1.93-1.73 (m, 2H), 1.71-1.47 (m, 2H), 1.32-1.18 (m, 3H).

Step 2. To a solution of methyl 1-[(4-methoxyphenyl) methyl]-2-methyl-piperidine-4-carboxylate (1.5 g, 5.41 mmol, 1 eq) in THF (15 mL) was added LiHMDS (4.1 mL, 8.11 mmol, 1.5 eq) dropwise at −45 °C and the mixture was stirred at −45 °C for 0.5 h. Then a solution of N-fluorobenzenesulfonimide (2.1 g, 6.76 mmol, 1.3 eq) in THF (15 mL) was added dropwise and the resulting solution was stirred at −45 °C for 0.5 h and −45 to 15 °C for 1 h. The reaction was quenched with sat. aq. $NH_4Cl$ (30 mL) and extracted with EtOAc (80 mL×2). The combined organic phases were washed with brine (50 mL×2), dried over $Na_2SO_4$, filtered, concentrated and purified by column chromatography (PE: EtOAc=9:1-7:3) to give methyl rac-(2R,4R)-4-fluoro-1-[(4-methoxyphenyl)methyl]-2-methyl-piperidine-4-carboxylate as a light yellow oil and methyl rac-(2S,4R)-4-fluoro-1-[(4-methoxyphenyl)methyl]-2-methyl-piperidine-4-carboxylate as a brown oil.

Step 3. A solution of methyl rac-(2R,4R)-4-fluoro-1-[(4-methoxyphenyl)methyl]-2-methyl-piperidine-4-carboxylate (1.7 g, 5.76 mmol, 1 eq) and LiOH·$H_2O$ (724 mg, 17.3 mmol, 3 eq) in THF (18 mL, 0.24 M) and $H_2O$ (6 mL, 0.24 M) was stirred at 25 °C for 2 h. The mixture was extracted with EtOAc (20 mL). The aqueous phase was adjusted with HCl (1 M) to pH=2. The resulting aqueous phase was extracted with EtOAc (30 mL×2). The combined organic phases were dried over $Na_2SO_4$ and filtered. The filtrate was concentrated. The crude product was purified by prep-HPLC to give rac-(2R,4R)-4-fluoro-1-[(4-methoxyphenyl)methyl]-2-methyl-piperidine-4-carboxylic acid (830 mg, 2.95 mmol, 51%) as a white solid. $^1$H NMR (400 MHz, DMSO-$d_6$) δ ppm 9.70-9.39 (m, 1H), 7.55-7.36 (m, 2H), 7.03 (d, J=8.6 Hz, 2H), 4.66-4.47 (m, 1H), 4.36-4.08 (m, 2H), 3.83-3.58 (m, 4H), 3.08-2.88 (m, 1H), 2.43-2.34 (m, 1H), 2.32-1.86 (m, 3H), 1.57-1.29 (m, 3H). [M+H] calculated for $C_{15}H_{20}FNO_3$, 281; found 282.

Step 4. To a solution of rac-(2R,4R)-4-fluoro-1-[(4-methoxyphenyl)methyl]-2-methyl-piperidine-4-carboxylic acid (830 mg, 2.95 mmol, 1 eq) and (Z,2R)-4-methylsulfonylbut-3-en-2-amine, 4-methylbenzenesulfonate (1.0 g, 3.25 mmol, 1.1 eq) in DCM (10 mL, 0.3 M) was added DIPEA (1.1 g, 8.85 mmol, 3 eq) and 2,4,6-tripropyl-1,3,5,2,4,6-trioxatriphosphorinane-2,4,6-trioxide (4.7 mg, 7.38 mmol, 2.5 eq). The mixture was stirred at 25 °C for 2 h. The reaction was poured into $H_2O$ (10 mL) and extracted with DCM (10 mL×3). The combined organic layers were dried over $Na_2SO_4$ and filtered. The filtrate was concentrated in vacuo to give a crude product, which was separated by SFC to give (2*R,4*R)-4-fluoro-1-[(4-methoxyphenyl)methyl]-2-methyl-N-[(Z,1R)-1-methyl-3-methylsulfonyl-allyl]piperidine-4-carboxamide (410 mg, 0.99 mmol, 34%) as a colorless oil $^1$H NMR (400 MHz, $CDCl_3$) δ ppm 7.77 (br d, J=7.9 Hz, 1H), 7.41 (br s, 1H), 7.22-7.19 (m, 1H), 6.85 (br d, J=8.5 Hz, 1H), 6.33-6.07 (m, 2H), 5.51-5.25 (m, 1H), 3.80 (s, 3H), 3.76-3.67 (m, 1H), 3.34-3.18 (m, 2H), 3.10 (br s, 3H), 2.41-2.35 (m, 3H), 2.22 (br s, 4H), 1.72-1.42 (m, 3H), 1.40-1.28 (m, 3H) and (2*S,4*S)-4-fluoro-1-[(4-methoxyphenyl)methyl]-2-methyl-N—[(Z,1R)-1-methyl-3-methylsulfonyl-allyl]piperidine-4-carboxamide (430 mg, 1.04 mmol, 35%) as a colorless oil $^1$H NMR (400 MHz, DMSO-$d_6$) δ ppm 7.47 (d, J=8.0 Hz, 2H), 7.11 (d, J=7.9 Hz, 2H), 6.52-6.43 (m, 1H), 6.31 (br t, J=10.3 Hz, 1H), 5.46-5.32 (m, 1H), 4.69-3.99 (m, 2H), 3.79-3.74 (m, 3H), 3.69-3.52 (m, 1H), 3.14-3.07 (m, 3H), 2.29 (s, 3H), 2.12-2.03 (m, 3H), 1.65-1.28 (m, 4H), 1.25-1.19 (m, 3H). [M+H] calculated for $C_{20}H_{29}FN_2O_4S$, 412; found 413.

Scheme 41. Synthesis of Intermediate (2*R,4*R)-4-fluoro-2-methyl-N-[(Z,1R)-1-methyl-3-methylsulfonyl-allyl]piperidine-4-carboxamide

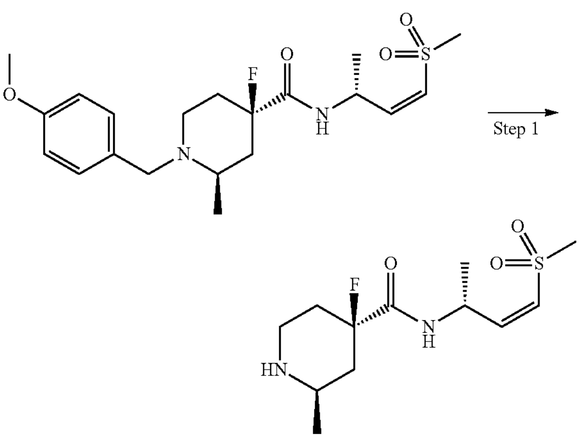

Step 1. Ammonium cerium(IV) nitrate (817 mg, 1.75 mmol, 3 eq) was added to a solution of (2*R,4*R)-4-fluoro- 1-[(4-methoxyphenyl)methyl]-2-methyl-N-[(Z,1R)-1-methyl-3-methylsulfonyl-allyl]piperidine-4-carboxamide (240 mg, 0.58 mmol, 1 eq) in MeCN/water (v/v 3:1, 3.2 mL, 0.18 M) at 0 °C and the mixture was stirred at 25 °C for 2 h. The reaction mixture was purified directly by prep-HPLC to give (2*R,4*R)-4-fluoro-2-methyl-N-[(Z,1R)-1-methyl-3-methylsulfonyl-allyl]piperidine-4-carboxamide (120 mg, 0.41 mmol, 70%) as a white solid. $^1$H NMR (400 MHz, DMSO-$d_6$) δ ppm 8.66-8.52 (m, 1H), 8.50-8.33 (m, 1H), 6.49 (d, J=11.3 Hz, 1H), 6.33 (dd, J=9.4, 11.1 Hz, 1H), 5.49-5.32 (m, 1H), 3.67-3.53 (m, 1H), 3.34-3.15 (m, 2H), 3.11 (s, 3H), 2.33-2.24 (m, 5H), 2.00-1.86 (m, 1H), 1.83-1.70 (m, 1H), 1.24 (s, 3H). [M+H] calculated for $C_{12}H_{21}FN_2O_3S$, 292; found 293.

Intermediate (2*S,4*S)-4-fluoro-2-methyl-N-[(Z,1R)-1-methyl-3-methylsulfonyl-allyl]piperidine-4-carboxamide was synthesized in an analogous manner using (2*S,4*S)-4-fluoro-1[(4-methoxyphenyl)methyl]-2-methyl-N-[(Z,1R)-1-methyl-3-methylsulfonyl-allyl]piperidine-4-carboxamide.

Compound 147 was synthesized from (2*R,4*R)-4-fluoro-2-methyl-N-[(Z,1R)-1-methyl-3-methylsulfonyl-allyl]piperidine-4-carboxamide in a manner analogous to Compound 141.

Compound 148 was synthesized from (2*S,4*S)-4-fluoro-2-methyl-N-[(Z,1R)-1-methyl-3-methylsulfonyl-allyl]piperidine-4-carboxamide in a manner analogous to Compound 141.

Scheme 42. Synthesis of Intermediate 2-(2-chlorophenyl)-4-(methoxymethyl)benzenesulfonyl chloride

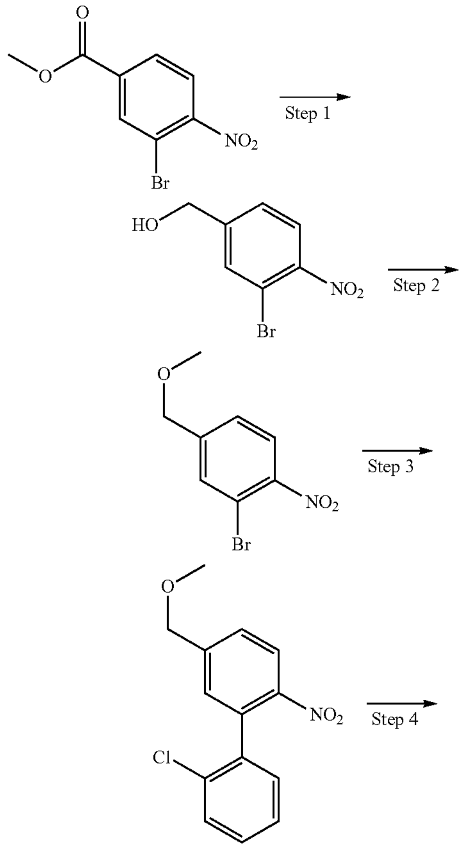

-continued

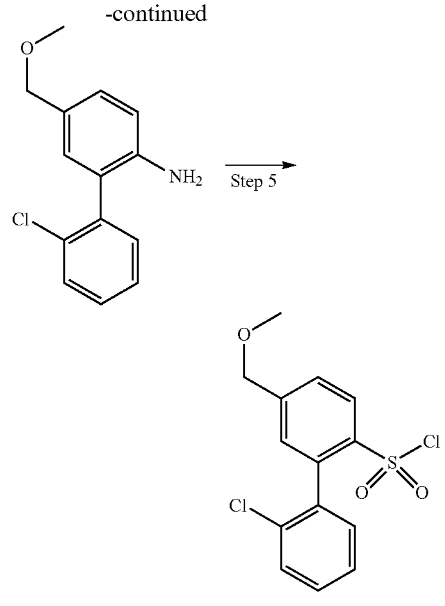

Step 1. To a solution of methyl 3-bromo-4-nitro-benzoate (5 g, 19.2 mmol, 1.0 eq) in methanol (80 mL, 0.24 M) was added sodium borohydride (7.5 g, 198 mmol, 10 eq) at 0 °C. The mixture was stirred at 25 °C for 6 h. The reaction mixture was quenched with water (100 mL) and extracted with EtOAc (60 mL×3). The combined organic layers were washed with brine (100 mL), dried over $Na_2SO_4$, filtered and concentrated under reduced pressure to give the crude product, which was purified by column chromatography (PE:EtOAc=100:1 to 0:1) to give (3-bromo-4-nitro-phenyl) methanol (3.8 g, 16.4 mmol, 85%) as a yellow solid. $^1$H NMR (400 MHz, $CDCl_3$) δ ppm 7.87 (d, J=8.4 Hz, 1H), 7.78 (d, J=0.8 Hz, 1H), 7.44 (dt, J=8.3, 0.8 Hz, 1H), 4.80 (s, 2H).

Step 2. To a solution of (3-bromo-4-nitro-phenyl)methanol (2.6 g, 11.2 mmol, 1.0 eq) in DMSO (20 mL, 0.6 M) was added iodomethane (6.4 g, 44.8 mmol, 4 eq) at 0 °C and the mixture was stirred for 1 h. Potassium hydroxide (2.5 g, 44.8 mmol, 4 eq) was added and the mixture was stirred at 20 °C for 2 h. The reaction mixture was quenched with water (200 mL) and extracted with EtOAc (100 mL×2). The combined organic layers were washed with brine (100 mL), dried over $Na_2SO_4$, filtered and concentrated under reduced pressure to give the crude product, which was purified by column chromatography (PE:EtOAc=100:1 to 1:1) to give 2-bromo-4-(methoxymethyl)-1-nitro-benzene (2.1 g, 8.5 mmol, 76%) as a yellow solid. $^1$H NMR (400 MHz, $CDCl_3$) δ ppm 7.86 (d, J=8.3 Hz, 1H), 7.74 (s, 1H), 7.41 (d, J=8.3 Hz, 1H), 4.51 (s, 2H), 3.45 (s, 3H).

Step 3. To a solution of methyl 2-bromo-4-(methoxymethyl)-1-nitro-benzene (2.1 g, 8.5 mmol, 1 eq), 2-chlorophenylboronic acid (2 g, 12.8 mmol, 1.5 eq) and potassium carbonate (2.4 g, 17 mmol, 2 eq) in toluene/water/ethanol (v/v/v 3:1:1, 40 mL, 0.2 M) was added tetrakis(triphenylphosphine)palladium(0) (986 mg, 0.85 mmol, 0.1 eq) at 25 °C. The suspension was purged with $N_2$ and stirred at 115 °C for 16 h. After cooling to rt, the reaction mixture was quenched with water (50 mL) and extracted with EtOAc (30 mL×3). The combined organic layers were washed with brine (50 mL), dried over $Na_2SO_4$, filtered and concentrated under reduced pressure to give the crude product, which was purified by column chromatography (PE:EtOAc=100:1 to 5:1) to give 2-(2-chlorophenyl)-4-(methoxymethyl)-1-nitro-benzene (2.20 g, 7.92 mmol, 93%) as a yellow oil. $^1$H NMR (400 MHz, $CDCl_3$) δ ppm 8.11 (d, J=8.5 Hz, 1H), 7.52 (dd, J=8.4, 1.3 Hz, 1H), 7.43-7.49 (m, 1H), 7.32-7.39 (m, 3H), 7.28-7.31 (m, 1H), 4.58 (s, 2H), 3.47 (s, 3H).

Step 4. To a solution of 2-(2-chlorophenyl)-4-(methoxymethyl)-1-nitro-benzene (2.2 g, 7.9 mmol, 1 eq) in ethanol/water (v/v 3:1, 40 mL, 0.2 M) was added ammonium chloride (2.1 g, 39.6 mmol, 5 eq) and iron powder (2.2 g, 39.6 mmol, 5 eq). The suspension was purged with $N_2$ and stirred at 80 °C for 2 h. After cooling to rt, the mixture reaction was filtered and the filtrate was concentrated under reduced pressure to remove EtOH. The crude was extracted with EtOAc (30 mL×3) and the combined organic layers were washed with brine (50 mL), dried over $Na_2SO_4$, filtered and concentrated under reduced pressure. The resulting residue was purified by column chromatography (PE:EtOAc=100:1 to 1:1) to give 2-(2-chlorophenyl)-4-(methoxymethyl)aniline (2 g, 7.27 mmol, 92%) as a yellow oil. $^1$H NMR (400 MHz, $CDCl_3$) δ ppm 7.48-7.53 (m, 1H), 7.30-7.36 (m, 3H), 7.20 (dd, J=8.1, 1.8 Hz, 1H), 7.05 (d, J=2.0 Hz, 1H), 6.79 (d, J=8.1 Hz, 1H), 4.38 (s, 2H), 3.38 (s, 3H).

Step 5. To a mixture of 2-(2-chlorophenyl)-4-(methoxymethyl)aniline (320 mg, 1.29 mmol, 1.0 eq) in HCl (6 N, 4 mL) and acetic acid (8 mL, 0.15 M) at 0 °C was added a solution of sodium nitrite (107 mg, 1.5 mmol, 1.2 eq) in water (0.5 mL, 0.15 M) dropwise at 0 °C. The reaction mixture (mixture 1) was stirred for 1.5 h at 0 °C. In a separate beaker (mixture 2), sulfur dioxide gas was bubbled through 10 mL of glacial acetic acid under vigorous stirring for 30 min. CuCl (76.7 mg, 0.77 mmol, 0.6 eq) was added and bubbling of sulfur dioxide gas was continued until the yellow-green suspension turned blue-green and most of the solids dissolved (about 1 h). Mixture 1 was added to mixture 2 at 0 °C and the reaction mixture was warmed to 20 °C and stirred for 1 h. The reaction was poured into ice-water (50 mL) and the precipitated gummy solid was extracted with MTBE (3×30 mL). The combined organic phase was washed with water (50 mL×3) and sat. $NaHCO_3$ (80 mL), dried over $Na_2SO_4$, filtered and concentrated to give crude product, which was purified by prep-TLC (PE:EtOAc=5:1) to give 2-(2-chlorophenyl)-4-(methoxymethyl)benzenesulfonyl chloride (25 mg, 0.075 mmol, 5.8%) as a yellow oil. $^1$H NMR (400 MHz, $CDCl_3$) δ ppm 8.22 (d, J=8.2 Hz, 1H), 7.58-7.63 (m, 1H), 7.47-7.52 (m, 1H), 7.33-7.42 (m, 4H), 4.60 (s, 2H), 3.47 (s, 3H).

Compound 149 was synthesized from 2-(2-chlorophenyl)-4-(methoxymethyl)benzenesulfonyl chloride in a manner analogous to Compound 141.

Compound 156 was synthesized from 2-(2-chlorophenyl)-4-(methoxymethyl)benzenesulfonyl chloride and (2R, 4S)-N-((R,E)-5-(3,3-difluoroazetidin-1-yl)-5-oxopent-3-en-2-yl)-4-fluoro-2-methylpiperidine-4-carboxamide in a manner analogous to Compound 141.

Scheme 43. Synthesis of Intermediate methyl (4*R)-4-fluoro-2,2-dimethyl-piperidine-4-carboxylate hydrochloride

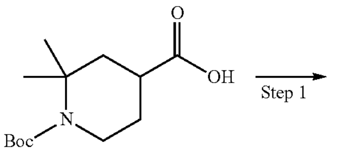

-continued

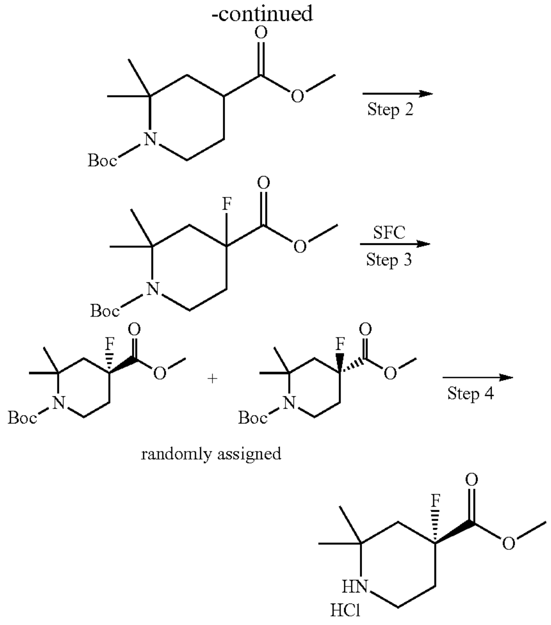

Step 1. To a solution of 1-tert-butoxycarbonyl-2,2-dimethyl-piperidine-4-carboxylic acid (150 mg, 0.58 mmol, 1 eq) in DCM (2 mL, 0.29 M) was added potassium carbonate (161 mg, 1.17 mmol, 2 eq) and iodomethane (165 mg, 1.17 mmol, 2 eq) and the mixture was stirred at 25 °C for 16 hours. The reaction mixture was concentrated under reduced pressure. The residue was purified by prep-TLC (PE:EA=5:1) to give 1-(tert-butyl) 4-methyl 2,2-dimethylpiperidine-1,4-dicarboxylate (60 mg, 0.22 mmol, 38%) as a colorless oil. $^1$H NMR (400 MHz, $CDCl_3$) δ ppm 3.70 (s, 3H), 3.63-3.69 (m, 1H), 3.30 (ddd, J=13.5, 8.9, 4.2 Hz, 1H), 2.58-2.69 (m, 1H), 1.90-2.00 (m, 1H), 1.66-1.85 (m, 3H), 1.51 (s, 3H), 1.43-1.49 (m, 9H), 1.34 (s, 3H).

Step 2. To a solution of 1-(tert-butyl) 4-methyl 2,2-dimethylpiperidine-1,4-dicarboxylate (100 mg, 0.37 mmol, 1 eq) in THF (1.5 mL, 0.25 M) was added LDA (2 M, 0.4 mL, 0.74 mmol, 2.0 eq) at −30 °C and this was stirred at −30 °C for 1.5 hours. To the mixture was added N-fluorobenzenesulfonimide (174 mg, 0.55 mmol, 1.5 eq) in THF (0.1 mL) dropwise at −30 °C and the reaction was stirred at 15 °C for 2 hours. The solution was diluted with sat. aq. $NH_4Cl$ (1 mL) and extracted with EtOAc (1 mL×3). The combined organic layers were washed with brine (1 mL×3), dried over $Na_2SO_4$, filtered, and concentrated under reduced pressure. The residue was purified by prep-TLC (PE:EtOAc=5:1) to give 1-(tert-butyl) 4-methyl 4-fluoro-2,2-dimethylpiperidine-1,4-dicarboxylate (20 mg, 0.07 mmol, 19%) as a colorless oil. $^1$H NMR (400 MHz, $CDCl_3$) δ ppm 3.61-3.76 (m, 3H), 3.35-3.54 (m, 2H), 1.80-2.24 (m, 4H), 1.34-1.40 (m, 15H).

Step 3. 1-(tert-Butyl) 4-methyl 4-fluoro-2,2-dimethylpiperidine-1,4-dicarboxylate (800 mg, 2.76 mmol) was separated by chiral SFC to give 1-tert-butyl 4-methyl(4*R)-4-fluoro-2,2-dimethyl-piperidine-1,4-dicarboxylate (400 mg, 1.38 mmol, 40% yield) as a yellow oil and 1-tert-butyl 4-methyl(4*S)-4-fluoro-2,2-dimethyl-piperidine-1,4-dicarboxylate (250 mg, 0.86 mmol, 25% yield) as a yellow oil.

Step 4. To a solution of 1-tert-butyl 4-methyl(4*R)-4-fluoro-2,2-dimethyl-piperidine-1,4-dicarboxylate (250 mg, 0.86 mmol, 1 eq) in methanol (2.5 mL, 0.35 M) was added HCl/MeOH (4 M, 1 mL) and the reaction was stirred at 25 °C for 2 hours. The reaction was concentrated under reduced pressure to give methyl(4*R)-4-fluoro-2,2-dimethyl-piperidine-4-carboxylate hydrochloride (190 mg, 0.84 mmol, 97%) as a yellow oil. $^1$H NMR (400 MHz, DMSO-$d_6$) δ ppm 9.48 (br s, 2H), 3.75 (s, 3H), 3.28-3.18 (m, 2H), 2.42-2.08 (m, 4H), 1.38 (d, J=2.6 Hz, 6H).

Compound 150 was synthesized by coupling 2'-chloro-5-methoxy-[1,1'-biphenyl]-2-sulfonyl chloride and methyl (4*R)-4-fluoro-2,2-dimethyl-piperidine-4-carboxylate hydrochloride in a manner analogous to Step 2, 4, and 5 of the synthesis of Compound 47.

Intermediate methyl(2R,4S)-4-fluoro-2-methylpiperidine-4-carboxylate was synthesized in a manner analogous to methyl(4*R)-4-fluoro-2,2-dimethyl-piperidine-4-carboxylate hydrochloride starting with 1-tert-butyl 4-methyl 4-fluoro-2-methyl-piperidine-1,4-dicarboxylate in Step 3.

Compound 250 was synthesized in a manner analogous to Compound 47 starting from methyl(2R,4S)-4-fluoro-2-methylpiperidine-4-carboxylate and 2-bromo-4-(trifluoromethoxy)benzenesulfonyl chloride in Step 2.

Compound 251 was synthesized in a manner analogous to Compound 134 starting from 2-bromo-4-(difluoromethoxy) benzenamine in Step 1 and using methyl(2R,4S)-4-fluoro-2-methylpiperidine-4-carboxylate in Step 2.

Intermediate (2R,4S)-1-((5-acetyl-2'-chloro-[1,1'-biphenyl]-2-yl)sulfonyl)-4-fluoro-2-methylpiperidine-4-carboxylic acid was synthesized in a manner analogous to 1-[2-(2-chlorophenyl)-4-(trifluoromethyl)phenyl]sulfonyl-4-fluoro-piperidine-4-carboxylic acid starting from 1-(4-amino-3-bromophenyl)ethanone in Step 1 and using methyl (2R,4S)-4-fluoro-2-methylpiperidine-4-carboxylate in Step 2.

Intermediate (2R,4S)-1-((2'-chloro-5-formyl-[1,1'-biphenyl]-2-yl)sulfonyl)-4-fluoro-2-methylpiperidine-4-carboxylic acid was synthesized in a manner analogous to 1-[2-(2-chlorophenyl)-4-(trifluoromethyl)phenyl]sulfonyl-4-fluoro-piperidine-4-carboxylic acid, Steps 1-3, starting from 4-amino-3-bromobenzaldehyde in Step 1 and using methyl (2R,4S)-4-fluoro-2-methylpiperidine-4-carboxylate in Step 2.

Scheme 44. Synthesis of Intermediate 5-bromobenzo[b]thiophene-6-sulfonyl chloride

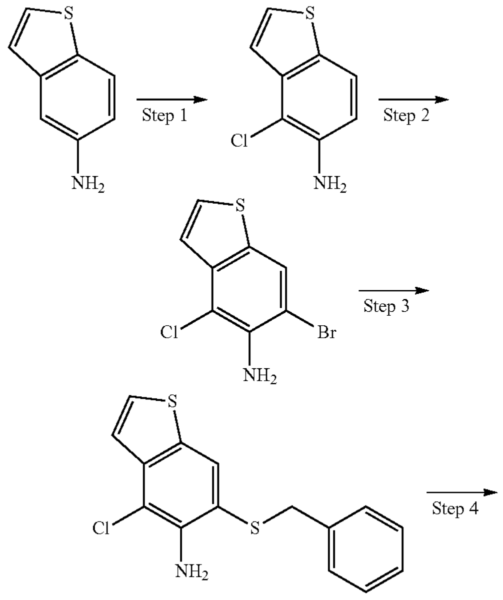

-continued

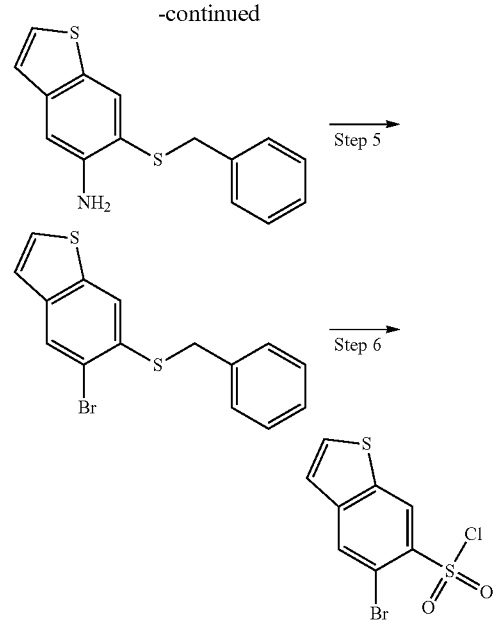

Step 1. A solution of benzothiophen-5-amine (11 g, 73.7 mmol, 1 eq) and NCS (9.8 g, 73.7 mmol, 1 eq) in acetonitrile (110 mL, 0.67 M) was stirred at 25 °C for 16 h. The mixture was diluted with $H_2O$ (10 mL) and extracted with EtOAc (20 mL×3). The extract was washed with brine (20 mL), dried over $Na_2SO_4$ and filtered. The filtrate was concentrated in vacuo. The residue was purified by column chromatography (PE:EtOAc=10:1-1:1) to afford 4-chlorobenzothiophen-5-amine (6.3 g, 34.3 mmol, 46%) as a yellow oil.

Step 2. A solution of 4-chlorobenzothiophen-5-amine (6.3 g, 34.3 mmol, 1 eq) and NBS (6.1 g, 34.3 mmol, 1 eq) in ACN (70 mL, 0.49 M) was stirred at 20 °C for 16 h under $N_2$. The mixture was diluted with $H_2O$ (10 mL) and extracted with EtOAc (20 mL). The extract was washed with brine (20 mL), dried over $Na_2SO_4$ and filtered. The filtrate was concentrated in vacuo. The residue was purified by column chromatography (PE:EtOAc=1:1) to afford 6-bromo-4-chloro-benzothiophen-5-amine (5.8 g, 22.1 mmol, 64%) as a yellow oil.

Step 3. A solution of 6-bromo-4-chloro-benzothiophen-5-amine (5.8 g, 22.1 mmol, 1 eq), benzyl mercaptan (3.6 g, 28.7 mmol, 1.3 eq), DIPEA (5.7 g, 44.2 mmol, 2 eq), 4,5-bis(diphenylphosphino)-9,9-dimethylxanthene (1.3 g, 2.21 mmol, 0.1 eq) and tris(dibenzylideneacetone)dipalladium (1 g, 1.1 mmol, 0.05 eq) in toluene (60 mL, 0.37 M) was stirred at 130 °C for 16 h under $N_2$. After cooling to rt, the reaction mixture was poured into water (500 mL) and extracted with EtOAc (500 mL×3). The combined organic layers were washed with brine (200 mL×2), dried over $Na_2SO_4$, filtered, and concentrated under reduced pressure. The residue was purified by column chromatography (PE: EtOAc=10:1) to afford 6-benzylsulfanyl-4-chloro-benzothiophen-5-amine (6.6 g, 21.6 mmol, 98%) as a yellow oil.

Step 4. To a solution of 6-benzylsulfanyl-4-chloro-benzothiophen-5-amine (4 g, 13.1 mmol, 1 eq) in 1,4-dioxane (40 mL, 0.33 M) was added triethylamine (2.6 g, 26.2 mmol, 2 eq), triethylsilane (7.6 g, 65.4 mmol, 5 eq), $Pd_2(dba)_3$ (0.6 g, 0.654 mmol, 0.05 eq) and XPhos (0.6 g, 1.31 mmol, 0.1 eq) under $N_2$. The reaction was stirred at 100 °C for 16 h under $N_2$. After cooling to rt, the reaction mixture was poured into water (300 mL) and extracted with EtOAc (200 mL×3). The combined organic layers were washed with brine (200 mL×2), dried over $Na_2SO_4$ and filtered. The filtrate was concentrated under reduced pressure. The residue was purified by column chromatography (PE:EtOAc=3:1) to give 6-benzylsulfanylbenzothiophen-5-amine (3 g, 11.1 mmol, 84%) as a yellow solid.

Step 5. A solution of 6-benzylsulfanylbenzothiophen-5-amine (1.5 g, 5.53 mmol, 1 eq), tert-butyl nitrite (855 mg, 8.29 mmol, 1.5 eq) and cuprous bromide (951 mg, 6.63 mmol, 1.2 eq) in ACN (30 mL, 0.18 M) was stirred at 65 °C for 2 h under $N_2$. The mixture was diluted with $H_2O$ (10 mL) and extracted with EtOAc (20 mL). The extract was washed with brine (20 mL), dried over $Na_2SO_4$ and filtered. The filtrate was concentrated in vacuo. The residue was purified by prep-TLC (PE:EtOAc=10:1) to afford 6-benzylsulfanyl-5-bromo-benzothiophene (120 mg, 0.36 mmol, 6.5%) as a yellow solid.

Step 6. To 6-benzylsulfanyl-5-bromo-benzothiophene (30 mg, 0.09 mmol, 1 eq) in acetic acid (1 mL) and water (0.3 mL) was added N-chlorosuccinimide (48 mg, 0.36 mmol, 4 eq). The mixture was stirred at 25 °C for 1 h. The mixture was diluted with water (20 mL) and extracted with EtOAc (20 mL). The extract was washed with brine (20 mL), dried over $Na_2SO_4$ and filtered. The filtrate was concentrated in vacuo to afford crude 5-bromobenzo[b]thiophene-6-sulfonyl chloride (20 mg, 0.064 mmol, 72% yield).

Compound 157 was synthesized in a manner analogous to Compound 47, Steps 2-5, using 5-bromobenzo[b]thiophene-6-sulfonyl chloride in Step 2.

Scheme 45. Synthesis of Intermediate 1-(tert-butyl) 3-ethyl (3R,4R)-4-(2-chlorophenyl)pyrrolidine-1,3-dicarboxylate

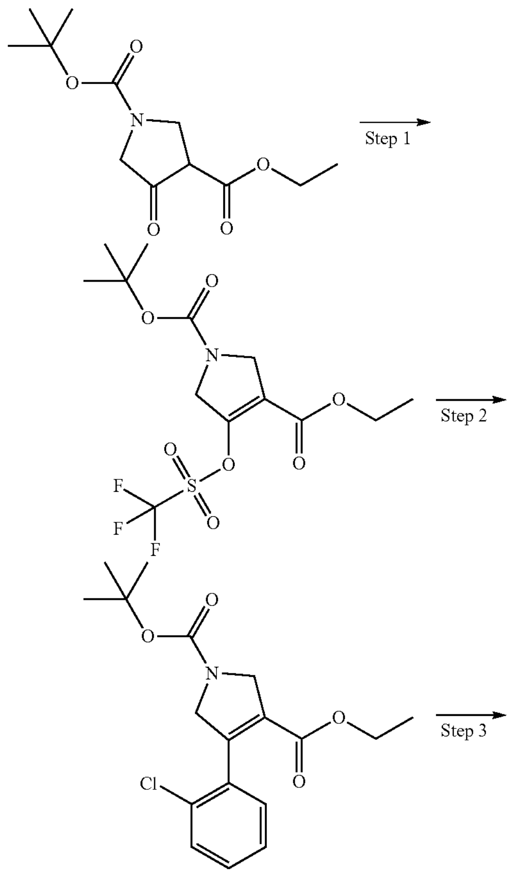

-continued

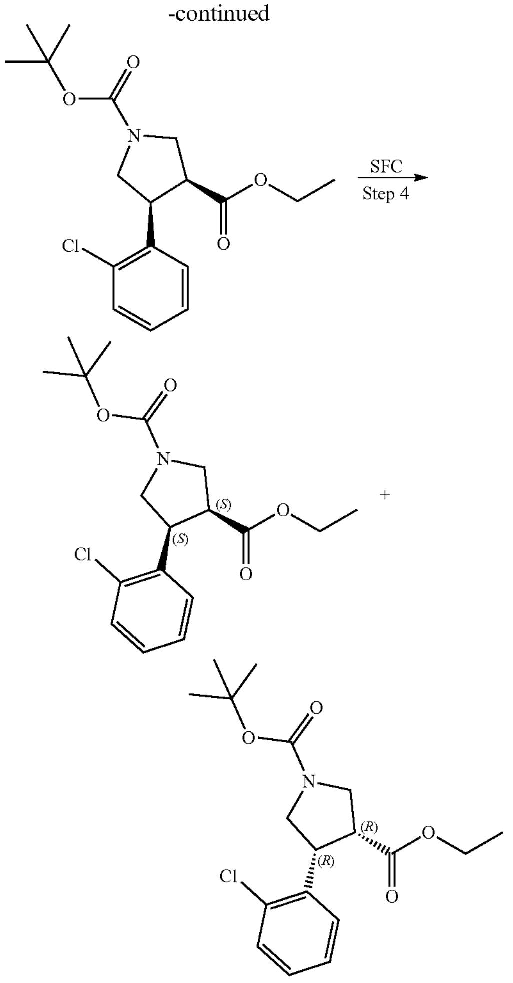

Step 1. To a solution of 1-(tert-butyl) 3-ethyl 4-oxopyrrolidine-1,3-dicarboxylate (100 g, 389 mmol, 1 eq) in toluene (2 L, 0.19 M) was added DIPEA (75.4 g, 583 mmol, 1.5 eq) and trifluoromethanesulfonic anhydride (132 g, 466 mmol, 1.2 eq) at 0 °C. The reaction was stirred at 20 °C for 16 h. The solution was evaporated to get the crude product 1-(tert-butyl) 3-ethyl 4-(trifluoromethylsulfonyloxy)-2,5-dihydropyrrole-1,3-dicarboxylate (150 g, 385 mmol, 99%) as a brown oil.

Step 2. To a solution of 1-(tert-butyl) 3-ethyl 4-(trifluoromethylsulfonyloxy)-2,5-dihydropyrrole-1,3-dicarboxylate (22 g, 56.5 mmol, 1 eq) in THF (360 mL, 0.16 M) was added 2-chlorophenylboronic acid (9.7 g, 62.2 mmol, 1.1 eq), potassium phosphate tribasic (164 g, 771 mmol, 2 eq) and tetrakis(triphenylphosphine)palladium(0) (22.3 g, 19.3 mmol, 0.05 eq). The reaction was stirred at 70 °C for 12 h under $N_2$. After cooling to rt, the solution was diluted with water (350 mL) and extracted with EtOAc (400 mL×3). The combined organic phases were washed with brine (150 mL×3), dried over $Na_2SO_4$, filtered, and concentrated. The crude product was purified by column chromatography (PE:EtOAc=1:0-1:1) to give 1-(tert-butyl) 3-ethyl 4-(2-chlorophenyl)-2,5-dihydro-1H-pyrrole-1,3-dicarboxylate (105 g, 298 mmol, 77%) as a yellow solid. $^1H$ NMR (400 MHz, $CDCl_3$) δ ppm 7.40-7.44 (m, 1H), 7.27-7.32 (m, 2H), 7.19 (br s, 1H), 4.43-4.62 (m, 4H), 4.05 (q, J=7.1 Hz, 2H), 1.51 (br d, J=11.3 Hz, 9H), 0.99-1.08 (m, 3H).

Step 3. To a solution of 1-(tert-butyl) 3-ethyl 4-(2-chlorophenyl)-2,5-dihydro-1H-pyrrole-1,3-dicarboxylate (25 g, 71.1 mmol, 1.0 eq) in ethanol (80 mL, 0.04 M) and ethyl acetate (240 mL, 0.04 M) was added $PtO_2$ (5 g, 35.5 mmol, 0.5 eq) and this was stirred at 20 °C for 16 h under $H_2$ (15 psi). The solution was filtered and evaporated. The residue was purified by prep-HPLC to give rac-1-(tert-butyl) 3-ethyl (3S,4S)-4-(2-chlorophenyl)pyrrolidine-1,3-dicarboxylate (7 g, 42.4 mmol, 30%) as a white solid. $^1H$ NMR (400 MHz, $CDCl_3$) δ ppm 7.36-7.42 (m, 1H), 7.18-7.25 (m, 3H), 3.54-3.90 (m, 8H), 1.50 (s, 9H), 0.89 (t, J=7.1 Hz, 3H).

Step 4. Rac-1-(tert-butyl) 3-ethyl(3S,4S)-4-(2-chlorophenyl)pyrrolidine-1,3-dicarboxylate (17 g, 48.0 mmol, 1 eq) was separated by SFC to give 1-(tert-butyl) 3-ethyl(3R,4R)-4-(2-chlorophenyl)pyrrolidine-1,3-dicarboxylate (8 g, 22.6 mmol, 47%) as a white solid $^1H$ NMR (400 MHz, $CDCl_3$) δ ppm 7.36-7.41 (m, 1H), 7.18-7.24 (m, 3H), 3.56-3.88 (m, 8H), 1.51 (s, 9H), 0.89 (t, J=7.1 Hz, 3H) and 1-(tert-butyl) 3-ethyl(3S,4S)-4-(2-chlorophenyl)pyrrolidine-1,3-dicarboxylate (8 g, 22.6 mmol, 47%) as a white solid $^1H$ NMR (400 MHz, $CDCl_3$) δ ppm 7.36-7.41 (m, 1H), 7.16-7.24 (m, 3H), 4.04-4.19 (m, 1H), 3.58-3.87 (m, 7H), 1.50 (s, 9H), 0.88 (t, J=7.1 Hz, 3H).

Intermediates rac-1-(tert-butyl) 3-ethyl(3S,4S)-4-(2-chloro-6-fluorophenyl)pyrrolidine-1,3-dicarboxylate, rac-1-(tert-butyl) 3-ethyl(3S,4S)-4-(2-chloro-5-fluorophenyl)pyrrolidine-1,3-dicarboxylate, rac-1-(tert-butyl) 3-ethyl(3S,4S)-4-(2-chloro-4-fluorophenyl)pyrrolidine-1,3-dicarboxylate, rac-1-(tert-butyl) 3-ethyl(3S,4S)-4-(2-chloro-3-fluorophenyl)pyrrolidine-1,3-dicarboxylate, rac-1-(tert-butyl) 3-ethyl(3S,4S)-4-(2-chloro-5-methylphenyl) pyrrolidine-1,3-dicarboxylate, rac-1-(tert-butyl) 3-ethyl(3S,4S)-4-(2-chloro-4-methylphenyl)pyrrolidine-1,3-dicarboxylate, rac-1-(tert-butyl) 3-ethyl(3S,4S)-4-(2-chloro-3-methylphenyl)pyrrolidine-1,3-dicarboxylate, and rac-1-(tert-butyl) 3-ethyl(3S,4S)-4-(2-fluoro-3-fluorophenyl) pyrrolidine-1,3-dicarboxylate were synthesized in a manner similar to rac-1-(tert-butyl) 3-ethyl(3S,4S)-4-(2-chlorophenyl)pyrrolidine-1,3-dicarboxylate.

Scheme 46. Synthesis of tert-butyl cis-(3RS,4RS)-3-(2-chlorophenyl)-4-(4-fluoro-4-(((R,Z)-4-(methylsulfonyl)but-3-en-2-yl)carbamoyl) piperidine-1-carbonyl)pyrrolidine-1-carboxylaye (Compound 158)

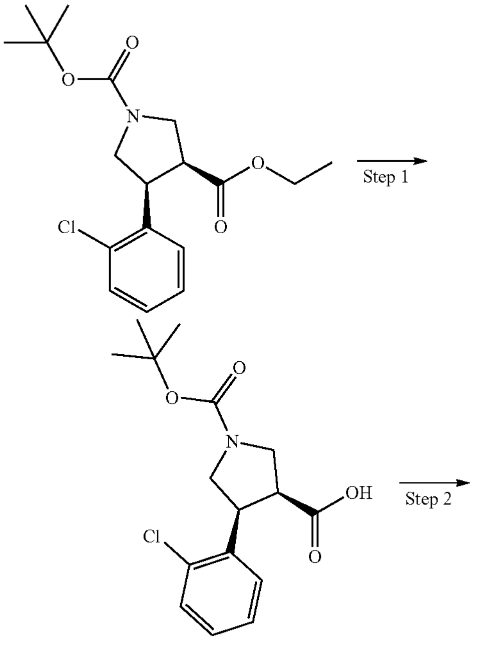

-continued

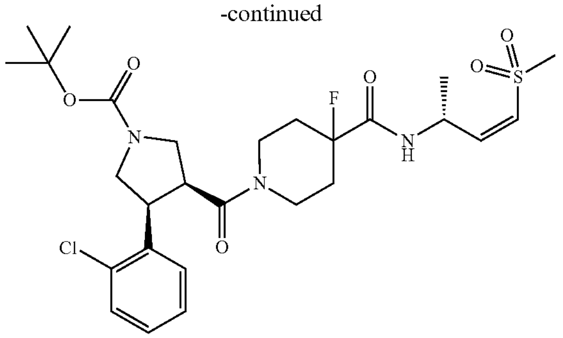

Step 1. To a solution of rac-1-(tert-butyl) 3-ethyl(3S,4S)-4-(2-chlorophenyl)pyrrolidine-1,3-dicarboxylate (250 mg, 0.71 mmol, 1 eq) in DCE (20 mL) was added trimethyltin hydroxide (650 mg, 2.13 mmol, 3 eq). The reaction was stirred at 70 °C for 72 h. The solution was filtered, diluted with water (20 mL) and extracted with EtOAc (30 mL×3). The combined organic layers were washed with brine (10 mL×3), dried over $Na_2SO_4$, filtered, and concentrated under reduced pressure to give rac-(3S,4S)-1-(tert-butoxycarbonyl)-4-(2-chlorophenyl)pyrrolidine-3-carboxylic acid (230 mg, 0.71 mmol, 100% yield).

Step 2. To a solution of rac-(3S,4S)-1-(tert-butoxycarbonyl)-4-(2-chlorophenyl)pyrrolidine-3-carboxylic acid (230 mg, 0.71 mmol, 1 eq) in DMF (5 mL, 0.14 M) was added HATU (350 mg, 1.06 mmol, 1.5 eq), DIPEA (0.3 mL, 2.13 mmol, 3 eq) and 4-fluoro-N-[(Z,1R)-1-methyl-3-methylsulfonyl-allyl]piperidine-4-carboxamide 4-methylbenzenesulfonic acid salt (318 mg, 0.71 mmol, 1 eq). The reaction was stirred at 20 °C for 2 h. The solution was diluted with water (10 mL) and extracted with EtOAc (20 mL×3). The combined organic layers were washed with brine (10 mL×3), dried over $Na_2SO_4$, filtered, and concentrated under reduced pressure. The residue was purified by prep-HPLC to give tert-butyl(3RS,4RS)-3-(2-chlorophenyl)-4-(4-fluoro-4-(((R,Z)-4-(methylsulfonyl)but-3-en-2-yl)carbamoyl)piperidine-1-carbonyl)pyrrolidine-1-carboxylate (Compound 158) (23 mg, 0.039 mmol, 5.6% yield). $^1H$ NMR (400 MHz, DMSO-$d_6$) δ ppm 8.39-8.17 (m, 1H), 7.50-7.40 (m, 1H), 7.20-7.14 (m, 1H), 7.36-7.13 (m, 2H), 6.50-6.40 (m, 1H), 6.31-6.20 (m, 1H), 5.32 (br d, J=8.5 Hz, 1H), 4.14-3.95 (m, 2H), 3.90 (br s, 1H), 3.74-3.45 (m, 5H), 3.29 (br s, 1H), 3.18-3.03 (m, 3H), 2.69-2.56 (m, 1H), 2.42-2.30 (m, 1H), 2.03-1.72 (m, 2H), 1.70-1.49 (m, 2H), 1.47-1.38 (m, 9H), 1.26-1.14 (m, 3H). [M+H] calculated for $C_{27}H_{37}ClFN_3O_6S$, 585.2; found 586.3.

Scheme 47. Synthesis of Intermediates tert-butyl (3*S,4*S)-3-(2-chlorophenyl)-4-(4-fluoro-4-(((R,Z)-4-(methylsulfonyl)but-3-en-2-yl)carbamoyl)piperidine-1-carbonyl)pyrrolidine-1-carboxylate and tert-butyl)(3*R,4*R)-3-(2-chlorophenyl)-4-(4-fluoro-4-(((R,Z)-4-(methylsulfonyl)but-3-en-2-yl)carbamoyl)piperidine-1-carbonyl)pyrrolidine-1-carboxylate

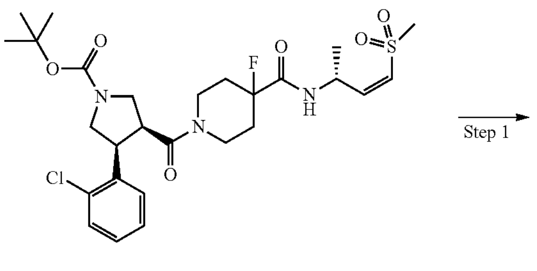

-continued

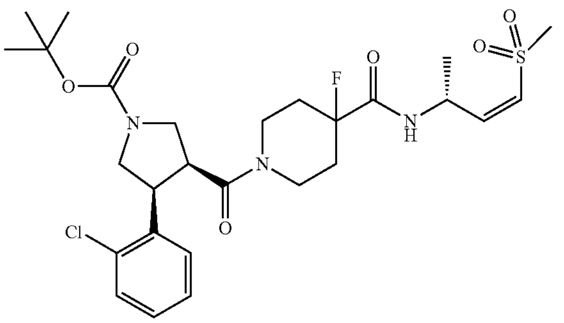

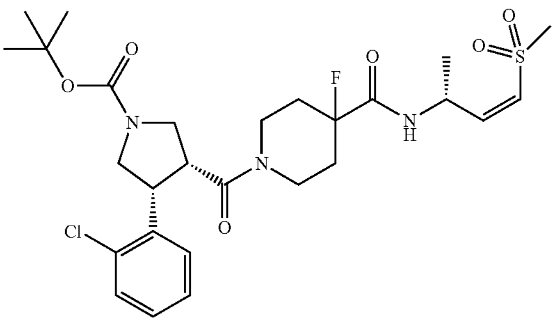

Step 1. tert-Butyl(3RS,4RS)-3-(2-chlorophenyl)-4-(4-fluoro-4-(((R,Z)-4-(methylsulfonyl)but-3-en-2-yl)carbamoyl)piperidine-1-carbonyl)pyrrolidine-1-carboxylate was separated by chiral SFC to give tert-butyl(3*S,4*S)-3-(2-chlorophenyl)-4-(4-fluoro-4-(((R,Z)-4-(methylsulfonyl)but-3-en-2-yl)carbamoyl)piperidine-1-carbonyl)pyrrolidine-1-carboxylate and tert-butyl(3*R,4*R)-3-(2-chlorophenyl)-4-(4-fluoro-4-(((R,Z)-4-(methylsulfonyl)but-3-en-2-yl)carbamoyl)piperidine-1-carbonyl)pyrrolidine-1-carboxylate.

Scheme 48. Synthesis of isopropyl (3R,4R)-3-(2-chlorophenyl)-4-(4-fluoro-4-(((R,Z)-4-(methylsulfonyl)but-3-en-2yl)carbamoyl)piperidine-1-carbonyl)pyrrolidine-1-carboxylate (Compound 159)

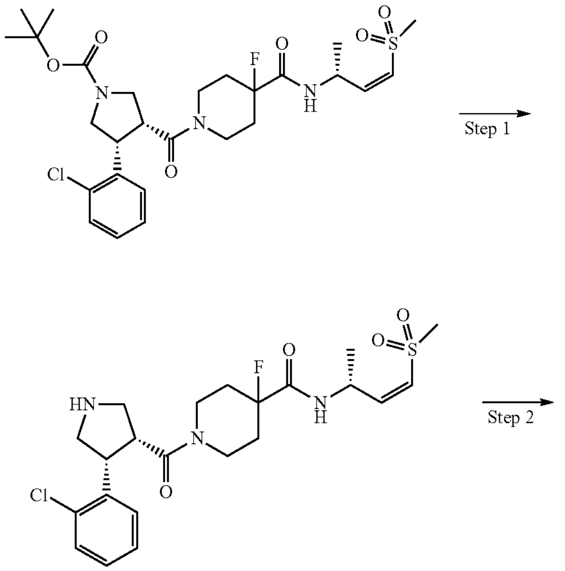

-continued

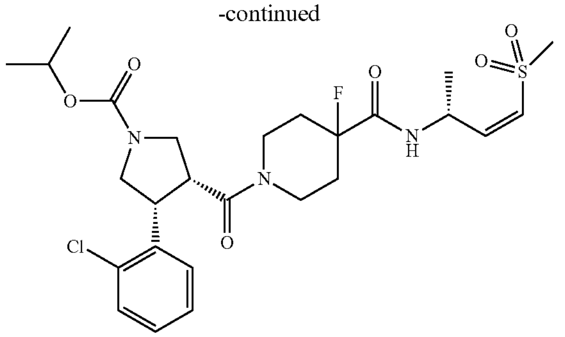

Step 1. To a solution of tert-butyl(3R,4R)-3-(2-chlorophenyl)-4-(4-fluoro-4-(((R,Z)-4-(methylsulfonyl)but-3-en-2-yl)carbamoyl)piperidine-1-carbonyl)pyrrolidine-1-carboxylate (600 mg, 1.02 mmol, 1 eq) in DCM (5 mL) was added TFA (3 mL). The mixture was stirred at 25 °C for 1 hr. The reaction mixture was concentrated under reduced pressure to give 1-((3R,4R)-4-(2-chlorophenyl)pyrrolidine-3-carbonyl)-4-fluoro-N-((R,Z)-4-(methylsulfonyl)but-3-en-2-yl)piperidine-4-carboxamide (480 mg, 0.988 mmol, 96% yield).

Step 2. To a solution of 1-((3R,4R)-4-(2-chlorophenyl)pyrrolidine-3-carbonyl)-4-fluoro-N-((R,Z)-4-(methylsulfonyl)but-3-en-2-yl)piperidine-4-carboxamide (120 mg, 0.25 mmol, 1 eq) in DCM (5 mL) was added isopropyl chloroformate (36 mg, 0.3 mmol, 1.2 eq) at 0 °C. After 10 mins, DIPEA (96 mg, 0.74 mmol, 3 eq) was added. The reaction was stirred at 25 °C for 1 hour. The mixture was concentrated and purified by prep-HPLC to give isopropyl(3R,4R)-3-(2-chlorophenyl)-4-(4-fluoro-4-(((R,Z)-4-(methylsulfonyl)but-3-en-2-yl)carbamoyl)piperidine-1-carbonyl)pyrrolidine-1-carboxylate (Compound 159) (88 mg, 0.15 mmol, 62% yield). $^{1}H$ NMR (400 MHz, DMSO-$d_6$) δ ppm 8.37-8.20 (m, 1H), 7.45 (br d, J=7.2 Hz, 1H), 7.34-7.13 (m, 3H), 6.45 (d, J=11.2 Hz, 1H), 6.31-6.21 (m, 1H), 5.33 (br s, 1H), 4.85-4.74 (m, 1H), 4.15-3.99 (m, 3H), 3.78-3.59 (m, 4H), 3.58-3.53 (m, 1H), 3.12 (d, J=17.9 Hz, 3H), 2.69-2.54 (m, 1H), 2.40-2.31 (m, 1H), 2.01-1.72 (m, 1H), 1.69-1.44 (m, 2H), 1.28-1.23 (m, 1H), 1.20 (t, J=7.3 Hz, 9H). [M+H] calculated for $C_{26}H_{35}ClFN_3O_6S$, 571; found 572.

Compounds 160-162 were synthesized in an analogous manner to Compound 159 using the appropriate chloroformate or acid chloride in the final step.

Compound 199 was synthesized in an analogous manner to Compound 159 using tert-butyl(3S,4S)-3-(2-chlorophenyl)-4-(4-fluoro-4-(((R,Z)-4-(methylsulfonyl)but-3-en-2-yl)carbamoyl)piperidine-1-carbonyl)pyrrolidine-1-carboxylate in Step 1.

Scheme 49. Synthesis of Intermediate (3R,4R)-4-(2-chlorophenyl)-1-(2,2,2-trifluoroethyl)pyrrolidine-3-carboxylic acid

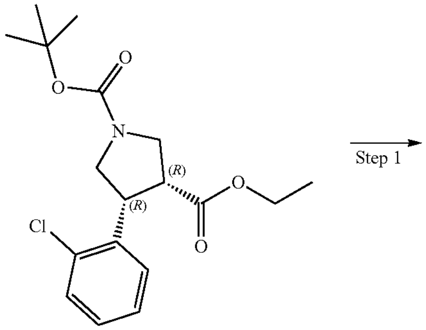

-continued

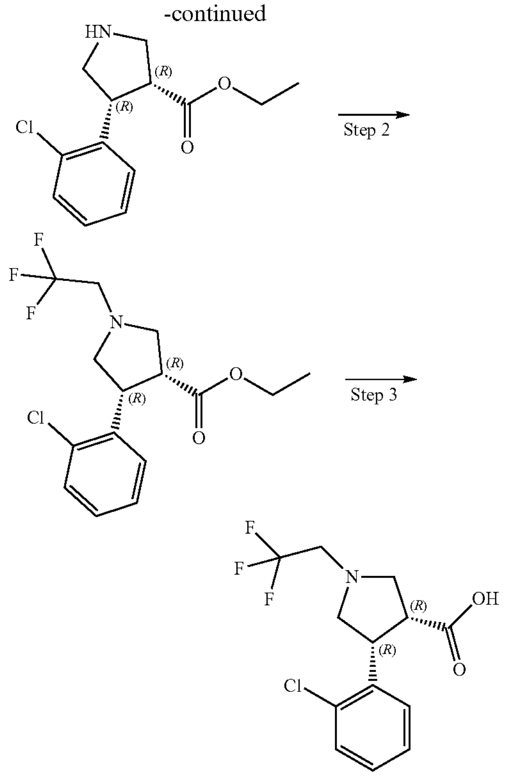

Step 1. To a solution of 1-(tert-butyl) 3-ethyl(3R,4R)-4-(2-chlorophenyl)pyrrolidine-1,3-dicarboxylate (7 g, 19.8 mmol, 1 eq) in DCM (70 mL, 0.28 M) was added TFA (20 ml) and the reaction was stirred at 25 °C for 3 h. The solution was quenched with sat. aq. sodium bicarbonate (5 mL) and extracted with EtOAc (5 mL×3). The combined organic phases were washed with brine (5 mL×3), dried over $Na_2SO_4$, and filtered. The filtrate was evaporated to get the crude product ethyl(3R,4R)-4-(2-chlorophenyl)pyrrolidine-3-carboxylate (5 g, 19.7 mmol, 100%) as a yellow oil, which was used in the next step directly.

Step 2. To a solution of ethyl(3R,4R)-4-(2-chlorophenyl) pyrrolidine-3-carboxylate (10 g, 39.4 mmol, 1 eq) in toluene (100 mL, 0.39 M) was added DIPEA (12 g, 118 mmol, 3 eq). The mixture was stirred at 20 °C for 5 min, cooled to 0 °C, and 2,2,2-trifluoroethyl trifluoromethanesulfonate (18.3 g, 78.8 mmol, 2 eq) was added. The mixture was stirred at 0 °C for 0.5 h, then stirred at 80 °C for 16 h. After cooling to rt, the mixture was partitioned between EtOAc (30 mL) and water (30 mL). The organic layer was concentrated under vacuum. The residue was purified by column chromatography (PE:EtOAc=1:0-5:1) to give ethyl(3R,4R)-4-(2-chlorophenyl)-1-(2,2,2-trifluoroethyl)pyrrolidine-3-carboxylate (10 g, 29.8 mmol, 76%) as a colorless oil. $^1H$ NMR (400 MHz, $CDCl_3$) δ ppm 7.27-7.31 (m, 1H), 7.21-7.24 (m, 1H), 7.02-7.16 (m, 2H), 4.15 (td, J=9.5, 6.5 Hz, 1H), 3.62 (dq, J=10.7, 7.2 Hz, 1H), 3.44-3.56 (m, 2H), 3.31 (br t, J=8.9 Hz, 1H), 2.99-3.25 (m, 5H), 0.71 (t, J=7.1 Hz, 3H).

Step 3. Ethyl(3R,4R)-4-(2-chlorophenyl)-1-(2,2,2-trifluoroethyl)pyrrolidine-3-carboxylate (2.3 g, 7.0 mmol, 1 eq) and trimethyltin hydroxide (6.3 g, 35.0 mmol, 5 eq) was combined in DCE (30 mL, 0.23 M). The mixture was heated to 110 °C for 24 h. After cooling to rt, the mixture was filtered and filtrate was concentrated in vacuo to afford crude product. Purification by prep-HPLC afforded (3R,4R)-4-(2-chlorophenyl)-1-(2,2,2-trifluoroethyl)pyrrolidine-3-carboxylic acid (2.1 g, 6.82 mmol, 97% yield).

Compound 163 was synthesized in a manner analogous to Step 2 of Compound 158 using (3R,4R)-4-(2-chlorophenyl)-1-(2,2,2-trifluoroethyl)pyrrolidine-3-carboxylic acid.

Scheme 50. Synthesis of 1-((3R,4R)-4-(2-chlorophenyl)-1-(2,2,2-trifluoroethyl)pyrrolidine-3-carbonyl)-N-((R)-1,1-dioxido-2,3-dihydrothiophen-3-yl)-4-fluoropiperidine-4-carboxamide (Compound64)

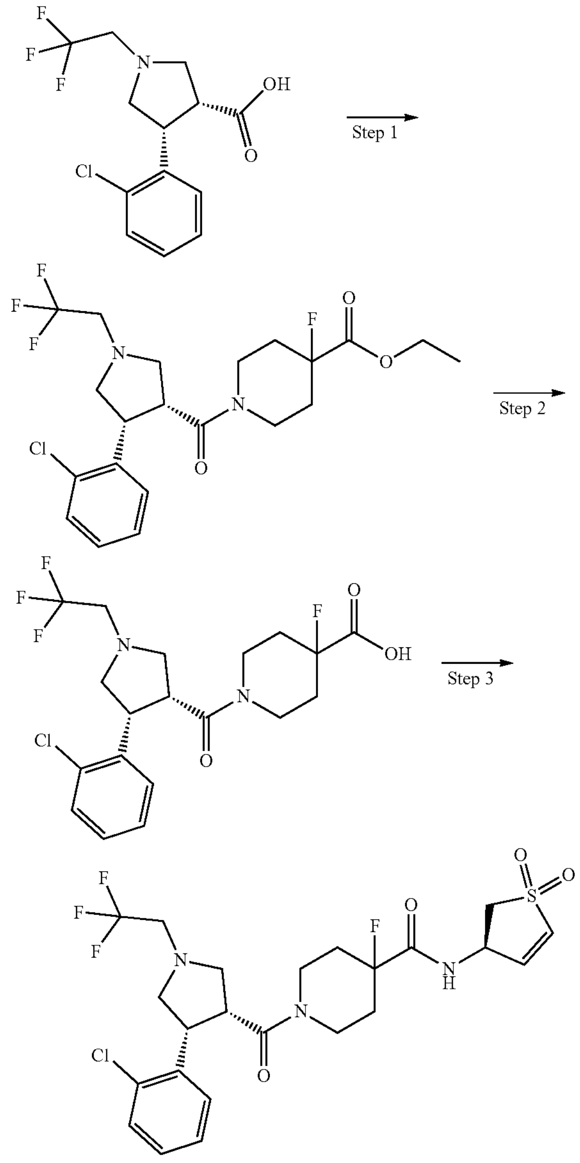

Step 1. To a solution of (3R,4R)-4-(2-chlorophenyl)-1-(2,2,2-trifluoroethyl)pyrrolidine-3-carboxylic acid (300 mg, 0.975 mmol, 1 eq) and ethyl 4-fluoropiperidine-4-carboxylate (171 mg, 0.975 mmol, 1 eq) in DCM (5 mL, 0.2 M) was added DIPEA (504 mg, 3.9 mmol, 4 eq) and 2,4,6-tripropyl-1,3,5,2,4,6-trioxatriphosphinane 2,4,6-trioxide (775 mg, 2.43 mmol, 2.5 eq). The reaction was stirred at 25 °C for 2 h. The reaction mixture was poured into water (5 mL) and extracted with DCM (15 mL×3). The combined organic layers were washed with brine (10 mL×2), dried over $Na_2SO_4$, filtered, and concentrated under reduced pressure.

The compound was purified by prep-TLC to give the product ethyl 1-((3R,4R)-4-(2-chlorophenyl)-1-(2,2,2-trifluoroethyl)pyrrolidine-3-carbonyl)-4-fluoropiperidine-4-carboxylate (150 mg, 0.323 mmol, 33% yield).

Step 2. To a solution of ethyl 1-((3R,4R)-4-(2-chlorophenyl)-1-(2,2,2-trifluoroethyl)pyrrolidine-3-carbonyl)-4-fluoropiperidine-4-carboxylate (150 mg, 0.323 mmol, 1 eq) in DCE (4 mL, 0.08 M) was added hydroxy(trimethyl)stannane (233 mg, 1.29 mmol, 4 eq). The reaction was stirred at 110 °C for 48 h. After cooling to rt, the reaction mixture was poured into water (1 mL) and extracted with DCM (10 mL×3). The combined organic layers were washed with brine (10 mL×2), dried over $Na_2SO_4$, filtered, and concentrated under reduced pressure to give 1-((3R,4R)-4-(2-chlorophenyl)-1-(2,2,2-trifluoroethyl)pyrrolidine-3-carbonyl)-4-fluoropiperidine-4-carboxylic acid (330 mg, 0.302 mmol, 94% yield).

Step 3. To a solution of 1-((3R,4R)-4-(2-chlorophenyl)-1-(2,2,2-trifluoroethyl)pyrrolidine-3-carbonyl)-4-fluoropiperidine-4-carboxylic acid (90 mg, 0.206 mmol, 1 eq) in DCM (3 mL, 0.07 M) was added (R)-3-amino-2,3-dihydrothiophene 1,1-dioxide (33 mg, 0.25 mmol, 1.2 eq), DIPEA (80 mg, 0.618 mmol, 3 eq), and 2,4,6-tripropyl-1,3,5,2,4,6-trioxatriphosphorinane-2,4,6-trioxide (131 mg, 0.412 mmol, 2 eq). The reaction was stirred at 25 °C for 2 h. The solution was diluted with water (10 mL) and extracted with DCM (10 mL×3). The combined organic layers were washed with brine (10 mL×3), dried over $Na_2SO_4$, and filtered. The solution was evaporated to get the crude product which was purified by prep-HPLC to give 1-((3R,4R)-4-(2-chlorophenyl)-1-(2,2,2-trifluoroethyl)pyrrolidine-3-carbonyl)-N-((R)-1,1-dioxido-2,3-dihydrothiophen-3-yl)-4-fluoropiperidine-4-carboxamide (Compound 164) (40 mg, 0.072 mmol, 35% yield). $^1$H NMR (400 MHz, DMSO-$d_6$) δ ppm 8.68-8.88 (m, 1H), 7.38-7.44 (m, 1H), 7.29-7.34 (m, 1H), 7.22-7.28 (m, 2H), 7.18 (dt, J=6.7, 2.3 Hz, 1H), 6.76 (td, J=6.4, 2.5 Hz, 1H), 5.05-5.22 (m, 1H), 3.96-4.24 (m, 2H), 3.53-3.93 (m, 3H), 3.41 (q, J=10.0 Hz, 2H), 3.06-3.25 (m, 4H), 2.80-2.98 (m, 1H), 2.56-2.66 (m, 1H), 2.12-2.25 (m, 1H), 1.67-2.07 (m, 1H), 1.49-1.64 (m, 2H), 0.98-1.17 (m, 1H). [M+H] calculated for $C_{23}H_{26}ClF_4N_3O_4S$, 551.1; found 552.1.

Compound 314 was synthesized in a manner analogous to Compound 164 using methyl 3-fluoro-3-pyrrolidinecarboxylate hydrochloride in Step 1 and (R,Z)-4-(methylsulfonyl)but-3-en-2-amine TsOH in Step 3.

Scheme 51. Synthesis of Intermediate di-tert-butyl (R)-4-fluoroazepane-1,4-dicarboxylate

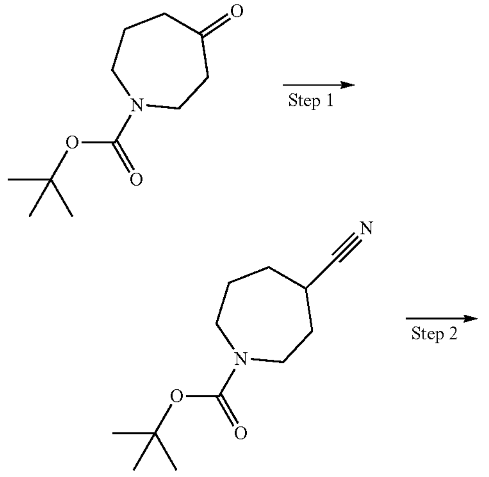

-continued

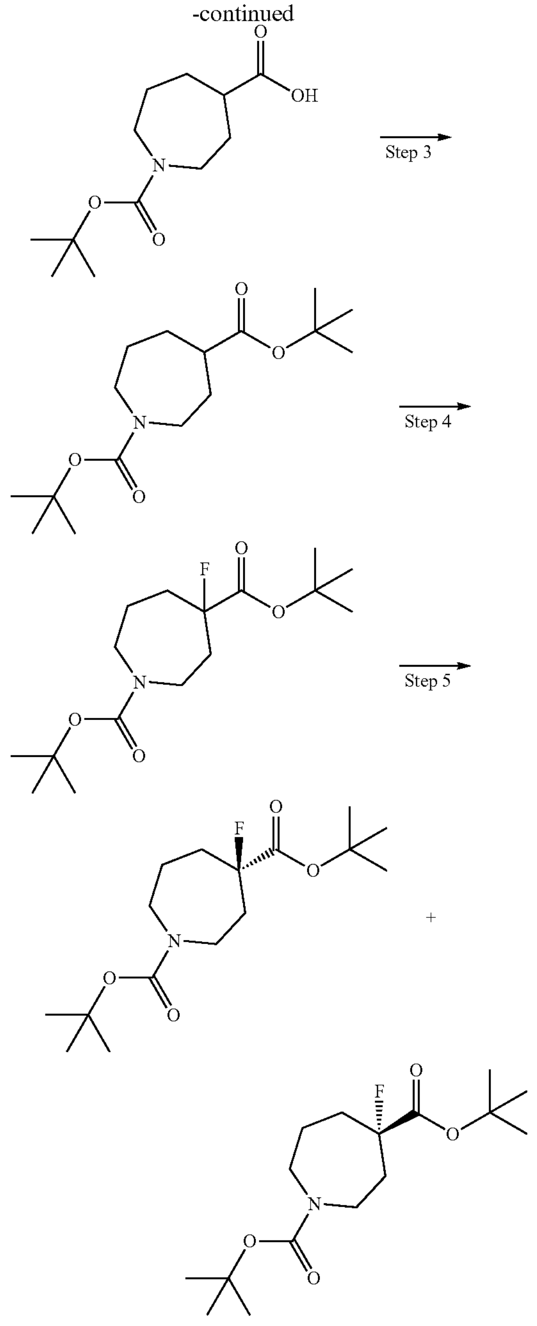

Step 1. To a solution of tert-butyl 4-oxoazepane-1-carboxylate (5.0 g, 23.4 mmol, 1.0 eq, available from a commercial source) in DME (60 mL, 0.39 M) was added 1-(isocyanomethane)sulfonyl-4-methylbenzene (5.7 g, 29.3 mmol, 1.25 eq) and ethanol (1.8 g, 39.9 mmol, 1.7 eq) at 15 °C. The mixture was cooled to 0 °C and 1M aq. potassium tert-butoxide (23.4 mL, 23.4 mmol, 1 eq) was added dropwise. The reaction was stirred at 40 °C for 16 h. After cooling to rt, the reaction mixture was filtered through celite, washed with MTBE (30 mL), and concentrated under reduced pressure. The resulting residue was purified by FCC to afford tert-butyl 4-cyanoazepane-1-carboxylate (3.4 g, 15.2 mmol, 65% yield).

Step 2. A solution of tert-butyl 4-cyanoazepane-1-carboxylate (7.5 g, 33.4 mmol, 1.0 eq) in 10% aq. NaOH (112.5 mL) was stirred at 100 °C for 16 h. After cooling to rt, the reaction mixture was concentrated in vacuo and the residue was dissolved in water (5 mL). The solution was adjusted to pH 2 and extracted with EtOAc (30 mL×2). The combined organic layers were dried over $Na_2SO_4$, filtered, and concentrated under reduced pressure to give 1-tert-butoxycarbonylazepane-4-carboxylic acid (6.5 g, 26.7 mmol, 80% yield).

Step 3. To a solution of 1-tert-butoxycarbonylazepane-4-carboxylic acid (2.0 g, 8.22 mmol, 1.0 eq) in tert-butanol (25 mL) was added di-tert-butyl dicarbonate (5.4 g, 24.7 mmol, 3.0 eq) and 4-(dimethylamino)pyridine (1.2 g, 9.86 mmol, 1.2 eq) slowly. The reaction was stirred at 15 °C for 8 h before being poured into water (30 mL) and extracted with EtOAc (20 mL×3). The combined organic layers were washed with brine (10 mL×2), dried over $Na_2SO_4$, filtered, and concentrated under reduced pressure. The resulting residue was purified by FCC to give di-tert-butyl azepane-1,4-dicarboxylate (1.2 g, 4.01 mmol, 76% yield).

Step 4. To a solution of di-tert-butyl azepane-1,4-dicarboxylate (23 g, 76.8 mmol, 1.0 eq) in THF (260 mL, 0.19 M) was added LDA (76.8 mL, 154 mmol, 2.0 eq) dropwise at −60 °C and the mixture was stirred at −45 °C for 1.5 h. To the mixture was added N-fluorobenzenesulfonimide (421 mg, 1.34 mmol, 2.0 eq) in THF (100 mL, 0.21 M) dropwise and the resulting solution was stirred at −45 °C for 1 h then allowed to warm to rt for 1 h. The reaction was quenched with sat. aq. ammonium chloride (200 mL) and extracted with EtOAc (150 mL×2). The combined organic phases were washed with brine (50 mL×2), dried over $Na_2SO_4$, filtered, and concentrated. The resulting residue was purified by FCC on silica (PE:EtOAc=1:0-95:5) to give di-tert-butyl 4-fluoroazepane-1,4-dicarboxylate (16 g, 50.4 mmol, 66% yield) as a colorless oil.

Step 5. Di-tert-butyl 4-fluoroazepane-1,4-dicarboxylate (30 g, 94.5 mmol, 1.0 eq) was separated by chiral SFC (Stationary phase: WHELK-O1 (25×5 cm); Mobile phase: 11% iPrOH/$CO_2$) to give di-tert-butyl(R)-4-fluoroazepane-1,4-dicarboxylate (Rt=5.9 min, 14 g, 44.1 mmol, 47% yield) as a colorless oil $^1H$ NMR (400 MHz, $CDCl_3$) δ ppm 3.81 (br d, J=14.2 Hz, 0.5H), 3.64 (br d, J=14.1 Hz, 1H), 3.54 (br d, J=1.1 Hz, 0.5H), 3.30 (br s, 1H), 3.12-3.22 (m, 1H), 1.84-2.17 (m, 5H), 1.77 (br s, 1H), 1.48 (d, J=4.2 Hz, 18H) and di-tert-butyl(S)-4-fluoroazepane-1,4-dicarboxylate (Rt=6.9 min, 14 g, 44.1 mmol, 47% yield) as a colorless oil.

-continued

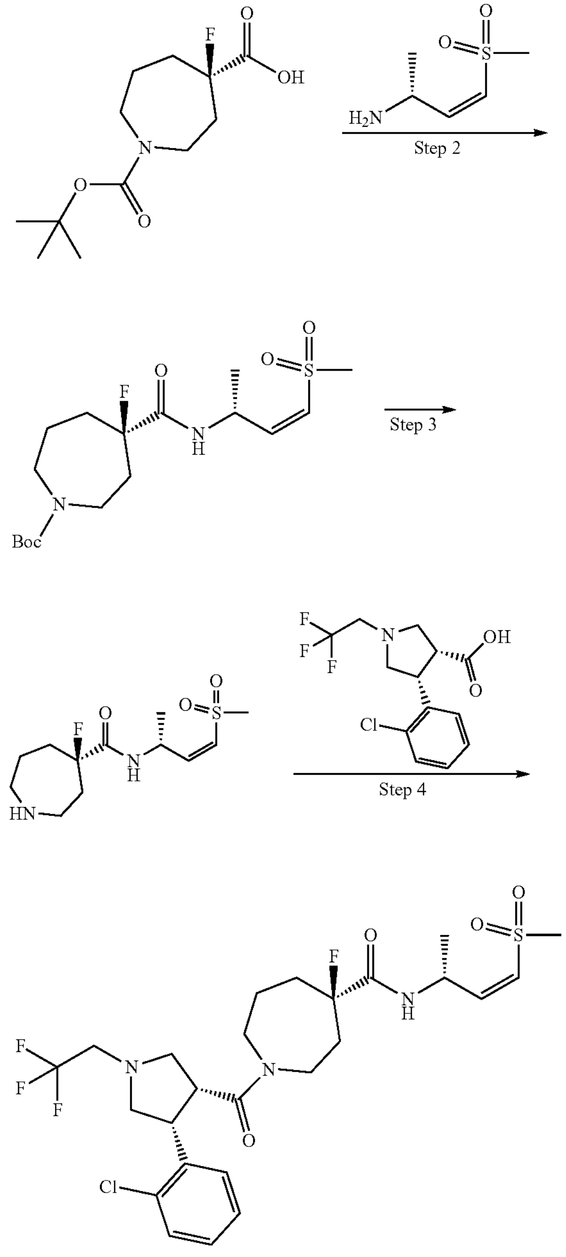

Scheme 52. Synthesis of (R)-1-((3R,4R)-4-(2-chlorophenyl)-1-(2,2,2-trifluoroethyl)pyrrolidine-3-carbonyl)-4-fluoro-N-((R,Z)-4-(methylsulfonyl)but-3-en-2-yl)azepane-4-carboxamide (Compound 165)

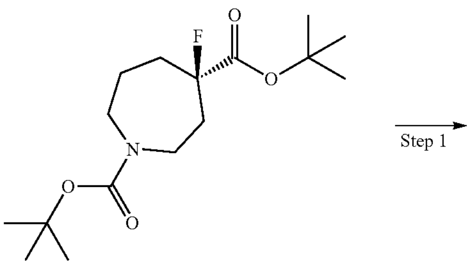

Step 1. To a solution of di-tert-butyl(R)-4-fluoroazepane-1,4-dicarboxylate (5.0 g, 15.7 mmol, 1.0 eq) in methanol (15 mL, 0.88 M) and water (3 mL, 0.88 M) was added potassium hydroxide (1.3 g, 23.6 mmol, 1.5 eq) at 15 °C. The reaction was placed under $N_2$ and stirred at 65 °C for 10 h. After cooling to rt, the mixture was concentrated under reduced pressure. The resulting residue was dissolved in water (5 mL) and acidified with 1N HCl to pH=2. The mixture was extracted with EtOAc (25 mL×2). The combined phases were dried over $Na_2SO_4$, filtered, and concentrated in vacuo to give (R)-1-tert-butoxycarbonyl-4-fluoro-azepane-4-carboxylic acid (4.0 g, 15.3 mmol, 97% yield). MS (ESI): mass calculated for $C_{12}H_{20}FNO_4$, 261.1; m/z found, 206.1 $[M+2H-tBu]^+$.

Step 2. To a solution of (R)-1-tert-butoxycarbonyl-4-fluoro-azepane-4-carboxylic acid (4.0 g, 15.3 mmol, 1.0 eq) in DCM (40 mL, 0.38 M) was added HATU (8.7 g, 23.0 mmol, 1.5 eq), DIPEA (5.0 g, 38.3 mmol, 2.5 eq) and (R,Z)-4-(methylsulfonyl)but-3-en-2-amine (TsOH salt, 3.0 g, 19.9 mmol, 1.3 eq) at 15 °C. The reaction was stirred at 15 °C for 4 h before being poured into water (15 mL) and extracted with DCM (20 mL×3). The combined organic layers were washed with brine (15 mL×2), dried over $Na_2SO_4$, filtered, and concentrated under reduced pressure. The resulting residue was purified by FCC on silica (PE: EtOAc=1:1-1:2) to give tert-butyl(R)-4-fluoro-4-(((R,Z)-4-(methylsulfonyl)but-3-en-2-yl)carbamoyl)azepane-1-carboxylate (5.0 g, 12.7 mmol, 83% yield) as a white solid. $^1H$ NMR (400 MHz, $CDCl_3$) δ ppm 6.46 (br s, 1H), 6.30 (d, J=11.1 Hz, 1H), 6.09 (t, J=10.3 Hz, 1H), 5.29-5.44 (m, 1H), 3.56-3.81 (m, 2H), 3.26-3.47 (m, 3H), 3.20 (s, 3H), 2.14-2.33 (m, 2H), 1.99 (br d, J=7.9 Hz, 3H), 1.46 (s, 9H), 1.41 (d, J=6.8 Hz, 3H).

Step 3. To a solution of tert-butyl(R)-4-fluoro-4-(((R,Z)-4-(methylsulfonyl)but-3-en-2-yl)carbamoyl)azepane-1-carboxylate (1.2 g, 3.06 mmol, 1.0 eq) in ACN (12 mL, 0.25 M) was added p-toluene sulfonic acid monohydrate (697 mg, 3.67 mmol, 1.2 eq). The mixture was stirred at 60 °C for 4 h. After cooling to rt, the reaction mixture was concentrated to dryness under reduced pressure. The resulting residue was washed with EtOAc (10 mL) to give the 4-methylbenzenesulfonate salt of (R)-4-fluoro-N-((R,Z)-4-(methylsulfonyl)but-3-en-2-yl)azepane-4-carboxamide (1.0 g, 2.26 mmol, 74% yield).

Step 4. To a solution of (3R,4R)-4-(2-chlorophenyl)-1-(2,2,2-trifluoroethyl)pyrrolidine-3-carboxylic acid (800 mg, 2.60 mmol, 1 eq) in DCM (3 mL, 0.87 M) was added HATU (1.5 g, 3.9 mmol, 1.5 eq), DIPEA (840 mg, 6.5 mmol, 2.5 eq) and (R)-4-fluoro-N-((R,Z)-4-(methylsulfonyl)but-3-en-2-yl)azepane-4-carboxamide (988 mg, 3.39 mmol, 1.3 eq). The mixture was stirred at 15 °C for 4 hours. The reaction mixture was poured into water (5 mL) and extracted with DCM (10 mL×3). The combined organic layers were washed with brine (10 mL×2), dried over $Na_2SO_4$, filtered and concentrated under reduced pressure. The residue was purified by prep-HPLC to give (R)-1-((3R,4R)-4-(2-chlorophenyl)-1-(2,2,2-trifluoroethyl)pyrrolidine-3-carbonyl)-4-fluoro-N-((R,Z)-4-(methylsulfonyl)but-3-en-2-yl)azepane-4-carboxamide (Compound 165) (648 mg, 1.11 mmol, 43%). $^1H$ NMR (400 MHz, DMSO-$d_6$) δ ppm 8.25 (br dd, J=7.6, 2.5 Hz, 1H), 7.30-7.44 (m, 2H), 7.18-7.29 (m, 2H), 6.40-6.52 (m, 1H), 6.21-6.33 (m, 1H), 5.24-5.37 (m, 1H), 4.00-4.16 (m, 1H), 3.70-3.90 (m, 1H), 3.48-3.61 (m, 1H), 3.34-3.48 (m, 3H), 3.18-3.28 (m, 3H), 3.08-3.15 (m, 3H), 2.82-3.05 (m, 2H), 2.68 (br dd, J=12.9, 11.7 Hz, 1H), 1.45-2.02 (m, 6H), 1.16-1.24 (m, 3H). [M+H] calculated for $C_{25}H_{32}ClF_4N_3O_4S$, 581; found 582.

Compound 198 was synthesized in a manner similar to Compound 165 using (R,Z)-1-(methylsulfonyl)pent-1-en-3-amine in Step 2.

Intermediate (R)—N-((R,E)-5-(3,3-difluoroazetidin-1-yl)-5-oxopent-3-en-2-yl)-4-fluoroazepane-4-carboxamide was synthesized in a manner analogous to (R)-4-fluoro-N-((R,Z)-4-(methylsulfonyl)but-3-en-2-yl)azepane-4-carboxamide using (E,4R)-4-amino-1-(3,3-difluoroazetidin-1-yl)pent-2-en-1-one in Step 3.

Compound 302 was synthesized in a manner analogous to Compound 165, Step 4, using (2S,4S)-4-fluoro-2-methyl-N-[(Z,1R)-1-methyl-3-methylsulfonyl-allyl]piperidine-4-carboxamide.

Scheme 53. Synthesis of Intermediate (3*R,4*R)-4-(2-chloro-5-fluorophenyl)-1-(2,2,2,-trifluoroethyl)pyrrolidine-3-carboxylic acid

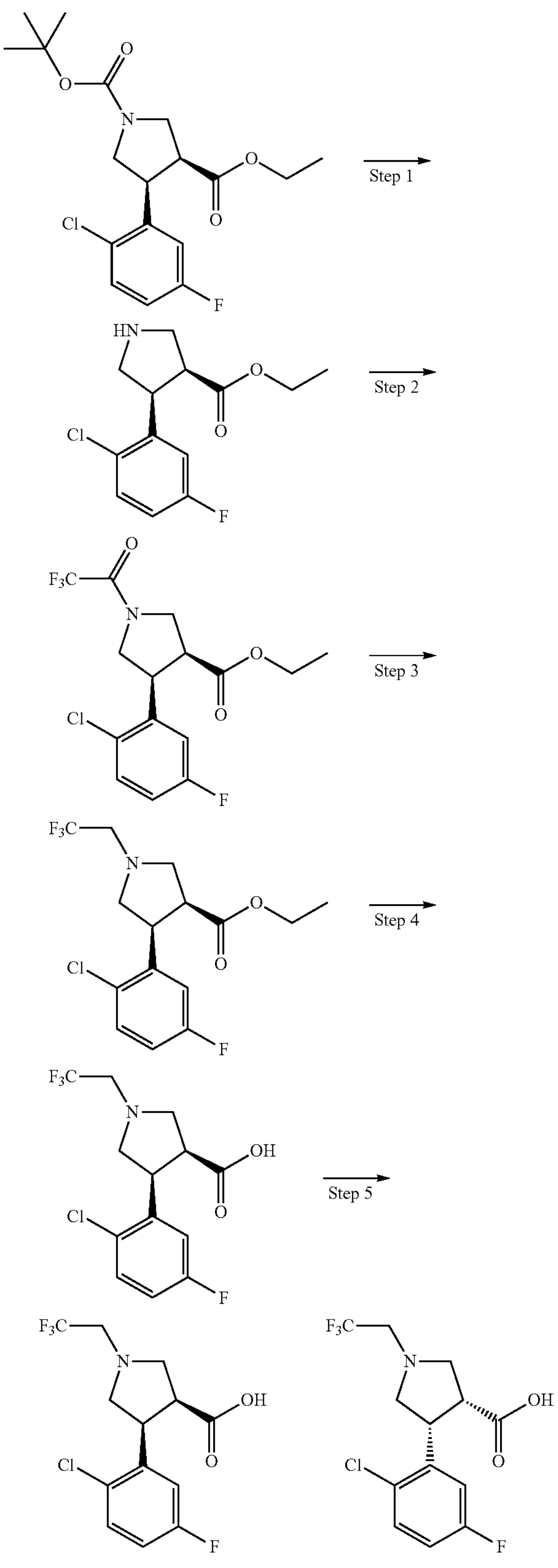

Step 1. To a solution of rac-1-(tert-butyl) 3-ethyl(3S,4S)-4-(2-chloro-5-fluorophenyl)pyrrolidine-1,3-dicarboxylate (2.0 g, 5.38 mmol, 1 eq) in DCM (20 mL) was added TFA (4 mL) under nitrogen. The reaction was stirred at 25 °C for 2 h. The reaction mixture was concentrated under reduced pressure to give crude rac-ethyl(3S,4S)-4-(2-chloro-5-fluorophenyl)pyrrolidin-1-ium-3-carboxylate 2,2,2-trifluoroacetate (2.0 g, 5.18 mmol, 96% yield).

Step 2. To a solution of rac-ethyl(3S,4S)-4-(2-chloro-5-fluorophenyl)pyrrolidin-1-ium-3-carboxylate 2,2,2-trifluoroacetate (2.0 g, 5.18 mmol, 1 eq) in DCM (20 mL) was added triethylamine (2.17 mL, 15.6 mmol, 3 eq) and trifluoroacetic anhydride (0.95 mL, 6.74 mmol, 1.3 eq) at 0 °C under nitrogen. The reaction was stirred at 25 °C for 2 h. The reaction mixture was poured into water (20 mL) and extracted with DCM (20 mL×3). The combined organic layers were washed with brine (50 mL), dried over $Na_2SO_4$, filtered, and concentrated under reduced pressure. The residue was purified by FCC to give rac-ethyl(3S,4S)-4-(2-chloro-5-fluorophenyl)-1-(2,2,2-trifluoroacetyl)pyrrolidine-3-carboxylate (1.8 g, 4.90 mmol, 94% yield).

Step 3. To a solution of rac-ethyl(3S,4S)-4-(2-chloro-5-fluorophenyl)-1-(2,2,2-trifluoroacetyl)pyrrolidine-3-carboxylate (1.8 g, 4.90 mmol, 1 eq) in THF (12 mL) was added 1 M borane tetrahydrofuran complex solution (7.34 mL, 7.34 mmol, 1.5 eq) at 0 °C under nitrogen. The reaction was stirred at 65 °C for 3.5 h. The reaction mixture was quenched with MeOH (7 mL) at 0 °C and concentrated under reduced pressure. The residue was purified by FCC to give rac-ethyl (3S,4S)-4-(2-chloro-5-fluoro-phenyl)-1-(2,2,2-trifluoroethyl)pyrrolidine-3-carboxylate (1.25 g, 3.53 mmol, 72% yield).

Step 4. To a solution of rac-ethyl(3S,4S)-4-(2-chloro-5-fluoro-phenyl)-1-(2,2,2-trifluoroethyl)pyrrolidine-3-carboxylate (1.25 g, 3.53 mmol, 1 eq) in DCE (15 mL) was added trimethyltin hydroxide (3.19 g, 17.7 mmol, 5 eq). The reaction was stirred at 110 °C for 16 h. After cooling to rt, the reaction was filtered, and the filtrate was concentrated. The residue was purified by prep-HPLC to give rac-(3S,4S)-4-(2-chloro-5-fluoro-phenyl)-1-(2,2,2-trifluoroethyl)pyrrolidine-3-carboxylic acid (850 mg, 2.61 mmol, 74% yield).

Step 5. Rac-(3S,4S)-4-(2-chloro-5-fluoro-phenyl)-1-(2,2,2-trifluoroethyl)pyrrolidine-3-carboxylic acid was separated by chiral SFC to give (3*S,4*S)-4-(2-chloro-5-fluoro-phenyl)-1-(2,2,2-trifluoroethyl)pyrrolidine-3-carboxylic acid (170 mg) and (3*R,4*R)-4-(2-chloro-5-fluorophenyl)-1-(2,2,2-trifluoroethyl)pyrrolidine-3-carboxylic acid (170 mg).

Intermediate (3*R,4*R)-4-(2-chloro-4-fluorophenyl)-1-(2,2,2-trifluoroethyl)pyrrolidine-3-carboxylic acid was synthesized in a manner similar to (3*R,4*R)-4-(2-chloro-5-fluorophenyl)-1-(2,2,2-trifluoroethyl)pyrrolidine-3-carboxylic acid.

Intermediate (3R,4R)-1-(2-chloro-2,2-difluoroethyl)-4-(2-chlorophenyl)pyrrolidine-3-carboxylic acid was synthesized in a manner similar to (3*R,4*R)-4-(2-chloro-5-fluorophenyl)-1-(2,2,2-trifluoroethyl)pyrrolidine-3-carboxylic acid using 1-(tert-butyl) 3-ethyl(3R,4R)-4-(2-chlorophenyl) pyrrolidine-1,3-dicarboxylate in Step 1 and 2-chloro-2,2-difluoroacetic anhydride in Step 2.

Compound 195 was synthesized in a manner analogous to Compound 165 using (3R,4R)-1-(2-chloro-2,2-difluoroethyl)-4-(2-chlorophenyl)pyrrolidine-3-carboxylic acid in Step 4.

Scheme 54. Synthesis of Intermediate methyl (R)-4-fluoroazepane-4-carboxylate

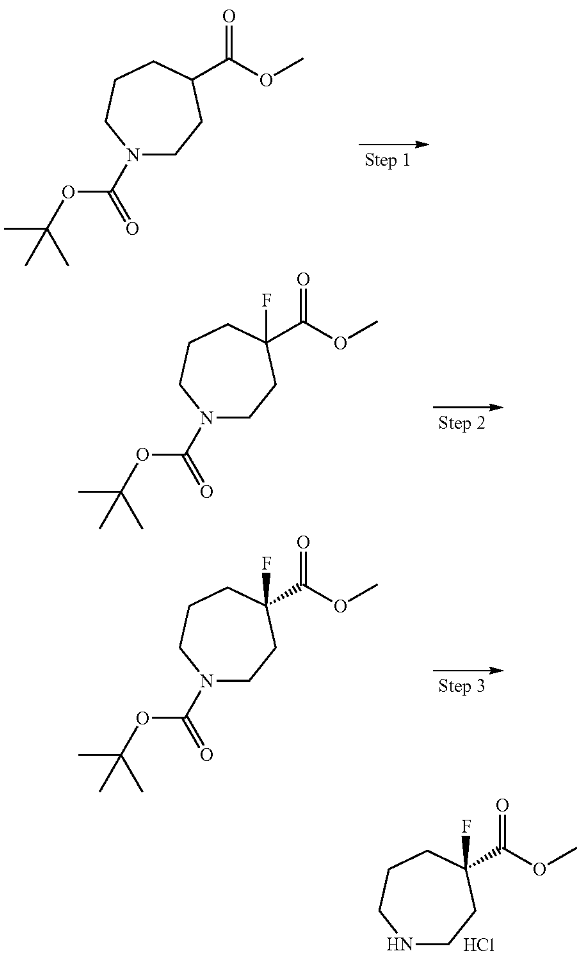

Step 1. To a solution of 1-(tert-butyl) 4-methyl azepane-1,4-dicarboxylate (9.0 g, 35.0 mmol, 1.0 eq) in THF (90 mL) was added LDA (26 mL, 52.5 mmol, 1.5 eq) dropwise at −45 °C. The mixture was stirred at −45 °C for 0.5 h before N-fluorobenzenesulfonimide (13.8 g, 43.7 mmol, 1.3 eq) in THF (90 mL) was added dropwise. The reaction was stirred at −45 °C for 1 h then allowed to warm to rt over 1 h. The reaction was quenched with sat. aq. $NH_4Cl$ (180 mL) and extracted with EtOAc (150 mL×2). The combined organic phases were washed with brine (300 mL×2), dried over $Na_2SO_4$, filtered, and concentrated under reduced pressure. The resulting residue was purified by FCC on silica (PE: EtOAc=100:0 to 87:13) to give 1-(tert-butyl) 4-methyl 4-fluoroazepane-1,4-dicarboxylate (5.0 g, 18.1 mmol, 52%) as a light yellow oil. MS (ESI): mass calculated for $C_{13}H_{22}FNO_4$, 275.2; m/z found, 220.2 $[M+2H-tBu]^+$. $^1H$ NMR (400 MHz, $CDCl_3$) δ ppm 3.79 (d, J=3.0 Hz, 3H), 3.73-3.47 (m, 2H), 3.40-3.14 (m, 2H), 2.27-1.86 (m, 5H), 1.77 (br d, J=10.9 Hz, 1H), 1.47 (s, 9H).

Step 2. 1-(tert-Butyl) 4-methyl 4-fluoroazepane-1,4-dicarboxylate (3.9 g, 14.2 mmol, 1.0 eq) was separated by chiral SFC to give 1-(tert-butyl) 4-methyl-(4R)-4-fluoroazepane-1,4-dicarboxylate (1.6 g, 5.81 mmol, 41% yield) as a colorless oil. MS (ESI): mass calculated for $C_{13}H_{22}FNO_4$, 275.2; m/z found, 220.1 $[M+2H-tBu]^+$.

Step 3. A solution of 1-(tert-butyl) 4-methyl-(4R)-4-fluoroazepane-1,4-dicarboxylate (500 mg, 1.82 mmol, 1.0 eq) in HCl (10 mL, 4M in EtOAC) was stirred at 25 °C for 0.5 h. The reaction was concentrated under reduced pressure to give methyl(R)-4-fluoroazepane-4-carboxylate, hydrochloride (380 mg, 1.80 mmol, quant. yield) as a white solid, which was used in the next step directly.

Intermediate methyl(S)-4-fluoroazepane-4-carboxylate was synthesized in a manner analogous to methyl(R)-4-fluoroazepane-4-carboxylate using the isolated opposite enantiomer from Step 2 in Step 3.

Scheme 55. Synthesis of Intermediate (3*R,4*R)-4-(2-chloro-3-fluorophenyl)-1-(2,2,2-trifluoroethyl)pyrrolidine-3-carboxylic acid

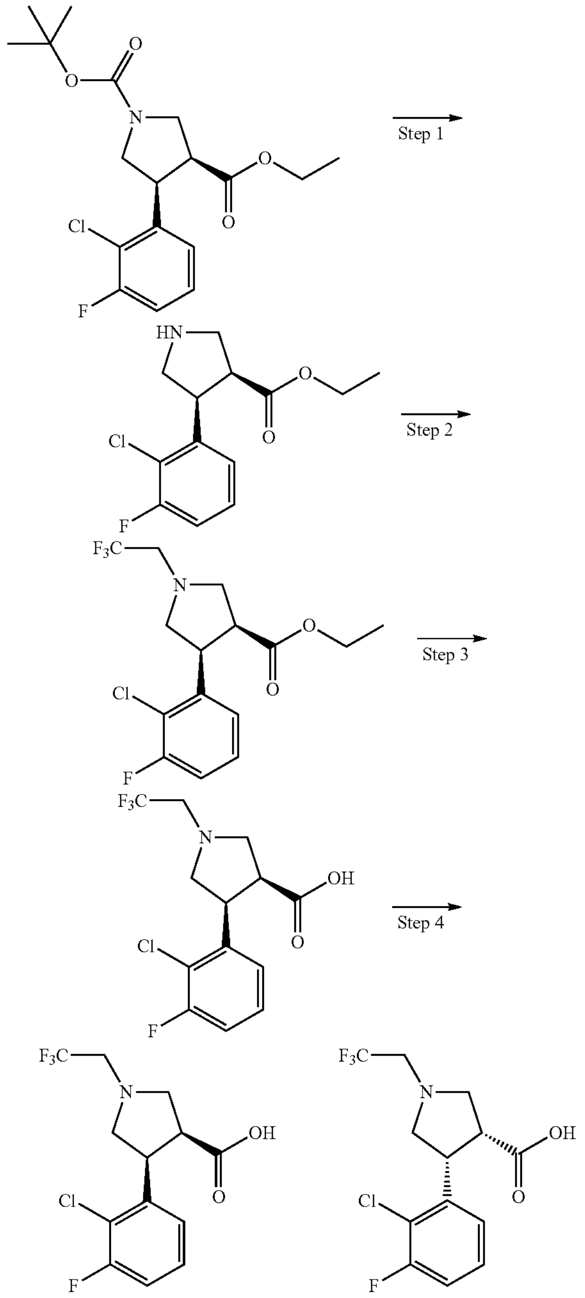

Step 1. Synthesized in a manner analogous to Step 1 of (3*R,4*R)-4-(2-chloro-5-fluorophenyl)-1-(2,2,2-trifluoroethyl)pyrrolidine-3-carboxylic acid.

Step 2. To a solution of rac-ethyl(3S,4S)-4-(2-chloro-3-fluorophenyl)pyrrolidine-3-carboxylate (1 g, 3.68 mmol, 1 eq) in toluene (30 mL) was added 2,2,2-trifluoroethyl trifluoromethanesulfonate (1.7 g, 7.36 mmol, 2 eq) and triethylamine (1.54 mL, 11.0 mmol, 3 eq). The mixture was stirred at 80 °C for 16 hrs. After cooling to rt, the reaction mixture was poured into water (50 mL) and extracted with EtOAc (30 mL×3). The combined organic layers were washed with brine (100 mL×2), dried over $Na_2SO_4$, filtered, and concentrated under reduced pressure. The residue was purified by column chromatography to give rac-ethyl(3S,4S)-4-(2-chloro-3-fluorophenyl)-1-(2,2,2-trifluoroethyl) pyrrolidine-3-carboxylate (1.1 g, 3.11 mmol, 84% yield).

Step 3. A solution of rac-ethyl(3S,4S)-4-(2-chloro-3-fluorophenyl)-1-(2,2,2-trifluoroethyl)pyrrolidine-3-carboxylate (1.1 g, 3.11 mmol, 1 eq) in $HBr/H_2O$ (10 mL) was stirred at 110 °C for 16 hrs. After cooling to rt, the reaction mixture was filtered and concentrated under reduced pressure to give rac-(3S,4S)-4-(2-chloro-3-fluorophenyl)-1-(2,2,2-trifluoroethyl)pyrrolidine-3-carboxylic acid (900 mg, 2.76 mmol, 89% yield).

Step 4. Rac-(3S,4S)-4-(2-chloro-3-fluorophenyl)-1-(2,2,2-trifluoroethyl)pyrrolidine-3-carboxylic acid was separated by chiral SFC to give (3*S,4*S)-4-(2-chloro-3-fluorophenyl)-1-(2,2,2-trifluoroethyl)pyrrolidine-3-carboxylic acid and (3*R,4*R)-4-(2-chloro-3-fluorophenyl)-1-(2,2,2-trifluoroethyl)pyrrolidine-3-carboxylic acid.

Intermediates (3*R,4*R)-4-(2-chloro-3-methylphenyl)-1-(2,2,2-trifluoroethyl)pyrrolidine-3-carboxylic acid, (3*R,4*R)-4-(2-chloro-4-methylphenyl)-1-(2,2,2-trifluoroethyl) pyrrolidine-3-carboxylic acid, (3*R,4*R)-4-(2-chloro-5-methylphenyl)-1-(2,2,2-trifluoroethyl)pyrrolidine-3-carboxylic acid, (3*R,4*R)-4-(2-fluoro-6-fluorophenyl)-1-(2,2,2-trifluoroethyl)pyrrolidine-3-carboxylic acid, (3*R,4*R)-4-(2,3-difluorophenyl)-1-(2,2,2-trifluoroethyl) pyrrolidine-3-carboxylic acid, and (3*R,4*R)-4-(2-fluoro-3-fluorophenyl)-1-(2,2,2-trifluoroethyl)pyrrolidine-3-carboxylic acid were synthesized in a manner similar to (3*R,4*R)-4-(2-chloro-3-fluorophenyl)-1-(2,2,2-trifluoroethyl)pyrrolidine-3-carboxylic acid using either HBr or trimethyltin hydroxide for the hydrolysis of the ester in Step 3.

Compounds 166-168, 170, and 172-173 were synthesized from the appropriate carboxylic acid in a manner similar to Compound 165.

Compounds 174-176 were synthesized in a manner analogous to Compound 164 using appropriate intermediates.

Compound 177 was synthesized in a manner analogous to Compound 165 using (R,E)-4-methylsulfonylbut-3-en-2-amine in Step 2.

Intermediate (3R,4R)-4-(2-chlorophenyl)-1-(3,3,3-trifluoropropyl)pyrrolidine-3-carboxylic acid was synthesized in a manner analogous to (3*R,4*R)-4-(2-chloro-3-fluorophenyl)-1-(2,2,2-trifluoroethyl)pyrrolidine-3-carboxylic acid using 1-(tert-butyl) 3-ethyl(3R,4R)-4-(2-chlorophenyl) pyrrolidine-1,3-dicarboxylate in Step 1 and 3,3,3-trifluoropropyl 1,1,1-trifluoromethanesulfonate in Step 2.

Compound 196 was synthesized in a manner analogous to Compound 165 using (3R,4R)-4-(2-chlorophenyl)-1-(3,3,3-trifluoropropyl)pyrrolidine-3-carboxylic acid in Step 4.

Intermediate (3R,4R)-4-(2-chlorophenyl)-1-(2,2-difluoroethyl)pyrrolidine-3-carboxylic acid was synthesized in a manner analogous to (3*R,4*R)-4-(2-chloro-3-fluorophenyl)-1-(2,2,2-trifluoroethyl)pyrrolidine-3-carboxylic acid using 1-(tert-butyl) 3-ethyl(3R,4R)-4-(2-chlorophenyl)pyrrolidine-1,3-dicarboxylate in Step 1, 2,2-difluoroethyl 1,1,1-trifluoromethanesulfonate in Step 2, and trimethyltin hydroxide for the hydrolysis of the ester in Step 3.

Compound 197 was synthesized in a manner analogous to Compound 165 using (3R,4R)-4-(2-chlorophenyl)-1-(2,2-difluoroethyl)pyrrolidine-3-carboxylic acid in Step 4.

Compound 206 was synthesized in a manner similar to Compound 165 starting from 4-fluoro-N—[(Z,1R)-1-methyl-3-methylsulfonyl-allyl]piperidine-4-carboxamide, 4-methylbenzenesulfonic acid salt and (3R,4R)-4-(2-chlorophenyl)-1-(2,2-difluoroethyl)pyrrolidine-3-carboxylic acid in Step 4.

Scheme 56. Synthesis of Intermediate (3R,4R)-4-(2-chlorophenyl)-1-(2,2-diflourobutyl)pyrrolidine-3-carboxylic acid

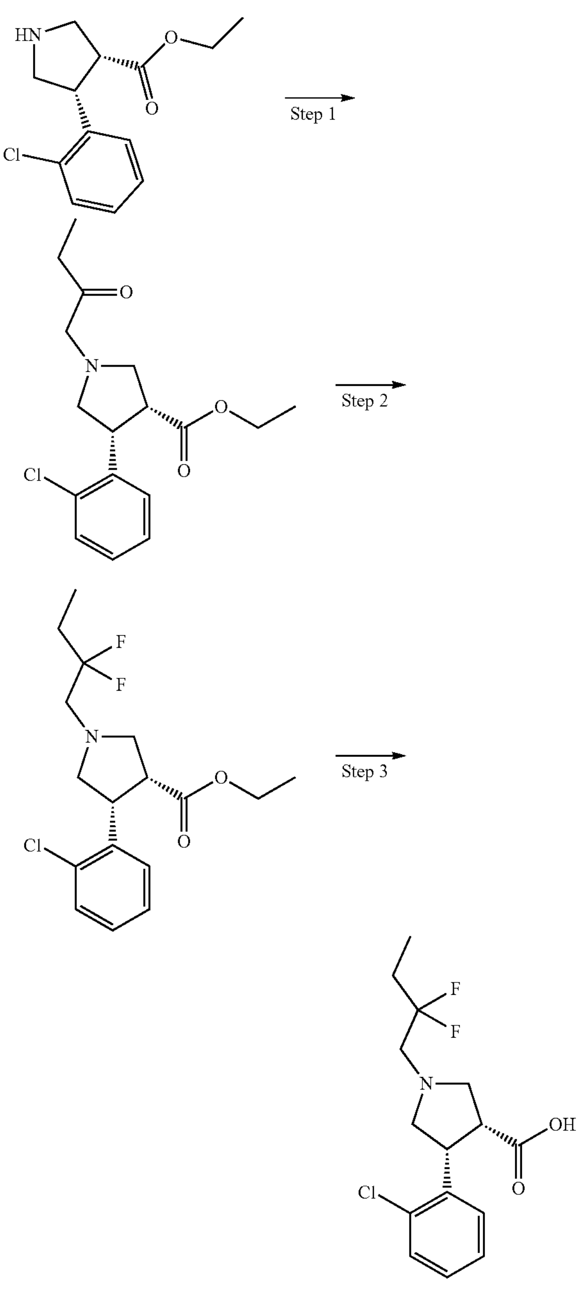

Step 1. To a solution of ethyl(3R,4R)-4-(2-chlorophenyl)pyrrolidine-3-carboxylate (350 mg, 1.38 mmol, 1 eq) in DCM (5 mL, 0.28 M) was added TEA (419 mg, 4.14 mmol, 3 eq) and 1-bromo-2-butanone (250 mg, 1.66 mmol, 1.2 eq) at 0 °C. The reaction was stirred at 25 °C for 30 min. The solution was diluted with water (15 mL) and extracted with DCM (20 mL×3). The combined organic layers were washed with brine (10 mL×3), dried over $Na_2SO_4$, filtered, and concentrated in vacuo to give a residue, which was purified by prep-TLC to give ethyl(3R,4R)-4-(2-chlorophenyl)-1-(2-oxobutyl)pyrrolidine-3-carboxylate (300 mg, 0.93 mmol, 67%) as a yellow oil.

Step 2. To a solution of ethyl(3R,4R)-4-(2-chlorophenyl)-1-(2-oxobutyl)pyrrolidine-3-carboxylate (200 mg, 0.62 mmol, 1 eq) in DCM (3 mL, 0.2 M) was added DAST (1.5 g, 9.26 mmol, 15 eq) at 0 °C and this was stirred at 25 °C for 16 h. The solution was diluted with water (10 mL) and extracted with DCM (10 mL×3). The combined organic layers were washed with brine (10 mL×3), dried over $Na_2SO_4$, filtered, and concentrated in vacuo to give a residue, which was purified by prep-TLC to give ethyl(3R,4R)-4-(2-chlorophenyl)-1-(2,2-difluorobutyl)pyrrolidine-3-carboxylate (100 mg, 0.29 mmol, 47% yield) as a yellow oil.

Step 3. To a solution of ethyl(3R,4R)-4-(2-chlorophenyl)-1-(2,2-difluorobutyl)pyrrolidine-3-carboxylate (100 mg, 0.29 mmol, 1.0 eq) in DCE (5 mL, 0.06 M) was added $Me_3SnOH$ (261 mg, 1.44 mmol, 5 eq) at 15 °C. The reaction was stirred at 110 °C for 48 h. After cooling to rt, the solution was filtered and concentrated in vacuo to give a residue, which was diluted with water (10 mL) and extracted with DCM (15 mL×3). The combined organic layers were washed with brine (10 mL×3), dried over $Na_2SO_4$, filtered, and concentrated in vacuo to give (3R,4R)-4-(2-chlorophenyl)-1-(2,2-difluorobutyl)pyrrolidine-3-carboxylic acid (120 mg, 0.26 mmol, 91%) as a yellow oil. $^1$HNMR (400 MHz, $CDCl_3$) δ ppm 7.44 (dd, J=1.8, 7.6 Hz, 1H), 7.33 (dd, J=1.7, 7.6 Hz, 1H), 7.21-7.10 (m, 2H), 4.16 (td, J=7.3, 9.9 Hz, 1H), 3.67-3.56 (m, 1H), 3.24-3.08 (m, 3H), 3.06-2.88 (m, 3H), 2.08-1.90 (m, 2H), 1.10-1.00 (m, 3H). [M+H] calculated for $C_{15}H_{18}ClF_2NO_2$, 317, found 318.

Compound 178 was synthesized from (3R,4R)-4-(2-chlorophenyl)-1-(2,2-difluorobutyl)pyrrolidine-3-carboxylic acid in a manner analogous to Compound 158, Step 2.

Intermediates (3R,4R)-4-(2-chlorophenyl)-1-(2,2-difluoropropyl)pyrrolidine-3-carboxylic acid, (3R,4R)-4-(2-chlorophenyl)-1-(2,2-difluoro-2-phenyl-ethyl)pyrrolidine-3-carboxylic acid, and (3R,4R)-4-(2-chloro-6-fluoro-phenyl)-1-(2,2-difluoropropyl)pyrrolidine-3-carboxylic acid were synthesized in a manner analogous to (3R,4R)-4-(2-chlorophenyl)-1-(2,2-difluorobutyl)pyrrolidine-3-carboxylic acid.

Compound 179 was synthesized from (3R,4R)-4-(2-chlorophenyl)-1-(2,2-difluoropropyl)pyrrolidine-3-carboxylic acid in a manner analogous to Compound 158, Step 2.

Compound 180 was synthesized in a manner analogous to Compound 165 using (3R,4R)-4-(2-chlorophenyl)-1-(2,2-difluoropropyl)pyrrolidine-3-carboxylic acid.

Compound 181 was synthesized from (3R,4R)-4-(2-chlorophenyl)-1-(2,2-difluoro-2-phenyl-ethyl)pyrrolidine-3-carboxylic acid in a manner analogous to Compound 158, Step 2.

Intermediate (3R,4R)-4-(2-chlorophenyl)-1-(2,2,3,3,3-pentafluoropropyl)pyrrolidine-3-carboxylic acid was synthesized in a manner similar to (3*R,4*R)-4-(2-chloro-5-fluorophenyl)-1-(2,2,2-trifluoroethyl)pyrrolidine-3-carboxylic acid starting with ethyl(3R,4R)-4-(2-chlorophenyl)pyrrolidine-3-carboxylate and pentafluoropropionic anhydride.

Compound 182 was synthesized from (3R,4R)-4-(2-chlorophenyl)-1-(2,2,3,3,3-pentafluoropropyl)pyrrolidine-3-carboxylic acid in a manner analogous to Compound 158, Step 2.

Compound 183 was synthesized from (3*R,4*R)-4-(2-chloro-6-fluorophenyl)-1-(2,2-difluoropropyl)pyrrolidine-3-carboxylic acid in a manner analogous to Compound 165.

Compound 221 was synthesized in a manner analogous to Compound 164 using methyl(2*R,4*S)-4-fluoro-2-methylpiperidine-4-carboxylate and (3R,4R)-4-(2-chlorophenyl)-1-(2,2-difluoropropyl)pyrrolidine-3-carboxylic acid in Step 1.

Intermediate (3*R,4*R)-4-(2-chloro-3-fluorophenyl)-1-(2,2-difluoropropyl)pyrrolidine-3-carboxylic acid was synthesized in a manner analogous to (3R,4R)-4-(2-chlorophenyl)-1-(2,2-difluorobutyl)pyrrolidine-3-carboxylic acid starting from rac-ethyl(3S,4S)-4-(2-chloro-3-fluorophenyl)-1-(2,2,2-trifluoroethyl)pyrrolidine-3-carboxylate and chloroacetone in Step 1.

Compound 222 was synthesized in a manner analogous to Compound 165 using (3*R,4*R)-4-(2-chloro-3-fluorophenyl)-1-(2,2-difluoropropyl)pyrrolidine-3-carboxylic acid in Step 4.

Compound 225 was synthesized in a manner analogous to Compound 164 using (3*R,4*R)-4-(2-chloro-3-fluorophenyl)-1-(2,2-difluoropropyl)pyrrolidine-3-carboxylic acid and methyl(2*R,4*S)-4-fluoro-2-methylpiperidine-4-carboxylate in Step 1.

Scheme 57. Synthesis of Intermediate ethyl (3*R,4*R)-4-(2-chloro-6-fluorophenyl)-1-(1-fluorocyclopropanecarbonyl) pyrrolidine-3-carboxylate

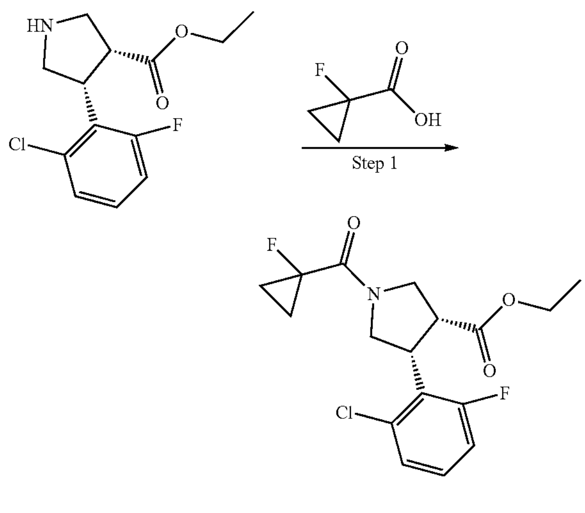

Step 1. To a solution of 1-fluorocyclopropane-1-carboxylic acid (129 mg, 1.24 mmol, 1.0 eq) in DCM (4 mL, 0.3 M) was added DIPEA (268 mg, 2.07 mmol, 2 eq) and HATU (591 mg, 1.56 mmol, 1.5 eq). The reaction solution was stirred at 20 °C for 10 min. Then to the solution was added ethyl(3*R,4*R)-4-(2-chloro-6-fluoro-phenyl)pyrrolidine-3-carboxylate; 2,2,2-trifluoroacetic acid (400 mg, 1.04 mmol, 1.2 eq). The reaction solution was stirred at 20 °C for 2 h. The reaction was quenched with water (10 mL) and extracted with DCM (5 mL×3). The combined organic phases were washed with brine (10 mL×2), dried over $Na_2SO_4$, and filtered. The filtrate was concentrated. The crude product was purified by column chromatography to give ethyl(3*R,4*R)-4-(2-chloro-6-fluorophenyl)-1-(1-fluorocyclopropanecarbonyl)pyrrolidine-3-carboxylate (300 mg, 0.84 mmol, 81%) as a yellow solid. $^1H$ NMR (400 MHz, $CDCl_3$) δ ppm 7.15-7.26 (m, 2H), 6.86-7.06 (m, 1H), 4.25-4.42 (m, 3H), 4.05-4.18 (m, 2H), 3.88-4.00 (m, 2H), 3.44-3.68 (m, 1H), 1.39-1.47 (m, 2H), 1.21-1.27 (m, 2H), 1.01 (t, J=7.2 Hz, 3H).

Intermediate (3*R,4*R)-4-(2-chloro-6-fluorophenyl)-1-((1-fluorocyclopropyl)methyl)pyrrolidine-3-carboxylic acid was synthesized from ethyl(3*R,4*R)-4-(2-chloro-6-fluorophenyl)-1-(1-fluorocyclopropanecarbonyl)pyrrolidine-3-carboxylate in a manner similar to Steps 3-5 of the synthesis of (3*R,4*R)-4-(2-chloro-5-fluorophenyl)-1-(2,2,2-trifluoroethyl)pyrrolidine-3-carboxylic acid.

Compound 184 was synthesized from (3*R,4*R)-4-(2-chloro-6-fluorophenyl)-1-((1-fluorocyclopropyl)methyl) pyrrolidine-3-carboxylic acid in a manner similar to Compound 165.

Intermediate (3R,4R)-4-(2-chlorophenyl)-1-((1-fluorocyclopropyl)methyl)pyrrolidine-3-carboxylic acid was synthesized in a manner similar to (3*R,4*R)-4-(2-chloro-6-fluorophenyl)-1-((1-fluorocyclopropyl)methyl)pyrrolidine-3-carboxylic acid.

Compound 185 was synthesized from (3R,4R)-4-(2-chlorophenyl)-1-((1-fluorocyclopropyl)methyl)pyrrolidine-3-carboxylic acid in a manner similar to Compound 165.

Scheme 58. Synthesis of (R,Z)-1-((4-(2-chlorophenyl)-6-methoxypyridin-3-yl)sulfonyl)-4-fluoro-N-(4-(methylsufonyl)but-3-en-2-yl)piperidine-4-carboxamide (Compound 186)

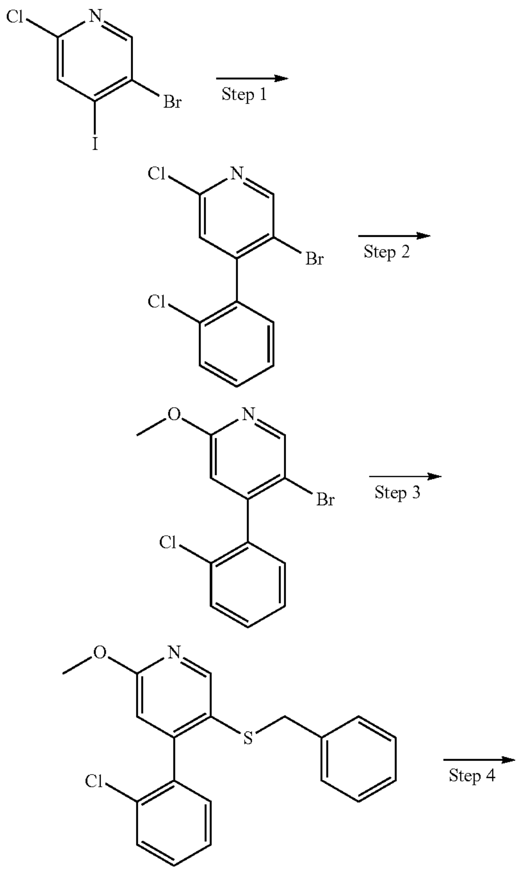

-continued

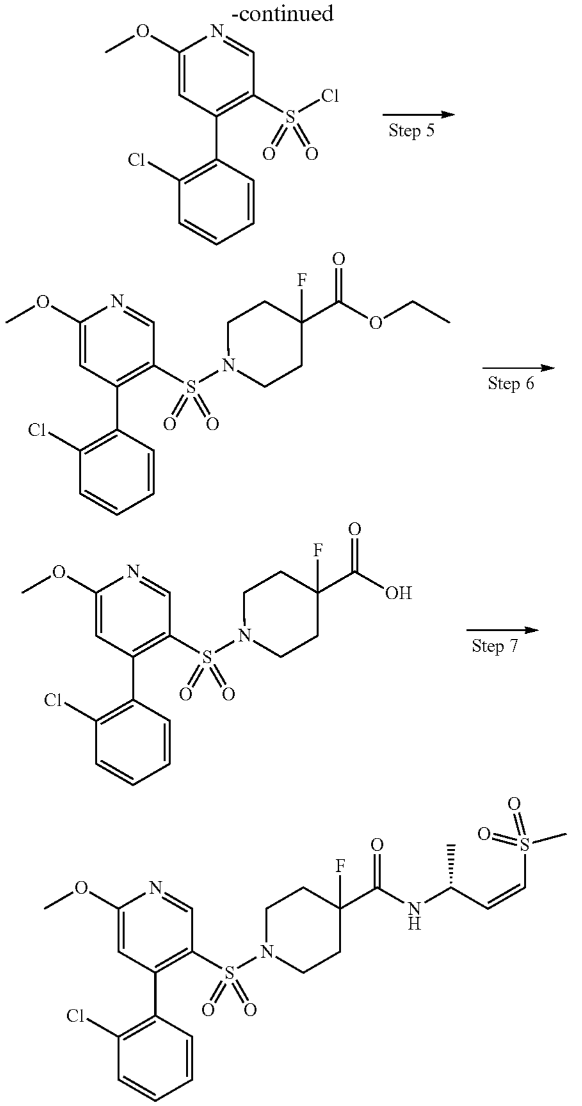

Step 1. To a solution of 5-bromo-2-chloro-4-iodopyridine (5 g, 15.7 mmol, 1 eq), (2-chlorophenyl)boronic acid (2.7 g, 17.3 mmol, 1.1 eq), $PPh_3$ (412 mg, 1.57 mmol, 0.1 eq) and $Pd(OAc)_2$ (176 mg, 0.79 mmol, 0.05 eq) in DME (100 mL, 0.16 M) was added 2 M $Na_2CO_3$ aq. (25 mL) and the mixture was stirred at 90 °C for 16 h. After cooling to rt, the mixture was diluted with water (300 mL) and extracted with EtOAc (200 mL×2). The combined organic phases were washed with brine (400 mL), dried over $Na_2SO_4$, filtered, concentrated and purified by column chromatography to give 5-bromo-2-chloro-4-(2-chlorophenyl)pyridine as a white solid (4 g, 13.2 mmol, 84% yield).

Step 2. To a solution of NaOMe (1.1 g, 19.8 mmol, 3.0 eq) in methanol (25 mL, 0.26 M) was added 5-bromo-2-chloro-4-(2-chlorophenyl)pyridine (2 g, 6.6 mmol, 1 eq) at 20 °C and the mixture was stirred at 120 °C for 24 h. After cooling to rt, the mixture was concentrated. The residue was dissolved with water (100 mL) and extracted with EtOAc (100 mL×2). The combined organic phases were washed with brine (100 mL×2), dried over $Na_2SO_4$, filtered, concentrated and purified by column chromatography (PE:EtOAc=98:2) to give 5-bromo-4-(2-chlorophenyl)-2-methoxy-pyridine as a white solid (1.9 g, 6.36 mmol, 96%).

Step 3. To a solution of 5-bromo-4-(2-chlorophenyl)-2-methoxy-pyridine (0.1 g, 0.33 mmol, 1 eq), DIPEA (130 mg, 1.01 mmol, 3 eq), $Pd_2(dba)_3$ (61 mg, 0.07 mmol, 0.2 eq) and XantPhos (77 mg, 0.13 mmol, 0.4 eq) in toluene (1 mL, 0.33 M) was added benzyl mercaptan (0.05 g, 0.37 mmol, 1.1 eq). The mixture was stirred at 140 °C under microwave irradiation for 1 h. After cooling to rt, the reaction was filtered. The filtrate was diluted with water (100 mL) and extracted with MTBE (100 mL×2). The combined organic phases were washed with brine (200 mL×2), dried over $Na_2SO_4$, filtered, concentrated and purified by FCC to give 5-benzylsulfanyl-4-(2-chlorophenyl)-2-methoxy-pyridine as a yellow oil (62 mg, 0.11 mmol, 54%).

Step 4. To a solution of 5-benzylsulfanyl-4-(2-chlorophenyl)-2-methoxy-pyridine (0.62 g, 1.81 mmol, 1 eq) in acetic acid (9 mL, 0.15 M) and water (3 mL, 0.15 M) was added NCS (969 mg, 7.25 mmol, 4 eq) at 0 °C and the mixture was stirred at 20 °C for 2 h. The mixture was diluted with water (60 mL) and extracted with ethyl acetate (30 mL×2). The extract was washed with brine (60 mL), dried over $Na_2SO_4$ and filtered. The filtrate was concentrated in vacuo. The residue was purified by column chromatography to afford 4-(2-chlorophenyl)-6-methoxy-pyridine-3-sulfonyl chloride (540 mg, 1.7 mmol, 94%) as a colorless oil, which was used in the next step directly.

Step 5. To a solution of ethyl 4-fluoropiperidine-4-carboxylate hydrochloride (467 mg, 2.21 mmol, 1.3 eq) in DCM (10 mL, 0.17 M) was added $Et_3N$ (515 mg, 5.09 mmol, 3 eq) and 4-(2-chlorophenyl)-6-methoxy-pyridine-3-sulfonyl chloride (540 mg, 1.7 mmol, 1 eq) in DCM (10 mL) at 0 °C. The mixture was stirred at 20 °C for 1 h. The reaction mixture was poured into water (30 mL) and extracted with EtOAc (20 mL×2). The combined organic layers were washed with brine (40 mL×2), dried over $Na_2SO_4$, filtered, and concentrated under reduced pressure. The residue was purified by column chromatography to afford ethyl 1-[[4-(2-chlorophenyl)-6-methoxy-3-pyridyl]sulfonyl]-4-fluoro-piperidine-4-carboxylate as a light yellow oil (700 mg, 1.53 mmol, 90%).

Step 6. To a solution of ethyl 1-[[4-(2-chlorophenyl)-6-methoxy-3-pyridyl]sulfonyl]-4-fluoro-piperidine-4-carboxylate (0.7 g, 1.53 mmol, 1 eq) in THF/water (v/v 3:1, 8 mL, 0.19 M) was added $LiOH/H_2O$ (88 mg, 2.1 mmol, 1.2 eq) and the mixture was stirred at 20 °C for 3 h. The mixture was concentrated in vacuo to give lithium 1-[[4-(2-chlorophenyl)-6-methoxy-3-pyridyl]sulfonyl]-4-fluoro-piperidine-4-carboxylate (660 mg, 1.52 mmol, 99%) as a light yellow solid, which was used in the next step directly.

Step 7. To a solution of lithium-1-[[4-(2-chlorophenyl)-6-methoxy-3-pyridyl]sulfonyl]-4-fluoro-piperidine-4-carboxylate (660 mg, 1.52 mmol, 1 eq) and (R,Z)-4-(methylsulfonyl)but-3-en-2-amine, TsOH salt (585 mg, 1.82 mmol, 1.2 eq) in DCM (8 mL, 0.19 M) was added DIPEA (588 mg, 4.55 mmol, 3 eq) and $T_3P$ (2.4 g, 3.79 mmol, 2.5 eq) and the mixture was stirred at 25 °C for 0.5 h. The mixture was quenched with water (20 mL) and extracted with DCM (10 mL×2). The combined organic phases were washed with brine (20 mL), dried over $Na_2SO_4$, filtered, concentrated and purified by column chromatography (PE:EtOAc=1:2) to give 1-[[4-(2-chlorophenyl)-6-methoxy-3-pyridyl]sulfonyl]-4-fluoro-N-[(Z,1R)-1-methyl-3-methylsulfonyl-allyl]piperidine-4-carboxamide (Compound 186) (700 mg, 1.25 mmol, 82%) as a white solid. $^1H$ NMR (400 MHz, DMSO-$d_6$) δ ppm 8.78 (s, 1H), 8.38 (br d, J=7.8 Hz, 1H), 7.56 (d, J=7.8 Hz, 1H), 7.51-7.32 (m, 3H), 6.86 (s, 1H), 6.45 (d, J=11.3 Hz, 1H), 6.36-6.20 (m, 1H), 5.46-5.26 (m, 1H), 3.99 (s, 3H), 3.26-2.97 (m, 5H), 2.79-2.66 (m, 1H), 2.59 (br t, J=12.3 Hz, 1H), 2.02-1.63 (m, 4H), 1.21 (d, J=6.9 Hz, 3H). [M+H] calculated for $C_{24}H_{28}ClFN_2O_6S_2$, 559; found 560.

Compounds 187-194 were synthesized in a manner analogous to Compound 186 using the appropriate boronic acid starting material and coupling with the appropriate amine in the final step.

Intermediate 4-(2-chlorophenyl)-6-(trifluoromethyl)pyridine-3-sulfonyl chloride was synthesized in a manner analogous to 4-(2-chlorophenyl)-6-methoxy-pyridine-3-sulfonyl chloride using 5-bromo-4-iodo-2-(trifluoromethyl)pyridine in Step 1 and excluding Step 2.

Compound 207 was synthesized in a manner analogous to Compound 186 using 5-bromo-4-iodo-2-(trifluoromethyl) pyridine in Step 1 and excluding Step 2.

Compound 208 was synthesized in a manner analogous to Compound 207 using (S,Z)-4-(methylsulfonyl)but-3-en-2-amine, 4-methylbenzenesulfonic acid salt in Step 7.

Compound 209 was synthesized in a manner analogous to Compound 207 using 2-chloro-3-fluorophenylboronic acid in Step 1.

Compound 210 was synthesized in a manner analogous to Compound 209 using (S,Z)-4-(methylsulfonyl)but-3-en-2-amine, 4-methylbenzenesulfonic acid salt in Step 7.

Compound 211 was synthesized in a manner analogous to Compound 207 using 2-chloro-4-fluorophenylboronic acid in Step 1.

Compound 212 was synthesized in a manner analogous to Compound 211 using (S,Z)-4-(methylsulfonyl)but-3-en-2-amine, 4-methylbenzenesulfonic acid salt in Step 7.

Compound 213 was synthesized in a manner analogous to Compound 207 using (E,4R)-4-amino-1-(3,3-difluoroazetidin-1-yl)pent-2-en-1-one in Step 7.

Compound 214 was synthesized in a manner analogous to Compound 141 from 4-(2-chlorophenyl)-6-(trifluoromethyl)pyridine-3-sulfonyl chloride.

Compound 215 was synthesized from 4-(2-chlorophenyl)-6-(trifluoromethyl)pyridine-3-sulfonyl chloride and (2R,4S)-N-((R,E)-5-(3,3-difluoroazetidin-1-yl)-5-oxopent-3-en-2-yl)-4-fluoro-2-methylpiperidine-4-carboxamide in a manner analogous to Compound 141.

Compounds 217-218 were synthesized in a manner analogous to Compound 186 using the appropriate starting material in Step 1 and excluding Step 2.

Compound 231 was synthesized in a manner analogous to Compound 186 excluding Step 2.

Compound 232 was synthesized in a manner analogous to Compound 231 using (E)-4-aminobut-2-enenitrile in Step 7.

Scheme 59. Synthesis of (R)-1-((3*R,4*R)-4-(2-chloro-4-methylphenyl)-1-(2,2,2-trifluoroethyl)pyrrolidine-3-carbonyl)-4-fluoro-N-((R,Z)-4-(methylsulfonyl)but-3-en-2-yl)azepane-4-carboxamide (Compound 169)

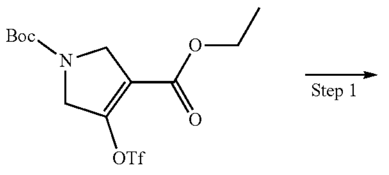

-continued

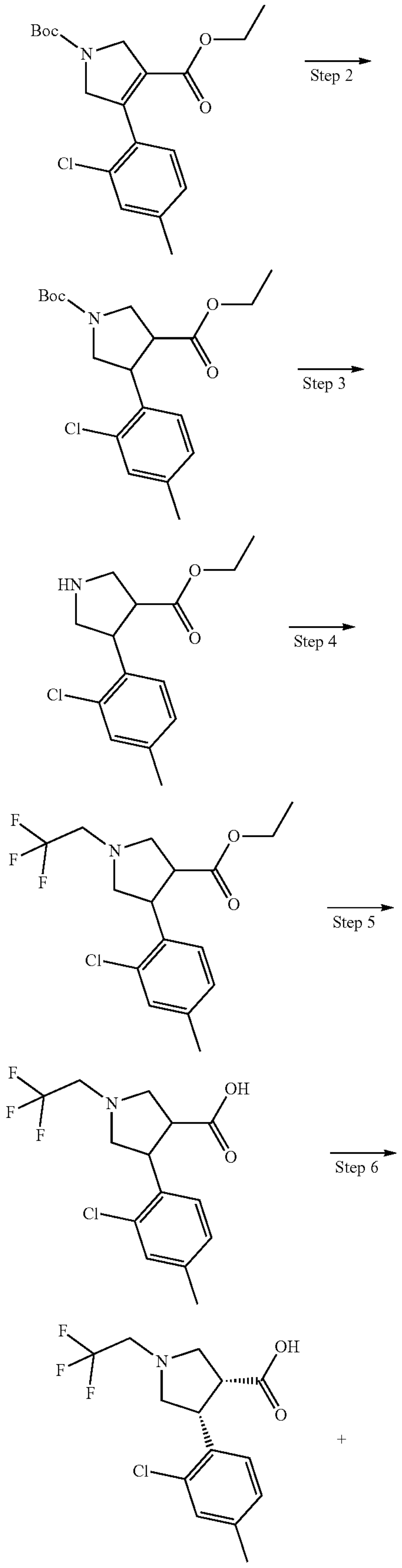

-continued

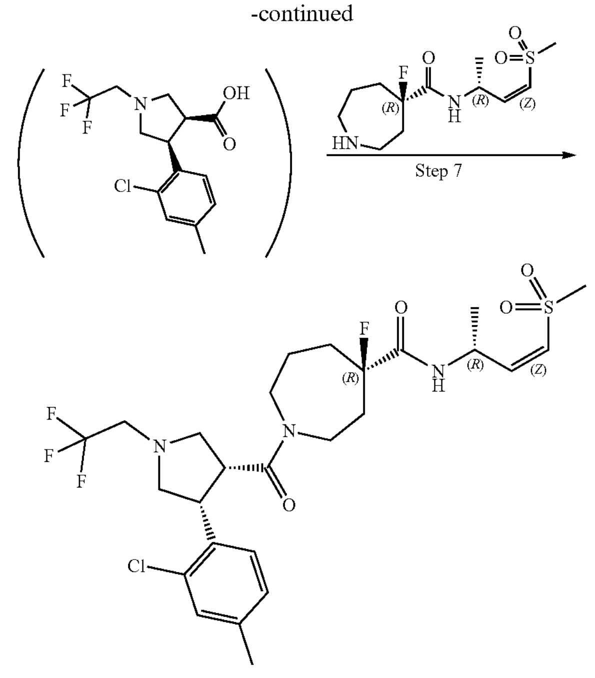

Step 1. To a solution of 1-tert-butyl 3-ethyl 4-(((trifluoromethyl)sulfonyl)oxy)-1H-pyrrole-1,3(2H,5H)-dicarboxylate (2.0 g, 5.30 mmol, 1.0 eq) in THF (20 mL, 0.26 M) was added (2-chloro-4-methyl-phenyl)boronic acid (993 mg, 5.83 mmol, 1.1 eq), $K_3PO_4$ (2.2 g, 10.6 mmol, 2.0 eq), and $Pd(PPh_3)_4$ (306 mg, 0.265 mmol, 0.05 eq). The reaction was placed under $N_2$ and stirred at 70 °C for 12 h. After cooling to rt, the solution was diluted with $H_2O$ (20 mL) and extracted with EtOAc (20 mL×3). The combined organic layers were washed with brine (20 mL×3), dried over $Na_2SO_4$, filtered, and concentrated under reduced pressure. The resulting residue was purified by FCC on silica (PE: EtOAc=1:0-5:1) to give 1-tert-butyl 3-ethyl 4-(2-chloro-4-methylphenyl)-1H-pyrrole-1,3(2H,5H)-dicarboxylate (1.6 g, 4.37 mmol, 83% yield) as a yellow oil. $^1H$ NMR (400 MHz, $CDCl_3$) δ ppm 7.26-7.22 (m, 1H), 7.14-6.97 (m, 2H), 4.61-4.40 (m, 4H), 4.11-4.01 (m, 2H), 2.38-2.32 (m, 3H), 1.50 (d, J=12.4 Hz, 9H), 1.13-1.03 (m, 3H).

Step 2. To a solution of 1-tert-butyl 3-ethyl 4-(2-chloro-4-methylphenyl)-1H-pyrrole-1,3(2H,5H)-dicarboxylate (500 mg, 1.37 mmol, 1.0 eq) in EtOAc:ethanol (3:1 v/v, 20 mL, 0.068 M) was added $PtO_2$ (155 mg, 0.683 mmol, 0.5 eq). The reaction was placed under $H_2$(15 psi) and stirred at 20 °C for 16 h before being filtered. The filtrate was concentrated and the resulting residue was purified by prep-TLC to give 1-tert-butyl 3-ethyl 4-(2-chloro-4-methylphenyl)pyrrolidine-1,3-dicarboxylate as a cis racemate (400 mg, 1.09 mmol, 80% yield) as a colorless oil. $^1H$ NMR (400 MHz, $CDCl_3$) δ ppm 7.24-7.18 (m, 1H), 7.15-7.08 (m, 1H), 7.05-6.97 (m, 1H), 4.13-4.02 (m, 1H), 3.91-3.73 (m, 5H), 3.72-3.62 (m, 1H), 3.60-3.49 (m, 1H), 2.35-2.26 (m, 3H), 1.50 (s, 9H), 0.92 (t, J=7.1 Hz, 3H).

Step 3. To a solution of 1-tert-butyl 3-ethyl 4-(2-chloro-4-methylphenyl)pyrrolidine-1,3-dicarboxylate (cis racemate) (400 mg, 1.09 mmol, 1.0 eq) in DCM (4.5 mL, 0.24 M) was added TFA (1.5 mL) and the reaction was stirred at 25 °C for 2 h. The reaction mixture was concentrated to obtain ethyl 4-(2-chloro-4-methylphenyl)pyrrolidine-3-carboxylate (cis racemate) (290 mg, 1.08 mmol, quant. yield) as a colorless oil, which was used directly in the next step. $^1H$ NMR (400 MHz, $CDCl_3$) δ ppm 7.18-6.93 (m, 3H), 4.35-4.25 (m, 1H), 3.90-3.79 (m, 4H), 3.77-3.70 (m, 3H), 2.35-2.32 (m, 3H), 0.86-0.79 (m, 3H).

Step 4. To ethyl 4-(2-chloro-4-methylphenyl)pyrrolidine-3-carboxylate (cis racemate) (290 mg, 1.08 mmol, 1.0 eq) in toluene (5.0 mL, 0.22 M) was added TEA (329 mg, 3.25 mmol, 3.0 eq) and 2,2,2-trifluoroethyl trifluoromethanesulfonate (502 mg, 2.17 mmol, 2.0 eq). The mixture was stirred at 80 °C for 16 h. After cooling to rt, the mixture was diluted with water (1.0 mL) and extracted with EtOAc (1.0 mL×3). The combined organic layers were washed with brine (2.0 mL), dried over $Na_2SO_4$, filtered, and concentrated under reduced pressure to give ethyl 4-(2-chloro-4-methylphenyl)-1-(2,2,2-trifluoroethyl)pyrrolidine-3-carboxylate (cis racemate) (300 mg, 0.858 mmol, 79% yield). This was used directly in the next step. MS (ESI): mass calculated for $C_{16}H_{19}ClF_3NO_2$, 349.1; m/z found, 350.1 $[M+H]^+$.

Step 5. To ethyl 4-(2-chloro-4-methylphenyl)-1-(2,2,2-trifluoroethyl)pyrrolidine-3-carboxylate (cis racemate) (300 mg, 0.858 mmol, 1.0 eq) was added HBr (3.0 mL, 48% solution). The mixture was stirred at 110 °C for 3 h. After cooling to rt, the mixture was concentrated under reduced pressure. The resulting residue was purified by prep-HPLC (15-45% ACN in 10 mM aq. $NH_4HCO_3$) to give 4-(2-chloro-4-methylphenyl)-1-(2,2,2-trifluoroethyl)pyrrolidine-3-carboxylic acid (cis racemate) (140 mg, 0.435 mmol, 51% yield) as a white solid. MS (ESI): mass calculated for $C_{14}H_{15}ClF_3NO_2$, 321.1; m/z found, 322.2 $[M+H]^+$.

Step 6. 4-(2-Chloro-4-methylphenyl)-1-(2,2,2-trifluoroethyl)pyrrolidine-3-carboxylic acid (cis racemate) (140 mg, 0.435 mmol, 1.0 eq) was separated by chiral SFC (Stationary phase: AD (250×30 mm), Mobile phase: 5-15% IPA/$CO_2$; Rt (P1)=8.37 min, Rt (P2)=9.37 min) to give two products. P1: (3*R,4*R)-4-(2-chloro-4-methylphenyl)-1-(2,2,2-trifluoroethyl)pyrrolidine-3-carboxylic acid (50 mg, 0.155 mmol, 36% yield) as a white solid. $^1H$ NMR (400 MHz, DMSO-$d_6$) δ ppm 7.23-7.16 (m, 2H), 7.06-6.98 (m, 1H), 4.29-4.17 (m, 1H), 3.62-3.47 (m, 1H), 3.33-3.12 (m, 6H), 2.30 (s, 3H).

Step 7. To a solution of (3*R,4*R)-4-(2-chloro-4-methylphenyl)-1-(2,2,2-trifluoroethyl)pyrrolidine-3-carboxylic acid (50 mg, 0.155 mmol, 1.0 eq) and (R)-4-fluoro-N-((R,Z)-4-(methylsulfonyl)but-3-en-2-yl)azepane-4-carboxamide (59 mg, 0.202 mmol, 1.3 eq) in DCM (1.0 mL, 0.16 M) was added DIPEA (60 mg, 0.466 mmol, 3.0 eq) and HATU (89 mg, 0.233 mmol, 1.5 eq). The reaction mixture was stirred under $N_2$ at 25 °C for 12 h. The mixture was quenched with water (1.0 mL) and extracted with DCM (1.0 mL×3). The combined organic layers were washed with brine (3.0 mL), dried over with $Na_2SO_4$, filtered, and concentrated under reduced pressure. The resulting residue was purified via prep-HPLC (20-50% ACN in 0.075% aq. TFA) to give (R)-1-((3*R,4*R)-4-(2-chloro-4-methylphenyl)-1-(2,2,2-trifluoroethyl)pyrrolidine-3-carbonyl)-4-fluoro-N-((R,Z)-4-(methylsulfonyl)but-3-en-2-yl)azepane-4-carboxamide (as TFA salt, 80 mg, 0.135 mmol, 87% yield) as a white solid. MS (ESI): mass calculated for $C_{26}H_{34}ClF_4N_3O_4S$, 595.2; m/z found, 596.4 $[M+H]^+$. $^1H$ NMR (400 MHz, DMSO-$d_6$) δ ppm 8.33-8.17 (m, 1H), 7.29-7.13 (m, 2H), 7.11-7.01 (m, 1H), 6.51-6.38 (m, 1H), 6.33-6.21 (m, 1H), 5.36-5.26 (m, 1H), 4.10 (br d, J=9.1 Hz, 2H), 3.86-3.81 (m, 2H), 3.73-3.61 (m, 3H), 3.49 (br d, J=10.6 Hz, 1H), 3.26-3.17 (m, 1H), 3.14-3.07 (m, 3H), 2.90-2.68 (m, 3H), 2.29-2.22 (m, 3H), 2.00-1.78 (m, 2H), 1.67-1.45 (m, 4H), 1.25-1.16 (m, 3H).

Compound 224 was synthesized in a manner analogous to Compound 169 using 2-methylphenylboronic acid in Step 1.

Scheme 60. Synthesis of (R)-1-((3R,4R)-4-(2-chloro-6-fluorophenyl)-1-(2,2,2-trifluoroethyl)pyrrolidine-3-carbonyl)-4-fluoro-N-((R,Z)-4-(methylsulfonyl)but-3-en-2-yl)azepane-4-carboxamide (Compound 171)

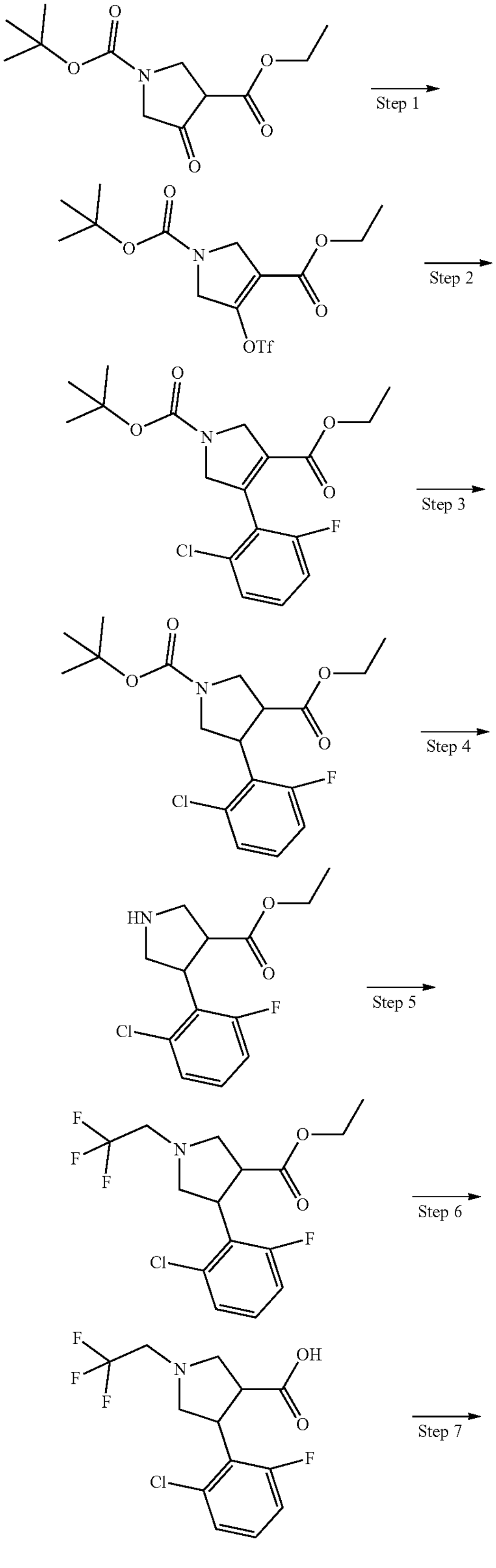

-continued

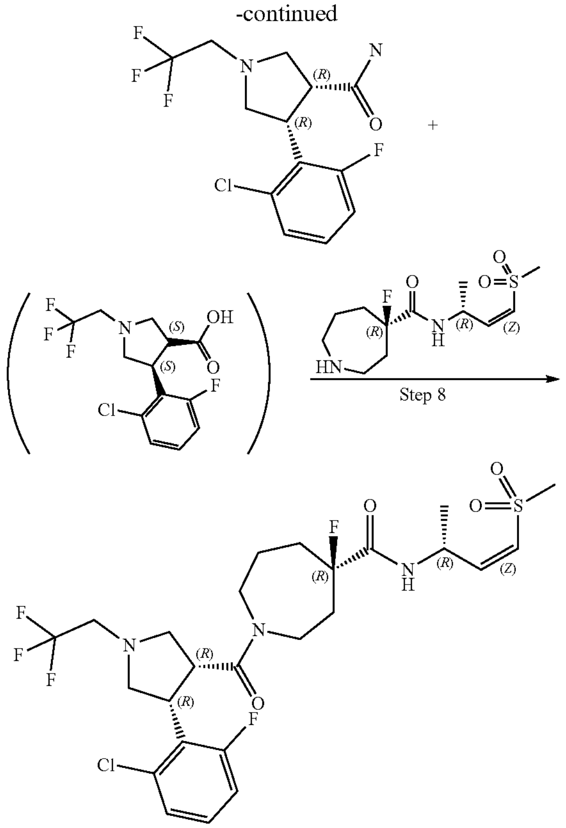

Step 1. To a solution of 1-tert-butyl 3-ethyl 4-oxopyrrolidine-1,3-dicarboxylate (5.0 g, 19.4 mmol, 1.0 eq) in toluene (100 mL, 0.19 M) was added DIPEA (3.8 g, 29.2 mmol, 1.5 eq) and trifluoromethanesulfonic anhydride (6.6 g, 23.3 mmol, 1.2 eq) at 0 °C. The reaction was allowed to warm to 20 °C and stirred for 16 h. The solution was evaporated to give 1-tert-butyl 3-ethyl 4-(((trifluoromethyl)sulfonyl)oxy)-1H-pyrrole-1,3(2H,5H)-dicarboxylate (7.5 g, 19.3 mmol, quant. yield) as a brown solid, which was used in the next step directly.

Step 2. To a solution of 1-tert-butyl 3-ethyl 4-(((trifluoromethyl)sulfonyl)oxy)-1H-pyrrole-1,3(2H,5H)-dicarboxylate (7.5 g, 19.3 mmol, 1.0 eq) in THF (80 mL, 0.24 M) was added (2-chloro-6-fluoro-phenyl)boronic acid (3.7 g, 21.2 mmol, 1.1 eq), $K_3PO_4$ (8.3 g, 38.5 mmol, 2.0 eq), and $Pd(PPh_3)_4$(1.1 g, 0.960 mmol, 0.05 eq). The reaction was placed under $N_2$ and heated to 80 °C for 12 h. After cooling to rt, the solution was diluted with $H_2O$ (100 mL) and extracted with EtOAc (100 mL×3). The combined organic phases were washed with brine (50 mL×3), dried over $Na_2SO_4$, filtered, and concentrated under reduced pressure. The resulting residue was purified by FCC on silica (PE: EtOAc=1:0-9:1) to provide 1-tert-butyl 3-ethyl 4-(2-chloro-6-fluorophenyl)-1H-pyrrole-1,3(2H,5H)-dicarboxylate (6.0 g, 16.2 mmol, 84% yield) as a yellow solid. $^1H$ NMR (400 MHz, $CDCl_3$) δ ppm 7.33-7.27 (m, 1H), 7.26-7.21 (m, 1H), 7.07-7.01 (m, 1H), 4.60-4.42 (m, 4H), 4.11-4.03 (m, 2H), 1.51 (d, J=11.8 Hz, 9H), 1.06 (dt, J=10.5, 7.1 Hz, 3H).

Step 3. To a solution of 1-tert-butyl 3-ethyl 4-(2-chloro-6-fluorophenyl)-1H-pyrrole-1,3(2H,5H)-dicarboxylate (1.0 g, 2.70 mmol, 1.0 eq) in ethanol (10 mL, 0.27 M) was added wet Rh/C (0.40 g, 1.35 mmol, 0.5 eq). The reaction was placed under $H_2$ (50 psi) and stirred at 25 °C for 16 h. The solution was filtered then evaporated under reduced pressure. The resulting residue was purified by prep-HPLC (40-75% ACN in 10 mM aq. $NH_4HCO_3$) to provide 1-tert-butyl 3-ethyl 4-(2-chloro-6-fluorophenyl)pyrrolidine-1,3-dicarboxylate as a cis racemate (900 mg, 2.42 mmol, 89% yield) as a colorless oil. $^1$H NMR (400 MHz, $CDCl_3$) δ ppm 7.23-7.14 (m, 2H), 6.96 (ddd, J=11.1, 7.9, 1.5 Hz, 1H), 4.27 (q, J=8.1 Hz, 1H), 3.99-3.82 (m, 5H), 3.75-3.64 (m, 1H), 3.56-3.47 (m, 1H), 1.50 (s, 9H), 0.99 (t, J=7.1 Hz, 3H).

Step 4. To a solution of 1-tert-butyl 3-ethyl 4-(2-chloro-6-fluorophenyl)pyrrolidine-1,3-dicarboxylate (cis racemate) (900 mg, 2.42 mmol, 1.0 eq) in DCM (10 mL, 0.24 M) was added TFA (3.0 mL, 39.2 mmol, 16 eq). The reaction was stirred at 25 °C for 3 h before being slowly poured into sat. aq. $NaHCO_3$ (50 mL) and extracted with EtOAc (50 mL×3). The combined organic layers were washed with brine (30 mL×2), dried over $Na_2SO_4$, and filtered. The filtrate was concentrated under reduced pressure to give ethyl 4-(2-chloro-6-fluorophenyl)pyrrolidine-3-carboxylate (cis racemate) (650 mg, 2.39 mmol, 98% yield) as a yellow oil. This was used in the next step directly without purification.

Step 5. To ethyl 4-(2-chloro-6-fluorophenyl)pyrrolidine-3-carboxylate (cis racemate) (650 mg, 2.39 mmol, 1.0 eq) in toluene (10 mL, 0.24 M) was added TEA (730 mg, 7.18 mmol, 3.0 eq) and 2,2,2-trifluoroethyl trifluoromethanesulfonate (1.1 g, 4.78 mmol, 2.0 eq) at 0 °C. The reaction was stirred at 80 °C for 16 h. After cooling to rt, the mixture was concentrated to remove solvent then diluted with water (30 mL) and extracted with DCM (20 mL×3). The combined organic layers were washed with brine (10 mL), dried over $Na_2SO_4$, filtered, and concentrated under reduced pressure. The resulting residue was purified by FCC on silica (PE: EtOAc=10:1-1:1) to give ethyl 4-(2-chloro-6-fluorophenyl)-1-(2,2,2-trifluoroethyl)pyrrolidine-3-carboxylate (cis racemate) (700 mg, 1.98 mmol, 83% yield) as a colorless oil. $^1$H NMR (400 MHz, $CDCl_3$) δ ppm 7.22-7.19 (m, 1H), 7.18-7.12 (m, 1H), 6.94 (ddd, J=10.9, 8.1, 1.3 Hz, 1H), 4.42-4.33 (m, 1H), 3.86-3.73 (m, 2H), 3.57 (dt, J=11.0, 8.3 Hz, 1H), 3.49-3.41 (m, 2H), 3.31-3.19 (m, 2H), 3.18-3.12 (m, 1H), 3.06 (td, J=9.5, 3.1 Hz, 1H), 0.86 (t, J=7.1 Hz, 3H).

Step 6. To a solution of ethyl 4-(2-chloro-6-fluorophenyl)-1-(2,2,2-trifluoroethyl)pyrrolidine-3-carboxylate (cis racemate) (700 mg, 1.98 mmol, 1.0 eq) in DCE (10 mL, 0.19 M) was added $Me_3SnOH$ (1.8 g, 9.89 mmol, 5.0 eq). The mixture was stirred at 110 °C for 48 h. After cooling to rt, the solution was filtered and evaporated under reduced pressure. The resulting residue was purified by prep-HPLC (25-70% ACN in 10 mM aq. TFA) to provide 4-(2-chloro-6-fluorophenyl)-1-(2,2,2-trifluoroethyl)pyrrolidine-3-carboxylic acid (cis racemate) (400 mg, 1.23 mmol, 62% yield) as a white solid. $^1$H NMR (400 MHz, $CDCl_3$) δ ppm 7.25-7.15 (m, 2H), 7.00-6.93 (m, 1H), 4.46-4.37 (m, 1H), 3.65-3.57 (m, 1H), 3.45-3.27 (m, 6H).

Step 7. 4-(2-Chloro-6-fluorophenyl)-1-(2,2,2-trifluoroethyl)pyrrolidine-3-carboxylic acid (cis racemate) (400 mg, 1.23 mmol, 1.0 eq) was separated by chiral SFC (Stationary phase: AD (250×30 mm); Mobile phase: 15% $MeOH/CO_2$, Rt (P1)=23.6 min, Rt (P2)=27.5 min) to give two products. P1: (3R,4R)-4-(2-chloro-6-fluorophenyl)-1-(2,2,2-trifluoroethyl)pyrrolidine-3-carboxylic acid (100 mg, 0.307 mmol, 25% yield) was obtained as a white solid. $^1$H NMR (400 MHz, $CDCl_3$) δ ppm 7.26-7.19 (m, 2H), 7.03-6.94 (m, 1H), 4.62 (q, J=9.0 Hz, 1H), 4.13 (q, J=7.1 Hz, 1H), 3.86 (br s, 2H), 3.79-3.51 (m, 4H). P2: (3S,4S)-4-(2-chloro-6-fluorophenyl)-1-(2,2,2-trifluoroethyl)pyrrolidine-3-carboxylic acid (100 mg, 0.307 mmol, 25% yield) was obtained as a white solid. $^1$H NMR (400 MHz, $CDCl_3$) δ ppm 7.24-7.14 (m, 2H), 6.99-6.91 (m, 1H), 4.43 (q, J=9.2 Hz, 1H), 3.69-3.55 (m, 1H), 3.46 (br s, 2H), 3.40-3.20 (m, 4H).

Step 8. To a mixture of (3R,4R)-4-(2-chloro-6-fluorophenyl)-1-(2,2,2-trifluoroethyl)pyrrolidine-3-carboxylic acid (100 mg, 0.307 mmol, 1.0 eq) in DCM (3.0 mL, 0.10 M) was added DIPEA (119 mg, 0.920 mmol, 3.0 eq), HATU (175 mg, 0.461 mmol, 1.5 eq), and (R)-4-fluoro-N-((R,Z)-4-(methylsulfonyl)but-3-en-2-yl)azepane-4-carboxamide, TsOH salt (90 mg, 0.307 mmol, 1.0 eq). The reaction was stirred at 20 °C for 2 h before being diluted with water (10 mL) and extracted with EtOAc (10 mL×3). The combined organic phases were washed with brine (5.0 mL), dried over $Na_2SO_4$, filtered, and concentrated under reduced pressure. The resulting residue was purified by prep-HPLC (10-55% ACN in 10 mM aq. TFA) to provide (R)-1-((3R,4R)-4-(2-chloro-6-fluorophenyl)-1-(2,2,2-trifluoroethyl)pyrrolidine-3-carbonyl)-4-fluoro-N-((R,Z)-4-(methylsulfonyl)but-3-en-2-yl)azepane-4-carboxamide (as TFA salt, 78 mg, 0.125 mmol, 40% yield) as a white solid. MS (ESI): mass calculated for $C_{25}H_{31}ClF_5N_3O_4S$, 599.2; m/z found, 600.2 $[M+H]^+$. $^1$H NMR (400 MHz, DMSO-$d_6$) δ ppm 8.17-8.36 (m, 1H), 7.24-7.34 (m, 2H), 7.06-7.17 (m, 1H), 6.40-6.48 (m, 1H), 6.21-6.32 (m, 1H), 5.25-5.37 (m, 1H), 4.08-4.22 (m, 1H), 3.79-3.92 (m, 1H), 3.54-3.62 (m, 3H), 3.30-3.34 (m, 1H), 3.17-3.27 (m, 2H), 3.09-3.12 (m, 3H), 2.75-2.85 (m, 1H), 2.68 (br d, J=12.8 Hz, 1H), 2.54-2.61 (m, 1H), 1.69-2.09 (m, 4H), 1.42-1.69 (m, 3H), 1.16-1.24 (m, 3H).

Compound 223 was synthesized in a manner analogous to Compound 171 using 2-fluorophenylboronic acid in Step 2.

Compound 226 was synthesized in a manner analogous to Compound 171 using (2-chloro-3,6-difluorophenyl)boronic acid in Step 2.

Compound 227 was synthesized in a manner analogous to Compound 171 using 2-(2-chloro-4,6-difluorophenyl)-4,4,5,5-tetramethyl-1,3,2-dioxaborolane in Step 2.

Compound 296 was synthesized in a manner analogous to Compound 164 using methyl(R)-4-fluoroazepane-4-carboxylate and (3R,4R)-4-(2-chloro-6-fluorophenyl)-1-(2,2,2-trifluoroethyl)pyrrolidine-3-carboxylic acid in Step 1 and (R,E)-4-methylsulfonylbut-3-en-2-amine in Step 3.

Compound 297 was synthesized in a manner analogous to Compound 296 using (S,Z)-4-(methylsulfonyl)but-3-en-2-amine in Step 3.

Scheme 61. Synthesis of (E)-4-fluoro-1-((3′-methoxy-[1,1′-biphenyl]-2-yl)sulfonyl)-N-(3-((1-methylpiperidin-4-yl)sulfonyl)allyl)piperidine-4-carboxamide (Compound 228)

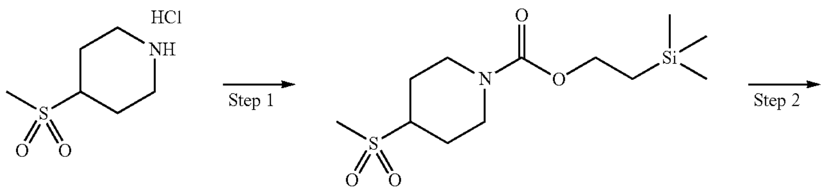

-continued

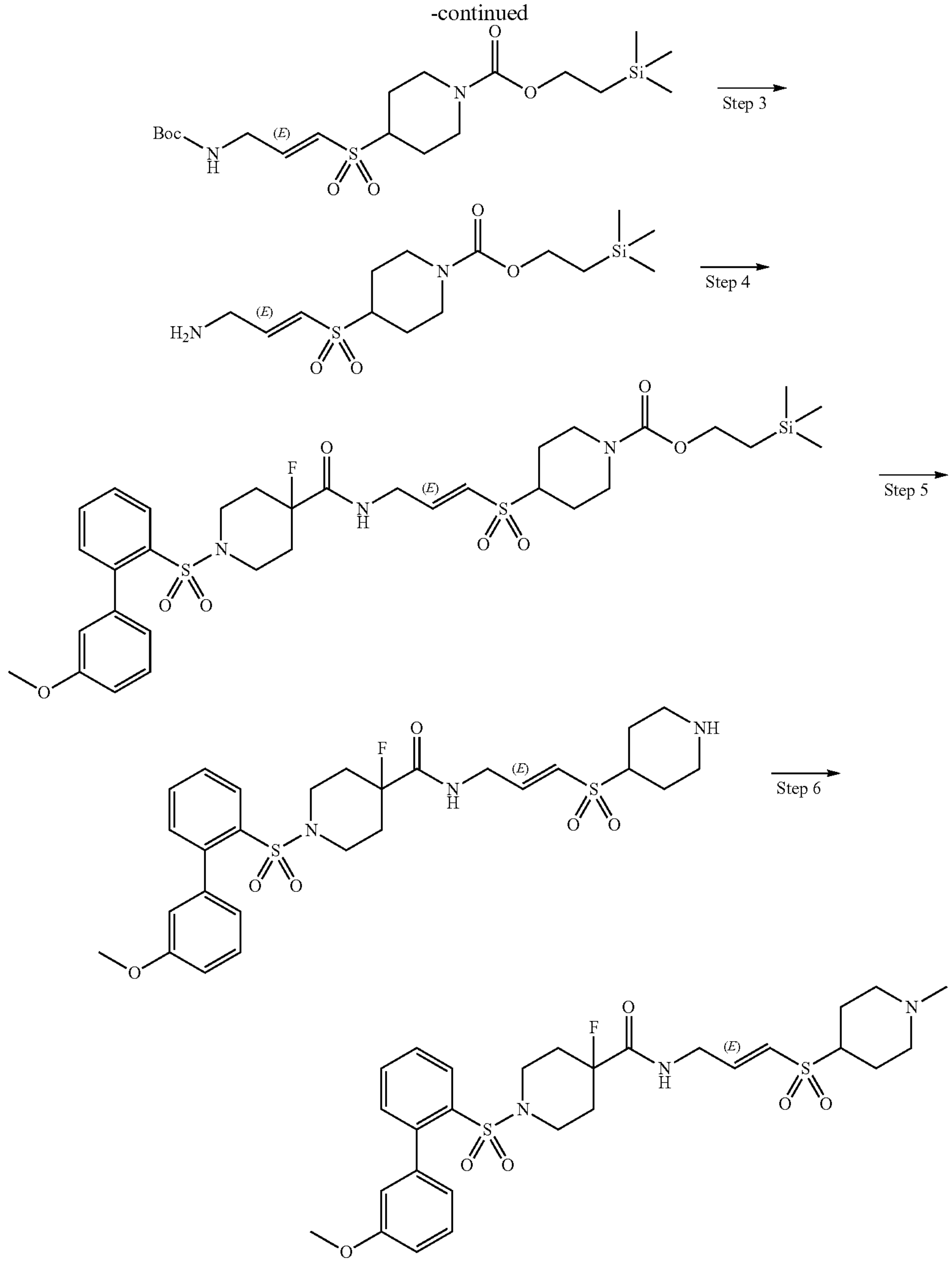

Step 1. At 0 °C, (2,5-dioxopyrrolidin-1-yl) 2-trimethylsilylethyl carbonate (2.7 g, 10.5 mmol, 1.05 eq) was added to the mixture of 4-methylsulfonylpiperidine hydrochloride (2.0 g, 10.0 mmol, 1 eq) and $Et_3N$ (1.2 g, 12.0 mmol, 1.2 eq) in DCM/MeOH (1:1 v/v, 20 mL). The resulting mixture was stirred at 25 °C for 16 h before being concentrated under reduced pressure. The resulting residue was purified by FCC on silica (PE:EtOAc=1:0-1:1) to provide 2-(trimethylsilyl)ethyl-4-(methylsulfonyl)piperidine-1-carboxylate (3.2 g, 10.4 mmol, quant. yield) as a white solid. $^1H$ NMR (400 MHz, $CDCl_3$) δ ppm 4.37 (br s, 2H), 4.24-4.16 (m, 2H), 2.99 (tt, J=3.6, 12.1 Hz, 1H), 2.85 (s, 3H), 2.84-2.73 (m, 2H), 2.15 (br d, J=13.6 Hz, 2H), 1.74 (dq, J=4.5, 12.4 Hz, 2H), 1.05-0.97 (m, 2H), 0.05 (s, 9H).

Step 2. To a solution of 2-trimethylsilylethyl 4-methylsulfonylpiperidine-1-carboxylate (1.4 g, 4.55 mmol) in THF (19 mL) was added LiHMDS (11 mL, 1 M) dropwise at −78 °C. The mixture was stirred at −78 °C for 40 min before diphenyl phosphorochloridate (1.3 g, 5 mmol) was added dropwise at −78 °C. The mixture was stirred at −78 °C for 40 min before a solution of N-boc-2-aminoacetaldehyde (797 mg, 5 mmol) in THF (2 mL) was added dropwise at −78 °C. The resulting mixture was stirred at −78 °C for 1 h. The reaction mixture was quenched with $NH_4Cl$ (100 mL) and extracted with EtOAc (80 mL×3). The combined organic layers were washed with brine (80 mL×2), dried over $Na_2SO_4$, filtered, and concentrated under reduced pressure. The resulting residue was stirred in DCM (20 mL) for 30 min and filtered. The residue was purified by FCC on silica (PE:EtOAc=1:0-7:3) to provide (E)-2-(trimethylsilyl) ethyl 4-((3-((tert-butoxycarbonyl)amino)prop-1-en-1-yl) sulfonyl)piperidine-1-carboxylate (400 mg, 0.890 mmol, 20% yield) as a colorless oil. $^1$H NMR (400 MHz, $CDCl_3$) δ ppm 6.84 (br d, J=15.4 Hz, 1H), 6.30 (br d, J=14.5 Hz, 1H), 4.76 (br s, 1H), 4.21-4.35 (m, 2H), 4.10-4.16 (m, 2H), 3.96 (br d, J=9.2 Hz, 2H), 2.89 (br t, J=12.0 Hz, 1H), 2.72 (br s, 2H), 1.99-2.10 (m, 2H), 1.55-1.79 (m, 2H), 1.41 (s, 9H), 0.96 (br t, J=8.19 Hz, 2H), 0.00 (s, 9H).

Step 3. To a solution of 2-trimethylsilylethyl 4-[(E)-3-(tert-butoxycarbonylamino)prop-1-enyl]sulfonylpiperidine-1-carboxylate (200 mg, 0.440 mmol, 1 eq) in MeCN (5 mL) was added 4-methylbenzenesulfonic acid (84 mg, 0.490 mmol, 1.1 eq). The reaction mixture was stirred for 12 h at 50 °C. After cooling to rt, the reaction mixture was concentrated to give (E)-2-(trimethylsilyl)ethyl 4-((3-aminoprop-1-en-1-yl)sulfonyl)piperidine-1-carboxylate (TsOH salt, 200 mg) as a yellow solid, which was used in the next step without purification.

Step 4. To a solution of 4-methylbenzenesulfonate[(E)-3-[[1-(2-trimethylsilylethoxycarbonyl)-4-piperidyl]sulfonyl] allyl]ammonium (150 mg, 0.290 mmol, 1.0 eq) in DCM (5 mL) was added DIPEA (0.860 mmol, 3.0 eq) and 4-fluoro-1-((3'-methoxy-[1,1'-biphenyl]-2-yl)sulfonyl)piperidine-4-carboxylic acid (113 mg, 0.290 mmol, 1.0 eq). HATU (165 mg, 0.430 mmol, 1.5 eq) was added and the reaction mixture was stirred for 2 h at 25 °C. The reaction mixture was quenched with water and extracted with DCM to give the crude product, which was purified by prep-TLC (PE:EtOAc=1:1) to give 2-trimethylsilylethyl 4-[(E)-3-[[4-fluoro-1-[2-(3-methoxyphenyl)phenyl]sulfonyl-piperidine-4-carbonyl]amino]prop-1-enyl]sulfonylpiperidine-1-carboxylate (60 mg, 29% yield) as a yellow solid.

Step 5. To a solution of 2-trimethylsilylethyl 4-[(E)-3-[[4-fluoro-1-[2-(3-methoxyphenyl)phenyl]sulfonyl-piperidine-4-carbonyl]amino]prop-1-enyl]sulfonylpiperidine-1-carboxylate (60 mg, 0.086 mmol, 1.0 eq) in DCM (2 mL) was added TFA (1 mL). The reaction mixture was stirred for 12 h at 25 °C before being concentrated under reduced pressure. The resulting residue was purified by prep-HPLC to give 4-fluoro-1-[2-(3-methoxyphenyl)phenyl]sulfonyl-N-[(E)-3-(4-piperidylsulfonyl)allyl]piperidine-4-carboxamide (50 mg, 0.086 mmol, quant. yield) as a yellow solid. $^1$H NMR (400 MHz, DMSO-$d_6$) δ ppm 8.99 (br s, 1H), 8.59 (br s, 2H), 8.04 (dd, J=7.8, 1.1 Hz, 1H), 7.59-7.79 (m, 2H), 7.28-7.43 (m, 2H), 6.88-7.03 (m, 3H), 6.75 (dt, J=15.3, 4.5 Hz, 1H), 6.50 (br d, J=15.3 Hz, 1H), 3.97 (br s, 2H), 3.79 (s, 3H), 3.27-3.34 (m, 1H), 3.16 (br d, J=13.0 Hz, 2H), 2.89 (q, J=11.7 Hz, 2H), 2.57-2.58 (m, 1H), 2.40-2.45 (m, 2H), 2.34 (br d, J=1.9 Hz, 4H), 2.06 (br d, J=11.6 Hz, 2H), 1.65-1.83 (m, 6H).

Step 6. To a solution of 4-fluoro-1-[2-(3-methoxyphenyl) phenyl]sulfonyl-N-[(E)-3-(4-piperidylsulfonyl)allyl]piperidine-4-carboxamide (60 mg, 0.10 mmol, 1.0 eq) in methanol (5 mL) was added HCHO (37% in water, 0.5 mL) and $NaBH_3CN$ (60 mg, 1.0 mmol, 10 eq). The reaction mixture was stirred for 16 h at 25 °C before being concentrated. The crude product was purified by prep-HPLC to provide 4-fluoro-1-[2-(3-methoxyphenyl)phenyl]sulfonyl-N-[(E)-3-[(1-methyl-4piperidyl)sulfonyl]allyl]piperidine-4-carboxamide (27 mg, 0.045 mmol, 44% yield) as a white solid. MS (ESI): mass calculated for $C_{25}H_{36}FN_3O_6S_2$, 593; m/z found, 594 $[M+H]^+$. $^1$H NMR (400 MHz, DMSO-$d_6$) δ ppm 10.35 (br s, 1H), 8.61 (br s, 1H), 8.05 (d, J=7.9 Hz, 1H), 7.57-7.80 (m, 2H), 7.27-7.46 (m, 2H), 6.84-7.03 (m, 3H), 6.66-6.81 (m, 1H), 6.53 (br d, J=15.3 Hz, 1H), 3.98 (br s, 2H), 3.80 (s, 3H), 3.53 (br d, J=11.9 Hz, 2H), 3.10-3.35 (m, 3H), 2.86-3.02 (m, 2H), 2.68-2.78 (m, 3H), 2.53-2.56 (m, 2H), 2.46-2.49 (m, 1H), 2.11 (br d, J=12.8 Hz, 2H), 1.65-1.93 (m, 6H).

Scheme 62. Synthesis of Intermediate 3-(aminomethyl)-2H-thiete 1,1-dioxide

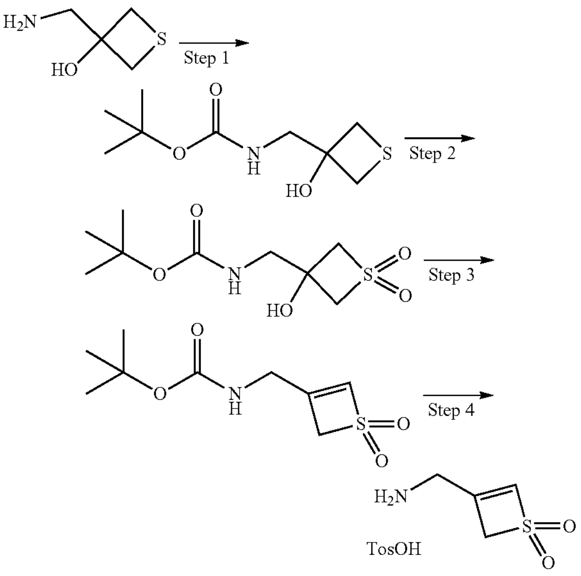

Step 1. To a solution of 3-(aminomethyl)thietan-3-ol (9.0 g, 75.5 mmol, 1.0 eq) and triethylamine (7.6 g, 75.5 mmol, 1.0 eq) in DCM (100 mL) was added di-tert-butyl dicarbonate (1.9 g, 86.8 mmol, 1.2 eq) at 0 °C. The reaction was stirred at 25 °C for 12 h before being concentrated under vacuum. The residue was purified by FCC on silica (PE: EtOAc=3:1-1:1) to give tert-butyl N-[(3-hydroxythietan-3-yl)methyl]carbamate (10 g, 45.6 mmol, 60% yield) as a light yellow solid. $^1$H NMR (400 MHz, $CDCl_3$) δ ppm 5.21 (br s, 1H), 4.88 (s, 1H), 3.60 (d, J=6.0 Hz, 2H), 3.42 (br d, J=9.8 Hz, 2H), 2.98 (br d, J=10.0 Hz, 2H), 1.39-1.49 (m, 9H).

Step 2. To a solution of tert-butyl N-[(3-hydroxythietan-3-yl)methyl]carbamate (10 g, 45.6 mmol, 1.0 eq) in EtOAc (150 mL, 0.3 M) was added 3-chloroperbenzoic acid (23 g, 114 mmol, 2.5 eq) in portions at 0 °C. The reaction was stirred at 20 °C for 2 h before being filtered. The filtrate was washed with a solution of disodium sulfite (8.6 g, 68.4 mmol, 1.5 eq) in $H_2O$ (150 mL) at 0 °C. The EtOAc layer was washed with sat. aq. $NaHCO_3$ (100 mL×2) and brine (150 mL), dried over $Na_2SO_4$, filtered, and concentrated under reduced pressure to give tert-butyl N-[(3-hydroxy-1,1-dioxo-thietan-3-yl)methyl]carbamate (8.0 g, 31.8 mmol, 70% yield).

Step 3. To a solution of tert-butyl N-[(3-hydroxy-1,1-dioxo-thietan-3-yl)methyl]carbamate (2.0 g, 7.96 mmol, 1.0 eq) in DCM (20 mL, 0.42 M) was added triethylamine (4.8 g, 47.7 mmol, 6.0 eq) at 0 °C followed by dropwise addition of methanesulfonyl chloride (3.2 mg, 27.5 mmol, 3.5 eq) in DCM (10 mL). The reaction was stirred at 20 °C for 4 h before being quenched with sat. aq. sodium bicarbonate (20 mL). The aq. phase was extracted with DCM (20 mL×2) and the combined organic layers were washed with brine (30 mL), dried over $Na_2SO_4$, filtered, and concentrated to give tert-butyl N-[(1,1-dioxo-2H-thiet-3-yl)methyl]carbamate (1.9 g, 8.20 mmol). This was used directly in the next step.

Step 4. To a solution of tert-butyl N-[(1,1-dioxo-2H-thiet-3-yl)methyl]carbamate (4.5 g, 19.3 mmol, 1.0 eq) in MeCN (8.0 mL, 2.4 M) was added p-toluenesulfonic acid monohydrate (4.4 g, 23.1 mmol, 1.2 eq). The reaction was stirred at 60 °C for 2 h before being cooled to 0 °C and filtered. The filter cake was concentrated under reduced pressure to give 3-(aminomethyl)-2H-thiete 1,1-dioxide; 4-methylbenzenesulfonate (4.3 g, 14.1 mmol, 73% yield) as a white solid. $^1H$ NMR (400 MHz, DMSO-$d_6$) δ ppm 8.25 (br s, 3H), 7.48 (d, J=8.0 Hz, 2H), 7.12 (d, J=7.8 Hz, 2H), 7.08 (t, J=1.8 Hz, 1H), 4.62 (s, 2H), 3.95 (br s, 2H), 2.29 (s, 3H).

Compound 233 was synthesized in a manner analogous to Compound 47 using 3-(aminomethyl)-2H-thiete 1,1-dioxide in Step 5.

Scheme 63. Synthesis of Intermediate (R)-3-(1-aminoethyl)-2H-thiete 1,1-dioxide

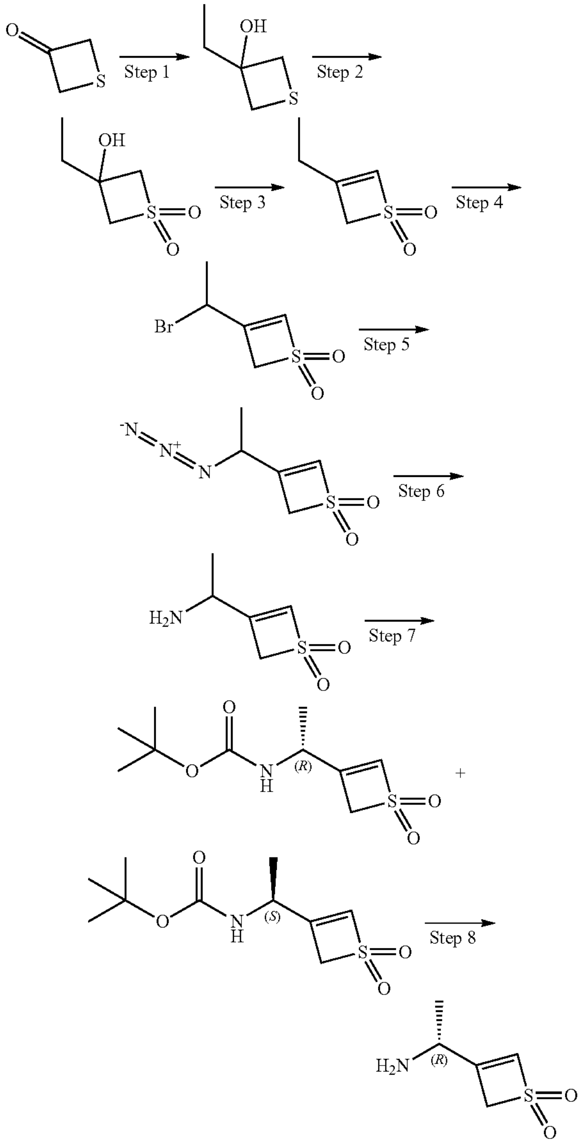

Step 1. To a solution of thietan-3-one (20 g, 227 mmol, 1.0 eq) in THF (150 mL) was added EtMgBr (76 mL, 227 mmol, 1.0 eq) dropwise at 0 °C under $N_2$. The reaction was stirred at 25 °C for 2 h before being quenched by sat. aq. $NH_4Cl$ (200 mL) and extracted with EtOAc (100 mL×2). The combined organic layers were washed with brine (100 mL), dried over $Na_2SO_4$, filtered, and concentrated under reduced pressure. The resulting residue was purified by FCC on silica (PE:EtOAc=1:0-5:1) to give 3-ethylthietan-3-ol (7.0 g, 59.2 mmol, 26% yield) as a colorless oil.

Step 2. To a solution of 3-ethylthietan-3-ol (7.0 g, 59.2 mmol, 1.0 eq) in ethyl acetate (140 mL) at 0 °C was added m-CPBA (28 g, 130 mmol, 2.2 eq) portionwise under $N_2$. The reaction was stirred at 25 °C for 2 h before being filtered. The filtrate was washed with $Na_2SO_3$ (80 mL) and extracted with ethyl acetate (80 mL). The combined organic layers were washed with brine (50 mL), dried over $Na_2SO_4$, filtered, and concentrated. The resulting residue was purified by FCC on silica (PE:EtOAc=9:1-7:3) to provide 3-ethyl-1,1-dioxo-thietan-3-ol (3.2 g, 21.3 mmol, 36% yield) as a yellow oil.

Step 3. To a solution of 3-ethyl-1,1-dioxo-thietan-3-ol (3.5 g, 23.3 mmol, 1.0 eq) in DCM (25 mL) at 0 °C was added $Et_3N$ (14 g, 140 mmol, 6.0 eq) followed by a solution of methanesulfonyl chloride (4.9 g, 43.3 mmol) in DCM (5 mL) dropwise under $N_2$. The reaction was stirred for at 25 °C for 2 h before being washed with $NaHCO_3$ (25 mL) and brine (25 mL). The organic layer was dried over $Na_2SO_4$, filtered, and concentrated under reduced pressure. The resulting residue was purified by FCC on silica (PE:EtOAc=1:1) to give 3-ethyl-2H-thiete 1,1-dioxide (2.7 g, 20.8 mmol, 89% yield) as a colorless oil.

Step 4. To a solution of 3-ethyl-2H-thiete 1,1-dioxide (2.7 g, 20.8 mmol, 1.0 eq) in MeCN (20 mL) was added a solution of N-bromosuccinimide (3.7 g, 20.8 mmol, 1.0 eq) and 2,2'-azobis(2-methylpropionitrile) (1.0 g, 6.24 mmol, 0.3 eq) in MeCN (20 mL). The reaction was stirred at 70 °C for 2 h. After cooling to rt, the mixture was concentrated under reduced pressure. The residue was purified by FCC on silica (PE:EtOAc=20:1 to 5:1) to give 3-(1-bromoethyl)-2H-thiete 1,1-dioxide (4.3 g, 20.4 mmol, 98% yield) as a colorless oil.

Step 5. A solution of 3-(1-bromoethyl)-2H-thiete 1,1-dioxide (4.3 g, 20.4 mmol, 1.0 eq) in THF (40 mL) was cooled to 0 °C and a solution of sodium azide (1.7 g, 25.7 mmol, 1.3 eq) in water (40 mL) was added dropwise under $N_2$. The mixture was stirred at 0 °C for 2 h before being poured into water (50 mL) and extracted with EtOAc (50 mL×2). The combined organic layers were washed with brine (50 mL), dried over $Na_2SO_4$, filtered, and concentrated to give 3-(1-azidoethyl)-2H-thiete 1,1-dioxide (2.0 g, 11.5 mmol, 57% yield) as a yellow oil. $^1H$ NMR (400 MHz, $CDCl_3$) δ ppm 6.71 (d, J=1.5 Hz, 1H), 4.44-4.53 (m, 2H), 4.41 (q, J=6.9 Hz, 1H), 1.52 (d, J=6.9 Hz, 3H)

Step 6. A mixture of 3-(1-azidoethyl)-2H-thiete 1,1-dioxide (1.0 g, 5.77 mmol, 1.0 eq) in ethanol (25 mL) were added zinc, granular (1.1 g, 17.3 mmol, 3.0 eq) and $NH_4Cl$ (1.5 g, 28.9 mmol, 1.3 eq) under $N_2$. The reaction was stirred at 20 °C for 20 h before being filtered. The filtrate was concentrated under reduced pressure to give 1-(1,1-dioxo-2H-thiet-3-yl)ethanamine (1.0 g, 7.13 mmol) as a yellow oil, which was used in the next step directly.

Step 7. To a solution of 1-(1,1-dioxo-2H-thiet-3-yl) ethanamine (800 mg, 5.43 mmol, 1.0 eq) and DIPEA (1.4 g, 10.9 mmol, 2.0 eq) in DCM (2 mL) was added di-tert-butyl dicarbonate (1.4 g, 6.52 mmol, 1.2 eq). The reaction was stirred at 18 °C for 6 h before being concentrated and purified by FCC on silica (PE:EtOAc=5:1 to 1:2). The resulting racemic product was separated by chiral SFC to give tert-butyl N-[(1R)-1-(1,1-dioxo-2H-thiet-3-yl)ethyl] carbamate (50 mg, 0.20 mmol, 4% yield) as a white solid, and tert-butyl N-[(1S)-1-(1,1-dioxo-2H-thiet-3-yl)ethyl]carbamate (50 mg, 0.20 mmol, 4% yield) as a white solid. $^1H$ NMR (400 MHz, $CDCl_3$) δ ppm 6.58 (s, 1H), 4.60-4.61 (m, 1H), 4.46 (s, 2H), 1.46 (s, 9H), 1.39-1.42 (m, 3H).

Step 8. A solution of tert-butyl N-[(1R)-1-(1,1-dioxo-2H-thiet-3-yl)ethyl]carbamate (50 mg, 0.200 mmol, 1.0 eq) and p-toluenesulfonic acid monohydrate (77 mg, 0.400 mmol, 2.0 eq) in ethyl acetate (2.0 mL) was stirred at 80 °C for 24 h. The mixture was concentrated under reduced pressure to provide (R)-3-(1-aminoethyl)-2H-thiete 1,1-dioxide (90 mg, 0.280 mmol, TsOH salt) as a white solid, which was used in the next step directly.

Compound 234 was synthesized in a manner analogous to Compound 47 using (*R)-3-(aminoethyl)-2H-thiete 1,1-dioxide in Step 5.

Compound 235 was synthesized in a manner analogous to Compound 1 using 1-((2'-chloro-5-methoxy-[1,1'-biphenyl]-2-yl)sulfonyl)-4-fluoropiperidine-4-carboxylic acid and (R)-3-(aminoethyl)-2H-thiete 1,1-dioxide in Step 5.

Compound 236 was synthesized in a manner analogous to Compound 134 using (R)-3-(aminoethyl)-2H-thiete 1,1-dioxide in Step 5.

Scheme 64. Synthesis of Intermediate (R,Z)-4-(((*R)-1-methylpyrrolidin-3-yl)sulfonyl)but-3-en-2-amine

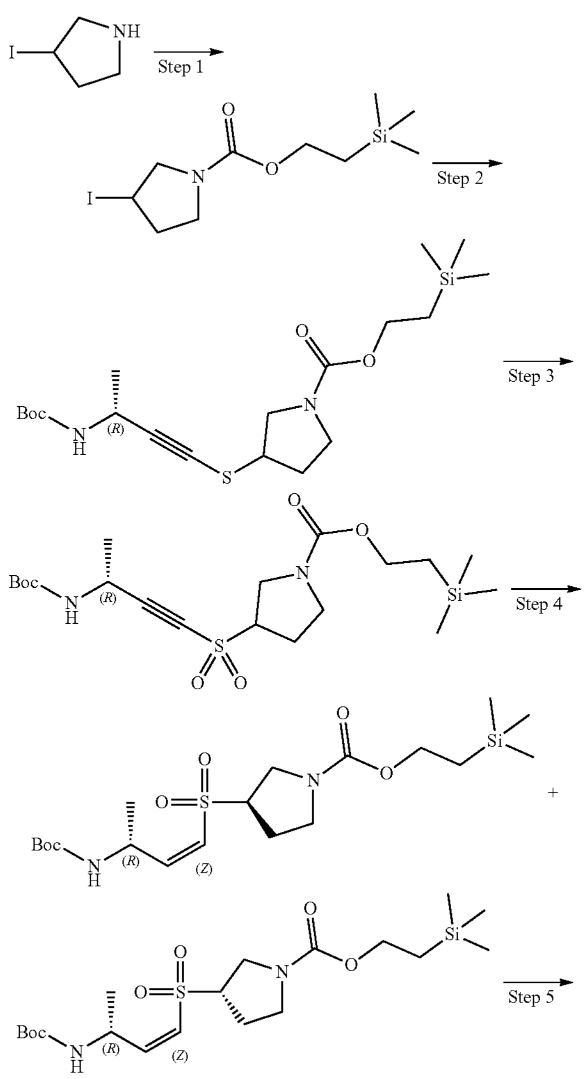

-continued

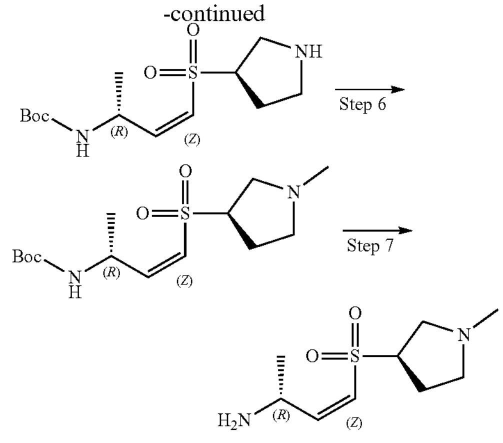

Step 1. To a solution of 3-iodopyrrolidine (4.0 g, 20.3 mmol, 1.0 eq) and (2,5-dioxopyrrolidin-1-yl)$_2$-trimethylsilylethyl carbonate (5.3 g, 20.3 mmol, 1.0 eq) in DCM (50 mL) was added triethylamine (5.1 g, 50.8 mmol, 2.5 eq). The reaction was stirred at 25 °C for 2 h before being quenched with $H_2O$ (10 mL) and extracted with DCM (10 mL×2). The combined organic layers were washed with brine, dried over $Na_2SO_4$, filtered, and concentrated under reduced pressure. The crude was purified by FCC on silica (PE:EtOAc=4:1-1:0) to afford 2-trimethylsilylethyl 3-iodopyrrolidine-1-carboxylate (5.3 g, 15.5 mmol, 76% yield) as a colorless oil. $^1H$ NMR (400 MHz, $CDCl_3$) δ ppm 4.38 (br s, 1H), 4.20 (br d, J=2.9 Hz, 2H), 3.83-3.91 (m, 1H), 3.40-3.81 (m, 3H), 2.21-2.29 (m, 2H), 0.96-1.07 (m, 2H), 0.04 (s, 9H).

Step 2. n-BuLi (10.4 mL, 26.0 mmol, 2.2 eq) was slowly added to a solution of tert-butyl(R)-but-3-yn-2-ylcarbamate (2.0 g, 11.8 mmol, 1.0 eq) in THF (20 mL, 0.59 M) under $N_2$ at −70 °C. The reaction was stirred for 1 h before $S_8$ (380 mg, 1.48 mmol, 0.13 eq) was added in batches. The solution became red and the mixture was stirred for 0.5 h at −70 °C then 0.5 h at 0 °C until complete consumption of sulfur (dark red solution). 2-Trimethylsilylethyl-3-iodopyrrolidine-1-carboxylate (4.0 g, 11.8 mmol, 1.0 eq) in THF (10 mL) was added and the reaction mixture was stirred at 0 °C for 2 h. Sat. aq. $NH_4Cl$ (30 mL) was added and the aq. phase was extracted with EtOAc (30 mL×3). The combined organic layers were washed with brine (10 mL), dried over $Na_2SO_4$, filtered, and concentrated in vacuo. The residue was purified by column chromatography (PE:EtOAc=95:5-9:1) to give 2-(trimethylsilyl)ethyl-3-(((R)-3-((tert-butoxycarbonyl)amino)but-1-yn-1-yl)thio)pyrrolidine-1-carboxylate (2.3 g, 5.55 mmol, 47% yield) as a yellow oil. $^1H$ NMR (400 MHz, $CDCl_3$) δ ppm 4.44-4.83 (m, 2H), 4.15-4.22 (m, 2H), 3.37-3.77 (m, 5H), 2.06-2.32 (m, 2H), 1.45 (s, 9H), 1.39 (d, J=6.9 Hz, 3H), 0.96-1.04 (m, 2H), 0.02-0.06 (m, 9H).

Step 3. To a solution of 2-(trimethylsilyl)ethyl-3-(((R)-3-((tert-butoxycarbonyl)amino)but-1-yn-1-yl)thio)pyrrolidine-1-carboxylate (2.0 g, 4.82 mmol, 1.0 eq) in DCM (20 mL, 0.24 M) was added 3-chloroperbenzoic acid (2.1 g, 12.1 mmol, 2.5 eq). The mixture was stirred at 25 °C for 2 h before being poured into sat. aq. $Na_2SO_3$ (10 mL) and extracted with DCM (10 mL×3). The combined organic layers were washed with sat. aq. $NaHCO_3$ (30 mL) and brine (30 mL), dried over $Na_2SO_4$, filtered, and concentrated under reduced pressure to give 2-(trimethylsilyl)ethyl 3-(((R)-3-((tert-butoxycarbonyl)amino)but-1-yn-1-yl)sulfonyl)pyrrolidine-1-carboxylate (2.0 g, 4.48 mmol, 93% yield) as a white solid. This was used in the next step directly.

Step 4. A mixture of 2-(trimethylsilyl)ethyl 3-(((R)-3-((tert-butoxycarbonyl)amino)but-1-yn-1-yl)sulfonyl)pyrrolidine-1-carboxylate (2.0 g, 4.48 mmol, 1.0 eq) and 5% Pd/C (2.0 g, with ~55% water) in THF (20 mL, 0.22 M) was stirred at 25 °C for 2 h under $H_2$ (15 psi). After filtration, the filtrate was concentrated under reduced pressure. The resulting residue was purified by FCC on silica (PE:EtOAc=4:1-1:0) to give 2-(trimethylsilyl)ethyl(*R)-3-(((R,Z)-3-((tert-butoxycarbonyl)amino)but-1-en-1-yl)sulfonyl)pyrrolidine-1-carboxylate (420 mg, 0.94 mmol, 21% yield) as a white solid. $^1$H NMR (400 MHz, $CDCl_3$) δ ppm 6.10-6.38 (m, 2H), 5.07 (br s, 1H), 4.62 (br s, 1H), 4.15-4.21 (m, 2H), 3.43-4.02 (m, 4H), 2.32 (br d, J=13.9 Hz, 2H), 1.39-1.46 (m, 9H), 1.32 (dd, J=6.8, 2.6 Hz, 3H), 0.95-1.04 (m, 2H), 0.04 (d, J=0.8 Hz, 9H).

Step 5. To a solution of 2-(trimethylsilyl)ethyl(*R)-3-(((R,Z)-3-((tert-butoxycarbonyl)amino)but-1-en-1-yl)sulfonyl)pyrrolidine-1-carboxylate (200 mg, 0.450 mmol, 1.0 eq) in THF (2.0 mL, 0.22 M) was added tetrabutylammonium fluoride (0.9 mL, 0.890 mmol, 2.0 eq). The mixture was stirred at 25 °C for 1 h before being concentrated under reduced pressure to give tert-butyl((R,Z)-4-(((*R)-pyrrolidin-3-yl)sulfonyl)but-3-en-2-yl)carbamate (140 mg, 0.460 mmol) as a white solid. This was used directly.

Step 6. A solution of tert-butyl((R,Z)-4-(((*R)-pyrrolidin-3-yl)sulfonyl)but-3-en-2-yl)carbamate (140 mg, 0.460 mmol, 1.0 eq) in methanol (2.0 mL, 0.23 M) was added formaldehyde (373 mg, 4.60 mmol, 10 eq) and sodium cyanoborohydride (116 mg, 1.84 mmol, 4.0 eq). The mixture was stirred at 25 °C for 1 h before being purified by prep-HPLC to afford tert-butyl((R,Z)-4-(((*R)-1-methylpyrrolidin-3-yl)sulfonyl)but-3-en-2-yl)carbamate (100 mg, 0.314 mmol, 68% yield) as a colorless oil. $^1$H NMR (400 MHz, $CDCl_3$) δ ppm 6.30-6.40 (m, 1H), 6.11-6.19 (m, 1H), 5.01-5.13 (m, 1H), 4.59-4.69 (m, 1H), 4.09-4.43 (m, 2H), 3.65-3.88 (m, 1H), 3.02-3.50 (m, 3H), 2.95 (s, 3H), 2.54-2.68 (m, 1H), 1.41 (s, 9H), 1.32 (d, J=6.9 Hz, 3H).

Step 7. To a solution of tert-butyl((R,Z)-4-(((*R)-1-methylpyrrolidin-3-yl)sulfonyl)but-3-en-2-yl)carbamate (100 mg, 0.310 mmol, 1.0 eq) in DCM (0.8 mL, 0.26 M) was added trifluoroacetic acid (0.4 mL, 0.26 M). The mixture was stirred at 25 °C for 1 h before being concentrated under reduced pressure to give (R,Z)-4-(((*R)-1-methylpyrrolidin-3-yl)sulfonyl)but-3-en-2-amine (70 mg, 0.320 mmol) as a colorless oil. This was used directly in the next step.

Compound 237 was synthesized in a manner analogous to Compound 47 using (R,Z)-4-(((*R)-1-methylpyrrolidin-3-yl)sulfonyl)but-3-en-2-amine in Step 5.

Intermediate (R,Z)-4-(((*S)-1-methylpyrrolidin-3-yl)sulfonyl)but-3-en-2-amine was synthesized in a manner analogous to (R,Z)-4-(((*R)-1-methylpyrrolidin-3-yl)sulfonyl)but-3-en-2-amine, elaborating the other diasteriomer obtained in Step 4.

Compound 238 was synthesized in a manner analogous to Compound 47 using (R,Z)-4-(((*S)-1-methylpyrrolidin-3-yl)sulfonyl)but-3-en-2-amine in Step 5.

Scheme 65. Synthesis of Intermediate (*S,Z)-5,5,5-trifluoro-1-(methylsulfonyl)pent-1-en-3-amine

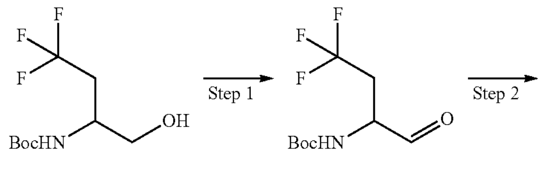

-continued

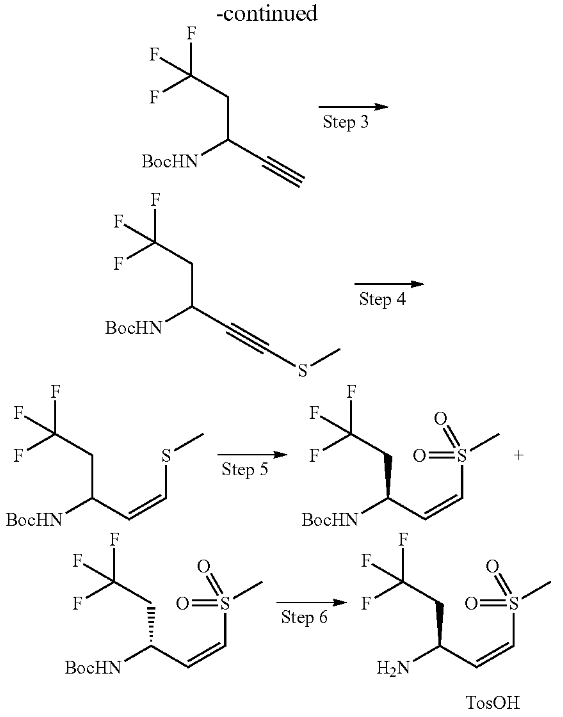

Step 1. To a solution of tert-butyl N-[3,3,3-trifluoro-1-(hydroxymethyl)propyl]carbamate (3.0 g, 12.3 mmol, 1.0 eq) in MeCN (60 mL) was added 1-hydroxy-1-oxo-15,2-benziodoxol-3-one (8.6 g, 30.8 mmol, 2.5 eq). The reaction was stirred at 65 °C for 6 h. After cooling to rt, the mixture was filtered and concentrated under reduced pressure to give tert-butyl N-(3,3,3-trifluoro-1-formyl-propyl)carbamate (2.4 g, 9.95 mmol, 81% yield) as a yellow oil. $^1$H NMR (400 MHz, $CDCl_3$) δ ppm 9.60 (s, 1H), 5.30 (br s, 1H), 4.22-4.14 (m, 1H), 2.91-2.77 (m, 1H), 2.66-2.53 (m, 1H), 1.47 (s, 9H).

Step 2. To a solution of tert-butyl N-(3,3,3-trifluoro-1-formyl-propyl)carbamate (2.0 g, 8.29 mmol, 1.0 eq) in methanol (16 mL, 0.52 M) was added dimethyl(1-diazo-2-oxopropyl)phosphonate (2.1 g, 10.8 mmol, 1.3 eq) and potassium carbonate (2.6 g, 19.1 mmol, 2.3 eq) at 0 °C. The reaction was stirred at 0-25 °C for 2 h before being diluted with MTBE (160 mL) and filtered. The filtrate was concentrated under reduced pressure. The resulting residue was purified by FCC on silica (PE:EtOAc=10:1-5:1) to give tert-butyl N-[1-(2,2,2-trifluoroethyl)prop-2-ynyl]carbamate (1.4 g, 5.9 mmol, 71% yield) as a white solid. $^1$H NMR (400 MHz, $CDCl_3$) δ ppm 4.91-4.72 (m, 2H), 2.65-2.50 (m, 2H), 2.39 (d, J=2.0 Hz, 1H), 1.46 (s, 9H).

Step 3. A solution of cuprous iodide (122 mg, 0.640 mmol, 0.2 eq) and 4,5-bis(diphenylphosphino)-9,9-dimethylxanthene (370 mg, 0.640 mmol, 0.2 eq) in DMSO (25 mL) was stirred for 0.5 h. tert-Butyl N-[1-(2,2,2-trifluoroethyl)prop-2-ynyl]carbamate (760 mg, 3.20 mmol, 1.0 eq), 1-methyl-4-methylsulfanylsulfonyl-benzene (972 mg, 4.81 mmol, 1.5 eq), and potassium carbonate (1.1 g, 8.00 mmol, 2.5 eq) were added at 25 °C under $O_2$ (15 psi). The reaction was stirred for 48 h before being poured into water (100 mL) and extracted with EtOAc (50 mL×3). The combined organic layers were washed brine (200 mL), dried over $Na_2SO_4$, filtered, and concentrated under reduced pressure. The residue was purified by column chromatography (PE: EtOAc=10:1-5:1) to give tert-butyl N-[3-methylsulfanyl-1-(2,2,2-trifluoroethyl)prop-2-ynyl]carbamate (500 mg, 1.76 mmol, 55% yield) as a yellow oil. $^1$H NMR (400 MHz, $CDCl_3$) δ ppm 4.85 (br s, 2H), 2.65-2.47 (m, 2H), 2.38 (s, 3H), 1.46 (s, 9H).

Step 4. tert-Butyl N-[3-methylsulfanyl-1-(2,2,2-trifluoroethyl)prop-2-ynyl]carbamate (300 mg, 1.06 mmol, 1.0 eq), quinoline (41 mg, 0.320 mmol, 0.3 eq), hexene (0.5 mL), and Lindlar catalyst (100 mg) were combined in methanol (20 mL). The mixture was stirred under $H_2$ (35 psi) at 25 °C for 2 h. The reaction was filtered to provide tert-butyl N-[(Z)-3-methylsulfanyl-1-(2,2,2-trifluoroethyl)allyl]carbamate (300 mg, 1.05 mmol, quant. yield) as a yellow oil, which was used directly in the next step. $^1$H NMR (400 MHz, CDCl3) δ ppm 6.12 (d, J=9.5 Hz, 1H), 5.58 (br d, J=6.5 Hz, 1H), 4.66-4.60 (m, 1H), 2.61-2.51 (m, 2H), 2.31 (s, 3H), 1.45 (s, 9H).

Step 5. To a solution of tert-butyl N-[(Z)-3-methylsulfanyl-1-(2,2,2-trifluoroethyl)allyl]carbamate (400 mg, 1.33 mmol, 1.0 eq) in DCM (5 mL) was added 3-chloroperbenzoic acid (676 mg, 3.33 mmol, 2.5 eq) at 0 °C. The mixture was stirred at 25 °C for 2 h before being quenched with 10% aq. $Na_2S_2O_3$ (5 mL) and sat. aq. $NaHCO_3$ (5 mL). The reaction was extracted with DCM (5 mL×3) and the combined organic layers were washed with brine (10 mL), dried over $Na_2SO_4$, filtered, and concentrated under reduced pressure. The residue was purified by column chromatography (PE:EtOAc=10:1-5:3) to give racemic product (400 mg). This was separated by chiral SFC to give tert-butyl N-[rac-(Z,1*S)-3-methylsulfonyl-1-(2,2,2-trifluoroethyl)allyl]carbamate (150 mg, 0.470 mmol, 35% yield) and tert-butyl N-[rac-(Z,1*R)-3-methylsulfonyl-1-(2,2,2-trifluoroethyl)allyl]carbamate (150 mg, 0.470 mmol, 35% yield). $^1$H NMR (400 MHz, $CDCl_3$) δ ppm 6.43-6.32 (m, 2H), 5.47-5.37 (m, 1H), 5.10 (br s, 1H), 3.13 (s, 3H), 2.73-2.56 (m, 2H), 1.44 (s, 9H). $^1$H NMR (400 MHz, $CDCl_3$) δ ppm 6.43-6.32 (m, 2H), 5.46-5.36 (m, 1H), 5.10 (br s, 1H), 3.13 (s, 3H), 2.73-2.55 (m, 2H), 1.44 (s, 9H).

Step 6. To a solution of tert-butyl N-[rac-(Z,1*S)-3-methylsulfonyl-1-(2,2,2-trifluoroethyl)allyl]carbamate (0.15 g, 0.470 mmol, 1.0 eq) in MeCN (3 mL) was added p-toluenesulfonic acid monohydrate (117 mg, 0.610 mmol, 1.3 eq). The mixture was stirred at 60 °C for 6 h. After cooling to rt, the mixture was concentrated under reduced pressure to give (*S,Z)-5,5,5-trifluoro-1-(methylsulfonyl)pent-1-en-3-amine, 4-methylbenzenesulfonate (180 mg, 0.460 mmol, 98% yield) as a yellow solid. $^1$H NMR (400 MHz, DMSO-$d_6$) δ ppm 8.36 (br s, 2H), 7.47 (d, J=8.1 Hz, 2H), 7.12 (d, J=7.8 Hz, 2H), 6.95 (d, J=11.2 Hz, 1H), 6.34 (t, J=10.8 Hz, 1H), 5.28 (br d, J=2.6 Hz, 1H), 3.14 (s, 3H), 2.80 (dq, J=7.3, 10.8 Hz, 3H), 2.29 (s, 3H).

Compound 239 was synthesized in a manner analogous to Compound 1 using 1-((2'-chloro-5-methoxy-[1,1'-biphenyl]-2-yl)sulfonyl)-4-fluoropiperidine-4-carboxylic acid and (*S,Z)-5,5,5-trifluoro-1-(methylsulfonyl)pent-1-en-3-amine in Step 5.

Compound 240 was synthesized in a manner analogous to Compound 47 using (*S,Z)-5,5,5-trifluoro-1-(methylsulfonyl)pent-1-en-3-amine in Step 5.

Intermediate (R,Z)-1-methoxy-4-(methylsulfonyl)but-3-en-2-amine was synthesized in a manner analogous to (*S,Z)-5,5,5-trifluoro-1-(methylsulfonyl)pent-1-en-3-amine using 1,1-dimethylethyl N-[(1S)-2-hydroxy-1-(methoxymethyl)ethyl]carbamate in Step 1.

Compound 246 was synthesized in a manner analogous to Compound 47 using (R,Z)-1-methoxy-4-(methylsulfonyl)but-3-en-2-amine in Step 5.

Compound 248 was synthesized in a manner analogous to Compound 1 using (R,Z)-1-methoxy-4-(methylsulfonyl)but-3-en-2-amine and 1-((2'-chloro-5-methoxy-[1,1'-biphenyl]-2-yl)sulfonyl)-4-fluoropiperidine-4-carboxylic acid in Step 5.

Intermediate (S,Z)-1-methoxy-4-(methylsulfonyl)but-3-en-2-amine was synthesized in a manner analogous to (*S,Z)-5,5,5-trifluoro-1-(methylsulfonyl)pent-1-en-3-amine using 1,1-dimethylethyl N-[(1R)-2-hydroxy-1-(methoxymethyl)ethyl]carbamate in Step 1.

Compound 247 was synthesized in a manner analogous to Compound 47 using (S,Z)-1-methoxy-4-(methylsulfonyl)but-3-en-2-amine in Step 5.

Scheme 66. Synthesis of Intermediate 5-bromo-2′-chloro-[1,1′-biphenyl]-2-carboxylic acid

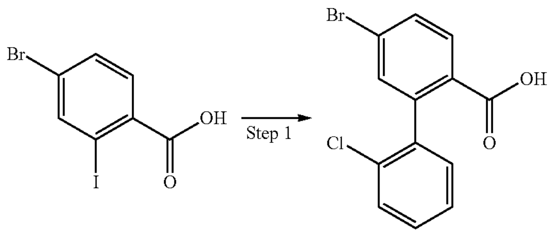

Step 1. To a solution of 4-bromo-2-iodo-benzoic acid (5.0 g, 15.3 mmol, 1.0 eq) in NMP/water (1:1 v/v, 50 mL, 0.31 M) was added 2-chlorophenylboronic acid (2.6 g, 16.8 mmol), LiOH·$H_2O$ (1.4 g, 33.6 mmol), and $Pd_2(dba)_3$ (140 mg, 0.150 mmol) under $N_2$. The mixture was stirred at 70 °C for 16 h. After cooling to rt, the reaction was poured into water (300 mL) and acidified with 2N HCl until pH=2. The mixture was extracted with EtOAc (200 mL×2) and the combined organic phases were dried over $Na_2SO_4$, filtered, concentrated under reduced pressure. Purification by column (PE:EtOAc=5:1-4:1) provided 5-bromo-2'-chloro-[1,1'-biphenyl]-2-carboxylic acid (3.5 g, 9.55 mmol, 62% yield) as a white solid. $^1$H NMR (400 MHz, $CDCl_3$) δ ppm 7.96 (d, J=8.5 Hz, 1H), 7.63 (dd, J=2.1, 8.4 Hz, 1H), 7.46 (d, J=2.0 Hz, 1H), 7.41 (s, 1H), 7.35-7.29 (m, 2H), 7.24 (s, 1H). [M+H] calculated for $C_{13}H_8BrClO_2$, 310; found 311.

Compound 241 was synthesized in a manner analogous to Compound 165 using 5-bromo-2'-chloro-[1,1'-biphenyl]-2-carboxylic acid in Step 4.

Compound 243 was synthesized in a manner analogous to Compound 241 using (R)—N-((R,E)-5-(3,3-difluoroazetidin-1-yl)-5-oxopent-3-en-2-yl)-4-fluoroazepane-4-carboxamide in Step 4.

Scheme 67. Synthesis of Intermediate 2-2(chlorophenyl)-4-methoxy-benzoic acid

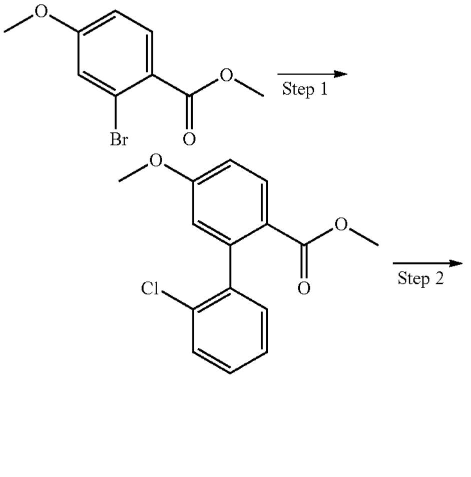

-continued

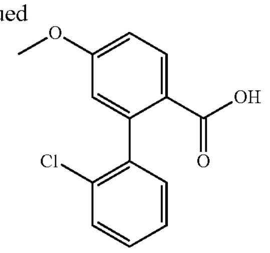

Step 1. To a solution of methyl 2-bromo-4-methoxy-benzoate (20 g, 81.6 mmol, 1.0 eq) in water (15 mL, 0.38 M) and 1,4-dioxane (200 mL, 0.38 M) was added 2-chlorophenylboronic acid (15 g, 97.9 mmol, 1.2 eq), potassium carbonate (23 g, 163 mmol, 2.0 eq), and Pd(dppf)$Cl_2$ (5.9 g, 8.16 mmol, 0.1 eq). The reaction was stirred at 80 °C for 16 h under $N_2$. After cooling to rt, the reaction was quenched with water (150 mL) and extracted with EtOAc (150 mL×2). The combined organic phases were washed with brine (300 mL×2), dried over $Na_2SO_4$, filtered, and concentrated under reduced pressure. The resulting residue was purified by FCC on silica (PE:EtOAc=5:1) to give methyl 2-(2-chlorophenyl)-4-methoxy-benzoate (18.5 g, 67.0 mmol, 82% yield) as a colorless oil. MS (ESI): mass calculated for $C_{15}H_{13}ClO_3$, 276.1; m/z found, 276.9 $[M+H]^+$. $^1H$ NMR (400 MHz, DMSO-$d_6$) δ ppm 7.96-7.89 (m, 1H), 7.49-7.43 (m, 1H), 7.40-7.34 (m, 2H), 7.31-7.25 (m, 1H), 7.11-7.01 (m, 1H), 6.80-6.75 (m, 1H), 3.86-3.79 (m, 3H), 3.58-3.51 (m, 3H).

Step 2. To a solution of methyl 2-(2-chlorophenyl)-4-methoxy-benzoate (20.6 g, 67.0 mmol, 1.0 eq) in THF/water/MeOH (v/v 2:1:1, 240 mL, 0.28 M) was added LiOH·$H_2O$ (8.4 g, 201 mmol, 3.0 eq). The reaction was stirred at 50 °C for 16 h. The reaction was concentrated under reduced pressure and the pH was adjusted to ~3-5 with 2M HCl. The mixture was filtered and purified by prep-HPLC to give 2-(2-chlorophenyl)-4-methoxy-benzoic acid (17 g, 65.2 mmol, 97% yield) as a pale yellow solid. MS (ESI): mass calculated for $C_{14}H_{13}ClO_3$, 262.0; m/z found, 262.9 $[M+H]^+$. $^1H$ NMR (400 MHz, DMSO-$d_6$) δ ppm 12.38-12.18 (m, 1H), 7.94 (d, J=8.8 Hz, 1H), 7.48-7.42 (m, 1H), 7.38-7.32 (m, 2H), 7.30-7.25 (m, 1H), 7.06 (dd, J=2.6, 8.7 Hz, 1H), 6.72 (d, J=2.6 Hz, 1H), 3.83 (s, 3H).

Compound 294 was synthesized in a manner analogous to Compound 164 using methyl(R)-4-fluoroazepane-4-carboxylate and 2-(2-chlorophenyl)-4-methoxy-benzoic acid in Step 1.

Compound 295 was synthesized in a manner analogous to Compound 164 using methyl(S)-4-fluoroazepane-4-carboxylate and 2-(2-chlorophenyl)-4-methoxy-benzoic acid in Step 1 and (R,Z)-4-(methylsulfonyl)but-3-en-2-amine in Step 3.

Intermediate 2'-chloro-5-(trifluoromethyl)-[1,1'-biphenyl]-2-carboxylic acid was synthesized in a manner analogous to 2-(2-chlorophenyl)-4-methoxy-benzoic acid using methyl 2-bromo-4-(trifluoromethyl)benzoate.

Compound 242 was synthesized in a manner analogous to Compound 165 using 2'-chloro-5-(trifluoromethyl)-[1,1'-biphenyl]-2-carboxylic acid in Step 4.

Compound 244 was synthesized in a manner analogous to Compound 242 using (R)—N-((R,E)-5-(3,3-difluoroazetidin-1-yl)-5-oxopent-3-en-2-yl)-4-fluoroazepane-4-carboxamide in Step 4.

Intermediate 2'-chloro-6'-fluoro-5-(trifluoromethyl)-[1,1'-biphenyl]-2-carboxylic acid was synthesized in a manner analogous to 2'-chloro-5-(trifluoromethyl)-[1,1'-biphenyl]-2-carboxylic acid using 2-chloro-6-fluorophenylboronic acid in Step 1.

Compound 245 was synthesized in a manner analogous to Compound 165 using 2'-chloro-6'-fluoro-5-(trifluoromethyl)-[1,1'-biphenyl]-2-carboxylic acid and (R)—N-((R,E)-5-(3,3-difluoroazetidin-1-yl)-5-oxopent-3-en-2-yl)-4-fluoroazepane-4-carboxamide in Step 4.

Scheme 68. Synthesis of Intermediate (2R,4S)-1-((2′-chloro-5-(difluoromethyl)-[1,1′-biphenyl]-2-yl)sulfonyl)-4-fluoro-2-methylpiperidine-4-carboxylic acid

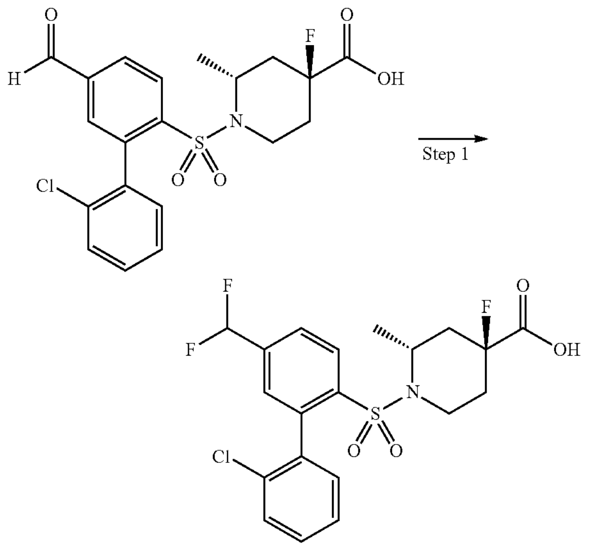

Step 1. To a solution of (2R,4S)-1-((2'-chloro-5-formyl-[1,1'-biphenyl]-2-yl)sulfonyl)-4-fluoro-2-methylpiperidine-4-carboxylic acid (150 mg, 0.340 mmol, 1.0 eq) in DCM (2.0 mL, 0.17 M) was added diethylaminosulfur trifluoride (549 mg, 3.40 mmol, 10 eq) and the solution was stirred at 25 °C for 16 h. The reaction was quenched with sat. aq. $NaHCO_3$ (3 mL) and extracted with DCM (1 mL×3). The combined organic layers were washed with brine (1 mL×2), dried over $Na_2SO_4$, filtered, and concentrated under reduced pressure. The resulting residue was purified by prep-TLC (PE:EtOAc=0:1) to give (2R,4S)-1-((2'-chloro-5-(difluoromethyl)-[1,1'-biphenyl]-2-yl)sulfonyl)-4-fluoro-2-methylpiperidine-4-carboxylic acid (110 mg, 0.240 mmol, 70% yield) as a pale yellow oil.

Compound 253 was synthesized in a manner analogous to Compound 134, Step 5, using (2R,4S)-1-((2'-chloro-5-(difluoromethyl)-[1,1'-biphenyl]-2-yl)sulfonyl)-4-fluoro-2-methylpiperidine-4-carboxylic acid.

Scheme 69. Synthesis of Intermediate 1-(tert-butyl) 3-ethyl (3R,4R)-4-(2-chlorophenyl)-3-methylpyrrolidine-1,3-dicarboxylate

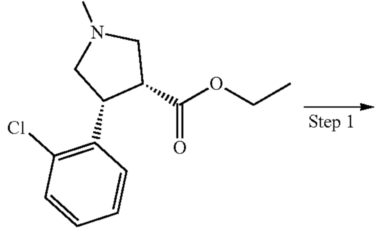

-continued

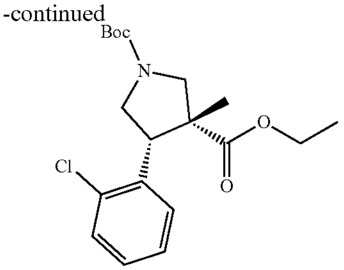

-continued

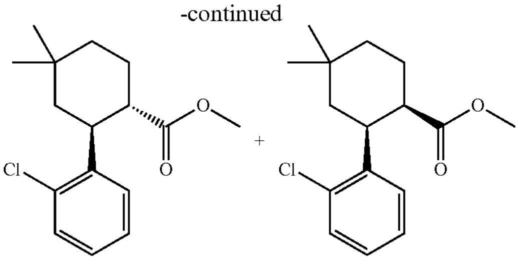

Step 1. To a solution of 1-(tert-butyl) 3-ethyl(3R,4R)-4-(2-chlorophenyl)pyrrolidine-1,3-dicarboxylate (300 mg, 0.880 mmol, 1.0 eq) and HMPA (506 mg, 2.83 mmol, 3.2 eq) in THF (10 mL, 0.09 M) was added LDA (2.2 mL, 4.41 mmol, 3.0 eq) at −78 °C. The solution was stirred at −78 °C for 1 h before MeI (250 mg, 1.77 mmol, 2.0 eq) was added. The reaction was stirred at 20 °C for 2 h before being poured into water (10 mL) and extracted with DCM (15 mL×3). The combined organic layers were washed with brine (10 mL), dried over $Na_2SO_4$, filtered, and concentrated under reduced pressure. The resulting residue was purified by prep-HPLC to give 1-(tert-butyl) 3-ethyl(3R,4R)-4-(2-chlorophenyl)-3-methylpyrrolidine-1,3-dicarboxylate (60 mg, 0.170 mmol, 19% yield) as a yellow oil. $^1$H NMR (400 MHz, $CDCl_3$) δ ppm 7.38 (br d, J=7.6 Hz, 1H), 7.16-7.22 (m, 3H), 4.01-4.09 (m, 2H), 3.85-3.97 (m, 3H), 3.70 (br d, J=6.8 Hz, 1H), 3.38 (br s, 1H), 1.51 (br s, 9H), 1.45 (s, 3H), 1.03 (t, J=7.2 Hz, 3H).

Intermediate (3R,4R)-4-(2-chlorophenyl)-3-methyl-1-(2,2,2-trifluoroethyl)pyrrolidine-3-carboxylic acid was synthesized in a manner analogous to (3R,4R)-4-(2-chlorophenyl)-1-(2,2,2-trifluoroethyl)pyrrolidine-3-carboxylic acid starting from 1-(tert-butyl) 3-ethyl(3R,4R)-4-(2-chlorophenyl)-3-methylpyrrolidine-1,3-dicarboxylate.

Compound 254 was synthesized in a manner analogous to Compound 165 using (3R,4R)-4-(2-chlorophenyl)-3-methyl-1-(2,2,2-trifluoroethyl)pyrrolidine-3-carboxylic acid in Step 4.

Scheme 70. Synthesis of Intermediate rac-methyl (1S,2S)-2-(2-chlorophenyl)-4,4-dimethylcyclohexane-1-carboxylate

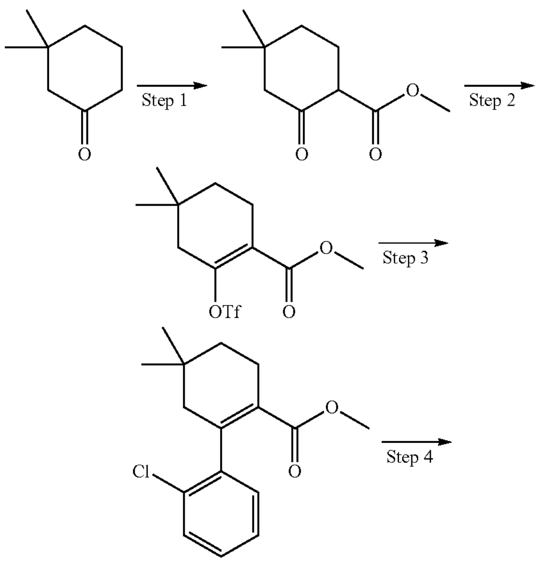

Step 1. To a solution of dimethyl carbonate (4.9 g, 547 mmol, 4.6 eq) in THF (112 mL, 1.0 M) was added NaH (9.6 g, 396 mmol, 2.0 eq, 60%) and 3,3-dimethylcyclohexanone (15 g, 119 mmol, 1.0 eq) at 0 °C. The reaction was stirred at 80 °C for 4 h. After cooling to rt, the solution was diluted with $NH_4Cl$(100 mL) and extracted with EtOAc (80 mL×3). The combined organic layers were washed with brine (50 mL×3), dried over $Na_2SO_4$, filtered, and concentrated under reduced pressure. The resulting residue was purified by FCC on silica (PE:EtOAc=0:1 to 5:1) to provide methyl 4,4-dimethyl-2-oxo-cyclohexanecarboxylate (14 g, 76.0 mmol, 64% yield) as a yellow oil. $^1$H NMR (400 MHz, $CDCl_3$) δ ppm 3.73-3.80 (m, 3H), 2.16-2.32 (m, 2H), 2.05 (d, J=2.8 Hz, 2H), 1.34-1.43 (m, 2H), 1.18-1.27 (m, 1H), 0.92-0.98 (m, 6H).

Step 2. To a solution of NaH (2.7 g, 68.4 mmol, 1.8 eq, 60%) in DCM (140 mL, 0.27 M) was added methyl 4,4-dimethyl-2-oxo-cyclohexanecarboxylate (7.0 g, 38.0 mmol, 1.0 eq) at 0 °C under $N_2$. The mixture was stirred at 0 °C for 1.5 h before being cooled to −65 °C and adding $Tf_2O$ (1.2 g, 42.2 mmol, 1.1 eq) dropwise. The reaction was stirred at −65 °C for 30 min then 25 °C for 16 h. The reaction was quenched with sat. aq. $NH_4Cl$ (150 mL) and extracted with EtOAc (300 mL×3). The combined organic layers were washed with brine (50 mL), dried over $Na_2SO_4$, filtered, and concentrated in vacuo to give methyl 4,4-dimethyl-2-(trifluoromethylsulfonyloxy)cyclohexene-1-carboxylate (12 g, 37.9 mmol, quant. yield) as a yellow oil.

Step 3. To a solution of methyl 4,4-dimethyl-2-(trifluoromethylsulfonyloxy)cyclohexene-1-carboxylate (12 g, 37.9 mmol, 1.0 eq), 2-chlorophenylboronic acid (7.1 g, 45.5 mmol, 1.2 eq), and $K_2CO_3$ (15.7 g, 114 mmol, 3.0 eq) in 1,4-dioxane (250 mL) and water (25 mL) was added Pd(dppf)$Cl_2$ (2.7 g, 3.79 mmol, 0.1 eq) under $N_2$. The reaction was stirred at 90 °C for 16 h. After cooling to rt, the reaction was filtered and concentrated in vacuo. The resulting residue was purified by FCC on silica (PE:EtOAc=100:1 to 10:1) to give methyl 2-(2-chlorophenyl)-4,4-dimethyl-cyclohexene-1-carboxylate (15 g, 53.8 mmol) as a yellow oil. $^1$H NMR (400 MHz, $CDCl_3$) δ ppm 7.36 (dd, J=1.6, 7.6 Hz, 1H), 7.20 (dq, J=1.8, 7.3 Hz, 2H), 7.01 (dd, J=2.1, 7.2 Hz, 1H), 3.46 (s, 3H), 2.56-2.48 (m, 2H), 2.28-2.19 (m, 1H), 2.04-1.96 (m, 1H), 1.55-1.44 (m, 2H), 1.03 (d, J=11.6 Hz, 6H).

Step 4. To a solution of methyl 2-(2-chlorophenyl)-4,4-dimethyl-cyclohexene-1-carboxylate (6.0 g, 21.5 mmol, 1.0 eq) in methanol (120 mL, 0.18 M) was added Mg (5.2 g, 215 mmol, 10 eq) at 0 °C under $N_2$. The mixture was stirred at 25 °C for 3 h before being quenched with 2M HCl (500 mL) and extracted with EtOAc (300 mL×3). The combined organic layers were washed with brine (100 mL), dried over $Na_2SO_4$, filtered, and concentrated in vacuo. The resulting residue was purified by prep-HPLC to give rac-methyl(1S,2S)-2-(2-chlorophenyl)-4,4-dimethylcyclohexane-1-carboxylate (5.0 g, 17.8 mmol, 83% yield) as a yellow oil. $^1$H NMR (400 MHz, $CDCl_3$) δ ppm 7.33 (dd, J=0.9, 7.9 Hz, 1H), 7.25-7.16 (m, 2H), 7.13-7.07 (m, 1H), 3.74-3.60 (m, 1H), 3.48 (s, 3H), 2.67 (br s, 1H), 1.99-1.79 (m, 2H), 1.68-1.50 (m, 2H), 1.40-1.31 (m, 1H), 1.12 (s, 4H), 0.95 (s, 3H).

Compound 255 was synthesized in a manner analogous to Compound 158 starting from rac-methyl(1S,2S)-2-(2-chlorophenyl)-4,4-dimethylcyclohexane-1-carboxylate.

Intermediate rac-methyl(3R,4S)-4-(2-chlorophenyl)-6,6-dimethyltetrahydro-2H-pyran-3-carboxylate was synthesized in a manner analogous to rac-methyl(1S,2S)-2-(2-chlorophenyl)-4,4-dimethylcyclohexane-1-carboxylate starting from 2,2-dimethyltetrahydropyran-4-one.

Compound 256 was synthesized in a manner analogous to Compound 158 starting from rac-methyl(3R,4S)-4-(2-chlorophenyl)-6,6-dimethyltetrahydro-2H-pyran-3-carboxylate.

Intermediate rac-methyl(6R,7R)-6-(2-chlorophenyl)spiro[3.5]nonane-7-carboxylate was synthesized in a manner analogous to rac-methyl(1S,2S)-2-(2-chlorophenyl)-4,4-dimethylcyclohexane-1-carboxylate starting from spiro[3.5]nonan-6-one.

Compound 257 was synthesized in a manner analogous to Compound 158 starting from rac-methyl(6R,7R)-6-(2-chlorophenyl)spiro[3.5]nonane-7-carboxylate.

Intermediate 1-(tert-butyl) 4-ethyl 5-(2-chlorophenyl)-3,4-dihydropyridine-1,4(2H)-dicarboxylate was synthesized in a manner analogous to rac-methyl(1S,2S)-2-(2-chlorophenyl)-4,4-dimethylcyclohexane-1-carboxylate, Steps 2-3, starting with 1-(1,1-dimethylethyl) 4-ethyl 3-oxo-1,4-piperidinedicarboxylate in Step 2.

Compound 258 was synthesized in a manner analogous to Compound 158 starting from 1-(tert-butyl) 4-ethyl 5-(2-chlorophenyl)-3,4-dihydropyridine-1,4(2H)-dicarboxylate.

Intermediate rac-1-(tert-butyl) 4-ethyl(3R,4S)-3-(2-chlorophenyl)piperidine-1,4-dicarboxylate was synthesized in a manner analogous to rac-methyl(1S,2S)-2-(2-chlorophenyl)-4,4-dimethylcyclohexane-1-carboxylate, Steps 2-4, starting with 1-(1,1-dimethylethyl) 4-ethyl 3-oxo-1,4-piperidinedicarboxylate in Step 2.

Compound 259 was synthesized in a manner analogous to Compound 158 starting from rac-1-(tert-butyl) 4-ethyl(3R,4S)-3-(2-chlorophenyl)piperidine-1,4-dicarboxylate.

Scheme 71. Synthesis of (S,Z)-1-((5-chloro-3′-(pyridin-3-ylmethoxy)-[1,1′-biphenyl]-2-yl)sulfonyl)-4-fluoro-N-(4-(methylsulfonyl)but-3-en-2-yl)piperidine-4-carboxamide (Compound 260)

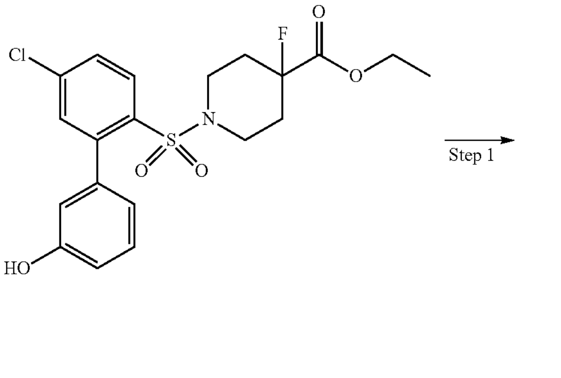

-continued

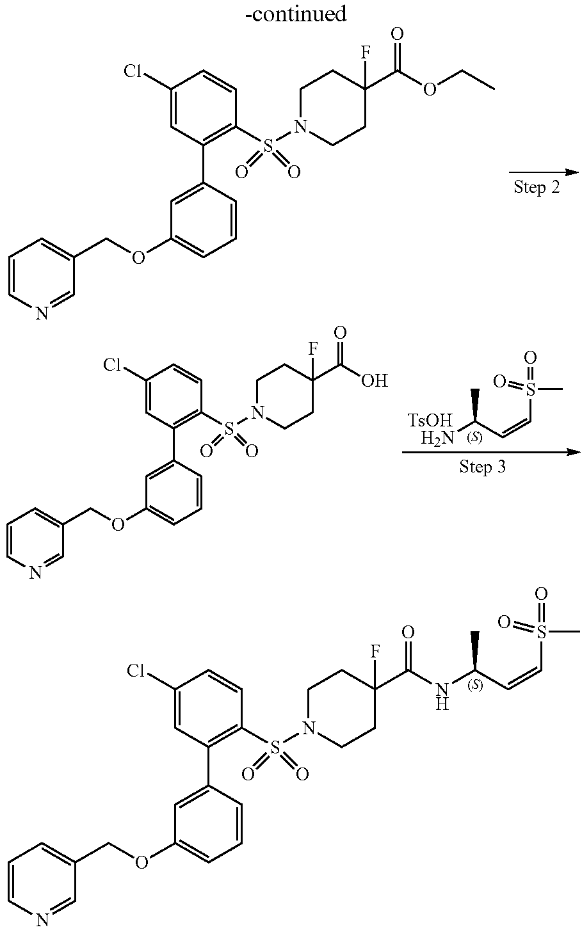

Step 1. To a solution of ethyl 1-((5-chloro-3'-hydroxy-[1,1'-biphenyl]-2-yl)sulfonyl)-4-fluoropiperidine-4-carboxylate (100 mg, 0.219 mmol, 1.0 eq) in DMF (1.5 mL, 0.15 M) was added 3-(bromomethyl)pyridine (45 mg, 0.263 mmol, 1.2 eq) and potassium carbonate (64 mg, 0.461 mmol, 2.1 eq). The mixture was stirred at 25 °C for 16 h before being diluted with $H_2O$ (5.0 mL) and extracted with EtOAc (5.0 mL×3). The combined organic layers were washed with brine (10 mL), dried over $Na_2SO_4$, filtered, and concentrated under vacuum. The resulting residue was purified by prep-TLC (PE:EtOAc=3:1, $R_f$=0.2) to give ethyl 1-((5-chloro-3'-(pyridin-3-ylmethoxy)-[1,1'-biphenyl]-2-yl)sulfonyl)-4-fluoropiperidine-4-carboxylate (60 mg, 0.113 mmol, 51% yield) as a colorless oil. $^1H$ NMR (400 MHz, $CDCl_3$) δ ppm 8.70 (d, J=1.6 Hz, 1H), 8.59 (dd, J=1.4, 4.8 Hz, 1H), 8.08 (d, J=8.6 Hz, 1H), 7.80 (td, J=1.9, 7.9 Hz, 1H), 7.47 (dd, J=2.3, 8.6 Hz, 1H), 7.39-7.29 (m, 3H), 7.12-7.06 (m, 1H), 7.05-6.97 (m, 2H), 5.13 (s, 2H), 4.20 (q, J=7.1 Hz, 2H), 3.17 (br d, J=13.2 Hz, 2H), 2.68-2.53 (m, 2H), 1.94-1.83 (m, 1H), 1.82-1.69 (m, 3H), 1.30-1.25 (m, 3H).

Step 2. To a solution of ethyl 1-((5-chloro-3'-(pyridin-3-ylmethoxy)-[1,1'-biphenyl]-2-yl)sulfonyl)-4-fluoropiperidine-4-carboxylate (60 mg, 0.113 mmol, 1.0 eq) in THF (1.5 mL, 0.063 M) and water (0.30 mL, 0.063 M) was added $LiOH·H_2O$ (14 mg, 0.338 mmol, 3.0 eq). The mixture was stirred at 25 °C for 2 h before being concentrated under reduced pressure. The resulting residue was acidified with 1N HCl until pH ~3-5. The resulting precipitate was collected by filtration and washed with water (5.0 mL) to afford 1-((5-chloro-3'-(pyridin-3-ylmethoxy)-[1,1'-biphenyl]-2-yl)

sulfonyl)-4-fluoropiperidine-4-carboxylic acid (40 mg, 0.079 mmol, 57% yield) as a white solid.

Step 3. To a solution of 1-((5-chloro-3'-(pyridin-3-ylmethoxy)-[1,1'-biphenyl]-2-yl)sulfonyl)-4-fluoropiperidine-4-carboxylic acid (40 mg, 0.079 mmol, 1.0 eq) in DCM (2.0 mL, 0.04 M) was added (S,Z)-4-(methylsulfonyl)but-3-en-2-amine (TsOH salt, 31 mg, 0.095 mmol, 1.2 eq), $T_3P$ (126 mg, 0.198 mmol, 2.5 eq), and DIPEA (31 mg, 0.238 mmol, 3.0 eq). The mixture was stirred at 25 °C for 1 h before being diluted with water (10 mL) and extracted with EtOAc (10 mL×3). The combined organic layers were washed with brine (10 mL×2), dried over $Na_2SO_4$, filtered, and concentrated in vacuo. The resulting residue was purified by prep-TLC (PE:EtOAc=1:2) to afford (S,Z)-1-((5-chloro-3'-(pyridin-3-ylmethoxy)-[1,1'-biphenyl]-2-yl)sulfonyl)-4-fluoro-N-(4-(methylsulfonyl)but-3-en-2-yl)piperidine-4-carboxamide (33 mg, 0.050 mmol, 63% yield) as a white solid. MS (ESI): mass calculated for $C_{29}H_{31}ClFN_3O_6S_2$, 635.1; m/z found, 636.2 $[M+H]^+$. $^1H$ NMR (400 MHz, DMSO-$d_6$) δ ppm 8.68 (s, 1H), 8.56 (d, J=3.6 Hz, 1H), 8.41-8.33 (m, 1H), 8.04 (d, J=8.6 Hz, 1H), 7.91 (d, J=7.9 Hz, 1H), 7.71 (dd, J=2.2, 8.6 Hz, 1H), 7.50-7.41 (m, 2H), 7.39-7.31 (m, 1H), 7.13-7.05 (m, 2H), 7.00 (d, J=7.6 Hz, 1H), 6.45 (d, J=10.9 Hz, 1H), 6.27 (dd, J=9.4, 11.1 Hz, 1H), 5.42-5.28 (m, 1H), 5.19 (s, 2H), 3.12 (br s, 2H), 3.09 (s, 3H), 2.58-2.52 (m, 1H), 2.48-2.45 (m, 1H), 1.82-1.69 (m, 1H), 1.68-1.55 (m, 3H), 1.19 (d, J=6.8 Hz, 3H).

Compounds 261-266 were synthesized in a manner analogous to Compound 260 using the appropriate bromide or benzyl chloride in Step 1.

Scheme 72. Synthesis of Intermediate ethyl 1-((5-chloro-3′-(pyridin-2-ylmethoxy)-[1,1′-biphenyl]-2-yl)sulfonyl)-4-fluoropiperidine-4-carboxylate

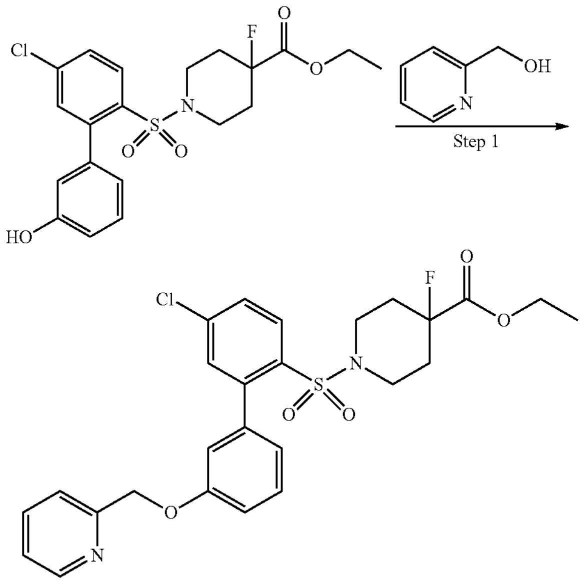

Step 1. To a solution of ethyl 1-((5-chloro-3'-hydroxy-[1,1'-biphenyl]-2-yl)sulfonyl)-4-fluoropiperidine-4-carboxylate (4.5 g, 10.2 mmol, 1.0 eq) in THF (60 mL, 0.17 M) was added 2-pyridinemethanol (1.0 mL, 10.2 mmol, 1.0 eq), triphenylphosphine (3.2 g, 12.2 mmol, 1.2 eq), and diisopropyl azodiccarboxylate (2.4 mL, 12.2 mmol, 1.2 eq) at 0 °C. The mixture was stirred at 25 °C for 3 h before being diluted with $H_2O$ (50 mL) and extracted with EtOAc (40 mL). The combined organic layers were washed with brine (20 mL), dried over $Na_2SO_4$, filtered, and concentrated in vacuo. The resulting residue was purified by FCC on silica (PE:EtOAc=40:60) to provide ethyl 1-((5-chloro-3'-(pyridin-2-ylmethoxy)-[1,1'-biphenyl]-2-yl)sulfonyl)-4-fluoropiperidine-4-carboxylate (4.1 g, 7.69 mmol, 75% yield) as a colorless oil. [M+H] calculated for $C_{26}H_{26}ClFN_2O_5S$, 532; found 533.

Compound 269 was synthesized in a manner analogous to Compound 260, Steps 2-3, using ethyl 1-((5-chloro-3'-(pyridin-2-ylmethoxy)-[1,1'-biphenyl]-2-yl)sulfonyl)-4-fluoropiperidine-4-carboxylate in Step 2.

Scheme 73. Synthesis of (S,Z)-1-((6-chloro-4-(3-methoxyphenyl)pyridin-3-yl)sulfonyl)-4-fluoro-N-(4-(methylsulfonyl)but-3-en-2-yl)piperidine-4-carboxamide (Compound 270) and (S,Z)-1-((6-chloro-4-(2-chloro-5-methoxyphenyl)pyridin-3-yl)sulfonyl)-4-fluoro-N-(4-(methylsulfonyl)but-3-en-2-yl)piperidine-4-carboxamdie (Compound 271)

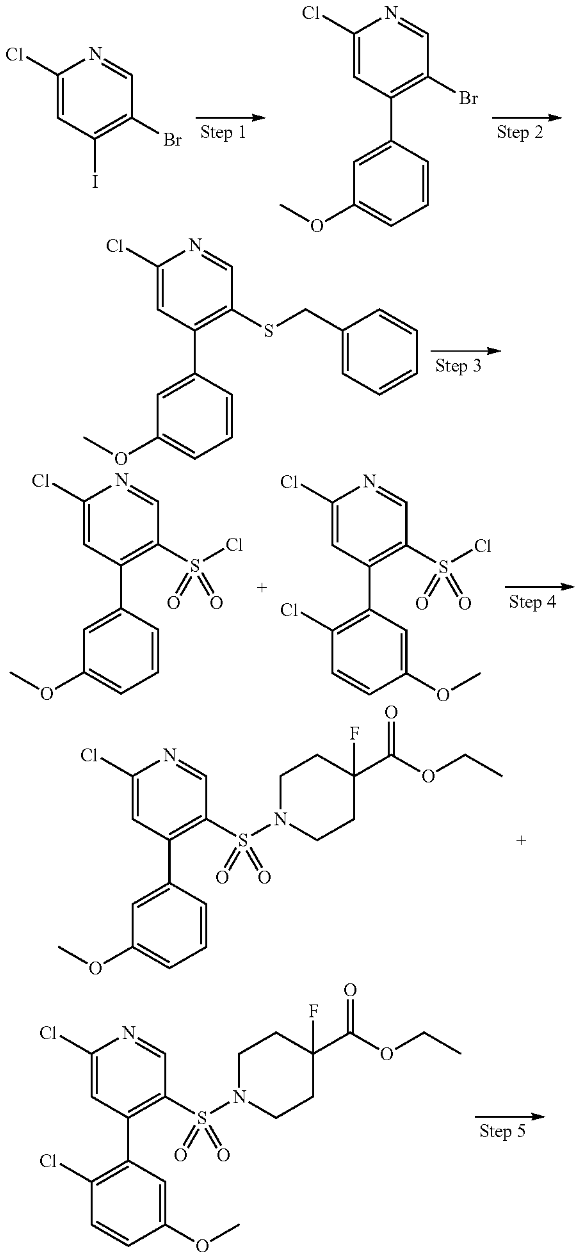

-continued

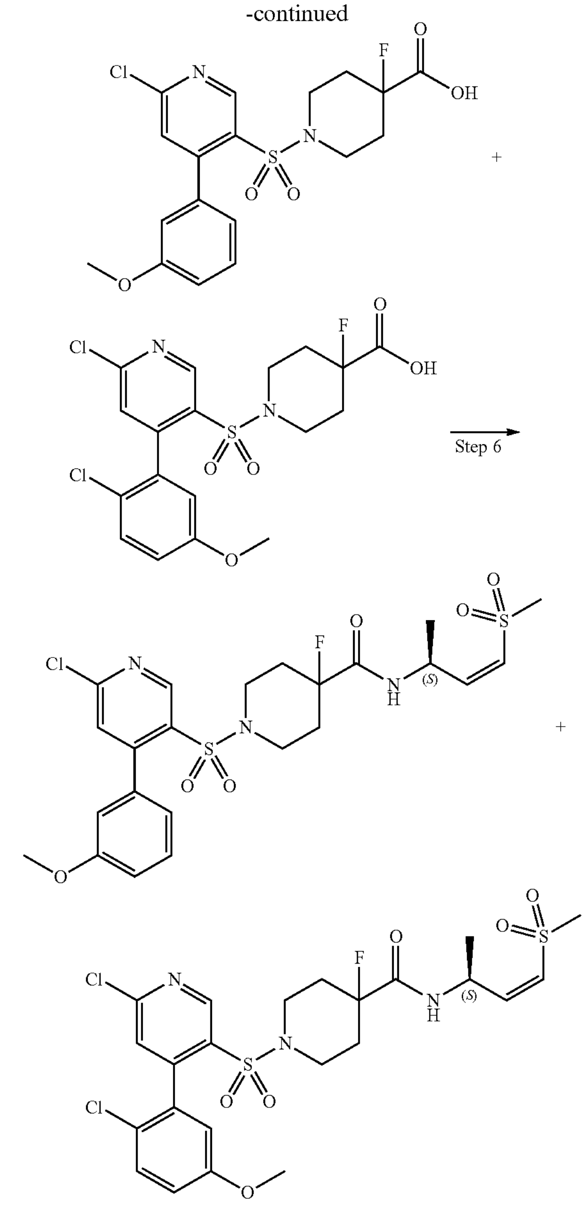

Step 1. To a solution of 5-bromo-2-chloro-4-iodo-pyridine (3.5 g, 11.0 mmol, 1.0 eq) and 3-methoxyphenylboronic acid (1.8 g, 12.1 mmol, 1.1 eq) in toluene/water (v/v 1:1, 42 mL, 0.26 M) was added $K_2CO_3$ (4.6 g, 33.0 mmol, 3.0 eq) and $Pd(PPh_3)_4$(1.3 g, 1.10 mmol, 0.1 eq) under $N_2$. The reaction was stirred at 90 °C for 16 h under $N_2$. After cooling to rt, the reaction was quenched with water (30 mL) and extracted with EtOAc (30 mL×3). The combined organic layers were washed with brine (30 mL), dried over $Na_2SO_4$, filtered, and concentrated under reduced pressure. The resulting residue was purified by column chromatography (PE:EtOAc=10:1) to give 5-bromo-2-chloro-4-(3-methoxyphenyl)pyridine (2.0 g, 6.70 mmol, 61% yield) as a yellow oil. $^1H$ NMR (400 MHz, $CDCl_3$) δ ppm 8.59 (s, 1H), 7.40 (t, J=7.9 Hz, 1H), 7.33 (s, 1H), 7.04-6.97 (m, 2H), 6.96-6.92 (m, 1H), 3.87 (s, 3H).

Step 2. To a solution of 5-bromo-2-chloro-4-(3-methoxyphenyl)pyridine (1.0 g, 3.35 mmol, 1.0 eq) in 1,4-dioxane (15 mL, 0.22 M) was added benzyl mercaptan (624 mg, 5.02 mmol, 1.5 eq), DIPEA (866 mg, 6.70 mmol, 2.0 eq), and XantPhos (194 mg, 0.335 mmol, 0.1 eq). The reaction was purged with $N_2$ before addition of $Pd_2(dba)_3$ (307 mg, 0.335 mmol, 0.1 eq). The mixture was stirred at 80 °C for 15 h. After cooling to rt, the mixture was poured into water (50 mL) and extracted with EtOAc (50 mL×3). The combined organic layers were washed with brine (50 mL×2), dried over $Na_2SO_4$, filtered, and concentrated under reduced pressure. The resulting residue was purified by prep-TLC ($SiO_2$, PE:EtOAc=8:1) to give 5-(benzylthio)-2-chloro-4-(3-methoxyphenyl)pyridine (500 mg, 1.46 mmol, 44% yield) as a yellow solid. $^1H$ NMR (400 MHz, $CDCl_3$) δ ppm 8.31 (s, 1H), 7.37 (t, J=7.9 Hz, 1H), 7.26-7.20 (m, 4H), 7.18-7.11 (m, 2H), 7.02-6.90 (m, 3H), 3.91 (s, 2H), 3.85 (s, 3H).

Step 3. To a solution of 5-benzylsulfanyl-2-chloro-4-(3-methoxyphenyl)pyridine (500 mg, 1.46 mmol, 1.0 eq) dissolved in $CCl_4$ (12 mL) was added water (4.0 mL) at 0 °C. Chlorine gas was passed through the stirred solution for 30 min at 0 °C before the solution was purged with $N_2$ to remove excess chlorine gas. The aq. layer was extracted with DCM (30 mL×2) and the combined organic layers were dried with anhydrous $Na_2SO_4$ and filtered. The filtrate was concentrated under reduced pressure to give a mixture of 6-chloro-4-(3-methoxyphenyl)pyridine-3-sulfonyl chloride and 6-chloro-4-(2-chloro-5-methoxyphenyl)pyridine-3-sulfonyl chloride in a 1:5 ratio (350 mg, 1.10 mmol, 75% yield).

Step 4. At 0 °C, a mixture of 6-chloro-4-(3-methoxyphenyl)pyridine-3-sulfonyl chloride and 6-chloro-4-(2-chloro-5-methoxyphenyl)pyridine-3-sulfonyl chloride (338 mg, 1.06 mmol, 1.5 eq) was added to ethyl 4-fluoropiperidine-4-carboxylate hydrochloride (150 mg, 0.709 mmol, 1.0 eq) and TEA (143 mg, 1.42 mmol, 2.0 eq) in DCM (5.0 mL, 0.14 M). The resulting mixture was stirred at 25 °C for 2 h before being poured into water (15 mL) and extracted with DCM (15 mL×3). The combined organic layers were washed with brine (10 mL×2), dried over $Na_2SO_4$, filtered, and concentrated under reduced pressure. The resulting residue was purified by prep-TLC ($SiO_2$, PE:EtOAc=3:1) to give a mixture of ethyl 1-((6-chloro-4-(3-methoxyphenyl)pyridin-3-yl)sulfonyl)-4-fluoropiperidine-4-carboxylate and ethyl 1-((6-chloro-4-(2-chloro-5-methoxyphenyl)pyridin-3-yl)sulfonyl)-4-fluoropiperidine-4-carboxylate in a 1:5 ratio (80 mg, 0.175 mmol, 25% yield).

Step 5. To a solution of ethyl 1-((6-chloro-4-(3-methoxyphenyl)pyridin-3-yl)sulfonyl)-4-fluoropiperidine-4-carboxylate and ethyl 1-((6-chloro-4-(2-chloro-5-methoxyphenyl)pyridin-3-yl)sulfonyl)-4-fluoropiperidine-4-carboxylate (80 mg, 0.175 mmol, 1.0 eq) in THF (3.2 mL, 0.041 M) and water (1.1 mL, 0.041 M) was added $LiOH{\cdot}H_2O$ (59 mg, 1.40 mmol, 8.0 eq). The mixture was stirred at 50 °C for 3 h. After cooling to rt, the mixture was acidified with 1N HCl to pH ~4 then poured into water (10 mL) and extracted with EtOAc (10 mL×3). The combined organic layers were washed with brine (10 mL×2), dried over $Na_2SO_4$, and filtered. The filtrate was concentrated under reduced pressure to give a mixture of 1-((6-chloro-4-(3-methoxyphenyl)pyridin-3-yl)sulfonyl)-4-fluoropiperidine-4-carboxylic acid and 1-((6-chloro-4-(2-chloro-5-methoxyphenyl)pyridin-3-yl)sulfonyl)-4-fluoropiperidine-4-carboxylic acid in a 1:5 ratio (75 mg, 0.187 mmol, quant. yield).

Step 6. HATU (106 mg, 0.280 mmol, 1.5 eq) was added to a mixture of 1-((6-chloro-4-(3-methoxyphenyl)pyridin-3-yl)sulfonyl)-4-fluoropiperidine-4-carboxylic acid and 1-((6-chloro-4-(2-chloro-5-methoxyphenyl)pyridin-3-yl)sulfonyl)-4-fluoropiperidine-4-carboxylic acid (80 mg, 0.187 mmol, 1.0 eq), (S,Z)-4-(methylsulfonyl)but-3-en-2-amine (as TsOH salt, 60 mg, 0.187 mmol, 1.0 eq), and DIPEA (60 mg, 0.466 mmol, 2.5 eq) in DCM (3.0 mL, 0.062 M). The reaction was stirred at 25 °C for 2 h before being poured into $H_2O$ (10 mL) and extracted with DCM (10 mL×3). The combined organic layers were washed with brine (10 mL), dried over $Na_2SO_4$, filtered, and concentrated under reduced pressure. The resulting residue was purified by prep-HPLC (32-62% ACN in 10 mM aq. $NH_4HCO_3$) to give two products: (S, Z)-1-((6-chloro-4-(3-methoxyphenyl)pyridin-3-yl)sulfonyl)-4-fluoro-N-(4-(methylsulfonyl)but-3-en-2-yl)piperidine-4-carboxamide (4.9 mg, 0.008 mmol, 4% yield) as a white solid. MS (ESI): mass calculated for $C_{23}H_{27}ClFN_3O_6S_2$, 559.1; m/z found, 560.1 $[M+H]^+$. $^1H$ NMR (400 MHz, DMSO-$d_6$) δ ppm 9.06-8.83 (m, 1H), 8.35 (br s, 1H), 7.63 (br d, J=11.9 Hz, 1H), 7.37 (br s, 1H), 7.03 (br s, 3H), 6.54-6.37 (m, 1H), 6.25 (br s, 1H), 5.33 (br s, 1H), 3.86-3.71 (m, 3H), 3.30 (br s, 3H), 3.20-3.07 (m, 4H), 1.64 (br s, 4H), 1.18 (br d, J=6.8 Hz, 3H) and (S, Z)-1-((6-chloro-4-(2-chloro-5-methoxyphenyl)pyridin-3-yl)sulfonyl)-4-fluoro-N-(4-(methylsulfonyl)but-3-en-2-yl)piperidine-4-carboxamide (25 mg, 0.041 mmol, 22% yield) as a white solid. MS (ESI): mass calculated for $C_{23}H_{26}Cl_2FN_3O_6S_2$, 593.1; m/z found, 594.1 $[M+H]^+$. $^1H$ NMR (400 MHz, Methanol-$d_4$) δ ppm 9.01 (s, 1H), 7.50 (s, 1H), 7.45 (d, J=8.8 Hz, 1H), 7.07-7.02 (m, 1H), 7.02-6.99 (m, 1H), 6.39 (d, J=11.0 Hz, 1H), 6.28-6.18 (m, 1H), 5.49-5.38 (m, 1H), 3.82 (s, 3H), 3.37 (br s, 1H), 3.24-3.15 (m, 2H), 3.13 (s, 3H), 2.92 (br t, J=13.0 Hz, 1H), 2.70 (br t, J=12.9 Hz, 1H), 2.15-1.89 (m, 2H), 1.83-1.65 (m, 2H), 1.31 (d, J=6.9 Hz, 3H).

Scheme 74. Synthesis of Intermediate tert-butyl 4-fluoroazocane-4-carboxylate

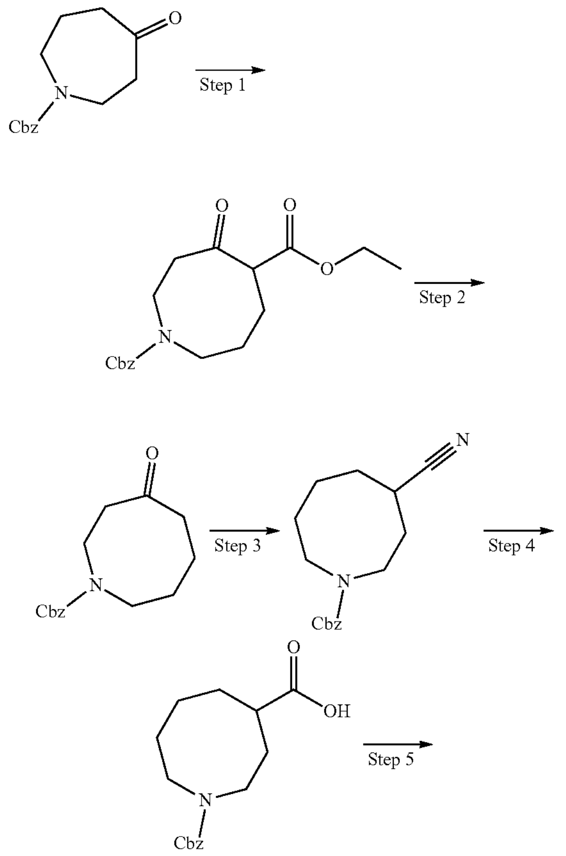

-continued

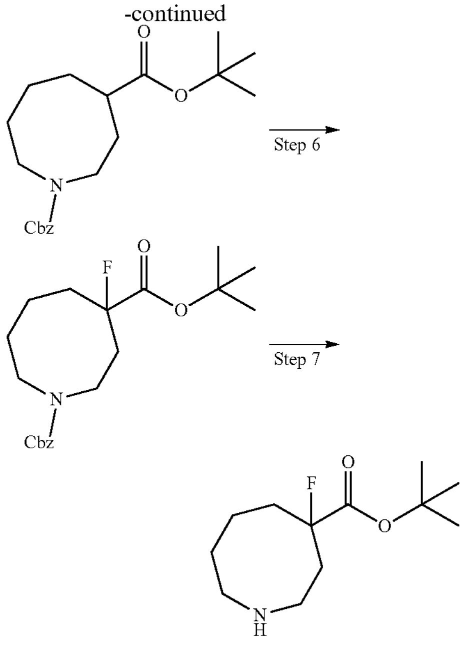

Step 1. A solution of benzyl 4-oxoazepane-1-carboxylate (6.0 g, 24.3 mmol, 1.0 eq) in THF (120 mL, 0.2 M) was placed under $N_2$ and cooled to −60 °C. To this was added ethyl diazoacetate (4.1 g, 34.0 mmol, 1.4 eq) and trifluoroborane (4.0 g, 27.9 mmol, 1.2 eq). The reaction was stirred at −60 °C for 1 hour then 25 °C for 16 hours. The mixture was diluted with $H_2O$ (150 mL) and extracted with EtOAc (200 mL×3). The combined organic layers were washed with brine (500 mL), dried over $Na_2SO_4$, filtered, and concentrated under reduced pressure. The resulting residue was purified by FCC on silica (PE:EtOAc=1:0-7:3) to give 1-benzyl 5-ethyl 4-oxoazocane-1,5-dicarboxylate (1.1 g, 3.30 mmol, 14% yield) as a yellow oil.

Step 2. To a solution of 1-benzyl 5-ethyl 4-oxoazocane-1,5-dicarboxylate (2.5 g, 7.50 mmol, 1.0 eq) in ethanol (25 mL, 0.3 M) was added potassium hydroxide (24 mL, 24 mmol, 3.2 eq). The reaction was stirred at 80 °C for 3 h. After cooling to rt, the mixture was evaporated, diluted with $H_2O$ (20 mL), and extracted with EtOAc (30 mL×3). The combined organic layers were washed with brine (80 mL), dried over $Na_2SO_4$, filtered, and concentrated under reduced pressure to give benzyl 4-oxoazocane-1-carboxylate (1.8 g, 6.89 mmol, 91% yield) as a colorless oil. $^1H$ NMR (400 MHz, $CDCl_3$) δ ppm 7.29-7.43 (m, 5H), 5.17 (s, 2H), 3.63-3.74 (m, 2H), 3.22 (dt, J=16.2, 6.2 Hz, 2H), 2.56-2.68 (m, 2H), 2.38-2.44 (m, 2H), 1.59-1.96 (m, 4H).

Step 3. To a solution of benzyl 4-oxoazocane-1-carboxylate (1.8 g, 6.89 mmol, 1.0 eq) in DME (18 mL) was added 1-(isocyanomethane)sulfonyl-4-methylbenzene (1.7 g, 8.61 mmol, 1.3 eq) and ethanol (0.5 g, 11.7 mmol, 1.7 eq) at 15 °C. The mixture was then cooled to 0 °C and potassium tert-butoxide (7.6 mL, 7.58 mmol, 1.1 eq) was added slowly. After stirring at 40 °C for 16 hours, the reaction was filtered through celite and washed with EtOAc (40 mL). The organic phase was concentrated under reduced pressure and the resulting residue was purified by FCC on silica (PE: EtOAc=1:0-7:3) to afford benzyl 4-cyanoazocane-1-carboxylate (1.5 g, 5.51 mmol, 80% yield) as a yellow oil. $^1H$ NMR (400 MHz, $CDCl_3$) δ ppm 7.22-7.35 (m, 5H), 5.01-5.16 (m, 2H), 3.27-3.63 (m, 3H), 3.07-3.25 (m, 1H), 2.61-2.82 (m, 1H), 1.61-2.12 (m, 8H).

Step 4. To a solution of benzyl 4-cyanoazocane-1-carboxylate (0.5 g, 1.84 mmol, 1.0 eq) in glycol/water (v/v 1:1, 10 mL, 0.22 M) was added potassium hydroxide (515 mg, 9.18 mmol, 5.0 eq) and the mixture was stirred at 120 °C for 16 hours under $N_2$. After cooling to rt, the reaction was diluted with water (10 mL) and acidified with 1N HCl until pH ~2. The mixture was extracted with EtOAc (30 mL×3) and the combined organic phases were dried over $Na_2SO_4$, filtered, and concentrated to give 1-((benzyloxy)carbonyl) azocane-4-carboxylic acid (0.2 g, 0.690 mmol, 37% yield) as a colorless oil. $^1H$ NMR (400 MHz, $CDCl_3$) δ 7.21-7.33 (m, 5H), 4.99-5.27 (m, 2H), 3.48-3.59 (m, 1H), 3.28-3.38 (m, 3H), 2.37-2.53 (m, 1H), 1.52-2.05 (m, 8H).

Step 5. To a solution of 1-((benzyloxy)carbonyl)azocane-4-carboxylic acid (1.2 g, 4.12 mmol, 1.0 eq) and 4-(dimethylamino)pyridine (302 mg, 2.47 mmol, 0.6 eq) in tert-butanol (20 mL, 0.21 M) was added di-tert-butyl dicarbonate (0.9 g, 4.12 mmol, 1.0 eq) in t-BuOH (200 mL) at 10-15 °C. The solution was stirred at 15 °C for 12 hours before being poured into water (50 mL) and extracted with EtOAc (50 mL×3). The combined organic layers were washed with brine (100 mL), dried over $Na_2SO_4$, filtered, and concentrated under reduced pressure. The resulting residue was purified by FCC on silica (PE:EtOAc=100:1-5:1) to give 1-benzyl 4-(tert-butyl) azocane-1,4-dicarboxylate (500 mg, 1.44 mmol, 35% yield) as a yellow oil. $^1H$ NMR (400 MHz, $CDCl_3$) δ ppm 7.30-7.49 (m, 5H), 5.10-5.24 (m, 2H), 3.52-3.70 (m, 1H), 3.32-3.51 (m, 3H), 2.34-2.47 (m, 1H), 1.60-2.05 (m, 8H), 1.43 (br d, J=5.8 Hz, 9H).

Step 6. To a solution of 1-benzyl 4-(tert-butyl) azocane-1,4-dicarboxylate (500 mg, 1.44 mmol, 1.0 eq) in THF (5 mL, 0.02 M) was added lithium diisopropylazanide (1.4 mL, 2.88 mmol, 2.0 eq) dropwise at −60 °C and the mixture was stirred at −45 °C for 1 hour. To the mixture was added N-fluorobenzenesulfonimide (681 mg, 2.16 mmol, 1.5 eq) in THF (3 mL, 0.21 M) dropwise and the resulting solution was stirred at −45 °C for 1 hour then 15 °C for 1 hour. The reaction was quenched with sat. aq. $NH_4Cl$(20 mL) and extracted with EtOAc (20 mL×3). The combined organic phases were washed with brine (50 mL×2), dried over $Na_2SO_4$, filtered, and concentrated under reduced pressure. The resulting residue was purified by FCC on silica (PE: EtOAc=100:0-19:1) to give 1-benzyl 4-(tert-butyl) 4-fluoroazocane-1,4-dicarboxylate (150 mg, 0.410 mmol, 28% yield) as a colorless oil. $^1H$ NMR (400 MHz, $CDCl_3$) δ ppm 7.19-7.47 (m, 5H), 5.04-5.28 (m, 2H), 3.51-3.80 (m, 4H), 2.13-2.44 (m, 1H), 1.90-2.09 (m, 3H), 1.52-1.73 (m, 4H), 1.33-1.47 (m, 9H).

Step 7. To a solution of 1-benzyl 4-(tert-butyl) 4-fluoroazocane-1,4-dicarboxylate (150 mg, 0.410 mmol, 1.0 eq) in methanol (20 mL, 0.02 M) was added 5% Pd/C (80 mg, with ca. 55% water). The reaction was stirred at 25 °C under $H_2$ (15 psi) for 16 hours. The mixture was filtered and the filtrate evaporated to give tert-butyl 4-fluoroazocane-4-carboxylate (80 mg, 0.350 mmol, 84% yield) as a pale yellow oil. $^1H$ NMR (400 MHz, $CDCl_3$) δ ppm 3.67 (dt, J=13.6, 6.8 Hz, 2H), 2.83-3.13 (m, 2H), 2.06-2.32 (m, 3H), 1.53-2.01 (m, 5H), 1.20 (d, J=6.8 Hz, 9H).

Compound 272 was synthesized in a manner analogous to Compound 164 using tert-butyl 4-fluoroazocane-4-carboxylate in Step 1 and (R,Z)-4-(methylsulfonyl)but-3-en-2-amine in Step 3.

Scheme 75. Synthesis of (R,Z)-1-((4-(2-chlorophenyl)-1-methyl-6-oxo-1,6-dihydropyridin-3-yl)sulfonyl)-4-fluoro-N-(4-methylsulfonyl)but-3-en-2-yl)piperidine-4-carboxamide (Compound 274)

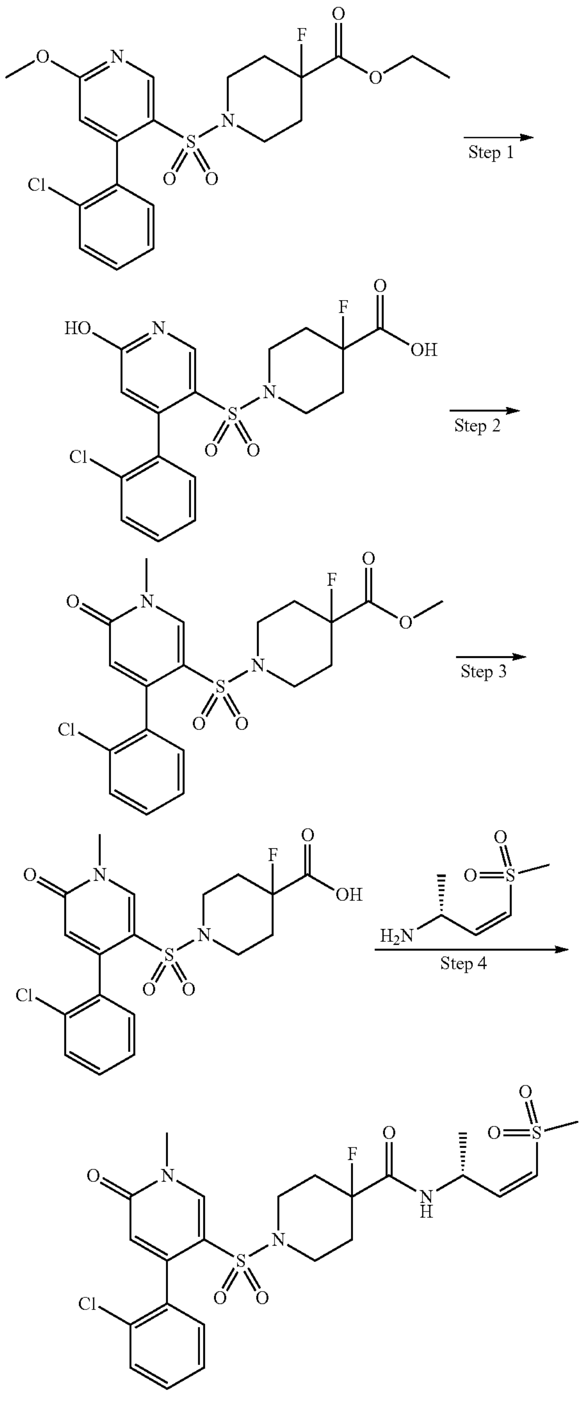

Step 1. To a solution of ethyl 1-[[4-(2-chlorophenyl)-6-methoxy-3-pyridyl]sulfonyl]-4-fluoro-piperidine-4-carboxylate (350 mg, 0.766 mmol, 1.0 eq) in acetic acid (4.0 mL, 0.19 M) was added HCl (4.0 mL, 0.19 M). The mixture was stirred at 80 °C for 3 h. After cooling to rt, the mixture was concentrated under reduced pressure to give 1-((4-(2-chlorophenyl)-6-hydroxypyridin-3-yl)sulfonyl)-4-fluoropiperidine-4-carboxylic acid (300 mg, 0.723 mmol, 94% yield) as a yellow solid. MS (ESI): mass calculated for $C_{18}H_{18}ClFN_2O_5S$, 428.1; m/z found, 429.1.

Step 2. A solution of 1-((4-(2-chlorophenyl)-6-hydroxypyridin-3-yl)sulfonyl)-4-fluoropiperidine-4-carboxylic acid (100 mg, 0.241 mmol, 1.0 eq) in DMF (2.0 mL, 0.12 M) was degassed and purged with $N_2$ for 3 times. NaH (29 mg, 0.723 mmol, 3.0 eq) was added to the mixture at 0 °C and this was stirred at 0 °C for 0.5 h. Iodomethane (171 mg, 1.20 mmol, 5.0 eq) was added dropwise and the mixture was stirred at 0 °C for 16 h. The mixture was diluted with $H_2O$ (10 mL) and extracted with EtOAc (20 mL). The extract was washed with brine (20 mL), dried over $Na_2SO_4$, filtered, and concentrated under reduced pressure. The resulting residue was purified by prep-TLC (PE:EtOAc=1:1) to afford methyl 1-((4-(2-chlorophenyl)-1-methyl-6-oxo-1,6-dihydropyridin-3-yl)sulfonyl)-4-fluoropiperidine-4-carboxylate (80 mg, 0.180 mmol, 75% yield) as a colorless oil. MS (ESI): mass calculated for $C_{19}H_{20}ClFN_2O_5S$, 442.1; m/z found, 443.1. $^1H$ NMR (400 MHz, $CDCl_3$) δ ppm 8.25 (s, 1H), 7.51-7.44 (m, 1H), 7.41-7.29 (m, 3H), 6.42 (s, 1H), 3.78 (s, 3H), 3.66 (s, 3H), 3.27-3.12 (m, 1H), 3.03-2.96 (m, 2H), 2.72-2.53 (m, 1H), 2.04-1.72 (m, 4H).

Step 3. To a solution of methyl 1-((4-(2-chlorophenyl)-1-methyl-6-oxo-1,6-dihydropyridin-3-yl)sulfonyl)-4-fluoropiperidine-4-carboxylate (80 mg, 0.181 mmol, 1.0 eq) in THF (2.0 mL, 0.067 M) and water (0.70 mL, 0.067 M) was added $LiOH \cdot H_2O$ (23 mg, 0.542 mmol, 3.0 eq). The reaction mixture was stirred at 25 °C for 2 h before being concentrated to remove THF. The resulting residue was acidified with 1N HCl until pH ~3-5. The resulting precipitate was collected by filtration to afford 1-((4-(2-chlorophenyl)-1-methyl-6-oxo-1,6-dihydropyridin-3-yl)sulfonyl)-4-fluoropiperidine-4-carboxylic acid (60 mg, 0.140 mmol, 77% yield) as a white solid.

Step 4. To a solution of 1-((4-(2-chlorophenyl)-1-methyl-6-oxo-1,6-dihydropyridin-3-yl)sulfonyl)-4-fluoropiperidine-4-carboxylic acid (60 mg, 0.140 mmol, 1.0 eq) in DCM (3.0 mL, 0.046 M) was added (R,Z)-4-(methylsulfonyl)but-3-en-2-amine (54 mg, 0.168 mmol, 1.2 eq), $T_3P$ (223 mg, 0.349 mmol, 2.5 eq), and DIPEA (541 mg, 0.419 mmol, 3.0 eq). The reaction was stirred at 25 °C for 1 h before being was diluted with $H_2O$ (10 mL) and extracted with EtOAc (10 mL×2). The combined organic layers were washed with brine (10 mL), dried over $Na_2SO_4$, filtered, and concentrated under vacuum. The resulting residue was purified by prep-TLC (PE:EtOAc=0:1) to afford (R,Z)-1-((4-(2-chlorophenyl)-1-methyl-6-oxo-1,6-dihydropyridin-3-yl)sulfonyl)-4-fluoro-N-(4-(methylsulfonyl)but-3-en-2-yl)piperidine-4-carboxamide (44 mg, 0.078 mmol, 56% yield) as a white solid. MS (ESI): mass calculated for $C_{23}H_{27}ClFN_3O_6S_2$, 559.1; m/z found, 560.0. $^1H$ NMR (400 MHz, DMSO-$d_6$) δ ppm 8.53 (s, 1H), 8.36 (br d, J=6.0 Hz, 1H), 7.53 (d, J=7.9 Hz, 1H), 7.48-7.31 (m, 3H), 6.46 (d, J=11.3 Hz, 1H), 6.35-6.22 (m, 2H), 5.49-5.23 (m, 1H), 3.58 (s, 3H), 3.18-2.96 (m, 5H), 2.73-2.55 (m, 2H), 1.98-1.66 (m, 4H), 1.21 (d, J=6.9 Hz, 3H).

Compound 276 was synthesized in a manner analogous to Compound 274, Step 5 using 1-((4-(2-chlorophenyl)-6-hydroxypyridin-3-yl)sulfonyl)-4-fluoropiperidine-4-carboxylic acid.

Scheme 76. Synthesis of Intermediate ethyl 1-((5-(2-chlorophenyl)-2-methoxypyridin-4-yl)sulfonyl)-4-fluoropiperidine-4-carboxylate

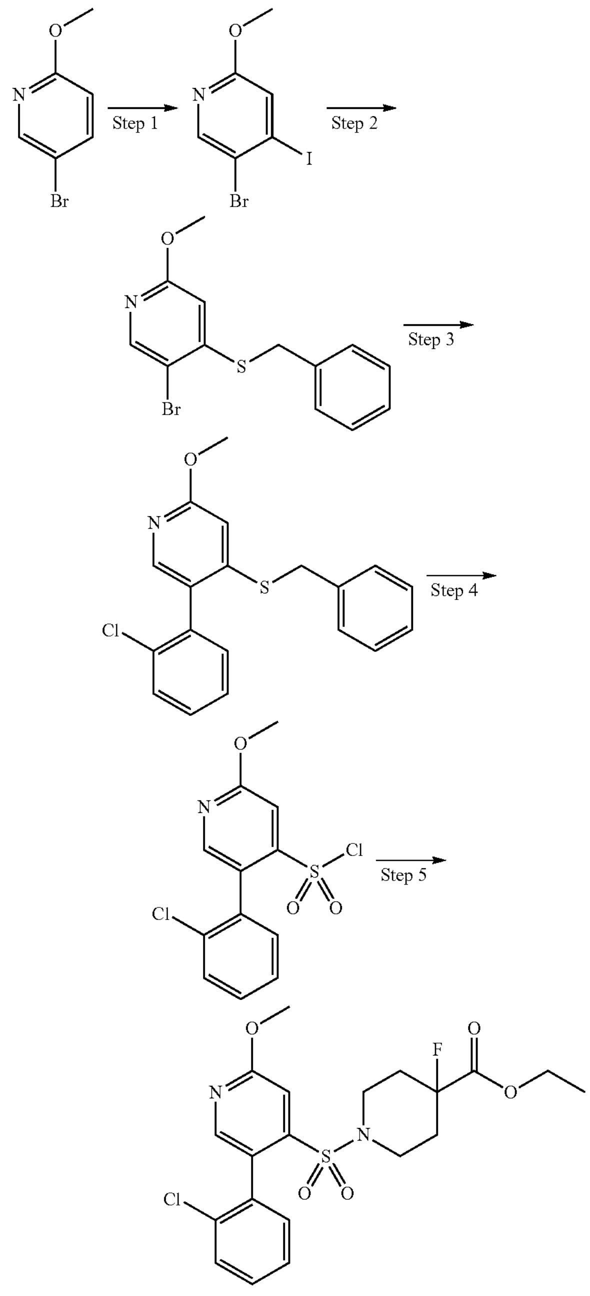

Step 1. A solution of 5-bromo-2-methoxypyridine (5.0 g, 26.6 mmol, 1.0 eq) in anhydrous THF (100 mL, 0.27 M) was degassed and purged with $N_2$. LDA (10.5 mL, 29.3 mmol, 1.1 eq, 2 M in THF) was added dropwise at −78 °C. The mixture was stirred for 1 h at −78 °C before a solution of iodine (6.7 g, 26.6 mmol, 1.0 eq) in anhydrous THF (30 mL) was added dropwise at over 30 min. The reaction was allowed to warm to rt and was stirred for 16 h. The reaction was quenched with sat. aq. $Na_2S_2O_3$ (60 mL) and extracted with MTBE (50 mL×3). The combined organic layers were washed with brine (60 mL), dried over $Na_2SO_4$, filtered, and concentration under reduced pressure. The resulting residue was purified by FCC on silica (PE:EtOAc=0:1) to give 5-bromo-4-iodo-2-methoxypyridine (7.7 g, 12.3 mmol, 46% yield) as a yellow solid. $^1$H NMR (400 MHz, $CDCl_3$) δ ppm 8.28-8.22 (m, 1H), 7.36-7.29 (m, 1H), 3.90-3.89 (m, 3H).

Step 2. To a stirred solution of 5-bromo-4-iodo-2-methoxypyridine (4.7 g, 9.73 mmol, 1.0 eq) in DMSO (47 mL, 0.20 M) was added phenylthioalcohol (1.2 g, 9.73 mmol, 1.0 eq) and $K_2CO_3$ (2.0 g, 14.6 mmol, 1.5 eq) at 0 °C. The reaction was stirred at 55 °C for 3 h. After cooling to rt, the mixture was poured into water (300 mL) and extracted with EtOAc (200 mL×3). The combined organic layers were washed with brine (600 mL×3), dried over $Na_2SO_4$, filtered, and concentrated under reduced pressure. The crude product was purified by FCC on silica (PE:EtOAc=1:0 to 20:1) to give 4-(benzylthio)-5-bromo-2-methoxypyridine (2.2 g, 7.22 mmol, 74% yield) as a yellow solid. MS (ESI): mass calculated for $C_{13}H_{12}BrNOS$, 309.0; m/z found, 310.0 $[M+H]^+$. $^1$H NMR (400 MHz, $CDCl_3$) δ ppm 8.10 (s, 1H), 7.50-7.40 (m, 2H), 7.40-7.28 (m, 3H), 6.55 (s, 1H), 4.16 (s, 2H), 3.89 (s, 3H).

Step 3. A mixture of 4-(benzylthio)-5-bromo-2-methoxypyridine (400 mg, 1.29 mmol, 1.0 eq), (2-chlorophenyl) boronic acid (242 mg, 1.55 mmol, 1.2 eq), $Pd(OAc)_2$ (29 mg, 0.129 mmol, 0.10 eq), $PPh_3$ (68 mg, 0.258 mmol, 0.20 eq), and $K_2CO_3$ (356 mg, 2.58 mmol, 2.0 eq) in toluene/water (v/v 10:1, 2.2 mL, 0.59 M) was placed under $N_2$. The reaction was stirred at 100 °C for 16 h. After cooling to rt, the mixture was filtered and the filtrate concentrated under reduced pressure. The resulting residue was purified by FCC on silica (PE:EtOAc=1:0 to 49:1) to give 4-(benzylthio)-5-(2-chlorophenyl)-2-methoxypyridine (250 mg, 0.731 mmol, 57% yield) as a colorless oil. MS (ESI): mass calculated for $C_{19}H_{16}ClNOS$, 341.1; m/z found, 342.1 $[M+H]^+$. $^1$H NMR (400 MHz, $CDCl_3$) δ ppm 7.84 (s, 1H), 7.48 (d, J=7.3 Hz, 1H), 7.40-7.27 (m, 7H), 7.26 (d, J=3.8 Hz, 1H), 6.66 (s, 1H), 4.13-4.10 (m, 2H), 3.96 (s, 3H).

Step 4. To a solution of 4-(benzylthio)-5-(2-chlorophenyl)-2-methoxypyridine (250 mg, 0.731 mmol, 1.0 eq) in acetic acid/water (v/v 3:1, 4.0 mL, 0.18 M) was added NCS (391 mg, 2.93 mmol, 4.0 eq) at 0 °C. The reaction was stirred at 25 °C for 2 h before being diluted with $H_2O$ (60 mL) and extracted with ethyl acetate (30 mL×2). The combined organic layers were washed with brine (60 mL), dried over $Na_2SO_4$, filtered, and concentrated under reduced pressure. The resulting residue was purified by FCC on silica (PE:EtOAc=1:0 to 49:1) to give 5-(2-chlorophenyl)-2-methoxypyridine-4-sulfonyl chloride (218 mg, 0.685 mmol, 94% yield) as a colorless oil. $^1$H NMR (400 MHz, $CDCl_3$) δ ppm 8.14 (s, 1H), 7.44-7.41 (m, 1H), 7.36-7.28 (m, 3H), 7.17 (s, 1H), 3.99 (s, 3H).

Step 5. To a solution of ethyl 4-fluoropiperidine-4-carboxylate HCl (160 mg, 0.754 mmol, 1.1 eq) in DCM (5.0 mL, 0.14 M) was added TEA (208 mg, 2.06 mmol, 3.0 eq) and 5-(2-chlorophenyl)-2-methoxypyridine-4-sulfonyl chloride (218 mg, 0.685 mmol, 1.0 eq) in DCM (5.0 mL, 0.14 M) at 0 °C. The reaction was stirred at 25 °C for 1 h before being poured into water (30 mL) and extracted with EtOAc (20 mL×2). The combined organic layers were washed with brine (40 mL×2), dried over $Na_2SO_4$, filtered, and concentrated under reduced pressure. The resulting residue was purified by FCC on silica (PE:EtOAc=1:0 to 5:1) to give ethyl 1-((5-(2-chlorophenyl)-2-methoxypyridin-4-yl)sulfonyl)-4-fluoropiperidine-4-carboxylate (230 mg, 0.503 mmol, 73% yield) as a colorless oil. MS (ESI): mass calculated for $C_{20}H_{22}ClFN_2O_5S$, 456.1; m/z found, 457.1 $[M+H]^+$. $^1$H NMR (400 MHz, $CDCl_3$) δ ppm 8.11 (s, 1H), 7.50 (dd, J=1.7, 7.6 Hz, 1H), 7.47-7.42 (m, 2H), 7.39-7.32 (m, 2H), 4.23 (q, J=7.1 Hz, 2H), 4.05 (s, 3H), 3.30 (td, J=2.3, 13.3 Hz, 1H), 3.09 (td, J=2.4, 13.4 Hz, 1H), 2.95 (dt, J=2.9, 12.7 Hz, 1H), 2.66 (dt, J=2.8, 12.9 Hz, 1H), 2.05-1.77 (m, 4H), 1.32-1.28 (m, 3H).

Compound 275 was synthesized in a manner analogous to Compound 274 starting with ethyl 1-((5-(2-chlorophenyl)-2-methoxypyridin-4-yl)sulfonyl)-4-fluoropiperidine-4-carboxylate in Step 1.

Scheme 77. Synthesis of (R,Z)-1-((6-bromo-4-(2-chlorophenyl)pyridin-3-yl)sulfonyl)-4-fluoro-N-(4-(methylsulfonyl)but-3-en-2yl)piperidine-4-carboxamide (Compound 277)

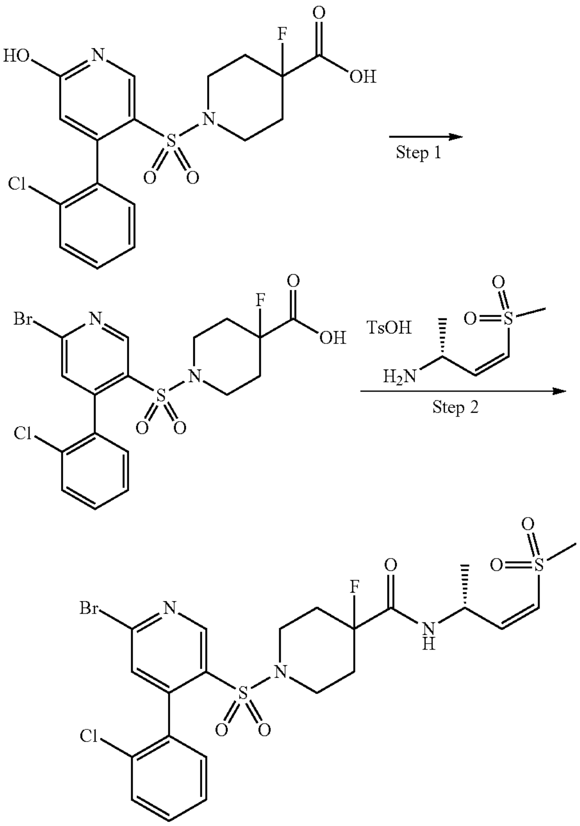

Step 1. To a solution of 1-((4-(2-chlorophenyl)-6-hydroxypyridin-3-yl)sulfonyl)-4-fluoropiperidine-4-carboxylic acid (100 mg, 0.241 mmol, 1.0 eq) in MeCN (1.0 mL, 0.24 M) was added $POBr_3$ (138 mg, 0.482 mmol, 2.0 eq). The reaction was stirred at 85 °C for 3 h under $N_2$. After cooling to rt, the mixture was quenched with $H_2O$ (5.0 mL) and extracted with EtOAc (5.0 mL×2). The combined organic layers were washed with brine (5.0 mL), dried over $Na_2SO_4$, filtered, and concentrated under reduced pressure. The resulting residue was purified by prep-TLC ($SiO_2$, PE:EtOAc=3:1) to give 1-((6-bromo-4-(2-chlorophenyl) pyridin-3-yl)sulfonyl)-4-fluoropiperidine-4-carboxylic acid (60 mg, 0.126 mmol, 52% yield) as a white solid. $^1$H NMR (400 MHz, $CDCl_3$) δ ppm 9.07 (s, 1H), 7.56-7.47 (m, 2H), 7.47-7.37 (m, 3H), 3.33 (br d, J=12.0 Hz, 1H), 3.12 (br d, J=14.3 Hz, 1H), 3.03-2.90 (m, 1H), 2.68 (br t, J=12.9 Hz, 1H), 2.02-1.80 (m, 4H).

Step 2. To a solution of 1-((6-bromo-4-(2-chlorophenyl) pyridin-3-yl)sulfonyl)-4-fluoropiperidine-4-carboxylic acid (60 mg, 0.126 mmol, 1.0 eq) in DCM (1.0 mL, 0.13 M) was added (R,Z)-4-(methylsulfonyl)but-3-en-2-amine (TsOH salt, 48 mg, 0.151 mmol, 1.2 eq), DIPEA (65 mg, 0.502 mmol, 4.0 eq), and $T_3P$ (80 mg, 0.251 mmol, 2.0 eq). The reaction was stirred at 25 °C for 1 h before being quenched with $H_2O$ (5.0 mL) and extracted with DCM (5.0 mL×2). The combined organic layers were washed with brine (5.0 mL), dried over $Na_2SO_4$, filtered, and concentrated under reduced pressure. The resulting residue was purified by prep-TLC (100% EtOAc) to give (R,Z)-1-((6-bromo-4-(2-chlorophenyl)pyridin-3-yl)sulfonyl)-4-fluoro-N-(4-(methylsulfonyl)but-3-en-2yl)piperidine-4-carboxamide (85 mg, 0.136 mmol, 97% yield) as a white solid. MS (ESI): mass calculated for $C_{22}H_{24}BrClFN_3O_5S_2$, 607.0; m/z found, 608.0 $[M+H]^+$. $^1H$ NMR (400 MHz, DMSO-$d_6$) δ ppm 8.95 (s, 1H), 8.44-8.35 (m, 1H), 7.86 (s, 1H), 7.61-7.57 (m, 1H), 7.53-7.47 (m, 1H), 7.44 (d, J=4.1 Hz, 2H), 6.45 (d, J=11.1 Hz, 1H), 6.28 (dd, J=9.4, 11.2 Hz, 1H), 5.38-5.29 (m, 1H), 3.20 (br d, J=13.0 Hz, 2H), 3.11 (s, 3H), 2.84-2.73 (m, 1H), 2.65 (br t, J=11.2 Hz, 1H), 1.95-1.67 (m, 4H), 1.20 (d, J=6.8 Hz, 3H).

Compound 278 was synthesized in a manner analogous to Compound 277 using (E)-4-aminobut-2-enenitrile in Step 2.

Scheme 78. Synthesis of Intermediate N-propyl-3-(4,4,5,5-tetramethyl-1,3,2-dioxaborolan-2-yl)benzamide

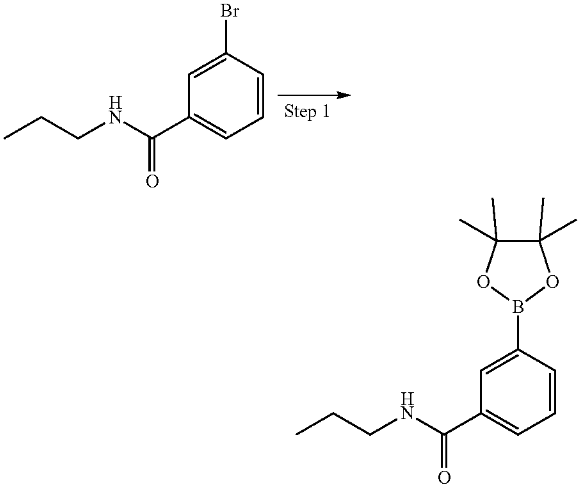

Step 1. To a solution of 3-bromo-N-propyl-benzamide (400 mg, 1.65 mmol, 1.0 eq) in 1,4-dioxane (10 mL, 0.17 M) was added bis(pinacolato)diboron (503 mg, 1.98 mmol, 1.2 eq), potassium acetate (515 mg, 4.95 mmol, 3.0 eq), and $Pd(dppf)Cl_2$ (100 mg, 0.165 mmol, 0.1 eq). The reaction was stirred at 100 °C under $N_2$ for 12 h. After cooling to rt, the mixture was diluted with water (10 mL) and extracted with EtOAc (15 mL×3). The combined organic layers were washed with brine (10 mL×2), dried over $Na_2SO_4$, filtered, and concentrated under reduced pressure. The resulting residue was purified by FCC on silica (PE:EtOAc=9:1-7:3) to give N-propyl-3-(4,4,5,5-tetramethyl-1,3,2-dioxaborolan-2-yl)benzamide (430 mg, 1.48 mmol, 90% yield) as a yellow oil. $^1H$ NMR (400 MHz, $CDCl_3$) δ ppm 8.07 (s, 1H), 8.01-7.89 (m, 2H), 7.46 (t, J=7.6 Hz, 1H), 6.25 (br s, 1H), 3.46-3.39 (m, 2H), 1.65 (dq, J=14.6, 7.4 Hz, 2H), 1.36 (s, 12H), 0.99 (t, J=7.4 Hz, 3H).

Compound 279 was synthesized in a manner analogous to Compound 1 using N-propyl-3-(4,4,5,5-tetramethyl-1,3,2-dioxaborolan-2-yl)benzamide in Step 3.

Scheme 79. Synthesis of Intermediate (R)-4-amino-N,N-dimethylpent-2-ynamide

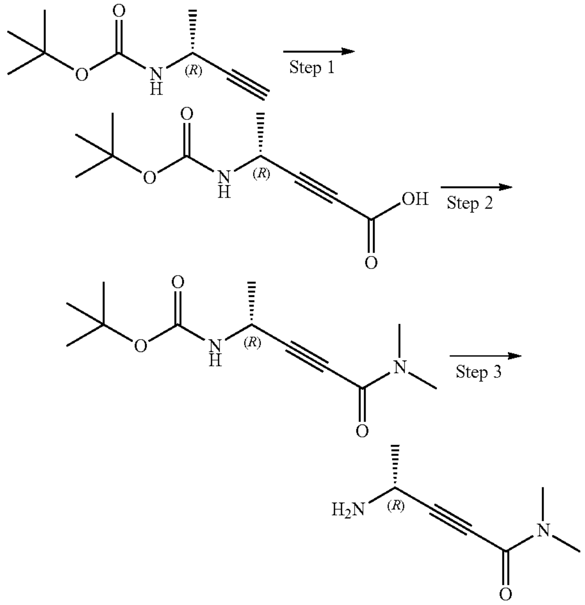

Step 1. A solution of tert-butyl N-[(1R)-1-methylprop-2-ynyl]carbamate (500 mg, 2.95 mmol, 1.0 eq) in anhydrous THF (8.0 mL, 0.37 M) was purged with $N_2$ and cooled to −60 °C. To the solution was added n-BuLi (2.6 mL, 5.9 mmol, 2.0 eq) and the mixture was stirred at −60 °C for 0.5 h. $CO_2$ (dry ice, ~5 g) was added and the mixture was stirred at 20 °C for 2 h. The reaction mixture was quenched with 1N HCl to adjust pH to 2-3 then extracted with ethyl acetate (50 mL×3). The combined organic layers were washed with brine (100 mL), dried over anhydrous $Na_2SO_4$, filtered, and concentrated to give (4R)-4-(tert-butoxycarbonylamino) pent-2-ynoic acid (400 mg, 1.88 mmol, 63% yield) as a yellow oil. $^1H$ NMR (400 MHz, $CDCl_3$) δ ppm 9.88 (br s, 1H), 4.97-4.54 (m, 1H), 1.65-1.49 (m, 3H), 1.48-1.44 (m, 9H).

Step 2. To a solution of (4R)-4-(tert-butoxycarbonylamino)pent-2-ynoic acid (200 mg, 0.938 mmol, 1.0 eq) in DMF (2.5 mL, 0.38 M) was added HATU (535 mg, 1.41 mmol, 1.5 eq), DIPEA (0.39 mL, 2.34 mmol, 2.5 eq), and dimethylamine (42 mg, 0.938 mmol, 1.0 eq). The reaction was stirred at 20 °C for 1 h before being diluted with $H_2O$ (40 mL) and extracted with EtOAc (80 mL). The combined organic layers were washed with brine (50 mL), dried over $Na_2SO_4$, filtered, and concentrated under reduced pressure. The resulting residue was purified by prep-TLC (DCM: MeOH=10:1) to afford tert-butyl N-[(1R)-4-(dimethylamino)-1-methyl-4-oxo-but-2-ynyl]carbamate (130 mg, 0.541 mmol, 58% yield) as a white solid. $^1H$ NMR (400 MHz, $CDCl_3$) δ ppm 4.82-4.61 (m, 1H), 2.81 (s, 6H), 1.72 (d, J=7.0 Hz, 3H), 1.48-1.46 (m, 9H).

Step 3. To a solution of tert-butyl N-[(1R)-4-(dimethylamino)-1-methyl-4-oxo-but-2-ynyl]carbamate (130 mg, 0.541 mmol, 1.0 eq) in DCM (3.0 mL, 0.21 M) was added trifluoroacetic acid (1.0 mL, 0.21 M). The reaction was stirred at 20 °C for 1 h before being concentrated in vacuo to afford (R)-4-amino-N,N-dimethylpent-2-ynamide (65 mg, 0.460 mmol, 86% yield) as a yellow oil. This was used in the next step directly. $^1H$ NMR (400 MHz, $CDCl_3$) δ ppm 4.50-4.42 (m, 1H), 2.92 (s, 3H), 2.81 (s, 3H), 1.82 (d, J=7.0 Hz, 3H).

Intermediate (S)-4-amino-N,N-dimethylpent-2-ynamide was synthesized in a manner analogous to (R)-4-amino-N,N-dimethylpent-2-ynamide starting with tert-butyl N-[(1S)-1-methylprop-2-ynyl]carbamate.

Compound 280 was synthesized in a manner analogous to Compound 47 using (R)-4-amino-N,N-dimethylpent-2-ynamide in Step 5.

Compound 281 was synthesized in a manner analogous to Compound 47 using (S)-4-amino-N,N-dimethylpent-2-ynamide in Step 5.

Scheme 80. Synthesis of Intermediate ethyl (Z)-4-aminobut-2-enoate

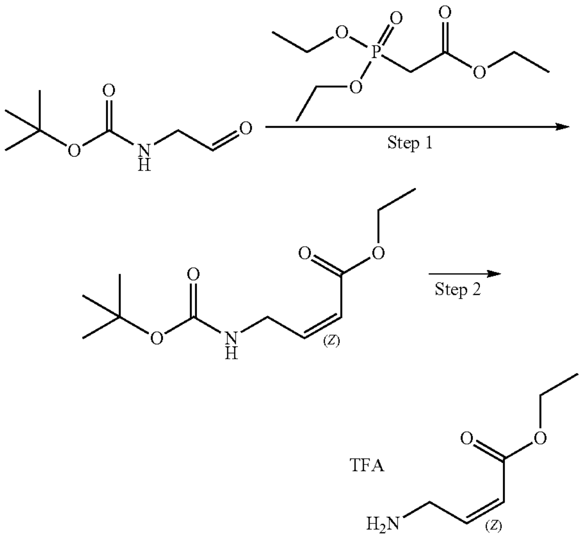

Step 1. To a solution of ethyl 2-(diethoxyphosphoryl) acetate (6.0 g, 26.8 mmol, 1.2 eq) in THF (40 mL, 0.56 M) was added LiHMDS (19 mL, 1.4 eq) at −70 °C. This was stirred 1 h before addition of tert-butyl(2-oxoethyl)carbamate (3.5 g, 22.0 mmol, 1.0 eq). The reaction was stirred at −70 °C for 1 h before being quenched with $NH_4Cl$ (40 mL) and extracted with EtOAc (100 mL×3). The combined organic layers were dried over $Na_2SO_4$, filtered, and concentrated under reduced pressure. The resulting residue was purified by FCC on silica (PE:EtOAc=1:0 to 5:1) to give (Z)-ethyl 4-((tert-butoxycarbonyl)amino)but-2-enoate (3.0 g, 13.1 mmol, 59% yield) as a colorless oil. $^1H$ NMR (400 MHz, DMSO-$d_6$) δ ppm 6.28 (dt, J=11.3, 5.8 Hz, 1H), 5.83 (dt, J=11.5, 1.8 Hz, 1H), 4.99 (br s, 1H), 4.25 (br t, J=4.9 Hz, 2H), 4.18 (q, J=7.1 Hz, 2H), 1.45 (s, 9H), 1.29 (t, J=7.1 Hz, 3H).

Step 2. A solution of (Z)-ethyl 4-((tert-butoxycarbonyl) amino)but-2-enoate (0.30 g, 1.31 mmol, 1.0 eq) in DCM (7.5 mL, 0.13 M) and trifluoroacetic acid (2.5 mL, 0.13 M) was stirred at 15 °C for 2 h. The solution was concentrated under reduced pressure to give (Z)-ethyl 4-aminobut-2-enoate (as TFA salt, 150 mg, 1.16 mmol, 89% yield). $^1H$ NMR (400 MHz, $CDCl_3$) δ ppm 8.24 (br s, 2H), 6.41-6.28 (m, 1H), 6.07 (br d, J=11.4 Hz, 1H), 4.19 (q, J=7.1 Hz, 2H), 4.12-4.04 (m, 2H), 1.29 (t, J=7.1 Hz, 3H).

Intermediate methyl(Z)-4-aminobut-2-enoate was synthesized in a manner analogous to ethyl(Z)-4-aminobut-2-enoate.

Scheme 81. Synthesis of (Z)-1-((2′-chloro-5-(trifluoromethyl)-[1,1′-biphenyl]-2-yl)sulfonyl)-N-(4-(3,3-difluoroazetidin-1-yl)-4-oxobut-2-en-1-yl)-4-fluoropiperidine-4-carboxamide (Compound 284)

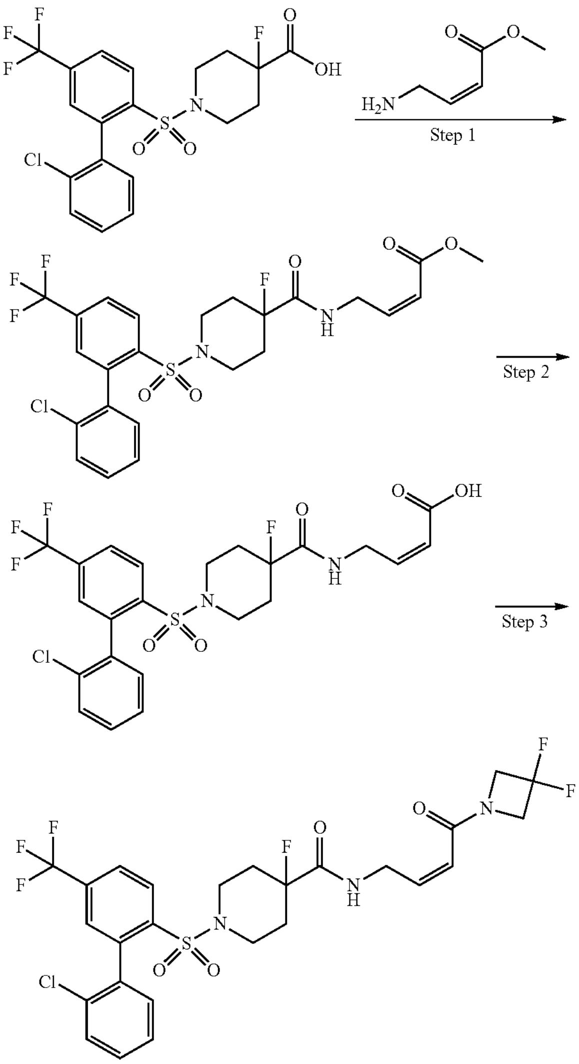

Step 1. To a solution of 1-[2-(2-chlorophenyl)-4-(trifluoromethyl)phenyl]sulfonyl-4-fluoro-piperidine-4-carboxylic acid (350 mg, 0.750 mmol, 1.0 eq) in DCM (5.0 mL, 0.15 M) was added methyl(Z)-4-aminobut-2-enoate (103 mg, 0.900 mmol, 1.2 eq), 2,4,6-tripropyl-1,3,5,2,4,6-trioxatriphosphorinane-2,4,6-trioxide (358 mg, 1.13 mmol, 1.5 eq), and DIPEA (243 mg, 1.88 mmol, 2.5 eq). The reaction was stirred at 25 °C for 1 h before being poured into water (5 mL) and extracted with DCM (15 mL×3). The combined organic layers were washed with brine (15 mL×2), dried over $Na_2SO_4$, filtered, and concentrated under reduced pressure. The resulting residue was purified by prep-TLC (PE:EtOAc=1:1) to afford methyl(Z)-4-[[1-[2-(2-chlorophenyl)-4-(trifluoromethyl)phenyl]sulfonyl-4-fluoro-piperidine-4-carbonyl]amino]but-2-enoate (240 mg, 0.430 mmol, 57% yield) as a white solid. $^1H$ NMR (400 MHz, $CDCl_3$) δ ppm 8.30 (d, J=8.4 Hz, 1H), 7.80 (dd, J=8.4, 1.3 Hz, 1H), 7.59 (d, J=1.1 Hz, 1H), 7.54 (dd, J=7.6, 1.6 Hz, 1H), 7.43-7.47 (m, 1H), 7.33-7.42 (m, 2H), 6.85-6.95 (t, 1H), 6.23 (dt, J=11.4, 6.5 Hz, 1H), 5.91 (d, J=11.5 Hz, 1H), 4.37 (td, J=6.3, 1.1 Hz, 2H), 3.74 (s, 3H), 3.28 (dt, J=13.2, 2.1 Hz, 1H), 3.12 (dt, J=13.2, 2.1 Hz, 1H), 2.92 (td, J=12.7, 2.9 Hz, 1H), 2.69 (td, J=12.8, 2.9 Hz, 1H), 1.93-2.30 (m, 2H), 1.70 (br s, 2H).

Step 2. To a solution of methyl(Z)-4-[[1-[2-(2-chlorophenyl)-4-(trifluoromethyl)phenyl]sulfonyl-4-fluoro-piperidine-4-carbonyl]amino]but-2-enoate (240 mg, 0.430 mmol, 1.0 eq) in DCE (10 mL, 0.04 M) was added hydroxy (trimethyl)stannane (385 mg, 2.13 mmol, 5.0 eq). The reaction was stirred at 110 °C under $N_2$ for 24 h. After cooling to rt, the mixture was poured into water (5 mL) and extracted with DCM (15 mL×3). The combined organic layers were washed with brine (15 mL×2), dried over $Na_2SO_4$, filtered, and concentrated under reduced pressure to give crude (Z)-4-[[1-[2-(2-chlorophenyl)-4-(trifluoromethyl)phenyl]sulfonyl-4-fluoro-piperidine-4-carbonyl] amino]but-2-enoic acid (220 mg, 0.401 mmol, 94% yield) as a white solid. $^1H$ NMR (400 MHz, $CDCl_3$) δ ppm 8.30 (d, J=8.4 Hz, 1H), 7.81 (s, 1H), 7.59 (s, 1H), 7.53-7.56 (m, 1H), 7.44-7.46 (m, 1H), 7.37-7.40 (m, 2H), 6.97-7.07 (m, 1H), 6.09-6.18 (m, 1H), 5.93 (d, J=11.4 Hz, 1H), 4.31 (t, J=6.13 Hz, 2H), 3.04 (dd, J=18.0, 7.3 Hz, 1H), 2.93 (br d, J=12.5 Hz, 1H), 2.66-2.74 (m, 2H), 2.10-2.31 (m, 2H), 1.89-2.03 (m, 1H), 1.68-1.73 (m, 2H).

Step 3. To a solution of (Z)-4-[[1-[2-(2-chlorophenyl)-4-(trifluoromethyl)phenyl]sulfonyl-4-fluoro-piperidine-4-carbonyl]amino]but-2-enoic acid (220 mg, 0.400 mmol, 1.0 eq) in DCM (5.0 mL, 0.08 M) was added 3,3-difluoroazetidine hydrochloride (62 mg, 0.480 mmol, 1.2 eq), 2,4,6-tripropyl-1,3,5,2,4,6-trioxatriphosphorinane-2,4,6-trioxide (191 mg, 0.600 mmol, 1.5 eq), and DIPEA (129 mg, 1.00 mmol, 2.5 eq). The reaction was stirred at 25 °C for 1 h before being poured into water (5 mL) and extracted with DCM (15 mL×3). The combined organic layers were washed with brine (15 mL×2), dried over $Na_2SO_4$, filtered, and concentrated under reduced pressure. The resulting residue was purified by prep-TLC (PE:EtOAc=2:1) to afford (Z)-1-((2'-chloro-5-(trifluoromethyl)-[1,1'-biphenyl]-2-yl)sulfonyl)-N-(4-(3,3-difluoroazetidin-1-yl)-4-oxobut-2-en-1-yl)-4-fluoropiperidine-4-carboxamide (63 mg, 0.100 mmol, 25% yield) as a white solid. $^1H$ NMR (400 MHz, DMSO-$d_6$) δ ppm 8.47-8.52 (m, 1H), 8.26 (d, J=8.5 Hz, 1H), 8.06 (dd, J=8.5, 1.6 Hz, 1H), 7.74 (d, J=1.3 Hz, 1H), 7.58 (d, J=7.9 Hz, 1H), 7.45-7.51 (m, 1H), 7.40-7.44 (m, 2H), 5.96-6.05 (m, 1H), 5.86-5.93 (m, 1H), 4.61 (br t, J=12.5 Hz, 2H), 4.31 (br t, J=12.8 Hz, 2H), 4.19-4.25 (m, 2H), 3.13-3.22 (m, 2H), 2.64-2.84 (m, 2H), 1.68-2.00 (m, 4H). [M+H] calculated for $C_{26}H_{24}ClF_6N_3O_4S$, 623; found 624.

Compound 285 was synthesized in a manner analogous to Compound 284 starting with 1-[4-bromo-2-(2-chlorophenyl)phenyl]sulfonyl-4-fluoro-piperidine-4-carboxylic acid and ethyl(Z)-4-aminobut-2-enoate.

Compound 286 was synthesized in a manner analogous to Compound 285 using azetidine in Step 3.

Scheme 82. Synthesis of Intermediate (S,Z)-4-amino-1-(3,3-difluoroazetidin-1-yl)pent-2-en-1-one

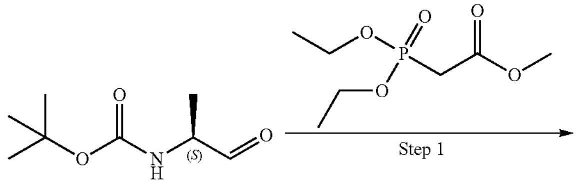

-continued

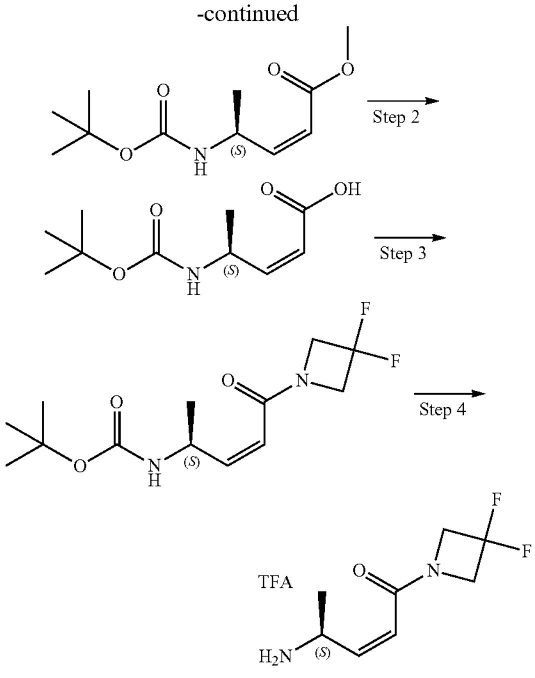

Step 1. A solution of trimethyl phosphonoacetate (6.2 g, 33.9 mmol, 1.2 eq) in THF (40 mL, 0.71 M) was placed under $N_2$ and cooled to −70 °C. LiHMDS (40 mL, 39.6 mmol, 1.4 eq, 1.0 M) was added and the solution was stirred at −70 °C for 1 h. tert-Butyl (S)-(1-oxopropan-2-yl)carbamate (4.9 g, 28.3 mmol, 1.0 eq) in THF (20 mL) was added and the reaction was stirred at −70 °C for 1 h. The reaction mixture was quenched with $NH_4Cl$(40 mL) and extracted with EtOAc (50 mL×3). The combined organic layers were washed with brine (100 mL), dried over $Na_2SO_4$, filtered, and concentrated under reduced pressure. The resulting residue was purified by FCC on silica (PE:EtOAc=1:0 to 5:1) to give methyl(S,Z)-4-((tert-butoxycarbonyl)amino) pent-2-enoate (2.0 g, 8.72 mmol, 31% yield) as a yellow oil. $^1H$ NMR (400 MHz, $CDCl_3$) δ ppm 6.19-6.06 (m, 1H), 5.76 (dd, J=11.6, 1.1 Hz, 1H), 5.22-5.11 (m, 1H), 4.77 (br s, 1H), 3.72 (s, 3H), 1.43 (s, 9H), 1.27 (br d, J=6.8 Hz, 3H).

Step 2. To a solution of methyl(S,Z)-4-((tert-butoxycarbonyl)amino)pent-2-enoate (1.5 g, 6.54 mmol, 1.0 eq) in DCE (20 mL, 0.33 M) under $N_2$ was added $Me_3SnOH$ (4.7 g, 26.2 mmol, 4.0 eq). The reaction was stirred at 85 °C for 96 h. After cooling to rt, the mixture was poured into water (50 mL) and extracted with DCM (35 mL×3). The combined organic layers were washed with brine (15 mL×2), dried over $Na_2SO_4$, filtered, and concentrated under reduced pressure to give crude (S,Z)-4-((tert-butoxycarbonyl)amino) pent-2-enoic acid (1.2 g, 5.57 mmol, 85% yield) as a white solid. $^1H$ NMR (400 MHz, $CDCl_3$) δ ppm 6.02 (br s, 1H), 5.78 (d, J=11.7 Hz, 1H), 5.18-4.83 (m, 2H), 1.43 (s, 9H), 1.26 (br d, J=6.7 Hz, 3H).

Step 3. To a solution of (S,Z)-4-((tert-butoxycarbonyl) amino)pent-2-enoic acid (1.2 g, 5.57 mmol, 1.0 eq) in DCM (20 mL, 0.28 M) was added 2,4,6-tripropyl-1,3,5,2,4,6-trioxatriphosphorinane-2,4,6-trioxide (2.7 g, 8.36 mmol, 1.5 eq), DIPEA (1.8 g, 13.9 mmol, 2.5 eq), and 3,3-difluoroazetidine (HCl salt, 867 mg, 6.69 mmol, 1.2 eq). The reaction was stirred at 25 °C for 1 h before being poured into water (50 mL) and extracted with DCM (20 mL×3). The combined organic layers were washed with brine (15 mL×2), dried over $Na_2SO_4$, filtered, and concentrated under reduced pressure. The resulting residue was purified by FCC on silica (PE:EtOAc=1:1) to afford tert-butyl(S,Z)-(5-(3,3-difluoroazetidin-1-yl)-5-oxopent-3-en-2-yl)carbamate (650 mg, 2.24 mmol, 40% yield) as a white solid. MS (ESI): mass calculated for $C_{13}H_{20}F_2N_2O_3$, 290.1; m/z found, 235.1 $[M+2H-tBu]^+$. $^1H$ NMR (400 MHz, $CDCl_3$) δ ppm 6.06 (br dd, J=11.1, 8.3 Hz, 1H), 5.72 (d, J=11.6 Hz, 1H), 5.04 (br s, 1H), 4.53-4.30 (m, 4H), 1.43 (s, 9H), 1.31-1.26 (m, 3H).

Step 4. To a solution of tert-butyl(S,Z)-(5-(3,3-difluoroazetidin-1-yl)-5-oxopent-3-en-2-yl)carbamate (450 mg, 1.55 mmol, 1.0 eq) in DCM (3.0 mL, 0.52 M) was added 2,2,2-trifluoroacetic acid (353 mg, 3.10 mmol, 2.0 eq) at 0 °C. The reaction was stirred at 25 °C for 1 h under $N_2$ before being concentrated to give (S,Z)-4-amino-1-(3,3-difluoroazetidin-1-yl)pent-2-en-1-one (TFA salt, 285 mg, 1.50 mmol, 97% yield) as a yellow oil. MS (ESI): mass calculated for $C_8H_{12}F_2N_2O$, 190.1; m/z found, 191.1 $[M+H]^+$.

Compound 287 was synthesized in a manner analogous to Compound 47 using (S,Z)-4-amino-1-(3,3-difluoroazetidin-1-yl)pent-2-en-1-one in Step 5.

Intermediate (Z)-4-amino-1-(3,3-difluoroazetidin-1-yl)but-2-en-1-one was synthesized in a manner analogous to (S,Z)-4-amino-1-(3,3-difluoroazetidin-1-yl)pent-2-en-1-one starting with (2-oxoethyl)carbamic acid tert-butyl ester.

Intermediate (2R,4S)-N-((Z)-4-(3,3-difluoroazetidin-1-yl)-4-oxobut-2-en-1-yl)-4-fluoro-2-methylpiperidine-4-carboxamide was synthesized in a manner analogous to (2R,4S)-4-fluoro-2-methyl-N-((R,Z)-4-(methylsulfonyl)but-3-en-2-yl)piperidine-4-carboxamide using (Z)-4-amino-1-(3,3-difluoroazetidin-1-yl)but-2-en-1-one and omitting the chiral separation.

Compound 288 was synthesized in a manner analogous to Compound 141 using (2R,4S)-N-((Z)-4-(3,3-difluoroazetidin-1-yl)-4-oxobut-2-en-1-yl)-4-fluoro-2-methylpiperidine-4-carboxamide.

Compounds 289-292 were synthesized in manner analogous to Compound 288 using the appropriate sulfonyl chloride.

Compound 293 was synthesized in a manner analogous to Compound 158 using methyl(3R,4S)-4-(2-chlorophenyl)-6,6-dimethyltetrahydro-2H-pyran-3-carboxylate in Step 1 and (2R,4S)-N-((Z)-4-(3,3-difluoroazetidin-1-yl)-4-oxobut-2-en-1-yl)-4-fluoro-2-methylpiperidine-4-carboxamide in Step 2.

Scheme 83. Synthesis of Intermediate 2-bromo-4-ethoxyaniline

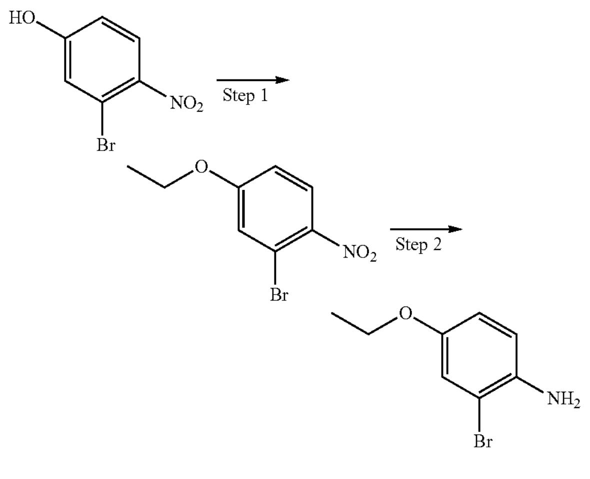

Step 1. To a solution of 3-bromo-4-nitrophenol (5.0 g, 22.9 mmol, 1.0 eq) in DMF (50 mL, 0.46 M) was added iodoethane (5.3 mL, 68.8 mmol, 3.0 eq) and $K_2CO_3$ (9.5 g, 68.8 mmol, 3.0 eq). The reaction was stirred at 20 °C for 16 h before being poured into water (200 mL) and extracted with EtOAc (50 mL×3). The combined organic layers were washed with brine (100 mL×2), dried over $Na_2SO_4$, filtered, and concentrated under reduced pressure. The resulting residue was purified by FCC on silica (PE:EtOAc=1:0 to 4:1) to give 2-bromo-4-ethoxy-1-nitrobenzene (5.7 g, 23.2 mmol, quant. yield) as a yellow solid. $^1H$ NMR (400 MHz, $CDCl_3$) δ ppm 8.00-7.93 (m, 1H), 7.19 (d, J=2.5 Hz, 1H), 6.89 (dd, J=9.1, 2.6 Hz, 1H), 4.10 (q, J=6.9 Hz, 2H), 1.49-1.41 (m, 3H).

Step 2. To a solution of 2-bromo-4-ethoxy-1-nitrobenzene (5.7 g, 23.2 mmol, 1.0 eq) in ethanol/water (v/v 1:1, 50 mL, 0.46 M) was added $NH_4Cl$ (6.2 g, 116 mmol, 5.0 eq) and iron powder (6.5 g, 116 mmol, 5.0 eq). The reaction was stirred at 80 °C for 1 h. After cooling to rt, the suspension was filtered through silica gel and washed with EtOH (50 mL). The filtrate was concentrated to dryness to give 2-bromo-4-ethoxyaniline (2.4 g, 11.1 mmol, 48% yield) as a yellow solid.

Compound 298 was synthesized in a manner analogous to Compound 134 using 2-bromo-4-ethoxyaniline in Step 1 and methyl(2R,4S)-4-fluoro-2-methylpiperidine-4-carboxylate in Step 2.

Compound 299 was synthesized in a manner analogous to Compound 298 using (R,Z)-4-(methylsulfonyl)but-3-en-2-amine in Step 5.

Intermediate 2-bromo-4-(methoxy-$d_3$)aniline was synthesized in a manner analogous to 2-bromo-4-ethoxyaniline using deuterated iodomethane in Step 1.

Compound 300 was synthesized in a manner analogous to Compound 134 using 2-bromo-4-(methoxy-$d_3$)aniline in Step 1 and methyl(2R,4S)-4-fluoro-2-methylpiperidine-4-carboxylate in Step 2.

Compound 301 was synthesized in a manner analogous to Compound 300 using (R,Z)-4-(methylsulfonyl)but-3-en-2-amine in Step 5.

Scheme 84. Synthesis of Intermediate (3R,4R)-4-(2-chlorophenyl)-1-cyclopropylpyrrolidine-3-carboxylic acid

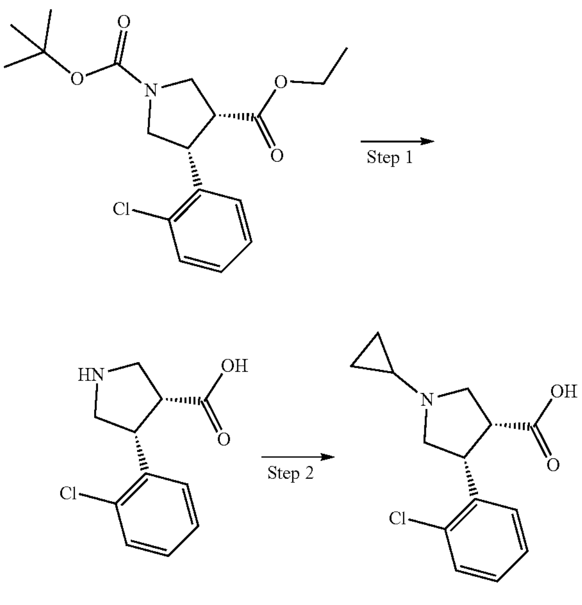

Step 1. A solution of 1-(tert-butyl) 3-ethyl(3R,4R)-4-(2-chlorophenyl)pyrrolidine-1,3-dicarboxylate (400 mg, 1.13 mmol, 1.0 eq) in HBr (3.0 mL, aq. in water) was stirred at 110 °C for 6 h. After cooling to rt, the mixture was concentrated in vacuo to give (3R,4R)-4-(2-chlorophenyl) pyrrolidine-3-carboxylic acid (250 mg, 1.11 mmol, 98% yield) as a pink solid. $^{1}$H NMR (400 MHz, Methanol-$d_4$) δ ppm 7.52-7.46 (m, 1H), 7.37-7.28 (m, 3H), 4.28 (dt, J=12.2, 7.5 Hz, 1H), 3.91-3.63 (m, 5H).

Step 2. To a solution of (3R,4R)-4-(2-chlorophenyl)pyrrolidine-3-carboxylic acid (250 mg, 1.11 mmol, 1.0 eq) and (1-ethoxycyclopropoxy)trimethylsilane (772 mg, 4.43 mmol, 4.0 eq) in methanol (5.0 mL, 0.22 M) was added acetic acid (1.3 mL, 22.2 mmol, 20 eq) and $NaBH_3CN$ (209 mg, 3.32 mmol, 3.0 eq) under $N_2$. The reaction was stirred at 60 °C for 4 h. After cooling to rt, the mixture was concentrated under reduced pressure. The resulting residue was purified by prep-HPLC (1-40% ACN in 0.1% aq. TFA) to give (3R,4R)-4-(2-chlorophenyl)-1-cyclopropylpyrrolidine-3-carboxylic acid (200 mg, 0.753 mmol, 68% yield) as a white solid. MS (ESI): mass calculated for $C_{14}H_{16}ClNO_2$, 265.1; m/z found, 266.2 $[M+H]^+$. $^{1}$H NMR (400 MHz, Methanol-$d_4$) δ ppm 7.51-7.45 (m, 1H), 7.35-7.29 (m, 3H), 4.41-4.26 (m, 1H), 4.14-3.89 (m, 4H), 3.85-3.76 (m, 1H), 3.20 (tt, J=7.3, 3.8 Hz, 1H), 1.13-0.98 (m, 4H).

Compound 303 was synthesized in a manner analogous to Compound 165 using (3R,4R)-4-(2-chlorophenyl)-1-cyclopropylpyrrolidine-3-carboxylic acid in Step 4.

Compound 304 was synthesized in a manner similar to Compound 165 starting from 4-fluoro-N—[(Z,1R)-1-methyl-3-methylsulfonyl-allyl]piperidine-4-carboxamide, 4-methylbenzenesulfonic acid salt and (3R,4R)-4-(2-chlorophenyl)-1-cyclopropylpyrrolidine-3-carboxylic acid in Step 4.

Scheme 85. Synthesis of Intermediate (3*R,4*R)-1-benzyl-4-(2-chlorophenyl)pyrrolidine-3-carboxylic acid

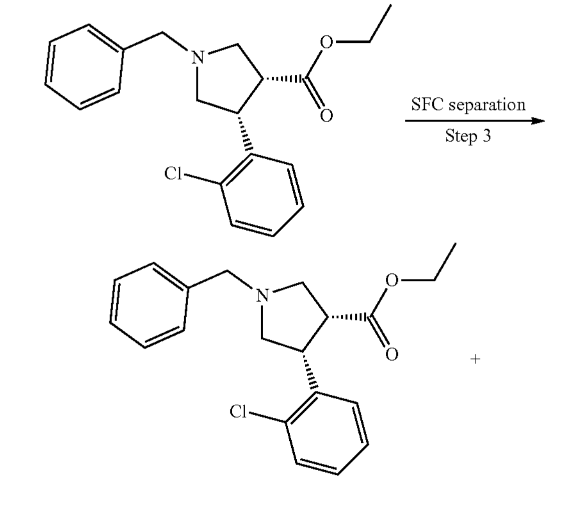

-continued

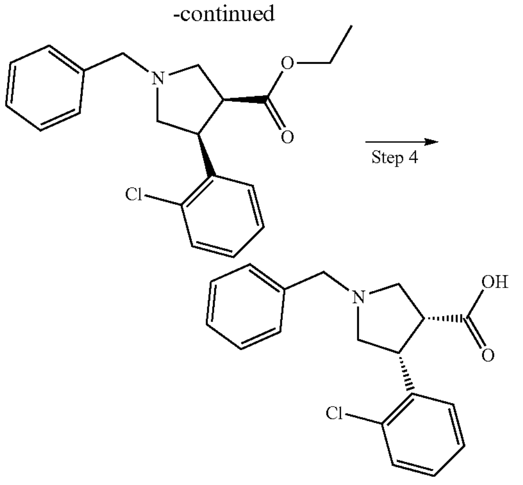

Step 1. A solution of ethyl(Z)-3-iodoprop-2-enoate (2.0 kg, 8.85 mol, 1.0 eq), 2-chlorophenylboronic acid (1.5 kg, 9.73 mol, 1.1 eq), and $K_3PO_4$ (5.6 kg, 26.5 mol, 3.0 eq) in toluene (3.5 L, 1.8 M) and water (1.5 L, 1.8 M) was purged with $N_2$. Pd(dppf)$Cl_2$·DCM (7.2 g, 8.85 mmol, 0.001 eq) was added and the reaction was heated to 60 °C for 16 h under $N_2$. After cooling to rt, the mixture was extracted with EtOAc (1.0 L×2). The combined organic layers were washed with brine (1.5 L), dried over anhydrous $Na_2SO_4$, and filtered. The filtrate was concentrated in vacuo to afford ethyl(Z)-3-(2-chlorophenyl)prop-2-enoate (1.7 kg, 7.91 mol, 89% yield) as a colorless oil. $^{1}$H NMR (400 MHz, $CDCl_3$) δ ppm 7.45 (dd, J=2.0, 7.3 Hz, 1H), 7.33 (dd, J=1.6, 7.7 Hz, 1H), 7.25-7.14 (m, 2H), 7.08 (d, J=12.3 Hz, 1H), 6.03 (d, J=12.3 Hz, 1H), 4.06 (q, J=7.1 Hz, 2H), 1.13 (t, J=7.1 Hz, 3H).

Step 2. To a solution of ethyl(Z)-3-(2-chlorophenyl)prop-2-enoate (23 g, 109 mmol, 1.0 eq) and 2,2,2-trifluoroacetic acid (1.25 g, 10.9 mmol, 0.1 eq) in toluene (300 mL, 0.36 M) was added N-(methoxymethyl)-N-(trimethylsilylmethyl) benzylamine (34.6 g, 131 mmol, 1.2 eq) dropwise at 50 °C. The reaction was stirred at 70 °C for 2 h. After cooling to rt, the mixture was quenched with water (200 mL) and extracted with toluene (200 mL×2). The combined organic layers were washed with brine (200 mL), dried over anhydrous $Na_2SO_4$, filtered, and concentrated under reduced pressure. The resulting residue was purified by FCC on silica (PE:EtOAc=1:0-3:1) to give ethyl rac-(3R,4R)-1-benzyl-4-(2-chlorophenyl)pyrrolidine-3-carboxylate (30 g, 87.2 mmol, 80% yield) as a colorless oil. $^{1}$H NMR (400 MHz, $CDCl_3$) δ ppm 7.47-7.41 (m, 3H), 7.34-7.27 (m, 6H), 4.26 (dt, J=6.6, 9.7 Hz, 1H), 3.82 (s, 2H), 3.75-3.51 (m, 3H), 3.22-3.13 (m, 1H), 3.12-3.05 (m, 2H), 2.91 (t, J=9.0 Hz, 1H), 0.82 (t, J=7.2 Hz, 3H).

Step 3. Ethyl rac-(3R,4R)-1-benzyl-4-(2-chlorophenyl) pyrrolidine-3-carboxylate (400 mg, 1.16 mmol, 1.0 eq) was separated by SFC (Stationary phase: OJ (250×30 mm); Mobile phase: 15% EtOH/$CO_2$) to give two enantiomers: P1, Rt=4.5 min: ethyl(3*R,4*R)-1-benzyl-4-(2-chlorophenyl)pyrrolidine-3-carboxylate (150 mg, 0.436 mmol, 38% yield) was obtained as colorless oil. $^{1}$H NMR (400 MHz, Methanol-$d_4$) δ ppm 7.42-7.07 (m, 9H), 4.22-4.04 (m, 1H), 3.79-3.66 (m, 2H), 3.62-3.37 (m, 3H), 3.10-2.72 (m, 4H), 0.79-0.63 (m, 3H). P2, Rt=5.9 min: ethyl(3*S,4*S)-1-benzyl-4-(2-chlorophenyl)pyrrolidine-3-carboxylate (120 mg, 0.349 mmol, 30% yield) was obtained as colorless oil. $^{1}$H NMR (400 MHz, Methanol-$d_4$) δ ppm 7.53-7.16 (m, 9H), 4.27-4.14 (m, 1H), 3.89-3.75 (m, 2H), 3.71-3.42 (m, 3H), 3.18-2.81 (m, 4H), 0.92-0.63 (m, 3H).

Step 4. To a solution of ethyl(3*R,4*R)-1-benzyl-4-(2-chlorophenyl)pyrrolidine-3-carboxylate (100 mg, 0.291 mmol, 1.0 eq) in DCE (5.0 mL, 0.058 M) was added trimethyltin hydroxide (263 mg, 1.45 mmol, 5.0 eq). The reaction was stirred at 110 °C for 48 h. After cooling to rt, the mixture was concentrated to give (3*R,4*R)-1-benzyl-4-(2-chlorophenyl)pyrrolidine-3-carboxylic acid (90 mg, 0.285 mmol, 98% yield) as a white solid. This was used in the next step without purification.

Compound 305 was synthesized in a manner analogous to Compound 165 using (3*R,4*R)-1-benzyl-4-(2-chlorophenyl)pyrrolidine-3-carboxylic acid in Step 4.

Scheme 86. Synthesis of Intermediate (3*R,4*R)-3-(2-chlorophenyl)-1-(2,2,2-trifluoroethyl)piperidine-4-carboxylic acid

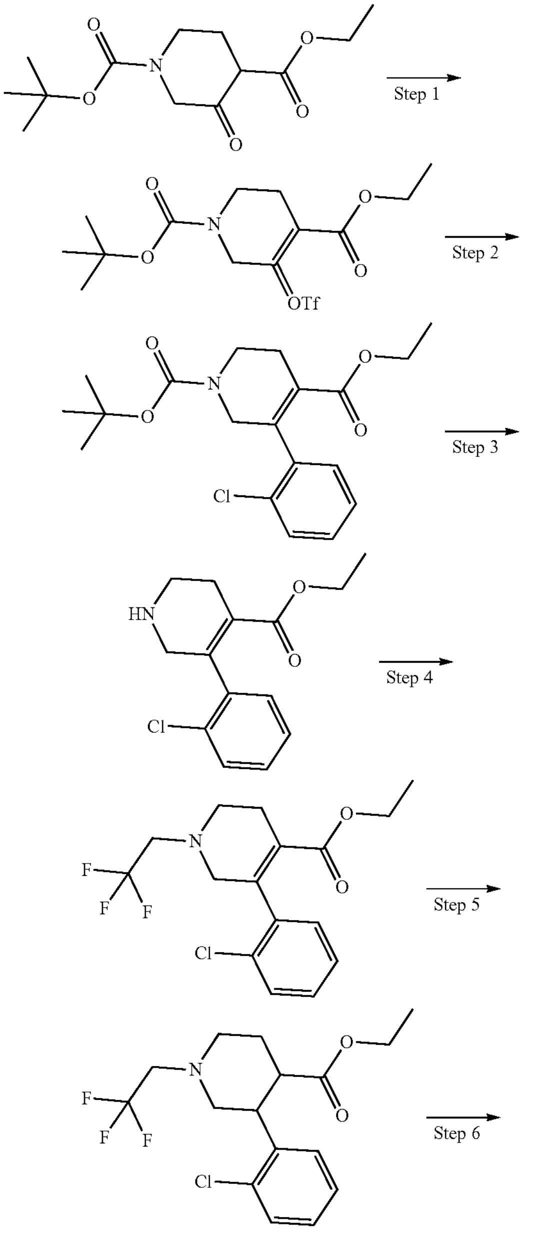

-continued

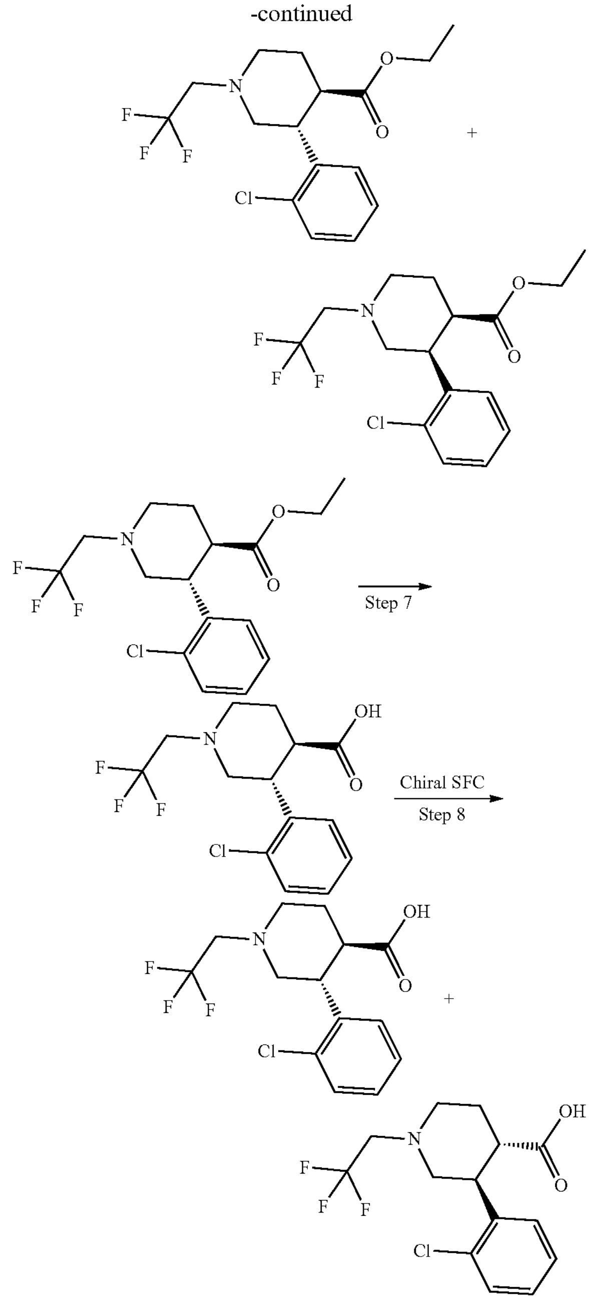

Step 1. To a solution of 1-(tert-butyl) 4-ethyl 3-oxopiperidine-1,4-dicarboxylate (10 g, 36.9 mmol, 1.0 eq) in toluene (120 mL, 0.31 M) was added DIPEA (7.1 g, 55.3 mmol, 1.5 eq) and $Tf_2O$ (12.5 g, 44.2 mmol, 1.2 eq) at 0 °C. The reaction was stirred at 20 °C for 16 h before being evaporated to give 1-(tert-butyl) 4-ethyl 5-(((trifluoromethyl)sulfonyl)oxy)-3,6-dihydropyridine-1,4(2H)-dicarboxylate (14.8 g, 36.7 mmol, 98% yield) as a brown oil.

Step 2. To a solution of 1-(tert-butyl) 4-ethyl 5-(((trifluoromethyl)sulfonyl)oxy)-3,6-dihydropyridine-1,4(2H)-dicarboxylate (30 g, 37.2 mmol, 1.0 eq) in THF (360 mL, 0.16 M) was added (2-chlorophenyl)boronic acid (6.4 g, 40.9 mmol, 1.1 eq), $K_3PO_4$ (15.8 g, 74.4 mmol, 2.0 eq), and $Pd(PPh_3)_4$ (1.3 g, 1.12 mmol, 0.03 eq). The reaction was placed under $N_2$ and stirred at 70 °C for 12 h. After cooling to rt, the solution was diluted with $H_2O$ (300 mL) and extracted with EtOAc (100 mL×3). The combined organic layers were washed with brine (150 mL), dried over $Na_2SO_4$, filtered, and concentrated under reduced pressure. The crude product was purified by FCC on silica (PE:EtOAc=1:0-5:1) to give 1-(tert-butyl) 4-ethyl 5-(2-chlorophenyl)-3,6-dihydropyridine-1,4(2H)-dicarboxylate (9.0 g, 24.6 mmol, 66% yield) as a yellow solid. MS (ESI): mass calculated for $C_{19}H_{24}ClNO_4$, 365.1; m/z found, 310.0 $[M+2H-tBu]^+$.

Step 3. To a solution of 1-(tert-butyl) 4-ethyl 5-(2-chlorophenyl)-3,6-dihydropyridine-1,4(2H)-dicarboxylate (6.0 g, 16.3 mmol, 1.0 eq) in DCM (30 mL, 0.54 M) was added TFA (10 mL). The reaction was stirred at 20 °C for 1 h. The mixture was filtered and concentrated under reduced pressure to give ethyl 5-(2-chlorophenyl)-1,2,3,6-tetrahydropyridine-4-carboxylate (as TFA salt, 5.6 g, 14.7 mmol, 98% yield) as a white solid. The product was used directly without further purification.

Step 4. To a solution of ethyl 5-(2-chlorophenyl)-1,2,3,6-tetrahydropyridine-4-carboxylate (5.6 g, 14.7 mmol, 1.0 eq) in MeCN (30 mL, 0.49 M) was added 2,2,2-trifluoroethyl trifluoromethanesulfonate (6.8 g, 29.5 mmol, 2.0 eq) and TEA (7.5 g, 73.7 mmol, 5.0 eq). The reaction was stirred at 80 °C for 12 h. After cooling to rt, the mixture was poured into water (100 mL) and extracted with EtOAc (100 mL×3). The combined organic layers were washed with brine (100 mL×2), dried over $Na_2SO_4$, filtered, and concentrated under reduced pressure. The resulting residue was purified by FCC on silica (PE:EtOAc=1:0-20:1) to give ethyl 5-(2-chlorophenyl)-1-(2,2,2-trifluoroethyl)-1,2,3,6-tetrahydropyridine-4-carboxylate (5.6 g, 16.1 mmol, 87% yield) as a yellow oil. $^1H$ NMR (400 MHz, DMSO-$d_6$) δ ppm 7.54-7.41 (m, 1H), 7.35-7.30 (m, 2H), 7.20-7.16 (m, 1H), 3.83-3.78 (m, 2H), 3.32-3.25 (m, 2H), 2.89 (t, J=5.8 Hz, 2H), 2.58-2.51 (m, 2H), 2.49-2.38 (m, 2H), 0.77 (t, J=7.1 Hz, 3H).

Step 5. To a solution of ethyl 5-(2-chlorophenyl)-1-(2,2,2-trifluoroethyl)-1,2,3,6-tetrahydropyridine-4-carboxylate (5.6 g, 16.1 mmol, 1.0 eq) in methanol (50 mL, 0.32 M) was added magnesium (3.9 g, 161 mmol, 10 eq) in portions and the reaction was stirred at 20 °C for 12 h. The mixture was filtered and concentrated under vacuum. The resulting residue was diluted with water (50 mL) and extracted with ethyl acetate (50 mL×3). The combined organic layers were dried over sodium sulfate, filtered, and concentrated in vacuo. The resulting residue was purified by FCC on silica (PE: EtOAc=1:0-50:1) to give ethyl 3-(2-chlorophenyl)-1-(2,2,2-trifluoroethyl)piperidine-4-carboxylate (2.0 g, 5.72 mmol, 35% yield) as a colorless oil. MS (ESI): mass calculated for $C_{16}H_{19}ClF_3NO_2$, 349.1; m/z found, 350.1 $[M+H]^+$. $^1H$ NMR (400 MHz, DMSO-$d_6$) δ ppm 7.53-7.40 (m, 2H), 7.31-7.18 (m, 2H), 3.91-3.69 (m, 2H), 3.60-3.44 (m, 1H), 3.29-3.15 (m, 3H), 3.03-2.63 (m, 4H), 2.02-1.61 (m, 2H), 0.93-0.85 (m, 3H).

Step 6. Ethyl 3-(2-chlorophenyl)-1-(2,2,2-trifluoroethyl) piperidine-4-carboxylate (2.0 g, 5.72 mmol) was separated by prep-HPLC (40-70% ACN in 10 mM aq. $NH_4HCO_3$) to give two products:

P1: ethyl(3*R,4*R)-3-(2-chlorophenyl)-1-(2,2,2-trifluoroethyl)piperidine-4-carboxylate (trans racemate, 330 mg, 0.943 mmol, 17% yield) was obtained as a white solid. $^1H$ NMR (400 MHz, DMSO-$d_6$) δ ppm 7.44-7.39 (m, 1H), 7.36 (dd, J=7.3, 1.9 Hz, 1H), 7.22-7.13 (m, 2H), 3.96-3.78 (m, 2H), 3.74-3.65 (m, 1H), 3.37 (t, J=10.4 Hz, 1H), 3.15-2.96 (m, 4H), 2.89 (dd, J=10.9, 3.6 Hz, 1H), 2.86-2.76 (m, 1H), 2.09-2.00 (m, 2H), 0.97 (t, J=7.2 Hz, 3H).

P2: ethyl(3*S,4*R)-3-(2-chlorophenyl)-1-(2,2,2-trifluoroethyl)piperidine-4-carboxylate (cis racemate, 1.50 g, 4.29 mmol, 75% yield) was obtained as a white solid. $^1H$ NMR (400 MHz, DMSO-$d_6$) δ ppm 7.36 (dd, J=7.9, 1.2 Hz, 1H), 7.29 (d, J=1.7 Hz, 1H), 7.27-7.12 (m, 2H), 3.95 (q, J=7.1 Hz, 2H), 3.73 (td, J=10.9, 3.2 Hz, 1H), 3.16-3.01 (m, 4H), 2.75 (br d, J=3.3 Hz, 1H), 2.59 (td, J=11.3, 3.7 Hz, 1H), 2.39 (br t, J=9.8 Hz, 1H), 2.07-1.92 (m, 2H), 1.04-0.98 (m, 3H).

Step 7. To a solution of ethyl(3*R,4*R)-3-(2-chlorophenyl)-1-(2,2,2-trifluoroethyl)piperidine-4-carboxylate (trans racemate, 330 mg, 0.945 mmol, 1.0 eq) in THF/water (v/v 3:1, 4.0 mL, 0.24 M) was added $LiOH \cdot H_2O$ (59 mg, 1.42 mmol, 1.5 eq). The reaction was stirred at 20 °C for 16 h before being acidified with 2N HCl to pH ~2. The white precipitate was collected via filtration to give (3*R,4*R)-3-(2-chlorophenyl)-1-(2,2,2-trifluoroethyl)piperidine-4-carboxylic acid (200 mg, 0.622 mmol, 66% yield) as a white solid.

Step 8. (3*R,4*R)-3-(2-Chlorophenyl)-1-(2,2,2-trifluoroethyl)piperidine-4-carboxylic acid (200 mg, 0.622 mmol, 1.0 eq) was separated by chiral SFC (Stationary phase: OZ (250×25 mm); Mobile phase: 10% $EtOH/CO_2$; Rt(P1)=4.26 min, Rt(P2)=6.75 min) to give P1: (3*R,4*R)-3-(2-chlorophenyl)-1-(2,2,2-trifluoroethyl)piperidine-4-carboxylic acid (65 mg, 0.202 mmol, 33% yield) as a white solid. MS (ESI): mass calculated for $C_{14}H_{15}ClF_3NO_2$, 321.1; m/z found, 322.1 $[M+H]^+$.

Compound 306 was synthesized in a manner analogous to Compound 165 using (3*R,4*R)-3-(2-chlorophenyl)-1-(2,2,2-trifluoroethyl)piperidine-4-carboxylic acid in Step 4.

Compound 307 was synthesized in a manner similar to Compound 165 starting from 4-fluoro-N—[(Z,1R)-1-methyl-3-methylsulfonyl-allyl]piperidine-4-carboxamide, 4-methylbenzenesulfonic acid salt and (3*R,4*R)-3-(2-chlorophenyl)-1-(2,2,2-trifluoroethyl)piperidine-4-carboxylic acid in Step 4.

Scheme 87. Synthesis of Intermediate (3*R,4*S)-4-(2-chlorophenyl)-1-(2,2,2-trifluoroethyl)piperidine-3-carboxylic acid

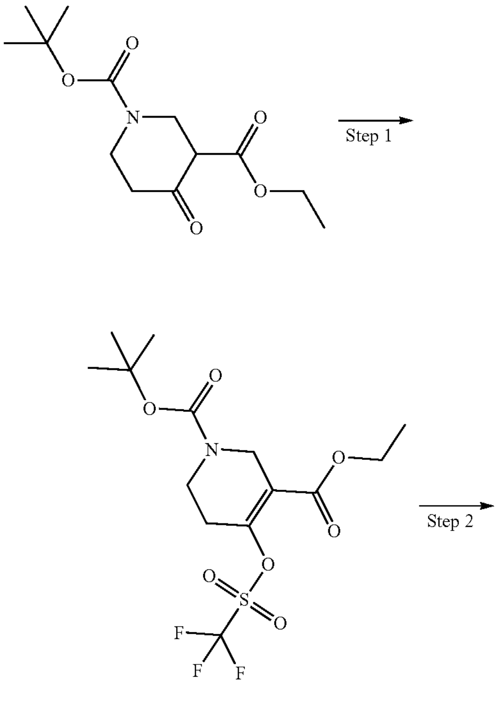

-continued

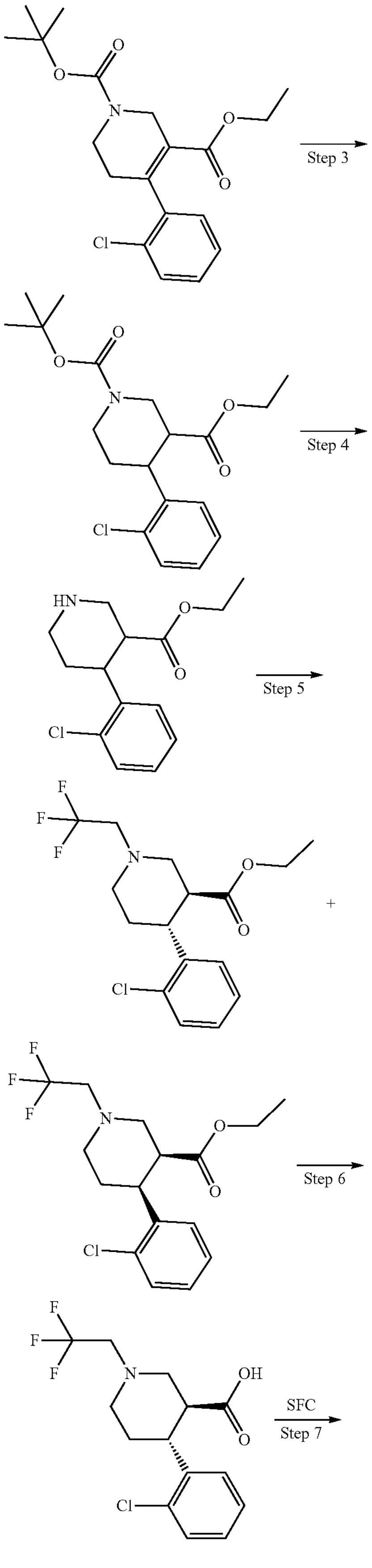

-continued

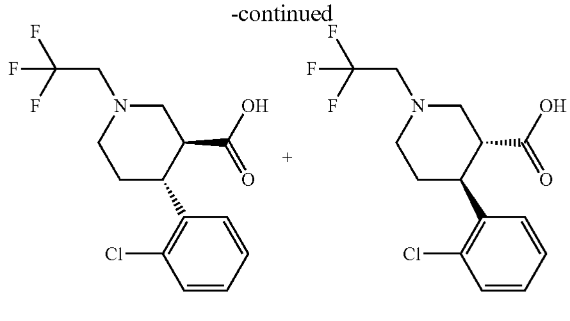

Step 1. A solution of 1-tert-butyl 3-ethyl 4-oxopiperidine-1,3-dicarboxylate (5.0 g, 18.4 mmol, 1.0 eq) and DIPEA (5.9 g, 46.1 mmol, 2.5 eq) in DCM (50 mL, 0.37 M) was placed under $N_2$. To this was added trifluoromethanesulfonic anhydride (6.8 g, 23.9 mmol, 1.3 eq) at −78 °C under $N_2$. The reaction was stirred at −78 °C for 0.5 h before being extracted with water (50 mL) and DCM (50 mL×3). The combined organic layers were washed with brine (50 mL), dried over with $Na_2SO_4$, filtered, and concentrated under reduced pressure. 1-tert-Butyl 3-ethyl 4-(((trifluoromethyl)sulfonyl)oxy)-5,6-dihydropyridine-1,3(2H)-dicarboxylate (7.4 g, 18.3 mmol, quant.) was obtained as a yellow solid.

Step 2. A mixture of 1-tert-butyl 3-ethyl 4-(((trifluoromethyl)sulfonyl)oxy)-5,6-dihydropyridine-1,3(2H)-dicarboxylate (7.4 g, 18.3 mmol, 1.0 eq) and (2-chlorophenyl)boronic acid (3.2 g, 20.2 mmol, 1.1 eq) in THF (75 mL, 0.24 M) was placed under $N_2$. To the mixture was added $K_3PO_4$ (7.8 g, 36.7 mmol, 2.0 eq) and $Pd(PPh_3)_4$(1.1 g, 0.917 mmol, 0.05 eq) and the reaction was heated to 65 °C for 12 h. After cooling to rt, the mixture was extracted with water (50 mL) and EtOAc (50 mL×3). The combined organic layers were washed with brine (50 mL), dried over with $Na_2SO_4$, filtered, and concentrated under reduced pressure. The residue was purified by FCC on silica (PE:EtOAc=1:0-5:1) to obtain 1-tert-butyl 3-ethyl 4-(2-chlorophenyl)-5,6-dihydropyridine-1,3(2H)-dicarboxylate (6.5 g, 17.8 mmol, 97% yield) as a yellow solid. MS (ESI): mass calculated for $C_{19}H_{24}C_1NO_4$, 365.1; m/z found, 309.9 $[M+2H-tBu]^+$. $^1H$ NMR (400 MHz, $CDCl_3$) δ ppm 7.34-7.27 (m, 1H), 7.16 (br dd, J=3.6, 5.5 Hz, 2H), 7.01-6.94 (m, 1H), 4.43-4.30 (m, 1H), 4.07-4.01 (m, 1H), 3.90-3.82 (m, 2H), 3.80-3.72 (m, 1H), 3.34 (td, J=4.4, 8.5 Hz, 1H), 2.43 (br s, 1H), 2.32 (br d, J=2.1 Hz, 1H), 1.44 (s, 9H), 0.83 (br s, 3H).

Step 3. To a solution of 1-tert-butyl 3-ethyl 4-(2-chlorophenyl)-5,6-dihydropyridine-1,3(2H)-dicarboxylate (4.5 g, 12.3 mmol, 1.0 eq) in methanol (45 mL, 0.27 M) was added magnesium (3.0 g, 123 mmol, 10 eq) at 0 °C. The reaction was stirred under $N_2$ at 25 °C for 3 h. The mixture was quenched with 1M HCl (50 mL) and extracted with EtOAc (50 mL×3). The combined organic layers were washed with brine (70 mL), dried over $Na_2SO_4$, filtered, and concentrated under reduced pressure. 1-tert-Butyl 3-ethyl 4-(2-chlorophenyl)piperidine-1,3-dicarboxylate (4.3 g, 11.7 mmol, 95% yield) was obtained as a yellow solid. MS (ESI): mass calculated for $C_{19}H_{26}C_1NO_4$, 367.1; m/z found, 312.2 $[M+2H-tBu]^+$.

Step 4. To a solution of 1-tert-butyl 3-ethyl 4-(2-chlorophenyl)piperidine-1,3-dicarboxylate (2.5 g, 6.83 mmol, 1.0 eq) in DCM (25 mL, 0.27 M) was added TFA (2.3 g, 20.5 mmol, 3.0 eq) under $N_2$. The reaction was stirred at 25 °C for 2 h before being concentrated under reduced pressure. The mixture was extracted with $H_2O$ (20 mL) and DCM (20 mL×3). The combined organic layers were washed with brine (50 mL), dried over with $Na_2SO_4$, filtered, and concentrated under reduced. Ethyl 4-(2-chlorophenyl)piperidine-3-carboxylate (2.5 g, 6.71 mmol, 98% yield) was obtained as a white solid.

Step 5. To ethyl 4-(2-chlorophenyl)piperidine-3-carboxylate (2.5 g, 6.58 mmol, 1.0 eq) in toluene (25 mL, 0.26 M) was added DIPEA (2.0 g, 19.7 mmol, 3.0 eq) and 2,2,2-trifluoroethyl trifluoromethanesulfonate (3.1 g, 13.2 mmol, 2.0 eq). The reaction was stirred at 80 °C for 16 h. After cooling to rt, the mixture was poured into $H_2O$ (30 mL) and extracted with EtOAc (30 mL×3). The combined organic layers were washed with brine (90 mL), dried over with $Na_2SO_4$, filtered, and concentrated under reduced pressure. The resulting residue was purified by FCC on silica (PE: EtOAc=1:0-3:1) to obtain ethyl 4-(2-chlorophenyl)-1-(2,2,2-trifluoroethyl)piperidine-3-carboxylate (trans racemate, 300 mg, 0.863 mmol, 13% yield) as a white solid and ethyl 4-(2-chlorophenyl)-1-(2,2,2-trifluoroethyl)piperidine-3-carboxylate (cis racemate, 1.5 g, 4.31 mmol, 65% yield) as a colorless oil. MS (ESI): mass calculated for $C_{16}H_{19}ClF_3NO_2$, 349.1; m/z found, 350.1 $[M+H]^+$.

Step 6. A solution of ethyl 4-(2-chlorophenyl)-1-(2,2,2-trifluoroethyl)piperidine-3-carboxylate (trans racemate, 300 mg, 0.858 mmol, 1.0 eq) in HBr (7.0 mL, 48% in water) was stirred at 110 °C for 2 h. After cooling to rt, the mixture was extracted with $H_2O$ (5.0 mL) and EtOAc (5.0 mL×3). The combined organic layers were washed with brine (15 mL), dried over with $Na_2SO_4$, filtered, and concentrated under reduced pressure. The resulting residue was purified via prep-HPLC (15-55% ACN in 10 mM aq. $NH_4HCO_3$) to obtain 4-(2-chlorophenyl)-1-(2,2,2-trifluoroethyl)piperidine-3-carboxylic acid (trans racemate, 150 mg, 0.466 mmol, 54% yield) as a white solid. $^1H$ NMR (400 MHz, $CDCl_3$) δ ppm 7.38-7.30 (m, 1H), 7.26 (br s, 2H), 7.17-7.11 (m, 1H), 3.42-3.33 (m, 1H), 3.33-3.27 (m, 1H), 3.14-3.01 (m, 4H), 2.72-2.65 (m, 1H), 2.64-2.56 (m, 1H), 1.94-1.86 (m, 1H), 1.68-1.55 (m, 1H).

Step 7. 4-(2-Chlorophenyl)-1-(2,2,2-trifluoroethyl)piperidine-3-carboxylic acid (trans racemate, 150 mg, 0.466 mmol) was purified by SFC (Stationary phase: AD (250×30 mm); Mobile phase: 11% $MeOH/CO_2$, 7 min) to give two products. P2: (3*R,4*S)-4-(2-chlorophenyl)-1-(2,2,2-trifluoroethyl)piperidine-3-carboxylic acid (40 mg, 0.124 mmol, 26% yield) as a pale yellow oil. MS (ESI): mass calculated for $C_{14}H_{15}ClF_3NO_2$, 321.1; m/z found, 322.1 $[M+H]^+$.

Compound 308 was synthesized in a manner analogous to Compound 165 using (3*R,4*S)-4-(2-chlorophenyl)-1-(2,2,2-trifluoroethyl)piperidine-3-carboxylic acid in Step 4.

Scheme 88. Synthesis of (R)-1-((*R)-2-(2-chlorophenyl)-4-(2,2,2-trifluoroethyl)piperazine-1-carbonyl)-4-fluoro-N-((R,Z)-4-(methylsulfonyl)but-3-en-2-yl)azepane-4-carboxamide (Compound 309)

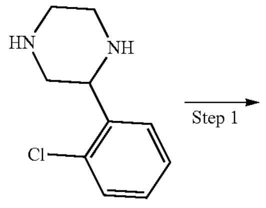

-continued

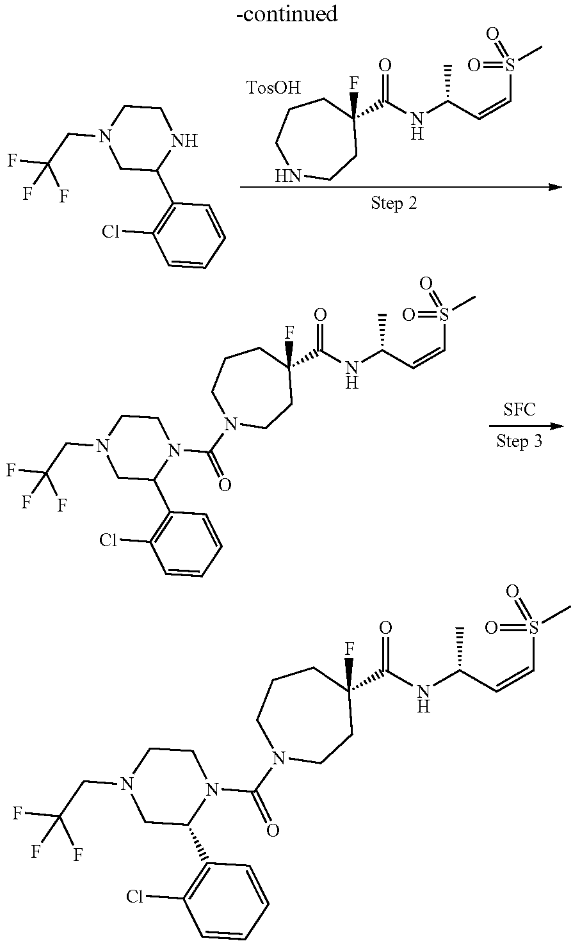

Step 1. To a solution of 2-(2-chlorophenyl)piperazine (1.4 g, 7.12 mmol, 1.0 eq) in toluene (15 mL, 0.47 M) was added TEA (3.0 mL, 21.4 mmol, 3.0 eq) and 2,2,2-trifluoroethyl trifluoromethanesulfonate (1.6 g, 7.12 mmol, 1.0 eq) at 15 °C. The reaction was stirred at 80 °C for 16 h. After cooling to rt, the mixture was poured into water (30 mL) and extracted with EtOAc (30 mL×3). The combined organic layers were washed brine (30 mL×2), dried over $Na_2SO_4$, filtered, and concentrated under reduced pressure. The resulting residue was purified by column chromatography to afford 3-(2-chlorophenyl)-1-(2,2,2-trifluoroethyl) piperazine (500 mg, 1.79 mmol, 25% yield) as a yellow oil.

Step 2. To a solution of 3-(2-chlorophenyl)-1-(2,2,2-trifluoroethyl)piperazine (200 mg, 0.718 mmol, 1.0 eq) in DCM (2.0 mL, 0.36 M) was added triphosgene (74.5 mg, 0.251 mmol, 0.4 eq) and DIPEA (0.4 mL, 2.15 mmol, 3.0 eq). The reaction was stirred at 25 °C for 0.5 h before (4R)-4-fluoro-N-[(Z,1R)-1-methyl-3-methylsulfonyl-allyl] azepane-4-carboxamide (TsOH salt, 333 mg, 0.718 mmol, 1.0 eq) was added. The reaction was stirred at 25 °C for 16 h before being poured into water (20 mL) and extracted with EtOAc (20 mL×3). The combined organic layers were washed with brine (20 mL×2), dried over $Na_2SO_4$, filtered, and concentrated under reduced pressure. The resulting residue was purified by prep-HPLC (35-65% ACN in 0.1% aq. TFA) to afford (4R)-1-[2-(2-chlorophenyl)-4-(2,2,2-trifluoroethyl)piperazine-1-carbonyl]-4-fluoro-N-[(Z,1R)-1-methyl-3-methylsulfonyl-allyl]azepane-4-carboxamide (200 mg, 0.335 mmol, 47% yield) as a colorless oil. MS (ESI): mass calculated for $C_{25}H_{33}ClF_4N_4O_4S$, 596.2; m/z found, 597.1 $[M+H]^+$.

Step 3. (4R)-1-[2-(2-chlorophenyl)-4-(2,2,2-trifluoroethyl)piperazine-1-carbonyl]-4-fluoro-N—[(Z,1R)-1-methyl-3-methylsulfonyl-allyl]azepane-4-carboxamide (200 mg, 0.335 mmol) was separated by SFC (Stationary phase: WHELK-01 (250×30 mm); Mobile phase: 50% IPA/$CO_2$; Rt (P1)=7.6 min, Rt (P2)=10.7 min) to give two products. P2: (R)-1-((*R)-2-(2-chlorophenyl)-4-(2,2,2-trifluoroethyl)piperazine-1-carbonyl)-4-fluoro-N-((R,Z)-4-(methylsulfonyl)but-3-en-2-yl)azepane-4-carboxamide (105 mg, 0.175 mmol, 52% yield) as a white solid. MS (ESI): mass calculated for $C_{25}H_{33}ClF_4N_4O_4S$, 596.2; m/z found, 597.1 $[M+H]^+$. $^1H$ NMR (400 MHz, DMSO-$d_6$) δ ppm 8.32 (dd, J=7.7, 2.1 Hz, 1H), 7.52 (dd, J=7.2, 2.0 Hz, 1H), 7.43-7.34 (m, 1H), 7.30-7.18 (m, 2H), 6.47 (d, J=11.2 Hz, 1H), 6.36-6.24 (m, 1H), 5.44-5.30 (m, 1H), 4.60 (dd, J=8.7, 3.2 Hz, 1H), 3.68-3.50 (m, 2H), 3.39-3.34 (m, 1H), 3.33-3.30 (m, 1H), 3.30-3.19 (m, 3H), 3.13 (s, 3H), 2.96-2.80 (m, 3H), 2.74-2.65 (m, 1H), 2.46 (br d, J=10.9 Hz, 1H), 2.13-1.83 (m, 4H), 1.75 (br s, 2H), 1.22 (d, J=6.8 Hz, 3H).

Scheme 89. Synthesis of (R)-1-((2′-chloro-5-(trifluoromethyl)-[1,1′-biphenyl]-2-yl)sulfonyl)-4-fluoro-N-((R,Z)-4-(methylsulfonyl)but-3-en-2-yl)azepane-4-carboxamide (Compound 310)

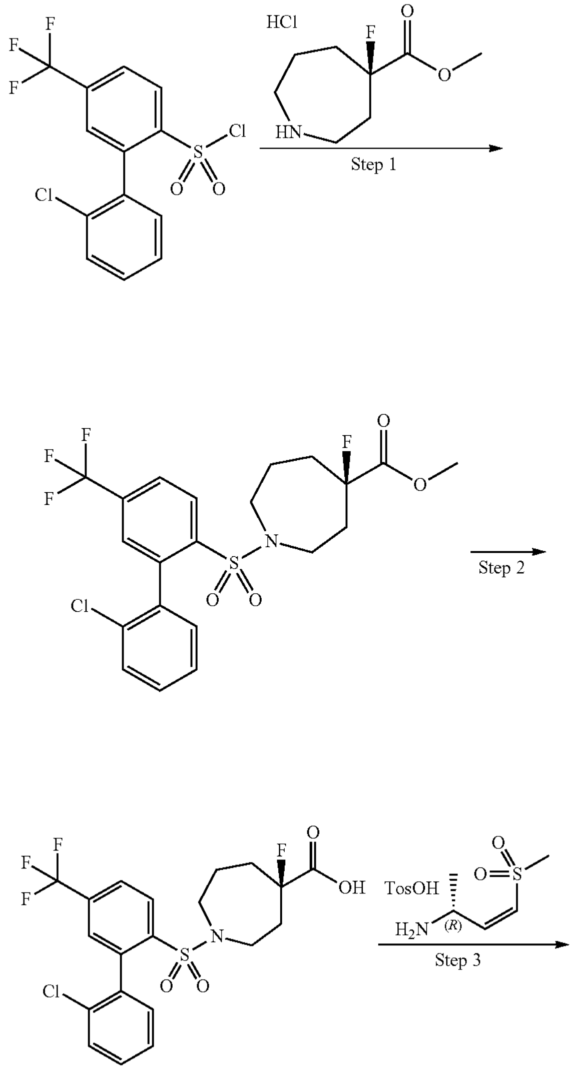

-continued

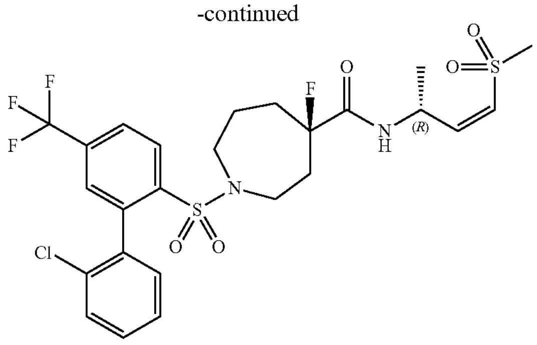

Step 1. To a solution of methyl(R)-4-fluoroazepane-4-carboxylate (HCl salt, 149 mg, 0.704 mmol, 1.0 eq) in DCM (5.0 mL, 0.14 M) was added DIPEA (273 mg, 2.11 mmol, 3.0 eq). 2-(2-Chlorophenyl)-4-(trifluoromethyl)benzenesulfonyl chloride (250 mg, 0.704 mmol, 1.0 eq) in DCM (2.0 mL) was added to the solution at 0 °C. The reaction was stirred at 20 °C for 2 h before being poured into water (10 mL) and extracted with DCM (10 mL×3). The combined organic layers were washed with brine (20 mL), dried over $Na_2SO_4$, filtered, and concentrated under reduced pressure. The resulting residue was purified by FCC on silica (PE: EtOAc=10:1) to give methyl(R)-1-((2'-chloro-5-(trifluoromethyl)-[1,1'-biphenyl]-2-yl)sulfonyl)-4-fluoroazepane-4-carboxylate (320 mg, 0.648 mmol, 92% yield) as a yellow oil. $^1H$ NMR (400 MHz, $CDCl_3$) δ ppm 8.33-8.25 (m, 1H), 7.79 (br d, J=8.0 Hz, 1H), 7.57 (s, 1H), 7.54-7.36 (m, 4H), 3.77 (d, J=5.2 Hz, 3H), 3.30-2.56 (m, 4H), 2.30-2.11 (m, 2H), 2.03-1.52 (m, 4H).

Step 2. To a solution of methyl(R)-1-((2'-chloro-5-(trifluoromethyl)-[1,1'-biphenyl]-2-yl)sulfonyl)-4-fluoroazepane-4-carboxylate (320 mg, 0.648 mmol, 1.0 eq) in THF/water (v/v 3:1, 4.0 mL, 0.16 M) was added $LiOH{\cdot}H_2O$ (33 mg, 0.778 mmol, 1.2 eq). The reaction was stirred at 20 °C for 3 h before being diluted with water (5 mL) and acidified with 1M aq. HCl until pH 3-4. The mixture was extracted with EtOAc (10 mL×3) and the combined organic layers were washed with brine (10 mL), dried over $Na_2SO_4$, and filtered. The filtrate was concentrated under reduced pressure to give (R)-1-((2'-chloro-5-(trifluoromethyl)-[1,1'-biphenyl]-2-yl)sulfonyl)-4-fluoroazepane-4-carboxylic acid (300 mg, 0.625 mmol, 96% yield) as a yellow oil. $^1H$ NMR (400 MHz, $CDCl_3$) δ ppm 8.34-8.24 (m, 1H), 7.80 (br d, J=8.4 Hz, 1H), 7.57 (s, 1H), 7.55-7.35 (m, 4H), 3.28-2.65 (m, 4H), 2.32-2.09 (m, 3H), 2.05-1.65 (m, 3H).

Step 3. To a solution of (R)-1-((2'-chloro-5-(trifluoromethyl)-[1,1'-biphenyl]-2-yl)sulfonyl)-4-fluoro-N-((R,Z)-4-(methylsulfonyl)but-3-en-2-yl)azepane-4-carboxamide (200 mg, 0.417 mmol, 1.0 eq) in DMF (3.0 mL, 0.14 M) was added $K_2CO_3$ (288 mg, 2.08 mmol, 5.0 eq) and HATU (476 mg, 1.25 mmol, 3.0 eq). The mixture was stirred at 20 °C for 10 mins before addition of (R,Z)-4-(methylsulfonyl)but-3-en-2-amine (TsOH salt, 174 mg, 0.542 mmol, 1.3 eq). The reaction was stirred at 20 °C for 1 h before being poured into water (20 mL) and extracted with EtOAc (10 mL×3). The combined organic layers were washed with brine (20 mL×3), dried over $Na_2SO_4$, filtered, and concentrated under reduced pressure. The crude product was purified by prep-HPLC (40-70% ACN in 10 mM aq. $NH_4HCO_3$) to give (R)-1-((2'-chloro-5-(trifluoromethyl)-[1,1'-biphenyl]-2-yl)sulfonyl)-4-fluoro-N-((R,Z)-4-(methylsulfonyl)but-3-en-2-yl)azepane-4-carboxamide (154 mg, 0.252 mmol, 62% yield) as a white solid. MS (ESI): mass calculated for $C_{25}H_{27}ClF_4N_2O_5S_2$, 610.1; m/z found, 611.3 $[M+H]^+$. $^1H$ NMR (400 MHz, DMSO-$d_6$) δ ppm 8.35-8.20 (m, 2H), 8.03 (br d, J=8.3 Hz, 1H), 7.73 (s, 1H), 7.63-7.56 (m, 1H), 7.52-7.39 (m, 3H), 6.44 (d, J=11.1 Hz, 1H), 6.33-6.23 (m, 1H), 5.39-5.26 (m, 1H), 3.11 (s, 3H), 3.09-2.83 (m, 4H), 2.12-1.82 (m, 4H), 1.79-1.60 (m, 2H), 1.20 (d, J=6.8 Hz, 3H).

Compound 311 was synthesized in a manner analogous to Compound 310 using methyl(S)-4-fluoroazepane-4-carboxylate in Step 1.

Compound 312 was synthesized in a manner analogous to Compound 310 using 2'-chloro-5-methoxy-[1,1'-biphenyl]-2-sulfonyl chloride in Step 1.

Compound 313 was synthesized in a manner analogous to Compound 312 using methyl(S)-4-fluoroazepane-4-carboxylate in Step 1.

Example 2. General Analytical Methods

The compounds were analyzed by LCMS using the following methods:

Method 1: Shimadzu LC-30AD MSD:LCMS-2020 with a Kinetex EVO C18 5 μm 2.1*30 mm column set to 40 °C with a mobile phase A of 0.04% TFA in water and mobile phase B of 0.02% TFA in ACN with a flow rate of 0. 8 mL/min used the following gradient:

| Time (min) | % B |
|---|---|
| 0.01 | 5 |
| 1.6 | 95 |
| 2.5 | 100 |
| 2.52 | 5 |
| 3 | 5 |

Method 2: Agilent 1200 HPLC MSD: 6120 single quadrupole with a Luna C18, 2.0*50 mm 5 m column set to 40 °C with a mobile phase A of 0.037% TFA in water and mobile phase B of 0.018% TFA in ACN with a flow rate of 1 mL/min used the following gradient:

| Time (min) | % B |
|---|---|
| 0.01 | 5 |
| 0.4 | 5 |
| 3 | 95 |
| 4 | 95 |
| 4.01 | 5 |
| 4.5 | 5 |

Method 3: Agilent 1200 HPLC MSD: 1956A single quadrupole MSD with a Luna C18, 2.0*50 mm 5 μm column set to 40 °C with a mobile phase A of 0.04% TFA in water and mobile phase B of 0.02% TFA in ACN with a flow rate of 1 mL/min used the following gradient:

| Time (min) | % B |
|---|---|
| 0.01 | 5 |
| 0.4 | 5 |
| 3 | 95 |
| 4 | 95 |
| 4.01 | 5 |
| 4.5 | 5 |

Method 4: Agilent 1260 HPLC MSD: 6125B single quadrupole MSD with a Xbridge C18, 2.1*50 mm 5 μm column set to 40 °C with a mobile phase A of 10 nM $NH_4HCO_3$ in water and mobile phase B of ACN with a flow rate of 0.8 mL/min used the following gradient:

| Time (min) | % B |
|---|---|
| 0.01 | 5 |
| 0.4 | 5 |
| 3.4 | 95 |
| 3.85 | 95 |
| 3.86 | 5 |
| 4.5 | 5 |

Method 5: Agilent 1260 HPLC MSD: 6125B single quadrupole MSD with a Luna C18, 2.0*50 mm 5 μm column set to 40 °C with a mobile phase A of 0.04% TFA in water and mobile phase B of 0.02% TFA in ACN with a flow rate of 1 mL/min used the following gradient:

| Time (min) | % B |
|---|---|
| 0.01 | 5 |
| 0.4 | 5 |
| 3 | 95 |
| 4 | 95 |
| 4.01 | 5 |
| 4.5 | 5 |

Method 6: Agilent 1260 HPLC MSD: 6120 single quadrupole MSD with a Xbridge C18, 2.1*50 mm 5 μm column set to 40 °C with a mobile phase A of 10 nM $NH_4HCO_3$ in water and mobile phase B of ACN with a flow rate of 0.8 mL/min used the following gradient:

| Time (min) | % B |
|---|---|
| 0.01 | 5 |
| 3.4 | 95 |
| 3.85 | 95 |
| 3.86 | 5 |
| 4.5 | 5 |

Method 8: 1260 HPLC MSD: 6135B single quadrupole MSD with a Luna C18, 2.0*50 mm 5 m column set to 40 °C with a mobile phase A of 0.04% TFA in water and mobile phase B of 0.02% TFA in ACN with a flow rate of 0.8 mL/min used the following gradient:

| Time (min) | % B |
|---|---|
| 0.01 | 5 |
| 0.4 | 5 |
| 3 | 95 |
| 4 | 95 |
| 4.01 | 5 |
| 4.5 | 5 |

Method 9: Agilent 1200 HPLC MSD: 6130 single quadrupole MSD with a Xbridge C18, 2.1*50 mm 5 μm column set to 40 °C with a mobile phase A of 10 nM $NH_4HCO_3$ in water and mobile phase B of ACN with a flow rate of 0.8 mL/min used the following gradient:

| Time (min) | % B |
|---|---|
| 0.01 | 5 |
| 0.4 | 5 |
| 3.4 | 95 |
| 3.85 | 95 |
| 3.86 | 5 |
| 4.5 | 5 |

Method 11: Shimadzu LC-20AD MSD:LCMS-2020 with a Xbridge C18, 2.1*50 mm 5 μm column set to 40 °C with a mobile phase A of 10 nM $NH_4HCO_3$ in water and mobile phase B of ACN with a flow rate of 1 mL/min used the following gradient:

| Time (min) | % B |
|---|---|
| 0.01 | 5 |
| 3.0 | 95 |
| 3.50 | 95 |
| 3.51 | 5 |
| 4.3 | 5 |

Method 12: Shimadzu LC-20ADXR MSD:LCMS-2020 set to 40 °C with a mobile phase A of 0.04% TFA in water and mobile phase B of 0.02% TFA in ACN with a flow rate of 1 mL/min used the following gradient:

| Time (min) | % B |
|---|---|
| 0.00 | 5 |
| 3.5 | 95 |
| 4.5 | 95 |

Method 13: Agilent 1200 & 6125B with a Ascentis Express C18 100*4.6 mm 2.7 m column set to 40 °C with a mobile phase A of 0.037% TFA in water and mobile phase B of 0.018% TFA in ACN with a flow rate of 1 mL/min used the following gradient:

| Time (min) | % B |
|---|---|
| 0.00 | 60 |
| 0.4 | 60 |
| 6.0 | 70 |
| 8.0 | 100 |
| 8.01 | 60 |
| 10 | 60 |

Method 14: Agilent 1260 HPLC (w 1290 Quad Pump) and 6120B Single Quad MSD. Equipped with a Infinity Lab Poroshell 120 EC-C18, 4.6×150 mm 4 m column using water with 0.1% formic acid as the mobile phase A, and acetonitrile with 0.1% formic acid as the mobile phase B. The gradient was 5-100% with mobile phase B over 10.5 min then held at 100% for 3.35 mins. The flow rate was 1 mL/min.

Method 15: Shimadzu LC-20AD set to 40 °C with a mobile phase A of 0.04% TFA in water and mobile phase B of 0.02% TFA in ACN used the following gradient:

| Time (min) | % B | Flow (mL/min) |
|---|---|---|
| 0.00 | 30 | 0.5 |
| 3.0 | 90 | 0.5 |
| 3.9 | 90 | 0.5 |
| 3.91 | 30 | 1 |
| 4.5 | 30 | 1 |

Method 16: Agilent 1200+6110MS with HALO 90A C18 5 μm 3*30 mm column set to 40 °C with a mobile phase A of 0.04% TFA in water and mobile phase B of 0.02% TFA in ACN used the following gradient:

| Time (min) | % B | Flow (mL/min) |
|---|---|---|
| 0.00 | 5 | 1.5 |
| 0.70 | 95 | 1.5 |
| 1.16 | 95 | 1.5 |
| 1.50 | 5 | 1.5 |

TABLE 3

Representative Analytical Data for Compounds of the Disclosure.

| Cmpd. No. | LCMS Method | LCMS retention time (min) | LCMS M + H | $^1$H NMR |
|---|---|---|---|---|
| 1 | Method 1 | 1.735 | 559.1 | $^1$H NMR (400 MHz, DMSO-$d_6$) δ ppm 8.36 (br d, J = 7.9 Hz, 1H), 8.04 (d, J = 8.5 Hz, 1H), 7.70 (dd, J = 8.6, 2.2 Hz, 1H), 7.47 (d, J = 2.3 Hz, 1H), 7.34 (t, J = 8.0 Hz, 1H), 6.93-7.03 (m, 3H), 6.45 (d, J = 11.2 Hz, 1H), 6.26 (dd, J = 11.1, 9.6 Hz, 1H), 5.25-5.41 (m, 1H), 3.78 (s, 3H), 3.12 (s, 5H), 2.52-2.56 (m, 2H), 1.58-1.84 (m, 4H), 1.20 (d, J = 6.78 Hz, 3H) |
| 2 | Method 1 | 1.728 | 529.1 | $^1$H NMR (400 MHz, DMSO-$d_6$) δ ppm 8.34 (br d, J = 7.8 Hz, 1H), 8.04 (d, J = 8.7 Hz, 1H), 7.71 (dd, J = 8.6, 2.2 Hz, 1H), 7.36-7.47 (m, 6H), 6.45 (d, J = 11.2 Hz, 1H), 6.21-6.31 (m, 1H), 5.23-5.44 (m, 1H), 3.30 (br s, 2H), 3.11 (s, 5H), 1.59-1.78 (m, 4H), 1.19 (d, J = 6.9 Hz, 3H) |
| 3 | Method 14 | 11.36 | 563 | $^1$H NMR (400 MHz, DMSO-$d_6$) δ ppm 8.30 (dd, J = 7.8, 2.4 Hz, 1H), 7.97 (d, J = 8.6 Hz, 1H), 7.67 (dd, J = 8.6, 2.3 Hz, 1H), 7.50-7.36 (m, 4H), 7.28 (dt, J = 7.3, 1.6 Hz, 1H), 6.38 (dd, J = 11.2, 1.0 Hz, 1H), 6.20 (dd, J = 11.2, 9.5 Hz, 1H), 5.27 (q, J = 7.7 Hz, 1H), 3.08 (d, J = 14.5 Hz, 2H), 3.04 (s, 3H), 2.53 (m, 2H), 1.78-1.56 (m, 4H), 1.13 (d, J = 6.8 Hz, 3H) |

TABLE 3-continued

| Cmpd. No. | LCMS Method | LCMS retention time (min) | LCMS M + H | $^1$H NMR |
|---|---|---|---|---|
| Representative Analytical Data for Compounds of the Disclosure. | | | | |
| 4 | Method 1 | 1.621 | 525.1 | $^1$H NMR (400 MHz, DMSO-$d_6$) δ ppm 8.32 (dd, J = 2.2, 7.5 Hz, 1H), 7.97 (d, J = 9.2 Hz, 1H), 7.46-7.32 (m, 5H), 7.14 (dd, J = 2.6, 8.8 Hz, 1H), 6.84 (d, J = 3.1 Hz, 1H), 6.44 (d, J = 11.4 Hz, 1H), 6.26 (dd, J = 9.4, 11.2 Hz, 1H), 5.39-5.27 (m, 1H), 3.86 (s, 3H), 3.11 (s, 3H), 3.05 (br d, J = 12.7 Hz, 2H), 2.47-2.36 (m, 2H), 1.81-1.56 (m, 4H), 1.19 (d, J = 7.0 Hz, 3H) |
| 5 | Method 1 | 1.625 | 555.1 | $^1$H NMR (400 MHz, DMSO-$d_6$) δ ppm 8.33 (br d, J = 7.9 Hz, 1H), 7.96 (d, J = 8.9 Hz, 1H), 7.30 (t, J = 7.9 Hz, 1H), 7.13 (dd, J = 2.7, 9.0 Hz, 1H), 6.98-6.91 (m, 3H), 6.86 (d, J = 2.6 Hz, 1H), 6.44 (d, J = 11.2 Hz, 1H), 6.29-6.21 (m, 1H), 5.38-5.26 (m, 1H), 3.86 (s, 3H), 3.77 (s, 3H), 3.11 (s, 3H), 3.07 (br d, J = 12.7 Hz, 2H), 2.46-2.40 (m, 2H), 1.77-1.54 (m, 4H), 1.18 (d, J = 6.9 Hz, 3H) |
| 6 | Method 15 | 2.844 | | $^1$H NMR (400 MHz, DMSO-$d_6$) δ ppm 8.37 (br d, J = 6.0 Hz, 1H), 8.04 (d, J = 8.6 Hz, 1H), 7.75 (dd, J = 8.6, 2.2 Hz, 1H), 7.55 (d, J = 7.9 Hz, 1H), 7.47-7.50 (m, 1H), 7.42-7.46 (m, 1H), 7.39 (d, J = 4.3 Hz, 2H), 6.45 (d, J = 11.3 Hz, 1H), 6.27 (dd, J = 11.0, 9.5 Hz, 1H), 5.29-5.40 (m, 1H), 3.12-3.19 (m, 2H), 3.10 (s, 3H), 2.58-2.76 (m, 2H), 1.64-1.99 (m, 4H), 1.20 (d, J = 6.7 Hz, 3H) |
| 7 | Method 1 | 1.692 | 559 | $^1$H NMR (400 MHz, DMSO-$d_6$) δ ppm 8.36 (br d, J = 5.9 Hz, 1H), 7.96 (d, J = 8.9 Hz, 1H), 7.39-7.52 (m, 3H), 7.32 (d, J = 7.1 Hz, 1H), 7.17 (dd, J = 8.9, 2.6 Hz, 1H), 6.90 (d, J = 2.6 Hz, 1H), 6.45 (d, J = 11.2 Hz, 1H), 6.21-6.31 (m, 1H), 5.25-5.41 (m, 1H), 3.87 (s, 3H), 3.11 (s, 5H), 2.52-2.58 (m, 2H), 1.61-1.88 (m, 4H), 1.19 (d, J = 6.9 Hz, 3H) |
| 8 | Method 13 | 2.28 | 554 | $^1$H NMR (400 MHz, DMSO-$d_6$) δ ppm 8.37 (br d, J = 6.3 Hz, 1H), 8.04 (d, J = 8.5 Hz, 1H), 7.86-7.93 (m, 2H), 7.71-7.79 (m, 2H), 7.60-7.68 (m, 1H), 7.57 (d, J = 2.1 Hz, 1H), 6.44 (d, J = 10.7 Hz, 1H), 6.22-6.31 (m, 1H), 5.33 (br d, J = 9.0 Hz, 1H), 3.11 (s, 5H), 2.58 (br s, 2H), 1.64-1.84 (m, 4H), 1.19 (d, J = 6.8 Hz, 3H) |
| 9 | Method 2 | 2.535 | 543.2 | $^1$H NMR (400 MHz, DMSO-$d_6$) δ ppm 8.33 (br d, J = 5.9 Hz, 1H), 8.10 (dd, J = 5.7, 8.9 Hz, 1H), 7.47 (dt, J = 2.8, 8.5 Hz, 1H), 7.37-7.24 (m, 2H), 7.02-6.92 (m, 3H), 6.45 (d, J = 11.1 Hz, 1H), 6.26 (dd, J = 9.5, 11.1 Hz, 1H), 5.39-5.27 (m, 1H), 3.78 (s, 3H), 3.11 (s, 5H), 2.59-2.51 (m, 2H), 1.82-1.57 (m, 4H), 1.19 (d, J = 6.8 Hz, 3H) |
| 10 | Method 2 | 2.739 | 573.2 | $^1$H NMR (400 MHz, DMSO-$d_6$) δ ppm 8.36 (dd, J = 7.8, 1.6 Hz, 1H), 8.03 (d, J = 8.6 Hz, 1H), 7.70 (dd, J = 8.6, 2.2 Hz, 1H), 7.46 (d, J = 2.2 Hz, 1H), 7.32 (t, J = 7.9 Hz, 1H), 6.90-7.00 (m, 3H), 6.45 (d, J = 11.1 Hz, 1H), 6.26 (dd, J = 10.9, 9.6 Hz, 1H), 5.25-5.41 (m, 1H), 4.05 (q, J = 7.0 Hz, 2H), 3.34-3.40 (m, 1H), 3.25-3.32 (m, 1H), 3.11 (s, 5H), 1.56-1.87 (m, 4H), 1.33 (t, J = 6.9 Hz, 3H), 1.19 (d, J = 6.7 Hz, 3H) |
| 11 | Method 3 | 2.519 | 559.1 | $^1$H NMR (400 MHz, DMSO-$d_6$) δ ppm 8.39 (br d, J = 6.3 Hz, 1H), 7.96 (d, J = 8.9 Hz, 1H), 7.52 (d, J = 8.0 Hz, 1H), 7.45-7.34 (m, 3H), 7.19 (dd, J = 2.6, 8.9 Hz, 1H), 6.85 (d, J = 2.5 Hz, 1H), 6.45 (d, J = 11.2 Hz, 1H), 6.32-6.24 (m, 1H), 5.40-5.30 (m, 1H), 3.86 (s, 3H), 3.11 (s, 5H), 2.66 (br d, J = 12.0 Hz, 2H), 1.95-1.67 (m, 4H), 1.20 (d, J = 6.8 Hz, 3H) |
| 12 | Method 3 | 2.539 | 539.2 | $^1$H NMR (400 MHz, DMSO-$d_6$) δ ppm 8.38 (dd, J = 2.1, 7.8 Hz, 1H), 7.96 (d, J = 8.9 Hz, 1H), 7.31-7.10 (m, 5H), 6.77 (d, J = 2.6 Hz, 1H), 6.45 (d, J = 11.2 Hz, 1H), 6.32-6.23 (m, 1H), 5.41-5.29 (m, 1H), 3.85 (s, 3H), 3.11 (s, 3H), 3.10-2.98 (m, 2H), 2.56 (br d, J = 2.6 Hz, 2H), 2.01 (s, 3H), 1.91-1.62 (m, 4H), 1.20 (d, J = 6.9 Hz, 3H) |
| 13 | Method 2 | 2.958 | 601.2 | $^1$H NMR (400 MHz, DMSO-$d_6$) δ ppm 8.34 (dd, J = 7.8, 2.0 Hz, 1H), 8.03 (d, J = 8.6 Hz, 1H), 7.69 (dd, J = 8.6, 2.3 Hz, 1H), 7.46 (d, J = 2.2 Hz, 1H), 7.31 (t, J = 7.9 Hz, 1H), 6.90-7.00 (m, 3H), 6.45 (dd, J = 11.1, 0.7 Hz, 1H), 6.27 (dd, J = 11.1, 9.4 Hz, 1H), |

TABLE 3-continued

Representative Analytical Data for Compounds of the Disclosure.

| Cmpd. No. | LCMS Method | LCMS retention time (min) | LCMS M + H | $^1$H NMR |
|---|---|---|---|---|
| | | | | 5.23-5.42 (m, 1H), 3.99 (t, J = 6.5 Hz, 2H), 3.11 (s, 5H), 2.55 (br s, 2H), 1.57-1.86 (m, 6H), 1.43 (dq, J = 14.9, 7.4 Hz, 2H), 1.19 (d, J = 6.8 Hz, 3H), 0.93 (t, J = 7.4 Hz, 3H) |
| 14 | Method 2 | 2.854 | 587.2 | $^1$H NMR (400 MHz, DMSO-$d_6$) δ ppm 8.34 (dd, J = 7.9, 2.0 Hz, 1H), 8.03 (d, J = 8.6 Hz, 1H), 7.70 (dd, J = 8.6, 2.2 Hz, 1H), 7.46 (d, J = 2.4 Hz, 1H), 7.32 (t, J = 7.8 Hz, 1H), 6.89-7.00 (m, 3H), 6.45 (d, J = 11.2 Hz, 1H), 6.26 (dd, J = 11.0, 9.5 Hz, 1H), 5.25-5.40 (m, 1H), 3.95 (t, J = 6.5 Hz, 2H), 3.05-3.31 (m, 6H), 1.54-1.88 (m, 7H), 1.19 (d, J = 6.8 Hz, 3H), 0.97 (t, J = 7.5 Hz, 3H) |
| 15 | Method 1 | 1.81 | 585.1 | $^1$H NMR (400 MHz, DMSO-$d_6$) δ ppm 8.35 (dd, J = 7.6, 1.9 Hz, 1H), 8.05 (d, J = 8.6 Hz, 1H), 7.70 (dd, J = 8.6, 2.2 Hz, 1H), 7.47 (d, J = 2.1 Hz, 1H), 7.35 (t, J = 7.9 Hz, 1H), 7.05-7.15 (m, 2H), 6.98 (d, J = 7.5 Hz, 1H), 6.45 (d, J = 11.1 Hz, 1H), 6.26 (dd, J = 11.0, 9.5 Hz, 1H), 5.33 (sxt, J = 7.6 Hz, 1H), 3.86 (tt, J = 5.9, 2.9 Hz, 1H), 3.06-3.17 (m, 5H), 2.45 (br s, 2H), 1.55-1.84 (m, 4H), 1.20 (d, J = 6.9 Hz, 3H), 0.61-0.84 (m, 4H) |
| 16 | Method 1 | 1.744 | 593.1 | $^1$H NMR (400 MHz, DMSO-$d_6$) δ ppm 8.37 (br d, J = 7.2 Hz, 1H), 8.03 (d, J = 8.5 Hz, 1H), 7.75 (dd, J = 8.6, 2.2 Hz, 1H), 7.38-7.51 (m, 2H), 6.95-7.08 (m, 2H), 6.45 (d, J = 11.1 Hz, 1H), 6.22-6.33 (m, 1H), 5.26-5.43 (m, 1H), 3.76 (s, 3H), 3.20 (br d, J = 11.8 Hz, 2H), 3.11 (s, 3H), 2.57-2.80 (m, 2H), 1.65-2.05 (m, 4H), 1.20 (d, J = 6.9 Hz, 3H) |
| 17 | Method 1 | 1.773 | 587.2 | $^1$H NMR (400 MHz, DMSO-$d_6$) δ ppm 8.36 (dd, J = 7.7, 1.7 Hz, 1H), 8.04 (d, J = 8.6 Hz, 1H), 7.71 (dd, J = 8.6, 2.2 Hz, 1H), 7.24-7.48 (m, 5H), 6.45 (d, J = 11.1 Hz, 1H), 6.21-6.31 (m, 1H), 5.23-5.45 (m, 1H), 4.51 (s, 2H), 3.50 (q, J = 6.9 Hz, 2H), 3.34 (s, 3H), 3.12 (s, 4H), 1.56-1.79 (m, 4H), 1.11-1.25 (m, 6H) |
| 18 | Method 1 | 1.715 | 597 | $^1$H NMR (400 MHz, DMSO-$d_6$) δ ppm 8.38 (dd, J = 7.8, 1.9 Hz, 1H), 8.27 (d, J = 8.2 Hz, 1H), 8.06 (dd, J = 8.4, 1.5 Hz, 1H), 7.74 (d, J = 1.4 Hz, 1H), 7.58 (d, J = 7.7 Hz, 1H), 7.48 (td, J = 5.4, 3.0 Hz, 1H), 7.39-7.45 (m, 2H), 6.45 (d, J = 11.1 Hz, 1H), 6.28 (dd, J = 11.1, 9.5 Hz, 1H), 5.28-5.41 (m, 1H), 3.15-3.24 (m, 2H), 3.11 (s, 3H), 2.78 (td, J = 12.6, 2.9 Hz, 1H), 2.62-2.68 (m, 1H), 1.81-2.02 (m, 2H), 1.67-1.80 (m, 2H), 1.21 (d, J = 6.9 Hz, 3H) |
| 19 | Method 14 | 9.798 | 525 | $^1$H NMR (400 MHz, DMSO-$d_6$) δ ppm 8.35 (dd, J = 7.9, 2.5 Hz, 1H), 8.04 (dd, J = 8.1, 1.4 Hz, 1H), 7.73 (td, J = 7.5, 1.4 Hz, 1H), 7.63 (td, J = 7.7, 1.4 Hz, 1H), 7.40 (dd, J = 7.6, 1.4 Hz, 1H), 7.33 (t, J = 8.1 Hz, 1H), 7.04-6.86 (m, 3H), 6.45 (d, J = 11.2 Hz, 1H), 6.27 (dd, J = 11.2, 9.4 Hz, 1H), 5.42-5.24 (m, 1H), 3.78 (s, 3H), 3.12 (s, 5H), 1.83-1.56 (m, 4H), 1.20 (d, J = 6.9 Hz, 3H) |
| 20 | Method 1 | 1.727 | 529.1 | $^1$H NMR (400 MHz, DMSO-$d_6$) δ ppm 8.34 (br d, J = 6.4 Hz, 1H), 8.04 (d, J = 8.5 Hz, 1H), 7.71 (dd, J = 8.6, 2.2 Hz, 1H), 7.35-7.49 (m, 6H), 6.45 (d, J = 11.2 Hz, 1H), 6.21-6.33 (m, 1H), 5.23-5.44 (m, 1H), 3.27-3.32 (m, 2H), 3.11 (s, 5H), 1.59-1.80 (m, 4H), 1.19 (d, J = 6.8 Hz, 3H) |
| 21 | Method 1 | 1.62 | 525.1 | $^1$H NMR (400 MHz, DMSO-$d_6$) δ ppm 8.33 (dd, J = 1.7, 7.6 Hz, 1H), 7.97 (d, J = 8.9 Hz, 1H), 7.44-7.34 (m, 5H), 7.14 (dd, J = 2.7, 9.0 Hz, 1H), 6.84 (d, J = 2.6 Hz, 1H), 6.45 (d, J = 11.3 Hz, 1H), 6.26 (dd, J = 9.6, 11.1 Hz, 1H), 5.40-5.28 (m, 1H), 3.86 (s, 3H), 3.11 (s, 3H), 3.05 (br d, J = 12.5 Hz, 2H), 2.46-2.38 (m, 2H), 1.79-1.56 (m, 4H), 1.19 (d, J = 6.9 Hz, 3H) |
| 22 | Method 1 | 1.697 | 559 | $^1$H NMR (400 MHz, DMSO-$d_6$) δ ppm 8.36 (br d, J = 7.8 Hz, 1H), 7.96 (d, J = 8.9 Hz, 1H), 7.39-7.50 (m, 3H), 7.32 (d, J = 7.3 Hz, 1H), 7.17 (dd, J = 8.9, 2.6 Hz, 1H), 6.90 (d, J = 2.6 Hz, 1H), 6.45 (d, J = 11.2 Hz, 1H), 6.22-6.33 (m, 1H), 5.27-5.41 (m, 1H), 3.87 (s, 3H), 3.06-3.17 (m, 5H), 2.55 (br s, 2H), 1.60-1.87 (m, 4H), 1.19 (d, J = 6.9 Hz, 3H) |

TABLE 3-continued

Representative Analytical Data for Compounds of the Disclosure.

| Cmpd. No. | LCMS Method | LCMS retention time (min) | LCMS M + H | $^1$H NMR |
|---|---|---|---|---|
| 23 | Method 1 | 1.736 | 563 | $^1$H NMR (400 MHz, DMSO-$d_6$) δ ppm 8.38 (br d, J = 6.8 Hz, 1H), 8.04 (d, J = 8.7 Hz, 1H), 7.75 (dd, J = 2.0, 8.5 Hz, 1H), 7.55 (d, J = 7.8 Hz, 1H), 7.51-7.42 (m, 2H), 7.40 (d, J = 4.1 Hz, 2H), 6.45 (d, J = 11.2 Hz, 1H), 6.31-6.23 (m, 1H), 5.35 (br d, J = 6.9 Hz, 1H), 3.11 (s, 5H), 2.76-2.58 (m, 2H), 1.72 (br d, J = 13.6 Hz, 4H), 1.20 (d, J = 6.9 Hz, 3H) |
| 24 | Method 1 | 1.645 | 539.2 | $^1$H NMR (400 MHz, DMSO-$d_6$) δ ppm 8.35 (br d, J = 5.9 Hz, 1H), 7.96 (d, J = 8.9 Hz, 1H), 7.32-7.08 (m, 5H), 6.77 (d, J = 2.8 Hz, 1H), 6.45 (d, J = 11.3 Hz, 1H), 6.33-6.22 (m, 1H), 5.44-5.26 (m, 1H), 3.85 (s, 3H), 3.11 (s, 3H), 3.03 (br d, J = 12.4 Hz, 2H), 2.61-2.53 (m, 2H), 2.02 (s, 3H), 1.94-1.73 (m, 2H), 1.68 (br d, J = 11.0 Hz, 2H), 1.20 (d, J = 6.8 Hz, 3H) |
| 25 | Method 1 | 1.635 | 559.1 | $^1$H NMR (400 MHz, DMSO-$d_6$) δ ppm 8.37 (br d, J = 7.9 Hz, 1H), 7.97 (d, J = 8.9 Hz, 1H), 7.58-7.48 (m, 1H), 7.46-7.31 (m, 3H), 7.19 (dd, J = 2.7, 8.9 Hz, 1H), 6.85 (d, J = 2.6 Hz, 1H), 6.45 (d, J = 11.1 Hz, 1H), 6.28 (dd, J = 9.5, 11.0 Hz, 1H), 5.43-5.27 (m, 1H), 3.86 (s, 3H), 3.11 (s, 5H), 2.60-2.52 (m, 2H), 2.01-1.79 (m, 2H), 1.78-1.68 (m, 2H), 1.21 (d, J = 6.9 Hz, 3H) |
| 26 | Method 1 | 1.655 | 577.1 | $^1$H NMR (400 MHz, DMSO-$d_6$) δ ppm 8.28-8.43 (m, 1H), 7.96 (d, J = 8.9 Hz, 1H), 7.32-7.51 (m, 2H), 7.17-7.28 (m, 2H), 6.91 (d, J = 2.8 Hz, 1H), 6.45 (d, J = 11.3 Hz, 1H), 6.18-6.34 (m, 1H), 5.35 (sxt, J = 7.5 Hz, 1H), 3.86 (s, 3H), 3.12-3.25 (m, 2H), 3.11 (s, 3H), 2.53-2.73 (m, 2H), 1.64-2.03 (m, 4H), 1.18-1.25 (m, 3H) |
| 27 | Method 1 | 1.677 | 577.2 | $^1$H NMR (400 MHz, DMSO-$d_6$) δ ppm 8.38 (br d, J = 6.5 Hz, 1H), 7.96 (d, J = 8.9 Hz, 1H), 7.53 (dd, J = 8.9, 2.5 Hz, 1H), 7.41 (dd, J = 8.5, 6.3 Hz, 1H), 7.15-7.30 (m, 2H), 6.88 (d, J = 2.6 Hz, 1H), 6.46 (d, J = 11.3 Hz, 1H), 6.29 (dd, J = 11.1, 9.5 Hz, 1H), 5.26-5.42 (m, 1H), 3.87 (s, 3H), 3.12-3.22 (m, 2H), 3.12 (s, 3H), 2.54-2.73 (m, 2H), 1.59-2.03 (m, 4H), 1.21 (d, J = 6.9 Hz, 3H) |
| 28 | Method 1 | 1.661 | 576.9 | $^1$H NMR (400 MHz, DMSO-$d_6$) δ ppm 8.37 (dd, J = 7.8, 2.1 Hz, 1H), 7.96 (d, J = 8.9 Hz, 1H), 7.56 (dd, J = 8.8, 5.1 Hz, 1H), 7.19-7.35 (m, 3H), 6.90 (d, J = 2.6 Hz, 1H), 6.45 (d, J = 11.3 Hz, 1H), 6.28 (dd, J = 11.1, 9.5 Hz, 1H), 5.30-5.40 (m, 1H), 3.86 (s, 3H), 3.14-3.22 (m, 2H), 3.11 (s, 3H), 2.57-2.74 (m, 2H), 1.70-2.00 (m, 4H), 1.21 (d, J = 6.9 Hz, 3H) |
| 29 | Method 1 | 1.709 | 593.1 | $^1$H NMR (400 MHz, DMSO-$d_6$) δ ppm 8.15 (s, 1H), 7.50 (br d, J = 7.3 Hz, 1H), 7.46-7.41 (m, 1H), 7.40-7.30 (m, 2H), 6.81 (s, 1H), 6.41 (br s, 1H), 6.29 (d, J = 11.0 Hz, 1H), 6.07 (ddd, J = 3.4, 9.5, 11.0 Hz, 1H), 5.41-5.27 (m, 1H), 3.95 (s, 3H), 3.29 (br s, 1H), 3.19 (s, 3H), 3.16-3.09 (m, 1H), 2.92-2.54 (m, 2H), 2.23-1.94 (m, 2H), 1.76-1.59 (m, 2H), 1.38 (d, J = 6.9 Hz, 3H) |
| 30 | Method 1 | 1.633 | 577.2 | $^1$H NMR (400 MHz, DMSO-$d_6$) δ ppm 8.38 (br d, J = 7.4 Hz, 1H), 7.98 (d, J = 8.9 Hz, 1H), 7.44-7.51 (m, 1H), 7.40 (d, J = 7.8 Hz, 1H), 7.20-7.31 (m, 2H), 6.96 (d, J = 2.6 Hz, 1H), 6.45 (d, J = 11.3 Hz, 1H), 6.24-6.32 (m, 1H), 5.35 (br d, J = 7.7 Hz, 1H), 3.87 (s, 3H), 3.11 (s, 3H), 2.63-2.71 (m, 1H), 1.79-2.05 (m, 4H), 1.73 (s, 1H), 1.23 (s, 3H) |
| 31 | Method 1 | 1.672 | 547.1 | $^1$H NMR (400 MHz, DMSO-$d_6$) δ ppm 8.36 (br d, J = 5.9 Hz, 1H), 8.11 (dd, J = 8.9, 5.7 Hz, 1H), 7.28-7.60 (m, 6H), 6.45 (d, J = 11.3 Hz, 1H), 6.28 (dd, J = 11.1, 9.5 Hz, 1H), 5.26-5.44 (m, 1H), 3.04-3.19 (m, 5H), 2.67-2.77 (m, 1H), 2.55-2.64 (m, 1H), 1.68-2.05 (m, 4H), 1.20 (d, J = 6.9 Hz, 3H) |
| 32 | Method 1 | 1.712 | 593 | $^1$H NMR (400 MHz, DMSO-$d_6$) δ ppm 8.35 (br d, J = 5.9 Hz, 1H), 7.99 (s, 1H), 7.50-7.60 (m, 1H), 7.34-7.47 (m, 3H), 7.10 (s, 1H), 6.45 (d, J = 11.3 Hz, 1H), 6.27 (dd, J = 11.1, 9.5 Hz, 1H), 5.24-5.45 (m, 1H), 3.93 (s, 3H), 3.10 (s, 5H), 2.64-2.74 (m, 2H), 1.66-1.97 (m, 4H), 1.20 (d, J = 6.9 Hz, 3H) |

TABLE 3-continued

| Cmpd. No. | LCMS Method | LCMS retention time (min) | LCMS M + H | $^1$H NMR |
|---|---|---|---|---|
| | | | | Representative Analytical Data for Compounds of the Disclosure. |
| 33 | Method 1 | 1.655 | 597 | $^1$H NMR (400 MHz, DMSO-$d_6$) δ ppm 8.35-8.41 (m, 1H), 8.26 (d, J = 8.4 Hz, 1H), 8.06 (dd, J = 8.4, 1.4 Hz, 1H), 7.75 (d, J = 1.2 Hz, 1H), 7.58 (d, J = 7.7 Hz, 1H), 7.45-7.51 (m, 1H), 7.40-7.45 (m, 2H), 6.45 (d, J = 11.3 Hz, 1H), 6.28 (dd, J = 11.1, 9.4 Hz, 1H), 5.28-5.41 (m, 1H), 3.13-3.24 (m, 2H), 3.11 (s, 3H), 2.78 (td, J = 12.6, 2.5 Hz, 1H), 2.58-2.65 (m, 1H), 1.79-2.02 (m, 2H), 1.65-1.78 (m, 2H), 1.20 (d, J = 6.7 Hz, 3H) |
| 34 | Method 1 | 1.674 | 613 | $^1$H NMR (400 MHz, DMSO-$d_6$) δ ppm 8.38 (br d, J = 6.1 Hz, 1H), 8.18 (d, J = 8.7 Hz, 1H), 7.68 (br d, J = 7.6 Hz, 1H), 7.57 (d, J = 7.7 Hz, 1H), 7.44-7.49 (m, 1H), 7.35-7.43 (m, 3H), 6.45 (d, J = 11.3 Hz, 1H), 6.23-6.32 (m, 1H), 5.29-5.41 (m, 1H), 3.04-3.23 (m, 5H), 2.69-2.84 (m, 1H), 2.55-2.64 (m, 1H), 1.64-2.05 (m, 4H), 1.20 (d, J = 6.9 Hz, 3H) |
| 35 | Method 1 | 1.545 | 554.1 | 1H NMR (400 MHz, DMSO-$d_6$) δ ppm 8.34-8.41 (m, 1H), 8.12-8.22 (m, 2H), 7.94-7.97 (m, 1H), 7.55-7.59 (m, 1H), 7.37-7.50 (m, 3H), 6.42-6.47 (m, 1H), 6.23-6.31 (m, 1H), 5.29-5.38 (m, 1H), 3.13-3.19 (m, 2H), 3.10 (s, 3H), 2.72-2.83 (m, 2H), 2.62-2.68 (m, 2H), 1.68-1.78 (m, 2H), 1.20 (d, J = 6.7 Hz, 3H) |
| 36 | Method 1 | 1.678 | 545 | $^1$H NMR (400 MHz, DMSO-$d_6$) δ ppm 8.56 (br s, 1H), 8.04 (d, J = 8.5 Hz, 1H), 7.70 (dd, J = 8.5, 2.3 Hz, 1H), 7.46 (d, J = 2.1 Hz, 1H), 7.30-7.38 (m, 1H), 6.94-7.02 (m, 3H), 6.64-6.73 (m, 1H), 6.55-6.62 (m, 1H), 3.91 (br s, 2H), 3.78 (s, 3H), 3.13 (br d, J = 13.2 Hz, 2H), 2.99 (s, 3H), 2.54 (br s, 2H), 1.65-1.86 (m, 4H) |
| 37 | Method 1 | 1.67 | 515.1 | $^1$H NMR (400 MHz, DMSO-$d_6$) δ ppm 8.55 (br s, 1H), 7.99-8.11 (m, 1H), 7.71 (dd, J = 8.6, 2.2 Hz, 1H), 7.33-7.52 (m, 6H), 6.65-6.73 (m, 1H), 6.54-6.63 (m, 1H), 3.92 (br s, 2H), 3.30 (br s, 2H), 3.10 (br d, J = 13.2 Hz, 2H), 2.99 (s, 3H), 1.62-1.85 (m, 4H) |
| 38 | Method 1 | 1.554 | 511.1 | $^1$H NMR (400 MHz, DMSO-$d_6$) δ ppm 8.54 (br t, J = 5.3 Hz, 1H), 7.98 (d, J = 8.8 Hz, 1H), 7.43-7.36 (m, 5H), 7.15 (dd, J = 2.6, 8.8 Hz, 1H), 6.85 (d, J = 2.6 Hz, 1H), 6.74-6.65 (m, 1H), 6.62-6.54 (m, 1H), 3.91 (br t, J = 4.4 Hz, 2H), 3.86 (s, 3H), 3.07 (br d, J = 12.7 Hz, 2H), 2.99 (s, 3H), 2.47-2.41 (m, 2H), 1.79-1.62 (m, 4H) |
| 39 | Method 1 | 1.568 | 541.1 | $^1$H NMR (400 MHz, DMSO-$d_6$) δ ppm 8.54 (br s, 1H), 7.97 (d, J = 8.9 Hz, 1H), 7.35-7.28 (m, 1H), 7.14 (dd, J = 2.6, 8.9 Hz, 1H), 6.98-6.92 (m, 3H), 6.87 (d, J = 2.6 Hz, 1H), 6.73-6.65 (m, 1H), 6.62-6.55 (m, 1H), 3.92 (br s, 2H), 3.86 (s, 3H), 3.78 (s, 3H), 3.10 (br d, J = 12.9 Hz, 2H), 2.99 (s, 3H), 2.45 (br s, 2H), 1.71 (br d, J = 17.6 Hz, 4H) |
| 40 | Method 14 | 10.593 | 549 | $^1$H NMR (400 MHz, DMSO-$d_6$) δ ppm 8.59 (d, J = 2.8 Hz, 1H), 8.05 (d, J = 8.6 Hz, 1H), 7.76 (dd, J = 8.6, 2.3 Hz, 1H), 7.60-7.54 (m, 1H), 7.53-7.38 (m, 4H), 6.71 (dt, J = 15.3, 4.2 Hz, 1H), 6.60 (dt, J = 15.2, 1.7 Hz, 1H), 3.98-3.91 (m, 2H), 3.18 (d, J = 12.8 Hz, 2H), 3.00 (s, 3H), 2.78-2.59 (m, 2H), 2.00-1.78 (m, 4H) |
| 41 | Method 1 | 1.628 | 545 | $^1$H NMR (400 MHz, DMSO-$d_6$) δ ppm 8.57 (br s, 1H), 7.97 (d, J = 8.9 Hz, 1H), 7.39-7.52 (m, 3H), 7.33 (d, J = 6.9 Hz, 1H), 7.17 (dd, J = 8.9, 2.6 Hz, 1H), 6.91 (d, J = 2.6 Hz, 1H), 6.65-6.76 (m, 1H), 6.55-6.64 (m, 1H), 3.92 (br s, 2H), 3.87 (s, 3H), 3.13 (br d, J = 12.9 Hz, 2H), 2.99 (s, 3H), 2.52-2.58 (m, 2H), 1.68-1.89 (m, 4H) |
| 42 | Method 1 | 1.608 | 525.1 | $^1$H NMR (400 MHz, DMSO-$d_6$) δ ppm 8.56 (br s, 1H), 7.92 (d, J = 8.2 Hz, 1H), 7.42 (d, J = 8.2 Hz, 1H), 7.32 (t, J = 8.0 Hz, 1H), 7.21 (s, 1H), 6.88-7.02 (m, 3H), 6.64-6.76 (m, 1H), 6.54-6.62 (m, 1H), 3.91 (br s, 2H), 3.77 (s, 3H), 3.31 (br s, 2H), 3.12 (br d, J = 12.7 Hz, 2H), 2.99 (s, 3H), 2.41 (s, 3H), 1.59-1.86 (m, 4H) |
| 43 | Method 3 | 2.42 | 545.1 | $^1$H NMR (400 MHz, DMSO-$d_6$) δ ppm 8.62-8.57 (m, 1H), 7.97 (d, J = 8.9 Hz, 1H), 7.52 (d, J = 7.4 Hz, 1H), 7.45-7.35 (m, 3H), 7.19 (dd, J = 2.6, 8.9 |

TABLE 3-continued

Representative Analytical Data for Compounds of the Disclosure.

| Cmpd. No. | LCMS Method | LCMS retention time (min) | LCMS M + H | $^1$H NMR |
|---|---|---|---|---|
| | | | | Hz, 1H), 6.85 (d, J = 2.6 Hz, 1H), 6.74-6.66 (m, 1H), 6.63-6.56 (m, 1H), 3.93 (br t, J = 4.1 Hz, 2H), 3.86 (s, 3H), 3.13 (br d, J = 12.3 Hz, 2H), 3.00 (s, 3H), 2.70-2.60 (m, 2H), 1.98-1.77 (m, 4H) |
| 44 | Method 1 | 1.596 | 525.1 | $^1$H NMR (400 MHz, DMSO-$d_6$) δ ppm 8.62-8.55 (m, 1H), 7.97 (d, J = 8.8 Hz, 1H), 7.29-7.23 (m, 2H), 7.20 (dt, J = 1.9, 7.1 Hz, 1H), 7.17-7.11 (m, 2H), 6.77 (d, J = 2.9 Hz, 1H), 6.74-6.66 (m, 1H), 6.62-6.55 (m, 1H), 3.93 (br t, J = 4.1 Hz, 2H), 3.85 (s, 3H), 3.15-3.01 (m, 2H), 2.99 (s, 3H), 2.61-2.53 (m, 2H), 2.02 (s, 3H), 1.96-1.73 (m, 4H) |
| 45 | Method 1 | 1.721 | 549 | $^1$H NMR (400 MHz, DMSO-$d_6$) δ ppm 8.59 (br s, 1H), 8.04 (d, J = 8.6 Hz, 1H), 7.73 (dd, J = 8.6, 2.2 Hz, 1H), 7.43-7.54 (m, 4H), 7.35 (d, J = 7.3 Hz, 1H), 6.66-6.74 (m, 1H), 6.56-6.62 (m, 1H), 3.92 (br s, 2H), 3.16 (br d, J = 12.8 Hz, 2H), 2.99 (s, 3H), 2.57 (br d, J = 12.6 Hz, 2H), 1.72-1.90 (m, 4H) |
| 46 | Method 1 | 1.741 | 553.1 | $^1$H NMR (400 MHz, DMSO-$d_6$) δ ppm 8.57 (br s, 1H), 8.03 (d, J = 8.5 Hz, 1H), 7.93-7.98 (m, 1H), 7.72 (dd, J = 8.5, 2.2 Hz, 1H), 7.27-7.52 (m, 5H), 6.65-6.75 (m, 1H), 6.54-6.63 (m, 1H), 3.92 (br s, 2H), 3.14 (br d, J = 12.8 Hz, 2H), 2.99 (s, 3H), 2.53-2.62 (m, 1H), 2.04 (s, 3H), 1.69-1.93 (m, 4H) |
| 47 | Method 1 | 1.592 | 607 | $^1$H NMR (400 MHz, DMSO-$d_6$) δ ppm 8.37 (br d, J = 6.0 Hz, 1H), 7.99-7.92 (m, 1H), 7.92-7.86 (m, 1H), 7.60 (d, J = 2.0 Hz, 1H), 7.58-7.51 (m, 1H), 7.49-7.41 (m, 1H), 7.39 (d, J = 4.1 Hz, 2H), 6.45 (d, J = 11.3 Hz, 1H), 6.28 (dd, J = 9.5, 11.1 Hz, 1H), 5.44-5.27 (m, 1H), 3.21-3.05 (m, 5H), 2.79-2.69 (m, 1H), 2.65-2.56 (m, 1H), 2.02-1.61 (m, 4H), 1.20 (d, J = 6.9 Hz, 3H) |
| 48 | Method 2 | 2.791 | 624.9 | $^1$H NMR (400 MHz, DMSO-$d_6$) δ ppm 8.39 (br d, J = 6.4 Hz, 1H), 7.89-7.96 (m, 2H), 7.67 (d, J = 1.7 Hz, 1H), 7.55-7.63 (m, 1H), 7.30-7.38 (m, 2H), 6.45 (d, J = 11.4 Hz, 1H), 6.23-6.32 (m, 1H), 5.28-5.40 (m, 1H), 3.21 (br s, 2H), 3.11 (s, 3H), 2.72-2.81 (m, 1H), 2.70 (br s, 1H), 1.70-1.96 (m, 4H), 1.20-1.26 (m, 3H) |
| 49 | Method 2 | 2.799 | 587 | $^1$H NMR (400 MHz, DMSO-$d_6$) δ ppm 8.37 (br d, J = 6.6 Hz, 1H), 7.96 (d, J = 8.5 Hz, 1H), 7.84 (dd, J = 8.5, 1.9 Hz, 1H), 7.52 (d, J = 1.9 Hz, 1H), 7.09-7.34 (m, 4H), 6.45 (d, J = 11.1 Hz, 1H), 6.21-6.33 (m, 1H), 5.27-5.40 (m, 1H), 3.43 (br s, 3H), 3.14 (br s, 1H), 3.06 (br d, J = 12.8 Hz, 1H), 2.61-2.67 (m, 2H), 2.01 (s, 3H), 1.66-1.95 (m, 4H), 1.20 (d, J = 6.9 Hz, 3H) |
| 50 | Method 1 | 1.678 | 625 | $^1$H NMR (400 MHz, DMSO-$d_6$) δ ppm 8.39 (br d, J = 6.5 Hz, 1H), 7.87-8.00 (m, 2H), 7.64 (d, J = 1.8 Hz, 1H), 7.56 (dd, J = 8.8, 2.4 Hz, 1H), 7.46 (dd, J = 8.7, 6.3 Hz, 1H), 7.25-7.34 (m, 1H), 6.46 (d, J = 11.4 Hz, 1H), 6.23-6.34 (m, 1H), 5.36 (br d, J = 8.4 Hz, 1H), 3.19 (br d, J = 5.1 Hz, 2H), 3.11 (s, 3H), 2.65-2.82 (m, 2H), 1.74-1.95 (m, 4H), 1.21 (d, J = 6.9 Hz, 3H) |
| 51 | Method 1 | 1.723 | 601 | $^1$H NMR (400 MHz, DMSO-$d_6$) δ ppm 8.38 (br d, J = 7.5 Hz, 1H), 7.96 (d, J = 8.7 Hz, 1H), 7.83-7.89 (m, 1H), 7.53 (d, J = 2.0 Hz, 1H), 7.29-7.42 (m, 2H), 7.23 (t, J = 8.0 Hz, 1H), 7.14 (d, J = 8.3 Hz, 1H), 6.46 (d, J = 11.4 Hz, 1H), 6.23-6.34 (m, 1H), 5.28-5.43 (m, 1H), 3.05-3.18 (m, 4H), 2.58 (br s, 3H), 2.22 (dq, J = 14.9, 7.5 Hz, 2H), 1.65-1.89 (m, 4H), 1.21 (d, J = 6.8 Hz, 3H), 1.06 (t, J = 7.5 Hz, 3H) |
| 52 | Method 1 | 1.669 | 625 | $^1$H NMR (400 MHz, DMSO-$d_6$) δ ppm 8.38 (dd, J = 7.9, 1.9 Hz, 1H), 7.88-8.00 (m, 2H), 7.69 (d, J = 1.9 Hz, 1H), 7.39-7.51 (m, 2H), 7.25 (d, J = 7.1 Hz, 1H), 6.45 (d, J = 11.4 Hz, 1H), 6.28 (dd, J = 11.1, 9.5 Hz, 1H), 5.29-5.40 (m, 1H), 3.14-3.27 (m, 2H), 3.11 (s, 3H), 2.69-2.80 (m, 1H), 2.57-2.66 (m, 1H), 1.70-2.02 (m, 4H), 1.21 (d, J = 6.9 Hz, 3H) |
| 53 | Method 1 | 1.732 | 621 | $^1$H NMR (400 MHz, DMSO-$d_6$) δ ppm 8.40 (br d, J = 7.3 Hz, 1H), 7.79-8.02 (m, 2H), 7.58 (d, J = 1.9 Hz, 1H), 7.40 (s, 1H), 7.19-7.31 (m, 2H), 6.47 (d, J = |

TABLE 3-continued

| Representative Analytical Data for Compounds of the Disclosure. | | | | |
|---|---|---|---|---|
| Cmpd. No. | LCMS Method | LCMS retention time (min) | LCMS M + H | $^1$H NMR |
| | | | | 11.4 Hz, 1H), 6.25-6.35 (m, 1H), 5.26-5.50 (m, 1H), 3.13 (s, 4H), 2.56-2.81 (m, 2H), 2.34-2.41 (m, 3H), 1.70-1.99 (m, 4H), 1.22 (d, J = 6.9 Hz, 3H) |
| 54 | Method 1 | 1.681 | 641 | $^1$H NMR (400 MHz, DMSO-$d_6$) δ ppm 8.39 (dd, J = 1.8, 7.8 Hz, 1H), 7.95-7.84 (m, 2H), 7.81 (d, J = 7.4 Hz, 1H), 7.74-7.61 (m, 2H), 7.59 (s, 1H), 7.44 (d, J = 7.3 Hz, 1H), 6.45 (d, J = 11.3 Hz, 1H), 6.28 (dd, J = 9.6, 11.1 Hz, 1H), 5.43-5.26 (m, 1H), 3.27 (br s, 1H), 3.16 (br d, J = 12.5 Hz, 1H), 3.12-3.06 (m, 3H), 2.80-2.61 (m, 2H), 2.02-1.67 (m, 4H), 1.21 (d, J = 6.8 Hz, 3H) |
| 55 | Method 1 | 1.725 | 607 | $^1$H NMR (400 MHz, DMSO-$d_6$) δ ppm 8.37 (dd, J = 7.8, 2.1 Hz, 1H), 7.93-7.96 (m, 1H), 7.85-7.89 (m, 1H), 7.64 (d, J = 2.0 Hz, 1H), 7.48-7.52 (m, 1H), 7.43-7.48 (m, 2H), 7.33-7.36 (m, 1H), 6.45 (dd, J = 11.1, 0.8 Hz, 1H), 6.27 (dd, J = 11.1, 9.5 Hz, 1H), 5.29-5.39 (m, 1H), 3.15 (br d, J = 13.0 Hz, 2H), 3.11 (s, 3H), 2.53-2.63 (m, 2H), 1.65-1.87 (m, 4H), 1.20 (d, J = 6.9 Hz, 3H) |
| 56 | Method 1 | 1.716 | 605.1 | $^1$H NMR (400 MHz, DMSO-$d_6$) δ ppm 8.38 (br d, J = 6.2 Hz, 1H), 7.83-8.00 (m, 2H), 7.57 (s, 1H), 7.16-7.32 (m, 2H), 7.02 (br d, J = 6.7 Hz, 1H), 6.45 (br d, J = 11.6 Hz, 1H), 6.28 (br t, J = 10.5 Hz, 1H), 5.34 (br d, J = 8.2 Hz, 1H), 3.20 (br d, J = 12.5 Hz, 4H), 3.11 (s, 3H), 1.90 (br s, 3H), 1.67-1.84 (m, 4H), 1.20 (br d, J = 6.7 Hz, 3H) |
| 57 | Method 1 | 1.658 | 573.1 | $^1$H NMR (400 MHz, DMSO-$d_6$) δ ppm 8.34 (br d, J = 7.6 Hz, 1H), 7.97 (d, J = 8.6 Hz, 1H), 7.85 (dd, J = 8.6, 2.1 Hz, 1H), 7.58 (d, J = 2.0 Hz, 1H), 7.42-7.47 (m, 3H), 7.38-7.41 (m, 2H), 6.45 (d, J = 11.3 Hz, 1H), 6.27 (dd, J = 10.9, 9.6 Hz, 1H), 5.29-5.41 (m, 1H), 3.30 (br s, 2H), 3.12 (s, 3H), 3.08 (br s, 2H), 1.59-1.81 (m, 4H), 1.20 (d, J = 6.9 Hz, 3H) |
| 58 | Method 1 | 1.865 | 650.9 | $^1$H NMR (400 MHz, DMSO-$d_6$) δ ppm 8.37 (dd, J = 7.7, 1.9 Hz, 1H), 7.91-7.99 (m, 1H), 7.83-7.89 (m, 1H), 7.57-7.70 (m, 3H), 7.34-7.45 (m, 2H), 6.45 (d, J = 11.5 Hz, 1H), 6.27 (dd, J = 11.7, 9.6 Hz, 1H), 5.25-5.42 (m, 1H), 3.09-3.19 (m, 5H), 2.58 (br t, J = 12.3 Hz, 2H), 1.58-1.92 (m, 4H), 1.20 (d, J = 6.9 Hz, 3H) |
| 59 | Method 1 | 1.179 | 621.1 | $^1$H NMR (400 MHz, DMSO-$d_6$) δ ppm 8.38 (br d, J = 7.7 Hz, 1H), 7.93-8.02 (m, 1H), 7.85-7.90 (m, 1H), 7.59 (d, J = 2.0 Hz, 1H), 7.41 (br d, J = 7.5 Hz, 1H), 7.29 (t, J = 7.6 Hz, 1H), 7.19-7.24 (m, 1H), 6.45 (d, J = 11.3 Hz, 1H), 6.22-6.33 (m, 1H), 5.27-5.40 (m, 1H), 3.11 (s, 3H), 2.65-2.75 (m, 4H), 2.39 (s, 3H), 1.65-1.93 (m, 4H), 1.20 (d, J = 6.9 Hz, 3H) |
| 60 | Method 1 | 1.769 | 621 | $^1$H NMR (400 MHz, DMSO-$d_6$) δ ppm 8.37 (br d, J = 7.7 Hz, 1H), 7.82-8.02 (m, 2H), 7.56 (d, J = 1.9 Hz, 1H), 7.38 (s, 1H), 7.15-7.29 (m, 2H), 6.45 (d, J = 11.1 Hz, 1H), 6.23-6.32 (m, 1H), 5.27-5.41 (m, 1H), 3.15 (br d, J = 11.5 Hz, 2H), 3.11 (s, 3H), 2.65-2.78 (m, 2H), 2.36 (s, 3H), 1.69-1.94 (m, 4H), 1.20 (d, J = 6.9 Hz, 3H) |
| 61 | Method 1 | 1.746 | 603 | $^1$H NMR (400 MHz, DMSO-$d_6$) δ ppm 8.37-8.33 (m, 1H), 7.95 (d, J = 8.6 Hz, 1H), 7.84 (dd, J = 2.1, 8.6 Hz, 1H), 7.59 (d, J = 2.0 Hz, 1H), 7.33 (t, J = 7.8 Hz, 1H), 7.01-6.93 (m, 3H), 6.45 (d, J = 11.1 Hz, 1H), 6.26 (dd, J = 9.6, 11.1 Hz, 1H), 5.38-5.28 (m, 1H), 3.78 (s, 3H), 3.14-3.12 (m, 1H), 3.11 (s, 3H), 3.11-3.08 (m, 1H), 2.53-2.52 (m, 2H), 1.80-1.59 (m, 4H), 1.19 (d, J = 6.8 Hz, 3H) |
| 62 | Method 1 | 1.568 | 607 | $^1$H NMR (400 MHz, DMSO-$d_6$) δ ppm 8.38 (dd, J = 7.9, 1.7 Hz, 1H), 7.93-7.99 (m, 1H), 7.86-7.92 (m, 1H), 7.61 (d, J = 2.0 Hz, 1H), 7.52-7.57 (m, 1H), 7.41-7.48 (m, 1H), 7.39 (d, J = 4.1 Hz, 2H), 6.45 (d, J = 11.1 Hz, 1H), 6.27 (dd, J = 11.1, 9.5 Hz, 1H), 5.28-5.40 (m, 1H), 3.06-3.21 (m, 5H), 2.72 (td, J = 12.6, 2.9 Hz, 1H), 2.59 (br t, J = 12.3 Hz, 1H), 1.80-2.01 (m, 2H), 1.66-1.78 (m, 2H), 1.20 (d, J = 6.9 Hz, 3H) |
| 63 | Method 1 | 1.68 | 589 | $^1$H NMR (400 MHz, DMSO-$d_6$) δ ppm 8.57 (br s, 1H), 7.76-8.04 (m, 2H), 7.59 (d, J = 1.7 Hz, 1H), |

TABLE 3-continued

Representative Analytical Data for Compounds of the Disclosure.

| Cmpd. No. | LCMS Method | LCMS retention time (min) | LCMS M + H | $^1$H NMR |
|---|---|---|---|---|
| | | | | 7.34 (t, J = 8.1 Hz, 1H), 6.89-7.08 (m, 3H), 6.65-6.77 (m, 1H), 6.54-6.63 (m, 1H), 3.84-3.98 (m, 2H), 3.78 (s, 3H), 3.13 (br d, J = 12.9 Hz, 2H), 2.99 (s, 3H), 2.54 (br d, J = 3.6 Hz, 2H), 1.63-1.84 (m, 4H |
| 64 | Method 3 | 2.736 | 592.9 | $^1$H NMR (400 MHz, DMSO-$d_6$) δ ppm 8.63-8.55 (m, 1H), 7.98-7.95 (m, 1H), 7.92-7.87 (m, 1H), 7.61 (d, J = 2.0 Hz, 1H), 7.56 (d, J = 7.7 Hz, 1H), 7.48-7.42 (m, 1H), 7.42-7.39 (m, 2H), 6.74-6.67 (m, 1H), 6.63-6.56 (m, 1H), 3.93 (br t, J = 4.2 Hz, 2H), 3.20-3.12 (m, 2H), 2.79-2.69 (m, 1H), 2.65-2.56 (m, 1H), 2.04-1.76 (m, 4H) |
| 65 | Method 2 | 2.713 | 590.9 | $^1$H NMR (400 MHz, DMSO-$d_6$) δ ppm 8.86 (br d, J = 6.6 Hz, 1H), 7.84-8.00 (m, 2H), 7.51-7.64 (m, 2H), 7.37-7.48 (m, 3H), 7.18 (dd, J = 6.6, 2.2 Hz, 1H), 6.78 (dd, J = 6.7, 2.3 Hz, 1H), 5.07-5.19 (m, 1H), 3.67-3.76 (m, 2H), 3.16 (br dd, J = 13.5, 5.6 Hz, 2H), 2.60-2.77 (m, 2H), 1.82-2.02 (m, 2H), 1.78 (br d, J = 12.1 Hz, 2H) |
| 66 | Method 1 | 1.657 | 591 | $^1$H NMR (400 MHz, DMSO-$d_6$) δ ppm 8.81-8.88 (m, 1H), 7.87-7.98 (m, 2H), 7.51-7.63 (m, 2H), 7.37-7.49 (m, 3H), 7.18 (dd, J = 6.7, 2.3 Hz, 1H), 6.78 (dd, J = 6.6, 2.4 Hz, 1H), 5.07-5.22 (m, 1H), 3.69 (dd, J = 13.6, 8.0 Hz, 1H), 3.16 (br dd, J = 13.5, 5.4 Hz, 3H), 2.69-2.78 (m, 1H), 2.55-2.65 (m, 1H), 1.71-2.02 (m, 4H) |
| 67 | Method 1 | 1.653 | 591 | $^1$H NMR (400 MHz, DMSO-$d_6$) δ ppm 8.85 (br d, J = 7.1 Hz, 1H), 7.85-8.00 (m, 2H), 7.52-7.63 (m, 2H), 7.37-7.48 (m, 3H), 7.18 (dd, J = 6.6, 2.2 Hz, 1H), 6.78 (dd, J = 6.7, 2.3 Hz, 1H), 5.14 (br d, J = 6.1 Hz, 1H), 3.69 (dd, J = 13.6, 8.0 Hz, 1H), 3.16 (br dd, J = 13.4, 5.6 Hz, 3H), 2.69-2.79 (m, 1H), 2.60-2.65 (m, 1H), 1.85-2.01 (m, 2H), 1.73 (br d, J = 1.0 Hz, 2H) |
| 68 | Method 1 | 1.588 | 542 | $^1$H NMR (400 MHz, DMSO-$d_6$) δ ppm 8.53 (br d, J = 2.1 Hz, 1H), 7.94-7.98 (m, 1H), 7.87-7.91 (m, 1H), 7.60 (d, J = 2.0 Hz, 1H), 7.53-7.57 (m, 1H), 7.42-7.48 (m, 1H), 7.37-7.42 (m, 2H), 6.83 (dt, J = 16.4, 4.6 Hz, 1H), 5.60 (dt, J = 16.5, 1.9 Hz, 1H), 3.82-3.91 (m, 2H), 3.10-3.21 (m, 2H), 2.61-2.80 (m, 2H), 1.75-2.01 (m, 4H) |
| 69 | Method 1 | 1.645 | 496 | $^1$H NMR (400 MHz, DMSO-$d_6$) δ ppm 8.54 (br d, J = 2.0 Hz, 1H), 8.04 (d, J = 8.5 Hz, 1H), 7.76 (dd, J = 8.6, 2.2 Hz, 1H), 7.54-7.57 (m, 1H), 7.49 (d, J = 2.3 Hz, 1H), 7.42-7.48 (m, 1H), 7.40 (d, J = 4.1 Hz, 2H), 6.83 (dt, J = 16.4, 4.5 Hz, 1H), 5.60 (dt, J = 16.4, 1.9 Hz, 1H), 3.86 (br t, J = 4.0 Hz, 2H), 3.08-3.23 (m, 2H), 2.69-2.81 (m, 1H), 2.55-2.65 (m, 1H), 1.75-1.98 (m, 4H) |
| 70 | Method 1 | 1.584 | 542 | $^1$H NMR (400 MHz, DMSO-$d_6$) δ ppm 8.60-8.66 (m, 1H), 7.93-7.99 (m, 1H), 7.85-7.92 (m, 1H), 7.60 (d, J = 2.0 Hz, 1H), 7.53-7.57 (m, 1H), 7.42-7.48 (m, 1H), 7.40 (d, J = 4.2 Hz, 2H), 6.46-6.54 (m, 1H), 5.75 (dt, J = 11.2, 1.6 Hz, 1H), 3.93-4.00 (m, 2H), 3.11-3.20 (m, 2H), 2.73 (td, J = 12.6, 2.7 Hz, 1H), 2.60 (td, J = 12.8, 2.9 Hz, 1H), 1.81-2.03 (m, 2H), 1.71-1.80 (m, 2H) |
| 71 | Method 1 | 1.507 | 492 | $^1$H NMR (400 MHz, DMSO-$d_6$) δ ppm 8.63 (br d, J = 2.1 Hz, 1H), 7.97 (d, J = 8.9 Hz, 1H), 7.53 (d, J = 7.4 Hz, 1H), 7.35-7.45 (m, 3H), 7.20 (dd, J = 8.9, 2.7 Hz, 1H), 6.85 (d, J = 2.6 Hz, 1H), 6.47-6.54 (m, 1H), 5.75 (dt, J = 11.2, 1.7 Hz, 1H), 3.95-4.00 (m, 2H), 3.86 (s, 3H), 3.13 (br d, J = 11.6 Hz, 2H), 2.54-2.71 (m, 2H), 1.72-2.01 (m, 4H) |
| 72 | Method 1 | 1.682 | 540 | $^1$H NMR (400 MHz, DMSO-$d_6$) δ ppm 8.70-8.79 (m, 1H), 7.93-7.99 (m, 1H), 7.86-7.92 (m, 1H), 7.61 (d, J = 2.0 Hz, 1H), 7.52-7.57 (m, 1H), 7.43-7.47 (m, 1H), 7.38-7.42 (m, 2H), 6.11 (s, 1H), 5.96 (t, J = 1.5 Hz, 1H), 3.88 (br d, J = 6.0 Hz, 2H), 3.15 (br d, J = 11.4 Hz, 2H), 2.74 (br dd, J = 12.4, 10.0 Hz, 2H), 1.70-1.97 (m, 4H) |
| 73 | Method 1 | 1.482 | 606 | $^1$H NMR (400 MHz, DMSO-$d_6$) δ ppm 8.56 (br t, J = 6.7 Hz, 1H), 8.01-7.92 (m, 1H), 7.92-7.86 (m, 1H), 7.61 (d, J = 1.9 Hz, 1H), 7.55 (d, J = 7.6 Hz, |

TABLE 3-continued

Representative Analytical Data for Compounds of the Disclosure.

| Cmpd. No. | LCMS Method | LCMS retention time (min) | LCMS M + H | $^1$H NMR |
|---|---|---|---|---|
| | | | | 1H), 7.49-7.42 (m, 1H), 7.39 (d, J = 4.4 Hz, 2H), 6.85-6.62 (m, 2H), 5.39-5.20 (m, 1H), 3.79-3.61 (m, 3H), 3.15 (br s, 2H), 2.76-2.56 (m, 3H), 2.01-1.63 (m, 4H), 1.25 (d, J = 6.8 Hz, 3H) |
| 74 | Method 1 | 1.486 | 606 | $^1$H NMR (400 MHz, DMSO-$d_6$) δ ppm 8.47 (dd, J = 7.6, 1.7 Hz, 1H), 7.94-8.02 (m, 1H), 7.91 (d, J = 2.0 Hz, 1H), 7.62 (d, J = 2.0 Hz, 1H), 7.53-7.58 (m, 1H), 7.42-7.49 (m, 1H), 7.40 (d, J = 4.1 Hz, 2H), 6.54-6.59 (m, 1H), 6.51 (s, 1H), 5.28-5.45 (m, 1H), 3.44 (s, 3H), 3.13-3.21 (m, 2H), 2.53-2.81 (m, 2H), 1.70-1.96 (m, 5H), 1.23 (d, J = 6.9 Hz, 3H) |
| 75 | Method 2 | 2.331 | 648 | $^1$H NMR (400 MHz, DMSO-$d_6$) δ ppm 9.18-8.98 (m, 2H), 8.52-8.42 (m, 1H), 7.97-7.85 (m, 2H), 7.59 (d, J = 2.0 Hz, 1H), 7.53 (d, J = 7.9 Hz, 1H), 7.48-7.35 (m, 3H), 6.85 (dd, J = 5.0, 15.2 Hz, 1H), 6.65 (dd, J = 1.2, 15.3 Hz, 1H), 4.65-4.54 (m, 1H), 4.49-4.37 (m, 1H), 4.29-4.18 (m, 2H), 4.12-4.00 (m, 2H), 3.19-3.09 (m, 2H), 2.78-2.67 (m, 1H), 2.63-2.52 (m, 1H), 1.97-1.67 (m, 4H), 1.22 (d, J = 7.0 Hz, 3H) |
| 76 | Method 2 | 2.327 | 648 | $^1$H NMR (400 MHz, DMSO-$d_6$) δ ppm 9.19-9.01 (m, 1H), 8.47 (dd, J = 1.8, 7.9 Hz, 1H), 7.98-7.87 (m, 2H), 7.61 (d, J = 2.0 Hz, 1H), 7.55 (d, J = 7.8 Hz, 1H), 7.48-7.37 (m, 3H), 6.87 (dd, J = 5.0, 15.3 Hz, 1H), 6.67 (dd, J = 1.3, 15.3 Hz, 1H), 4.66-4.57 (m, 1H), 4.50-4.39 (m, 1H), 4.30-4.21 (m, 2H), 4.13-4.01 (m, 2H), 3.22-3.09 (m, 2H), 2.73 (dt, J = 2.7, 12.4 Hz, 1H), 2.64-2.56 (m, 1H), 2.00-1.72 (m, 4H), 1.24 (d, J = 7.0 Hz, 3H) |
| 77 | Method 3 | 2.388 | 662 | $^1$H NMR (400 MHz, DMSO-$d_6$) δ ppm 9.23-8.94 (m, 2H), 8.41-8.33 (m, 1H), 7.99-7.94 (m, 1H), 7.93-7.88 (m, 1H), 7.62 (d, J = 2.0 Hz, 1H), 7.55 (d, J = 7.8 Hz, 1H), 7.45 (qd, J = 4.1, 8.1 Hz, 1H), 7.42-7.37 (m, 2H), 6.89-6.82 (m, 1H), 6.74-6.66 (m, 1H), 4.49-4.40 (m, 2H), 4.30-4.21 (m, 2H), 4.13-4.01 (m, 2H), 3.22-3.11 (m, 2H), 2.81-2.70 (m, 1H), 2.64-2.57 (m, 1H), 2.02-1.72 (m, 4H), 1.70-1.51 (m, 2H), 0.81 (t, J = 7.3 Hz, 3H) |
| 78 | Method 3 | 2.382 | 662 | $^1$H NMR (400 MHz, DMSO-$d_6$) δ ppm 9.25-8.94 (m, 2H), 8.37 (dd, J = 2.1, 8.4 Hz, 1H), 7.98-7.93 (m, 1H), 7.91-7.87 (m, 1H), 7.61 (d, J = 2.0 Hz, 1H), 7.54 (d, J = 7.8 Hz, 1H), 7.48-7.41 (m, 1H), 7.40-7.37 (m, 2H), 6.88-6.81 (m, 1H), 6.73-6.66 (m, 1H), 4.49-4.39 (m, 2H), 4.29-4.21 (m, 2H), 4.06 (td, J = 6.1, 11.6 Hz, 2H), 3.22-3.10 (m, 2H), 2.79-2.68 (m, 1H), 2.64-2.55 (m, 1H), 2.00-1.71 (m, 4H), 1.69-1.51 (m, 2H), 0.80 (t, J = 7.3 Hz, 3H |
| 79 | Method 2 | 2.746 | 606.9 | $^1$H NMR (400 MHz, DMSO-$d_6$) δ ppm 8.46 (dd, J = 1.9, 8.3 Hz, 1H), 7.99-7.93 (m, 1H), 7.92-7.87 (m, 1H), 7.61 (d, J = 2.0 Hz, 1H), 7.55 (d, J = 7.7 Hz, 1H), 7.48-7.42 (m, 1H), 7.42-7.38 (m, 2H), 6.76-6.58 (m, 2H), 4.68-4.56 (m, 1H), 3.24-3.08 (m, 2H), 3.04-2.94 (m, 3H), 2.79-2.68 (m, 1H), 2.65-2.54 (m, 1H), 2.05-1.68 (m, 4H), 1.22 (d, J = 7.1 Hz, 3H) |
| 80 | Method 3 | 2.397 | 559.2 | $^1$H NMR (400 MHz, DMSO-$d_6$) δ ppm 8.42 (br d, J = 6.1 Hz, 1H), 8.04 (d, J = 8.6 Hz, 1H), 7.70 (dd, J = 8.6, 2.2 Hz, 1H), 7.47 (d, J = 2.2 Hz, 1H), 7.31-7.37 (m, 1H), 6.94-7.01 (m, 3H), 6.66-6.74 (m, 1H), 6.58-6.65 (m, 1H), 4.51-4.68 (m, 1H), 3.78 (s, 3H), 3.13 (br d, J = 12.8 Hz, 2H), 2.99 (s, 3H), 2.54 (br s, 2H), 1.62-1.84 (m, 4H), 1.21 (d, J = 7.0 Hz, 3H) |
| 81 | Method 2 | 2.744 | 607 | $^1$H NMR (400 MHz, DMSO-$d_6$) δ ppm 8.46 (br d, J = 8.4 Hz, 1H), 7.98-7.88 (m, 2H), 7.61 (d, J = 2.0 Hz, 1H), 7.55 (d, J = 7.7 Hz, 1H), 7.48-7.37 (m, 3H), 6.74-6.61 (m, 2H), 4.66-4.57 (m, 1H), 3.21-3.11 (m, 2H), 3.00 (s, 3H), 2.77-2.67 (m, 1H), 2.64-2.54 (m, 1H), 1.98-1.71 (m, 4H), 1.22 (d, J = 7.1 Hz, 3H) |
| 82 | Method 2 | 2.809 | 620.9 | $^1$H NMR (400 MHz, DMSO-$d_6$) δ ppm 8.26-8.33 (m, 1H), 7.93-7.97 (m, 1H), 7.87-7.91 (m, 1H), |

TABLE 3-continued

Representative Analytical Data for Compounds of the Disclosure.

| Cmpd. No. | LCMS Method | LCMS retention time (min) | LCMS M + H | $^1$H NMR |
|---|---|---|---|---|
| | | | | 7.61 (d, J = 2.2 Hz, 1H), 7.52-7.56 (m, 1H), 7.41-7.47 (m, 1H), 7.39 (d, J = 3.9 Hz, 2H), 6.49 (d, J = 11.2 Hz, 1H), 6.23 (dd, J = 11.2, 9.9 Hz, 1H), 5.21 (br dd, J = 8.9, 6.5 Hz, 1H), 3.11-3.19 (m, 2H), 3.09 (s, 3H), 2.53-2.78 (m, 2H), 1.80-2.02 (m, 2H), 1.65-1.78 (m, 2H), 1.45-1.63 (m, 2H), 0.79 (t, J = 7.4 Hz, 3H) |
| 83 | Method 1 | 1.761 | 573.1 | $^1$H NMR (400 MHz, DMSO-$d_6$) δ ppm 8.27 (dd, J = 8.4, 2.0 Hz, 1H), 8.04 (d, J = 8.6 Hz, 1H), 7.70 (dd, J = 8.6, 2.2 Hz, 1H), 7.46 (d, J = 2.1 Hz, 1H), 7.25-7.39 (m, 1H), 6.86-7.07 (m, 3H), 6.49 (d, J = 11.1 Hz, 1H), 6.11-6.32 (m, 1H), 5.08-5.31 (m, 1H), 3.77 (s, 3H), 3.03-3.17 (m, 5H), 2.53 (br s, 2H), 1.43-1.81 (m, 6H), 0.78 (t, J = 7.3 Hz, 3H) |
| 84 | Method 1 | 1.755 | 543.2 | $^1$H NMR (400 MHz, DMSO-$d_6$) δ ppm 8.27 (dd, J = 8.4, 2.1 Hz, 1H), 8.05 (d, J = 8.6 Hz, 1H), 7.71 (dd, J = 8.6, 2.2 Hz, 1H), 7.32-7.50 (m, 6H), 6.49 (d, J = 11.1 Hz, 1H), 6.12-6.31 (m, 1H), 5.12-5.30 (m, 1H), 2.99-3.16 (m, 5H), 2.45 (br s, 2H), 1.45-1.80 (m, 6H), 0.78 (t, J = 7.3 Hz, 3H) |
| 85 | Method 1 | 1.701 | 586.1 | $^1$H NMR (400 MHz, DMSO-$d_6$) δ ppm 8.26 (dd, J = 8.3, 1.7 Hz, 1H), 7.76 (d, J = 9.0 Hz, 1H), 7.46-7.50 (m, 1H), 7.35-7.41 (m, 1H), 7.31-7.35 (m, 2H), 6.82 (dd, J = 9.1, 2.6 Hz, 1H), 6.49 (d, J = 11.1 Hz, 1H), 6.43 (d, J = 2.6 Hz, 1H), 6.24 (dd, J = 11.0, 10.0 Hz, 1H), 5.17-5.27 (m, 1H), 3.09 (s, 5H), 3.00 (s, 6H), 2.52-2.67 (m, 2H), 1.67-2.04 (m, 4H), 1.46-1.65 (m, 2H), 0.79 (t, J = 7.4 Hz, 3H) |
| 86 | Method 2 | 2.506 | 568.3 | $^1$H NMR (400 MHz, DMSO-$d_6$) δ ppm 8.32 (br d, J = 7.7 Hz, 1H), 7.78 (d, J = 9.0 Hz, 1H), 7.31-7.24 (m, 1H), 6.96-6.89 (m, 3H), 6.78 (dd, J = 2.8, 9.2 Hz, 1H), 6.50-6.41 (m, 2H), 6.26 (dd, J = 9.6, 11.1 Hz, 1H), 5.40-5.26 (m, 1H), 3.77 (s, 3H), 3.12 (s, 3H), 3.06 (br d, J = 12.7 Hz, 2H), 3.01 (s, 6H), 2.43 (br d, J = 12.7 Hz, 2H), 1.75-1.56 (m, 4H), 1.19 (d, J = 6.9 Hz, 3H) |
| 87 | Method 1 | 1.67 | 602.2 | $^1$H NMR (400 MHz, DMSO-$d_6$) δ ppm 8.36 (br d, J = 6.1 Hz, 1H), 7.75 (d, J = 9.1 Hz, 1H), 7.36 (d, J = 8.9 Hz, 1H), 6.95 (dd, J = 8.8, 2.9 Hz, 1H), 6.89 (d, J = 3.0 Hz, 1H), 6.82 (dd, J = 9.1, 2.6 Hz, 1H), 6.41-6.49 (m, 2H), 6.23-6.33 (m, 1H), 5.26-5.42 (m, 1H), 3.75 (s, 3H), 3.09-3.21 (m, 5H), 3.00 (s, 6H), 2.55-2.70 (m, 2H), 1.62-2.02 (m, 4H), 1.15-1.26 (m, 3H) |
| 88 | Method 1 | 1.625 | 538.2 | $^1$H NMR (400 MHz, DMSO-$d_6$) δ ppm 8.31 (br d, J = 7.7 Hz, 1H), 7.78 (d, J = 9.01 Hz, 1H), 7.36 (s, 5H), 6.79 (dd, J = 9.1, 2.6 Hz, 1H), 6.40-6.52 (m, 2H), 6.21-6.30 (m, 1H), 5.26-5.41 (m, 1H), 3.11 (s, 3H), 3.01 (s, 8H), 2.39 (br t, J = 12.1 Hz, 2H), 1.54-1.75 (m, 4H), 1.16-1.24 (m, 3H) |
| 89 | Method 1 | 1.657 | 572.2 | $^1$H NMR (400 MHz, DMSO-$d_6$) δ ppm 8.35 (br d, J = 6.4 Hz, 1H), 7.76 (d, J = 9.0 Hz, 1H), 7.48 (d, J = 7.5 Hz, 1H), 7.27-7.42 (m, 3H), 6.82 (dd, J = 9.1, 2.6 Hz, 1H), 6.40-6.50 (m, 2H), 6.22-6.35 (m, 1H), 5.25-5.45 (m, 1H), 3.05-3.18 (m, 5H), 3.00 (s, 6H), 2.54-2.69 (m, 2H), 1.61-1.99 (m, 4H), 1.18-1.23 (m, 3H) |
| 90 | Method 1 | 1.637 | 602.1 | $^1$H NMR (400 MHz, DMSO-$d_6$) δ ppm 8.35 (br d, J = 5.9 Hz, 1H), 7.74 (d, J = 9.0 Hz, 1H), 7.25-7.31 (m, 1H), 7.12 (d, J = 7.9 Hz, 1H), 6.89 (d, J = 6.6 Hz, 1H), 6.81 (dd, J = 9.1, 2.6 Hz, 1H), 6.38-6.48 (m, 2H), 6.23-6.32 (m, 1H), 5.29-5.38 (m, 1H), 3.87 (s, 3H), 3.12-3.19 (m, 2H), 3.11 (d, J = 1.3 Hz, 3H), 2.99 (s, 6H), 2.52-2.71 (m, 2H), 1.63-1.98 (m, 4H), 1.20 (d, J = 6.9 Hz, 3H) |
| 91 | Method 1 | 1.63 | 538.2 | $^1$H NMR (400 MHz, DMSO-$d_6$) δ ppm 8.32 (br d, J = 6.0 Hz, 1H), 7.78 (d, J = 9.0 Hz, 1H), 7.36 (s, 5H), 6.79 (dd, J = 9.1, 2.6 Hz, 1H), 6.37-6.51 (m, 2H), 6.20-6.33 (m, 1H), 5.25-5.42 (m, 1H), 3.11 (s, 3H), 3.01 (s, 8H), 2.32-2.43 (m, 2H), 1.54-1.78 (m, 4H), 1.19 (d, J = 6.9 Hz, 3H) |
| 92 | Method 1 | 1.655 | 572.1 | $^1$H NMR (400 MHz, DMSO-$d_6$) δ ppm 8.35 (br d, J = 6.2 Hz, 1H), 7.76 (d, J = 9.0 Hz, 1H), 7.48 (d, J = 7.6 Hz, 1H), 7.29-7.42 (m, 3H), 6.82 (dd, J = 9.1, |

TABLE 3-continued

| Representative Analytical Data for Compounds of the Disclosure. | | | | |
|---|---|---|---|---|
| Cmpd. No. | LCMS Method | LCMS retention time (min) | LCMS M + H | $^1$H NMR |
| | | | | 2.6 Hz, 1H), 6.41-6.49 (m, 2H), 6.23-6.32 (m, 1H), 5.24-5.46 (m, 1H), 3.05-3.19 (m, 5H), 3.00 (s, 6H), 2.53-2.69 (m, 2H), 1.63-1.99 (m, 4H), 1.17-1.23 (m, 3H) |
| 93 | Method 1 | 1.688 | 552 | $^1$H NMR (400 MHz, DMSO-$d_6$) δ ppm 8.33 (br d, J = 5.9 Hz, 1H), 7.77 (d, J = 9.0 Hz, 1H), 7.13-7.27 (m, 3H), 7.07-7.11 (m, 1H), 6.78 (dd, J = 9.1, 2.8 Hz, 1H), 6.44 (d, J = 11.3 Hz, 1H), 6.36 (d, J = 2.6 Hz, 1H), 6.23-6.30 (m, 1H), 5.29-5.40 (m, 1H), 3.10 (s, 5H), 2.99 (s, 6H), 2.43-2.48 (m, 2H), 2.03 (s, 3H), 1.62-1.88 (m, 4H), 1.20 (d, J = 6.9 Hz, 3H) |
| 94 | Method 1 | 1.563 | 524.2 | $^1$H NMR (400 MHz, DMSO-$d_6$) δ ppm 8.53 (br s, 1H), 7.79 (d, J = 9.0 Hz, 1H), 7.37 (s, 5H), 6.79 (dd, J = 8.8, 2.7 Hz, 1H), 6.64-6.74 (m, 1H), 6.54-6.62 (m, 1H), 6.45 (d, J = 2.6 Hz, 1H), 3.91 (br s, 2H), 3.06 (br s, 2H), 3.01 (s, 6H), 2.99 (s, 3H), 2.38 (br s, 2H), 1.69 (br d, J = 18.4 Hz, 4H) |
| 95 | Method 1 | 1.592 | 558.1 | $^1$H NMR (400 MHz, DMSO-$d_6$) δ ppm 8.57 (br s, 1H), 7.76 (d, J = 9.1 Hz, 1H), 7.45-7.53 (m, 1H), 7.31-7.42 (m, 3H), 6.82 (dd, J = 9.1, 2.4 Hz, 1H), 6.65-6.75 (m, 1H), 6.55-6.63 (m, 1H), 6.44 (d, J = 2.6 Hz, 1H), 3.93 (br s, 2H), 3.07-3.16 (m, 2H), 2.96-3.03 (m, 9H), 2.60 (br s, 2H), 1.69-2.02 (m, 4H) |
| 96 | Method 1 | 1.567 | 554.2 | $^1$H NMR (400 MHz, DMSO-$d_6$) δ ppm 8.54 (br s, 1H), 7.79 (d, J = 9.2 Hz, 1H), 7.25-7.33 (m, 1H), 6.91-6.96 (m, 3H), 6.79 (dd, J = 9.1, 2.7 Hz, 1H), 6.66-6.74 (m, 1H), 6.54-6.62 (m, 1H), 6.48 (d, J = 2.6 Hz, 1H), 3.92 (br s, 2H), 3.77 (s, 3H), 3.08 (br d, J = 12.4 Hz, 2H), 3.02 (s, 6H), 3.00 (s, 3H), 2.37-2.44 (m, 2H), 1.64-1.77 (m, 4H) |
| 97 | Method 2 | 2.67 | 505 | $^1$H NMR (400 MHz, DMSO-$d_6$) δ ppm 8.51 (br s, 1H), 7.76 (d, J = 9.0 Hz, 1H), 7.41-7.52 (m, 1H), 7.29-7.40 (m, 3H), 6.77-6.85 (m, 2H), 6.44 (d, J = 2.6 Hz, 1H), 5.59 (d, J = 16.5 Hz, 1H), 3.86 (br s, 2H), 3.05-3.16 (m, 2H), 3.00 (s, 6H), 2.65-2.71 (m, 2H), 1.82-2.00 (m, 2H), 1.76-1.81 (m, 2H) |
| 98 | Method 1 | 1.848 | 583.2 | $^1$H NMR (400 MHz, DMSO-$d_6$) δ ppm 8.34 (br d, J = 5.7 Hz, 1H), 7.94 (d, J = 8.3 Hz, 1H), 7.45-7.55 (m, 2H), 7.30-7.44 (m, 3H), 7.14 (s, 1H), 6.44 (d, J = 11.8 Hz, 1H), 6.16-6.30 (m, 1H), 5.34 (s, 1H), 3.56-3.71 (m, 1H), 3.03-3.18 (m, 5H), 2.61-2.74 (m, 1H), 2.23-2.38 (m, 3H), 2.11 (br s, 2H), 1.62-2.02 (m, 6H), 1.19 (d, J = 6.6 Hz, 3H) |
| 99 | Method 1 | 1.757 | 584.2 (M-Boc) | $^1$H NMR (400 MHz, DMSO-$d_6$) δ ppm 8.36 (br d, J = 7.9 Hz, 1H), 8.02 (d, J = 8.3 Hz, 1H), 7.68-7.62 (m, 1H), 7.54 (d, J = 8.1 Hz, 1H), 7.48-7.36 (m, 3H), 7.30 (d, J = 1.5 Hz, 1H), 6.45 (d, J = 11.4 Hz, 1H), 6.33-6.23 (m, 1H), 5.43-5.25 (m, 1H), 4.27 (br t, J = 8.0 Hz, 2H), 4.02-3.79 (m, 3H), 3.11 (s, 5H), 2.76-2.54 (m, 2H), 1.80-1.65 (m, 2H), 2.02-1.64 (m, 2H), 1.39 (s, 9H), 1.21 (d, J = 6.8 Hz, 3H) |
| 100 | Method 1 | 1.8 | 567.1 | $^1$H NMR (400 MHz, DMSO-$d_6$) δ ppm 8.36 (dd, J = 7.7, 1.9 Hz, 1H), 8.03 (d, J = 8.6 Hz, 1H), 7.71 (dd, J = 8.6, 2.2 Hz, 1H), 7.45-7.49 (m, 1H), 7.36-7.45 (m, 3H), 7.30-7.35 (m, 1H), 6.44 (d, J = 11.3 Hz, 1H), 6.26 (dd, J = 11.1, 9.4 Hz, 1H), 5.27-5.39 (m, 1H), 3.11 (s, 5H), 2.51-2.58 (m, 2H), 2.04 (s, 3H), 1.60-1.90 (m, 4H), 1.18-1.23 (m, 3H) |
| 101 | Method 1 | 1.729 | 585.2 | $^1$H NMR (400 MHz, DMSO-$d_6$) δ ppm 8.35 (br d, J = 5.9 Hz, 1H), 7.98 (d, J = 8.9 Hz, 1H), 7.47-7.57 (m, 1H), 7.27-7.46 (m, 4H), 6.93 (d, J = 2.6 Hz, 1H), 6.45 (d, J = 11.1 Hz, 1H), 6.28 (dd, J = 11.1, 9.5 Hz, 1H), 5.25-5.43 (m, 1H), 3.91-4.05 (m, 1H), 3.11 (s, 5H), 2.55-2.72 (m, 2H), 1.67-2.01 (m, 4H), 1.20 (d, J = 6.9 Hz, 3H), 0.78-0.86 (m, 2H), 0.63-0.77 (m, 2H) |
| 102 | Method 1 | 1.718 | 553 | $^1$H NMR (400 MHz, DMSO-$d_6$) δ ppm 8.36 (dd, J = 7.8, 2.0 Hz, 1H), 7.94 (d, J = 8.9 Hz, 1H), 7.16-7.30 (m, 3H), 7.09-7.14 (m, 2H), 6.73 (d, J = 2.6 Hz, 1H), 6.45 (d, J = 11.3 Hz, 1H), 6.24-6.31 (m, 1H), 5.29-5.40 (m, 1H), 4.13 (q, J = 7.0 Hz, 2H), 3.11 (s, 3H), 3.03 (br d, J = 13.1 Hz, 2H), 2.52- |

TABLE 3-continued

Representative Analytical Data for Compounds of the Disclosure.

| Cmpd. No. | LCMS Method | LCMS retention time (min) | LCMS M + H | $^1$H NMR |
|---|---|---|---|---|
| | | | | 2.59 (m, 2H), 2.01 (s, 3H), 1.62-1.89 (m, 4H), 1.33 (t, J = 6.9 Hz, 3H), 1.20 (d, J = 6.9 Hz, 3H) |
| 103 | Method 1 | 1.765 | 567 | $^1$H NMR (400 MHz, DMSO-$d_6$) δ ppm 8.36 (dd, J = 7.7, 1.9 Hz, 1H), 7.93 (d, J = 9.0 Hz, 1H), 7.22-7.30 (m, 2H), 7.16-7.21 (m, 1H), 7.08-7.14 (m, 2H), 6.71 (d, J = 2.6 Hz, 1H), 6.45 (d, J = 11.1 Hz, 1H), 6.24-6.31 (m, 1H), 5.29-5.40 (m, 1H), 4.76 (sept, J = 6.0 Hz, 1H), 3.11 (s, 3H), 2.98-3.10 (m, 2H), 2.52-2.59 (m, 2H), 2.02 (s, 3H), 1.62-1.94 (m, 4H), 1.28 (t, J = 5.4 Hz, 6H), 1.20 (d, J = 6.9 Hz, 3H) |
| 104 | Method 1 | 1.347 | 545 | $^1$H NMR (400 MHz, DMSO-$d_6$) δ ppm 10.67 (br s, 1H), 8.35 (br d, J = 5.7 Hz, 1H), 7.85 (d, J = 8.9 Hz, 1H), 7.50 (d, J = 7.4 Hz, 1H), 7.30-7.45 (m, 3H), 6.97 (dd, J = 8.8, 2.6 Hz, 1H), 6.62 (d, J = 2.5 Hz, 1H), 6.45 (d, J = 11.3 Hz, 1H), 6.28 (dd, J = 11.1, 9.5 Hz, 1H), 5.26-5.45 (m, 1H), 3.11 (s, 5H), 2.55-2.70 (m, 2H), 1.68-2.02 (m, 4H), 1.20 (d, J = 6.9 Hz, 3H) |
| 105 | Method 1 | 1.759 | 587 | $^1$H NMR (400 MHz, DMSO-$d_6$) δ ppm 8.36 (br d, J = 5.6 Hz, 1H), 7.93 (d, J = 8.9 Hz, 1H), 7.51 (d, J = 7.6 Hz, 1H), 7.32-7.43 (m, 3H), 7.15 (dd, J = 9.0, 2.6 Hz, 1H), 6.79 (d, J = 2.6 Hz, 1H), 6.45 (d, J = 11.1 Hz, 1H), 6.20-6.33 (m, 1H), 5.29-5.41 (m, 1H), 4.76 (dt, J = 12.0, 6.0 Hz, 1H), 3.11 (s, 5H), 2.61-2.72 (m, 2H), 1.64-2.03 (m, 4H), 1.29 (t, J = 6.1 Hz, 6H), 1.20 (d, J = 6.7 Hz, 3H) |
| 106 | Method 1 | 1.619 | 565 | $^1$H NMR (400 MHz, DMSO-$d_6$) δ ppm 8.37 (br d, J = 9.8 Hz, 1H), 7.98 (d, J = 8.9 Hz, 1H), 7.24-7.29 (m, 3H), 7.18-7.23 (m, 1H), 7.12-7.16 (m, 1H), 6.88 (d, J = 2.5 Hz, 1H), 6.46 (d, J = 11.2 Hz, 1H), 6.23-6.33 (m, 1H), 5.35 (br d, J = 7.9 Hz, 1H), 3.99 (dt, J = 6.0, 3.0 Hz, 1H), 3.12 (s, 3H), 3.01-3.11 (m, 2H), 2.53-2.61 (m, 2H), 2.03 (s, 3H), 1.63-1.96 (m, 4H), 1.21 (d, J = 6.9 Hz, 3H), 0.65-0.86 (m, 4H) |
| 107 | Method 2 | 2.66 | 555 | $^1$H NMR (400 MHz, DMSO-$d_6$) δ ppm 8.35 (dd, J = 7.8, 1.9 Hz, 1H), 7.98 (d, J = 8.2 Hz, 1H), 7.76 (dd, J = 8.3, 1.7 Hz, 1H), 7.49-7.57 (m, 1H), 7.33-7.48 (m, 4H), 6.84 (dd, J = 17.8, 11.0 Hz, 1H), 6.44 (d, J = 11.3 Hz, 1H), 6.27 (dd, J = 11.1, 9.5 Hz, 1H), 6.07 (d, J = 17.6 Hz, 1H), 5.48 (d, J = 11.1 Hz, 1H), 5.28-5.41 (m, 1H), 3.07-3.21 (m, 5H), 2.65-2.75 (m, 1H), 2.58 (br t, J = 12.6 Hz, 1H), 1.66-1.99 (m, 4H), 1.20 (d, J = 6.7 Hz, 3H) |
| 108 | Method 1 | 1.74 | 535 | $^1$H NMR (400 MHz, DMSO-$d_6$) δ ppm 8.36 (br d, J = 5.6 Hz, 1H), 7.96-8.02 (m, 1H), 7.67-7.76 (m, 1H), 7.35-7.38 (m, 1H), 7.25-7.30 (m, 2H), 7.18-7.24 (m, 1H), 7.11-7.17 (m, 1H), 6.83 (dd, J = 17.6, 11.1 Hz, 1H), 6.45 (d, J = 11.3 Hz, 1H), 6.23-6.33 (m, 1H), 6.06 (d, J = 17.8 Hz, 1H), 5.47 (d, J = 11.3 Hz, 1H), 5.27-5.39 (m, 1H), 3.15 (br s, 1H), 3.11 (s, 3H), 3.05 (br s, 1H), 2.55-2.62 (m, 2H), 2.00 (s, 3H), 1.76-1.96 (m, 2H), 1.70 (br s, 2H), 1.20 (d, J = 6.9 Hz, 3H) |
| 109 | Method 1 | 1.775 | 569 | $^1$H NMR (400 MHz, DMSO-$d_6$) δ ppm 8.37 (br d, J = 6.5 Hz, 1H), 8.00 (br d, J = 8.3 Hz, 1H), 7.77 (br d, J = 8.2 Hz, 1H), 7.54 (br d, J = 7.2 Hz, 1H), 7.41 (br d, J = 10.9 Hz, 3H), 6.45 (br d, J = 10.9 Hz, 1H), 6.28 (br t, J = 10.3 Hz, 1H), 5.63 (br s, 1H), 5.24-5.42 (m, 2H), 3.97-4.07 (m, 1H), 3.05-3.19 (m, 4H), 2.65-2.77 (m, 2H), 2.60 (br s, 1H), 2.14 (br s, 3H), 1.65-2.01 (m, 4H), 1.15-1.22 (m, 3H) |
| 110 | Method 1 | 1.796 | 549 | $^1$H NMR (400 MHz, DMSO-$d_6$) δ ppm 8.37 (br d, J = 6.0 Hz, 1H), 8.00 (d, J = 8.5 Hz, 1H), 7.73 (dd, J = 8.4, 2.0 Hz, 1H), 7.34 (d, J = 1.9 Hz, 1H), 7.24-7.31 (m, 2H), 7.21 (td, J = 6.9, 2.2 Hz, 1H), 7.13-7.17 (m, 1H), 6.45 (d, J = 11.3 Hz, 1H), 6.23-6.32 (m, 1H), 5.62 (s, 1H), 5.31-5.40 (m, 1H), 5.28 (s, 1H), 3.02-3.19 (m, 5H), 2.58 (br t, J = 12.7 Hz, 2H), 2.13 (s, 3H), 2.00 (s, 3H), 1.62-1.96 (m, 4H), 1.20 (d, J = 6.7 Hz, 3H) |
| 111 | Method 1 | 1.755 | 557.2 | $^1$H NMR (400 MHz, DMSO-$d_6$) δ ppm 8.34 (br d, J = 5.9 Hz, 1H), 7.94 (d, J = 8.1 Hz, 1H), 7.48-7.55 |

TABLE 3-continued

Representative Analytical Data for Compounds of the Disclosure.

| Cmpd. No. | LCMS Method | LCMS retention time (min) | LCMS M + H | $^1$H NMR |
|---|---|---|---|---|
| | | | | (m, 2H), 7.31-7.45 (m, 3H), 7.18 (d, J = 1.5 Hz, 1H), 6.45 (d, J = 11.3 Hz, 1H), 6.28 (dd, J = 11.1, 9.6 Hz, 1H), 5.29-5.40 (m, 1H), 3.10 (s, 5H), 2.70-2.76 (m, 2H), 2.64-2.69 (m, 1H), 2.55-2.60 (m, 1H), 1.79-2.01 (m, 2H), 1.71 (br d, J = 10.4 Hz, 2H), 1.17-1.24 (m, 6H) |
| 112 | Method 1 | 1.713 | 523.1 | $^1$H NMR (400 MHz, DMSO-$d_6$) δ ppm 8.34 (dd, J = 7.7, 1.9 Hz, 1H), 7.95 (d, J = 8.1 Hz, 1H), 7.46 (dd, J = 8.2, 1.7 Hz, 1H), 7.38-7.43 (m, 3H), 7.34-7.38 (m, 2H), 7.20 (d, J = 1.6 Hz, 1H), 6.45 (d, J = 11.1 Hz, 1H), 6.26 (dd, J = 11.1, 9.5 Hz, 1H), 5.27-5.39 (m, 1H), 3.11 (s, 3H), 3.08 (br d, J = 12.8 Hz, 2H), 2.66-2.77 (m, 2H), 2.37-2.46 (m, 2H), 1.57-1.80 (m, 4H), 1.17-1.24 (m, 6H) |
| 113 | Method 2 | 2.743 | 537 | $^1$H NMR (400 MHz, DMSO-$d_6$) δ ppm 8.34 (br d, J = 5.6 Hz, 1H), 7.93 (d, J = 8.2 Hz, 1H), 7.44 (dd, J = 8.3, 1.6 Hz, 1H), 7.23-7.29 (m, 2H), 7.16-7.22 (m, 1H), 7.08-7.14 (m, 2H), 6.44 (d, J = 11.1 Hz, 1H), 6.23-6.30 (m, 1H), 5.28-5.38 (m, 1H), 3.03-3.15 (m, 5H), 2.65-2.74 (m, 2H), 2.54-2.60 (m, 2H), 1.98 (s, 3H), 1.76-1.95 (m, 2H), 1.67 (br d, J = 11.1 Hz, 2H), 1.17-1.23 (m, 6H) |
| 114 | Method 1 | 1.808 | 57 | $^1$H NMR (400 MHz, DMSO-$d_6$) δ ppm 8.35 (br d, J = 6.0 Hz, 1H), 7.95 (d, J = 8.2 Hz, 1H), 7.49-7.56 (m, 2H), 7.34-7.45 (m, 3H), 7.20 (d, J = 1.5 Hz, 1H), 6.45 (d, J = 11.3 Hz, 1H), 6.28 (dd, J = 11.1, 9.6 Hz, 1H), 5.28-5.40 (m, 1H), 3.09-3.21 (m, 5H), 3.02 (dt, J = 13.7, 6.8 Hz, 1H), 2.64-2.75 (m, 1H), 2.54-2.61 (m, 1H), 1.64-2.00 (m, 4H), 1.17-1.25 (m, 9H) |
| 115 | Method 1 | 1.823 | 551 | $^1$H NMR (400 MHz, DMSO-$d_6$) δ ppm 8.30-8.39 (m, 1H), 7.95 (br d, J = 8.2 Hz, 1H), 7.48 (br d, J = 8.1 Hz, 1H), 7.10-7.29 (m, 5H), 6.45 (br d, J = 11.1 Hz, 1H), 6.20-6.35 (m, 1H), 5.26-5.41 (m, 1H), 3.11 (s, 5H), 2.95-3.03 (m, 1H), 2.54-2.63 (m, 2H), 1.99 (s, 3H), 1.64-1.88 (m, 4H), 1.16-1.27 (m, 9H) |
| 116 | Method 1 | 1.726 | 564.2 | $^1$H NMR (400 MHz, DMSO-$d_6$) δ ppm 8.34 (br d, J = 5.7 Hz, 1H), 7.76 (d, J = 8.8 Hz, 1H), 7.04-7.27 (m, 4H), 6.41-6.53 (m, 2H), 6.22-6.34 (m, 1H), 6.07 (d, J = 2.4 Hz, 1H), 5.27-5.41 (m, 1H), 3.93 (t, J = 7.3 Hz, 4H), 2.93-3.13 (m, 5H), 2.47 (br s, 2H), 2.34 (quin, J = 7.3 Hz, 2H), 1.96-2.06 (m, 3H), 1.59-1.95 (m, 4H), 1.20 (d, J = 6.9 Hz, 3H) |
| 117 | Method 1 | 1.728 | 564.2 | $^1$H NMR (400 MHz, DMSO-$d_6$) δ ppm 8.34 (br d, J = 7.8 Hz, 1H), 7.78 (d, J = 8.9 Hz, 1H), 7.39-7.31 (m, 5H), 6.64 (dd, J = 2.5, 9.0 Hz, 1H), 6.46 (d, J = 11.1 Hz, 1H), 6.36-6.20 (m, 2H), 5.43-5.25 (m, 1H), 3.31 (br s, 4H), 3.12 (s, 3H), 3.03 (br d, J = 12.5 Hz, 1H), 3.08-2.96 (m, 1H), 2.41 (br d, J = 13.0 Hz, 2H), 1.99-1.91 (m, 4H), 1.81-1.57 (m, 4H), 1.19 (d, J = 6.8 Hz, 3H) |
| 118 | Method 1 | 1.645 | 713 | $^1$H NMR (400 MHz, DMSO-$d_6$) δ ppm 8.34 (br d, J = 7.9 Hz, 1H), 7.80 (d, J = 9.0 Hz, 1H), 7.49 (d, J = 7.4 Hz, 1H), 7.29-7.41 (m, 3H), 7.06 (dd, J = 9.1, 2.6 Hz, 1H), 6.73 (d, J = 2.5 Hz, 1H), 6.45 (d, J = 11.0 Hz, 1H), 6.28 (dd, J = 11.1, 9.6 Hz, 1H), 5.28-5.42 (m, 1H), 3.43 (br d, J = 5.2 Hz, 4H), 3.34-3.38 (m, 4H), 3.11 (s, 5H), 2.54-2.68 (m, 2H), 1.63-1.87 (m, 4H), 1.41 (s, 9H), 1.20 (br d, J = 6.9 Hz, 3H) |
| 119 | Method 1 | 1.759 | 598.2 | $^1$H NMR (400 MHz, DMSO-$d_6$) δ ppm 8.35 (br d, J = 7.7 Hz, 1H), 7.74 (d, J = 8.9 Hz, 1H), 7.44-7.53 (m, 1H), 7.29-7.40 (m, 3H), 6.66 (dd, J = 9.0, 2.5 Hz, 1H), 6.45 (d, J = 11.1 Hz, 1H), 6.20-6.34 (m, 2H), 5.25-5.44 (m, 1H), 3.29 (br d, J = 4.5 Hz, 4H), 3.11 (s, 5H), 2.52-2.64 (m, 2H), 1.96 (br t, J = 6.4 Hz, 4H), 1.63-1.92 (m, 4H), 1.20 (d, J = 6.9 Hz, 3H) |
| 120 | Method 1 | 1.779 | 578 | $^1$H NMR (400 MHz, DMSO-$d_6$) δ ppm 8.36 (dd, J = 7.8, 2.1 Hz, 1H), 7.76 (d, J = 8.9 Hz, 1H), 7.13-7.28 (m, 3H), 7.06-7.12 (m, 1H), 6.63 (dd, J = 9.0, 2.5 Hz, 1H), 6.45 (d, J = 11.1 Hz, 1H), 6.24-6.34 (m, 1H), 6.22 (d, J = 2.5 Hz, 1H), 5.29-5.41 (m, |

TABLE 3-continued

Representative Analytical Data for Compounds of the Disclosure.

| Cmpd. No. | LCMS Method | LCMS retention time (min) | LCMS M + H | $^1$H NMR |
| --- | --- | --- | --- | --- |
| | | | | 1H), 3.29 (br t, J = 6.3 Hz, 4H), 3.11 (d, J = 1.1 Hz, 3H), 2.99 (br d, J = 12.6 Hz, 1H), 2.46 (br s, 2H), 2.04 (s, 3H), 1.95 (br t, J = 6.4 Hz, 4H), 1.92-1.99 (m, 1H), 1.60-1.91 (m, 4H), 1.20 (d, J = 6.9 Hz, 3H |
| 121 | Method 1 | 1.6 | 614 | $^1$H NMR (400 MHz, DMSO-$d_6$) δ ppm 8.36 (br d, J = 6.3 Hz, 1H), 7.80 (d, J = 9.0 Hz, 1H), 7.54-7.45 (m, 1H), 7.42-7.28 (m, 3H), 7.08 (dd, J = 2.5, 9.1 Hz, 1H), 6.75 (d, J = 2.4 Hz, 1H), 6.45 (d, J = 11.3 Hz, 1H), 6.33-6.22 (m, 1H), 5.44-5.26 (m, 1H), 3.70 (br t, J = 4.6 Hz, 4H), 3.29 (br d, J = 2.3 Hz, 5H), 3.11 (s, 4H), 2.69-2.52 (m, 2H), 2.01-1.68 (m, 4H), 1.20 (d, J = 6.9 Hz, 3H) |
| 122 | Method 1 | 1.608 | 594 | $^1$H NMR (400 MHz, DMSO-$d_6$) δ ppm 8.36 (dd, J = 7.8, 1.9 Hz, 1H), 7.82 (d, J = 9.0 Hz, 1H), 7.20-7.27 (m, 2H), 7.14-7.20 (m, 1H), 7.09-7.12 (m, 1H), 7.05 (dd, J = 9.1, 2.6 Hz, 1H), 6.67 (d, J = 2.5 Hz, 1H), 6.45 (d, J = 11.1 Hz, 1H), 6.24-6.31 (m, 1H), 5.29-5.40 (m, 1H), 3.70 (t, J = 4.7 Hz, 4H), 3.25-3.31 (m, 4H), 3.11 (s, 3H), 2.97-3.10 (m, 2H), 2.54 (br d, J = 3.0 Hz, 2H), 2.03 (s, 3H), 1.76-1.97 (m, 2H), 1.62-1.72 (m, 2H), 1.20 (d, J = 6.9 Hz, 3H) |
| 123 | Method 1 | 1.655 | 616 | $^1$H NMR (400 MHz, DMSO-$d_6$) δ ppm 8.35 (br d, J = 5.9 Hz, 1H), 7.73 (d, J = 8.9 Hz, 1H), 7.45 (dd, J = 8.9, 2.6 Hz, 1H), 7.35 (dd, J = 8.5, 6.3 Hz, 1H), 7.21 (td, J = 8.5, 2.6 Hz, 1H), 6.67 (dd, J = 8.9, 2.4 Hz, 1H), 6.45 (d, J = 11.4 Hz, 1H), 6.22-6.32 (m, 2H), 5.28-5.40 (m, 1H), 3.29 (br d, J = 4.5 Hz, 4H), 3.16 (br d, J = 12.1 Hz, 2H), 3.10 (s, 3H), 2.53-2.63 (m, 2H), 1.64-1.99 (m, 8H), 1.20 (d, J = 6.9 Hz, 3H) |
| 124 | Method 1 | 1.707 | 584.2 | $^1$H NMR (400 MHz, DMSO-$d_6$) δ ppm 8.32 (dd, J = 7.8, 2.3 Hz, 1H), 7.72 (d, J = 8.8 Hz, 1H), 7.44 (dd, J = 7.9, 1.1 Hz, 1H), 7.26-7.37 (m, 3H), 6.39-6.49 (m, 2H), 6.24 (dd, J = 11.1, 9.5 Hz, 1H), 6.10 (d, J = 2.4 Hz, 1H), 5.26-5.37 (m, 1H), 3.85-3.95 (m, 4H), 3.08 (s, 5H), 2.48-2.61 (m, 2H), 2.27-2.36 (m, 2H), 1.59-1.96 (m, 4H), 1.17 (d, J = 6.8 Hz, 3H) |
| 125 | Method 3 | 2.451 | 587.2 | $^1$H NMR (400 MHz, DMSO-$d_6$) δ ppm 8.33 (br d, J = 5.9 Hz, 1H), 8.05 (d, J = 8.6 Hz, 1H), 7.70 (dd, J = 8.5, 2.2 Hz, 1H), 7.44 (d, J = 2.2 Hz, 1H), 7.18-7.36 (m, 4H), 6.44 (d, J = 11.3 Hz, 1H), 6.26 (dd, J = 11.1, 9.6 Hz, 1H), 5.27-5.39 (m, 1H), 3.57 (t, J = 6.7 Hz, 2H), 3.24 (s, 3H), 3.02-3.13 (m, 5H), 2.85 (t, J = 6.7 Hz, 2H), 2.38-2.46 (m, 2H), 1.53-1.78 (m, 4H), 1.19 (d, J = 6.7 Hz, 3H) |
| 126 | Method 1 | 1.709 | 573.1 | $^1$H NMR (400 MHz, DMSO-$d_6$) δ ppm 8.36 (br d, J = 8.2 Hz, 1H), 8.05 (d, J = 8.5 Hz, 1H), 7.71 (dd, J = 8.6, 2.1 Hz, 1H), 7.30-7.47 (m, 5H), 6.45 (d, J = 11.1 Hz, 1H), 6.19-6.32 (m, 1H), 5.25-5.41 (m, 1H), 4.47 (s, 2H), 3.30 (s, 3H), 3.05-3.13 (m, 5H), 2.36-2.46 (m, 2H), 1.58-1.75 (m, 4H), 1.19 (d, J = 6.9 Hz, 3H) |
| 127 | Method 2 | 2.722 | 586.2 | $^1$H NMR (400 MHz, DMSO-$d_6$) δ ppm 8.35 (dd, J = 7.8, 2.1 Hz, 1H), 8.26 (s, 1H), 8.05 (d, J = 8.5 Hz, 1H), 7.73 (dd, J = 8.5, 2.3 Hz, 1H), 7.64-7.68 (m, 1H), 7.60 (s, 1H), 7.40-7.51 (m, 3H), 6.44 (dd, J = 11.1, 0.8 Hz, 1H), 6.26 (dd, J = 11.2, 9.5 Hz, 1H), 5.26-5.38 (m, 1H), 3.89 (s, 3H), 3.11 (s, 5H), 2.52-2.60 (m, 2H), 1.60-1.86 (m, 4H), 1.19 (d, J = 6.8 Hz, 3H) |
| 128 | Method 1 | 1.423 | 573.2 | $^1$H NMR (400 MHz, DMSO-$d_6$) δ ppm 8.39-8.49 (m, 1H), 7.99 (d, J = 8.1 Hz, 1H), 7.54-7.63 (m, 2H), 7.38-7.52 (m, 3H), 7.26 (d, J = 1.4 Hz, 1H), 6.52 (d, J = 11.1 Hz, 1H), 6.34 (dd, J = 11.1, 9.5 Hz, 1H), 5.33-5.50 (m, 1H), 4.78 (t, J = 5.1 Hz, 1H), 3.67-3.78 (m, 2H), 3.15-3.27 (m, 5H), 2.90 (t, J = 6.6 Hz, 2H), 2.61-2.75 (m, 2H), 1.67-2.10 (m, 4H), 1.27 (d, J = 6.9 Hz, 3H) |
| 129 | Method 1 | 1.444 | 573.1 | $^1$H NMR (400 MHz, DMSO-$d_6$) δ ppm 8.34-8.44 (m, 1H), 7.98 (d, J = 8.2 Hz, 1H), 7.62 (dd, J = 8.2, 1.6 Hz, 1H), 7.54 (d, J = 7.7 Hz, 1H), 7.33-7.48 (m, 3H), 7.29 (d, J = 1.2 Hz, 1H), 6.46 (d, J = 11.1 |

TABLE 3-continued

Representative Analytical Data for Compounds of the Disclosure.

| Cmpd. No. | LCMS Method | LCMS retention time (min) | LCMS M + H | $^1$H NMR |
|---|---|---|---|---|
| | | | | Hz, 1H), 6.28 (dd, J = 11.0, 9.6 Hz, 1H), 5.45 (dd, J = 4.4, 2.9 Hz, 1H), 5.28-5.41 (m, 1H), 4.79 (s, 1H), 3.07-3.19 (m, 5H), 2.58-2.70 (m, 2H), 1.63-2.04 (m, 4H), 1.35 (dd, J = 6.4, 2.1 Hz, 3H), 1.21 (d, J = 6.7 Hz, 3H) |
| 130 | Method 1 | 1.405 | 559.1 | $^1$H NMR (400 MHz, DMSO-$d_6$) δ ppm 8.34-8.39 (m, 1H), 7.96-8.01 (m, 1H), 7.57-7.61 (m, 1H), 7.53 (dd, J = 7.8, 1.2 Hz, 1H), 7.32-7.45 (m, 3H), 7.24-7.27 (m, 1H), 6.41-6.49 (m, 1H), 6.23-6.32 (m, 1H), 5.44-5.51 (m, 1H), 5.27-5.38 (m, 1H), 4.58-4.66 (m, 2H), 3.12-3.19 (m, 2H), 3.09-3.12 (m, 3H), 2.63-2.73 (m, 1H), 2.54-2.61 (m, 1H), 1.68-2.00 (m, 4H), 1.20 (d, J = 6.9 Hz, 3H) |
| 131 | Method 1 | 1.619 | 567 | $^1$H NMR (400 MHz, DMSO-$d_6$) δ ppm 8.36 (br d, J = 7.0 Hz, 1H), 7.93-8.01 (m, 1H), 7.62-7.92 (m, 1H), 7.38-7.62 (m, 4H), 7.28-7.37 (m, 1H), 6.45 (d, J = 11.1 Hz, 1H), 6.20-6.34 (m, 1H), 5.27-5.42 (m, 1H), 3.11 (s, 5H), 2.69 (br d, J = 16.6 Hz, 1H), 2.58-2.64 (m, 1H), 1.54-2.19 (m, 7H), 1.20 (d, J = 6.9 Hz, 3H) |
| 132 | Method 1 | 1.408 | 585 | $^1$H NMR (400 MHz, DMSO-$d_6$) δ ppm 8.42-8.29 (m, 1H), 8.04 (d, J = 8.3 Hz, 1H), 7.79-7.67 (m, 1H), 7.54 (d, J = 7.6 Hz, 1H), 7.46-7.29 (m, 4H), 6.45 (d, J = 11.4 Hz, 1H), 6.32-6.23 (m, 1H), 5.39-5.29 (m, 1H), 4.96 (ddd, J = 1.6, 6.2, 8.1 Hz, 2H), 4.63 (td, J = 6.3, 14.4 Hz, 2H), 4.43-4.33 (m, 1H), 3.28-3.25 (m, 1H), 3.20-3.02 (m, 4H), 2.74-2.65 (m, 1H), 2.61-2.57 (m, 1H), 1.98-1.68 (m, 4H), 1.23 (s, 3H) |
| 133 | Method 1 | 1.649 | 619 | $^1$H NMR (400 MHz, DMSO-$d_6$) δ ppm 8.11 (d, J = 8.3 Hz, 1H), 7.81-7.94 (m, 2H), 7.56 (d, J = 1.7 Hz, 1H), 7.48-7.53 (m, 1H), 7.37-7.44 (m, 1H), 7.32-7.36 (m, 2H), 6.40 (d, J = 11.0 Hz, 1H), 6.24 (d, J = 9.4 Hz, 1H), 5.25-5.35 (m, 1H), 3.08 (s, 3H), 2.99 (s, 3H), 2.92-2.98 (m, 2H), 2.50-2.54 (m, 2H), 1.61-1.71 (m, 4H), 1.15 (d, J = 6.8 Hz, 3H) |
| 134 | Method 1 | 1.71 | 638.2 | $^1$H NMR (400 MHz, DMSO-$d_6$) δ ppm 8.34 (dd, J = 1.7, 8.2 Hz, 1H), 8.26 (d, J = 8.4 Hz, 1H), 8.06 (dd, J = 1.4, 8.4 Hz, 1H), 7.74 (s, 1H), 7.58 (d, J = 7.9 Hz, 1H), 7.52-7.39 (m, 3H), 6.66 (dd, J = 5.9, 15.5 Hz, 1H), 5.93 (dd, J = 1.2, 15.4 Hz, 1H), 4.62 (br t, J = 10.9 Hz, 2H), 4.56-4.48 (m, 1H), 4.31 (br t, J = 11.4 Hz, 2H), 3.24-3.18 (m, 2H), 2.78 (dt, J = 2.6, 12.6 Hz, 1H), 2.69-2.58 (m, 1H), 2.06-1.75 (m, 4H), 1.19 (d, J = 7.0 Hz, 3H) |
| 135 | Method 1 | 1.698 | 648 | $^1$H NMR (400 MHz, $CD_3SOCD_3$) δ ppm 8.35 (br d, J = 7.2 Hz, 1H), 7.98-7.94 (m, 1H), 7.91-7.87 (m, 1H), 7.61 (d, J = 1.8 Hz, 1H), 7.55 (d, J = 7.9 Hz, 1H), 7.48-7.42 (m, 1H), 7.40 (d, J = 4.6 Hz, 2H), 6.66 (dd, J = 6.0, 15.2 Hz, 1H), 5.94 (d, J = 15.3 Hz, 1H), 4.66-4.59 (m, 2H), 4.56-4.49 (m, 1H), 4.36-4.28 (m, 2H), 3.19-3.13 (m, 2H), 2.77-2.69 (m, 1H), 2.64-2.56 (m, 1H), 2.02-1.81 (m, 2H), 1.80-1.72 (m, 2H), 1.19 (d, J = 7.0 Hz, 3H) |
| 136 | Method 1 | 1.549 | 595.2 | $^1$H NMR (400 MHz, DMSO-$d_6$) δ ppm 8.33-8.40 (m, 1H), 8.19-8.24 (m, 1H), 8.13-8.17 (m, 1H), 7.97 (d, J = 1.5 Hz, 1H), 7.55-7.61 (m, 1H), 7.41-7.50 (m, 3H), 6.66 (dd, J = 15.4, 5.8 Hz, 1H), 5.93 (dd, J = 15.4, 0.9 Hz, 1H), 4.57-4.68 (m, 2H), 4.49-4.56 (m, 1H), 4.25-4.37 (m, 2H), 3.14-3.22 (m, 2H), 2.73-2.84 (m, 1H), 2.57-2.68 (m, 1H), 1.71-1.95 (m, 4H), 1.19 (d, J = 7.0 Hz, 3H) |
| 137 | Method 1 | 1.571 | 600.2 | $^1$H NMR (400 MHz, DMSO-$d_6$) δ ppm 8.30-8.38 (m, 1H), 7.92-8.01 (m, 1H), 7.52 (d, J = 7.5 Hz, 1H), 7.39-7.45 (m, 1H), 7.34-7.38 (m, 2H), 7.19 (dd, J = 8.9, 2.6 Hz, 1H), 6.85 (d, J = 2.6 Hz, 1H), 6.66 (dd, J = 15.4, 5.9 Hz, 1H), 5.93 (d, J = 15.4 Hz, 1H), 4.56-4.70 (m, 2H), 4.47-4.56 (m, 1H), 4.31 (br t, J = 12.0 Hz, 2H), 3.86 (s, 3H), 3.13 (br d, J = 12.0 Hz, 2H), 2.53-2.73 (m, 2H), 1.81-2.03 (m, 2H), 1.68-1.78 (m, 2H), 1.19 (d, J = 6.9 Hz, 3H) |
| 138 | Method 4 | 2.949 | 612.2 | $^1$H NMR (400 MHz, DMSO-$d_6$) δ ppm 8.34 (br d, J = 6.6 Hz, 1H), 8.14-8.23 (m, 2H), 7.82 (s, 1H), |

TABLE 3-continued

| Representative Analytical Data for Compounds of the Disclosure. | | | | |
|---|---|---|---|---|
| Cmpd. No. | LCMS Method | LCMS retention time (min) | LCMS M + H | $^1$H NMR |
| | | | | 7.57 (d, J = 7.5 Hz, 1H), 7.37-7.51 (m, 3H), 6.66 (dd, J = 15.4, 5.9 Hz, 1H), 5.94 (dd, J = 15.4, 1.1 Hz, 1H), 4.45-4.74 (m, 3H), 4.31 (br t, J = 11.8 Hz, 2H), 3.20 (br d, J = 11.5 Hz, 2H), 2.75 (br t, J = 11.5 Hz, 1H), 2.55-2.67 (m, 4H), 1.69-2.06 (m, 4H), 1.19 (d, J = 7.0 Hz, 3H) |
| 139 | Method 3 | 2.884 | 609 | $^1$H NMR (400 MHz, DMSO-$d_6$) δ ppm 8.23 (d, J = 8.5 Hz, 1H), 8.14 (d, J = 8.3 Hz, 1H), 8.02-8.07 (m, 1H), 7.73 (s, 1H), 7.56 (d, J = 7.9 Hz, 1H), 7.43-7.50 (m, 1H), 7.40-7.42 (m, 2H), 6.40-6.45 (m, 1H), 6.21-6.29 (m, 1H), 5.28-5.38 (m, 1H), 3.10 (s, 3H), 2.97-3.06 (m, 5H), 2.68-2.79 (m, 1H), 2.57-2.62 (m, 1H), 1.60-1.76 (m, 4H), 1.18 (d, J = 7.0 Hz, 3H) |
| 140 | Method 4 | 2.789 | 614.2 | $^1$H NMR (400 MHz, DMSO-$d_6$) δ ppm 8.28-8.36 (m, 1H), 7.98 (d, J = 8.3 Hz, 1H), 7.62 (dd, J = 8.3, 1.5 Hz, 1H), 7.53 (d, J = 7.9 Hz, 1H), 7.34-7.45 (m, 3H), 7.29 (d, J = 1.4 Hz, 1H), 6.66 (dd, J = 15.4, 5.9 Hz, 1H), 5.93 (dd, J = 15.5, 1.3 Hz, 1H), 5.43 (dd, J = 4.4, 2.9 Hz, 1H), 4.78-4.90 (m, 1H), 4.46-4.68 (m, 3H), 4.24-4.40 (m, 2H), 3.16 (br s, 2H), 2.69 (br t, J = 11.4 Hz, 1H), 2.56 (br t, J = 12.5 Hz, 1H), 1.68-2.03 (m, 4H), 1.35 (dd, J = 6.5, 2.1 Hz, 3H), 1.19 (d, J = 7.0 Hz, 3H) |
| 141 | Method 3 | 2.734, 2.781 | 573 | $^1$H NMR (400 MHz, DMSO-$d_6$) δ ppm 8.35 (br dd, J = 2.6, 7.6 Hz, 1H), 8.05-7.92 (m, 1H), 7.62-7.49 (m, 1H), 7.46-7.31 (m, 3H), 7.19-7.11 (m, 1H), 6.89-6.75 (m, 1H), 6.44 (d, J = 11.1 Hz, 1H), 6.26 (dd, J = 9.6, 11.1 Hz, 1H), 5.41-5.25 (m, 1H), 3.85 (s, 3H), 3.15-3.07 (m, 3H), 2.95-2.72 (m, 1H), 2.31-2.23 (m, 1H), 2.13-1.74 (m, 2H), 1.74-1.44 (m, 3H), 1.24-1.15 (m, 3H), 1.08-0.97 (m, 3H) |
| 142 | Method 1 | 1.714 | 611.1 | $^1$H NMR (400 MHz, $CD_3SOCD_3$, 298K) δ ppm 8.43 (br d, J = 5.5 Hz, 1H), 8.35 (d, J = 8.4 Hz, 1H), 8.10 (dd, J = 1.3, 8.4 Hz, 1H), 7.80 (s, 1H), 7.72-7.61 (m, 1H), 7.59-7.44 (m, 3H), 6.51 (d, J = 11.1 Hz, 1H), 6.32 (dd, J = 9.6, 11.0 Hz, 1H), 5.40 (td, J = 7.5, 15.5 Hz, 1H), 3.57-3.45 (m, 1H), 3.18 (d, J = 1.5 Hz, 3H), 3.08-2.82 (m, 1H), 2.47-2.35 (m, 1H), 2.21-2.02 (m, 1H), 2.01-1.83 (m, 1H), 1.82-1.74 (m, 1H), 1.72-1.62 (m, 1H), 1.27 (d, J = 6.9 Hz, 3H), 1.15-1.06 (m, 3H) |
| 143 | Method 1 | 1.704 | 621 | $^1$H NMR (400 MHz, DMSO-$d_6$) δ ppm 8.37 (br d, J = 5.4 Hz, 1H), 7.98 (d, J = 8.5 Hz, 1H), 7.86 (br d, J = 8.7 Hz, 1H), 7.51-7.64 (m, 2H), 7.32-7.50 (m, 3H), 6.45 (d, J = 11.2 Hz, 1H), 6.26 (t, J = 10.3 Hz, 1H), 5.26-5.42 (m, 1H), 3.40 (br dd, J = 10.4, 7.3 Hz, 1H), 3.11 (d, J = 2.0 Hz, 3H), 2.60-2.99 (m, 1H), 2.33 (br s, 1H), 1.76-2.16 (m, 2H), 1.50-1.72 (m, 2H), 1.20 (d, J = 6.9 Hz, 3H), 1.00-1.09 (m, 3H) |
| 144 | Method 1 | 1.566 | 568.1 | $^1$H NMR (400 MHz, DMSO-$d_6$) δ ppm 8.36-8.41 (m, 1H), 8.23 (d, J = 8.3 Hz, 1H), 8.13 (dd, J = 8.3, 1.8 Hz, 1H), 7.95 (d, J = 1.2 Hz, 1H), 7.56-7.67 (m, 1H), 7.35-7.52 (m, 3H), 6.45 (d, J = 11.2 Hz, 1H), 6.26 (dd, J = 11.1, 9.6 Hz, 1H), 5.28-5.39 (m, 1H), 3.38-3.52 (m, 1H), 3.10-3.13 (m, 3H), 2.65-2.99 (m, 1H), 2.31-2.41 (m, 1H), 1.57-2.11 (m, 4H), 1.20 (d, J = 6.8 Hz, 3H), 1.00-1.06 (m, 3H) |
| 145 | Method 1 | 1.903 | 621.2 | $^1$H NMR (400 MHz, DMSO-$d_6$) δ ppm 8.38 (br d, J = 7.6 Hz, 1H), 7.96 (d, J = 8.4 Hz, 1H), 7.85 (dd, J = 8.8, 2.0 Hz, 1H), 7.62 (d, J = 2.0 Hz, 1H), 7.41-7.55 (m, 3H), 7.35 (d, J = 7.2 Hz, 1H), 6.44 (d, J = 11.2 Hz, 1H), 6.20-6.29 (m, 1H), 5.26-5.41 (m, 1H), 3.32-3.40 (m, 1H), 3.11 (s, 3H), 3.05-3.11 (m, 1H), 2.55 (br d, J = 2.8 Hz, 1H), 1.52-1.98 (m, 4H), 1.12-1.26 (m, 3H), 0.93 (d, J = 6.8 Hz, 3H) |
| 146 | Method 1 | 1.567 | 571 | $^1$H NMR (400 MHz, DMSO-$d_6$) δ ppm 8.11 (d, J = 8.0 Hz, 1H), 7.93 (d, J = 8.9 Hz, 1H), 7.50 (d, J = 7.7 Hz, 1H), 7.44-7.31 (m, 3H), 7.18 (dd, J = 2.7, 9.0 Hz, 1H), 6.83 (d, J = 2.6 Hz, 1H), 6.43 (d, J = 11.2 Hz, 1H), 6.30-6.23 (m, 1H), 5.40-5.28 (m, 1H), 3.85 (s, 3H), 3.11 (s, 3H), 3.02 (s, 3H), 3.00- |

TABLE 3-continued

Representative Analytical Data for Compounds of the Disclosure.

| Cmpd. No. | LCMS Method | LCMS retention time (min) | LCMS M + H | $^1$H NMR |
|---|---|---|---|---|
| | | | | 2.92 (m, 2H), 2.65-2.52 (m, 2H), 1.74-1.56 (m, 4H), 1.19 (d, J = 6.9 Hz, 3H) |
| 147 | Method 12 | 2.592 | 573 | $^1$H NMR (400 MHz, DMSO-$d_6$) δ ppm 8.37 (ddd, J = 2.4, 7.7, 15.0 Hz, 1H), 7.99 (d, J = 8.9 Hz, 1H), 7.54-7.46 (m, 1H), 7.45-7.23 (m, 3H), 7.21-7.14 (m, 1H), 6.83 (dd, J = 2.7, 9.8 Hz, 1H), 6.45 (d, J = 11.1 Hz, 1H), 6.28 (ddd, J = 4.0, 9.5, 11.1 Hz, 1H), 5.42-5.27 (m, 1H), 3.85 (s, 3H), 3.77-3.59 (m, 1H), 3.16-3.10 (m, 3H), 3.06-2.91 (m, 2H), 2.09-1.57 (m, 4H), 1.23-1.16 (m, 3H), 1.14-1.00 (m, 3H) |
| 148 | Method 2 | 2.652 | 573 | $^1$H NMR (400 MHz, DMSO-$d_6$) δ ppm 8.38 (ddd, J = 2.3, 8.0, 16.0 Hz, 1H), 7.99 (d, J = 8.9 Hz, 1H), 7.51 (d, J = 7.8 Hz, 1H), 7.45-7.23 (m, 3H), 7.17 (td, J = 2.1, 9.0 Hz, 1H), 6.83 (dd, J = 2.6, 9.3 Hz, 1H), 6.45 (d, J = 11.1 Hz, 1H), 6.28 (ddd, J = 2.4, 9.3, 11.3 Hz, 1H), 5.44-5.27 (m, 1H), 3.85 (s, 3H), 3.75-3.61 (m, 1H), 3.15-3.07 (m, 3H), 3.06-2.94 (m, 2H), 2.13-1.58 (m, 4H), 1.24-1.16 (m, 3H), 1.15-0.99 (m, 3H) |
| 149 | Method 1 | 1.72 | 587.3 | $^1$H NMR (400 MHz, DMSO-$d_6$) δ ppm 8.35 (br dd, J = 7.5, 2.5 Hz, 1H), 8.03 (d, J = 8.2 Hz, 1H), 7.52-7.63 (m, 2H), 7.33-7.47 (m, 3H), 7.22-7.27 (m, 1H), 6.44 (d, J = 11.1 Hz, 1H), 6.26 (dd, J = 11.1, 9.6 Hz, 1H), 5.34 (dt, J = 15.6, 7.6 Hz, 1H), 4.53 (s, 2H), 3.33 (s, 2H), 3.11 (d, J = 2.1 Hz, 3H), 2.65-3.00 (m, 2H), 2.25-2.37 (m, 1H), 1.94-2.13 (m, 1H), 1.49-1.90 (m, 4H), 1.20 (d, J = 6.9 Hz, 3H), 1.04 (br d, J = 7.1 Hz, 3H) |
| 150 | Method 1 | 1.741 | 587.3 | $^1$H NMR (400 MHz, DMSO-$d_6$) δ ppm 8.45-8.26 (m, 1H), 8.08-7.95 (m, 1H), 7.58-7.33 (m, 4H), 7.25-7.11 (m, 1H), 6.85-6.78 (m, 1H), 6.46 (d, J = 11.2 Hz, 1H), 6.32-6.18 (m, 1H), 5.44-5.30 (m, 1H), 3.85 (s, 3H), 3.19-3.11 (m, 3H), 3.11-2.84 (m, 2H), 2.10-1.50 (m, 3H), 1.48-1.39 (m, 1H), 1.36-1.28 (m, 3H), 1.23-1.18 (m, 3H), 1.14-1.03 (m, 3H) |
| 151 | Method 1 | 1.624 | 614.2 | $^1$H NMR (400 MHz, DMSO-$d_6$) δ ppm 8.32 (br d, J = 7.7 Hz, 1H), 7.98 (dd, J = 8.8, 1.8 Hz, 1H), 7.31-7.64 (m, 4H), 7.16 (dt, J = 8.8, 3.3 Hz, 1H), 6.83 (t, J = 3.1 Hz, 1H), 6.56-6.72 (m, 1H), 5.82-6.03 (m, 1H), 4.62 (br t, J = 11.6 Hz, 2H), 4.44-4.55 (m, 1H), 4.31 (br t, J = 11.6 Hz, 2H), 3.85 (s, 3H), 3.34-3.39 (m, 1H), 2.73-2.94 (m, 1H), 2.22-2.35 (m, 1H), 1.66-2.16 (m, 3H), 1.51-1.61 (m, 1H), 1.19 (d, J = 6.9 Hz, 3H), 0.96-1.09 (m, 3H) |
| 152 | Method 5 | 2.948,2.83 | 652.2 | $^1$H NMR (400 MHz, DMSO-$d_6$) δ ppm 8.26-8.37 (m, 2 H) 8.04 (br d, J = 8.1 Hz, 1H), 7.74 (s, 1H), 7.55-7.67 (m, 1H), 7.38-7.52 (m, 3H), 6.66 (dd, J = 15.4, 6.1 Hz, 1H), 5.96 (d, J = 15.4 Hz, 1H), 4.47-4.71 (m, 3H), 4.24-4.39 (m, 2H), 3.37-3.51 (m, 1H), 2.67-3.01 (m, 1H), 2.29-2.40 (m, 1H), 1.56-1.67 (m, 1H), 1.55-2.17 (m, 3H), 1.19 (d, J = 6.9 Hz, 3H), 1.01-1.09 (m, 3H) |
| 153 | Method 1 | 1.733 | 662.1 | $^1$H NMR (400 MHz, DMSO-$d_6$) δ ppm 8.29-8.36 (m, 1H), 7.99 (d, J = 8.6 Hz, 1H), 7.84-7.90 (m, 1H), 7.52-7.64 (m, 2H), 7.32-7.51 (m, 3H), 6.65 (ddd, J = 15.4, 6.1, 1.2 Hz, 1H), 5.96 (dd, J = 15.4, 1.0 Hz, 1H), 4.44-4.71 (m, 3H), 4.31 (br t, J = 11.5 Hz, 2H), 3.41 (td, J = 7.3, 3.7 Hz, 1H), 2.94 (dt, J = 13.4, 4.2 Hz, 1H), 2.78 (dt, J = 13.8, 3.8 Hz, 1H), 2.33 (br t, J = 11.8 Hz, 1H), 1.83-2.18 (m, 1H), 1.69-1.79 (m, 1H), 1.49-1.66 (m, 1H), 1.19 (d, J = 6.9 Hz, 3H), 0.99-1.10 (m, 3H) |
| 154 | Method 1 | 1.596 | 609.2 | $^1$H NMR (400 MHz, DMSO-$d_6$) δ ppm 8.29-8.39 (m, 1H), 8.24 (d, J = 8.2 Hz, 1H), 8.13 (dd, J = 8.2, 1.2 Hz, 1H), 7.95 (s, 1H), 7.55-7.66 (m, 1H), 7.35-7.52 (m, 3H), 6.65 (dd, J = 15.5, 6.1 Hz, 1H), 5.96 (d, J = 15.4 Hz, 1H), 4.58-4.68 (m, 2H), 4.48-4.54 (m, 1H), 4.33 (br d, J = 11.1 Hz, 2H), 3.38-3.53 (m, 1H), 2.64-3.03 (m, 2H), 2.36 (br t, J = 11.6 Hz, 1H), 1.85-2.12 (m, 1H), 1.70-1.82 (m, 1H), 1.54-1.66 (m, 1H), 1.19 (d, J = 6.7 Hz, 3H), 0.97-1.09 (m, 3H) |

TABLE 3-continued

Representative Analytical Data for Compounds of the Disclosure.

| Cmpd. No. | LCMS Method | LCMS retention time (min) | LCMS M + H | $^1$H NMR |
|---|---|---|---|---|
| 155 | Method 4 | 3.428 | 661.9 | $^1$H NMR (400 MHz, DMSO-$d_6$) δ ppm 8.34 (br d, J = 7.8 Hz, 1H), 7.97 (d, J = 8.5 Hz, 1H), 7.85 (br d, J = 8.4 Hz, 1H), 7.61 (s, 1H), 7.43-7.57 (m, 3H), 7.35 (br d, J = 7.0 Hz, 1H), 6.65 (dd, J = 15.4, 6.1 Hz, 1H), 5.95 (br d, J = 15.3 Hz, 1H), 4.44-4.72 (m, 3H), 4.22-4.42 (m, 2H), 3.35 (br dd, J = 6.8, 3.6 Hz, 1H), 3.05-3.15 (m, 1H), 2.54 (br s, 1H), 1.79-2.00 (m, 1H), 1.50-1.77 (m, 3H), 1.14-1.24 (m, 3H), 0.95 (br d, J = 6.7 Hz, 3H) |
| 156 | Method 1 | 1.74 | 628.3 | $^1$H NMR (400 MHz, DMSO-$d_6$) δ ppm 8.24-8.38 (m, 1H), 8.04 (br d, J = 8.0 Hz, 1H), 7.50-7.64 (m, 2H), 7.31-7.48 (m, 3H), 7.24 (br d, J = 5.2 Hz, 1H), 6.65 (br dd, J = 15.3, 5.9 Hz, 1H), 5.95 (br d, J = 15.3 Hz, 1H), 4.57-4.73 (m, 2H), 4.45-4.56 (m, 3H), 4.21-4.41 (m, 2H), 3.38-3.46 (m, 2H), 2.66-3.05 (m, 2H), 2.27-2.44 (m, 1H), 1.82-2.17 (m, 2H), 1.47-1.79 (m, 3H), 1.19 (br d, J = 6.6 Hz, 3H) 0.97-1.08 (m, 3H) |
| 157 | Method 1 | 1.637 | 585.1 | $^1$H NMR (400 MHz, DMSO-$d_6$) δ ppm 8.80 (s, 1H), 8.37 (dd, J = 7.9, 2.3 Hz, 1H), 8.15 (d, J = 5.4 Hz, 1H), 7.84 (s, 1H), 7.52-7.64 (m, 2H), 7.35-7.48 (m, 3H), 6.45 (dd, J = 11.2, 0.7 Hz, 1H), 6.27 (dd, J = 11.1, 9.5 Hz, 1H), 5.25-5.41 (m, 1H), 3.06-3.20 (m, 5H), 2.68-2.79 (m, 1H), 2.56-2.65 (m, 1H), 1.78-2.07 (m, 2H), 1.64-1.77 (m, 2H), 1.20 (d, J = 6.9 Hz, 3H) |
| 158 | Method 1 | 1.536 | 586.3 | $^1$H NMR (400 MHz, DMSO-$d_6$) δ ppm 8.39-8.17 (m, 1H), 7.50-7.40 (m, 1H), 7.20-7.14 (m, 1H), 7.36-7.13 (m, 2H), 6.50-6.40 (m, 1H), 6.31-6.20 (m, 1H), 5.32 (br d, J = 8.5 Hz, 1H), 4.14-3.95 (m, 2H), 3.90 (br s, 1H), 3.74-3.45 (m, 5H), 3.29 (br s, 1H), 3.18-3.03 (m, 3H), 2.69-2.56 (m, 1H), 2.42-2.30 (m, 1H), 2.03-1.72 (m, 2H), 1.70-1.49 (m, 2H), 1.47-1.38 (m, 9H), 1.26-1.14 (m, 3H) |
| 159 | Method 1 | 1.478 | 572 | $^1$H NMR (400 MHz, DMSO-$d_6$) δ ppm 8.37-8.20 (m, 1H), 7.45 (br d, J = 7.2 Hz, 1H), 7.34-7.13 (m, 3H), 6.45 (d, J = 11.2 Hz, 1H), 6.31-6.21 (m, 1H), 5.33 (br s, 1H), 4.85-4.74 (m, 1H), 4.15-3.99 (m, 3H), 3.78-3.59 (m, 4H), 3.58-3.53 (m, 1H), 3.12 (d, J = 17.9 Hz, 3H), 2.69-2.54 (m, 1H), 2.40-2.31 (m, 1H), 2.01-1.72 (m, 1H), 1.69-1.44 (m, 2H), 1.28-1.23 (m, 1H), 1.20 (t, J = 7.3 Hz, 9H) |
| 160 | Method 1 | 1.429 | 558 | $^1$H NMR (400 MHz, DMSO-$d_6$) δ ppm 8.37-8.21 (m, 1H), 7.47-7.42 (m, 1H), 7.33-7.15 (m, 3H), 6.45 (d, J = 11.2 Hz, 1H), 6.32-6.21 (m, 1H), 5.33 (br d, J = 6.3 Hz, 1H), 4.15-4.01 (m, 4H), 3.91 (br s, 1H), 3.80-3.50 (m, 5H), 3.12 (d, J = 18.1 Hz, 3H), 2.69-2.52 (m, 1H), 2.40-2.30 (m, 1H), 2.01-1.73 (m, 1H), 1.70-1.56 (m, 1H), 1.53 (br d, J = 12.2 Hz, 1H), 1.32-1.22 (m, 0.5H), 1.22-1.14 (m, 6H), 0.94-0.70 (m, 0.5H) |
| 161 | Method 1 | 1.439 | 570 | $^1$H NMR (400 MHz, DMSO-$d_6$) δ ppm 8.38-8.23 (m, 1H), 7.44 (br t, J = 7.3 Hz, 1H), 7.35-7.14 (m, 3H), 6.45 (d, J = 11.0 Hz, 1H), 6.27 (dt, J = 5.5, 10.3 Hz, 1H), 5.33 (br s, 1H), 4.18-3.98 (m, 3H), 3.96-3.53 (m, 5H), 3.12 (d, J = 16.9 Hz, 3H), 2.62 (br s, 1H), 2.43-2.34 (m, 1H), 2.04-1.76 (m, 1H), 1.69-1.47 (m, 2H), 1.35 (br s, 1H), 1.24-1.07 (m, 12H) |
| 162 | Method 1 | 1.439 | 590 | $^1$H NMR (400 MHz, DMSO-$d_6$) δ ppm 8.36-8.21 (m, 1H), 7.61-7.52 (m, 2H), 7.50-7.40 (m, 4H), 7.38-7.14 (m, 3H), 6.48-6.41 (m, 1H), 6.32-6.22 (m, 1H), 5.32 (br d, J = 6.7 Hz, 1H), 4.26-3.98 (m, 3H), 3.95-3.66 (m, 4H), 3.64-3.43 (m, 1H), 3.17-3.06 (m, 3H), 2.48-2.45 (m, 1H), 2.38 (br d, J = 12.4 Hz, 1H), 1.98-1.84 (m, 1H), 1.76-1.58 (m, 1H), 1.49 (br s, 2H), 1.19 (td, J = 3.5, 6.8 Hz, 3H) |
| 163 | Method 3 | 2.151 | 568 | $^1$H NMR (400 MHz, DMSO-$d_6$) δ ppm 8.39-8.16 (m, 1H), 7.52-7.39 (m, 1H), 7.34-7.20 (m, 3H), 6.45 (d, J = 11.2 Hz, 1H), 6.26 (ddd, J = 4.1, 9.5, 11.1 Hz, 1H), 5.36-5.31 (m, 1H), 4.25-4.11 (m, 1H), 4.05 (br d, J = 13.0 Hz, 1H), 3.99-3.60 (m, 4H), 3.58-3.41 (m, 4H), 3.34-3.15 (m, 1H), 3.12 (d, J = 17.5 Hz, 3H), 2.65-2.56 (m, 1H), 2.39-2.32 |

TABLE 3-continued

Representative Analytical Data for Compounds of the Disclosure.

| Cmpd. No. | LCMS Method | LCMS retention time (min) | LCMS M + H | $^1$H NMR |
|---|---|---|---|---|
| | | | | (m, 1H), 2.19 (dt, J = 2.8, 12.7 Hz, 1H), 2.00-1.66 (m, 1H), 1.63-1.45 (m, 2H), 1.25-1.13 (m, 3H), 1.10-0.84 (m, 1H) |
| 164 | Method 1 | 1.249 | 552.1 | $^1$H NMR (400 MHz, DMSO-$d_6$) δ ppm 8.68-8.88 (m, 1H), 7.38-7.44 (m, 1H), 7.29-7.34 (m, 1H), 7.22-7.28 (m, 2H), 7.18 (dt, J = 6.7, 2.3 Hz, 1H), 6.76 (td, J = 6.4, 2.5 Hz, 1H), 5.05-5.22 (m, 1H), 3.96-4.24 (m, 2H), 3.53-3.93 (m, 3H), 3.41 (q, J = 10.0 Hz, 2H), 3.06-3.25 (m, 4H), 2.80-2.98 (m, 1H), 2.56-2.66 (m, 1H), 2.12-2.25 (m, 1H), 1.67-2.07 (m, 1H), 1.49-1.64 (m, 2H), 0.98-1.17 (m, 1H) |
| 165 | Method 1 | 1.326 | 582.2 | $^1$H NMR (400 MHz, DMSO-$d_6$) δ ppm 8.24 (br d, J = 4.8 Hz, 1H), 7.44-7.29 (m, 2H), 7.26-7.18 (m, 2H), 6.48-6.38 (m, 1H), 6.34-6.18 (m, 1H), 5.36-5.24 (m, 1H), 4.14-3.97 (m, 1H), 3.87-3.69 (m, 1H), 3.59-3.45 (m, 1H), 3.39 (br d, J = 10.2 Hz, 2H), 3.31-3.16 (m, 4H), 3.15-2.98 (m, 3H), 2.86 (q, J = 9.0 Hz, 2H), 2.74-2.62 (m, 1H), 2.01-1.45 (m, 6H), 1.26-1.13 (m, 3H) |
| 166 | Method 4 | 3.04 | 600.2 | $^1$H NMR (400 MHz, DMSO-$d_6$) δ ppm 8.22-8.33 (m, 1H), 7.37-7.47 (m, 1H), 7.16-7.27 (m, 1H), 7.05-7.14 (m, 1H), 6.39-6.48 (m, 1H), 6.22-6.31 (m, 1H), 5.31 (dt, J = 15.6, 7.7 Hz, 1H), 3.77-4.09 (m, 2H), 3.51-3.63 (m, 1H), 3.35-3.46 (m, 3H), 3.26-3.30 (m, 1H), 3.14-3.22 (m, 2H), 3.08-3.13 (m, 3H), 2.97-3.06 (m, 1H), 2.62-2.88 (m, 2H), 1.55-2.04 (m, 6H), 1.17-1.23 (m, 3H) |
| 167 | Method 1 | 1.434 | 600.1 | $^1$H NMR (400 MHz, DMSO-$d_6$) δ ppm 8.32-8.21 (m, 1H), 7.45-7.29 (m, 2H), 7.20-7.08 (m, 1H), 6.50-6.37 (m, 1H), 6.32-6.20 (m, 1H), 5.38-5.23 (m, 1H), 4.10-3.93 (m, 1H), 3.88-3.71 (m, 1H), 3.57-3.50 (m, 1H), 3.43-3.36 (m, 3H), 3.26 (br dd, J = 6.7, 9.4 Hz, 1H), 3.22-3.16 (m, 2H), 3.14-3.08 (m, 3H), 3.02-2.91 (m, 1H), 2.88-2.64 (m, 2H), 2.01-1.53 (m, 6H), 1.24-1.15 (m, 3H) |
| 168 | Method 2 | 2.344 | 600.1 | $^1$H NMR (400 MHz, DMSO-$d_6$) δ ppm 8.18-8.30 (m, 1H), 7.14-7.36 (m, 3H), 6.38-6.50 (m, 1H), 6.21-6.33 (m, 1H), 5.24-5.39 (m, 1H), 3.97-4.17 (m, 1H), 3.74-3.91 (m, 1H), 3.48-3.57 (m, 1H), 3.34-3.47 (m, 3H), 3.17-3.29 (m, 3H), 3.12 (s, 1H), 3.09 (s, 2H), 2.83-3.06 (m, 2H), 2.64-2.80 (m, 1H), 1.46-2.02 (m, 6H), 1.14-1.25 (m, 3H) |
| 169 | Method 1 | 1.438 | 596.2 | $^1$H NMR (400 MHz, DMSO-$d_6$) δ ppm 8.17-8.33 (m, 1H), 7.13-7.29 (m, 2H), 7.01-7.11 (m, 1H), 6.38-6.51 (m, 1H), 6.21-6.33 (m, 1H), 5.26-5.36 (m, 1H), 4.10 (br d, J = 9.1 Hz, 2H), 3.81-3.86 (m, 2H), 3.61-3.73 (m, 3H), 3.49 (br d, J = 10.6 Hz, 1H), 3.17-3.26 (m, 1H), 3.07-3.14 (m, 3H), 2.68-2.90 (m, 3H), 2.22-2.29 (m, 3H), 1.78-2.00 (m, 2H), 1.45-1.67 (m, 4H), 1.16-1.25 (m, 3H) |
| 170 | Method 4 | 3.117 | 596.2 | $^1$H NMR (400 MHz, DMSO-$d_6$) δ ppm 8.20-8.28 (m, 1H), 7.22-7.30 (m, 1H), 7.12-7.17 (m, 1H), 6.99-7.08 (m, 1H), 6.39-6.49 (m, 1H), 6.19-6.32 (m, 1H), 5.24-5.40 (m, 1H), 3.94-4.09 (m, 1H), 3.69-3.83 (m, 1H), 3.40-3.54 (m, 4H), 3.17-3.25 (m, 3H), 3.09-3.14 (m, 3H), 2.70-2.90 (m, 2H), 2.22 (s, 3H), 1.66-2.11 (m, 3H), 1.31-1.64 (m, 4H), 1.14-1.22 (m, 3H) |
| 171 | Method 5 | 2.224 | 600.1 | $^1$H NMR (400 MHz, DMSO-$d_6$) δ ppm 8.17-8.36 (m, 1H), 7.24-7.34 (m, 2H), 7.06-7.17 (m, 1H), 6.40-6.48 (m, 1H), 6.21-6.32 (m, 1H), 5.25-5.37 (m, 1H), 4.08-4.22 (m, 1H), 3.79-3.92 (m, 1H), 3.54-3.62 (m, 3H), 3.30-3.34 (m, 1H), 3.17-3.27 (m, 2H), 3.09-3.12 (m, 3H), 2.75-2.85 (m, 1H), 2.68 (br d, J = 12.8 Hz, 1H), 2.54-2.61 (m, 1H), 1.69-2.09 (m, 4H), 1.42-1.69 (m, 3H), 1.16-1.24 (m, 3H) |
| 172 | Method 5 | 2.283 | 596.2 | $^1$H NMR (400 MHz, DMSO-$d_6$) δ ppm 8.25 (br d, J = 7.1 Hz, 1H), 7.10-7.29 (m, 3H), 6.40-6.49 (m, 1H), 6.20-6.30 (m, 1H), 5.27-5.36 (m, 1H), 4.17 (br dd, J = 9.1, 7.5 Hz, 1H), 3.83-3.91 (m, 1H), 3.64-3.79 (m, 2H), 3.33-3.50 (m, 4H), 3.22-3.31 (m, 1H), 3.13 (s, 1H), 3.09 (s, 2H), 2.71-2.86 (m, |

TABLE 3-continued

Representative Analytical Data for Compounds of the Disclosure.

| Cmpd. No. | LCMS Method | LCMS retention time (min) | LCMS M + H | $^1$H NMR |
|---|---|---|---|---|
| | | | | 2H), 2.28-2.40 (m, 3H), 1.69-2.07 (m, 3H), 1.35-1.67 (m, 4H), 1.14-1.26 (m, 3H) |
| 173 | Method 1 | 1.415 | 584.1 | $^1$H NMR (400 MHz, DMSO-$d_6$) δ ppm 8.13-8.40 (m, 1H), 7.04-7.29 (m, 3H), 6.40-6.48 (m, 1H), 6.23-6.32 (m, 1H), 5.22-5.40 (m, 1H), 3.90-4.03 (m, 1H), 3.70-3.85 (m, 1H), 3.49-3.65 (m, 1H), 3.34-3.46 (m, 3H), 3.21-3.30 (m, 2H), 3.08-3.20 (m, 4H), 2.96-3.08 (m, 1H), 2.81-2.92 (m, 1H), 2.58-2.78 (m, 1H), 1.82-2.04 (m, 2H), 1.43-1.81 (m, 4H), 1.11-1.28 (m, 3H) |
| 174 | Method 8 | 2.061 | 566.2 | $^1$H NMR (400 MHz, DMSO-$d_6$) δ ppm 8.69-8.84 (m, 1H), 7.27-7.45 (m, 2H), 7.20-7.26 (m, 2H), 7.14-7.19 (m, 1H), 6.70-6.82 (m, 1H), 5.10 (br d, J = 5.1 Hz, 1H), 4.53 (br t, J = 6.9 Hz, 0.5H), 3.95-4.23 (m, 2H), 3.78-3.93 (m, 1.5H), 3.65-3.72 (m, 1H), 3.39-3.49 (m, 2H), 3.20-3.27 (m, 2H), 3.09-3.18 (m, 2H), 2.64-2.90 (m, 2H), 1.50-2.06 (m, 4H), 1.14-1.24 (m, 1H), 0.40 (dd, J = 7.1, 1.5 Hz, 2H) |
| 175 | Method 8 | 2.167 | 584.2 | $^1$H NMR (400 MHz, DMSO-$d_6$) δ ppm 8.72-8.86 (m, 1H), 7.20-7.34 (m, 3H), 7.11-7.18 (m, 1H), 6.67-6.83 (m, 1H), 5.11 (br d, J = 5.6 Hz, 1H), 4.54 (br t, J = 7.0 Hz, 0.5H), 4.06-4.27 (m, 2H), 3.86-4.02 (m, 2H), 3.77-3.85 (m, 1.5H), 3.38-3.44 (m, 2H), 3.34 (br s, 1H), 3.11-3.20 (m, 2H), 2.92 (br d, J = 7.7 Hz, 1H), 2.65-2.74 (m, 1H), 1.61-2.00 (m, 4H), 1.17 (br d, J = 6.5 Hz, 1H), 0.45 (br d, J = 7.1 Hz, 2H) |
| 176 | Method 1 | 1.34 | 566.3 | $^1$H NMR (400 MHz, DMSO-$d_6$) δ ppm 8.71 (br d, J = 6.4 Hz, 1H), 7.36-7.44 (m, 1H), 7.20-7.33 (m, 3H), 7.10-7.18 (m, 1H), 6.69-6.79 (m, 1H), 5.06 (br dd, J = 5.3, 2.0 Hz, 1H), 4.00-4.15 (m, 1H), 3.75-3.92 (m, 1H), 3.46-3.72 (m, 4H), 2.75-3.45 (m, 7H), 2.57-2.69 (m, 1H), 1.49-1.96 (m, 6H) |
| 177 | Method 1 | 1.373 | 582.2 | $^1$H NMR (400 MHz, DMSO-$d_6$) δ ppm 8.31 (br dd, J = 7.9, 2.6 Hz, 1H), 7.29-7.44 (m, 2H), 7.16-7.27 (m, 2H), 6.66-6.74 (m, 1H), 6.57-6.65 (m, 1H), 4.48-4.64 (m, 1H), 3.97-4.14 (m, 1H), 3.72-3.88 (m, 1H), 3.47-3.62 (m, 1H), 3.40 (q, J = 10.3 Hz, 3H), 3.11-3.29 (m, 4H), 2.97-3.02 (m, 3H), 2.84-2.91 (m, 1H), 2.61-2.71 (m, 1H), 1.73-2.03 (m, 3H), 1.44-1.71 (m, 3H), 1.17-1.26 (m, 3H) |
| 178 | Method 6 | 3.078 | 578.3 | $^1$H NMR (400 MHz, DMSO-$d_6$) δ ppm 8.38-8.20 (m, 1H), 7.43-7.29 (m, 2H), 7.27-7.18 (m, 2H), 6.45 (br d, J = 11.4 Hz, 1H), 6.33-6.19 (m, 1H), 5.39-5.24 (m, 1H), 4.16-3.96 (m, 2H), 3.90-3.54 (m, 2H), 3.24-3.04 (m, 8H), 2.96 (br t, J = 14.5 Hz, 3H), 2.80-2.65 (m, 1H), 2.23-1.86 (m, 3H), 1.55 (br s, 2H), 1.19 (br d, J = 6.8 Hz, 3H), 1.03-0.90 (m, 3H) |
| 179 | Method 6 | 2.902 | 564.3 | $^1$H NMR (400 MHz, DMSO-$d_6$) δ ppm 8.35-8.20 (m, 1H), 7.42-7.17 (m, 3H), 6.44 (d, J = 11.1 Hz, 1H), 6.26 (dt, J = 6.1, 10.3 Hz, 1H), 5.40-5.26 (m, 1H), 4.20-3.97 (m, 2H), 3.88-3.55 (m, 2H), 3.26-3.03 (m, 7H), 2.96 (br t, J = 14.2 Hz, 2H), 2.84-2.63 (m, 3H), 2.21-1.78 (m, 2H), 1.75-1.58 (m, 4H), 1.47 (br s, 1H), 1.19 (d, J = 6.8 Hz, 3H) |
| 180 | Method 1 | 1.224 | 578.2 | $^1$H NMR (400 MHz, DMSO-$d_6$) δ ppm 8.19-8.28 (m, 1H), 7.30-7.43 (m, 2H), 7.16-7.27 (m, 2H), 6.40-6.47 (m, 1H), 6.22-6.31 (m, 1H), 5.24-5.36 (m, 1H), 3.97-4.15 (m, 1H), 3.68-3.89 (m, 1H), 3.48-3.62 (m, 1H), 3.35-3.42 (m, 1H), 3.05-3.26 (m, 6H), 2.86-3.02 (m, 3H), 2.53-2.78 (m, 2H), 1.45-2.00 (m, 9H), 1.14-1.26 (m, 3H) |
| 181 | Method 6 | 3.204 | 626.3 | $^1$H NMR (400 MHz, DMSO-$d_6$) δ ppm 8.36-8.19 (m, 1H), 7.57 (br s, 2H), 7.50 (br s, 3H), 7.36 (br d, J = 6.6 Hz, 1H), 7.28-7.10 (m, 3H), 6.44 (br d, J = 10.8 Hz, 1H), 6.34-6.17 (m, 1H), 5.40-5.22 (m, 1H), 4.07-3.90 (m, 2H), 3.85-3.52 (m, 2H), 3.29-3.17 (m, 2H), 3.16-3.02 (m, 6H), 2.82-2.58 (m, 1H), 2.14 (br t, J = 12.3 Hz, 1H), 1.95-1.62 (m, 2H), 1.61-1.44 (m, 2H), 1.18 (br d, J = 6.4 Hz, 3H), 1.12-0.87 (m, 1H) |

TABLE 3-continued

Representative Analytical Data for Compounds of the Disclosure.

| Cmpd. No. | LCMS Method | LCMS retention time (min) | LCMS M + H | $^1H$ NMR |
|---|---|---|---|---|
| 182 | Method 9 | 3.047 | 618.2 | $^1H$ NMR (400 MHz, DMSO-$d_6$) δ ppm 8.40-8.17 (m, 1H), 7.48-7.36 (m, 1H), 7.34-7.16 (m, 3H), 6.45 (d, J = 11.1 Hz, 1H), 6.27 (br dd, J = 5.4, 9.5 Hz, 1H), 5.42-5.26 (m, 1H), 4.17-3.96 (m, 2H), 3.91-3.57 (m, 2H), 3.46 (br t, J = 16.4 Hz, 2H), 3.30-3.16 (m, 3H), 3.11 (d, J = 14.8 Hz, 3H), 2.99-2.81 (m, 1H), 2.59 (br d, J = 10.8 Hz, 1H), 2.44-2.11 (m, 1H), 1.98-1.45 (m, 3H), 1.19 (d, J = 6.9 Hz, 2H), 1.23 (br s, 1H), 1.15-0.95 (m, 1H) |
| 183 | Method 1 | 1.212 | 596 | $^1H$ NMR (400 MHz, DMSO-$d_6$) δ ppm 8.28 (d, J = 6.3 Hz, 1H), 7.32-7.47 (m, 2H), 7.13-7.26 (m, 1H), 6.40-6.50 (m, 1H), 6.21-6.34 (m, 1H), 5.26-5.37 (m, 1H), 4.23 (dd, J = 16.5, 12.9 Hz, 2H), 3.78-4.11 (m, 5H), 3.52-3.71 (m, 2H), 3.33-3.44 (m, 1H), 3.04-3.16 (m, 3H), 2.76 (t, J = 12.7 Hz, 1H), 2.54 (s, 1H), 1.45-2.15 (m, 9H), 1.12-1.25 (m, 3H) |
| 184 | Method 1 | 1.208 | 590 | $^1H$ NMR (400 MHz, DMSO-$d_6$) δ ppm 10.07-10.48 (m, 1H), 8.29 (br d, J = 7.6 Hz, 1H), 7.36-7.47 (m, 2H), 7.19-7.29 (m, 1H), 6.37-6.52 (m, 1H), 6.20-6.32 (m, 1H), 5.22-5.42 (m, 1H), 4.21-4.67 (m, 1H), 3.86-4.15 (m, 5H), 3.53-3.82 (m, 4H), 3.35-3.49 (m, 1H), 3.05-3.20 (m, 3H), 2.67-2.84 (m, 1H), 2.53-2.62 (m, 1H), 1.59-2.12 (m, 5H), 1.18-1.27 (m, 4H), 0.95-1.08 (m, 2H) |
| 185 | Method 1 | 1.225 | 572.2 | $^1H$ NMR (400 MHz, DMSO-$d_6$) δ ppm 8.17-8.31 (m, 1H), 7.14-7.42 (m, 4H), 6.19-6.52 (m, 2H), 5.24-5.36 (m, 1H), 3.99-4.15 (m, 1H), 3.69-3.87 (m, 1H), 3.42-3.62 (m, 2H), 3.05-3.27 (m, 7H), 2.81-2.97 (m, 3H), 1.48-1.96 (m, 7H), 1.15-1.21 (m, 3H), 0.91-1.02 (m, 2H), 0.62-0.73 (m, 2H) |
| 186 | Method 1 | 1.636 | 560.1 | $^1H$ NMR (400 MHz, DMSO-$d_6$) δ ppm 8.78 (s, 1H), 8.37 (dd, J = 1.9, 7.8 Hz, 1H), 7.60-7.52 (m, 1H), 7.50-7.35 (m, 3H), 6.86 (s, 1H), 6.45 (d, J = 11.2 Hz, 1H),6.28 (dd, J = 9.4, 11.2 Hz, 1H), 5.43-5.27 (m, 1H), 4.00 (s, 3H), 3.20-3.05 (m, 5H), 2.78-2.66 (m, 1H), 2.64-2.54 (m, 1H), 2.01-1.65 (m, 4H), 1.20 (d, J = 6.8 Hz, 3H) |
| 187 | Method 3 | 2.497 | 560.1 | $^1H$ NMR (400 MHz, DMSO-$d_6$) δ ppm 8.78 (s, 1H), 8.36 (br d, J = 6.4 Hz, 1H), 7.53-7.59 (m, 1H), 7.44-7.49 (m, 1H), 7.36-7.43 (m, 2H), 6.86 (s, 1H), 6.45 (d, J = 11.1 Hz, 1H), 6.21-6.35 (m, 1H), 5.28-5.42 (m, 1H), 4.00 (s, 3H), 3.14 (br s, 2H), 3.11 (s, 3H), 2.65-2.77 (m, 2H), 1.70-1.94 (m, 4H), 1.21 (d, J = 6.8 Hz, 3H) |
| 188 | Method 3 | 2.390 | 546.1 | $^1H$ NMR (400 MHz, DMSO-$d_6$) δ ppm 8.78 (s, 1H), 8.57 (br d, J = 2.2 Hz, 1H), 7.53-7.60 (m, 1H), 7.46 (td, J = 7.4, 2.3 Hz, 1H), 7.35-7.43 (m, 2H), 6.86 (s, 1H), 6.66-6.76 (m, 1H), 6.53-6.64 (m, 1H), 4.00 (s, 3H), 3.89-3.95 (m, 2H), 3.14 (br d, J = 5.1 Hz, 2H), 2.99 (s, 3H), 2.59-2.77 (m, 2H), 1.74-1.97 (m, 4H) |
| 189 | Method 1 | 1.571 | 526.1 | $^1H$ NMR (400 MHz, DMSO-$d_6$) δ ppm 8.77 (s, 1H), 8.59 (br d, J = 1.9 Hz, 1H), 7.11-7.36 (m, 4H), 6.77 (s, 1H), 6.66-6.74 (m, 1H), 6.54-6.63 (m, 1H), 3.98 (s, 3H), 3.88-3.96 (m, 2H), 3.02-3.18 (m, 2H), 2.99 (s, 3H), 2.55-2.64 (m, 2H), 2.04 (s, 3H), 1.71-1.99 (m, 4H) |
| 190 | Method 2 | 2.512 | 540.2 | $^1H$ NMR (400 MHz, DMSO-$d_6$) δ ppm 8.77 (s, 1H), 8.32-8.43 (m, 1H), 7.31 (dd, J = 7.5, 6.2 Hz, 2H), 7.24 (s, 1H), 7.11-7.19 (m, 1H), 6.78 (s, 1H), 6.46 (d, J = 11.2 Hz, 1H), 6.24-6.34 (m, 1H), 5.28-5.43 (m, 1H), 3.99 (s, 3H), 3.01-3.19 (m, 5H), 2.59 (br t, J = 12.5 Hz, 2H), 2.05 (s, 3H), 1.76-2.00 (m, 2H), 1.53-1.73 (m, 2H), 1.21 (d, J = 6.9 Hz, 3H) |
| 191 | Method 2 | 2.310 | 512.2 | $^1H$ NMR (400 MHz, DMSO-$d_6$) δ ppm 8.76 (s, 1H), 8.53 (br d, J = 2.4 Hz, 1H), 7.47-7.41 (m, 5H), 6.81 (s, 1H), 6.69 (td, J = 4.3, 15.3 Hz, 1H), 6.63-6.55 (m, 1H), 3.99 (s, 3H), 3.92 (br t, J = 4.2 Hz, 2H), 3.30 (s, 2H), 3.12 (br d, J = 12.8 Hz, 2H), 2.99 (s, 3H), 1.76-1.65 (m, 4H) |
| 192 | Method 2 | 2.419 | 526.2 | $^1H$ NMR (400 MHz, DMSO-$d_6$) δ ppm 8.75 (s, 1H), 8.31 (dd, J = 2.0, 7.8 Hz, 1H), 7.48-7.40 (m, 5H), 6.80 (s, 1H), 6.44 (d, J = 11.1 Hz, 1H), 6.26 (dd, J = |

TABLE 3-continued

Representative Analytical Data for Compounds of the Disclosure.

| Cmpd. No. | LCMS Method | LCMS retention time (min) | LCMS M + H | $^1$H NMR |
|---|---|---|---|---|
| | | | | 9.5, 11.2 Hz, 1H), 5.39-5.28 (m, 1H), 3.99 (s, 3H), 3.11 m, 7H), 1.74-1.57 (m, 4H), 1.19 (d, J = 6.8 Hz, 3H) |
| 193 | Method 1 | 1.634 | 540.2 | $^1$H NMR (400 MHz, DMSO-$d_6$) δ ppm 8.76 (s, 1H), 8.36 (br d, J = 5.8 Hz, 1H), 7.36-7.18 (m, 3H), 7.17-7.10 (m, 1H), 6.76 (s, 1H), 6.45 (d, J = 11.1 Hz, 1H), 6.34-6.22 (m, 1H), 5.42-5.27 (m, 1H), 3.98 (s, 3H), 3.17-2.99 (m, 5H), 2.63-2.55 (m, 2H), 2.03 (s, 3H), 1.93-1.73 (m, 2H), 1.69 (br s, 2H), 1.20 (d, J = 6.9 Hz, 3H) |
| 194 | Method 1 | 1.476 | 493 | $^1$H NMR (400 MHz, DMSO-$d_6$) δ ppm 8.78 (s, 1H), 8.64 (br s, 1H), 7.56 (d, J = 7.9 Hz, 1H), 7.50-7.32 (m, 3H), 6.87 (s, 1H), 6.56-6.45 (m, 1H), 5.75 (d, J = 11.3 Hz, 1H), 4.11-3.89 (m, 5H), 3.14 (br d, J = 11.1 Hz, 2H), 2.67 (br s, 2H), 2.03-1.84 (m, 2H), 1.81-1.68 (m, 2H) |
| 195 | Method 6 | 3.134 | 598 | $^1$H NMR (400 MHz, DMSO-$d_6$) δ ppm 8.25 (br dd, J = 7.8, 2.1 Hz, 1H), 7.16-7.42 (m, 4H), 6.39-6.49 (m, 1H), 6.20-6.32 (m, 1H), 5.23-5.38 (m, 1H), 3.98-4.12 (m, 1H), 3.66-3.89 (m, 1H), 3.46-3.62 (m, 4H), 3.19-3.30 (m, 3H), 2.84-3.15 (m, 5H), 2.61-2.72 (m, 1H), 1.45-2.03 (m, 6H), 1.10-1.29 (m, 3H) |
| 196 | Method 1 | 1.227 | 596 | $^1$H NMR (400 MHz, DMSO-$d_6$) δ ppm 8.16-8.30 (m, 1H), 7.29-7.43 (m, 2H), 7.14-7.26 (m, 2H), 6.37-6.49 (m, 1H), 6.20-6.31 (m, 1H), 5.21-5.39 (m, 1H), 3.98-4.14 (m, 1H), 3.68-3.84 (m, 1H), 3.46-3.61 (m, 1H), 3.34-3.42 (m, 1H), 3.19-3.29 (m, 1H), 3.00-3.16 (m, 5H), 2.85-2.96 (m, 1H), 2.60-2.79 (m, 3H), 2.52-2.55 (m, 1H), 2.42-2.49 (m, 2H), 1.47-2.05 (m, 6H), 1.14-1.23 (m, 3H) |
| 197 | Method 5 | 1.982 | 564 | $^1$H NMR (400 MHz, DMSO-$d_6$) δ ppm 8.19-8.34 (m, 1H), 7.44-7.55 (m, 1H), 7.24-7.38 (m, 3H), 6.41-6.47 (m, 1H), 6.38 (br s, 1H), 6.22-6.30 (m, 1H), 5.22-5.42 (m, 1H), 4.20-4.36 (m, 2H), 4.02-4.10 (m, 1H), 3.87 (br d, J = 8.2 Hz, 1H), 3.77 (br s, 3H), 3.30-3.51 (m, 2H), 3.13 (s, 1H), 3.09 (s, 2H), 2.57-2.72 (m, 2H), 1.78-2.06 (m, 2H), 1.36-1.77 (m, 5H), 1.15-1.23 (m, 3H) |
| 198 | Method 1 | 1.424 | 596 | $^1$H NMR (400 MHz, DMSO-$d_6$) δ ppm 8.16 (dd, J = 8.5, 2.5 Hz, 1H), 7.35-7.45 (m, 1H), 7.29-7.34 (m, 1H), 7.20-7.29 (m, 2H), 6.48 (d, J = 11.1 Hz, 1H), 6.22 (br dd, J = 11.1, 9.9 Hz, 1H), 5.14-5.23 (m, 1H), 4.05-4.16 (m, 1H), 3.79-3.95 (m, 1H), 3.55-3.71 (m, 2H), 3.41 (br d, J = 2.5 Hz, 2H), 3.37 (br d, J = 5.2 Hz, 2H), 3.13-3.30 (m, 1H), 3.09-3.13 (m, 1H), 3.07 (s, 3H), 2.74-2.88 (m, 1H), 2.67 (br t, J = 12.3 Hz, 1H), 1.76-2.08 (m, 2H), 1.42-1.71 (m, 6H), 0.74-0.85 (m, 3H) |
| 199 | Method 2 | 2.464 | 572 | $^1$H NMR (400 MHz, DMSO-$d_6$) δ ppm 8.23-8.46 (m, 1H), 7.44-7.53 (m, 1H), 7.19-7.40 (m, 3H), 6.46-6.55 (m, 1H), 6.31 (t, J = 10.3 Hz, 1H), 5.34-5.44 (m, 1H), 4.82-4.89 (m, 1H), 3.88-4.24 (m, 3H), 3.47-3.87 (m, 5H), 3.12-3.24 (m, 3H), 2.58-2.75 (m, 1H), 2.41 (br dd, J = 12.9, 10.6 Hz, 1H), 1.75-2.10 (m, 1H), 1.46-1.73 (m, 2H), 1.19-1.34 (m, 9H), 0.63-1.15 (m, 1H) |
| 200 | Method 2 | 2.555 | 560 | $^1$H NMR (400 MHz, DMSO-$d_6$) δ ppm 8.79 (d, J = 2.3 Hz, 1H), 8.42 (br d, J = 7.8 Hz, 1H), 8.15 (d, J = 2.2 Hz, 1H), 7.37 (t, J = 8.0 Hz, 1H), 7.04-7.11 (m, 2H), 7.02 (br d, J = 8.1 Hz, 1H), 6.47 (d, J = 10.9 Hz, 1H), 6.23-6.37 (m, 1H), 5.31-5.49 (m, 1H), 3.79 (s, 3H), 3.69 (br d, J = 12.7 Hz, 2H), 3.19-3.27 (m, 2H), 3.12 (s, 3H), 1.78-2.05 (m, 4H), 1.23 (d, J = 6.8 Hz, 3H) |
| 201 | Method 1 | 1.721 | 555 | $^1$H NMR (400 MHz, DMSO-$d_6$) δ ppm 7.99 (d, J = 8.7 Hz, 1H), 7.59-7.72 (m, 2H), 7.44 (d, J = 2.1 Hz, 1H), 7.32 (t, J = 7.8 Hz, 1H), 6.87-7.03 (m, 3H), 6.87-7.03 (m, 1H), 6.42 (d, J = 11.0 Hz, 1H), 6.36-6.46 (m, 1H), 6.16 (t, J = 10.4 Hz, 1H), 5.18-5.35 (m, 1H), 3.78 (s, 3H), 3.12 (s, 3H), 2.87 (br d, J = 12.9 Hz, 2H), 2.29-2.44 (m, 2H), 1.82 (br d, J = 13.9 Hz, 2H), 1.17 (d, J = 6.8 Hz, 3H), 0.99-1.10 (m, 2H), 0.99-1.10 (m, 1H), 0.96 (s, 3H) |

TABLE 3-continued

| Cmpd. No. | LCMS Method | LCMS retention time (min) | LCMS M + H | $^1$H NMR |
|---|---|---|---|---|
| Representative Analytical Data for Compounds of the Disclosure. | | | | |
| 202 | Method 1 | 1.591 | 589 | $^1$H NMR (400 MHz, DMSO-$d_6$) δ ppm 8.37 (dd, J = 1.8, 7.8 Hz, 1H), 7.51 (d, J = 7.5 Hz, 1H), 7.46-7.31 (m, 4H), 6.86 (s, 1H), 6.45 (d, J = 11.1 Hz, 1H), 6.33-6.22 (m, 1H), 5.42-5.28 (m, 1H), 3.89 (s, 3H), 3.81 (s, 3H), 3.17 (br d, J = 12.1 Hz, 2H), 3.11 (s, 3H), 2.71-2.61 (m, 1H), 2.60-2.53 (m, 1H), 2.03-1.62 (m, 4H), 1.20 (d, J = 6.8 Hz, 3H) |
| 203 | Method 1 | 1.717 | 555 | $^1$H NMR (400 MHz, DMSO-$d_6$) δ ppm 7.99 (d, J = 8.7 Hz, 1H), 7.72-7.60 (m, 2H), 7.44 (d, J = 2.1 Hz, 1H), 7.32 (t, J = 7.8 Hz, 1H), 7.02-6.90 (m, 3H), 6.42 (d, J = 11.2 Hz, 1H), 6.20-6.11 (m, 1H), 5.20-5.34 (m, 1H), 3.78 (s, 3H), 3.12 (s, 3H), 2.91-2.81 (m, 2H), 2.31-2.46 (m, 2H), 1.82 (br d, J = 13.8 Hz, 2H), 1.17 (d, J = 6.9 Hz, 3H), 1.10-0.99 (m, 2H), 0.96 (s, 3H) |
| 204 | Method 1 | 1.418 | 610 | $^1$H NMR (400 MHz, DMSO-$d_6$) δ ppm 8.54 (dd, J = 4.7, 1.2 Hz, 1H), 8.36-8.41 (m, 1H), 8.02 (dd, J = 8.2, 1.3 Hz, 1H), 7.93-7.98 (m, 1H), 7.89-7.93 (m, 1H), 7.72 (d, J = 1.9 Hz, 1H), 7.50 (dd, J = 8.1, 4.7 Hz, 1H), 6.45 (d, J = 11.8 Hz, 1H), 6.24-6.33 (m, 1H), 5.28-5.40 (m, 1H), 3.47-3.58 (m, 1H), 3.10 (s, 4H), 2.68-2.78 (m, 2H), 1.87-2.05 (m, 2H), 1.77-1.85 (m, 2H), 1.21 (d, J = 6.9 Hz, 3H) |
| 205 | Method 1 | 1.481 | 612 | $^1$H NMR (400 MHz, DMSO-$d_6$) δ ppm 8.36 (dd, J = 7.7, 1.9 Hz, 1H), 8.01 (d, J = 8.9 Hz, 1H), 7.84 (dd, J = 8.9, 2.4 Hz, 1H), 7.78 (d, J = 2.2 Hz, 1H), 7.51-7.56 (m, 1H), 7.33-7.46 (m, 3H), 6.45 (d, J = 11.1 Hz, 1H), 6.27 (dd, J = 11.1, 9.5 Hz, 1H), 5.24-5.41 (m, 1H), 3.81-3.97 (m, 2H), 3.07-3.20 (m, 5H), 2.59-2.72 (m, 2H), 2.56 (s, 2H), 2.07 (quin, J = 7.5 Hz, 2H), 1.63-1.95 (m, 4H), 1.20 (d, J = 6.7 Hz, 3H) |
| 206 | Method 9 | 2.532 | 550 | $^1$H NMR (400 MHz, DMSO-$d_6$) δ ppm 8.16-8.38 (m, 1H), 7.36-7.45 (m, 1H), 7.27-7.35 (m, 1H), 7.16-7.27 (m, 2H), 6.44 (d, J = 11.2 Hz, 1H), 6.24-6.30 (m, 1H), 5.95-6.23 (m, 1H), 5.24-5.39 (m, 1H), 3.93-4.18 (m, 2H), 3.55-3.89 (m, 2H), 3.07-3.20 (m, 6H), 2.97 (m, 2H), 2.58-2.81 (m, 2H), 2.07-2.38 (m, 1H), 1.64-1.97 (m, 1H), 1.42-1.62 (m, 2H), 1.19 (d, J = 6.9 Hz, 3H), 0.90-1.14 (m, 1H) |
| 207 | Method 1 | 1.646 | 598 | $^1$H NMR (400 MHz, DMSO-$d_6$) δ ppm 9.34 (s, 1H), 8.39 (br d, J = 6.0 Hz, 1H), 8.08 (s, 1H), 7.62 (d, J = 7.9 Hz, 1H), 7.57-7.41 (m, 3H), 6.45 (d, J = 11.3 Hz, 1H), 6.28 (dd, J = 9.5, 11.1 Hz, 1H), 5.50-5.18 (m, 1H), 3.27 (br d, J = 13.7 Hz, 2H), 3.11 (s, 3H), 2.84 (br t, J = 11.4 Hz, 1H), 2.73-2.63 (m, 1H), 2.03-1.71 (m, 4H), 1.30-1.19 (m, 3H) |
| 208 | Method 1 | 1.616 | 598 | $^1$H NMR (400 MHz, DMSO-$d_6$) δ ppm 9.34 (s, 1H), 8.39 (br d, J = 7.0 Hz, 1H), 8.09 (s, 1H), 7.62 (d, J = 7.9 Hz, 1H), 7.57-7.46 (m, 3H), 6.45 (d, J = 11.0 Hz, 1H), 6.34-6.22 (m, 1H), 5.47-5.24 (m, 1H), 3.27 (br d, J = 11.7 Hz, 2H), 3.11 (s, 3H), 2.89-2.79 (m, 1H), 2.68 (br d, J = 12.0 Hz, 1H), 1.96-1.70 (m, 4H), 1.21(d, J = 6.8 Hz, 3H) |
| 209 | Method 1 | 1.641 | 616 | $^1$H NMR (400 MHz, DMSO-$d_6$) δ ppm 9.31-9.39 (m, 1H), 8.33-8.47 (m, 1H), 8.14-8.21 (m, 1H), 7.48-7.61 (m, 2H), 7.30-7.39 (m, 1H), 6.41-6.51 (m, 1H), 6.24-6.32 (m, 1H), 5.30-5.43 (m, 1H), 3.24-3.29 (m, 2H), 3.09-3.13 (m, 3H), 2.72-2.91 (m, 2H), 1.74-1.99 (m, 4H), 1.20-1.24 (m, 3H) |
| 210 | Method 1 | 1.645 | 616 | $^1$H NMR (400 MHz, DMSO-$d_6$) δ ppm 9.30-9.39 (m, 1H), 8.32-8.46 (m, 1H), 8.17 (s, 1H), 7.48-7.64 (m, 2H), 7.34 (br d, J = 7.2 Hz, 1H), 6.45 (d, J = 11.0 Hz, 1H), 6.28 (dd, J = 11.0, 9.5 Hz, 1H), 5.30-5.44 (m, 1H), 3.20-3.24 (m, 2H), 3.10 (s, 3H), 2.90 (br s, 2H), 1.75-1.96 (m, 4H), 1.21 (d, J = 6.7 Hz, 3H) |
| 211 | Method 1 | 1.650 | 616 | $^1$H NMR (400 MHz, DMSO-$d_6$) δ ppm 9.33 (s, 1H), 8.40 (br d, J = 7.7 Hz, 1H), 8.12 (s, 1H), 7.65 (dd, J = 8.8, 2.4 Hz, 1H), 7.55 (dd, J = 8.6, 6.1 Hz, 1H), 7.38 (td, J = 8.5, 2.4 Hz, 1H), 6.45 (d, J = 11.3 Hz, 1H), 6.28 (dd, J = 11.0, 9.6 Hz, 1H), 5.30-5.41 (m, |

TABLE 3-continued

| Cmpd. No. | LCMS Method | LCMS retention time (min) | LCMS M + H | $^1$H NMR |
|---|---|---|---|---|
| Representative Analytical Data for Compounds of the Disclosure. | | | | |
| | | | | 1H), 3.11 (s, 3H), 2.70-2.92 (m, 4H), 1.85-2.02 (m, 2H), 1.75-1.84 (m, 2H), 1.21 (d, J = 6.9 Hz, 3H) |
| 212 | Method 1 | 1.649 | 616 | $^1$H NMR (400 MHz, DMSO-$d_6$) δ ppm 9.33 (s, 1H), 8.34-8.44 (m, 1H), 8.12 (s, 1H), 7.65 (dd, J = 8.7, 2.4 Hz, 1H), 7.55 (dd, J = 8.6, 6.1 Hz, 1H), 7.38 (td, J = 8.5, 2.4 Hz, 1H), 6.46 (d, J = 11.1 Hz, 1H), 6.24-6.34 (m, 1H), 5.27-5.42 (m, 1H), 3.11 (s, 3 H), 2.82-2.91 (m, 2H), 2.77 (br d, J = 12.3 Hz, 2H), 1.86-2.03 (m, 2H), 1.76-1.85 (m, 2H), 1.18-1.25 (m, 3H) |
| 213 | Method 1 | 1.773 | 639 | $^1$H NMR (400 MHz, DMSO-$d_6$) δ ppm 9.34 (s, 1H), 8.31-8.40 (m, 1H), 8.09 (s, 1H), 7.63 (d, J = 7.9 Hz, 1H), 7.43-7.58 (m, 3H), 6.67 (dd, J = 15.4, 5.9 Hz, 1H), 5.94 (dd, J = 15.4, 1.2 Hz, 1H), 4.55-4.72 (m, 2H), 4.48-4.55 (m, 1H), 4.32 (br t, J = 11.1 Hz, 2H), 3.28 (br d, J = 12.1 Hz, 2H), 2.80-2.90 (m, 1H), 2.65-2.76 (m, 1H), 1.72-2.04 (m, 4H), 1.20 (d, J = 7.0 Hz, 3H) |
| 214 | Method 1 | 1.638 | 612 | $^1$H NMR (400 MHz, DMSO-$d_6$) δ ppm 9.36 (d, J = 2.7 Hz, 1H), 8.34-8.48 (m, 1H), 8.09 (d, J = 3.0 Hz, 1H), 7.60-7.71 (m, 1H), 7.42-7.58 (m, 3H), 6.45 (d, J = 11.1 Hz, 1H), 6.21-6.32 (m, 1H), 5.35 (dt, J = 14.6, 7.5 Hz, 1H), 3.40-3.64 (m, 1H), 3.32 (s, 1H), 2.73-3.07 (m, 2H), 2.40-2.48 (m, 1H), 1.55-2.17 (m, 5H), 1.21 (br d, J = 6.9 Hz, 3H), 1.07 (br dd, J = 6.6, 3.2 Hz, 3H) |
| 215 | Method 1 | 1.672 | 653 | $^1$H NMR (400 MHz, DMSO-$d_6$) δ ppm 9.36 (d, J = 2.6 Hz, 1H), 8.29-8.43 (m, 1H), 8.10 (d, J = 3.5 Hz, 1H), 7.60-7.71 (m, 1H), 7.42-7.58 (m, 3H), 6.66 (ddd, J = 15.4, 6.2, 1.8 Hz, 1H), 5.96 (dd, J = 15.4, 1.2 Hz, 1H), 4.46-4.72 (m, 3H), 4.32 (br t, J = 11.8 Hz, 2H), 3.41-3.63 (m, 1H), 2.72-3.10 (m, 1H), 2.39-2.47 (m, 1H), 1.59-2.17 (m, 4H), 1.19 (d, J = 6.9 Hz, 3H), 1.08 (dd, J = 6.6, 3.4 Hz, 3H) |
| 216 | Method 1 | 1.770 | 620 | $^1$H NMR (400 MHz, $CD_3SOCD_3$, 298K) δ ppm 8.34 (br d, J = 7.6 Hz, 1H), 8.27 (d, J = 8.4 Hz, 1H), 8.07 (br d, J = 7.6 Hz, 1H), 7.76 (s, 1H), 7.59 (d, J = 8.0 Hz, 1H), 7.52-7.41 (m, 3H), 6.62 (dd, J = 6.0, 15.5 Hz, 1H), 5.92 (br d, J = 15.2 Hz, 1H), 5.52-5.29 (m, 1H), 4.57-4.39 (m, 2H), 4.31-4.15 (m, 2H), 3.99-3.84 (m, 1H), 3.25-3.14 (m, 2H), 2.86-2.59 (m, 2H), 2.03-1.73 (m, 4H), 1.19 (d, J = 7.2 Hz, 3H) |
| 217 | Method 1 | 1.683 | 594 | $^1$H NMR (400 MHz, DMSO-$d_6$) δ ppm 8.98 (s, 1H), 8.38 (br d, J = 7.6 Hz, 1H), 7.72 (s, 1H), 7.52-7.37 (m, 1H), 7.15-6.94 (m, 2H), 6.45 (d, J = 11.3 Hz, 1H), 6.28 (t, J = 10.3 Hz, 1H), 5.45-5.24 (m, 1H), 3.76 (s, 3H), 3.26 (br d, J = 13.0 Hz, 2H), 3.11 (s, 3H), 2.80 (br t, J = 11.6 Hz, 1H), 2.73-2.61 (m, 1H), 2.04-1.63 (m, 4H), 1.23-1.16 (m, 3H) |
| 218 | Method 1 | 1.519 | 610 | $^1$H NMR (400 MHz, DMSO-$d_6$) δ ppm 8.96 (d, J = 2.0 Hz, 1H), 8.41 (br d, J = 8.3 Hz, 1H), 8.30 (d, J = 2.1 Hz, 1H), 7.61-7.51 (m, 1H), 7.49-7.31 (m, 3H), 6.46 (d, J = 11.3 Hz, 1H), 6.30 (t, J = 10.2 Hz, 1H), 5.46-5.27 (m, 1H), 3.66 (br s, 2H), 3.26-3.07 (m, 5H), 2.07-1.92 (m, 2H), 1.90-1.81 (m, 2H), 1.22 (d, J = 6.9 Hz, 4H) |
| 219 | Method 3 | 2.442 | 555 | $^1$H NMR (400 MHz, DMSO-$d_6$) δ ppm 8.38 (br d, J = 6.3 Hz, 1H), 7.94 (d, J = 8.9 Hz, 1H), 7.36 (br t, J = 7.9 Hz, 1H), 7.15 (dd, J = 7.5, 1.6 Hz, 1H), 7.11 (dd, J = 8.9, 2.7 Hz, 1H), 7.05 (dd, J = 8.3, 1.7 Hz, 1H), 6.95 (t, J = 7.4 Hz, 1 H), 6.77 (d, J = 2.6 Hz, 1H), 6.45 (dd, J = 11.3, 1.9 Hz, 1H), 6.27 (dd, J = 11.1, 9.5 Hz, 1H), 5.29-5.40 (m, 1H), 3.83 (s, 3H), 3.70 (d, J = 2.2 Hz, 3H), 3.12 (d, J = 3.8 Hz, 3H), 3.03 (br s, 2H), 2.43-2.36 (m, 2H), 1.59-1.77 (m, 4H), 1.19 (d, J = 6.9 Hz, 3H) |
| 220 | Method 1 | 1.585 | 573 | $^1$H NMR (400 MHz, DMSO-$d_6$) δ ppm 8.34 (br d, J = 6.0 Hz, 1H), 8.04 (d, J = 8.5 Hz, 1H), 7.70 (dd, J = 8.6, 2.3 Hz, 1H), 7.44 (d, J = 2.1 Hz, 1H), 7.36-7.19 (m, 4H), 6.44 (d, J = 11.1 Hz, 1H), 6.26 (dd, J = 11.1, 9.6 Hz, 1H), 5.38-5.27 (m, 1H), 4.62 (t, J = 5.2 Hz, 1H), 3.69-3.58 (m, 2H), 3.29 (s, 2H), 3.11 |

TABLE 3-continued

Representative Analytical Data for Compounds of the Disclosure.

| Cmpd. No. | LCMS Method | LCMS retention time (min) | LCMS M + H | $^1$H NMR |
|---|---|---|---|---|
| | | | | (s, 5H), 2.77 (t, J = 7.1 Hz, 2H), 1.52-1.82 (m, 4H), 1.19 (d, J = 6.8 Hz, 3H) |
| 221 | Method 1 | 1.185 | 562 | $^1$H NMR (400 MHz, DMSO-$d_6$) δ ppm 8.87-8.72 (m, 1H), 7.54-7.46 (m, 1H), 7.38-7.24 (m, 3H), 7.18 (dd, J = 6.7, 2.3 Hz, 1H), 6.74 (dt, J = 6.7, 2.6 Hz, 1H), 5.16-5.05 (m, 1H), 4.59 (dt, J = 14.0, 7.0 Hz, 1H), 4.32-4.07 (m, 4H), 3.83-3.54 (m, 6H), 3.18-3.10 (m, 1H), 2.72-2.52 (m, 1H), 2.13-1.87 (m, 1H), 1.86-1.59 (m, 5H), 1.18 (br d, J = 6.0 Hz, 1H), 1.14-0.73 (m, 1H), 0.51 (br d, J = 6.8 Hz, 2H) |
| 222 | Method 1 | 1.237 | 596 | $^1$H NMR (400 MHz, DMSO-$d_6$) δ ppm 8.33-8.20 (m, 1H), 7.44-7.26 (m, 2H), 7.13 (br s, 1H), 6.48-6.40 (m, 1H), 6.26 (t, J = 10.4 Hz, 1H), 5.37-5.25 (m, 1H), 4.34-4.19 (m, 1H), 4.11-3.94 (m, 2H), 3.93-3.59 (m, 4H), 3.55-3.22 (m, 3H), 3.17-3.06 (m, 3H), 2.83-2.63 (m, 2H), 2.10-1.39 (m, 9H), 1.25-1.14 (m, 3H) |
| 223 | Method 1 | 1.339 | 566 | $^1$H NMR (400 MHz, DMSO-$d_6$) δ ppm 8.27 (br dd, J = 7.5, 2.1 Hz, 1H), 7.41-7.21 (m, 2H), 7.15-7.03 (m, 2H), 6.51-6.37 (m, 1H), 6.36-6.18 (m, 1H), 5.39-5.24 (m, 1H), 4.07-3.94 (m, 1H), 3.88-3.75 (m, 1H), 3.68 (br d, J = 4.3 Hz, 2H), 3.60-3.51 (m, 1H), 3.42 (br d, J = 8.3 Hz, 3H), 3.36-3.18 (m, 2H), 3.14-3.08 (m, 3H), 2.93-2.83 (m, 1H), 2.70-2.60 (m, 1H), 2.07-1.79 (m, 2H), 1.79-1.70 (m, 1H), 1.69-1.45 (m, 3H), 1.25-1.15 (m, 3H) |
| 224 | Method 1 | 1.283 | 562 | $^1$H NMR (400 MHz, DMSO-$d_6$) δ ppm 8.31-8.17 (m, 1H), 7.18-6.99 (m, 4H), 6.48-6.39 (m, 1H), 6.30-6.17 (m, 1H), 5.42-5.21 (m, 1H), 4.00-3.87 (m, 2H), 3.85-3.63 (m, 3H), 3.51-3.24 (m, 5H), 3.14-3.08 (m, 3H), 3.05-2.88 (m, 1H), 2.71-2.60 (m, 1H), 2.48-2.41 (m, 1H), 2.37 (s, 3H), 2.05-1.83 (m, 1H), 1.81-1.67 (m, 1H), 1.67-1.46 (m, 3H), 1.40-1.29 (m, 1H), 1.26-1.14 (m, 3H) |
| 225 | Method 1 | 1.203 | 580 | $^1$H NMR (400 MHz, DMSO-$d_6$) δ ppm 8.91-8.75 (m, 1H), 7.37 (br d, J = 6.0 Hz, 2H), 7.26-7.10 (m, 2H), 6.80-6.71 (m, 1H), 5.11 (br d, J = 5.6 Hz, 1H), 4.68-4.54 (m, 1H), 4.39-4.07 (m, 3H), 3.62-4.00 (m, 7H), 3.09-3.21 (m, 1H), 2.77-2.56 (m, 1H), 2.00-1.55 (m, 6H), 1.30-1.14 (m, 1H), 1.10-0.75 (m, 1H), 0.52 (br d, J = 6.5 Hz, 2H) |
| 226 | Method 1 | 1.447 | 618 | $^1$H NMR (400 MHz, DMSO-$d_6$) δ ppm 8.37-8.22 (m, 1H), 7.46-7.22 (m, 1H), 7.25-7.12 (m, 1H), 6.49-6.38 (m, 1H), 6.32-6.22 (m, 1H), 5.42-5.21 (m, 1H), 4.19-4.02 (m, 1H), 3.93-3.75 (m, 1H), 3.67-3.50 (m, 1H), 3.48-3.36 (m, 3H), 3.35-3.23 (m, 3H), 3.19-3.11 (m, 2H), 3.07 (br d, J = 2.3 Hz, 1H), 3.04-2.86 (m, 2H), 2.81-2.62 (m, 1H), 2.09-1.81 (m, 2H), 1.80-1.44 (m, 4H), 1.25-1.15 (m, 3H) |
| 227 | Method 1 | 1.446 | 618 | $^1$H NMR (400 MHz, DMSO-$d_6$) δ ppm 8.40-8.10 (m, 1H), 7.38-7.14 (m, 2H), 6.51-6.36 (m, 1H), 6.32-6.21 (m, 1H), 5.31 (dt, J = 15.9, 7.9 Hz, 1H), 4.18-3.96 (m, 1H), 3.80 (dt, J = 18.1, 9.0 Hz, 1H), 3.64-3.43 (m, 2H), 3.42-3.33 (m, 2H), 3.30-3.22 (m, 2H), 3.16-3.05 (m, 4H), 3.02-2.85 (m, 2H), 2.82-2.62 (m, 1H), 2.12-1.81 (m, 2H), 1.80-1.62 (m, 3H), 1.62-1.45 (m, 1H), 1.26-1.15 (m, 3H) |
| 228 | Method 1 | 1.411 | 594 | $^1$H NMR (400 MHz, DMSO-$d_6$) δ ppm 10.35 (br s, 1H), 8.61 (br s, 1H), 8.05 (d, J = 7.9 Hz, 1H), 7.57-7.80 (m, 2H), 7.27-7.46 (m, 2H), 6.84-7.03 (m, 3H), 6.66-6.81 (m, 1H), 6.53 (br d, J = 15.3 Hz, 1H), 3.98 (br s, 2H), 3.80 (s, 3H), 3.53 (br d, J = 11.9 Hz, 2H), 3.10-3.35 (m, 3H), 2.86-3.02 (m, 2H), 2.68-2.78 (m, 3H), 2.53-2.56 (m, 2H), 2.46-2.49 (m, 1H), 2.11 (br d, J = 12.8 Hz, 2H), 1.65-1.93 (m, 6H) |
| 229 | Method 1 | 1.702 | 506 | $^1$H NMR (400 MHz, DMSO-$d_6$) δ ppm 8.37 (br d, J = 6.5 Hz, 1H), 7.97 (d, J = 8.9 Hz, 1H), 7.47-7.57 (m, 1H), 7.40-7.46 (m, 1H), 7.29-7.40 (m, 2H), 7.20 (dd, J = 9.0, 2.7 Hz, 1H), 6.77-6.89 (m, 2H), 5.63 (d, J = 16.6 Hz, 1H), 4.45-4.57 (m, 1H), 3.86 (s, 3H), 3.13 (br d, J = 12.0 Hz, 2H), 2.52-2.72 (m, 2H), 1.65-1.98 (m, 4H), 1.19 (d, J = 7.2 Hz, 3H) |

TABLE 3-continued

Representative Analytical Data for Compounds of the Disclosure.

| Cmpd. No. | LCMS Method | LCMS retention time (min) | LCMS M + H | $^1$H NMR |
|---|---|---|---|---|
| 230 | Method 1 | 1.452 | 571 | $^1$H NMR (400 MHz, DMSO-$d_6$) δ ppm 7.95 (d, J = 8.9 Hz, 1H), 7.55-7.49 (m, 1H), 7.45-7.33 (m, 3H), 7.18 (dd, J = 2.7, 8.9 Hz, 1H), 6.84 (d, J = 2.6 Hz, 1H), 6.77 (dd, J = 8.8, 11.0 Hz, 1H), 6.57 (d, J = 11.5 Hz, 1H), 4.60-4.47 (m, 1H), 4.29-4.07 (m, 3H), 3.85 (s, 3H), 3.76 (dd, J = 5.5, 9.5 Hz, 1H), 3.18-2.99 (m, 5H), 2.65-2.54 (m, 2H), 1.95-1.69 (m, 4H) |
| 231 | Method 1 | 1.650 | 564 | $^1$H NMR (400 MHz, DMSO-$d_6$) δ ppm 8.99 (s, 1H), 8.46-8.36 (m, 1H), 7.75 (s, 1H), 7.60 (d, J = 7.9 Hz, 1H), 7.54-7.48 (m, 1H), 7.47 (br d, J = 1.3 Hz, 2H), 6.49-6.41 (m, 1H), 6.28 (dd, J = 9.5, 11.1 Hz, 1H), 5.41-5.28 (m, 1H), 3.25-3.16 (m, 2H), 3.11 (s, 3H), 2.84-2.73 (m, 1H), 2.70-2.59 (m, 1H), 1.97-1.72 (m, 4H), 1.23-1.19 (m, 3H) |
| 232 | Method 1 | 1.568 | 497 | $^1$H NMR (400 MHz, DMSO-$d_6$) δ ppm 9.00 (s, 1H), 8.55 (br d, J = 2.1 Hz, 1H), 7.74 (s, 1H), 7.57-7.63 (m, 1H), 7.49-7.55 (m, 1H), 7.45 (d, J = 4.1 Hz, 2H), 6.84 (dt, J = 16.5, 4.5 Hz, 1H), 5.60 (dt, J = 16.5, 2.0 Hz, 1H), 3.87 (br t, J = 4.0 Hz, 2H), 3.21 (br d, J = 12.8 Hz, 2H), 2.74-2.85 (m, 1H), 2.64-2.72 (m, 1H), 2.04-1.77 (m, 4H) |
| 233 | Method 3 | 2.763 | 593 | $^1$H NMR (400 MHz, DMSO-$d_6$) δ ppm 8.79-8.70 (m, 1H), 7.99-7.94 (m, 1H), 7.93-7.88 (m, 1H), 7.62 (d, J = 2.0 Hz, 1H), 7.56 (d, J = 7.7 Hz, 1H), 7.49-7.43 (m, 1H), 7.40 (d, J = 4.2 Hz, 2H), 6.89 (s, 1H), 4.51 (s, 2H), 4.07 (br d, J = 5.3 Hz, 2H), 3.22-3.11 (m, 2H), 2.79-2.70 (m, 1H), 2.65-2.56 (m, 1H), 2.03-1.77 (m, 4H) |
| 234 | Method 1 | 1.681 | 605 | $^1$H NMR (400 MHz, DMSO-$d_6$) δ ppm 8.63 (br d, J = 8.6 Hz, 1H), 7.94-7.99 (m, 1H), 7.88-7.93 (m, 1H), 7.61 (d, J = 1.9 Hz, 1H), 7.56 (d, J = 7.9 Hz, 1H), 7.42-7.49 (m, 1H), 7.40 (d, J = 4.3 Hz, 2H), 6.93 (s, 1H), 4.76 (br t, J = 6.9 Hz, 1H), 4.50 (s, 2H), 3.12-3.20 (m, 2H), 2.72-2.77 (m, 2H), 1.71-1.94 (m, 4H), 1.28 (d, J = 7.0 Hz, 3H) |
| 235 | Method 1 | 1.534 | 557 | $^1$H NMR (400 MHz, DMSO-$d_6$) δ ppm 8.62 (br dd, J = 8.1, 1.7 Hz, 1H), 7.97 (d, J = 8.9 Hz, 1H), 7.52 (d, J = 7.4 Hz, 1H), 7.32-7.46 (m, 3H), 7.19 (dd, J = 8.9, 2.7 Hz, 1H), 6.93 (s, 1H), 6.85 (d, J = 2.6 Hz, 1H), 4.76 (br t, J = 7.1 Hz, 1H), 4.49 (s, 2H), 3.86 (s, 3H), 3.02-3.21 (m, 2H), 2.55-2.65 (m, 2H), 1.68-2.00 (m, 4H), 1.28 (d, J = 7.0 Hz, 3H) |
| 236 | Method 1 | 1.652 | 595 | $^1$H NMR (400 MHz, DMSO-$d_6$) δ ppm 8.61-8.68 (m, 1H), 8.27 (d, J = 8.4 Hz, 1H), 8.06 (d, J = 8.6 Hz, 1H), 7.75 (s, 1H), 7.58 (d, J = 7.6 Hz, 1H), 7.38-7.53 (m, 3H), 6.90-6.96 (m, 1H), 4.76 (br t, J = 7.2 Hz, 1H), 4.50 (s, 2H), 3.11-3.25 (m, 2H), 2.73-2.84 (m, 1H), 2.59-2.68 (m, 1H), 1.72-2.00 (m, 4H), 1.28 (d, J = 7.1 Hz, 3H) |
| 237 | Method 1 | 1.428 | 676 | $^1$H NMR (400 MHz, DMSO-$d_6$) δ ppm 9.70-10.14 (m, 1H), 8.40-8.51 (m, 1H), 7.92-7.97 (m, 1H), 7.86-7.91 (m, 1H), 7.61 (d, J = 1.9 Hz, 1H), 7.51-7.57 (m, 1H), 7.41-7.49 (m, 1H), 7.34-7.41 (m, 2H), 6.40-6.64 (m, 2H), 5.22-5.37 (m, 1H), 4.18-4.40 (m, 1H), 3.84-4.04 (m, 1H), 3.55-3.69 (m, 1H), 3.08-3.26 (m, 4H), 2.81-2.93 (m, 3H), 2.58-2.80 (m, 4H), 1.80-2.07 (m, 2H), 1.67-1.79 (m, 2H), 1.20-1.25 (m, 3H) |
| 238 | Method 1 | 1.438 | 676 | $^1$H NMR (400 MHz, DMSO-$d_6$) δ ppm 9.81-10.30 (m, 1H), 8.43-8.53 (m, 1H), 7.94-7.98 (m, 1H), 7.87-7.91 (m, 1H), 7.59-7.63 (m, 1H), 7.52-7.57 (m, 1H), 7.44-7.49 (m, 1H), 7.36-7.42 (m, 2H), 6.45-6.57 (m, 2H), 5.26-5.42 (m, 1H), 4.25-4.36 (m, 1H), 3.10-3.22 (m, 4H), 2.87 (s, 3H), 2.61-2.78 (m, 6H), 1.81 (br s, 2H), 1.72-1.80 (m, 2H), 1.23 (d, J = 6.9 Hz, 3H) |
| 239 | Method 6 | 3.159 | 627 | $^1$H NMR (400 MHz, DMSO-$d_6$) δ ppm 8.59 (dd, J = 2.3, 8.5 Hz, 1H), 7.96 (d, J = 9.0 Hz, 1H), 7.55-7.49 (m, 1H), 7.44-7.33 (m, 3H), 7.19 (dd, J = 2.7, 8.9 Hz, 1H), 6.84 (d, J = 2.6 Hz, 1H), 6.59 (d, J = 11.1 Hz, 1H), 6.32-6.22 (m, 1H), 5.76 (dq, J = 3.4, |

TABLE 3-continued

Representative Analytical Data for Compounds of the Disclosure.

| Cmpd. No. | LCMS Method | LCMS retention time (min) | LCMS M + H | $^1H$ NMR |
|---|---|---|---|---|
| | | | | 9.2 Hz, 1H), 3.86 (s, 3H), 3.16-3.08 (m, 5H), 2.84-2.61 (m, 2H), 2.60-2.53 (m, 1H), 2.47-2.38 (m, 1H), 1.99-1.75 (m, 2H), 1.75-1.61 (m, 2H) |
| 240 | Method 6 | 3.411 | 675 | $^1H$ NMR (400 MHz, DMSO-$d_6$) δ ppm 8.61 (dd, J = 2.0, 8.5 Hz, 1H), 7.99-7.93 (m, 1H), 7.92-7.86 (m, 1H), 7.61 (d, J = 2.0 Hz, 1H), 7.57-7.52 (m, 1H), 7.48-7.41 (m, 1H), 7.39 (d, J = 4.6 Hz, 2H), 6.60 (d, J = 10.9 Hz, 1H), 6.32-6.22 (m, 1H), 5.81-5.69 (m, 1H), 3.19-3.13 (m, 2H), 3.12 (s, 3H), 2.84-2.67 (m, 2H), 2.66-2.52 (m, 2H), 2.01-1.78 (m, 2H), 1.76-1.63 (m, 2H) |
| 241 | Method 1 | 1.597 | 587 | $^1H$ NMR (400 MHz, DMSO-$d_6$) δ ppm 8.28 (br s, 1H), 7.78-7.66 (m, 1H), 7.64-7.48 (m, 2H), 7.47-7.22 (m, 4H), 6.54-6.41 (m, 1H), 6.27 (t, J = 10.3 Hz, 1H), 5.45-5.21 (m, 1H), 3.68 (br s, 2H), 3.24-3.02 (m, 5H), 2.03-1.35 (m, 6H), 1.20 (br d, J = 6.9 Hz, 3H) |
| 242 | Method 1 | 1.614 | 575 | $^1H$ NMR (400 MHz, DMSO-$d_6$) δ ppm 8.27 (br s, 1H), 7.87 (br d, J = 7.0 Hz, 1H), 7.78-7.54 (m, 3H), 7.47-7.30 (m, 3H), 6.51-6.41 (m, 1H), 6.34-6.19 (m, 1H), 5.42-5.24 (m, 1H), 3.32-3.07 (m, 7H), 1.97-1.42 (m, 6H), 1.23-1.18 (m, 3H) |
| 243 | Method 1 | 1.725 | 626 | $^1H$ NMR (400 MHz, DMSO-$d_6$) δ ppm 8.15-8.28 (m, 1H), 7.67-7.75 (m, 2H), 7.48-7.62 (m, 2H), 7.33-7.41 (m, 3H), 6.67 (br dd, J = 15.3, 5.9 Hz, 1H), 5.95 (br d, J = 15.3 Hz, 1H), 4.56-4.72 (m, 2H), 4.51 (br d, J = 4.2 Hz, 1H), 4.25-4.39 (m, 2H), 3.38 (br s, 3H), 3.11-3.26 (m, 2H), 1.56-1.92 (m, 5H), 1.20 (br d, J = 6.6 Hz, 3H) |
| 244 | Method 1 | 1.742 | 616 | $^1H$ NMR (400 MHz, DMSO-$d_6$) δ ppm 8.23 (br s, 1H), 7.88 (br d, J = 7.5 Hz, 1H), 7.73-7.79 (m, 1H), 7.53-7.69 (m, 2H), 7.38-7.50 (m, 2H), 7.30-7.37 (m, 1H), 6.67 (dd, J = 15.4, 5.9 Hz, 1H), 5.96 (br d, J = 15.2 Hz, 1H), 4.63 (br s, 2H), 4.52 (br d, J = 5.9 Hz, 1H), 4.24-4.38 (m, 2H), 3.52-3.87 (m, 1H), 2.93-3.41 (m, 3H), 1.41-2.13 (m, 6H), 1.16-1.25 (m, 3H) |
| 245 | Method 2 | 2.725 | 634 | $^1H$ NMR (400 MHz, DMSO-$d_6$) δ ppm 8.19-8.32 (m, 1H), 7.88-7.96 (m, 1H), 7.79 (br d, J = 7.9 Hz, 1H), 7.68-7.76 (m, 1H), 7.35-7.52 (m, 2H), 7.21-7.34 (m, 1H), 6.69 (ddd, J = 15.4, 5.9, 3.9 Hz, 1H), 5.91-6.01 (m, 1H), 4.49-4.74 (m, 3H), 4.33 (br d, J = 9.5 Hz, 2H), 3.65-3.83 (m, 1H), 3.14-3.31 (m, 3H), 1.66-2.07 (m, 6H), 1.21 (dd, J = 6.9, 2.9 Hz, 3H) |
| 246 | Method 2 | 2.801 | 637 | $^1H$ NMR (400 MHz, DMSO-$d_6$) δ ppm 8.29 (dd, J = 2.3, 8.1 Hz, 1H), 7.99-7.93 (m, 1H), 7.92-7.87 (m, 1H), 7.61 (d, J = 2.0 Hz, 1H), 7.57-7.53 (m, 1H), 7.48-7.42 (m, 1H), 7.39 (d, J = 4.2 Hz, 2H), 6.59 (dd, J = 0.7, 11.3 Hz, 1H), 6.26 (dd, J = 9.5, 11.2 Hz, 1H), 5.62-5.52 (m, 1H), 3.47 (dd, J = 7.5, 10.0 Hz, 1H), 3.36 (dd, J = 5.1, 10.0 Hz, 1H), 3.23 (s, 3H), 3.20-3.12 (m, 2H), 3.09 (s, 3H), 2.78-2.56 (m, 2H), 2.02-1.78 (m, 2H), 1.78-1.68 (m, 2H) |
| 247 | Method 2 | 2.801 | 637 | $^1H$ NMR (400 MHz, DMSO-$d_6$) δ ppm 8.30 (dd, J = 2.1, 8.1 Hz, 1H), 7.99-7.93 (m, 1H), 7.92-7.87 (m, 1H), 7.61 (d, J = 2.1 Hz, 1H), 7.58-7.53 (m, 1H), 7.49-7.42 (m, 1H), 7.39 (d, J = 4.2 Hz, 2H), 6.59 (d, J = 11.2 Hz, 1H), 6.26 (dd, J = 9.6, 11.2 Hz, 1H), 5.64-5.52 (m, 1H), 3.47 (dd, J = 7.5, 10.0 Hz, 1H), 3.36 (dd, J = 5.2, 10.0 Hz, 1H), 3.23 (s, 3H), 3.20-3.12 (m, 2H), 3.09 (s, 3H), 2.78-2.56 (m, 2H), 2.03-1.79 (m, 2H), 1.78-1.67 (m, 2H) |
| 248 | Method 6 | 3.007 | 589 | $^1H$ NMR (400 MHz, DMSO-$d_6$) δ ppm 8.29 (dd, J = 8.1, 2.0 Hz, 1H), 7.96 (d, J = 8.9 Hz, 1H), 7.48-7.54 (m, 1H), 7.32-7.45 (m, 3H), 7.19 (dd, J = 8.9, 2.7 Hz, 1H), 6.84 (d, J = 2.6 Hz, 1H), 6.58 (d, J = 11.3 Hz, 1H), 6.26 (dd, J = 11.2, 9.6 Hz, 1H), 5.50-5.62 (m, 1H), 3.85 (s, 3H), 3.34-3.50 (m, 2H), 3.22 (s, 3H), 3.13 (br s, 2H), 3.09 (s, 3H), 2.52-2.71 (m, 2H), 1.72 (br d, J = 13.5 Hz, 4H) |
| 249 | Method 1 | 1.890 | 652 | $^1H$ NMR (400 MHz, DMSO-$d_6$) δ ppm 8.27 (d, J = 8.4 Hz, 1H), 8.06 (dd, J = 8.4, 1.4 Hz, 1H), 7.74 (d, J = 1.9 Hz, 2H), 7.58 (d, J = 7.9 Hz, 1H), 7.39-7.51 |

TABLE 3-continued

| Representative Analytical Data for Compounds of the Disclosure. | | | | |
|---|---|---|---|---|
| Cmpd. No. | LCMS Method | LCMS retention time (min) | LCMS M + H | $^1$H NMR |
| | | | | (m, 3H), 6.78 (d, J = 15.6 Hz, 1H), 5.82 (d, J = 15.6 Hz, 1H), 4.61 (br t, J = 11.6 Hz, 2H), 4.31 (br t, J = 11.9 Hz, 2H), 3.19 (br t, J = 12.6 Hz, 2H), 2.72-2.82 (m, 1H), 2.62 (td, J = 12.5, 2.6 Hz, 1H), 1.74-2.00 (m, 4H), 1.36 (s, 6H) |
| 250 | Method 1 | 1.900 | 627 | $^1$H NMR (400 MHz, DMSO-$d_6$) δ ppm 8.31-8.41 (m, 1H), 8.14-8.23 (m, 1H), 7.62-7.67 (m, 1H), 7.53-7.62 (m, 1H), 7.46-7.50 (m, 1H), 7.44 (dt, J = 9.0, 1.6 Hz, 1H), 7.40 (dd, J = 10.1, 2.3 Hz, 1H), 7.37 (d, J = 2.0 Hz, 1H), 6.44 (d, J = 11.1 Hz, 1H), 6.25 (dd, J = 11.1, 9.6 Hz, 1H), 5.26-5.39 (m, 1H), 3.06-3.14 (m, 3H), 2.89-3.04 (m, 1H), 2.72-2.82 (m, 1H), 2.26-2.34 (m, 1H), 1.94-2.11 (m, 1H), 1.75-1.93 (m, 1H), 1.65-1.74 (m, 1H), 1.56-1.64 (m, 1H), 1.16-1.23 (m, 3H), 0.98-1.07 (m, 3H) |
| 251 | Method 1 | 1.767 | 650 | $^1$H NMR (400 MHz, DMSO-$d_6$) δ ppm 8.26-8.37 (m, 1H), 8.12 (dd, J = 8.9, 1.4 Hz, 1H), 7.53-7.66 (m, 1H), 7.25-7.51 (m, 5H), 7.15 (t, J = 2.2 Hz, 1H), 6.65 (ddd, J = 15.5, 6.2, 1.4 Hz, 1H), 5.96 (dd, J = 15.4, 1.3 Hz, 1H), 4.55-4.69 (m, 2H), 4.48-4.54 (m, 1H), 4.19-4.40 (m, 2H), 3.37-3.44 (m, 1H), 2.72-3.00 (m, 1H), 2.61-2.70 (m, 0.5H), 2.23-2.41 (m, 1H), 1.82-2.16 (m, 1.5H), 1.68-1.77 (m, 1H), 1.55-1.63 (m, 1H), 1.19 (d, J = 6.9 Hz, 3H), 0.96-1.10 (m, 3H) |
| 252 | Method 4 | 2.833 | 628 | $^1$H NMR (400 MHz, DMSO-$d_6$) δ ppm 8.26-8.35 (m, 1H), 8.00 (dd, J = 8.3, 2.3 Hz, 1H), 7.49-7.63 (m, 2H), 7.30-7.47 (m, 3H), 7.23-7.28 (m, 1H), 6.65 (ddd, J = 15.4, 6.1, 1.9 Hz, 1H), 5.91-6.00 (m, 1H), 5.42 (t, J = 4.4 Hz, 1H), 4.83 (br dd, J = 10.2, 3.9 Hz, 1H), 4.47-4.69 (m, 3H), 4.24-4.40 (m, 2H), 3.34-3.44 (m, 1H), 2.59-3.02 (m, 2H), 1.66-2.38 (m, 3H), 1.46-1.61 (m, 1H), 1.34 (dd, J = 6.4, 3.1 Hz, 3H), 1.19 (d, J = 7.0 Hz, 3H), 1.00-1.08 (m, 3H) |
| 253 | Method 1 | 1.761 | 634 | $^1$H NMR (400 MHz, DMSO-$d_6$) δ ppm 8.29-8.39 (m, 1H), 8.17-8.27 (m, 1H), 7.81-7.90 (m, 1H), 7.34-7.67 (m, 5H), 7.17 (t, J = 55.3 Hz, 1H), 6.66 (dd, J = 15.5, 6.1 Hz, 1H), 5.96 (dd, J = 15.5, 1.1 Hz, 1H), 4.47-4.71 (m, 3H), 4.25-4.40 (m, 2H), 2.65-3.04 (m, 2H), 2.26-2.40 (m, 1H), 2.08 (s, 4H), 1.20 (d, J = 6.9 Hz, 3H), 1.00-1.09 (m, 3H) |
| 254 | Method 1 | 1.725 | 596 | $^1$H NMR (400 MHz, DMSO-$d_6$) δ ppm 8.23 (dd, J = 7.8, 2.2 Hz, 1H), 7.41 (br d, J = 7.8 Hz, 1H), 7.18-7.29 (m, 3H), 6.43 (d, J = 11.1 Hz, 1H), 6.25 (t, J = 10.3 Hz, 1H), 5.24-5.36 (m, 1H), 3.71 (br d, J = 10.3 Hz, 2H), 3.56-3.60 (m, 1H), 3.33-3.48 (m, 3H), 3.19-3.30 (m, 1H), 3.09 (s, 3H), 2.77-2.89 (m, 2H), 2.59 (br d, J = 13.1 Hz, 1H), 2.41 (br dd, J = 9.2, 5.6 Hz, 1H), 1.94-2.12 (m, 1H), 1.69-1.84 (m, 1H), 1.51-1.65 (m, 6H), 1.16-1.24 (m, 4H) |
| 255 | Method 1 | 1.663 | 527 | $^1$H NMR (400 MHz, DMSO-$d_6$) δ ppm 8.35-8.46 (m, 1H), 7.12-7.38 (m, 4H), 6.41-6.52 (m, 1H), 6.23-6.36 (m, 1H), 5.30-5.45 (m, 1H), 4.13 (br d, J = 10.3 Hz, 2H), 3.59 (br s, 1H), 3.25 (br d, J = 12.9 Hz, 2H), 3.12 (s, 3H), 2.56-2.71 (m, 1H), 1.58-1.97 (m, 5H), 1.29-1.49 (m, 4H), 1.11-1.26 (m, 4H), 1.04 (s, 3H), 0.91 (s, 3H) |
| 256 | Method 1 | 1.473 | 529 | $^1$H NMR (400 MHz, DMSO-$d_6$) δ ppm 8.39 (br s, 1H), 7.33-7.49 (m, 2H), 7.08-7.32 (m, 2H), 6.46 (br dd, J = 10.9, 6.6 Hz, 1H), 6.24-6.35 (m, 1H), 5.36 (br d, J = 6.7 Hz, 1H), 4.03-4.22 (m, 2H), 3.73-3.94 (m, 2H), 3.50-3.67 (m, 2H), 3.27 (br s, 1H), 3.12 (s, 3H), 2.58-2.76 (m, 1H), 1.59-1.82 (m, 4H), 1.41 (br d, J = 13.1 Hz, 2H), 1.30 (s, 3H), 1.22 (br d, J = 6.0 Hz, 3H), 1.17 (s, 3H) |
| 257 | Method 1 | 1.676 | 539 | $^1$H NMR (400 MHz, DMSO-$d_6$) δ ppm 8.34-8.43 (m, 1H), 7.19-7.37 (m, 3H), 7.12-7.17 (m, 1H), 6.43-6.49 (m, 1H), 6.25-6.34 (m, 1H), 5.32-5.42 (m, 1H), 4.04-4.19 (m, 2H), 3.37 (br d, J = 10.5 Hz, 1H), 3.18-3.30 (m, 2H), 3.12 (s, 3H), 2.56-2.69 (m, 1H), 1.79-1.98 (m, 8H), 1.64-1.77 (m, 4H), 1.35-1.61 (m, 3H), 1.22 (br dd, J = 6.4, 3.8 Hz, 4H) |

TABLE 3-continued

Representative Analytical Data for Compounds of the Disclosure.

| Cmpd. No. | LCMS Method | LCMS retention time (min) | LCMS M + H | $^1$H NMR |
|---|---|---|---|---|
| 258 | Method 2 | 2.680 | 498 | $^1$H NMR (400 MHz, DMSO-$d_6$) δ ppm 8.41-8.28 (m, 1H), 7.45-7.38 (m, 1H), 7.30-7.18 (m, 3H), 6.93-6.80 (m, 1H), 6.45 (br d, J = 10.9 Hz, 1H), 6.27 (br t, J = 9.8 Hz, 1H), 5.43-5.25 (m, 1H), 4.26-4.12 (m, 1H), 4.11-3.98 (m, 1H), 3.85-3.50 (m, 3H), 3.29-3.16 (m, 1H), 3.16-3.09 (m, 3H), 3.08-2.77 (m, 1H), 2.66-2.54 (m, 1H), 2.03-1.88 (m, 3H), 1.88-1.51 (m, 3H), 1.45 (br d, J = 7.9 Hz, 9H), 1.20 (br s, 3H) |
| 259 | Method 2 | 2.695 | [M + H − 56] = 544 | $^1$H NMR (400 MHz, DMSO-$d_6$) δ ppm 8.20-8.45 (m, 1H), 7.41-7.46 (m, 1H), 7.19-7.32 (m, 3H), 6.44 (d, J = 11.1 Hz, 1H), 6.22-6.30 (m, 1H), 5.24-5.40 (m, 1H), 3.78-4.25 (m, 2H), 3.43-3.76 (m, 5H), 3.06-3.19 (m, 3H), 2.37-2.43 (m, 2H), 1.54-1.92 (m, 6H), 1.29-1.45 (m, 9H), 1.15-1.22 (m, 3H), 0.67-1.09 (m, 1H) |
| 260 | Method 1 | 1.467 | 636.2 | $^1$H NMR (400 MHz, DMSO-$d_6$) δ ppm 8.68 (s, 1H), 8.56 (d, J = 3.6 Hz, 1H), 8.41-8.33 (m, 1H), 8.04 (d, J = 8.6 Hz, 1H), 7.91 (d, J = 7.9 Hz, 1H), 7.71 (dd, J = 2.2, 8.6 Hz, 1H), 7.50-7.41 (m, 2H), 7.39-7.31 (m, 1H), 7.13-7.05 (m, 2H), 7.00 (d, J = 7.6 Hz, 1H), 6.45 (d, J = 10.9 Hz, 1H), 6.27 (dd, J = 9.4, 11.1 Hz, 1H), 5.42-5.28 (m, 1H), 5.19 (s, 2H), 3.12 (br s, 2H), 3.09 (s, 3H), 2.58-2.52 (m, 1H), 2.48-2.45 (m, 1H), 1.82-1.69 (m, 1H), 1.68-1.55 (m, 3H), 1.19 (d, J = 6.8 Hz, 3H) |
| 261 | Method 1 | 1.872 | 665 | $^1$H NMR (400 MHz, DMSO-$d_6$) δ ppm 8.36 (dd, J = 2.2, 7.8 Hz, 1H), 8.04 (d, J = 8.6 Hz, 1H), 7.70 (dd, J = 2.3, 8.5 Hz, 1H), 7.46 (d, J = 2.3 Hz, 1H), 7.37-7.27 (m, 2H), 7.08-7.00 (m, 4H), 6.97 (d, J = 7.6 Hz, 1H), 6.89 (dd, J = 1.9, 8.1 Hz, 1H), 6.45 (d, J = 11.8 Hz, 1H), 6.27 (dd, J = 9.4, 11.2 Hz, 1H), 5.41-5.27 (m, 1H), 5.11 (s, 2H), 3.75 (s, 3H), 3.12 (br s, 2H), 3.09 (s, 3H), 2.52 (br s, 1H), 2.47 (br s, 1H), 1.83-1.69 (m, 1H), 1.68-1.55 (m, 3H), 1.19 (d, J = 6.8 Hz, 3H) |
| 262 | Method 2 | 3.053 | 615 | $^1$H NMR (400 MHz, DMSO-$d_6$) δ ppm 8.33 (br d, J = 6.4 Hz, 1H), 8.03 (d, J = 8.7 Hz, 1H), 7.69 (dd, J = 8.6, 2.3 Hz, 1H), 7.46 (d, J = 2.2 Hz, 1H), 7.31 (t, J = 7.8 Hz, 1H), 6.89-7.01 (m, 3H), 6.45 (d, J = 11.2 Hz, 1H), 6.27 (dd, J = 11.1, 9.5 Hz, 1H), 5.24-5.40 (m, 1H), 3.99 (t, J = 6.5 Hz, 2H), 3.10 (s, 5H), 2.55 (br s, 2H), 1.61-1.80 (m, 6H), 1.30-1.42 (m, 4H), 1.19 (d, J = 6.9 Hz, 3H), 0.83-0.93 (m, 3H) |
| 263 | Method 1 | 1.872 | 599 | $^1$H NMR (400 MHz, DMSO-$d_6$) δ ppm 8.36 (br d, J = 8.2 Hz, 1 H), 8.04 (d, J = 8.7 Hz, 1 H), 7.70 (dd, J = 8.6, 2.3 Hz, 1 H), 7.45 (d, J = 2.2 Hz, 1 H), 7.32 (t, J = 8.0 Hz, 1 H), 6.83-6.97 (m, 3 H), 6.45 (d, J = 11.3 Hz, 1 H), 6.27 (dd, J = 11.1, 9.5 Hz, 1 H), 5.28-5.40 (m, 1 H), 4.72 (t, J = 7.0 Hz, 1 H), 3.30 (s, 2 H), 3.12 (s, 5 H), 2.41-2.46 (m, 2 H), 2.05 (quin, J = 9.8 Hz, 2 H), 1.71-1.86 (m, 2 H), 1.56-1.70 (m, 4 H), 1.20 (d, J = 6.9 Hz, 3 H) |
| 264 | Method 1 | 1.800 | 597 | $^1$H NMR (400 MHz, DMSO-$d_6$) δ ppm 8.35 (br d, J = 5.8 Hz, 1H), 8.04 (d, J = 8.5 Hz, 1H), 7.70 (dd, J = 8.6, 2.2 Hz, 1H), 7.46 (d, J = 2.3 Hz, 1H), 7.28-7.40 (m, 1H), 6.95-7.06 (m, 3H), 6.45 (d, J = 11.2 Hz, 1H), 6.26 (dd, J = 11.1, 9.5 Hz, 1H), 5.25-5.40 (m, 1H), 4.75 (d, J = 2.4 Hz, 2H), 3.29-3.32 (m, 2H), 3.11 (s, 5H), 1.58-1.86 (m, 7H), 1.19 (d, J = 6.9 Hz, 3H) |
| 265 | Method 1 | 1.944 | 669 | $^1$H NMR (400 MHz, DMSO-$d_6$) δ ppm 8.31-8.39 (m, 1H), 8.04 (d, J = 8.6 Hz, 1H), 7.71 (dd, J = 8.6, 2.3 Hz, 1H), 7.59-7.66 (m, 1H), 7.46-7.56 (m, 2H), 7.32-7.44 (m, 3H), 7.05-7.13 (m, 2H), 7.00 (d, J = 7.5 Hz, 1H), 6.45 (d, J = 11.2 Hz, 1H), 6.27 (dd, J = 11.1, 9.5 Hz, 1H), 5.29-5.41 (m, 1H), 5.19 (s, 2H), 3.07-3.17 (m, 5H), 2.52-2.58 (m, 2H), 1.57-1.84 (m, 4H), 1.19 (d, J = 6.8 Hz, 3H) |
| 266 | Method 1 | 1.948 | 669 | $^1$H NMR (400 MHz, DMSO-$d_6$) δ ppm 8.34 (br d, J = 5.8 Hz, 1H), 8.04 (d, J = 8.6 Hz, 1H), 7.70 (dd, J = 2.1, 8.6 Hz, 1H), 7.52 (s, 1H), 7.48-7.27 (m, 5H), 7.12-7.04 (m, 2H), 6.99 (d, J = 7.5 Hz, 1H), 6.45 (d, J = 11.3 Hz, 1H), 6.33-6.21 (m, 1H), 5.41-5.27 |

TABLE 3-continued

Representative Analytical Data for Compounds of the Disclosure.

| Cmpd. No. | LCMS Method | LCMS retention time (min) | LCMS M + H | $^1$H NMR |
|---|---|---|---|---|
| | | | | (m, 1H), 5.16 (s, 2H), 3.08 (s, 5H), 2.54 (br s, 2H), 1.84-1.70 (m, 1H), 1.70-1.51 (m, 3H), 1.19 (d, J = 6.9 Hz, 3H) |
| 267 | Method 14 | 12.064 | 621.0 | $^1$H NMR (400 MHz, DMSO-$d_6$) δ ppm 8.39 (dd, J = 7.9, 2.4 Hz, 1H), 8.01 (d, J = 8.6 Hz, 1H), 7.70 (dd, J = 8.6, 2.3 Hz, 1H), 7.49 (d, J = 2.2 Hz, 1H), 7.47-7.37 (m, 3H), 7.20-7.11 (m, 2H), 7.11-7.03 (m, 3H), 6.99 (t, J = 2.1 Hz, 1H), 6.46 (d, J = 11.2 Hz, 1H), 6.28 (dd, J = 11.2, 9.4 Hz, 1H), 5.35 (h, J = 7.1 Hz, 1H), 3.17 (d, J = 13.2 Hz, 2H), 3.11 (s, 3H), 2.60-2.51 (m, 2H), 1.90-1.76 (m, 1H), 1.77-1.61 (m, 3H), 1.20 (d, J = 6.8 Hz, 3H) |
| 268 | Method 14 | 12.076 | 635.0 | $^1$H NMR (400 MHz, DMSO-$d_6$) δ ppm 8.37 (dd, J = 7.9, 2.5 Hz, 1H), 8.04 (d, J = 8.6 Hz, 1H), 7.70 (dd, J = 8.6, 2.3 Hz, 1H), 7.50-7.44 (m, 3H), 7.44-7.37 (m, 2H), 7.37-7.29 (m, 2H), 7.10-7.02 (m, 2H), 6.98 (dt, J = 7.5, 1.2 Hz, 1H), 6.45 (dd, J = 11.1, 1.0 Hz, 1H), 6.27 (dd, J = 11.1, 9.4 Hz, 1H), 5.35 (h, J = 7.1 Hz, 1H), 5.13 (s, 2H), 3.15-3.06 (m, 5H), 2.56-2.45 (m, 2H), 1.81-1.69 (m, 1H), 1.69-1.56 (m, 3H), 1.19 (d, J = 6.8 Hz, 3H) |
| 269 | Method 1 | 1.515 | 636 | $^1$H NMR (400 MHz, DMSO-$d_6$) δ ppm 8.58 (d, J = 4.4 Hz, 1H), 8.35 (br d, J = 8.0 Hz, 1H), 8.04 (d, J = 8.6 Hz, 1H), 7.84 (dt, J = 1.8, 7.7 Hz, 1H), 7.71 (dd, J = 2.3, 8.6 Hz, 1H), 7.55 (d, J = 7.8 Hz, 1H), 7.46 (d, J = 2.1 Hz, 1H), 7.40-7.30 (m, 2H), 7.13-7.05 (m, 2H), 7.00 (d, J = 7.6 Hz, 1H), 6.45 (d, J = 11.0 Hz, 1H), 6.32-6.23 (m, 1H), 5.38-5.30 (m, 1H), 5.22 (s, 2H), 3.09 (s, 5H), 2.60-2.53 (m, 2H), 1.87-1.71 (m, 1H), 1.69-1.53 (m, 3H), 1.20 (d, J = 6.9 Hz, 3H) |
| 270 | Method 1 | 1.639 | 560.1 | $^1$H NMR (400 MHz, DMSO-$d_6$) δ ppm 9.06-8.83 (m, 1H), 8.35 (br s, 1H), 7.63 (br d, J = 11.9 Hz, 1H), 7.37 (br s, 1H), 7.03 (br s, 3H), 6.54-6.37 (m, 1H), 6.25 (br s, 1H), 5.33 (br s, 1H), 3.86-3.71 (m, 3H), 3.30-3.27 (m, 1H), 3.30 (br s, 3H), 3.20-3.07 (m, 3H), 1.64 (br s, 4H), 1.18 (br d, J = 6.8 Hz, 3H) |
| 271 | Method 2 | 2.577 | 594.1 | $^1$H NMR (400 MHz, Methanol-$d_4$) δ ppm 9.01 (s, 1H), 7.50 (s, 1H), 7.45 (d, J = 8.8 Hz, 1H), 7.07-7.02 (m, 1H), 7.02-6.99 (m, 1H), 6.39 (d, J = 11.0 Hz, 1H), 6.28-6.18 (m, 1H), 5.49-5.38 (m, 1H), 3.82 (s, 3H), 3.37 (br s, 1H), 3.24-3.15 (m, 2H), 3.13 (s, 3H), 2.92 (br t, J = 13.0 Hz, 1H), 2.70 (br t, J = 12.9 Hz, 1H), 2.15-1.89 (m, 2H), 1.83-1.65 (m, 2H), 1.31 (d, J = 6.9 Hz, 3H) |
| 272 | Method 4 | 3.112 | 596 | $^1$H NMR (400 MHz, $CDCl_3$) δ ppm 7.30-7.45 (m, 2H), 7.10-7.21 (m, 2H), 6.21-6.44 (m, 2H), 6.07 (td, J = 10.2, 5.4 Hz, 1H), 5.21-5.39 (m, 1H), 4.19-4.35 (m, 1H), 3.44-3.81 (m, 3H), 3.24-3.40 (m, 3H), 3.17 (br d, J = 4.1 Hz, 3H), 2.90-3.07 (m, 1H), 2.63-2.81 (m, 1H), 2.16-2.50 (m, 2H), 1.60-2.05 (m, 8H), 1.39 (br dd, J = 10.9, 6.9 Hz, 3H), 1.26 (s, 1H) |
| 273 | Method 14 | 11.103 | 604.8 | $^1$H NMR (400 MHz, DMSO-$d_6$) δ ppm 8.01 (d, J = 8.6 Hz, 1H), 7.67 (dd, J = 8.5, 2.1 Hz, 1H), 7.54-7.45 (m, 2H), 7.42 (dd, J = 7.0, 2.4 Hz, 1H), 7.39-7.29 (m, 2H), 6.32 (d, J = 10.3 Hz, 1H), 5.29 (s, 1H), 5.01 (d, J = 11.6 Hz, 1H), 4.73 (s, 1H), 3.25 (d, J = 14.0 Hz, 1H), 3.09 (d, J = 13.5 Hz, 1H), 2.97 (s, 1H), 2.88 (t, J = 11.5 Hz, 1H), 2.72-2.57 (m, 1H), 2.25-1.91 (m, 3H), 1.81-1.64 (m, 2H) |
| 274 | Method 2 | 2.137 | 560.0 | $^1$H NMR (400 MHz, DMSO-$d_6$) δ ppm 8.53 (s, 1H), 8.36 (br d, J = 6.0 Hz, 1H), 7.53 (d, J = 7.9 Hz, 1H), 7.48-7.31 (m, 3H), 6.46 (d, J = 11.3 Hz, 1H), 6.35-6.22 (m, 2H), 5.49-5.23 (m, 1H), 3.58 (s, 3H), 3.18-2.96 (m, 5H), 2.73-2.55 (m, 2H), 1.98-1.66 (m, 4H), 1.21 (d, J = 6.9 Hz, 3H) |
| 275 | Method 1 | 1.263 | 560.1 | $^1$H NMR (400 MHz, DMSO-$d_6$) δ ppm 8.38 (dd, J = 1.9, 7.8 Hz, 1H), 7.91 (s, 1H), 7.58-7.51 (m, 1H), 7.47-7.33 (m, 3H), 6.93 (s, 1H), 6.45 (d, J = 11.2 Hz, 1H), 6.28 (dd, J = 9.4, 11.2 Hz, 1H), 5.35 (br d, J = 8.2 Hz, 1H), 3.50 (s, 3H), 3.22-3.05 (m, 5H), 2.87-2.75 (m, 1H), 2.71-2.60 (m, 1H), 2.02-1.65 (m, 4H), 1.21 (d, J = 6.9 Hz, 3H) |

TABLE 3-continued

Representative Analytical Data for Compounds of the Disclosure.

| Cmpd. No. | LCMS Method | LCMS retention time (min) | LCMS M + H | $^1$H NMR |
|---|---|---|---|---|
| 276 | Method 1 | 1.375 | 546 | $^1$H NMR (400 MHz, DMSO-d$_6$) δ ppm 12.44 (br s, 1H), 8.37 (br d, J = 6.1 Hz, 1H), 8.06 (s, 1H), 7.53 (d, J = 7.9 Hz, 1H), 7.47-7.29 (m, 3H), 6.45 (d, J = 11.4 Hz, 1H), 6.28 (dd, J = 9.6, 11.1 Hz, 1H), 6.21 (s, 1H), 5.45-5.25 (m, 1H), 3.13-2.99 (m, 5H), 2.78-2.68 (m, 1H), 2.62-2.56 (m, 1H), 2.01-1.65 (m, 4H), 1.21 (d, J = 6.9 Hz, 3H) |
| 277 | Method 1 | 1.488 | 610 | $^1$H NMR (400 MHz, DMSO-d$_6$) δ ppm 8.95 (s, 1H), 8.44-8.35 (m, 1H), 7.86 (s, 1H), 7.61-7.57 (m, 1H), 7.53-7.47 (m, 1H), 7.44 (d, J = 4.1 Hz, 2H), 6.45 (d, J = 11.1 Hz, 1H), 6.28 (dd, J = 9.4, 11.2 Hz, 1H), 5.38-5.29 (m, 1H), 3.20 (br d, J = 13.0 Hz, 2H), 3.11 (s, 3H), 2.84-2.73 (m, 1H), 2.65 (br t, J = 11.2 Hz, 1H), 1.95-1.67 (m, 4H), 1.20 (d, J = 6.8 Hz, 3H) |
| 278 | Method 1 | 1.583 | 430 | $^1$H NMR (400 MHz, DMSO-d$_6$) δ ppm 9.73-9.94 (m, 1H), 7.45-7.53 (m, 1H), 7.29-7.40 (m, 2H), 7.14-7.24 (m, 1H), 6.17-6.30 (m, 1H), 6.01-6.11 (m, 1H), 5.64 (br d, J = 10.3 Hz, 1H), 4.76 (br s, 1H), 3.78-3.92 (m, 3H), 3.00-3.47 (m, 10H), 2.82 (br dd, J = 9.9, 3.1 Hz, 1H), 1.66-1.94 (m, 5H), 1.14-1.57 (m, 4H), 0.53-0.73 (m, 1H) |
| 279 | Method 1 | 1.607 | 614 | $^1$H NMR (400 MHz, DMSO-d$_6$) δ ppm 8.46 (t, J = 5.7 Hz, 1H), 8.35 (br d, J = 7.7 Hz, 1H), 8.05 (d, J = 8.7 Hz, 1H), 7.92-7.84 (m, 2H), 7.74 (dd, J = 8.6, 2.1 Hz, 1H), 7.55-7.48 (m, 3H), 6.45 (d, J = 11.1 Hz, 1H), 6.30-6.23 (m, 1H), 5.39-5.27 (m, 1H), 3.22 (q, J = 6.5 Hz, 2H), 3.10 (s, 5H), 2.61-2.52 (m, 2H), 1.89-1.59 (m, 4H), 1.53 (sxt, J = 7.3 Hz, 2H), 1.19 (d, J = 6.9 Hz, 3H), 0.88 (t, J = 7.4 Hz, 3H) |
| 280 | Method 1 | 1.706 | 598 | $^1$H NMR (400 MHz, DMSO-d$_6$) δ ppm 8.80 (br d, J = 7.8 Hz, 1H), 7.99-7.94 (m, 1H), 7.92-7.88 (m, 1H), 7.61 (d, J = 2.0 Hz, 1H), 7.56 (d, J = 7.8 Hz, 1H), 7.48-7.43 (m, 1H), 7.40 (d, J = 4.1 Hz, 2H), 4.85-4.73 (m, 1H), 3.16 (br d, J = 11.8 Hz, 2H), 3.10 (s, 3H), 2.83 (s, 3H), 2.77-2.64 (m, 2H), 1.92-1.73 (m, 4H), 1.37 (d, J = 7.1 Hz, 3H) |
| 281 | Method 1 | 1.687 | 598 | $^1$H NMR (400 MHz, DMSO-d$_6$) δ ppm 8.81 (d, J = 7.7 Hz, 1H), 7.97-7.94 (m, 1H), 7.91-7.88 (m, 1H), 7.61 (d, J = 2.2 Hz, 1H), 7.57-7.54 (m, 1H), 7.48-7.43 (m, 1H), 7.41-7.39 (m, 2H), 4.81-4.75 (m, 1H), 3.15 (br d, J = 14.5 Hz, 2H), 3.10 (s, 3H), 2.83 (s, 3H), 2.52-2.76 (m, 3H), 1.68-2.08 (m, 3H), 1.36 (d, J = 7.0 Hz, 3H) |
| 282 | Method 1 | 1.663 | 634 | $^1$H NMR (400 MHz, DMSO-d$_6$) δ ppm 8.52 (br d, J = 5.3 Hz, 1H), 7.87-8.01 (m, 2H), 7.54-7.63 (m, 2H), 7.36-7.45 (m, 3H), 6.57-6.67 (m, 1H), 5.92 (br d, J = 15.4 Hz, 1H), 4.56-4.67 (m, 2H), 4.27-4.37 (m, 2H), 3.85 (br s, 2H), 2.62-2.74 (m, 4H), 1.79-1.99 (m, 4H) |
| 283 | Method 1 | 1.668 | 624 | $^1$H NMR (400 MHz, DMSO-d$_6$) δ ppm 8.53 (td, J = 5.6, 2.4 Hz, 1H), 8.28 (d, J = 8.4 Hz, 1H), 8.07 (dd, J = 8.4, 1.5 Hz, 1H), 7.75 (d, J = 1.5 Hz, 1H), 7.59 (d, J = 7.8 Hz, 1H), 7.41-7.53 (m, 3H), 6.63 (dt, J = 15.4, 5.0 Hz, 1H), 5.93 (dt, J = 15.4, 1.7 Hz, 1H), 4.51-4.72 (m, 2H), 4.25-4.42 (m, 2H), 3.87 (br t, J = 4.6 Hz, 2H), 3.14-3.26 (m, 2H), 2.75-2.86 (m, 1H), 2.61-2.70 (m, 1H), 1.74-2.04 (m, 4H) |
| 284 | Method 1 | 1.720 | 624 | $^1$H NMR (400 MHz, DMSO-d$_6$) δ ppm 8.47-8.52 (m, 1H), 8.26 (d, J = 8.5 Hz, 1H), 8.06 (dd, J = 8.5, 1.6 Hz, 1H), 7.74 (d, J = 1.3 Hz, 1H), 7.58 (d, J = 7.9 Hz, 1H), 7.45-7.51 (m, 1H), 7.40-7.44 (m, 2H), 5.96-6.05 (m, 1H), 5.86-5.93 (m, 1H), 4.61 (br t, J = 12.5 Hz, 2H), 4.31 (br t, J = 12.8 Hz, 2H), 4.19-4.25 (m, 2H), 3.13-3.22 (m, 2H), 2.64-2.84 (m, 2H), 1.68-2.00 (m, 4H). |
| 285 | Method 1 | 1.720 | 634 | $^1$H NMR (400 MHz, DMSO-d$_6$) δ ppm 8.50 (br d, J = 1.9 Hz, 1H), 7.98-7.93 (m, 1H), 7.92-7.86 (m, 1H), 7.61 (d, J = 2.0 Hz, 1H), 7.55 (d, J = 7.7 Hz, 1H), 7.49-7.37 (m, 3H), 6.05-5.95 (m, 1H), 5.94- |

TABLE 3-continued

Representative Analytical Data for Compounds of the Disclosure.

| Cmpd. No. | LCMS Method | LCMS retention time (min) | LCMS M + H | $^1$H NMR |
|---|---|---|---|---|
| | | | | 5.86 (m, 1H), 4.61 (br t, J = 12.5 Hz, 2H), 4.31 (br t, J = 12.4 Hz, 2H), 4.22 (br t, J = 4.6 Hz, 2H), 3.15 (br d, J = 12.2 Hz, 2H), 2.78-2.68 (m, 1H), 2.62 (br s, 1H), 2.02-1.83 (m, 2H), 1.77-1.67 (m, 2H) |
| 286 | Method 1 | 1.657 | 598 | $^1$H NMR (400 MHz, DMSO-$d_6$) δ ppm 8.49 (br d, J = 2.4 Hz, 1H), 7.99-7.93 (m, 1H), 7.92-7.86 (m, 1H), 7.61 (d, J = 2.0 Hz, 1H), 7.58-7.53 (m, 1H), 7.48-7.36 (m, 3H), 5.95-5.77 (m, 2H), 4.21 (br t, J = 4.7 Hz, 2H), 4.12 (t, J = 7.6 Hz, 2H), 3.87 (t, J = 7.7 Hz, 2H), 3.14 (br d, J = 11.2 Hz, 2H), 2.78-2.69 (m, 1H), 2.63-2.55 (m, 1H), 2.18 (quin, J = 7.7 Hz, 2H), 2.04-1.69 (m, 4H) |
| 287 | Method 1 | 1.743 | 648 | $^1$H NMR (400 MHz, DMSO-$d_6$) δ ppm 8.27 (dd, J = 8.3, 2.3 Hz, 1H), 7.91-7.97 (m, 1H), 7.85-7.90 (m, 1H), 7.59 (d, J = 2.0 Hz, 1H), 7.51-7.55 (m, 1H), 7.39-7.46 (m, 1H), 7.37 (d, J = 4.3 Hz, 2H), 6.09 (dd, J = 11.5, 8.5 Hz, 1H), 5.81 (dd, J = 11.6, 0.7 Hz, 1H), 5.25-5.44 (m, 1H), 4.43-4.71 (m, 2H), 4.30 (br t, J = 12.8 Hz, 2H), 3.12 (br dd, J = 9.6, 3.5 Hz, 2H), 2.55-2.75 (m, 2H), 1.64-1.97 (m, 4H), 1.13 (d, J = 6.8 Hz, 3H) |
| 288 | Method 1 | 1.624 | 600 | $^1$H NMR (400 MHz, DMSO-$d_6$) δ ppm 8.42-8.51 (m, 1H), 7.93-8.01 (m, 1H), 7.48-7.61 (m, 1H), 7.30-7.45 (m, 3H), 7.11-7.19 (m, 1H), 6.78-6.85 (m, 1H), 5.95-6.03 (m, 1H), 5.85-5.93 (m, 1H), 4.61 (br t, J = 12.5 Hz, 2H), 4.31 (br t, J = 12.3 Hz, 2H), 4.21 (br t, J = 4.9 Hz, 2H), 3.85 (s, 3H), 3.28-3.42 (m, 1H), 2.72-2.96 (m, 1H), 2.26-2.35 (m, 1H), 1.97-2.17 (m, 1H), 1.95 (s, 1H), 1.58-1.72 (m, 1H), 1.43-1.57 (m, 1H), 0.97-1.10 (m, 3H) |
| 289 | Method 1 | 1.670 | 639 | $^1$H NMR (400 MHz, DMSO-$d_6$) δ ppm 9.36 (d, J = 2.5 Hz, 1H), 8.47-8.57 (m, 1H), 8.10 (d, J = 3.5 Hz, 1H), 7.60-7.73 (m, 1H), 7.42-7.58 (m, 3H), 5.95-6.04 (m, 1H), 5.85-5.94 (m, 1H), 4.62 (br t, J = 12.4 Hz, 2H), 4.31 (br t, J = 12.6 Hz, 2H), 4.22 (br t, J = 5.1 Hz, 2H), 3.40-3.62 (m, 1H), 2.72-3.06 (m, 1H), 2.37-2.48 (m, 1H), 1.58-2.16 (m, 4H), 1.08 (br d, J = 6.9 Hz, 3H) |
| 290 | Method 1 | 1.743 | 638 | $^1$H NMR (400 MHz, DMSO-$d_6$) δ ppm 8.49 (br s, 1H), 8.29 (d, J = 8.4 Hz, 1H), 8.04 (br d, J = 8.4 Hz, 1H), 7.73 (s, 1H), 7.55-7.68 (m, 1H), 7.37-7.54 (m, 3H), 5.95-6.03 (m, 1H), 5.86-5.93 (m, 1H), 4.61 (br t, J = 12.4 Hz, 2H), 4.31 (br t, J = 12.6 Hz, 2H), 4.17-4.25 (m, 2H), 3.44 (br d, J = 8.4 Hz, 1H), 2.76-3.04 (m, 1H), 2.33 (br t, J = 12.1 Hz, 1H), 2.01-2.20 (m, 1H), 1.50-1.79 (m, 3H), 0.98-1.13 (m, 3H) |
| 291 | Method 1 | 1.736 | 650 | $^1$H NMR (400 MHz, DMSO-$d_6$) δ ppm 8.49 (br s, 1H), 7.98 (d, J = 8.4 Hz, 1H), 7.81-7.90 (m, 1H), 7.52-7.64 (m, 2H), 7.28-7.50 (m, 3H), 5.93-6.04 (m, 1H), 5.86-5.92 (m, 1H), 4.61 (br t, J = 12.4 Hz, 2H), 4.31 (br t, J = 12.4 Hz, 2H), 4.21 (br t, J = 4.4 Hz, 2H), 3.35-3.46 (m, 1H), 2.56-3.00 (m, 1H), 1.48-2.37 (m, 5H), 0.98-1.10 (m, 3H) |
| 292 | Method 1 | 1.595 | 595 | $^1$H NMR (400 MHz, DMSO-$d_6$) δ ppm 8.46-8.52 (m, 1H), 8.23 (d, J = 8.3 Hz, 1H), 8.13 (dd, J = 8.3, 1.6 Hz, 1H), 7.95 (d, J = 1.4 Hz, 1H), 7.55-7.67 (m, 1H), 7.42-7.52 (m, 2H), 7.34-7.42 (m, 1H), 5.95-6.02 (m, 1H), 5.91 (br d, J = 1.5 Hz, 1H), 4.61 (br t, J = 12.3 Hz, 2H), 4.30 (br d, J = 13.0 Hz, 2H), 4.22 (br s, 2H), 3.37-3.50 (m, 1H), 2.93-3.00 (m, 0.5H), 2.66-2.80 (m, 1H), 2.31-2.37 (m, 0.5H), 1.89-2.12 (m, 1H), 1.55-1.77 (m, 3H), 1.02-1.06 (m, 3H) |
| 293 | Method 1 | 1.515 | 570 | $^1$H NMR (400 MHz, DMSO-$d_6$) δ ppm 8.50 (br s, 1H), 7.31-7.42 (m, 2H), 7.26 (t, J = 7.1 Hz, 1H), 7.14-7.21 (m, 1H), 6.97-6.05 (m, 1H), 5.87-5.94 (m, 1H), 4.62 (br t, J = 12.5 Hz, 2H), 4.32 (br t, J = 12.6 Hz, 2H), 4.24 (br t, J = 4.8 Hz, 2H), 4.14-4.02 (m, 1H), 3.89-3.81 (m, 2H), 3.70-3.60 (m, 2H), 3.41 (td, J = 10.6, 4.2 Hz, 1H), 3.27-2.96 (m, 1H), 2.30-2.11 (m, 1H), 2.02-1.59 (m, 4H), 1.52-1.39 (m, 1H), 1.32 (s, 3H), 1.18 (s, 3H), 0.51-0.75 (m, 2H) |

TABLE 3-continued

Representative Analytical Data for Compounds of the Disclosure.

| Cmpd. No. | LCMS Method | LCMS retention time (min) | LCMS M + H | $^1$H NMR |
|---|---|---|---|---|
| 294 | Method 1 | 1.445 | 521.1 | $^1$H NMR (400 MHz, DMSO-$d_6$) δ ppm 8.69-8.78 (m, 1H), 7.52 (br d, J = 7.4 Hz, 1H), 7.24-7.41 (m, 4H), 7.17 (dd, J = 6.6, 2.2 Hz, 1H), 7.04 (dd, J = 8.5, 2.2 Hz, 1H), 6.88-6.92 (m, 1H), 6.78 (dd, J = 6.6, 2.2 Hz, 1H), 5.02-5.15 (m, 1H), 3.80 (s, 3H), 3.61-3.73 (m, 2H), 3.07-3.30 (m, 4H), 1.55-2.07 (m, 6H) |
| 295 | Method 2 | 2.446 | 537 | $^1$H NMR (400 MHz, DMSO-$d_6$) δ ppm 8.34-8.20 (m, 1H), 7.56-7.47 (m, 1H), 7.41-7.24 (m, 4H), 7.04 (br dd, J = 2.3, 8.4 Hz, 1H), 6.90 (br s, 1H), 6.46 (br d, J = 11.2 Hz, 1H), 6.33-6.23 (m, 1H), 5.38-5.29 (m, 1H), 3.80 (s, 3H), 3.72-3.58 (m, 1H), 3.14 (br d, J = 16.1 Hz, 6H), 2.11-1.42 (m, 6H), 1.20 (br d, J = 6.7 Hz, 3H) |
| 296 | Method 16 | 0.798 | 600.2 | $^1$H NMR (400 MHz, DMSO-$d_6$) δ ppm 8.39-8.28 (m, 1H), 7.34-7.22 (m, 2H), 7.17-7.05 (m, 1H), 6.75-6.66 (m, 1H), 6.66-6.57 (m, 1H), 4.66-4.52 (m, 1H), 4.20-4.06 (m, 1H), 3.89-3.73 (m, 1H), 3.66-3.53 (m, 1H), 3.52-3.44 (m, 1H), 3.43-3.33 (m, 2H), 3.31-3.20 (m, 2H), 3.19-3.09 (m, 1H), 3.06-2.92 (m, 3H), 2.87-2.81 (m, 1H), 2.75-2.57 (m, 1H), 2.10-2.00 (m, 1H), 1.96-1.75 (m, 3H), 1.73-1.45 (m, 3H), 1.26-1.19 (m, 3H) |
| 297 | Method 16 | 0.795 | 600.2 | $^1$H NMR (400 MHz, DMSO-$d_6$) δ ppm 8.33-8.19 (m, 1H), 7.34-7.20 (m, 2H), 7.16-7.04 (m, 1H), 6.51-6.38 (m, 1H), 6.35-6.21 (m, 1H), 5.43-5.23 (m, 1H), 4.20-3.99 (m, 1H), 3.91-3.68 (m, 1H), 3.64-3.53 (m, 1H), 3.51-3.43 (m, 1H), 3.43-3.33 (m, 2H), 3.31-3.20 (m, 2H), 3.18-3.07 (m, 4H), 3.06-2.90 (m, 1H), 2.87-2.76 (m, 1H), 2.74-2.57 (m, 1H), 2.07-1.44 (m, 6H), 1.24-1.16 (m, 3H) |
| 298 | Method 1 | 1.820 | 628.1 | $^1$H NMR (400 MHz, DMSO-$d_6$) δ ppm 8.36-8.27 (m, 1H), 7.96 (dd, J = 8.9, 1.8 Hz, 1H), 7.62-7.49 (m, 1H), 7.46-7.31 (m, 3H), 7.14 (dt, J = 8.9, 3.2 Hz, 1H), 6.80 (dd, J = 4.1, 2.7 Hz, 1H), 6.65 (ddd, J = 15.4, 6.1, 1.6 Hz, 1H), 5.95 (dd, J = 15.4, 1.4 Hz, 1H), 4.74-4.45 (m, 3H), 4.40-4.23 (m, 2H), 4.20-4.07 (m, 2H), 3.44-3.33 (m, 1H), 2.98-2.74 (m, 1H), 2.34-2.25 (m, 1H), 2.14-1.48 (m, 4H), 1.33 (t, J = 6.9 Hz, 3H), 1.19 (d, J = 6.9 Hz, 3H), 1.08-1.00 (m, 3H) |
| 299 | Method 1 | 1.810 | 587 | $^1$H NMR (400 MHz, DMSO-$d_6$) δ ppm 8.29-8.40 (m, 1H), 7.91-8.00 (m, 1H), 7.49-7.63 (m, 1H), 7.30-7.46 (m, 3H), 7.13 (dt, J = 8.9, 3.0 Hz, 1H), 6.76-6.82 (m, 1H), 6.44 (d, J = 11.1 Hz, 1H), 6.26 (dd, J = 11.1, 9.7 Hz, 1H), 5.34 (dt, J = 15.8, 8.0 Hz, 1H), 4.07-4.19 (m, 2H), 3.33-3.41 (m, 1H), 3.09-3.13 (m, 3H), 2.72-2.96 (m, 1H), 2.56-2.67 (m, 0.5H), 2.24-2.36 (m, 0.5H), 1.48-2.13 (m, 4H), 1.33 (t, J = 7.0 Hz, 3H), 1.20 (d, J = 6.9 Hz, 3H), 0.98-1.08 (m, 3H) |
| 300 | Method 1 | 1.743 | 617 | $^1$H NMR (400 MHz, DMSO-$d_6$) δ ppm 8.23-8.38 (m, 1H), 7.88-8.07 (m, 1H), 7.48-7.63 (m, 1H), 7.32-7.45 (m, 3H), 7.15 (ddd, J = 8.9, 3.8, 2.8 Hz, 1H), 6.78-6.86 (m, 1H), 6.65 (ddd, J = 15.4, 6.1, 1.6 Hz, 1H), 5.95 (dd, J = 15.4, 1.4 Hz, 1H), 4.62 (br t, J = 10.2 Hz, 2H), 4.52 (dq, J = 13.8, 6.8 Hz, 1H), 4.38-4.26 (m, 2H), 3.27-3.44 (m, 1H), 2.95-2.72 (m, 1H), 2.38-2.24 (m, 1H), 2.15-1.81 (m, 2H), 1.78-1.65 (m, 1H), 1.61-1.50 (m, 1H), 1.19 (d, J = 7.0 Hz, 3H), 0.98-1.08 (m, 3H) |
| 301 | Method 1 | 1.715 | 576 | $^1$H NMR (400 MHz, DMSO-$d_6$) δ ppm 8.33-8.41 (m, 1H), 7.98 (dd, J = 9.0, 2.1 Hz, 1H), 7.48-7.63 (m, 1H), 7.31-7.47 (m, 3H), 7.08-7.19 (m, 1H), 6.78-6.86 (m, 1H), 6.45 (d, J = 11.2 Hz, 1H), 6.26 (dd, J = 11.1, 9.6 Hz, 1H), 5.34 (dquin, J = 15.6, 7.6, Hz, 1H), 3.31-3.41 (m, 1H), 3.09-3.16 (m, 3H), 2.97-2.73 (m, 1H), 2.66-2.55 (m, 0.5H), 2.35-2.31 (m, 0.5H), 2.12-1.73 (m, 2H), 1.71-1.53 (m, 2H), 1.20 (d, J = 6.9 Hz, 3H), 1.00-1.07 (m, 3H) |
| 302 | Method 1 | 1.571 | 582 | $^1$H NMR (400 MHz, $CD_3SOCD_3$, 298K) δ ppm 8.35-8.21 (m, 1H), 7.64-7.15 (m, 4H), 6.50-6.41 (m, 1H), 6.34-6.20 (m, 1H), 5.41-5.25 (m, 1H), 4.83-4.26 (m, 1H), 4.21-3.50 (m, 3H), 3.45-3.34 (m, |

TABLE 3-continued

| Representative Analytical Data for Compounds of the Disclosure. | | | | |
|---|---|---|---|---|
| Cmpd. No. | LCMS Method | LCMS retention time (min) | LCMS M + H | $^1$H NMR |
| | | | | 3H), 3.27-3.07 (m, 5H), 2.91-2.59 (m, 2H), 1.97-1.49 (m, 3H), 1.26-0.37 (m, 7H) |
| 303 | Method 4 | 2.767 | 540 | $^1$H NMR (400 MHz, DMSO-$d_6$) δ ppm 8.18-8.28 (m, 1H), 7.31-7.40 (m, 2H), 7.21 (m, 2H), 6.40-6.46 (m, 1H), 6.21-6.31 (m, 1H), 5.24-5.39 (m, 1H), 3.89-4.08 (m, 1H), 3.67-3.81 (m, 1H), 3.38-3.59 (m, 2H), 3.11-3.24 (m, 3H), 3.09 (s, 3H), 2.85-2.98 (m, 1H), 2.53-2.77 (m, 2H), 1.77-2.01 (m, 3H), 1.48-1.76 (m, 4H), 1.15-1.25 (m, 3H), 0.29-0.46 (m, 4H) |
| 304 | Method 6 | 2.717 | 526 | $^1$H NMR (400 MHz, DMSO-$d_6$) δ ppm 8.37-8.21 (m, 1H), 7.42-7.27 (m, 2H), 7.26-7.17 (m, 2H), 6.44 (br d, J = 11.1 Hz, 1H), 6.25 (dt, J = 5.4, 10.3 Hz, 1H), 5.37-5.25 (m, 1H), 4.10-3.96 (m, 2H), 3.86-3.55 (m, 2H), 3.29-3.01 (m, 7H), 2.83-2.60 (m, 2H), 2.29-2.01 (m, 1H), 1.95-1.46 (m, 4H), 1.19 (br d, J = 6.8 Hz, 3H), 0.48-0.28 (m, 4H) |
| 305 | Method 1 | 1.299 | 590 | $^1$H NMR (400 MHz, DMSO-$d_6$) δ ppm 8.17-8.33 (m, 1H), 7.12-7.45 (m, 9H), 6.36-6.54 (m, 1H), 6.15-6.33 (m, 1H), 5.19-5.41 (m, 1H), 4.00-4.18 (m, 1H), 3.43-3.88 (m, 5H), 2.83-3.17 (m, 7H), 2.56-2.76 (m, 2H), 1.42-2.03 (m, 6H), 1.09-1.26 (m, 3H) |
| 306 | Method 14 | 2.408 | 596.3 | $^1$H NMR (400 MHz, DMSO-$d_6$) δ ppm 8.39-8.21 (m, 1H), 7.42-7.31 (m, 2H), 7.29-7.11 (m, 2H), 6.53-6.40 (m, 1H), 6.36-6.24 (m, 1H), 5.45-5.24 (m, 1H), 3.77-3.35 (m, 4H), 3.30-3.07 (m, 7H), 3.01-2.88 (m, 2H), 2.60 (br d, J = 12.5 Hz, 1H), 2.39-2.27 (m, 1H), 2.22-1.95 (m, 1H), 1.94-1.45 (m, 7H), 1.29-1.12 (m, 3H) |
| 307 | Method 1 | 1.370 | 582 | $^1$H NMR (400 MHz, DMSO-$d_6$) δ ppm 8.32-8.43 (m, 1H), 7.16-7.44 (m, 4H), 6.24-6.56 (m, 2H), 5.25-5.40 (m, 1H), 4.13 (br d, J = 12.0 Hz, 2H), 3.54-3.67 (m, 1H), 3.35-3.44 (m, 1H), 3.10-3.29 (m, 6H), 2.86-3.03 (m, 2H), 2.56-2.65 (m, 2H), 1.29-2.02 (m, 7H), 1.23 (br d, J = 6.7 Hz, 3H) |
| 308 | Method 7 | 2.074 | 596.2 | $^1$H NMR (400 MHz, DMSO-$d_6$) δ ppm 8.34-8.22 (m, 1H), 7.45-7.38 (m, 1H), 7.37-7.33 (m, 1H), 7.28-7.21 (m, 1H), 7.19-7.13 (m, 1H), 6.49-6.42 (m, 1H), 6.34-6.25 (m, 1H), 5.45-5.25 (m, 1H), 3.73-3.53 (m, 2H), 3.52-3.46 (m, 1H), 3.37 (br s, 2H), 3.36-3.33 (m, 1H), 3.27 (br s, 2H), 3.23 (br d, J = 4.9 Hz, 1H), 3.17-3.09 (m, 4H), 3.06-2.92 (m, 2H), 2.15-1.92 (m, 1H), 1.92-1.78 (m, 3H), 1.71 (br d, J = 13.1 Hz, 2H), 1.67-1.59 (m, 1H), 1.58-1.47 (m, 1H), 1.26-1.18 (m, 3H) |
| 309 | Method 1 | 1.648 | 597.1 | $^1$H NMR (400 MHz, DMSO-$d_6$) δ ppm 8.32 (dd, J = 7.7, 2.1 Hz, 1H), 7.52 (dd, J = 7.2, 2.0 Hz, 1H), 7.43-7.34 (m, 1H), 7.30-7.18 (m, 2H), 6.47 (d, J = 11.2 Hz, 1H), 6.36-6.24 (m, 1H), 5.44-5.30 (m, 1H), 4.60 (dd, J = 8.7, 3.2 Hz, 1H), 3.68-3.50 (m, 2H), 3.39-3.34 (m, 1H), 3.33-3.30 (m, 1H), 3.30-3.19 (m, 3H), 3.13 (s, 3H), 2.96-2.80 (m, 3H), 2.74-2.65 (m, 1H), 2.46 (br d, J = 10.9 Hz, 1H), 2.13-1.83 (m, 4H), 1.75 (br s, 2H), 1.22 (d, J = 6.8 Hz, 3H) |
| 310 | Method 3 | 2.929 | 611 | $^1$H NMR (400 MHz, DMSO-$d_6$) δ ppm 8.20-8.35 (m, 2H), 8.03 (br d, J = 8.3 Hz, 1H), 7.73 (s, 1H), 7.56-7.63 (m, 1H), 7.39-7.52 (m, 3H), 6.44 (d, J = 11.1 Hz, 1H), 6.23-6.33 (m, 1H), 5.26-5.39 (m, 1H), 3.11 (s, 3H), 2.83-3.09 (m, 4H), 1.82-2.12 (m, 4H), 1.60-1.79 (m, 2H), 1.20 (d, J = 6.7 Hz, 3H |
| 311 | Method 3 | 2.929 | 611 | $^1$H NMR (400 MHz, DMSO-$d_6$) δ ppm 8.19-8.35 (m, 2H), 8.03 (dd, J = 8.5, 1.3 Hz, 1H), 7.73 (s, 1H), 7.55-7.62 (m, 1H), 7.38-7.52 (m, 3H), 6.44 (d, J = 11.1 Hz, 1H), 6.22-6.33 (m, 1H), 5.33 (sxt, J = 7.3 Hz, 1H), 3.11 (s, 3H), 2.81-3.09 (m, 4H), 1.80-2.08 (m, 4H), 1.65-1.79 (m, 2H), 1.20 (d, J = 6.8 Hz, 3H) |
| 312 | Method 3 | 2.698 | 573 | $^1$H NMR (400 MHz, DMSO-$d_6$) δ ppm 8.27 (br d, J = 7.8 Hz, 1H), 7.95 (dd, J = 9.0, 3.1 Hz, 1H), 7.51-7.60 (m, 1H), 7.31-7.46 (m, 3H), 7.15 (dd, J = 8.9, 2.6 Hz, 1H), 6.81 (t, J = 2.5 Hz, 1H), 6.44 (d, J = |

TABLE 3-continued

Representative Analytical Data for Compounds of the Disclosure.

| Cmpd. No. | LCMS Method | LCMS retention time (min) | LCMS M + H | $^1$H NMR |
|---|---|---|---|---|
| | | | | 11.3 Hz, 1H), 6.23-6.31 (m, 1H), 5.21-5.39 (m, 1H), 3.84 (s, 3H), 3.10 (s, 3H), 2.71-3.03 (m, 4H), 1.63-2.10 (m, 6H), 1.19 (d, J = 6.8 Hz, 3H) |
| 313 | Method 3 | 2.702 | 573 | $^1$H NMR (400 MHz, DMSO-$d_6$) δ ppm 8.28 (br d, J = 8.2 Hz, 1H), 7.95 (dd, J = 8.9, 3.4 Hz, 1H), 7.54 (ddd, J = 7.5, 4.3, 1.6 Hz, 1H), 7.31-7.49 (m, 3H), 7.16 (dd, J = 8.9, 2.5 Hz, 1H), 6.82 (t, J = 2.5 Hz, 1H), 6.44 (d, J = 11.3 Hz, 1H), 6.21-6.33 (m, 1H), 5.33 (br d, J = 7.6 Hz, 1H), 3.85 (s, 3H), 3.11 (s, 3H), 2.94-3.05 (m, 1H), 2.70-2.92 (m, 3H), 1.86-2.11 (m, 3H), 1.61-1.84 (m, 3H), 1.20 (d, J = 6.9 Hz, 3H) |
| 314 | Method 14 | 2.123 | 554.2 | $^1$H NMR (400 MHz, $CDCl_3$) δ ppm 7.39-7.27 (m, 2H), 7.22-7.13 (m, 2H), 6.63-6.43 (m, 1H), 6.34-6.24 (m, 1H), 6.15-6.02 (m, 1H), 5.43-5.27 (m, 1H), 4.35-4.18 (m, 1H), 3.79-3.27 (m, 8H), 3.27-3.04 (m, 6H), 2.48-2.12 (m, 1H), 2.06-1.85 (m, 1H), 1.38 (dd, J = 12.5, 6.9 Hz, 3H) |

Example 3. In Vitro ELISA Target Engagement Assay for PIKKA

Engagement of compounds on PIK3CA were assessed in Jurkat cellular lysate via a sandwich ELISA.

Synthesis of PIK3CA Biotin Probe

Scheme 90. Synthesis of (R,Z)-4-((4-(1,3-dioxolan-2-yl)butyl)sulfonyl)but-3-en-2-amine

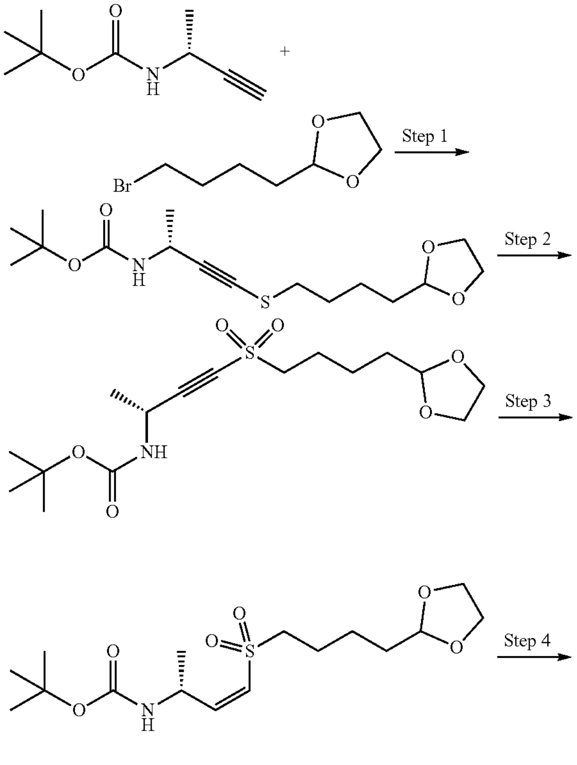

-continued

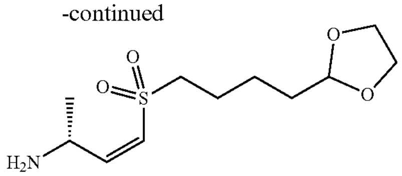

Step 1. To a solution of tert-butyl(R)-but-3-yn-2-ylcarbamate (0.90 g, 5.32 mmol, 1.0 eq) in THF (50 mL, 0.09 M) under nitrogen at −70 °C was slowly added 2.5M n-butyllithium (4.7 mL, 11.7 mmol, 2.2 eq). The mixture was stirred for 1 h before sulfur (171 mg, 0.660 mmol, 0.12 eq) was added, causing the solution to become red. The reaction mixture was stirred 30 min at −70 °C then 30 min at 0 °C until consumption of sulfur was complete (dark red solution). 2-(4-Bromobutyl)-1,3-dioxolane (1.1 g, 5.32 mmol, 1.0 eq) in THF (10 mL) was added and the reaction mixture was stirred at 0 °C for 2 h. Sat. aq. ammonium chloride was added and the aq. phase was extracted with EtOAc. The combined organic layers were washed with brine, dried over $Na_2SO_4$, filtered, and concentrated under reduced pressure. The resulting residue was purified by column chromatography to give tert-butyl (R)-(4-((4-(1,3-dioxolan-2-yl)butyl)thio)but-3-yn-2-yl)carbamate (1.0 g, 57% yield).

Step 2. To a solution of tert-butyl (R)-(4-((4-(1,3-dioxolan-2-yl)butyl)thio)but-3-yn-2-yl)carbamate (200 mg, 0.610 mmol, 1.0 eq) in ethyl acetate (2.0 mL, 0.3 M) was added 3-chloroperbenzoic acid (262 mg, 1.52 mmol, 2.5 eq) at 0 °C. The mixture was allowed to warm to rt and stirred 16 hours. The mixture was poured into sat. aq. $Na_2SO_3$ and extracted with ethyl acetate. The combined organic layers were washed with sat. aq. sodium bicarbonate, dried over $Na_2SO_4$, filtered, and concentrated under reduced pressure. The crude product tert-butyl (R)-(4-((4-(1,3-dioxolan-2-yl)butyl)sulfonyl)but-3-yn-2-yl)carbamate (250 mg, quant. yield) was used the next step directly without further purification.

Step 3. To a solution of tert-butyl (R)-(4-((4-(1,3-dioxolan-2-yl)butyl)sulfonyl)but-3-yn-2-yl)carbamate (250 mg, 0.690 mmol, 1.0 eq) in THF (3.0 mL, 0.23 M) was added Pd/C (250 mg) and the reaction was stirred at rt for 30 min under $H_2$ (50 psi). The solution was filtered to get the crude product which was purified by FCC (0-25% EtOAc in PE) to provide tert-butyl(R,Z)-(4-((4-(1,3-dioxolan-2-yl)butyl) sulfonyl)but-3-en-2-yl)carbamate (130 mg, 52% yield) as a white solid.

Step 4. To a solution of tert-butyl(R,Z)-(4-((4-(1,3-dioxolan-2-yl)butyl)sulfonyl)but-3-en-2-yl)carbamate (130 mg, 0.358 mmol, 1.0 eq) in acetonitrile (2.0 mL, 0.18 M) was added p-toluenesulfonic acid monohydrate (82 mg, 0.430 mmol, 1.2 eq) and the reaction was stirred at 50 °C for 2 h. The crude solution was evaporated to get the 4-methylbenzenesulfonic acid salt of (R,Z)-4-((4-(1,3-dioxolan-2-yl) butyl)sulfonyl)but-3-en-2-amine (160 mg, quant. yield).

Scheme 91. Synthesis of 1-((5-bromo-2'-chloro-[1, 1'-biphenyl]-2-yl)sulfonyl)-4-fluoro-N-((R,Z)-4-((5-(4-(2-(2-(2-(5-((3aS,4S,6aR)-2-oxohexahydro-1H-thieno[3,4-d]imidazol-4-yl)pentanamido)ethoxy) ethoxy)acetyl)piperazin-1-yl)pentyl)sulfonyl)but-3-en-2-yl)piperidine-4-carboxamide (PIK3CA Biotin Probe)

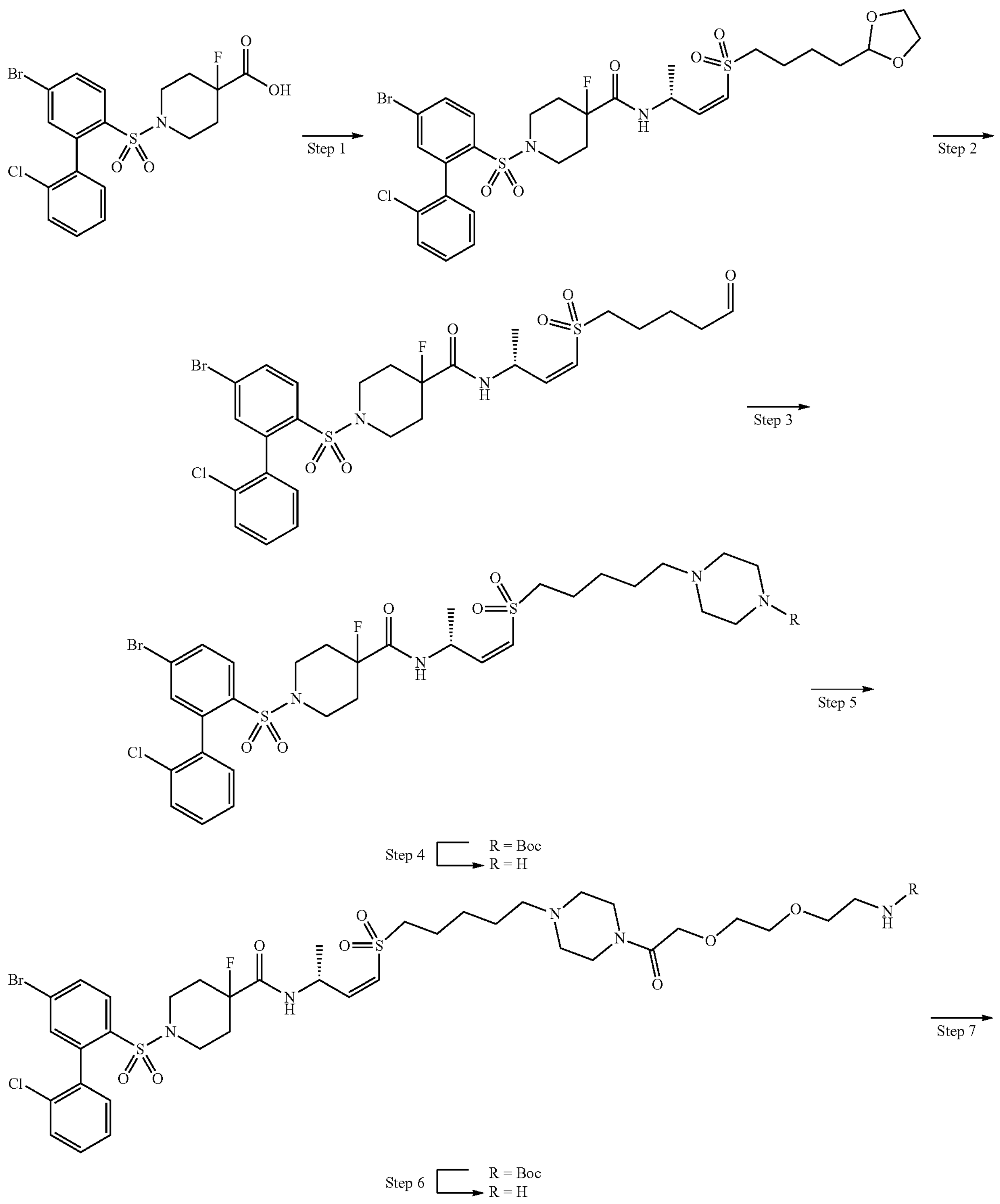

-continued

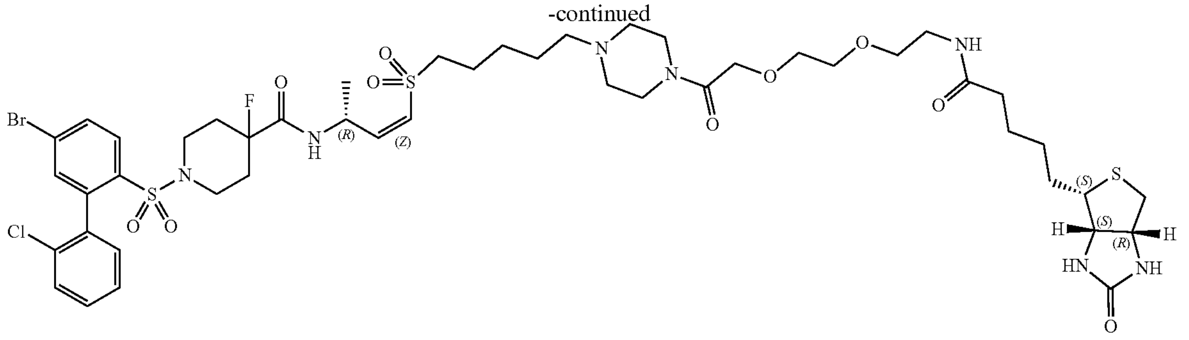

Step 1. To a solution of (R,Z)-4-((4-(1,3-dioxolan-2-yl)butyl)sulfonyl)but-3-en-2-amine, 4-methylbenzenesulfonic acid (153 mg, 0.352 mmol, 1.2 eq) in DCM (5.0 mL, 0.06 M) was added HATU (167 mg, 0.440 mmol, 1.5 eq) and DIPEA (0.13 mL, 0.734 mmol, 2.5 eq). After 5 mins, 1-[4-bromo-2-(2-chlorophenyl)phenyl]sulfonyl-4-fluoro-piperidine-4-carboxylic acid (140 mg, 0.294 mmol, 1.0 eq) was added and the reaction was stirred at rt for 2 h. The reaction was quenched with sat. aq. ammonium chloride and extracted with EtOAc. The combined organic layers were washed with brine, dried over $Na_2SO_4$, filtered, and concentrated under vacuum. The resulting residue was purified by prep-TLC ($SiO_2$, PE:EtOAc=1:1) to give (R,Z)—N-(4-((4-(1,3-dioxolan-2-yl)butyl)sulfonyl)but-3-en-2-yl)-1-((5-bromo-2'-chloro-[1,1'-biphenyl]-2-yl)sulfonyl)-4-fluoropiperidine-4-carboxamide (210 mg, quant. yield).

Step 2. To a solution of (R,Z)—N-(4-((4-(1,3-dioxolan-2-yl)butyl)sulfonyl)but-3-en-2-yl)-1-((5-bromo-2'-chloro-[1,1'-biphenyl]-2-yl)sulfonyl)-4-fluoropiperidine-4-carboxamide (210 mg, 0.290 mmol, 1.0 eq) in trifluoroacetic acid (3.0 mL, 0.02 M) was added concentrated HCl (0.6 mL) under nitrogen. The reaction was stirred at rt for 2 h before being filtered and the filtrate concentrated to provide (R,Z)-1-((5-bromo-2'-chloro-[1,1'-biphenyl]-2-yl)sulfonyl)-4-fluoro-N-(4-((5-oxopentyl)sulfonyl)but-3-en-2-yl)piperidine-4-carboxamide (200 mg, 96% yield).

Step 3. To a solution of (R,Z)-1-((5-bromo-2'-chloro-[1,1'-biphenyl]-2-yl)sulfonyl)-4-fluoro-N-(4-((5-oxopentyl)sulfonyl)but-3-en-2-yl)piperidine-4-carboxamide (200 mg, 0.300 mmol, 1.0 eq) in THF/DCE (1:1, 4.0 mL, 0.07 M) was added tert-butyl piperazine-1-carboxylate (66 mg, 0.354 mmol, 1.2 eq). DIPEA was added until pH ~5 and the mixture was stirred for 5 min at rt. $NaBH(OAc)_3$ (248 mg, 4.0 eq) was added and the mixture was stirred at rt for 1 hour. The reaction was quenched with the water and extracted with DCM. The combined organic layers were dried over $Na_2SO_4$, filtered, and concentrated under vacuum. The resulting residue was purified by prep-HPLC to give tert-butyl(R,Z)-4-(5-((3-(1-((5-bromo-2'-chloro-[1,1'-biphenyl]-2-yl)sulfonyl)-4-fluoropiperidine-4-carboxamido)but-1-en-1-yl)sulfonyl)pentyl)piperazine-1-carboxylate (160 mg, 64% yield).

Step 4. To a solution of tert-butyl(R,Z)-4-(5-((3-(1-((5-bromo-2'-chloro-[1,1'-biphenyl]-2-yl)sulfonyl)-4-fluoropiperidine-4-carboxamido)but-1-en-1-yl)sulfonyl)pentyl)piperazine-1-carboxylate (160 mg, 0.190 mmol, 1.0 eq) in acetonitrile (2.0 mL, 0.09 M) was added 4-methylbenzenesulfonic acid (39 mg, 0.230 mmol, 1.2 eq). The reaction was stirred at 50 °C for 30 min before the solution was evaporated to provide (R,Z)-1-((5-bromo-2'-chloro-[1,1'-biphenyl]-2-yl)sulfonyl)-4-fluoro-N-(4-((5-(piperazin-1-yl)pentyl)sulfonyl)but-3-en-2-yl)piperidine-4-carboxamide (150 mg, quant. yield), which was used in the next step without further purification.

Step 5. To a solution of (R,Z)-1-((5-bromo-2'-chloro-[1,1'-biphenyl]-2-yl)sulfonyl)-4-fluoro-N-(4-((5-(piperazin-1-yl)pentyl)sulfonyl)but-3-en-2-yl)piperidine-4-carboxamide (142 mg, 0.190 mmol, 1 eq) in DCM (5.0 mL, 0.04 M) was added HATU (108 mg, 0.280 mmol, 1.5 eq) and DIPEA (83 μL, 0.470 mmol, 2.5 eq). After 5 min, 2-[2-[2-(tert-butoxycarbonylamino)ethoxy]ethoxy]acetic acid (50 mg, 0.190 mmol, 1 eq) was added and the reaction mixture was stirred at rt for 2 h. The reaction was quenched with sat. aq. $NH_4Cl$ extracted with EtOAc. The combined organic layers were washed with brine, dried over $Na_2SO_4$, filtered, and concentrated under vacuum. The resulting residue was purified by prep-TLC to give tert-butyl(R,Z)-(2-(2-(2-(4-(5-((3-(1-((5-bromo-2'-chloro-[1,1'-biphenyl]-2-yl)sulfonyl)-4-fluoropiperidine-4-carboxamido)but-1-en-1-yl)sulfonyl)pentyl)piperazin-1-yl)-2-oxoethoxy)ethoxy)ethyl)carbamate (110 mg, 58% yield).

Step 6. To a solution of tert-butyl(R,Z)-(2-(2-(2-(4-(5-((3-(1-((5-bromo-2'-chloro-[1,1'-biphenyl]-2-yl)sulfonyl)-4-fluoropiperidine-4-carboxamido)but-1-en-1-yl)sulfonyl)pentyl)piperazin-1-yl)-2-oxoethoxy)ethoxy)ethyl)carbamate (110 mg, 0.110 mmol, 1.0 eq) in MeCN (20 mL, 0.006 M) was added 4-methylbenzenesulfonic acid (23 mg, 0.130 mmol, 1.2 eq). The reaction was stirred at 50 °C for 2 h before the solvent was evaporated to provide (R,Z)—N-(4-((5-(4-(2-(2-(2-aminoethoxy)ethoxy)acetyl)piperazin-1-yl)pentyl)sulfonyl)but-3-en-2-yl)-1-((5-bromo-2'-chloro-[1,1'-biphenyl]-2-yl)sulfonyl)-4-fluoropiperidine-4-carboxamide (90 mg, 91% yield), which was used in the next step without further purification.

Step 7. To a solution of (R,Z)—N-(4-((5-(4-(2-(2-(2-aminoethoxy)ethoxy)acetyl)piperazin-1-yl)pentyl)sulfonyl)but-3-en-2-yl)-1-((5-bromo-2'-chloro-[1,1'-biphenyl]-2-yl)sulfonyl)-4-fluoropiperidine-4-carboxamide (88 mg, 0.098 mmol, 1.2 eq) in DCM (5.0 mL, 0.02 M) was added HATU (47 mg, 0.120 mmol, 1.5 eq) and DIPEA (36 μL, 0.200 mmol, 2.5 eq). After 5 min, D-Biotin (20 mg, 0.082 mmol, 1.0 eq) was added and the reaction was stirred at RT for 2 h. The reaction was quenched with sat. aq. $NH_4Cl$ and extracted with EtOAc. The combined organic layers wre washed with brine, dried over $Na_2SO_4$, filtered, and concentrated under vacuum. The resulting residue was purified by prep-TLC to give 1-((5-bromo-2'-chloro-[1,1'-biphenyl]-2-yl)sulfonyl)-4-fluoro-N-((R,Z)-4-((5-(4-(2-(2-(2-(5-((3aS,4S,6aR)-2-oxohexahydro-1H-thieno[3,4-d]imidazol-4-yl)pentanamido)ethoxy)ethoxy)acetyl)piperazin-1-yl)pentyl)sulfonyl)but-3-en-2-yl)piperidine-4-carboxamide (PIK3CA Biotin Probe) (10.9 mg, 12% yield). MS (ESI): mass calculated for $C_{47}H_{66}BrClFN_7O_{10}S_3$, 1119; m/z found, 1120 $[M+H]^+$.

Biochemical Assay

A solution of PIK3CA Biotin Probe was generated at 10 mM and used in the biological testing.

TABLE 4

Materials and Methods.

| Reagents | Reagent Working Solutions | Supplier and Catalog Number | Stock Conc. |
|---|---|---|---|
| Plating Buffer | 1) 10 mL 0.2M solution of anhydrous sodium carbonate (2.2 g/100 mL)<br>2) 115 mL 0.2M solution of sodium bicarbonate<br>3) 375 mL DI water | | |
| PIK3CA Capture Antibody | Diluted in Plating Buffer 1:83 | Cell Signaling #4249S | |
| 500 mL-Pierce 20X PBS Tween 20 Buffer (PBST) | | Thermo Fisher #29352 | |
| Intercept (PBS) Blocking Buffer | | Fisher Scientific #NC1660556 | |
| Dilution Buffer | 1:1 mixture of 1X PBST and Intercept Blocking Buffer | | |
| Pierce NeutrAvidin High Sensitivity Protein HRP Conjugates (Neutravidin HRP) | Diluted in Dilution Buffer | Thermo Scientific #PI31030 | 1:500 |
| SuperSignal West Pico PLUS Chemiluminescent Substrate (HRP Substrate) | | Thermo Fisher #34580 | 1:1 A/B |

Treatment Protocol: Jurkat cellular lysate was generated from frozen cell pellets. Cells were thawed on ice and resuspended in cold Dulbecco's phosphate buffered saline (DPBS) (12 mL/300e^6 cells) then lysed by probe sonication (12×3 second pulses). Jurkat lysate was plated (50 μl/well) in Armadillo 96 well PCR plates (Thermo Fisher catalog number AB2396). The lysate was treated with serial dilutions of test compounds up to 200 μM and incubated for 1 hour at rt. Following compound incubation, PIK3CA Biotin Probe was added to a final concentration of 500 nM, and lysate was mixed by pipetting gently and incubated for an additional 1 hour at rt. The mixture was then diluted in 75 μL Dilution buffer. The mixture was centrifuged for 5 minutes at 4122 g and stored at −80 °C until ELISA TE detection.

le;1.5qELISA TE Detection: Quantification of PIK3CA TE was initiated by coating of the ELISA plate (Thermo Scientific White 384-Well Immuno plates; Thermo Fisher catalog number 460372). The capture antibody was diluted in plating buffer (1:83) and added to the ELISA plate, 20 μl/well, overnight at 4 °C. The plate was then washed twice with PBST, 100 μl/well, and blocked with addition of blocking buffer (100 μl/well, 1 hour at rt). During block, treated and probe labeled lysate was thawed. After Block, the block buffer was removed and the thawed lysate was added to the ELISA plate, 30 μl/well, for 1.5 hours at rt. Following lysate incubation, the assay plate was washed 3 times with PBST, 100 μl/well. The Neutravidin-HRP was then diluted (1:500 in dilution buffer) and added for 1 hour at rt, 20 μl/well. Following incubation, the assay plate was washed 4 times with PBST, 100 μl/well, HRP substrate was added to plate, 20 μl/well and luminescence signal was read (Clariostar Plate Reader). For each compound the potency of target engagement ($TE_{50}$) was determined using Graphpad Prism.

Example 4. Proteomic $TE_{50}$

In vitro $TE_{50}$ values for PIK3CA_C242 were obtained by treating 500 μg of cell lysate generated from Jurkat cells with DMSO or compound for 1 hour at rt followed by the addition of 200 μM desthiobiotin polyethyleneoxide iodoacetamide (IA-DTB) in DMSO for one hour at rt. Compounds were serially diluted 1:5 for a total of 7 points in order to generate dose response curves. Samples were then precipitated by the addition of 8× ice cold acetone and incubated at −80 °C for two hours. Protein was then pelleted by centrifugation (4,200 RPM, 45 min, 4 °C). The pelleted material was resuspended in 9M urea, 50 mM ammonium bicarbonate and proteins were reduced and alkylated by the addition of DTT and iodoacetamide (10 and 30 mM, respectively). Following reduction and alkylation, samples were exchanged into 2M urea (Zeba spin desalting plates, Thermo Fisher) and digested with Trypsin. IA-DTB labeled peptides were isolated with streptavidin agarose resin. Enriched peptides were eluted by the addition of 50% acetonitrile (ACN) 0.1% formic acid (FA) and dried in a SpeedVac vacuum concentrator.

Dried peptides were resuspended in 0.2 M EPPS pH 8.5 and each sample was labelled with 6.5 μL of 16-plex tandem mass tag (TMT, Thermo Fisher; 8.3 μg/μL in anhydrous ACN) for 1-2 hours at rt. Reactions were quenched by the addition of 6.5 μL of 5% hydroxylamine. Samples were then combined and desalted on a Evolute express ABN plate (Biotage, 600-0010-PX01).

Targeted TMT measurements were collected using an Orbitrap Lumos Tribrid Mass Spectrometer (Thermo Scientific) coupled to an UltiMate 3000 Series Rapid Separation LC system and autosampler (Thermo Scientific Dionex). Peptides were eluted onto a custom C18 capillary analytical column (75-μm inner diameter fused silica, packed with Acclaim PepMap C18 resin; Thermo Scientific) using an Acclaim PepMap 100 (Thermo 164535) loading column, and separated at a flow rate of 1.0 l/min. Data were acquired using a specific MS3-based TMT method targeting the peptide containing PIK3CA_C242 (LC[+324.2]VLEYQGK, +2 charge state) where MS2 peptide fragmentation is triggered upon detection of the peptide precursor ion. Subsequent MS3 analysis was then performed using pre-selected peptide fragment ions that were isolated for fragmentation using synchronous precursor selection. RAW files were converted to MZXML format and searched with the SEQUEST algorithm using the MassPike software package. TMT quantitation was performed with a filter requiring at least ten summed signal-to-noise (S/N) for control channels. $TE_{50}$ values were calculated from 7-point dose response curves created using the reporter ion S/N for each channel.

Representative proteomic data and Elisa target engagement is presented in Table 5.

TABLE 5

Representative Proteomic Biochemical Data.

| Compound No. | Elisa Target Engagement Assay (μM) | Proteomic $TE_{50}$ (μM) |
|---|---|---|
| 1 | 0.11 | 0.2455 |
| 2 | | 0.08852 |
| 3 | 0.09 | 0.11 |
| 4 | 0.14 | 0.2063 |
| 5 | 0.2 | 0.1866 |
| 6 | 0.05 | 0.026 |
| 7 | 0.09 | 0.1069 |
| 8 | 0.69 | 1.354 |
| 9 | 0.57 | 0.5074 |
| 10 | 0.32 | 0.275 |
| 11 | | 0.07014 |
| 12 | | 0.066 |
| 13 | 0.48 | 0.34 |
| 14 | 0.47 | 0.33 |
| 15 | 0.41 | 0.4 |
| 16 | 0.2 | 0.21 |
| 17 | 0.76 | |
| 18 | 0.038 | |
| 19 | 0.7436 | |
| 20 | 0.68 | 0.4618 |
| 21 | 1 | 1.23 |
| 22 | 0.77 | 0.7848 |
| 23 | 0.091 | |
| 24 | 0.17 | 0.232 |
| 25 | 0.29 | 0.2379 |
| 26 | 0.3842 | 0.3709 |
| 27 | 0.45 | 0.4299 |
| 28 | | 0.63 |
| 29 | 0.57 | 0.39 |
| 30 | 0.56 | 0.34 |
| 31 | 0.76 | 0.62 |
| 32 | 0.93 | 0.82 |
| 33 | 0.158 | 0.1327 |
| 34 | 0.55 | 0.7 |
| 35 | 0.1645 | 0.14 |
| 36 | | 0.7504 |
| 37 | | 0.2973 |
| 38 | | 0.6437 |
| 39 | | 0.7155 |
| 40 | | 0.21 |
| 41 | | 0.2904 |
| 42 | | 0.6239 |
| 43 | | 0.2642 |
| 44 | | 0.313 |
| 45 | | 0.42 |
| 46 | | 0.46 |
| 47 | 0.09897 | 0.09829 |
| 48 | 0.4815 | |
| 49 | 0.1249 | |
| 50 | 0.3194 | |
| 51 | 0.55 | |
| 52 | 0.14 | |
| 53 | 0.96 | |
| 54 | 0.86 | |
| 55 | 0.71 | |
| 56 | 0.15 | |
| 57 | 0.58 | |
| 58 | 0.85 | |
| 59 | 0.71 | |

TABLE 5-continued

Representative Proteomic Biochemical Data.

| Compound No. | Elisa Target Engagement Assay (μM) | Proteomic $TE_{50}$ (μM) |
|---|---|---|
| 60 | 0.81 | |
| 61 | | 0.06672 |
| 62 | 0.03453 | 0.028 |
| 63 | | 0.36 |
| 64 | 0.075 | |
| 65 | 0.054 | |
| 66 | 0.03795 | |
| 67 | 0.09555 | |
| 68 | 0.465 | 0.33 |
| 69 | | 0.52 |
| 70 | 0.095 | 0.07 |
| 71 | | 0.16 |
| 72 | 0.67 | |
| 73 | 0.3041 | |
| 74 | 0.41 | |
| 75 | 0.14 | |
| 76 | 0.032 | |
| 77 | 0.1285 | |
| 78 | 0.4613 | |
| 79 | 0.13 | |
| 80 | | 0.51 |
| 81 | 0.34 | |
| 82 | 0.1977 | |
| 83 | 0.52 | 0.54 |
| 84 | 0.51 | 0.45 |
| 85 | | 0.93 |
| 86 | 0.06 | 0.1066 |
| 87 | 0.39 | 0.4 |
| 88 | 0.079 | 0.086 |
| 89 | | 0.047 |
| 90 | 0.25 | 0.33 |
| 91 | 0.28 | 0.43 |
| 92 | 0.13 | 0.139 |
| 93 | 0.1497 | 0.0755 |
| 94 | | 0.19 |
| 95 | | 0.1 |
| 96 | | 0.41 |
| 97 | | 0.37 |
| 98 | | 0.52 |
| 99 | | 0.83 |
| 100 | 0.099 | 0.096 |
| 101 | | 0.86 |
| 102 | 0.73 | 0.61 |
| 103 | | 0.83 |
| 104 | | 0.62 |
| 105 | | 0.78 |
| 106 | 0.8205 | 0.31 |
| 107 | 0.2 | 0.32 |
| 108 | | 0.12 |
| 109 | 0.36 | 0.28 |
| 110 | 0.83 | 0.3633 |
| 111 | 0.32 | 0.21 |
| 112 | 0.78 | 0.66 |
| 113 | | 0.17 |
| 114 | 0.61 | 0.68 |
| 115 | 0.52 | 0.41 |
| 116 | 0.34 | 0.2615 |
| 117 | 0.83 | 0.81 |
| 118 | | 0.43 |
| 119 | 0.67 | 0.46 |
| 120 | | 0.25 |
| 121 | 1 | 0.88 |
| 122 | 0.61 | 0.49 |
| 123 | 0.82 | 0.063 |
| 124 | 0.32 | 0.15 |
| 125 | 0.61 | |
| 126 | 0.43 | 0.8165 |
| 127 | 1.1 | 0.96 |
| 128 | 0.28 | |
| 129 | 0.44 | |
| 130 | 0.47 | |
| 131 | | 0.2092 |
| 132 | 0.5244 | 0.4682 |
| 133 | 0.22 | |
| 134 | 0.1767 | 0.15 |

TABLE 5-continued

Representative Proteomic Biochemical Data.

| Compound No. | Elisa Target Engagement Assay (μM) | Proteomic $TE_{50}$ (μM) |
|---|---|---|
| 135 | 0.08718 | 0.12 |
| 136 | 0.19 | |
| 137 | 0.38 | |
| 138 | 0.34 | |
| 139 | 0.33 | |
| 140 | 0.35 | |
| 141 | 0.07498 | 0.05 |
| 142 | 0.12 | |
| 143 | 0.06648 | |
| 144 | 0.055 | |
| 145 | 0.27 | |
| 146 | 0.61 | |
| 147 | 0.39 | |
| 148 | 0.6 | |
| 149 | 0.1612 | |
| 150 | 0.31 | |
| 151 | 0.2261 | 0.2 |
| 152 | 0.45 | |
| 153 | 0.1833 | |
| 154 | 0.19 | |
| 155 | 0.3 | |
| 156 | 0.52 | |
| 157 | 0.2 | |
| 158 | | 0.8947 |
| 159 | 0.98 | |
| 160 | 0.67 | |
| 161 | 0.8 | |
| 162 | 0.77 | |
| 163 | 0.5 | |
| 164 | 0.37 | |
| 165 | 0.164 | |
| 166 | 0.3 | |
| 167 | 0.58 | |
| 168 | 0.2149 | |
| 169 | 0.21 | |
| 170 | 0.76 | |
| 171 | 0.09274 | |
| 172 | 0.58 | |
| 173 | 0.54 | |
| 174 | 0.2764 | |
| 175 | 0.62 | |
| 176 | 0.75 | |
| 177 | 0.79 | |
| 178 | 0.54 | |
| 179 | 0.39 | |
| 180 | 0.1272 | |
| 181 | 0.7 | |
| 182 | 0.91 | |
| 183 | 0.078 | |
| 184 | 0.085 | |
| 185 | 0.29 | |
| 186 | 0.4934 | 0.2256 |
| 187 | | 0.06809 |
| 188 | | 0.1889 |
| 189 | | 0.2632 |
| 190 | 0.11 | 0.061 |
| 191 | | 0.95 |
| 192 | 0.28 | 0.24 |
| 193 | 0.29 | 0.2843 |
| 194 | | 0.27 |
| 195 | 0.19 | |
| 196 | 0.53 | |
| 197 | 0.1342 | |
| 198 | 0.54 | |
| 199 | 0.9 | |
| 200 | | 0.7884 |
| 201 | 0.35 | 0.31 |
| 202 | 0.18 | 0.18 |
| 203 | 0.98 | 1.11 |
| 204 | 0.34 | 0.7297 |
| 205 | 0.65 | |
| 206 | 0.8 | |
| 207 | 0.1844 | 0.15 |
| 208 | 0.05367 | |
| 209 | 0.24 | |
| 210 | 0.11 | |
| 211 | 1 | |
| 212 | 0.38 | |
| 213 | 0.23 | |
| 214 | 0.22 | |
| 215 | 0.49 | |
| 216 | 0.55 | |
| 217 | 1.449 | 0.98 |
| 218 | 0.56 | 0.44 |
| 219 | 0.97 | 1.09 |
| 220 | 0.92 | 1.528 |
| 221 | 0.21 | |
| 222 | 0.21 | |
| 223 | 0.51 | |
| 224 | 0.52 | |
| 225 | 0.64 | |
| 226 | 0.17 | |
| 227 | 0.34 | |
| 228 | | 0.69 |
| 229 | 1.1 | 0.97 |
| 230 | | 0.14 |
| 231 | 0.13 | 0.1137 |
| 232 | 0.52 | |
| 233 | 0.29 | |
| 234 | 0.14 | |
| 235 | 0.37 | |
| 236 | 0.39 | |
| 237 | 0.055 | |
| 238 | 0.025 | |
| 239 | 0.28 | |
| 240 | 0.12 | |
| 241 | 0.062 | |
| 242 | 0.072 | |
| 243 | 0.67 | |
| 244 | 0.78 | |
| 245 | 0.62 | |
| 246 | 0.042 | |
| 247 | 0.41 | |
| 248 | 0.17 | |
| 249 | 0.62 | |
| 250 | 0.35 | |
| 251 | 0.26 | |
| 252 | 0.28 | |
| 253 | 0.16 | |
| 254 | 0.88 | |
| 255 | 0.43 | |
| 256 | 0.78 | |
| 257 | 0.42 | |
| 258 | 0.8832 | |
| 259 | 0.66 | |
| 260 | 0.15 | 0.21 |
| 261 | 0.48 | 0.73 |
| 262 | 0.78 | 0.43 |
| 263 | 1 | 0.93 |
| 264 | 0.48 | 0.51 |
| 265 | 0.33 | 0.39 |
| 266 | 0.75 | 0.6 |
| 267 | | 0.7029 |
| 268 | | 0.3561 |
| 269 | 0.09001 | 0.063 |
| 270 | | 0.55 |
| 271 | 0.17 | 0.2089 |
| 272 | 0.88 | |
| 273 | 0.83 | |
| 274 | 1.1 | 0.57 |
| 275 | 1.3 | 0.91 |
| 276 | | 0.57 |
| 277 | 0.097 | 0.082 |
| 278 | | 0.24 |
| 279 | 1 | 1.53 |
| 280 | 0.15 | |
| 281 | 0.16 | |
| 282 | 0.14 | |
| 283 | 0.2 | |
| 284 | 0.061 | |

TABLE 5-continued

| Representative Proteomic Biochemical Data. | | |
|---|---|---|
| Compound No. | Elisa Target Engagement Assay (μM) | Proteomic $TE_{50}$ (μM) |
| 285 | 0.05411 | |
| 286 | 0.64 | |
| 287 | 0.83 | |
| 288 | 0.49 | |
| 289 | 0.46 | |
| 290 | 1 | |
| 291 | 0.32 | |
| 292 | 0.16 | |
| 293 | 0.82 | |
| 294 | 0.12 | |
| 295 | 0.35 | |
| 296 | 0.4 | |
| 297 | 0.91 | |
| 298 | 0.72 | |
| 299 | 0.21 | |
| 300 | 0.31 | |
| 301 | 0.077 | |
| 302 | 0.44 | |
| 303 | 0.5572 | |
| 304 | 0.74 | |
| 305 | 0.65 | |
| 306 | 0.31 | |
| 307 | 0.8449 | |
| 308 | 0.85 | |
| 309 | 0.39 | |
| 310 | 0.085 | |
| 311 | 0.82 | |
| 312 | 0.08 | |
| 313 | 0.53 | |
| 314 | 1.1 | |

Example 5. In Vitro Phosgho-AKT(S473) Analysis

Functional activity of the compounds to inhibit pAKT were assessed in FaDu or H358 cell lines as indicated below.

Materials

- Complete Media
- FBS, Corning catalog #35-010-CV
- Anti-Anti, Gibco catalog #15240-062
- 96 well plate, Corning catalog #3610
- TrypLE, Gibco catalog #12604013
- Phospho-AKT(S473) HTRF kit, Cisbio catalog #64AKSPET Cells were detached from the tissue culture flask with TrypLE. The cells were pelleted at 500×g for 5 min, TrypLe was removed and then resuspended in the necessary volume of media+1% FBS to give the appropriate cell density (17,500 cells/mL for FaDu; 20,000 cells/mL for H358). 100 μL of cell suspension/well was dispensed into the 96-well plate while keeping the outer wells of the plate free of cells and filled with PBS to prevent evaporation of interior wells. The plate was incubated at 37 °C and allowed to adhere overnight. The cells were treated with a dose response of compound and incubated at 37 °C for 30 minutes. The cells were then processed and pAKT(S473) levels were assessed following the specifications of the Cisbio HTRF kit.

1-[4-Bromo-2-(2-chlorophenyl)phenyl]sulfonyl-4-fluoro-N-[(Z,1R)-1-methyl-3-methylsulfonyl-allyl]piperidine-4-carboxamide (Compound 47) was used as an internal standard for the assay to normalize Imax and the absolute inhibition of pAKT for 1-[4-bromo-2-(2-chlorophenyl)phenyl]sulfonyl-4-fluoro-N—[(Z,1R)-1-methyl-3-methylsulfonyl-allyl]piperidine-4-carboxamide varied from 40-89% for the H358 cell line and 43-98% for the FaDu cell line.

Representative biochemical data for inhibition of pAKT is presented in Table 6.

TABLE 6

| Representative pAKT Inhibition Data. | | | | |
|---|---|---|---|---|
| Compound Number | H358 pAKT $IC_{50}$ (μM) | H358 pAKT Imax % control | FaDu pAKT $IC_{50}$ (μM) | FaDu pAKT Imax % control |
| 33 | | | 0.4091 | 86.2 |
| 35 | | | 0.3301 | 103.1 |
| 47 | | | 0.09648 | 100 |
| 58 | | | 0.7433 | 97.55 |
| 62 | | | 0.02754 | 85.2 |
| 134 | | | 0.3479 | 96.27 |
| 138 | | | 0.2921 | 93.55 |
| 140 | | | 0.4271 | 87.65 |
| 141 | | | 0.08243 | 102.5 |
| 143 | | | 0.1172 | 111.2 |
| 145 | | | 0.1307 | 102.3 |
| 149 | | | 0.2478 | 108.8 |
| 151 | | | 0.2843 | 100.5 |
| 153 | | | 0.2045 | 103.6 |
| 155 | | | 0.3046 | 105.5 |
| 156 | | | 0.3475 | 99.2 |
| 164 | | | 0.8341 | 103.1 |
| 165 | 0.115 | 95.68 | 0.2137 | 96.65 |
| 166 | | | 0.1872 | 78.9 |
| 167 | | | 0.5181 | 93.6 |
| 168 | | | 0.1359 | 90.6 |
| 169 | 0.2023 | 106 | 0.1545 | 107.5 |
| 170 | | | 0.4838 | 83.2 |
| 171 | 0.0826 | 100.6 | 0.07892 | 97.8 |
| 172 | | | 0.5052 | 97.9 |
| 173 | 0.4642 | 85.55 | | |
| 174 | | | 0.168 | 91.75 |
| 175 | 0.1508 | 75.6 | | |
| 176 | | | 0.6789 | 83.3 |
| 177 | | | 0.672 | 69.45 |
| 179 | 0.1651 | 106.2 | | |
| 180 | | | 0.1357 | 96.9 |
| 183 | 0.0566 | 93.2 | | |
| 184 | 0.0646 | 102 | | |
| 185 | 0.1233 | 95.63 | | |
| 187 | | | 0.1521 | 70.1 |
| 195 | 0.123 | 85.05 | 0.1129 | 96.9 |
| 196 | 0.3288 | 96.3 | 0.4498 | 86.4 |
| 197 | 0.1026 | 91.4 | 0.1291 | 89 |
| 198 | | | 0.472 | 95.25 |
| 205 | | | 1.122 | |
| 206 | | | 0.7178 | 105.6 |
| 207 | | | 0.8028 | 75.2 |
| 208 | 0.08157 | 95.9 | 0.08823 | |
| 210 | | | 0.214 | |
| 213 | | | 0.2907 | 90.8 |
| 216 | | | 0.6883 | 107.6 |
| 217 | 0.9533 | 74.6 | | |
| 221 | 0.123 | 85 | | |
| 222 | 0.1465 | 91 | | |
| 223 | 0.3457 | 87.5 | | |
| 224 | 0.3264 | 81.2 | | |
| 225 | 0.4647 | 78.8 | | |
| 227 | 0.2504 | 101.6 | | |
| 234 | | | 0.1001 | |
| 237 | | | 0.07363 | |
| 238 | | | 0.02921 | |
| 240 | | | 0.4374 | |
| 241 | | | 0.2812 | 95.3 |
| 242 | | | 0.1376 | |
| 243 | | | 0.7608 | 68.7 |
| 244 | | | 1.199 | 76.3 |
| 245 | | | 0.9215 | 86.15 |
| 246 | | | 0.1632 | |
| 248 | | | 0.5574 | |
| 249 | | | 1.2 | 82.75 |
| 250 | | | 1.645 | 96.8 |
| 251 | | | 0.2488 | 102.5 |
| 252 | | | 0.2485 | 85.85 |
| 253 | | | 0.2669 | 77.25 |
| 254 | | | 0.9109 | 92.5 |
| 255 | 0.06705 | 86.65 | | |
| 272 | 0.6944 | 89.85 | | |
| 282 | | | 0.3673 | |

TABLE 6-continued

Representative pAKT Inhibition Data.

| Compound Number | H358 pAKT $IC_{50}$ (μM) | H358 pAKT Imax % control | FaDu pAKT $IC_{50}$ (μM) | FaDu pAKT Imax % control |
|---|---|---|---|---|
| 284 | | | 0.0674 | |
| 285 | | | 0.1238 | |
| 294 | | | 2.119 | |
| 296 | 0.6416 | 69.4 | | |
| 297 | 1.501 | 87.6 | | |
| 298 | | | 0.3215 | 101.5 |
| 299 | | | 0.1465 | 99.6 |
| 300 | | | 0.4177 | 94.25 |
| 301 | | | 0.117 | 99.75 |
| 302 | 0.4639 | 87.15 | 0.6955 | 100.8 |
| 303 | | | 0.243 | 101.8 |
| 305 | 0.3955 | 90.7 | 0.4281 | 94.35 |
| 306 | 0.2631 | 88.03 | 0.3336 | 93 |
| 308 | 0.4077 | 91.05 | 0.5804 | 93.4 |
| 309 | 0.2759 | 91.75 | | |
| 310 | | | 0.07707 | |
| 312 | | | 0.1405 | |
| 314 | 0.622 | 100.4 | | |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound of Formula (I), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof:

Formula (I)

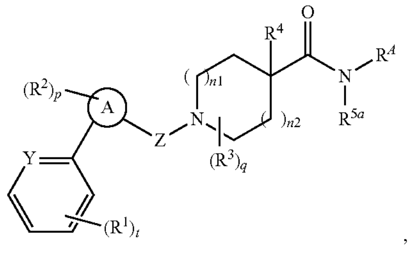

wherein,

Z is C(=O) or $S(=O)_2$;

Ring A is phenyl, 5 to 10-membered heteroaryl, $C_3$-$C_8$ cycloalkyl, C8-C9 spirocyclyl, or 5 to 8-membered heterocycloalkyl;

Y is N, CH, or $CR^1$;

each R1 is independently halogen, —CN, —OH, —$OR^a$, —SH, —$SR^a$, —$NO_2$, —$N(R^b)_2$, —C(=O)$R^a$, —C(=O)$OR^a$, —C(=O)$NR^aR^b$, optionally substituted $C_1$-$C_6$ alkyl, optionally substituted $C_1$-$C_6$ deuteroalkyl, optionally substituted $C_2$-$C_6$ alkenyl, optionally substituted $C_2$-$C_6$ alkynyl, optionally substituted $C_1$-$C_6$ haloalkyl, optionally substituted $C_1$-$C_6$ hydroxyalkyl or optionally substituted $C_3$-$C_6$ cycloalkyl;

each $R^2$ is independently halogen, —CN, —OH, —$OR^a$, —SH, —$SR^a$, —$NO_2$, —$N(R^b)_2$, —$S(=O)_2R^a$, —C(=O)$R^a$, —C(=O)$OR^a$, —C(=O)$NR^aR^b$, oxo (=O), optionally substituted $C_1$-$C_6$ alkyl, optionally substituted $C_1$-$C_6$ deuteroalkyl, optionally substituted $C_2$-$C_6$ alkenyl, optionally substituted $C_2$-$C_6$ alkynyl, optionally substituted $C_1$-$C_6$ alkylamino, optionally substituted $C_1$-$C_6$ haloalkyl, optionally substituted $C_1$-$C_6$ hydroxyalkyl, optionally substituted $C_3$-$C_6$ cycloalkyl, optionally substituted arylalkyl or optionally substituted 4 to 6-membered heterocycloalkyl;

or two $R^2$ together with the atom(s) to which they are attached combine to form a $C_3$-$C_5$ cycloalkyl, 4 to 5-membered heterocycloalkyl, or a 5-membered heteroaryl ring;

each $R^3$ is independently halogen, —CN, —OH, —$OR^a$, $C_1$-$C_6$ alkyl, $C_1$-$C_6$ deuteroalkyl, or $C_1$-$C_6$ haloalkyl;

$R^4$ is H, halogen, —OH, —$OR^a$, or $C_1$-$C_6$ alkyl;

$R^A$ is

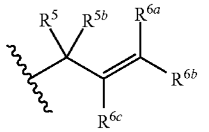

or

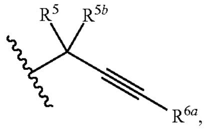

wherein $R^5$ is H, optionally substituted $C_1$-$C_3$ alkyl, optionally substituted $C_1$-$C_3$ haloalkyl, or optionally substituted $C_1$-$C_3$ hydroxyalkyl;

$R^{6a}$ and $R^{6b}$ are each independently H, —CN, —C(=O)$OR^7$, —C(=O)$N(R^7)_2$, —S(=O) $R^7$, —$S(=O)_2R^7$, or —S(=O)(=NH)$R^7$; wherein each $R^7$ is independently optionally substituted $C_1$-$C_6$ alkyl, optionally substituted $C_3$-$C_6$ cycloalkyl, or optionally substituted 4 to 6-membered heterocycloalkyl ring;

or two $R^7$ together with the nitrogen atom to which they are attached combine to form an optionally substituted 4 to 5-membered heterocycloalkyl ring;

or $R^5$ and $R^7$ together with the atoms to which they are attached combine to form a 5-membered heterocycloalkyl ring;

$R^{6c}$ is H or —CN;

or $R^{6c}$ and $R^7$ together with the atoms to which they are attached combine to form a 4-membered heterocycloalkyl ring;

$R^{5a}$ is H; or $R^{5a}$ and $R^{6c}$ together with the nitrogen atom to which they are $R^{5a}$ is attached and the two carbons linking $R^6$ to the nitrogen atom to which $R^{5a}$ is attached combine to form a 4-membered heterocycloalkyl ring; or $R^{5a}$ is absent and $R^{6c}$ is bound directly to the nitrogen to which $R^A$ is attached to form a 4-membered heterocyclic ring;

or $R^{5a}$ and $R^5$ together with the nitrogen and carbon atoms to which they are attached form a 4-membered heterocyclic ring;

$R^{5b}$ is H or $C_1$-$C_3$ alkyl;

each $R^a$ is independently H, $C_1$-$C_6$ alkyl, $C_1$-$C_6$ deuteroalkyl, $C_1$-$C_6$ haloalkyl, $C_1$-$C_6$ heteroalkyl, $C_2$-$C_6$ alkenyl, $C_2$-$C_6$ alkynyl, $C_3$-$C_6$ cycloalkyl, $C_3$-$C_6$ heterocycloalkyl, $C_5$-$C_8$ aryl, $C_5$-$C_8$ heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl(heterocycloalkyl); wherein each alkyl, deuteroalkyl, haloalkyl, heteroalkyl, cycloalkyl, heterocycloalkyl, aryl, heteroaryl, alkyl(aryl), alkyl (heteroaryl), alkyl(cycloalkyl) and alkyl(heterocycloalkyl) is independently optionally substituted with one, two, or three halogen, —OH, $C_1$-$C_6$ alkyl, $C_1$-$C_6$ haloalkyl, or $C_1$-$C_6$ alkoxy;

each $R^b$ is independently H, $C_1$-$C_6$ alkyl, $C_1$-$C_6$ haloalkyl, $C_1$-$C_6$ heteroalkyl, cycloalkyl, heterocycloalkyl, aryl, or heteroaryl; wherein the alkyl, heteroalkyl, cycloalkyl, heterocycloalkyl, aryl, and heteroaryl is independently optionally substituted with one, two, or three halogen, —OH, $C_1$-$C_6$ alkyl, or $C_1$-$C_6$ haloalkyl;

or two $R^b$ groups on a nitrogen atom are taken together with the nitrogen atom to which they are attached to form a heterocycloalkyl which is optionally substituted with one, two, or three $C_1$-$C_6$ alkyl, or $C_1$-$C_6$ haloalkyl;

n1 and n2 are each independently 0, 1, 2, or 3;

p is 0, 1, 2, or 3;

q is 0, 1, or 2; and t is 0, 1, 2, or 3.

2. The compound of claim 1, or a pharmaceutically acceptable salt thereof, wherein $R^4$ is halogen.

3. The compound of claim 1, or a pharmaceutically acceptable salt thereof, wherein $R^{5a}$ and $R^{5b}$ are each H, and $R^5$ is $C_1$-$C_3$ alkyl.

4. The compound of claim 1, wherein the compound has the structure of Formula (Ia), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof:

Formula (Ia)

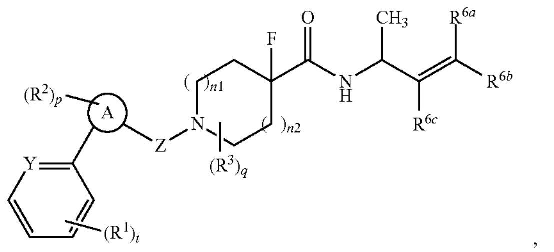

, wherein,

Z is C(═O) or S(═O)$_2$;

Ring A is phenyl, 5 to 10-membered heteroaryl, $C_3$-$C_8$ cycloalkyl, C8-C9 spirocyclyl, or 5 to 8-membered heterocycloalkyl;

Y is CH or $CR^1$;

each $R^1$ is independently halogen, —CN, —OH, —$OR^a$, —SH, —$SR^a$, —$NO_2$, —$N(R^b)_2$, —C(═O)$R^a$, —C(═O)$OR^a$, —C(═O)$NR^aR^b$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ haloalkyl, optionally substituted $C_1$-$C_6$ hydroxyalkyl or optionally substituted $C_3$-$C_6$ cycloalkyl;

each $R^2$ is independently halogen, —CN, —OH, —$OR^a$, —SH, —$SR^a$, —$NO_2$, —$N(R^b)_2$, —S(═O)$_2R^a$, —C(═O)$R^a$, —C(═O)$OR^a$, —C(═O)$NR^aR^b$, oxo (═O), optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkylamino, optionally substituted $C_1$-$C_6$ haloalkyl, optionally substituted $C_1$-$C_6$ hydroxyalkyl, optionally substituted $C_3$-$C_6$ cycloalkyl, optionally substituted arylalkyl or optionally substituted 4 to 6-membered heterocycloalkyl;

or two $R^2$ together with the atom(s) to which they are attached combine to form a $C_3$-$C_5$ cycloalkyl, 4 to 5-membered heterocycloalkyl, or a 5-membered heteroaryl ring;

each $R^3$ is independently halogen, —CN, —OH, —$OR^a$, $C_1$-$C_6$ alkyl, or $C_1$-$C_6$ haloalkyl;

$R^{6a}$ and $R^{6b}$ are each independently H, —CN, —C(═O)$OR^7$, —C(═O)N($R^7$) 2, —S(═O)$R^7$, —S(═O)$_2R^7$, or —S(═O)(═NH)$R^7$; wherein each $R^7$ is independently optionally substituted $C_1$-$C_6$ alkyl, optionally substituted $C_3$-$C_6$ cycloalkyl, or optionally substituted 4 to 6-membered heterocycloalkyl ring;

or two $R^7$ together with the nitrogen atom to which they are attached combine to form an optionally substituted 4 to 5-membered heterocycloalkyl ring;

or $R^5$ and $R^7$ together with the atoms to which they are attached combine to form a 5-membered heterocycloalkyl ring;

$R^{6c}$ is H or —CN;

or $R^{6c}$ and $R^7$ together with the atoms to which they are attached combine to form a 4-membered heterocycloalkyl ring;

each $R^a$ is independently H, $C_1$-$C_6$ alkyl, $C_1$-$C_6$ deuteroalkyl, $C_1$-$C_6$ haloalkyl, $C_1$-$C_6$ heteroalkyl, $C_2$-$C_6$ alkenyl, $C_2$-$C_6$ alkynyl, $C_3$-$C_6$ cycloalkyl, $C_3$-$C_6$ heterocycloalkyl, $C_5$-$C_8$ aryl, $C_5$-$C_8$ heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl(heterocycloalkyl); wherein each alkyl, deuteroalkyl, haloalkyl, heteroalkyl, cycloalkyl, heterocycloalkyl, aryl, heteroaryl, alkyl(aryl), alkyl (heteroaryl), alkyl(cycloalkyl) and alkyl(heterocycloalkyl) is independently optionally substituted with one, two, or three halogen, —OH, $C_1$-$C_6$ alkyl, $C_1$-$C_6$ haloalkyl, or $C_1$-$C_6$ alkoxy;

each $R^b$ is independently H, $C_1$-$C_6$ alkyl, $C_1$-$C_6$ haloalkyl, $C_1$-$C_6$ heteroalkyl, cycloalkyl, heterocycloalkyl, aryl, or heteroaryl; wherein the alkyl, heteroalkyl, cycloalkyl, heterocycloalkyl, aryl, and heteroaryl is independently optionally substituted with one, two, or three halogen, —OH, $C_1$-$C_6$ alkyl, or $C_1$-$C_6$ haloalkyl;

or two $R^b$ groups on a nitrogen atom are taken together with the nitrogen atom to which they are attached to form a heterocycloalkyl which is optionally substituted with one, two, or three $C_1$-$C_6$ alkyl, or $C_1$-$C_6$ haloalkyl;

n1 and n2 are each independently 0, 1, 2, or 3;

p is 0, 1, 2, or 3;

q is 0, 1, or 2; and t is 0, 1, 2, or 3.

5. The compound of claim 1, or a pharmaceutically acceptable salt thereof, wherein ring A is a C5-C7 cycloalkyl or 5 to 7-membered heterocycloalkyl.

6. The compound of claim 1, wherein the compound has the structure of Formula (II), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof:

Formula (II)

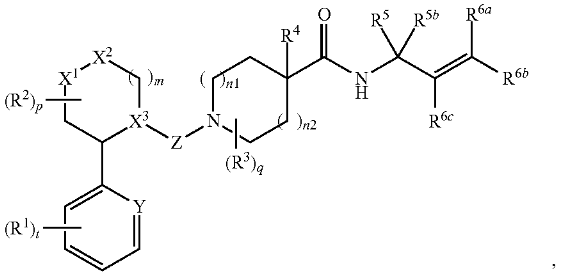

wherein, $X^1$ and $X^2$ are each independently $CH_2$, $CHR^2$, $CR^2R^2$, O, or $NR^{2a}$, wherein at least one of $X^1$ or $X^2$ is $CH_2$, $CHR^2$, or $CR^2R^2$;

$X^3$ is $CR^8$ or N, provided that when $X^3$ is N, $R^8$ is absent;

Y is N, CH, or $CR^1$;

Z is C(═O) or $S(═O)_2$;

each $R^1$ is independently halogen, —CN, —OH, —$OR^a$, optionally substituted $C_1$-$C_6$ alkyl, optionally substituted $C_1$-$C_6$ deuteroalkyl, optionally substituted $C_2$-$C_6$ alkynyl, optionally substituted $C_1$-$C_6$ haloalkyl, or optionally substituted $C_1$-$C_6$ hydroxyalkyl or optionally substituted $C_3$-$C_6$ cycloalkyl;

each $R^2$ is independently halogen, —CN, —OH, —$OR^a$, —$N(R^b)_2$, optionally substituted $C_1$-$C_6$ alkyl, optionally substituted $C_1$-$C_6$ deuteroalkyl, optionally substituted $C_2$-$C_6$ alkenyl, optionally substituted $C_2$-$C_6$ alkynyl, optionally substituted $C_1$-$C_6$ haloalkyl, optionally substituted $C_1$-$C_6$ hydroxyalkyl, optionally substituted $C_3$-$C_6$ cycloalkyl, optionally substituted arylalkyl or optionally substituted 4 to 6-membered heterocycloalkyl;

or two $R^2$ together with the atom(s) to which they are attached combine to form a $C_3$-$C_5$ cycloalkyl;

$R^{2a}$ is H, —$S(═O)_2R^a$, —C(═O)$R^a$, —C(═O)$OR^a$, —C(═O)$NR^aR^b$, optionally substituted $C_1$-$C_6$ alkyl, optionally substituted $C_1$-$C_6$ haloalkyl, $C_3$-$C_6$ cycloalkyl, or phenyl;

each $R^3$ is independently halogen, —CN, —OH, —$OR^a$, $C_1$-$C_6$ alkyl, $C_1$-$C_6$ deuteroalkyl, or $C_1$-$C_6$ haloalkyl;

$R^4$ is H, halogen, —OH, —$OR^a$, or $C_1$-$C_6$ alkyl;

$R^5$ is H, $C_1$-$C_3$ alkyl, $C_1$-$C_3$ haloalkyl, or $C_1$-$C_3$ hydroxyalkyl;

$R^{5b}$ is H or $C_1$-$C_3$ alkyl;

$R^{6a}$ and $R^{6b}$ are each independently H, —CN, —C(═O)$OR^7$, —C(═O)$N(R^7)_2$, —S(═O)$R^7$, —$S(═O)_2R^7$, or —S(═O)(═NH)$R^7$; wherein each $R^7$ is independently optionally substituted $C_1$-$C_6$ alkyl, optionally substituted $C_3$-$C_6$ cycloalkyl, or optionally substituted 4 to 6-membered heterocycloalkyl ring;

or two $R^7$ together with the nitrogen atom to which they are attached combine to form an optionally substituted 4 to 5-membered heterocycloalkyl ring;

or $R^5$ and $R^7$ together with the atoms to which they are attached combine to form a 5-membered heterocycloalkyl ring;

$R^{6c}$ is H or —CN;

or $R^{6c}$ and $R^7$ together with the atoms to which they are attached combine to form a 4-membered heterocycloalkyl ring;

$R^8$ is absent, H, halogen, —$OCH_3$, or —$CH_3$;

each $R^a$ is independently H, $C_1$-$C_6$ alkyl, $C_1$-$C_6$ deuteroalkyl, $C_1$-$C_6$ haloalkyl, $C_1$-$C_6$ heteroalkyl, $C_2$-$C_6$ alkenyl, $C_2$-$C_6$ alkynyl, $C_3$-$C_6$ cycloalkyl, $C_3$-$C_6$ heterocycloalkyl, $C_5$-$C_8$ aryl, $C_5$-$C_8$ heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl(heterocycloalkyl); wherein each alkyl, deuteroalkyl, haloalkyl, heteroalkyl, cycloalkyl, heterocycloalkyl, aryl, heteroaryl, alkyl(aryl), alkyl(heteroaryl), alkyl(cycloalkyl) and alkyl(heterocycloalkyl) is independently optionally substituted with one, two, or three halogen, —OH, $C_1$-$C_6$ alkyl, $C_1$-$C_6$ haloalkyl, or $C_1$-$C_6$ alkoxyl;

each $R^b$ is independently H, $C_1$-$C_6$ alkyl, $C_1$-$C_6$ haloalkyl, $C_1$-$C_6$ heteroalkyl, cycloalkyl, heterocycloalkyl, aryl, or heteroaryl; wherein the alkyl, heteroalkyl, cycloalkyl, heterocycloalkyl, aryl, and heteroaryl is independently optionally substituted with one, two, or three halogen, —OH, $C_1$-$C_6$ alkyl, or $C_1$-$C_6$ haloalkyl;

or two $R^b$ groups on a nitrogen atom are taken together with the nitrogen atom to which they are attached to form a heterocycloalkyl which is optionally substituted with one, two, or three $C_1$-$C_6$ alkyl, or $C_1$-$C_6$ haloalkyl;

m is 0 or 1;

n1 and n2 are each independently 0, 1, 2, or 3;

p is 0, 1, 2, or 3;

q is 0, 1, or 2; and t is 1, 2, or 3.

7. The compound of claim 6, wherein the compound has the structure of Formula (IIb), or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof:

Formula (IIb)

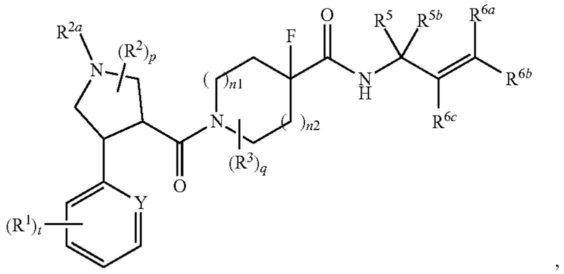

wherein,

Y is CH or $CR^1$;

each $R^1$ is independently halogen, —CN, —OH, —$OR^a$, optionally substituted $C_1$-$C_6$ alkyl, optionally substituted $C_1$-$C_6$ deuteroalkyl, optionally substituted $C_2$-$C_6$ alkynyl, optionally substituted $C_1$-$C_6$ haloalkyl, or $C_1$-$C_6$ hydroxyalkyl;

each $R^2$ is independently optionally substituted $C_1$-$C_6$ alkyl, optionally substituted $C_1$-$C_6$ deuteroalkyl, optionally substituted $C_1$-$C_6$ haloalkyl, or optionally substituted $C_3$-$C_6$ cycloalkyl;

$R^{2a}$ is H, —C(═O)$OR^a$, —C(═O)$NR^aR^b$, optionally substituted $C_1$-$C_6$ alkyl, optionally substituted $C_1$-$C_6$ haloalkyl, optionally substituted arylalkyl, or optionally substituted $C_3$-$C_6$ cycloalkyl;

each $R^3$ is independently $C_1$-$C_3$ alkyl or $C_1$-$C_3$ deuteroalkyl;

$R^5$ is H, $C_1$-$C_3$ alkyl, $C_1$-$C_3$ haloalkyl, or $C_1$-$C_3$ hydroxyalkyl;

$R^{5b}$ is H or $C_1$-$C_3$ alkyl;

$R^{6a}$ and $R^{6b}$ are each independently H, —CN, —C(═O)$OR^7$, —C(—O)N($R^7$) 2, —S(═O)$R^7$, —S(═O)$_2R^7$, or —S(═O)(═NH)$R^7$; wherein each $R^7$ is independently optionally substituted $C_1$-$C_6$ alkyl, optionally substituted $C_3$-C6 cycloalkyl, or optionally substituted 4 to 6-membered heterocycloalkyl ring;

or two $R^7$ together with the nitrogen atom to which they are attached combine to form an optionally substituted 4 to 5-membered heterocycloalkyl ring;

or $R^5$ and $R^7$ together with the atoms to which they are attached combine to form a 5-membered heterocycloalkyl ring;

$R^{6c}$ is H or —CN;

or $R^{6c}$ and $R^7$ together with the atoms to which they are attached combine to form a 4-membered heterocycloalkyl ring;

each $R^a$ is independently H, $C_1$-$C_6$ alkyl, $C_1$-$C_6$ deuteroalkyl, $C_1$-$C_6$ haloalkyl, $C_1$-$C_6$ heteroalkyl, $C_2$-$C_6$ alkenyl, $C_2$-$C_6$ alkynyl, $C_3$-$C_6$ cycloalkyl, $C_3$-$C_6$ heterocycloalkyl, $C_5$-$C_8$ aryl, $C_5$-$C_8$ heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl(heterocycloalkyl); wherein each alkyl, deuteroalkyl, haloalkyl, heteroalkyl, cycloalkyl, heterocycloalkyl, aryl, heteroaryl, alkyl(aryl), alkyl(heteroaryl), alkyl(cycloalkyl) and alkyl(heterocycloalkyl) is independently optionally substituted with one, two, or three halogen, —OH, $C_1$-$C_6$ alkyl, $C_1$-$C_6$ haloalkyl, or $C_1$-$C_6$ alkoxyl;

each $R^b$ is independently H, $C_1$-$C_6$ alkyl, $C_1$-$C_6$ haloalkyl, $C_1$-$C_6$ heteroalkyl, cycloalkyl, heterocycloalkyl, aryl, or heteroaryl; wherein the alkyl, heteroalkyl, cycloalkyl, heterocycloalkyl, aryl, and heteroaryl is independently optionally substituted with one, two, or three halogen, —OH, $C_1$-$C_6$ alkyl, or $C_1$-$C_6$ haloalkyl;

n1 and n2 are each independently 0, 1, 2, or 3;

p is 0, 1, 2, or 3;

q is 0, 1, or 2; and t is 1, 2, or 3.

8. The compound of claim 7 or a pharmaceutically acceptable salt thereof, wherein Y is CH or $CR^1$;

$R^1$ is halogen;

$R^{2a}$ is $C_1$-$C_6$ haloalkyl;

$R^5$ is $C_1$-$C_3$ alkyl;

$R^{5b}$ is H;

$R^{6a}$ and $R^{6b}$ are each independently H or —S(═O)(═NH)$R^7$ wherein each $R^7$ is independently $C_1$-$C_6$ alkyl, or $R^5$ and $R^7$ together with the atoms to which they are attached combine to form a 5-membered heterocycloalkyl ring;

$R^{6c}$ is H;

n1 and n2 are each independently 1 or 2;

p is 0 or 1;

q is 0 or 1; and t is 1 or 2.

9. The compound of claim 6, or a pharmaceutically acceptable salt thereof, wherein $R^{2a}$ is —C(═O)$R^a$, —C(═O)O$R^a$, optionally substituted $C_1$-$C_6$ alkyl, optionally substituted $C_1$-$C_6$ haloalkyl, or optionally substituted $C_3$-$C_6$ cycloalkyl; wherein each $R^a$ is independently $C_1$-$C_6$ alkyl or aryl.

10. The compound of claim 7, or a pharmaceutically acceptable salt thereof, wherein $R^{2a}$ is

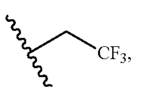
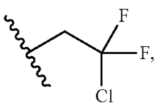
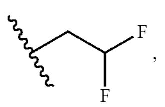
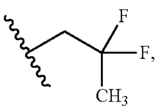
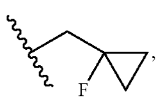
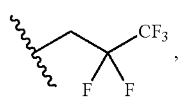
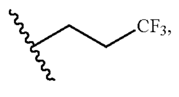
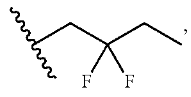
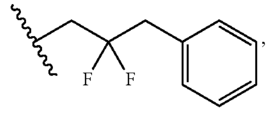
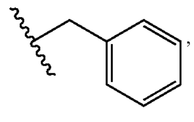
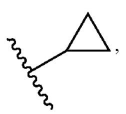
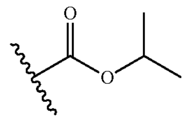
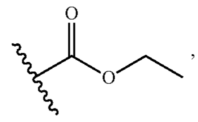
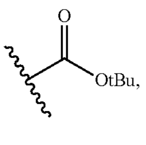
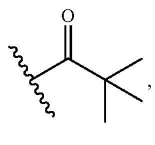
or
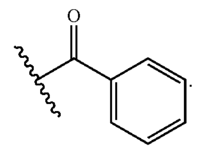

11. The compound of claim 7, or a pharmaceutically acceptable salt thereof, wherein p is 0.

12. The compound of claim 1, or a pharmaceutically acceptable salt thereof, wherein each $R^1$ is independently halogen, —CN, —OH, —O$R^a$, —C(═O)O$R^a$, —C(═O)N$R^aR^b$, optionally substituted $C_1$-$C_6$ alkyl, optionally substituted $C_2$-$C_6$ alkenyl, optionally substituted $C_2$-$C_6$ alkynyl, or optionally substituted $C_1$-$C_6$ haloalkyl.

13. The compound of claim 1, or a pharmaceutically acceptable salt thereof, wherein t is 1 or 2.

14. The compound of claim 1, or a pharmaceutically acceptable salt thereof, wherein q is 0.

15. The compound of claim 1, or a pharmaceutically acceptable salt thereof, wherein $R^A$ is:

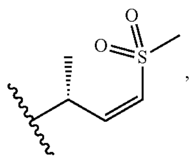
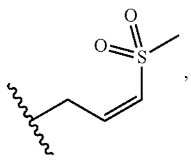
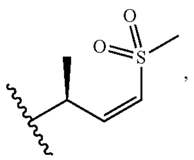
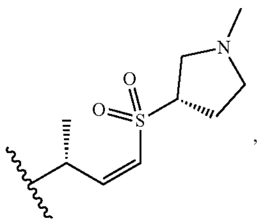

-continued

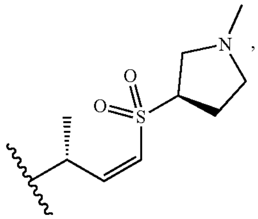,
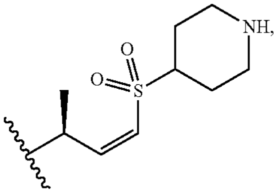
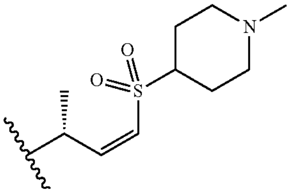,
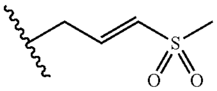,
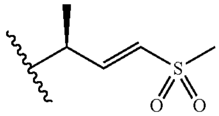,
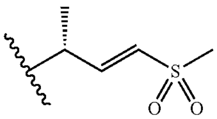,
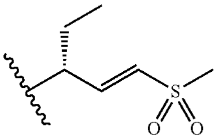,
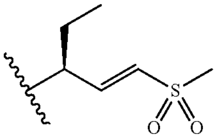,
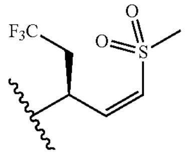,
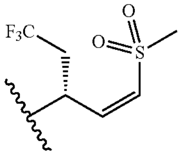,
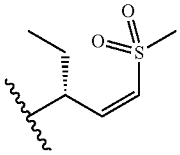,
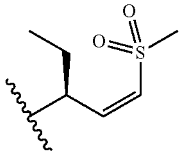,
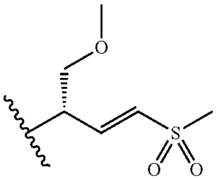,
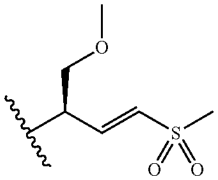,
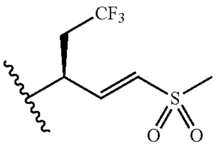,
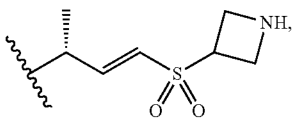
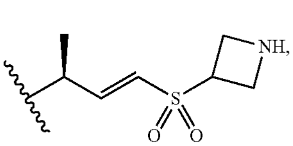
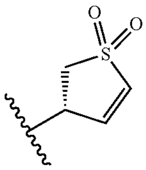, -continued

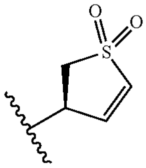,
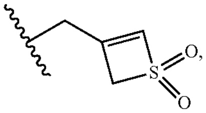
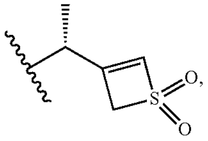
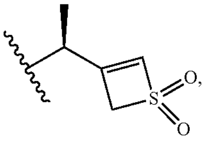
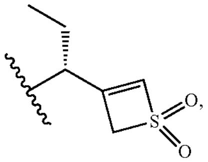
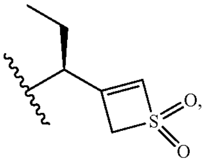
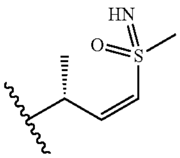,
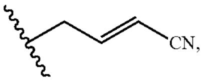
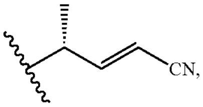
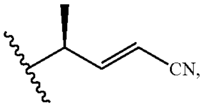
,
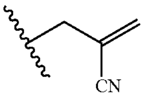
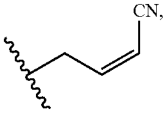
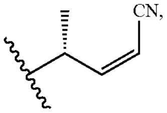
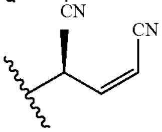,
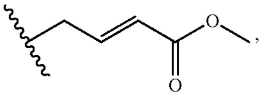
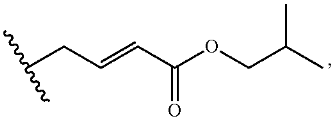
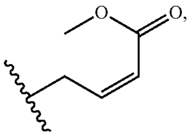
or
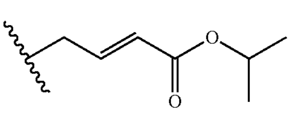.

16. The compound of claim 1, or a pharmaceutically acceptable salt thereof, wherein the compound is:

(S,Z)-1-((5-chloro-3'-methoxy-[1,1'-biphenyl]-2-yl)sulfonyl)-4-fluoro-N-(4-(methylsulfonyl)but-3-en-2-yl)piperidine-4-carboxamide, (S,Z)-1-((5-chloro-[1,1'-biphenyl]-2-yl)sulfonyl)-4-fluoro-N-(4-(methylsulfonyl)but-3-en-2-yl)piperidine-4-carboxamide, (S,Z)-1-((3',5-dichloro-[1,1'-biphenyl]-2-yl)sulfonyl)-4-fluoro-N-(4-(methylsulfonyl)but-3-en-2-yl)piperidine-4-carboxamide, (S,Z)-4-fluoro-1-((5-methoxy-[1,1'-biphenyl]-2-yl)sulfonyl)-N-(4-(methylsulfonyl)but-3-en-2-yl)piperidine-4-carboxamide, (S,Z)-1-((3',5-dimethoxy-[1,1'-biphenyl]-2-yl)sulfonyl)-4-fluoro-N-(4-(methylsulfonyl)but-3-en-2-yl)piperidine-4-carboxamide, (S,Z)-1-((2',5-dichloro-[1,1'-biphenyl]-2-yl)sulfonyl)-4-fluoro-N-(4-(methylsulfonyl)but-3-en-2-yl)piperidine-4-carboxamide, (S,Z)-1-((3'-chloro-5-methoxy-[1,1'-biphenyl]-2-yl)sulfonyl)-4-fluoro-N-(4-(methylsulfonyl)but-3-en-2-yl)piperidine-4-carboxamide, (S,Z)-1-((5-chloro-3'-cyano-[1,1'-biphenyl]-2-yl)sulfonyl)-4-fluoro-N-(4-(methylsulfonyl)but-3-en-2-yl)piperidine-4-carboxamide, (S,Z)-4-fluoro-1-((5-fluoro-3'-methoxy-[1,1'-biphenyl]-2-yl)sulfonyl)-N-(4-(methylsulfonyl)but-3-en-2-yl)piperidine-4-carboxamide, (S,Z)-1-((5-chloro-3'-ethoxy-[1,1'-biphenyl]-2-yl)sulfonyl)-4-fluoro-N-(4-(methylsulfonyl)but-3-en-2-yl)piperidine-4-carboxamide, (S,Z)-1-((2'-chloro-5-methoxy-[1,1'-biphenyl]-2-yl)sulfonyl)-4-fluoro-N-(4-(methylsulfonyl)but-3-en-2-yl)piperidine-4-carboxamide, (S,Z)-4-fluoro-1-((5-methoxy-2'-methyl-[1,1'-biphenyl]-2-yl)sulfonyl)-N-(4-(methylsulfonyl)but-3-en-2-yl)piperidine-4-carboxamide, (S,Z)-1-((5-chloro-3'-propoxy-[1,1'-biphenyl]-2-yl)sulfonyl)-4-fluoro-N-(4-(methylsulfonyl)but-3-en-2-yl)piperidine-4-carboxamide, (S,Z)-1-((5-chloro-3'-cyclopropoxy-[1,1'-biphenyl]-2-yl)sulfonyl)-4-fluoro-N-(4-(methylsulfonyl)but-3-en-2-yl)piperidine-4-carboxamide, (S,Z)-1-((2',5-dichloro-5'-methoxy-[1,1'-biphenyl]-2-yl)sulfonyl)-4-fluoro-N-(4-(methylsulfonyl)but-3-en-2-yl)piperidine-4-carboxamide, (S,Z)-1-((5-chloro-3'-(ethoxymethyl)-[1,1'-biphenyl]-2-yl)sulfonyl)-4-fluoro-N-(4-(methylsulfonyl)but-3-en-2-yl)piperidine-4-carboxamide, (S,Z)-1-((2'-chloro-5-(trifluoromethyl)-[1,1'-biphenyl]-2-yl)sulfonyl)-4-fluoro-N-(4-(methylsulfonyl)but-3-en-2-yl)piperidine-4-carboxamide, (S,Z)-4-fluoro-1-((3'-methoxy-[1,1'-biphenyl]-2-yl)sulfonyl)-N-(4-(methylsulfonyl)but-3-en-2-yl)piperidine-4-carboxamide, (R,Z)-1-((5-chloro-[1,1'-biphenyl]-2-yl)sulfonyl)-4-fluoro-N-(4-(methylsulfonyl)but-3-en-2-yl)piperidine-4-carboxamide, (R,Z)-4-fluoro-1-((5-methoxy-[1,1'-biphenyl]-2-yl)sulfonyl)-N-(4-(methylsulfonyl)but-3-en-2-yl)piperidine-4-carboxamide, (R,Z)-1-((3'-chloro-5-methoxy-[1,1'-biphenyl]-2-yl)sulfonyl)-4-fluoro-N-(4-(methylsulfonyl)but-3-en-2-yl)piperidine-4-carboxamide, (R,Z)-1-((2',5-dichloro-[1,1'-biphenyl]-2-yl)sulfonyl)-4-fluoro-N-(4-(methylsulfonyl)but-3-en-2-yl)piperidine-4-carboxamide, (R,Z)-4-fluoro-1-((5-methoxy-2'-methyl-[1,1'-biphenyl]-2-yl)sulfonyl)-N-(4-(methylsulfonyl)but-3-en-2-yl)piperidine-4-carboxamide, (R,Z)-1-((2'-chloro-5-methoxy-[1,1'-biphenyl]-2-yl)sulfonyl)-4-fluoro-N-(4-(methylsulfonyl)but-3-en-2-yl)piperidine-4-carboxamide, (R,Z)-1-((2'-chloro-3'-fluoro-5-methoxy-[1,1'-biphenyl]-2-yl)sulfonyl)-4-fluoro-N-(4-(methylsulfonyl)but-3-en-2-yl)piperidine-4-carboxamide, (R,Z)-1-((2'-chloro-4'-fluoro-5-methoxy-[1,1'-biphenyl]-2-yl)sulfonyl)-4-fluoro-N-(4-(methylsulfonyl)but-3-en-2-yl)piperidine-4-carboxamide, (R,Z)-1-((2'-chloro-5'-fluoro-5-methoxy-[1,1'-biphenyl]-2-yl)sulfonyl)-4-fluoro-N-(4-(methylsulfonyl)but-3-en-2-yl)piperidine-4-carboxamide, (R,Z)-1-((2',4-dichloro-5-methoxy-[1,1'-biphenyl]-2-yl)sulfonyl)-4-fluoro-N-(4-(methylsulfonyl)but-3-en-2-yl)piperidine-4-carboxamide, 1-((2'-chloro-6'-fluoro-5-methoxy-[1,1'-biphenyl]-2-yl)sulfonyl)-4-fluoro-N-((R,Z)-4-(methylsulfonyl)but-3-en-2-yl)piperidine-4-carboxamide, (R,Z)-1-((2'-chloro-5-fluoro-[1,1'-biphenyl]-2-yl)sulfonyl)-4-fluoro-N-(4-(methylsulfonyl)but-3-en-2-yl)piperidine-4-carboxamide, 1-((2',6-dichloro-5-methoxy-[1,1'-biphenyl]-2-yl)sulfonyl)-4-fluoro-N-((R,Z)-4-(methylsulfonyl)but-3-en-2-yl)piperidine-4-carboxamide, (R,Z)-1-((2'-chloro-5-(trifluoromethyl)-[1,1'-biphenyl]-2-yl)sulfonyl)-4-fluoro-N-(4-(methylsulfonyl)but-3-en-2-yl)piperidine-4-carboxamide, (R,Z)-1-((2'-chloro-5-(trifluoromethoxy)-[1,1'-biphenyl]-2-yl)sulfonyl)-4-fluoro-N-(4-(methylsulfonyl)but-3-en-2-yl)piperidine-4-carboxamide, (R,Z)-1-((2'-chloro-5-cyano-[1,1'-biphenyl]-2-yl)sulfonyl)-4-fluoro-N-(4-(methylsulfonyl)but-3-en-2-yl)piperidine-4-carboxamide, (E)-1-((5-chloro-3'-methoxy-[1,1'-biphenyl]-2-yl)sulfonyl)-4-fluoro-N-(3-(methylsulfonyl)allyl)piperidine-4-carboxamide, (E)-1-((5-chloro-[1,1'-biphenyl]-2-yl)sulfonyl)-4-fluoro-N-(3-(methylsulfonyl)allyl)piperidine-4-carboxamide, (E)-4-fluoro-1-((5-methoxy-[1,1'-biphenyl]-2-yl)sulfonyl)-N-(3-(methylsulfonyl)allyl)piperidine-4-carboxamide, (E)-1-((3',5-dimethoxy-[1,1'-biphenyl]-2-yl)sulfonyl)-4-fluoro-N-(3-(methylsulfonyl)allyl)piperidine-4-carboxamide, (E)-1-((2',5-dichloro-[1,1'-biphenyl]-2-yl)sulfonyl)-4-fluoro-N-(3-(methylsulfonyl)allyl)piperidine-4-carboxamide, (E)-1-((3'-chloro-5-methoxy-[1,1'-biphenyl]-2-yl)sulfonyl)-4-fluoro-N-(3-(methylsulfonyl)allyl)piperidine-4-carboxamide, (E)-4-fluoro-1-((3'-methoxy-5-methyl-[1,1'-biphenyl]-2-yl)sulfonyl)-N-(3-(methylsulfonyl)allyl)piperidine-4-carboxamide, (E)-1-((2'-chloro-5-methoxy-[1,1'-biphenyl]-2-yl)sulfonyl)-4-fluoro-N-(3-(methylsulfonyl)allyl)piperidine-4-carboxamide, (E)-4-fluoro-1-((5-methoxy-2'-methyl-[1,1'-biphenyl]-2-yl)sulfonyl)-N-(3-(methylsulfonyl)allyl)piperidine-4-carboxamide, (E)-1-((3',5-dichloro-[1,1'-biphenyl]-2-yl)sulfonyl)-4-fluoro-N-(3-(methylsulfonyl)allyl)piperidine-4-carboxamide, (E)-1-((5-chloro-3'-(prop-1-yn-1-yl)-[1,1'-biphenyl]-2-yl)sulfonyl)-4-fluoro-N-(3-(methylsulfonyl)allyl)piperidine-4-carboxamide, (R,Z)-1-((5-bromo-2'-chloro-[1,1'-biphenyl]-2-yl)sulfonyl)-4-fluoro-N-(4-(methylsulfonyl)but-3-en-2-yl)piperidine-4-carboxamide, (R,Z)-1-((5-bromo-2'-chloro-5'-fluoro-[1,1'-biphenyl]-2-yl)sulfonyl)-4-fluoro-N-(4-(methylsulfonyl)but-3-en-2-yl)piperidine-4-carboxamide, (R,Z)-1-((5-bromo-2'-methyl-[1,1'-biphenyl]-2-yl)sulfonyl)-4-fluoro-N-(4-(methylsulfonyl)but-3-en-2-yl)piperidine-4-carboxamide, (R,Z)-1-((5-bromo-2'-chloro-4'-fluoro-[1,1'-biphenyl]-2-yl)sulfonyl)-4-fluoro-N-(4-(methylsulfonyl)but-3-en-2-yl)piperidine-4-carboxamide, (R,Z)-1-((5-bromo-2'-ethyl-[1,1'-biphenyl]-2-yl)sulfonyl)-4-fluoro-N-(4-(methylsulfonyl)but-3-en-2-yl)piperidine-4-carboxamide, (R,Z)-1-((5-bromo-2'-chloro-3'-fluoro-[1,1'-biphenyl]-2-yl)sulfonyl)-4-fluoro-N-(4-(methylsulfonyl)but-3-en-2-yl)piperidine-4-carboxamide, (R,Z)-1-((5-bromo-2'-chloro-4'-methyl-[1,1'-biphenyl]-2-yl)sulfonyl)-4-fluoro-N-(4-(methylsulfonyl)but-3-en-2-yl)piperidine-4-carboxamide, (R,Z)-1-((5-bromo-2'-(trifluoromethyl)-[1,1'-biphenyl]-2-yl)sulfonyl)-4-fluoro-N-(4-(methylsulfonyl)but-3-en-2-yl)piperidine-4-carboxamide, (R,Z)-1-((5-bromo-3'-chloro-[1,1'-biphenyl]-2-yl)sulfonyl)-4-fluoro-N-(4-(methylsulfonyl)but-3-en-2-yl)piperidine-4-carboxamide, (R,Z)-1-((5-bromo-3'-fluoro-2'-methyl-[1,1'-biphenyl]-2-yl)sulfonyl)-4-fluoro-N-(4-(methylsulfonyl)but-3-en-2-yl)piperidine-4-carboxamide, (R,Z)-1-((5-bromo-[1,1'-biphenyl]-2-yl)sulfonyl)-4-fluoro-N-(4-(methylsulfonyl)but-3-en-2-yl)piperidine-4-carboxamide, (R,Z)-1-((3',5-dibromo-[1,1'-biphenyl]-2-yl)sulfonyl)-4-fluoro-N-(4-(methylsulfonyl)but-3-en-2-yl)piperidine-4-carboxamide, (R,Z)-1-((5-bromo-2'-chloro-3'-methyl-[1,1'-biphenyl]-2-yl)sulfonyl)-4-fluoro-N-(4-(methylsulfonyl)but-3-en-2-yl)piperidine-4-carboxamide, 1-((5-bromo-2'-chloro-6'-methyl-[1,1'-biphenyl]-2-yl)sulfonyl)-4-fluoro-N-((R,Z)-4-(methylsulfonyl)but-3-en-2-yl)piperidine-4-carboxamide, (S,Z)-1-((5-bromo-3'-methoxy-[1,1'-biphenyl]-2-yl)sulfonyl)-4-fluoro-N-(4-(methylsulfonyl)but-3-en-2-yl)piperidine-4-carboxamide, (S,Z)-1-((5-bromo-2'-chloro-[1,1'-biphenyl]-2-yl)sulfonyl)-4-fluoro-N-(4-(methylsulfonyl)but-3-en-2-yl)piperidine-4-carboxamide, (E)-1-((5-bromo-3'-methoxy-[1,1'-biphenyl]-2-yl)sulfonyl)-4-fluoro-N-(3-(methylsulfonyl)allyl)piperidine-4-carboxamide, (E)-1-((5-bromo-2'-chloro-[1,1'-biphenyl]-2-yl)sulfonyl)-4-fluoro-N-(3-(methylsulfonyl)allyl)piperidine-4-carboxamide, 1-((5-bromo-2'-chloro-[1,1'-biphenyl]-2-yl)sulfonyl)-N-(1,1-dioxido-2,3-dihydrothiophen-3-yl)-4-fluoropiperidine-4-carboxamide, (R)-1-((5-bromo-2'-chloro-[1,1'-biphenyl]-2-yl)sulfonyl)-N-(1,1-dioxido-2,3-dihydrothiophen-3-yl)-4-fluoropiperidine-4-carboxamide, (S)-1-((5-bromo-2'-chloro-[1,1'-biphenyl]-2-yl)sulfonyl)-N-(1,1-dioxido-2,3-dihydrothiophen-3-yl)-4-fluoropiperidine-4-carboxamide, (E)-1-((5-bromo-2'-chloro-[1,1'-biphenyl]-2-yl)sulfonyl)-N-(3-cyanoallyl)-4-fluoropiperidine-4-carboxamide, (E)-N-(3-cyanoallyl)-1-((2',5-dichloro-[1,1'-biphenyl]-2-yl)sulfonyl)-4-fluoropiperidine-4-carboxamide, (Z)-1-((5-bromo-2'-chloro-[1,1'-biphenyl]-2-yl)sulfonyl)-N-(3-cyanoallyl)-4-fluoropiperidine-4-carboxamide, (Z)-1-((2'-chloro-5-methoxy-[1,1'-biphenyl]-2-yl)sulfonyl)-N-(3-cyanoallyl)-4-fluoropiperidine-4-carboxamide, 1-((5-bromo-2'-chloro-[1,1'-biphenyl]-2-yl)sulfonyl)-N-(2-cyanoallyl)-4-fluoropiperidine-4-carboxamide, 1-((5-bromo-2'-chloro-[1,1'-biphenyl]-2-yl)sulfonyl)-4-fluoro-N-((2R,Z)-4-(S-methylsulfonimidoyl) but-3-en-2-yl)piperidine-4-carboxamide, 1-((5-bromo-2'-chloro-[1,1'-biphenyl]-2-yl)sulfonyl)-4-fluoro-N-((R,Z)-4-((R)—S-methylsulfonimidoyl) but-3-en-2-yl)piperidine-4-carboxamide, (S,E)-N-(4-(azetidin-3-ylsulfonyl)but-3-en-2-yl)-1-((5-bromo-2'-chloro-[1,1'-biphenyl]-2-yl)sulfonyl)-4-fluoropiperidine-4-carboxamide, (R,E)-N-(4-(azetidin-3-ylsulfonyl)but-3-en-2-yl)-1-((5-bromo-2'-chloro-[1,1'-biphenyl]-2-yl)sulfonyl)-4-fluoropiperidine-4-carboxamide, (R,E)-N-(1-(azetidin-3-ylsulfonyl)pent-1-en-3-yl)-1-((5-bromo-2'-chloro-[1,1'-biphenyl]-2-yl)sulfonyl)-4-fluoropiperidine-4-carboxamide, (S,E)-N-(1-(azetidin-3-ylsulfonyl)pent-1-en-3-yl)-1-((5-bromo-2'-chloro-[1,1'-biphenyl]-2-yl)sulfonyl)-4-fluoropiperidine-4-carboxamide, (R,E)-1-((5-bromo-2'-chloro-[1,1'-biphenyl]-2-yl)sulfonyl)-4-fluoro-N-(4-(methylsulfonyl)but-3-en-2-yl)piperidine-4-carboxamide, (R,E)-1-((5-chloro-3'-methoxy-[1,1'-biphenyl]-2-yl)sulfonyl)-4-fluoro-N-(4-(methylsulfonyl)but-3-en-2-yl)piperidine-4-carboxamide, (S,E)-1-((5-bromo-2'-chloro-[1,1'-biphenyl]-2-yl)sulfonyl)-4-fluoro-N-(4-(methylsulfonyl)but-3-en-2-yl)piperidine-4-carboxamide, (S,Z)-1-((5-bromo-2'-chloro-[1,1'-biphenyl]-2-yl)sulfonyl)-4-fluoro-N-(1-(methylsulfonyl)pent-1-en-3-yl)piperidine-4-carboxamide, (S,Z)-1-((5-chloro-3'-methoxy-[1,1'-biphenyl]-2-yl)sulfonyl)-4-fluoro-N-(1-(methylsulfonyl)pent-1-en-3-yl)piperidine-4-carboxamide, (S,Z)-1-((5-chloro-[1,1'-biphenyl]-2-yl)sulfonyl)-4-fluoro-N-(1-(methylsulfonyl)pent-1-en-3-yl)piperidine-4-carboxamide, (R,Z)-1-((2'-chloro-5-(dimethylamino)-[1,1'-biphenyl]-2-yl)sulfonyl)-4-fluoro-N-(1-(methylsulfonyl)pent-1-en-3-yl)piperidine-4-carboxamide, (S,Z)-1-((5-(dimethylamino)-3'-methoxy-[1,1'-biphenyl]-2-yl)sulfonyl)-4-fluoro-N-(4-(methylsulfonyl)but-3-en-2-yl)piperidine-4-carboxamide, (S,Z)-1-((2'-chloro-5-(dimethylamino)-5'-methoxy-[1,1'-biphenyl]-2-yl)sulfonyl)-4-fluoro-N-(4-(methylsulfonyl)but-3-en-2-yl)piperidine-4-carboxamide, (S,Z)-1-((5-(dimethylamino)-[1,1'-biphenyl]-2-yl)sulfonyl)-4-fluoro-N-(4-(methylsulfonyl)but-3-en-2-yl)piperidine-4-carboxamide, (S,Z)-1-((2'-chloro-5-(dimethylamino)-[1,1'-biphenyl]-2-yl)sulfonyl)-4-fluoro-N-(4-(methylsulfonyl)but-3-en-2-yl)piperidine-4-carboxamide, (S,Z)-1-((2'-chloro-5-(dimethylamino)-3'-methoxy-[1,1'-biphenyl]-2-yl)sulfonyl)-4-fluoro-N-(4-(methylsulfonyl)but-3-en-2-yl)piperidine-4-carboxamide, (R,Z)-1-((5-(dimethylamino)-[1,1'-biphenyl]-2-yl)sulfonyl)-4-fluoro-N-(4-(methylsulfonyl)but-3-en-2-yl)piperidine-4-carboxamide, (R,Z)-1-((2'-chloro-5-(dimethylamino)-[1,1'-biphenyl]-2-yl)sulfonyl)-4-fluoro-N-(4-(methylsulfonyl)but-3-en-2-yl)piperidine-4-carboxamide, (R,Z)-1-((5-(dimethylamino)-2'-methyl-[1,1'-biphenyl]-2-yl)sulfonyl)-4-fluoro-N-(4-(methylsulfonyl)but-3-en-2-yl)piperidine-4-carboxamide, (E)-1-((5-(dimethylamino)-[1,1'-biphenyl]-2-yl)sulfonyl)-4-fluoro-N-(3-(methylsulfonyl)allyl)piperidine-4-carboxamide, (E)-1-((2'-chloro-5-(dimethylamino)-[1,1'-biphenyl]-2-yl)sulfonyl)-4-fluoro-N-(3-(methylsulfonyl)allyl)piperidine-4-carboxamide, (E)-1-((5-(dimethylamino)-3'-methoxy-[1,1'-biphenyl]-2-yl)sulfonyl)-4-fluoro-N-(3-(methylsulfonyl)allyl)piperidine-4-carboxamide, (E)-1-((2'-chloro-5-(dimethylamino)-[1,1'-biphenyl]-2-yl)sulfonyl)-N-(3-cyanoallyl)-4-fluoropiperidine-4-carboxamide, (R,Z)-1-((2'-chloro-5-cyclobutyl-[1,1'-biphenyl]-2-yl)sulfonyl)-4-fluoro-N-(4-(methylsulfonyl)but-3-en-2-yl)piperidine-4-carboxamide, tert-butyl (R,Z)-3-(2'-chloro-6-((4-fluoro-4-((4-(methylsulfonyl)but-3-en-2-yl) carbamoyl)piperidin-1-yl)sulfonyl)-[1,1'-biphenyl]-3-yl)azetidine-1-carboxylate, (S,Z)-1-((5-chloro-3'-(prop-1-yn-1-yl)-[1,1'-biphenyl]-2-yl)sulfonyl)-4-fluoro-N-(4-(methylsulfonyl)but-3-en-2-yl)piperidine-4-carboxamide, (R,Z)-1-((2'-chloro-5-cyclopropoxy-[1,1'-biphenyl]-2-yl)sulfonyl)-4-fluoro-N-(4-(methylsulfonyl)but-3-en-2-yl)piperidine-4-carboxamide, (R,Z)-1-((5-ethoxy-2'-methyl-[1,1'-biphenyl]-2-yl)sulfonyl)-4-fluoro-N-(4-(methylsulfonyl)but-3-en-2-yl)piperidine-4-carboxamide, (R,Z)-4-fluoro-1-((5-isopropoxy-2'-methyl-[1,1'-biphenyl]-2-yl)sulfonyl)-N-(4-(methylsulfonyl)but-3-en-2-yl)piperidine-4-carboxamide, (R,Z)-1-((2'-chloro-5-hydroxy-[1,1'-biphenyl]-2-yl)sulfonyl)-4-fluoro-N-(4-(methylsulfonyl)but-3-en-2-yl)piperidine-4-carboxamide, (R,Z)-1-((2'-chloro-5-isopropoxy-[1,1'-biphenyl]-2-yl)sulfonyl)-4-fluoro-N-(4-(methylsulfonyl)but-3-en-2-yl)piperidine-4-carboxamide, (R,Z)-1-((5-cyclopropoxy-2'-methyl-[1,1'-biphenyl]-2-yl)sulfonyl)-4-fluoro-N-(4-(methylsulfonyl)but-3-en-2-yl)piperidine-4-carboxamide, (R,Z)-1-((2'-chloro-5-vinyl-[1,1'-biphenyl]-2-yl)sulfonyl)-4-fluoro-N-(4-(methylsulfonyl)but-3-en-2-yl)piperidine-4-carboxamide, (R,Z)-4-fluoro-1-((2'-methyl-5-vinyl-[1,1'-biphenyl]-2-yl)sulfonyl)-N-(4-(methylsulfonyl)but-3-en-2-yl)piperidine-4-carboxamide, (R,Z)-1-((2'-chloro-5-(prop-1-en-2-yl)-[1,1'-biphenyl]-2-yl)sulfonyl)-4-fluoro-N-(4-(methylsulfonyl)but-3-en-2-yl)piperidine-4-carboxamide, (R,Z)-4-fluoro-1-((2'-methyl-5-(prop-1-en-2-yl)-[1,1'-biphenyl]-2-yl)sulfonyl)-N-(4-(methylsulfonyl)but-3-en-2-yl)piperidine-4-carboxamide, (R,Z)-1-((2'-chloro-5-ethyl-[1,1'-biphenyl]-2-yl)sulfonyl)-4-fluoro-N-(4-(methylsulfonyl)but-3-en-2-yl)piperidine-4-carboxamide, (R,Z)-1-((5-ethyl-[1,1'-biphenyl]-2-yl)sulfonyl)-4-fluoro-N-(4-(methylsulfonyl)but-3-en-2-yl)piperidine-4-carboxamide, (R,Z)-1-((5-ethyl-2'-methyl-[1,1'-biphenyl]-2-yl)sulfonyl)-4-fluoro-N-(4-(methylsulfonyl)but-3-en-2-yl)piperidine-4-carboxamide, (R,Z)-1-((2'-chloro-5-isopropyl-[1,1'-biphenyl]-2-yl)sulfonyl)-4-fluoro-N-(4-(methylsulfonyl)but-3-en-2-yl)piperidine-4-carboxamide, (R,Z)-4-fluoro-1-((5-isopropyl-2'-methyl-[1,1'-biphenyl]-2-yl)sulfonyl)-N-(4-(methylsulfonyl)but-3-en-2-yl)piperidine-4-carboxamide, (R,Z)-1-((5-(azetidin-1-yl)-2'-methyl-[1,1'-biphenyl]-2-yl)sulfonyl)-4-fluoro-N-(4-(methylsulfonyl)but-3-en-2-yl)piperidine-4-carboxamide, (R,Z)-4-fluoro-N-(4-(methylsulfonyl)but-3-en-2-yl)-1-((5-(pyrrolidin-1-yl)-[1,1'-biphenyl]-2-yl)sulfonyl)piperidine-4-carboxamide, tert-butyl (R,Z)-4-(2'-chloro-6-((4-fluoro-4-((4-(methylsulfonyl)but-3-en-2-yl) carbamoyl)piperidin-1-yl)sulfonyl)-[1,1'-biphenyl]-3-yl)piperazine-1-carboxylate, (R,Z)-1-((2'-chloro-5-(pyrrolidin-1-yl)-[1,1'-biphenyl]-2-yl)sulfonyl)-4-fluoro-N-(4-(methylsulfonyl)but-3-en-2-yl)piperidine-4-carboxamide, (R,Z)-4-fluoro-1-((2'-methyl-5-(pyrrolidin-1-yl)-[1,1'-biphenyl]-2-yl)sulfonyl)-N-(4-(methylsulfonyl)but-3-en-2-yl)piperidine-4-carboxamide, (R,Z)-1-((2'-chloro-5-morpholino-[1,1'-biphenyl]-2-yl)sulfonyl)-4-fluoro-N-(4-(methylsulfonyl)but-3-en-2-yl)piperidine-4-carboxamide, (R,Z)-4-fluoro-1-((2'-methyl-5-morpholino-[1,1'-biphenyl]-2-yl)sulfonyl)-N-(4-(methylsulfonyl)but-3-en-2-yl)piperidine-4-carboxamide, (R,Z)-1-((2'-chloro-4'-fluoro-5-(pyrrolidin-1-yl)-[1,1'-biphenyl]-2-yl)sulfonyl)-4-fluoro-N-(4-(methylsulfonyl)but-3-en-2-yl)piperidine-4-carboxamide, (R,Z)-1-((5-(azetidin-1-yl)-2'-chloro-[1,1'-biphenyl]-2-yl)sulfonyl)-4-fluoro-N-(4-(methylsulfonyl)but-3-en-2-yl)piperidine-4-carboxamide, (S,Z)-1-((5-chloro-3'-(2-methoxyethyl)-[1,1'-biphenyl]-2-yl)sulfonyl)-4-fluoro-N-(4-(methylsulfonyl)but-3-en-2-yl)piperidine-4-carboxamide, (S,Z)-1-((5-chloro-3'-(methoxymethyl)-[1,1'-biphenyl]-2-yl)sulfonyl)-4-fluoro-N-(4-(methylsulfonyl)but-3-en-2-yl)piperidine-4-carboxamide, 1-((5-chloro-3'-((E)-(methoxyimino)methyl)-[1,1'-biphenyl]-2-yl)sulfonyl)-4-fluoro-N—((S,Z)-4-(methylsulfonyl)but-3-en-2-yl)piperidine-4-carboxamide, (R,Z)-1-((2'-chloro-5-(2-hydroxyethyl)-[1,1'-biphenyl]-2-yl)sulfonyl)-4-fluoro-N-(4-(methylsulfonyl)but-3-en-2-yl)piperidine-4-carboxamide, 1-((2'-chloro-5-(1-hydroxyethyl)-[1,1'-biphenyl]-2-yl)sulfonyl)-4-fluoro-N-((R,Z)-4-(methylsulfonyl)but-3-en-2-yl)piperidine-4-carboxamide, (R,Z)-1-((2'-chloro-5-(hydroxymethyl)-[1,1'-biphenyl]-2-yl)sulfonyl)-4-fluoro-N-(4-(methylsulfonyl)but-3-en-2-yl)piperidine-4-carboxamide, (R,Z)-1-((2'-chloro-5-(prop-1-yn-1-yl)-[1,1'-biphenyl]-2-yl)sulfonyl)-4-fluoro-N-(4-(methylsulfonyl)but-3-en-2-yl)piperidine-4-carboxamide, (R,Z)-1-((2'-chloro-5-(oxetan-3-yl)-[1,1'-biphenyl]-2-yl)sulfonyl)-4-fluoro-N-(4-(methylsulfonyl)but-3-en-2-yl)piperidine-4-carboxamide, (R,Z)-1-((5-bromo-2'-chloro-[1,1'-biphenyl]-2-yl)sulfonyl)-4-methoxy-N-(4-(methylsulfonyl)but-3-en-2-yl)piperidine-4-carboxamide, (R,E)-1-((2'-chloro-5-(trifluoromethyl)-[1,1'-biphenyl]-2-yl)sulfonyl)-N-(5-(3,3-difluoroazetidin-1-yl)-5-oxopent-3-en-2-yl)-4-fluoropiperidine-4-carboxamide, (R,E)-1-((5-bromo-2'-chloro-[1,1'-biphenyl]-2-yl)sulfonyl)-N-(5-(3,3-difluoroazetidin-1-yl)-5-oxopent-3-en-2-yl)-4-fluoropiperidine-4-carboxamide, (R,E)-1-((2'-chloro-5-cyano-[1,1'-biphenyl]-2-yl)sulfonyl)-N-(5-(3,3-difluoroazetidin-1-yl)-5-oxopent-3-en-2-yl)-4-fluoropiperidine-4-carboxamide, (R,E)-1-((2'-chloro-5-methoxy-[1,1'-biphenyl]-2-yl)sulfonyl)-N-(5-(3,3-difluoroazetidin-1-yl)-5-oxopent-3-en-2-yl)-4-fluoropiperidine-4-carboxamide, (R,E)-1-((5-acetyl-2'-chloro-[1,1'-biphenyl]-2-yl)sulfonyl)-N-(5-(3,3-difluoroazetidin-1-yl)-5-oxopent-3-en-2-yl)-4-fluoropiperidine-4-carboxamide, (R,Z)-1-((2'-chloro-5-(trifluoromethyl)-[1,1'-biphenyl]-2-yl)sulfonyl)-4-methoxy-N-(4-(methylsulfonyl)but-3-en-2-yl)piperidine-4-carboxamide, 1-((2'-chloro-5-(1-hydroxyethyl)-[1,1'-biphenyl]-2-yl)sulfonyl)-N-((R,E)-5-(3,3-difluoroazetidin-1-yl)-5-oxopent-3-en-2-yl)-4-fluoropiperidine-4-carboxamide, (2R,4S)-1-((2'-chloro-5-methoxy-[1,1'-biphenyl]-2-yl)sulfonyl)-4-fluoro-2-methyl-N-((R,Z)-4-(methylsulfonyl)but-3-en-2-yl)piperidine-4-carboxamide, (2R,4S)-1-((2'-chloro-5-(trifluoromethyl)-[1,1'-biphenyl]-2-yl)sulfonyl)-4-fluoro-2-methyl-N-((R,Z)-4-(methylsulfonyl)but-3-en-2-yl)piperidine-4-carboxamide, (2R,4S)-1-((5-bromo-2'-chloro-[1,1'-biphenyl]-2-yl)sulfonyl)-4-fluoro-2-methyl-N-((R,Z)-4-(methylsulfonyl)but-3-en-2-yl)piperidine-4-carboxamide, (2R,4S)-1-((2'-chloro-5-cyano-[1,1'-biphenyl]-2-yl)sulfonyl)-4-fluoro-2-methyl-N-((R,Z)-4-(methylsulfonyl)but-3-en-2-yl)piperidine-4-carboxamide, (2R,4S)-1-((5-bromo-3'-chloro-[1,1'-biphenyl]-2-yl)sulfonyl)-4-fluoro-2-methyl-N-((R,Z)-4-(methylsulfonyl)but-3-en-2-yl)piperidine-4-carboxamide, (R,Z)-1-((2'-chloro-5-methoxy-[1,1'-biphenyl]-2-yl)sulfonyl)-4-methoxy-N-(4-(methylsulfonyl)but-3-en-2-yl)piperidine-4-carboxamide, (2R,4R)-1-((2'-chloro-5-methoxy-[1,1'-biphenyl]-2-yl)sulfonyl)-4-fluoro-2-methyl-N-((R,Z)-4-(methylsulfonyl)but-3-en-2-yl)piperidine-4-carboxamide, (2S,4S)-1-((2'-chloro-5-methoxy-[1,1'-biphenyl]-2-yl)sulfonyl)-4-fluoro-2-methyl-N-((R,Z)-4-(methylsulfonyl)but-3-en-2-yl)piperidine-4-carboxamide, (2R,4S)-1-((2'-chloro-5-(methoxymethyl)-[1,1'-biphenyl]-2-yl)sulfonyl)-4-fluoro-2-methyl-N-((R,Z)-4-(methylsulfonyl)but-3-en-2-yl)piperidine-4-carboxamide, (R)-1-((2'-chloro-5-methoxy-[1,1'-biphenyl]-2-yl)sulfonyl)-4-fluoro-2,2-dimethyl-N-((R,Z)-4-(methylsulfonyl)but-3-en-2-yl)piperidine-4-carboxamide, (2R,4S)-1-((2'-chloro-5-methoxy-[1,1'-biphenyl]-2-yl)sulfonyl)-N-((R,E)-5-(3,3-difluoroazetidin-1-yl)-5-oxopent-3-en-2-yl)-4-fluoro-2-methylpiperidine-4-carboxamide, (2R,4S)-1-((2'-chloro-5-(trifluoromethyl)-[1,1'-biphenyl]-2-yl)sulfonyl)-N-((R,E)-5-(3,3-difluoroazetidin-1-yl)-5-oxopent-3-en-2-yl)-4-fluoro-2-methylpiperidine-4-carboxamide, (2R,4S)-1-((5-bromo-2'-chloro-[1,1'-biphenyl]-2-yl)sulfonyl)-N-((R,E)-5-(3,3-difluoroazetidin-1-yl)-5-oxopent-3-en-2-yl)-4-fluoro-2-methylpiperidine-4-carboxamide, (2R,4S)-1-((2'-chloro-5-cyano-[1,1'-biphenyl]-2-yl)sulfonyl)-N-((R,E)-5-(3,3-difluoroazetidin-1-yl)-5-oxopent-3-en-2-yl)-4-fluoro-2-methylpiperidine-4-carboxamide, (2R,4S)-1-((5-bromo-3'-chloro-[1,1'-biphenyl]-2-yl)sulfonyl)-N-((R,E)-5-(3,3-difluoroazetidin-1-yl)-5-oxopent-3-en-2-yl)-4-fluoro-2-methylpiperidine-4-carboxamide, (2R,4S)-1-((2'-chloro-5-(methoxymethyl)-[1,1'-biphenyl]-2-yl)sulfonyl)-N-((R,E)-5-(3,3-difluoroazetidin-1-yl)-5-oxopent-3-en-2-yl)-4-fluoro-2-methylpiperidine-4-carboxamide, (R,Z)-1-((5-(2-chlorophenyl)benzo[b]thiophen-6-yl)sulfonyl)-4-fluoro-N-(4-(methylsulfonyl)but-3-en-2-yl)piperidine-4-carboxamide, tert-butyl cis-(3RS,4RS)-3-(2-chlorophenyl)-4-(4-fluoro-4-(((R,Z)-4-(methylsulfonyl)but-3-en-2-yl) carbamoyl)piperidine-1-carbonyl)pyrrolidine-1-carboxylate;

isopropyl (3R,4R)-3-(2-chlorophenyl)-4-(4-fluoro-4-(((R,Z)-4-(methylsulfonyl)but-3-en-2-yl) carbamoyl)piperidine-1-carbonyl)pyrrolidine-1-carboxylate;

ethyl (3R,4R)-3-(2-chlorophenyl)-4-(4-fluoro-4-(((R,Z)-4-(methylsulfonyl)but-3-en-2-yl) carbamoyl)piperidine-1-carbonyl)pyrrolidine-1-carboxylate;

1-((3R,4R)-4-(2-chlorophenyl)-1-pivaloylpyrrolidine-3-carbonyl)-4-fluoro-N-((R,Z)-4-(methylsulfonyl)but-3-en-2-yl)piperidine-4-carboxamide;

1-((3R,4R)-1-benzoyl-4-(2-chlorophenyl)pyrrolidine-3-carbonyl)-4-fluoro-N-((R,Z)-4-(methylsulfonyl)but-3-en-2-yl)piperidine-4-carboxamide;

1-((3R,4R)-4-(2-chlorophenyl)-1-(2,2,2-trifluoroethyl)pyrrolidine-3-carbonyl)-4-fluoro-N-((R,Z)-4-(methylsulfonyl)but-3-en-2-yl)piperidine-4-carboxamide;

1-((3R,4R)-4-(2-chlorophenyl)-1-(2,2,2-trifluoroethyl)pyrrolidine-3-carbonyl)-N-((R)-1,1-dioxido-2,3-dihydrothiophen-3-yl)-4-fluoropiperidine-4-carboxamide;

(R)-1-((3R,4R)-4-(2-chlorophenyl)-1-(2,2,2-trifluoroethyl)pyrrolidine-3-carbonyl)-4-fluoro-N-((R,Z)-4-(methylsulfonyl)but-3-en-2-yl)azepane-4-carboxamide;

(R)-1-((3*R,4*R)-4-(2-chloro-5-fluorophenyl)-1-(2,2,2-trifluoroethyl)pyrrolidine-3-carbonyl)-4-fluoro-N-((R,Z)-4-(methylsulfonyl)but-3-en-2-yl)azepane-4-carboxamide;

(R)-1-((3*R,4*R)-4-(2-chloro-4-fluorophenyl)-1-(2,2,2-trifluoroethyl)pyrrolidine-3-carbonyl)-4-fluoro-N-((R,Z)-4-(methylsulfonyl)but-3-en-2-yl)azepane-4-carboxamide;

(R)-1-((3*R,4*R)-4-(2-chloro-3-fluorophenyl)-1-(2,2,2-trifluoroethyl)pyrrolidine-3-carbonyl)-4-fluoro-N-((R,Z)-4-(methylsulfonyl)but-3-en-2-yl)azepane-4-carboxamide;

(R)-1-((3*R,4*R)-4-(2-chloro-4-methylphenyl)-1-(2,2,2-trifluoroethyl)pyrrolidine-3-carbonyl)-4-fluoro-N-((R,Z)-4-(methylsulfonyl)but-3-en-2-yl)azepane-4-carboxamide;

(R)-1-((3*R,4*R)-4-(2-chloro-5-methylphenyl)-1-(2,2,2-trifluoroethyl)pyrrolidine-3-carbonyl)-4-fluoro-N-((R,Z)-4-(methylsulfonyl)but-3-en-2-yl)azepane-4-carboxamide;

(R)-1-((3R,4R)-4-(2-chloro-6-fluorophenyl)-1-(2,2,2-trifluoroethyl)pyrrolidine-3-carbonyl)-4-fluoro-N-((R,Z)-4-(methylsulfonyl)but-3-en-2-yl)azepane-4-carboxamide;

(R)-1-((3*R,4*R)-4-(2-chloro-3-methylphenyl)-1-(2,2,2-trifluoroethyl)pyrrolidine-3-carbonyl)-4-fluoro-N-((R,Z)-4-(methylsulfonyl)but-3-en-2-yl)azepane-4-carboxamide;

(R)-1-((3*R,4*R)-4-(2,3-difluorophenyl)-1-(2,2,2-trifluoroethyl)pyrrolidine-3-carbonyl)-4-fluoro-N-((R,Z)-4-(methylsulfonyl)but-3-en-2-yl)azepane-4-carboxamide;

(2*S,4*S)-1-((3R,4R)-4-(2-chlorophenyl)-1-(2,2,2-trifluoroethyl)pyrrolidine-3-carbonyl)-N-((R)-1,1-dioxido-2,3-dihydrothiophen-3-yl)-4-fluoro-2-methylpiperidine-4-carboxamide;

(2*S,4*S)-1-((3*R,4*R)-4-(2-chloro-3-fluorophenyl)-1-(2,2,2-trifluoroethyl)pyrrolidine-3-carbonyl)-N-((R)-1,1-dioxido-2,3-dihydrothiophen-3-yl)-4-fluoro-2-methylpiperidine-4-carboxamide;

(R)-1-((3R,4R)-4-(2-chlorophenyl)-1-(2,2,2-trifluoroethyl)pyrrolidine-3-carbonyl)-N-((R)-1,1-dioxido-2,3-dihydrothiophen-3-yl)-4-fluoroazepane-4-carboxamide;

(R)-1-((3R,4R)-4-(2-chlorophenyl)-1-(2,2,2-trifluoroethyl)pyrrolidine-3-carbonyl)-4-fluoro-N-((R,E)-4-(methylsulfonyl)but-3-en-2-yl)azepane-4-carboxamide;

1-((3R,4R)-4-(2-chlorophenyl)-1-(2,2-difluorobutyl) pyrrolidine-3-carbonyl)-4-fluoro-N-((R,Z)-4-(methylsulfonyl)but-3-en-2-yl)piperidine-4-carboxamide;

1-((3R,4R)-4-(2-chlorophenyl)-1-(2,2-difluoropropyl) pyrrolidine-3-carbonyl)-4-fluoro-N-((R,Z)-4-(methylsulfonyl)but-3-en-2-yl)piperidine-4-carboxamide;

(R)-1-((3R,4R)-4-(2-chlorophenyl)-1-(2,2-difluoropropyl) pyrrolidine-3-carbonyl)-4-fluoro-N-((R,Z)-4-(methylsulfonyl)but-3-en-2-yl)azepane-4-carboxamide;

1-((3R,4R)-4-(2-chlorophenyl)-1-(2,2-difluoro-2-phenylethyl)pyrrolidine-3-carbonyl)-4-fluoro-N-((R,Z)-4-(methylsulfonyl)but-3-en-2-yl)piperidine-4-carboxamide;

1-((3R,4R)-4-(2-chlorophenyl)-1-(2,2,3,3,3-pentafluoropropyl) pyrrolidine-3-carbonyl)-4-fluoro-N-((R,Z)-4-(methylsulfonyl)but-3-en-2-yl)piperidine-4-carboxamide;

(R)-1-((3R,4R)-4-(2-chloro-6-fluorophenyl)-1-(2,2-difluoropropyl) pyrrolidine-3-carbonyl)-4-fluoro-N-((R,Z)-4-(methylsulfonyl)but-3-en-2-yl)azepane-4-carboxamide;

(R)-1-((3*R,4*R)-4-(2-chloro-6-fluorophenyl)-1-((1-fluorocyclopropyl)methyl)pyrrolidine-3-carbonyl)-4-fluoro-N-((R,Z)-4-(methylsulfonyl)but-3-en-2-yl) azepane-4-carboxamide;

(R)-1-((3R,4R)-4-(2-chlorophenyl)-1-((1-fluorocyclopropyl)methyl)pyrrolidine-3-carbonyl)-4-fluoro-N-((R,Z)-4-(methylsulfonyl)but-3-en-2-yl)azepane-4-carboxamide;

(R,Z)-1-((4-(2-chlorophenyl)-6-methoxypyridin-3-yl) sulfonyl)-4-fluoro-N-(4-(methylsulfonyl)but-3-en-2-yl)piperidine-4-carboxamide;

(S,Z)-1-((4-(2-chlorophenyl)-6-methoxypyridin-3-yl) sulfonyl)-4-fluoro-N-(4-(methylsulfonyl)but-3-en-2-yl)piperidine-4-carboxamide;

(E)-1-((4-(2-chlorophenyl)-6-methoxypyridin-3-yl)sulfonyl)-4-fluoro-N-(3-(methylsulfonyl)allyl)piperidine-4-carboxamide;

(E)-4-fluoro-1-((6-methoxy-4-(o-tolyl)pyridin-3-yl) sulfonyl)-N-(3-(methylsulfonyl)allyl)piperidine-4-carboxamide;

(S,Z)-4-fluoro-1-((6-methoxy-4-(o-tolyl)pyridin-3-yl) sulfonyl)-N-(4-(methylsulfonyl)but-3-en-2-yl)piperidine-4-carboxamide;

(E)-4-fluoro-1-((6-methoxy-4-phenylpyridin-3-yl)sulfonyl)-N-(3-(methylsulfonyl)allyl)piperidine-4-carboxamide;

(S,Z)-4-fluoro-1-((6-methoxy-4-phenylpyridin-3-yl) sulfonyl)-N-(4-(methylsulfonyl)but-3-en-2-yl)piperidine-4-carboxamide;

(R,Z)-4-fluoro-1-((6-methoxy-4-(o-tolyl)pyridin-3-yl) sulfonyl)-N-(4-(methylsulfonyl)but-3-en-2-yl)piperidine-4-carboxamide;

(Z)-1-((4-(2-chlorophenyl)-6-methoxypyridin-3-yl)sulfonyl)-N-(3-cyanoallyl)-4-fluoropiperidine-4-carboxamide;

(R)-1-((3R,4R)-1-(2-chloro-2,2-difluoroethyl)-4-(2-chlorophenyl)pyrrolidine-3-carbonyl)-4-fluoro-N-((R,Z)-4-(methylsulfonyl)but-3-en-2-yl)azepane-4-carboxamide;

(R)-1-((3R,4R)-4-(2-chlorophenyl)-1-(3,3,3-trifluoropropyl) pyrrolidine-3-carbonyl)-4-fluoro-N-((R,Z)-4-(methylsulfonyl)but-3-en-2-yl)azepane-4-carboxamide;

(R)-1-((3R,4R)-4-(2-chlorophenyl)-1-(2,2-difluoroethyl) pyrrolidine-3-carbonyl)-4-fluoro-N-((R,Z)-4-(methylsulfonyl)but-3-en-2-yl)azepane-4-carboxamide;

(R)-1-((3R,4R)-4-(2-chlorophenyl)-1-(2,2,2-trifluoroethyl)pyrrolidine-3-carbonyl)-4-fluoro-N-((R,Z)-1-(methylsulfonyl)pent-1-en-3-yl)azepane-4-carboxamide;

isopropyl (3S,4S)-3-(2-chlorophenyl)-4-(4-fluoro-4-(((R,Z)-4-(methylsulfonyl)but-3-en-2-yl) carbamoyl)piperidine-1-carbonyl)pyrrolidine-1-carboxylate;

(S,Z)-1-((5-chloro-3-(3-methoxyphenyl)pyridin-2-yl) sulfonyl)-4-fluoro-N-(4-(methylsulfonyl)but-3-en-2-yl)piperidine-4-carboxamide;

(S,Z)-1-((5-chloro-3'-methoxy-[1,1'-biphenyl]-2-yl) sulfonyl)-4-methyl-N-(4-(methylsulfonyl)but-3-en-2-yl)piperidine-4-carboxamide;

(R,Z)-1-((2'-chloro-4,5-dimethoxy-[1,1'-biphenyl]-2-yl) sulfonyl)-4-fluoro-N-(4-(methylsulfonyl)but-3-en-2-yl)piperidine-4-carboxamide;

(R,Z)-1-((5-chloro-3'-methoxy-[1,1'-biphenyl]-2-yl) sulfonyl)-4-methyl-N-(4-(methylsulfonyl)but-3-en-2-yl)piperidine-4-carboxamide;

(R,Z)-1-((4-bromo-2-(3-chloropyridin-2-yl)phenyl)sulfonyl)-4-fluoro-N-(4-(methylsulfonyl)but-3-en-2-yl)piperidine-4-carboxamide;

(R,Z)-1-((2'-chloro-5-(2-oxopyrrolidin-1-yl)-[1,1'-biphenyl]-2-yl)sulfonyl)-4-fluoro-N-(4-(methylsulfonyl)but-3-en-2-yl)piperidine-4-carboxamide;

1-((3R,4R)-4-(2-chlorophenyl)-1-(2,2-difluoroethyl)pyrrolidine-3-carbonyl)-4-fluoro-N-((R,Z)-4-(methylsulfonyl)but-3-en-2-yl)piperidine-4-carboxamide;

(R,Z)-1-((4-(2-chlorophenyl)-6-(trifluoromethyl)pyridin-3-yl)sulfonyl)-4-fluoro-N-(4-(methylsulfonyl)but-3-en-2-yl)piperidine-4-carboxamide;

(S,Z)-1-((4-(2-chlorophenyl)-6-(trifluoromethyl)pyridin-3-yl)sulfonyl)-4-fluoro-N-(4-(methylsulfonyl)but-3-en-2-yl)piperidine-4-carboxamide;

(R,Z)-1-((4-(2-chloro-3-fluorophenyl)-6-(trifluoromethyl)pyridin-3-yl)sulfonyl)-4-fluoro-N-(4-(methylsulfonyl)but-3-en-2-yl)piperidine-4-carboxamide;

(S,Z)-1-((4-(2-chloro-3-fluorophenyl)-6-(trifluoromethyl)pyridin-3-yl)sulfonyl)-4-fluoro-N-(4-(methylsulfonyl)but-3-en-2-yl)piperidine-4-carboxamide;

(R,Z)-1-((4-(2-chloro-4-fluorophenyl)-6-(trifluoromethyl)pyridin-3-yl)sulfonyl)-4-fluoro-N-(4-(methylsulfonyl)but-3-en-2-yl)piperidine-4-carboxamide;

(S,Z)-1-((4-(2-chloro-4-fluorophenyl)-6-(trifluoromethyl)pyridin-3-yl)sulfonyl)-4-fluoro-N-(4-(methylsulfonyl)but-3-en-2-yl)piperidine-4-carboxamide;

(R,E)-1-((4-(2-chlorophenyl)-6-(trifluoromethyl)pyridin-3-yl)sulfonyl)-N-(5-(3,3-difluoroazetidin-1-yl)-5-oxopent-3-en-2-yl)-4-fluoropiperidine-4-carboxamide;

(2R,4S)-1-((4-(2-chlorophenyl)-6-(trifluoromethyl)pyridin-3-yl)sulfonyl)-4-fluoro-2-methyl-N-((R,Z)-4-(methylsulfonyl)but-3-en-2-yl)piperidine-4-carboxamide;

(2R,4S)-1-((4-(2-chlorophenyl)-6-(trifluoromethyl)pyridin-3-yl)sulfonyl)-N-((R,E)-5-(3,3-difluoroazetidin-1-yl)-5-oxopent-3-en-2-yl)-4-fluoro-2-methylpiperidine-4-carboxamide;

(R,E)-1-((2'-chloro-5-(trifluoromethyl)-[1,1'-biphenyl]-2-yl)sulfonyl)-4-fluoro-N-(5-(3-fluoroazetidin-1-yl)-5-oxopent-3-en-2-yl)piperidine-4-carboxamide;

(R,Z)-1-((6-chloro-4-(2-chloro-5-methoxyphenyl)pyridin-3-yl)sulfonyl)-4-fluoro-N-(4-(methylsulfonyl)but-3-en-2-yl)piperidine-4-carboxamide;

(R,Z)-1-((5-bromo-3-(2-chlorophenyl)pyridin-2-yl)sulfonyl)-4-fluoro-N-(4-(methylsulfonyl)but-3-en-2-yl)piperidine-4-carboxamide;

(S,Z)-1-((2',5-dimethoxy-[1,1'-biphenyl]-2-yl)sulfonyl)-4-fluoro-N-(4-(methylsulfonyl)but-3-en-2-yl)piperidine-4-carboxamide;

(S,Z)-1-((5-chloro-3'-(2-hydroxyethyl)-[1,1'-biphenyl]-2-yl)sulfonyl)-4-fluoro-N-(4-(methylsulfonyl)but-3-en-2-yl)piperidine-4-carboxamide;

(2*S,4*S)-1-((3R,4R)-4-(2-chlorophenyl)-1-(2,2-difluoropropyl) pyrrolidine-3-carbonyl)-N-((R)-1,1-dioxido-2,3-dihydrothiophen-3-yl)-4-fluoro-2-methylpiperidine-4-carboxamide;

(R)-1-((3*S,4*S)-4-(2-chloro-3-fluorophenyl)-1-(2,2-difluoropropyl) pyrrolidine-3-carbonyl)-4-fluoro-N-((R,Z)-4-(methylsulfonyl)but-3-en-2-yl)azepane-4-carboxamide;

(R)-4-fluoro-1-((3*R,4*R)-4-(2-fluorophenyl)-1-(2,2,2-trifluoroethyl)pyrrolidine-3-carbonyl)-N-((R,Z)-4-(methylsulfonyl)but-3-en-2-yl)azepane-4-carboxamide;

(R)-4-fluoro-N-((R,Z)-4-(methylsulfonyl)but-3-en-2-yl)-1-((3*R,4*R)-4-(o-tolyl)-1-(2,2,2-trifluoroethyl)pyrrolidine-3-carbonyl)azepane-4-carboxamide;

(2*S,4*S)-1-((3*S,4*S)-4-(2-chloro-3-fluorophenyl)-1-(2,2-difluoropropyl) pyrrolidine-3-carbonyl)-N-((R)-1,1-dioxido-2,3-dihydrothiophen-3-yl)-4-fluoro-2-methylpiperidine-4-carboxamide;

(R)-1-((3*S,4*S)-4-(2-chloro-3,6-difluorophenyl)-1-(2,2,2-trifluoroethyl)pyrrolidine-3-carbonyl)-4-fluoro-N-((R,Z)-4-(methylsulfonyl)but-3-en-2-yl)azepane-4-carboxamide;

(R)-1-((3*S,4*S)-4-(2-chloro-4,6-difluorophenyl)-1-(2,2,2-trifluoroethyl)pyrrolidine-3-carbonyl)-4-fluoro-N-((R,Z)-4-(methylsulfonyl)but-3-en-2-yl)azepane-4-carboxamide;

(E)-4-fluoro-1-((3'-methoxy-[1,1'-biphenyl]-2-yl)sulfonyl)-N-(3-((1-methylpiperidin-4-yl)sulfonyl)allyl)piperidine-4-carboxamide;

(R,E)-1-((2'-chloro-5-methoxy-[1,1'-biphenyl]-2-yl)sulfonyl)-N-(4-cyanobut-3-en-2-yl)-4-fluoropiperidine-4-carboxamide;

(Z)-(1-((2'-chloro-5-methoxy-[1,1'-biphenyl]-2-yl)sulfonyl)-4-fluoropiperidin-4-yl) (3-(2-(methylsulfonyl)vinyl)azetidin-1-yl) methanone;

(R,Z)-1-((6-chloro-4-(2-chlorophenyl)pyridin-3-yl)sulfonyl)-4-fluoro-N-(4-(methylsulfonyl)but-3-en-2-yl)piperidine-4-carboxamide;

(E)-1-((6-chloro-4-(2-chlorophenyl)pyridin-3-yl)sulfonyl)-N-(3-cyanoallyl)-4-fluoropiperidine-4-carboxamide;

1-((5-bromo-2'-chloro-[1,1'-biphenyl]-2-yl)sulfonyl)-N-((1,1-dioxido-2H-thiet-3-yl)methyl)-4-fluoropiperidine-4-carboxamide;

(*R)-1-((5-bromo-2'-chloro-[1,1'-biphenyl]-2-yl)sulfonyl)-N-(1-(1,1-dioxido-2H-thiet-3-yl)ethyl)-4-fluoropiperidine-4-carboxamide;

(R)-1-((2'-chloro-5-methoxy-[1,1'-biphenyl]-2-yl)sulfonyl)-N-(1-(1,1-dioxido-2H-thiet-3-yl)ethyl)-4-fluoropiperidine-4-carboxamide;

(R)-1-((2'-chloro-5-(trifluoromethyl)-[1,1'-biphenyl]-2-yl)sulfonyl)-N-(1-(1,1-dioxido-2H-thiet-3-yl)ethyl)-4-fluoropiperidine-4-carboxamide;

1-((5-bromo-2'-chloro-[1,1'-biphenyl]-2-yl)sulfonyl)-4-fluoro-N-((R,Z)-4-(((*R)-1-methylpyrrolidin-3-yl)sulfonyl)but-3-en-2-yl)piperidine-4-carboxamide;

1-((5-bromo-2'-chloro-[1,1'-biphenyl]-2-yl)sulfonyl)-4-fluoro-N-((R,Z)-4-(((*S)-1-methylpyrrolidin-3-yl)sulfonyl)but-3-en-2-yl)piperidine-4-carboxamide;

(*S,Z)-1-((2'-chloro-5-methoxy-[1,1'-biphenyl]-2-yl)sulfonyl)-4-fluoro-N-(5,5,5-trifluoro-1-(methylsulfonyl)pent-1-en-3-yl)piperidine-4-carboxamide;

(*S,Z)-1-((5-bromo-2'-chloro-[1,1'-biphenyl]-2-yl)sulfonyl)-4-fluoro-N-(5,5,5-trifluoro-1-(methylsulfonyl)pent-1-en-3-yl)piperidine-4-carboxamide;

(R)-1-(5-bromo-2'-chloro-[1,1'-biphenyl]-2-carbonyl)-4-fluoro-N-((R,Z)-4-(methylsulfonyl)but-3-en-2-yl)azepane-4-carboxamide;

(R)-1-(2'-chloro-5-(trifluoromethyl)-[1,1'-biphenyl]-2-carbonyl)-4-fluoro-N-((R,Z)-4-(methylsulfonyl)but-3-en-2-yl)azepane-4-carboxamide;

(R)-1-(5-bromo-2'-chloro-[1,1'-biphenyl]-2-carbonyl)-N-((R,E)-5-(3,3-difluoroazetidin-1-yl)-5-oxopent-3-en-2-yl)-4-fluoroazepane-4-carboxamide;

(R)-1-(2'-chloro-5-(trifluoromethyl)-[1,1'-biphenyl]-2-carbonyl)-N-((R,E)-5-(3,3-difluoroazetidin-1-yl)-5-oxopent-3-en-2-yl)-4-fluoroazepane-4-carboxamide;

(4R)-1-(2'-chloro-6'-fluoro-5-(trifluoromethyl)-[1,1'-biphenyl]-2-carbonyl)-N-((R,E)-5-(3,3-difluoroazetidin-1-yl)-5-oxopent-3-en-2-yl)-4-fluoroazepane-4-carboxamide;

(R,Z)-1-((5-bromo-2'-chloro-[1,1'-biphenyl]-2-yl)sulfonyl)-4-fluoro-N-(1-methoxy-4-(methylsulfonyl)but-3-en-2-yl)piperidine-4-carboxamide;

(S,Z)-1-((5-bromo-2'-chloro-[1,1'-biphenyl]-2-yl)sulfonyl)-4-fluoro-N-(1-methoxy-4-(methylsulfonyl)but-3-en-2-yl)piperidine-4-carboxamide;

(R,Z)-1-((2'-chloro-5-methoxy-[1,1'-biphenyl]-2-yl)sulfonyl)-4-fluoro-N-(1-methoxy-4-(methylsulfonyl)but-3-en-2-yl)piperidine-4-carboxamide;

(E)-1-((2'-chloro-5-(trifluoromethyl)-[1,1'-biphenyl]-2-yl)sulfonyl)-N-(5-(3,3-difluoroazetidin-1-yl)-2-methyl-5-oxopent-3-en-2-yl)-4-fluoropiperidine-4-carboxamide;

(2R,4S)-1-((2'-chloro-5-(trifluoromethoxy)-[1,1'-biphenyl]-2-yl)sulfonyl)-4-fluoro-2-methyl-N-((R,Z)-4-(methylsulfonyl)but-3-en-2-yl)piperidine-4-carboxamide;

(2R,4S)-1-((2'-chloro-5-(difluoromethoxy)-[1,1'-biphenyl]-2-yl)sulfonyl)-N-((R,E)-5-(3,3-difluoroazetidin-1-yl)-5-oxopent-3-en-2-yl)-4-fluoro-2-methylpiperidine-4-carboxamide;

(2R,4S)-1-((2'-chloro-5-((RS)-1-hydroxyethyl)-[1,1'-biphenyl]-2-yl)sulfonyl)-N-((R,E)-5-(3,3-difluoroazetidin-1-yl)-5-oxopent-3-en-2-yl)-4-fluoro-2-methylpiperidine-4-carboxamide;

(2R,4S)-1-((2'-chloro-5-(difluoromethyl)-[1,1'-biphenyl]-2-yl)sulfonyl)-N-((R,E)-5-(3,3-difluoroazetidin-1-yl)-5-oxopent-3-en-2-yl)-4-fluoro-2-methylpiperidine-4-carboxamide;

(R)-1-((3R,4R)-4-(2-chlorophenyl)-3-methyl-1-(2,2,2-trifluoroethyl)pyrrolidine-3-carbonyl)-4-fluoro-N-((R,Z)-4-(methylsulfonyl)but-3-en-2-yl)azepane-4-carboxamide;

1-((1*S,2*S)-2-(2-chlorophenyl)-4,4-dimethylcyclohexane-1-carbonyl)-4-fluoro-N-((R,Z)-4-(methylsulfonyl)but-3-en-2-yl)piperidine-4-carboxamide;

1-((3*R,4*S)-4-(2-chlorophenyl)-6,6-dimethyltetrahydro-2H-pyran-3-carbonyl)-4-fluoro-N-((R,Z)-4-(methylsulfonyl)but-3-en-2-yl)piperidine-4-carboxamide;

1-((6*R,7*R)-6-(2-chlorophenyl)spiro[3.5]nonane-7-carbonyl)-4-fluoro-N-((R,Z)-4-(methylsulfonyl)but-3-en-2-yl)piperidine-4-carboxamide;

tert-butyl 5-(2-chlorophenyl)-4-(4-fluoro-4-(((R,Z)-4-(methylsulfonyl)but-3-en-2-yl) carbamoyl)piperidine-1-carbonyl)-3,4-dihydropyridine-1 (2H)-carboxylate;

tert-butyl (3*R,4*S)-3-(2-chlorophenyl)-4-(4-fluoro-4-(((R,Z)-4-(methylsulfonyl)but-3-en-2-yl) carbamoyl) piperidine-1-carbonyl)piperidine-1-carboxylate;

(S,Z)-1-((5-chloro-3'-(pyridin-3-ylmethoxy)-[1,1'-biphenyl]-2-yl)sulfonyl)-4-fluoro-N-(4-(methylsulfonyl)but-3-en-2-yl)piperidine-4-carboxamide;

(S,Z)-1-((5-chloro-3'-((3-methoxybenzyl)oxy)-[1,1'-biphenyl]-2-yl)sulfonyl)-4-fluoro-N-(4-(methylsulfonyl) but-3-en-2-yl)piperidine-4-carboxamide;

(S,Z)-1-((5-chloro-3'-(pentyloxy)-[1,1'-biphenyl]-2-yl) sulfonyl)-4-fluoro-N-(4-(methylsulfonyl)but-3-en-2-yl)piperidine-4-carboxamide;

(S,Z)-1-((5-chloro-3'-cyclobutoxy-[1,1'-biphenyl]-2-yl) sulfonyl)-4-fluoro-N-(4-(methylsulfonyl)but-3-en-2-yl)piperidine-4-carboxamide;

(S,Z)-1-((3'-(but-2-yn-1-yloxy)-5-chloro-[1,1'-biphenyl]-2-yl)sulfonyl)-4-fluoro-N-(4-(methylsulfonyl)but-3-en-2-yl)piperidine-4-carboxamide;

(S,Z)-1-((5-chloro-3'-((2-chlorobenzyl)oxy)-[1,1'-biphenyl]-2-yl)sulfonyl)-4-fluoro-N-(4-(methylsulfonyl)but-3-en-2-yl)piperidine-4-carboxamide;

(S,Z)-1-((5-chloro-3'-((3-chlorobenzyl)oxy)-[1,1'-biphenyl]-2-yl)sulfonyl)-4-fluoro-N-(4-(methylsulfonyl)but-3-en-2-yl)piperidine-4-carboxamide;

(S,Z)-1-((5-chloro-3'-phenoxy-[1,1'-biphenyl]-2-yl)sulfonyl)-4-fluoro-N-(4-(methylsulfonyl)but-3-en-2-yl)piperidine-4-carboxamide;

(S,Z)-1-((3'-(benzyloxy)-5-chloro-[1,1'-biphenyl]-2-yl) sulfonyl)-4-fluoro-N-(4-(methylsulfonyl)but-3-en-2-yl)piperidine-4-carboxamide;

(S,Z)-1-((5-chloro-3'-(pyridin-2-ylmethoxy)-[1,1'-biphenyl]-2-yl)sulfonyl)-4-fluoro-N-(4-(methylsulfonyl)but-3-en-2-yl)piperidine-4-carboxamide;

(S,Z)-1-((6-chloro-4-(3-methoxyphenyl)pyridin-3-yl) sulfonyl)-4-fluoro-N-(4-(methylsulfonyl)but-3-en-2-yl)piperidine-4-carboxamide;

(S,Z)-1-((6-chloro-4-(2-chloro-5-methoxyphenyl)pyridin-3-yl)sulfonyl)-4-fluoro-N-(4-(methylsulfonyl)but-3-en-2-yl)piperidine-4-carboxamide;

(*R)-1-((3R,4R)-4-(2-chlorophenyl)-1-(2,2,2-trifluoroethyl)pyrrolidine-3-carbonyl)-4-fluoro-N-((R,Z)-4-(methylsulfonyl)but-3-en-2-yl) azocane-4-carboxamide;

(1-((5-bromo-2'-chloro-[1,1'-biphenyl]-2-yl)sulfonyl)-4-fluoropiperidin-4-yl) (3-((methylsulfonyl)methylene) azetidin-1-yl) methanone;

(R,Z)-1-((4-(2-chlorophenyl)-1-methyl-6-oxo-1,6-dihydropyridin-3-yl)sulfonyl)-4-fluoro-N-(4-(methylsulfonyl)but-3-en-2-yl)piperidine-4-carboxamide;

(R,Z)-1-((5-(2-chlorophenyl)-1-methyl-2-oxo-1,2-dihydropyridin-4-yl)sulfonyl)-4-fluoro-N-(4-(methylsulfonyl)but-3-en-2-yl)piperidine-4-carboxamide;

(R,Z)-1-((4-(2-chlorophenyl)-6-hydroxypyridin-3-yl) sulfonyl)-4-fluoro-N-(4-(methylsulfonyl)but-3-en-2-yl)piperidine-4-carboxamide;

(R,Z)-1-((6-bromo-4-(2-chlorophenyl)pyridin-3-yl)sulfonyl)-4-fluoro-N-(4-(methylsulfonyl)but-3-en-2-yl)piperidine-4-carboxamide;

(E)-1-((6-bromo-4-(2-chlorophenyl)pyridin-3-yl)sulfonyl)-N-(3-cyanoallyl)-4-fluoropiperidine-4-carboxamide;

(S,Z)-1-((5-chloro-3'-(propylcarbamoyl)-[1,1'-biphenyl]-2-yl)sulfonyl)-4-fluoro-N-(4-(methylsulfonyl)but-3-en-2-yl)piperidine-4-carboxamide;

(R)-1-((5-bromo-2'-chloro-[1,1'-biphenyl]-2-yl)sulfonyl)-N-(5-(dimethylamino)-5-oxopent-3-yn-2-yl)-4-fluoropiperidine-4-carboxamide;

(S)-1-((5-bromo-2'-chloro-[1,1'-biphenyl]-2-yl)sulfonyl)-N-(5-(dimethylamino)-5-oxopent-3-yn-2-yl)-4-fluoropiperidine-4-carboxamide;

(E)-1-((5-bromo-2'-chloro-[1,1'-biphenyl]-2-yl)sulfonyl)-N-(4-(3,3-difluoroazetidin-1-yl)-4-oxobut-2-en-1-yl)-4-fluoropiperidine-4-carboxamide;

(E)-1-((2'-chloro-5-(trifluoromethyl)-[1,1'-biphenyl]-2-yl)sulfonyl)-N-(4-(3,3-difluoroazetidin-1-yl)-4-oxobut-2-en-1-yl)-4-fluoropiperidine-4-carboxamide;

(Z)-1-((2'-chloro-5-(trifluoromethyl)-[1,1'-biphenyl]-2-yl)sulfonyl)-N-(4-(3,3-difluoroazetidin-1-yl)-4-oxobut-2-en-1-yl)-4-fluoropiperidine-4-carboxamide;

(Z)-1-((5-bromo-2'-chloro-[1,1'-biphenyl]-2-yl)sulfonyl)-N-(4-(3,3-difluoroazetidin-1-yl)-4-oxobut-2-en-1-yl)-4-fluoropiperidine-4-carboxamide;

(Z)—N-(4-(azetidin-1-yl)-4-oxobut-2-en-1-yl)-1-((5-bromo-2'-chloro-[1,1'-biphenyl]-2-yl)sulfonyl)-4-fluoropiperidine-4-carboxamide;

(S,Z)-1-((5-bromo-2'-chloro-[1,1'-biphenyl]-2-yl)sulfonyl)-N-(5-(3,3-difluoroazetidin-1-yl)-5-oxopent-3-en-2-yl)-4-fluoropiperidine-4-carboxamide;

(2R,4S)-1-((2'-chloro-5-methoxy-[1,1'-biphenyl]-2-yl) sulfonyl)-N-((Z)-4-(3,3-difluoroazetidin-1-yl)-4-oxobut-2-en-1-yl)-4-fluoro-2-methylpiperidine-4-carboxamide;

(2R,4S)-1-((4-(2-chlorophenyl)-6-(trifluoromethyl)pyridin-3-yl)sulfonyl)-N-((Z)-4-(3,3-difluoroazetidin-1-yl)-4-oxobut-2-en-1-yl)-4-fluoro-2-methylpiperidine-4-carboxamide;

(2R,4S)-1-((2'-chloro-5-(trifluoromethyl)-[1,1'-biphenyl]-2-yl)sulfonyl)-N-((Z)-4-(3,3-difluoroazetidin-1-yl)-4-oxobut-2-en-1-yl)-4-fluoro-2-methylpiperidine-4-carboxamide;

(2R,4S)-1-((5-bromo-2'-chloro-[1,1'-biphenyl]-2-yl) sulfonyl)-N-((Z)-4-(3,3-difluoroazetidin-1-yl)-4-oxobut-2-en-1-yl)-4-fluoro-2-methylpiperidine-4-carboxamide;

(2R,4S)-1-((2'-chloro-5-cyano-[1,1'-biphenyl]-2-yl)sulfonyl)-N-((Z)-4-(3,3-difluoroazetidin-1-yl)-4-oxobut-2-en-1-yl)-4-fluoro-2-methylpiperidine-4-carboxamide;

(2*R,4*S)-1-((3*R,4*S)-4-(2-chlorophenyl)-6,6-dimethyltetrahydro-2H-pyran-3-carbonyl)-N-((Z)-4-(3,3-difluoroazetidin-1-yl)-4-oxobut-2-en-1-yl)-4-fluoro-2-methylpiperidine-4-carboxamide;

(R)-1-(2'-chloro-5-methoxy-[1,1'-biphenyl]-2-carbonyl)-N-((R)-1,1-dioxido-2,3-dihydrothiophen-3-yl)-4-fluoroazepane-4-carboxamide;

(R)-1-(2'-chloro-5-methoxy-[1,1'-biphenyl]-2-carbonyl)-4-fluoro-N-((R,Z)-4-(methylsulfonyl)but-3-en-2-yl) azepane-4-carboxamide;

(R)-1-((3R,4R)-4-(2-chloro-6-fluorophenyl)-1-(2,2,2-trifluoroethyl)pyrrolidine-3-carbonyl)-4-fluoro-N-((R,E)-4-(methylsulfonyl)but-3-en-2-yl)azepane-4-carboxamide;

(R)-1-((3R,4R)-4-(2-chloro-6-fluorophenyl)-1-(2,2,2-trifluoroethyl)pyrrolidine-3-carbonyl)-4-fluoro-N—((S,Z)-4-(methylsulfonyl)but-3-en-2-yl)azepane-4-carboxamide;

(2R,4S)-1-((2'-chloro-5-ethoxy-[1,1'-biphenyl]-2-yl)sulfonyl)-N-((R,E)-5-(3,3-difluoroazetidin-1-yl)-5-oxopent-3-en-2-yl)-4-fluoro-2-methylpiperidine-4-carboxamide;

(2R,4S)-1-((2'-chloro-5-ethoxy-[1,1'-biphenyl]-2-yl)sulfonyl)-4-fluoro-2-methyl-N-((R,Z)-4-(methylsulfonyl)but-3-en-2-yl)piperidine-4-carboxamide;

(2R,4S)-1-((2'-chloro-5-(methoxy-d3)-[1,1'-biphenyl]-2-yl)sulfonyl)-N-((R,E)-5-(3,3-difluoroazetidin-1-yl)-5-oxopent-3-en-2-yl)-4-fluoro-2-methylpiperidine-4-carboxamide;

(2R,4S)-1-((2'-chloro-5-(methoxy-d3)-[1,1'-biphenyl]-2-yl)sulfonyl)-4-fluoro-2-methyl-N-((R,Z)-4-(methylsulfonyl)but-3-en-2-yl)piperidine-4-carboxamide;

(2*S,4*S)-1-((3R,4R)-4-(2-chlorophenyl)-1-(2,2,2-trifluoroethyl)pyrrolidine-3-carbonyl)-4-fluoro-2-methyl-N-((R,Z)-4-(methylsulfonyl)but-3-en-2-yl)piperidine-4-carboxamide;

(R)-1-((3R,4R)-4-(2-chlorophenyl)-1-cyclopropylpyrrolidine-3-carbonyl)-4-fluoro-N-((R,Z)-4-(methylsulfonyl)but-3-en-2-yl)azepane-4-carboxamide;

1-((3R,4R)-4-(2-chlorophenyl)-1-cyclopropylpyrrolidine-3-carbonyl)-4-fluoro-N-((R,Z)-4-(methylsulfonyl)but-3-en-2-yl)piperidine-4-carboxamide;

(R)-1-((3*R,4*R)-1-benzyl-4-(2-chlorophenyl)pyrrolidine-3-carbonyl)-4-fluoro-N-((R,Z)-4-(methylsulfonyl)but-3-en-2-yl)azepane-4-carboxamide;

(R)-1-((3*R,4*R)-3-(2-chlorophenyl)-1-(2,2,2-trifluoroethyl)piperidine-4-carbonyl)-4-fluoro-N-((R,Z)-4-(methylsulfonyl)but-3-en-2-yl)azepane-4-carboxamide;

1-((3*S,4*S)-3-(2-chlorophenyl)-1-(2,2,2-trifluoroethyl)piperidine-4-carbonyl)-4-fluoro-N-((R,Z)-4-(methylsulfonyl)but-3-en-2-yl)piperidine-4-carboxamide;

(R)-1-((3*R,4*S)-4-(2-chlorophenyl)-1-(2,2,2-trifluoroethyl)piperidine-3-carbonyl)-4-fluoro-N-((R,Z)-4-(methylsulfonyl)but-3-en-2-yl)azepane-4-carboxamide;

(R)-1-((*R)-2-(2-chlorophenyl)-4-(2,2,2-trifluoroethyl)piperazine-1-carbonyl)-4-fluoro-N-((R,Z)-4-(methylsulfonyl)but-3-en-2-yl)azepane-4-carboxamide;

(R)-1-((2'-chloro-5-(trifluoromethyl)-[1,1'-biphenyl]-2-yl)sulfonyl)-4-fluoro-N-((R,Z)-4-(methylsulfonyl)but-3-en-2-yl)azepane-4-carboxamide;

(S)-1-((2'-chloro-5-(trifluoromethyl)-[1,1'-biphenyl]-2-yl)sulfonyl)-4-fluoro-N-((R,Z)-4-(methylsulfonyl)but-3-en-2-yl)azepane-4-carboxamide;

(R)-1-((2'-chloro-5-methoxy-[1,1'-biphenyl]-2-yl)sulfonyl)-4-fluoro-N-((R,Z)-4-(methylsulfonyl)but-3-en-2-yl)azepane-4-carboxamide;

(S)-1-((2'-chloro-5-methoxy-[1,1'-biphenyl]-2-yl)sulfonyl)-4-fluoro-N-((R,Z)-4-(methylsulfonyl)but-3-en-2-yl)azepane-4-carboxamide;

1-((3R,4R)-4-(2-chlorophenyl)-1-(2,2,2-trifluoroethyl)pyrrolidine-3-carbonyl)-3-fluoro-N-((R,Z)-4-(methylsulfonyl)but-3-en-2-yl) pyrrolidine-3-carboxamide;

or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof.

17. A pharmaceutical composition comprising a compound of claim 1, or a pharmaceutically acceptable salt thereof, or a stereoisomer thereof, or a pharmaceutically acceptable salt of a stereoisomer thereof, or an atropisomer thereof, or a pharmaceutically acceptable salt of an atropisomer thereof; and a pharmaceutically acceptable excipient or carrier.

* * * * *